United States Patent
Harvey et al.

(10) Patent No.: US 11,685,732 B2
(45) Date of Patent: Jun. 27, 2023

(54) MYST FAMILY HISTONE ACETYLTRANSFERASE INHIBITORS

(71) Applicant: Epizyme, Inc., Cambridge, MA (US)

(72) Inventors: Darren Martin Harvey, Acton, MA (US); John Emmerson Campbell, Cambridge, MA (US); Kenneth William Duncan, Westwood, MA (US)

(73) Assignee: Epizyme, Inc., Cambridge, MA (US)

( * ) Notice: Subject to any disclaimer, the term of this patent is extended or adjusted under 35 U.S.C. 154(b) by 208 days.

(21) Appl. No.: 16/766,890

(22) PCT Filed: Nov. 29, 2018

(86) PCT No.: PCT/US2018/063110
§ 371 (c)(1),
(2) Date: May 26, 2020

(87) PCT Pub. No.: WO2019/108824
PCT Pub. Date: Jun. 6, 2019

(65) Prior Publication Data
US 2022/0162197 A1    May 26, 2022

Related U.S. Application Data

(60) Provisional application No. 62/592,215, filed on Nov. 29, 2017.

(51) Int. Cl.
| | | |
|---|---|---|
| *C07D 403/12* | (2006.01) |
| *C07D 309/06* | (2006.01) |
| *C07D 309/08* | (2006.01) |
| *C07D 231/12* | (2006.01) |
| *C07D 231/56* | (2006.01) |
| *C07D 471/10* | (2006.01) |
| *C07D 263/28* | (2006.01) |
| *C07D 263/50* | (2006.01) |
| *C07D 205/04* | (2006.01) |
| *C07D 265/30* | (2006.01) |
| *C07D 207/08* | (2006.01) |
| *C07D 275/03* | (2006.01) |
| *C07C 311/19* | (2006.01) |
| *C07C 311/32* | (2006.01) |
| *C07C 311/49* | (2006.01) |
| *C07C 255/00* | (2006.01) |
| *C07C 307/02* | (2006.01) |
| *C07C 317/50* | (2006.01) |
| *A61K 31/40* | (2006.01) |
| *A61K 31/18* | (2006.01) |
| *A61K 31/165* | (2006.01) |
| *A61P 35/00* | (2006.01) |
| *C07D 405/12* | (2006.01) |
| *C07D 211/24* | (2006.01) |
| *C07D 213/54* | (2006.01) |
| *C07D 223/04* | (2006.01) |
| *C07D 233/64* | (2006.01) |
| *C07D 241/04* | (2006.01) |
| *C07D 257/04* | (2006.01) |
| *C07D 401/12* | (2006.01) |
| *C07D 401/14* | (2006.01) |
| *C07D 403/14* | (2006.01) |
| *C07D 405/14* | (2006.01) |
| *C07D 413/12* | (2006.01) |
| *C07D 417/12* | (2006.01) |

(52) U.S. Cl.
CPC .......... *C07D 405/12* (2013.01); *C07C 311/49* (2013.01); *C07D 205/04* (2013.01); *C07D 207/08* (2013.01); *C07D 211/24* (2013.01); *C07D 213/54* (2013.01); *C07D 223/04* (2013.01); *C07D 231/12* (2013.01); *C07D 233/64* (2013.01); *C07D 241/04* (2013.01); *C07D 257/04* (2013.01); *C07D 265/30* (2013.01); *C07D 401/12* (2013.01); *C07D 401/14* (2013.01); *C07D 403/12* (2013.01); *C07D 403/14* (2013.01); *C07D 405/14* (2013.01); *C07D 413/12* (2013.01); *C07D 417/12* (2013.01)

(58) Field of Classification Search
CPC .. C07D 403/12; C07D 309/06; C07D 309/08; C07D 231/12; C07D 231/56; C07D 471/10; C07D 263/28; C07D 263/50; C07D 205/04; C07D 265/30; C07D 207/08; C07D 275/03; C07C 311/19; C07C 311/32; C07C 311/49; C07C 255/00; C07C 307/02; C07C 317/50; A61P 35/00; A61K 31/165; A61K 31/18; A61K 31/40
See application file for complete search history.

(56) References Cited

U.S. PATENT DOCUMENTS

| | | |
|---|---|---|
| 4,735,959 A | 4/1988 | Grell et al. |
| 2002/0120007 A1 | 8/2002 | Beight et al. |

FOREIGN PATENT DOCUMENTS

WO    WO 2016198507    * 12/2016

OTHER PUBLICATIONS

International Search Report and Written Opinion for Application No. PCT/US2017/063721, dated Feb. 2, 2018.
International Search Report and Written Opinion for Application No. PCT/US2018/063110, dated Mar. 5, 2019.
No Author Listed, PUBCHEM, Substance Record for SID 5798273. Available Date: Sep. 12, 2005. [retrieved Jan. 3, 2019). Retrieved from the Internet: <https://pubchem.ncbi.nlm.nih.gov/substance/5798273>.

(Continued)

*Primary Examiner* — Bruck Kifle
(74) *Attorney, Agent, or Firm* — Wolf, Greenfield & Sacks, P.C.

(57) ABSTRACT

The present disclosure provides compounds, pharmaceutically acceptable compositions thereof, and methods of using the same.

8 Claims, 1 Drawing Sheet
Specification includes a Sequence Listing.

(56) References Cited

OTHER PUBLICATIONS

Bocanegra-Garcia et al., Synthesis and biological evaluation of new sulfonamide derivatives as potential anti-Trypanosoma cruzi agents. Med Chem. Nov. 2012;8(6):1039-44. doi: 10.2174/1573406411208061039.

Brown et al., Targeting cancer using KAT inhibitors to mimic lethal knockouts. Biochem Soc Trans. Aug. 15, 2016;44(4):979-86. doi: 10.1042/BST20160081.

Cheng et al., Discovery and structure-activity relationships of phenyl benzenesulfonylhydrazides as novel indoleamine 2,3-dioxygenase inhibitors. Bioorg Med Chem Lett. Aug. 1, 2014;24(15):3403-6. doi: 10.1016/j.bmcl.2014.05.084. Epub Jun. 4, 2014.

Gemma et al., Discovery of potent nucleotide-mimicking competitive inhibitors of hepatitis C virus NS3 helicase. Bioorg Med Chem Lett. May 1, 2011;21(9):2776-9. doi: 10.1016/j.bmcl.2010.09.002. Epub Sep. 6, 2010.

Kim et al., Hit-to-lead optimization of phenylsulfonyl hydrazides for a potent suppressor of PGE2 production: Synthesis, biological activity, and molecular docking study. Bioorg Med Chem Lett. Jan 1, 2016;26(1):94-9. doi: 10.1016/j.bmcl.2015.11.024. Epub Nov. 10, 2015.

Lin et al., Phenyl Benzenesulfonylhydrazides Exhibit Selective Indoleamine 2,3-Dioxygenase Inhibition with Potent in Vivo Pharmacodynamic Activity and Antitumor Efficacy. J Med Chem. Jan. 14, 2016;59(1):419-30. doi: 10.1021/acs.jmedchem.5b01640. Epub Dec. 23, 2015. With supplemental information.

Ukhin et al., Synthesis of new 3,4-di-and 1,2,3,4-tetrahydroquinazolin-4-one derivatives and X-ray diffraction study of crystal solvates of 3-methylsulfonylamino-2-(2-methylsulfonylaminophenyl)-1,2,3,4-tetrahydroquinazolin-4-one. Russian Chemical Bulletin. Jul. 2006; 55(7): 1229-1238. DOI:10.1007/S11172-006-0404-Y.

Zaharia et al., Synthesis of some p-toluenesulfonyl-hydrazinothiazoles and hydrazino-bis-thiazoles and their anticancer activity. Eur J Med Chem. Nov. 2010;45(11):5080-5. doi: 10.1016/j.ejmech.2010.08.017. Epub Aug. 12, 2010.

Zhou et al., Novel parallel synthesis of N-(4-oxo-2-substituted-4H-quinazolin-3-yl)-substituted sulfonamides. Tetrahedron Letters. Oct. 2004; 45(43):8049-8051.

* cited by examiner

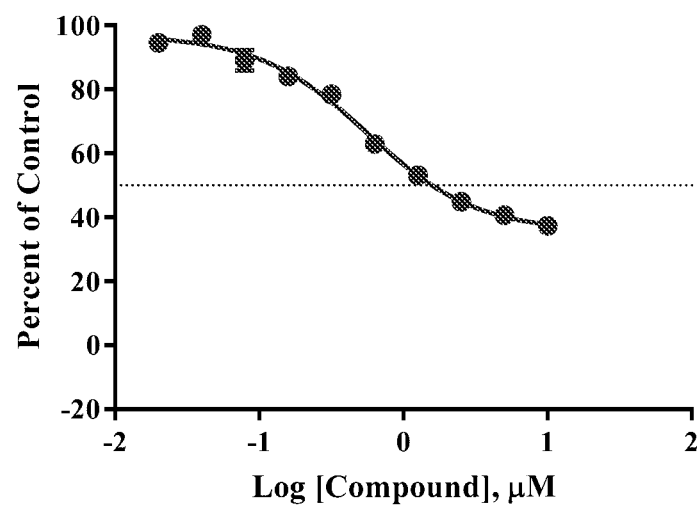

SEQUENCE LISTING

```
<160> NUMBER OF SEQ ID NOS: 17

<210> SEQ ID NO 1
<211> LENGTH: 611
<212> TYPE: PRT
<213> ORGANISM: Homo sapiens

<400> SEQUENCE: 1

Met Pro Arg Arg Lys Arg Asn Ala Gly Ser Ser Ser Asp Gly Thr Glu
1               5                   10                  15

Asp Ser Asp Phe Ser Thr Asp Leu Glu His Thr Asp Ser Ser Glu Ser
            20                  25                  30

Asp Gly Thr Ser Arg Arg Ser Ala Arg Val Thr Arg Ser Ser Ala Arg
        35                  40                  45

Leu Ser Gln Ser Ser Gln Asp Ser Ser Pro Val Arg Asn Leu Gln Ser
    50                  55                  60

Phe Gly Thr Glu Glu Pro Ala Tyr Ser Thr Arg Arg Val Thr Arg Ser
65                  70                  75                  80

Gln Gln Gln Pro Thr Pro Val Thr Pro Lys Lys Tyr Pro Leu Arg Gln
                85                  90                  95
```

```
Thr Arg Ser Ser Gly Ser Glu Thr Glu Gln Val Val Asp Phe Ser Asp
            100                 105                 110

Arg Glu Thr Lys Asn Thr Ala Asp His Asp Glu Ser Pro Pro Arg Thr
            115                 120                 125

Pro Thr Gly Asn Ala Pro Ser Ser Glu Ser Asp Ile Asp Ile Ser Ser
            130                 135                 140

Pro Asn Val Ser His Asp Glu Ser Ile Ala Lys Asp Met Ser Leu Lys
145                 150                 155                 160

Asp Ser Gly Ser Asp Leu Ser His Arg Pro Lys Arg Arg Phe His
                165                 170                 175

Glu Ser Tyr Asn Phe Asn Met Lys Cys Pro Thr Pro Gly Cys Asn Ser
            180                 185                 190

Leu Gly His Leu Thr Gly Lys His Glu Arg His Phe Ser Ile Ser Gly
            195                 200                 205

Cys Pro Leu Tyr His Asn Leu Ser Ala Asp Glu Cys Lys Val Arg Ala
210                 215                 220

Gln Ser Arg Asp Lys Gln Ile Glu Glu Arg Met Leu Ser His Arg Gln
225                 230                 235                 240

Asp Asp Asn Asn Arg His Ala Thr Arg His Gln Ala Pro Thr Glu Arg
                245                 250                 255

Gln Leu Arg Tyr Lys Glu Lys Val Ala Glu Leu Arg Lys Lys Arg Asn
            260                 265                 270

Ser Gly Leu Ser Lys Glu Gln Lys Glu Lys Tyr Met Glu His Arg Gln
            275                 280                 285

Thr Tyr Gly Asn Thr Arg Glu Pro Leu Leu Glu Asn Leu Thr Ser Glu
290                 295                 300

Tyr Asp Leu Asp Leu Phe Arg Arg Ala Gln Ala Arg Ala Ser Glu Asp
305                 310                 315                 320

Leu Glu Lys Leu Arg Leu Gln Gly Gln Ile Thr Glu Gly Ser Asn Met
            325                 330                 335

Ile Lys Thr Ile Ala Phe Gly Arg Tyr Glu Leu Asp Thr Trp Tyr His
            340                 345                 350

Ser Pro Tyr Pro Glu Glu Tyr Ala Arg Leu Gly Arg Leu Tyr Met Cys
            355                 360                 365

Glu Phe Cys Leu Lys Tyr Met Lys Ser Gln Thr Ile Leu Arg Arg His
370                 375                 380

Met Ala Lys Cys Val Trp Lys His Pro Pro Gly Asp Glu Ile Tyr Arg
385                 390                 395                 400

Lys Gly Ser Ile Ser Val Phe Glu Val Asp Gly Lys Lys Asn Lys Ile
            405                 410                 415

Tyr Cys Gln Asn Leu Cys Leu Leu Ala Lys Leu Phe Leu Asp His Lys
            420                 425                 430

Thr Leu Tyr Tyr Asp Val Glu Pro Phe Leu Phe Tyr Val Met Thr Glu
            435                 440                 445

Ala Asp Asn Thr Gly Cys His Leu Ile Gly Tyr Phe Ser Lys Glu Lys
450                 455                 460

Asn Ser Phe Leu Asn Tyr Asn Val Ser Cys Ile Leu Thr Met Pro Gln
465                 470                 475                 480

Tyr Met Arg Gln Gly Tyr Gly Lys Met Leu Ile Asp Phe Ser Tyr Leu
            485                 490                 495

Leu Ser Lys Val Glu Glu Lys Val Gly Ser Pro Glu Arg Pro Leu Ser
            500                 505                 510

Asp Leu Gly Leu Ile Ser Tyr Arg Ser Tyr Trp Lys Glu Val Leu Leu
```

```
                515                 520                 525

Arg Tyr Leu His Asn Phe Gln Gly Lys Glu Ile Ser Ile Lys Glu Ile
    530                 535                 540

Ser Gln Glu Thr Ala Val Asn Pro Val Asp Ile Val Ser Thr Leu Gln
545                 550                 555                 560

Ala Leu Gln Met Leu Lys Tyr Trp Lys Gly Lys His Leu Val Leu Lys
                565                 570                 575

Arg Gln Asp Leu Ile Asp Glu Trp Ile Ala Lys Glu Ala Lys Arg Ser
            580                 585                 590

Asn Ser Asn Lys Thr Met Asp Pro Ser Cys Leu Lys Trp Thr Pro Pro
        595                 600                 605

Lys Gly Thr
    610

<210> SEQ ID NO 2
<211> LENGTH: 581
<212> TYPE: PRT
<213> ORGANISM: Homo sapiens

<400> SEQUENCE: 2

Met Pro Arg Arg Lys Arg Asn Ala Gly Ser Ser Asp Gly Thr Glu
1               5                   10                  15

Asp Ser Asp Phe Ser Thr Asp Leu Glu His Thr Asp Ser Ser Glu Ser
                20                  25                  30

Asp Gly Thr Ser Arg Arg Ser Ala Arg Val Thr Arg Ser Ser Ala Arg
            35                  40                  45

Leu Ser Gln Ser Ser Gln Asp Ser Ser Pro Val Arg Asn Leu Gln Ser
        50                  55                  60

Phe Gly Thr Glu Glu Pro Ala Tyr Ser Thr Arg Arg Val Thr Arg Ser
65                  70                  75                  80

Gln Gln Gln Pro Thr Pro Val Thr Pro Lys Lys Tyr Pro Leu Arg Gln
                85                  90                  95

Thr Arg Ser Ser Gly Ser Glu Thr Glu Gln Val Val Asp Phe Ser Asp
                100                 105                 110

Arg Glu Thr Lys Asn Thr Ala Asp His Asp Glu Ser Pro Pro Arg Thr
            115                 120                 125

Pro Thr Gly Asn Ala Pro Ser Ser Glu Ser Asp Ile Asp Ile Ser Ser
        130                 135                 140

Pro Asn Val Ser His Asp Glu Ser Ile Ala Lys Asp Met Ser Leu Lys
145                 150                 155                 160

Asp Ser Gly Ser Asp Leu Ser His Arg Pro Lys Arg Arg Arg Phe His
                165                 170                 175

Glu Ser Tyr Asn Phe Asn Met Lys Cys Pro Thr Pro Gly Cys Asn Ser
                180                 185                 190

Leu Gly His Leu Thr Gly Lys His Glu Arg His Phe Ser Ile Ser Gly
            195                 200                 205

Cys Pro Leu Tyr His Asn Leu Ser Ala Asp Glu Cys Lys Ala Pro Thr
        210                 215                 220

Glu Arg Gln Leu Arg Tyr Lys Glu Lys Val Ala Glu Leu Arg Lys Lys
225                 230                 235                 240

Arg Asn Ser Gly Leu Ser Lys Glu Gln Lys Glu Lys Tyr Met Glu His
                245                 250                 255

Arg Gln Thr Tyr Gly Asn Thr Arg Glu Pro Leu Leu Glu Asn Leu Thr
            260                 265                 270
```

```
Ser Glu Tyr Asp Leu Asp Leu Phe Arg Arg Ala Gln Ala Arg Ala Ser
        275                 280                 285
Glu Asp Leu Glu Lys Leu Arg Leu Gln Gly Gln Ile Thr Glu Gly Ser
290                 295                 300
Asn Met Ile Lys Thr Ile Ala Phe Gly Arg Tyr Glu Leu Asp Thr Trp
305                 310                 315                 320
Tyr His Ser Pro Tyr Pro Glu Tyr Ala Arg Leu Gly Arg Leu Tyr
                325                 330                 335
Met Cys Glu Phe Cys Leu Lys Tyr Met Lys Ser Gln Thr Ile Leu Arg
            340                 345                 350
Arg His Met Ala Lys Cys Val Trp Lys His Pro Pro Gly Asp Glu Ile
        355                 360                 365
Tyr Arg Lys Gly Ser Ile Ser Val Phe Glu Val Asp Gly Lys Lys Asn
        370                 375                 380
Lys Ile Tyr Cys Gln Asn Leu Cys Leu Leu Ala Lys Leu Phe Leu Asp
385                 390                 395                 400
His Lys Thr Leu Tyr Tyr Asp Val Glu Pro Phe Leu Phe Tyr Val Met
                405                 410                 415
Thr Glu Ala Asp Asn Thr Gly Cys His Leu Ile Gly Tyr Phe Ser Lys
            420                 425                 430
Glu Lys Asn Ser Phe Leu Asn Tyr Asn Val Ser Cys Ile Leu Thr Met
        435                 440                 445
Pro Gln Tyr Met Arg Gln Gly Tyr Gly Lys Met Leu Ile Asp Phe Ser
        450                 455                 460
Tyr Leu Leu Ser Lys Val Glu Lys Val Gly Ser Pro Glu Arg Pro
465                 470                 475                 480
Leu Ser Asp Leu Gly Leu Ile Ser Tyr Arg Ser Tyr Trp Lys Glu Val
                485                 490                 495
Leu Leu Arg Tyr Leu His Asn Phe Gln Gly Lys Glu Ile Ser Ile Lys
            500                 505                 510
Glu Ile Ser Gln Glu Thr Ala Val Asn Pro Val Asp Ile Val Ser Thr
        515                 520                 525
Leu Gln Ala Leu Gln Met Leu Lys Tyr Trp Lys Gly Lys His Leu Val
530                 535                 540
Leu Lys Arg Gln Asp Leu Ile Asp Glu Trp Ile Ala Lys Glu Ala Lys
545                 550                 555                 560
Arg Ser Asn Ser Asn Lys Thr Met Asp Pro Ser Cys Leu Lys Trp Thr
                565                 570                 575
Pro Pro Lys Gly Thr
            580

<210> SEQ ID NO 3
<211> LENGTH: 472
<212> TYPE: PRT
<213> ORGANISM: Homo sapiens

<400> SEQUENCE: 3

Met Pro Arg Arg Lys Arg Asn Ala Gly Ser Ser Asp Gly Thr Glu
1               5                   10                  15
Asp Ser Asp Phe Ser Thr Asp Leu Glu His Thr Asp Ser Glu Ser
            20                  25                  30
Asp Gly Thr Ser Arg Arg Ser Ala Arg Val Thr Arg Ser Ser Ala Arg
        35                  40                  45
Leu Ser Gln Ser Ser Gln Gly His Leu Thr Gly Lys His Glu Arg His
50                  55                  60
```

```
Phe Ser Ile Ser Gly Cys Pro Leu Tyr His Asn Leu Ser Ala Asp Glu
 65                  70                  75                  80

Cys Lys Val Arg Ala Gln Ser Arg Asp Lys Gln Ile Glu Glu Arg Met
                 85                  90                  95

Leu Ser His Arg Gln Asp Asp Asn Asn Arg His Ala Thr Arg His Gln
            100                 105                 110

Ala Pro Thr Glu Arg Gln Leu Arg Tyr Lys Glu Lys Val Ala Glu Leu
        115                 120                 125

Arg Lys Lys Arg Asn Ser Gly Leu Ser Lys Glu Gln Lys Glu Lys Tyr
130                 135                 140

Met Glu His Arg Gln Thr Tyr Gly Asn Thr Arg Glu Pro Leu Leu Glu
145                 150                 155                 160

Asn Leu Thr Ser Glu Tyr Asp Leu Asp Leu Phe Arg Arg Ala Gln Ala
                165                 170                 175

Arg Ala Ser Glu Asp Leu Glu Lys Leu Arg Leu Gln Gly Gln Ile Thr
            180                 185                 190

Glu Gly Ser Asn Met Ile Lys Thr Ile Ala Phe Gly Arg Tyr Glu Leu
        195                 200                 205

Asp Thr Trp Tyr His Ser Pro Tyr Pro Glu Glu Tyr Ala Arg Leu Gly
210                 215                 220

Arg Leu Tyr Met Cys Glu Phe Cys Leu Lys Tyr Met Lys Ser Gln Thr
225                 230                 235                 240

Ile Leu Arg Arg His Met Ala Lys Cys Val Trp Lys His Pro Pro Gly
                245                 250                 255

Asp Glu Ile Tyr Arg Lys Gly Ser Ile Ser Val Phe Glu Val Asp Gly
            260                 265                 270

Lys Lys Asn Lys Ile Tyr Cys Gln Asn Leu Cys Leu Leu Ala Lys Leu
        275                 280                 285

Phe Leu Asp His Lys Thr Leu Tyr Tyr Asp Val Glu Pro Phe Leu Phe
290                 295                 300

Tyr Val Met Thr Glu Ala Asp Asn Thr Gly Cys His Leu Ile Gly Tyr
305                 310                 315                 320

Phe Ser Lys Glu Lys Asn Ser Phe Leu Asn Tyr Asn Val Ser Cys Ile
                325                 330                 335

Leu Thr Met Pro Gln Tyr Met Arg Gln Gly Tyr Gly Lys Met Leu Ile
            340                 345                 350

Asp Phe Ser Tyr Leu Leu Ser Lys Val Glu Glu Lys Val Gly Ser Pro
        355                 360                 365

Glu Arg Pro Leu Ser Asp Leu Gly Leu Ile Ser Tyr Arg Ser Tyr Trp
370                 375                 380

Lys Glu Val Leu Leu Arg Tyr Leu His Asn Phe Gln Gly Lys Glu Ile
385                 390                 395                 400

Ser Ile Lys Glu Ile Ser Gln Glu Thr Ala Val Asn Pro Val Asp Ile
                405                 410                 415

Val Ser Thr Leu Gln Ala Leu Gln Met Leu Lys Tyr Trp Lys Gly Lys
            420                 425                 430

His Leu Val Leu Lys Arg Gln Asp Leu Ile Asp Glu Trp Ile Ala Lys
        435                 440                 445

Glu Ala Lys Arg Ser Asn Ser Asn Lys Thr Met Asp Pro Ser Cys Leu
450                 455                 460

Lys Trp Thr Pro Pro Lys Gly Thr
465                 470
```

```
<210> SEQ ID NO 4
<211> LENGTH: 501
<212> TYPE: PRT
<213> ORGANISM: Homo sapiens

<400> SEQUENCE: 4

Met Pro Arg Arg Lys Arg Asn Ala Gly Ser Ser Asp Gly Thr Glu
1               5                   10                  15

Asp Ser Asp Phe Ser Thr Asp Leu Glu His Thr Asp Ser Ser Glu Ser
            20                  25                  30

Asp Gly Thr Ser Arg Arg Ser Ala Arg Val Thr Arg Ser Ser Ala Arg
        35                  40                  45

Leu Ser Gln Ser Ser Gln Asp Ser Ser Pro Val Arg Asn Leu Gln Ser
    50                  55                  60

Phe Gly Thr Glu Glu Pro Ala Tyr Ser Thr Arg Arg Val Thr Arg Ser
65                  70                  75                  80

Gln Gln Gln Pro Thr Pro Val Thr Pro Lys Lys Tyr Pro Leu Arg Gln
                85                  90                  95

Thr Arg Ser Ser Gly Ser Glu Thr Glu Gln Val Val Asp Phe Ser Asp
            100                 105                 110

Arg Gly His Leu Thr Gly Lys His Glu Arg His Phe Ser Ile Ser Gly
        115                 120                 125

Cys Pro Leu Tyr His Asn Leu Ser Ala Asp Glu Cys Lys Ala Pro Thr
130                 135                 140

Glu Arg Gln Leu Arg Tyr Lys Glu Lys Val Ala Glu Leu Arg Lys Lys
145                 150                 155                 160

Arg Asn Ser Gly Leu Ser Lys Glu Gln Lys Glu Lys Tyr Met Glu His
                165                 170                 175

Arg Gln Thr Tyr Gly Asn Thr Arg Glu Pro Leu Leu Glu Asn Leu Thr
            180                 185                 190

Ser Glu Tyr Asp Leu Asp Leu Phe Arg Arg Ala Gln Ala Arg Ala Ser
        195                 200                 205

Glu Asp Leu Glu Lys Leu Arg Leu Gln Gly Gln Ile Thr Glu Gly Ser
    210                 215                 220

Asn Met Ile Lys Thr Ile Ala Phe Gly Arg Tyr Glu Leu Asp Thr Trp
225                 230                 235                 240

Tyr His Ser Pro Tyr Pro Glu Glu Tyr Ala Arg Leu Gly Arg Leu Tyr
                245                 250                 255

Met Cys Glu Phe Cys Leu Lys Tyr Met Lys Ser Gln Thr Ile Leu Arg
            260                 265                 270

Arg His Met Ala Lys Cys Val Trp Lys His Pro Pro Gly Asp Glu Ile
        275                 280                 285

Tyr Arg Lys Gly Ser Ile Ser Val Phe Glu Val Asp Gly Lys Lys Asn
    290                 295                 300

Lys Ile Tyr Cys Gln Asn Leu Cys Leu Leu Ala Lys Leu Phe Leu Asp
305                 310                 315                 320

His Lys Thr Leu Tyr Tyr Asp Val Glu Pro Phe Leu Phe Tyr Val Met
                325                 330                 335

Thr Glu Ala Asp Asn Thr Gly Cys His Leu Ile Gly Tyr Phe Ser Lys
            340                 345                 350

Glu Lys Asn Ser Phe Leu Asn Tyr Asn Val Ser Cys Ile Leu Thr Met
        355                 360                 365

Pro Gln Tyr Met Arg Gln Gly Tyr Gly Lys Met Leu Ile Asp Phe Ser
    370                 375                 380
```

Tyr Leu Leu Ser Lys Val Glu Glu Lys Val Gly Ser Pro Glu Arg Pro
385                 390                 395                 400

Leu Ser Asp Leu Gly Leu Ile Ser Tyr Arg Ser Tyr Trp Lys Glu Val
                405                 410                 415

Leu Leu Arg Tyr Leu His Asn Phe Gln Gly Lys Glu Ile Ser Ile Lys
            420                 425                 430

Glu Ile Ser Gln Glu Thr Ala Val Asn Pro Val Asp Ile Val Ser Thr
        435                 440                 445

Leu Gln Ala Leu Gln Met Leu Lys Tyr Trp Lys Gly Lys His Leu Val
450                 455                 460

Leu Lys Arg Gln Asp Leu Ile Asp Glu Trp Ile Ala Lys Glu Ala Lys
465                 470                 475                 480

Arg Ser Asn Ser Asn Lys Thr Met Asp Pro Ser Cys Leu Lys Trp Thr
                485                 490                 495

Pro Pro Lys Gly Thr
            500

<210> SEQ ID NO 5
<211> LENGTH: 442
<212> TYPE: PRT
<213> ORGANISM: Homo sapiens

<400> SEQUENCE: 5

Met Pro Arg Arg Lys Arg Asn Ala Gly Ser Ser Asp Gly Thr Glu
1               5                   10                  15

Asp Ser Asp Phe Ser Thr Asp Leu Glu His Thr Asp Ser Ser Glu Ser
                20                  25                  30

Asp Gly Thr Ser Arg Arg Ser Ala Arg Val Thr Arg Ser Ser Ala Arg
            35                  40                  45

Leu Ser Gln Ser Ser Gln Gly His Leu Thr Gly Lys His Glu Arg His
50                  55                  60

Phe Ser Ile Ser Gly Cys Pro Leu Tyr His Asn Leu Ser Ala Asp Glu
65                  70                  75                  80

Cys Lys Ala Pro Thr Glu Arg Gln Leu Arg Tyr Lys Glu Lys Val Ala
                85                  90                  95

Glu Leu Arg Lys Lys Arg Asn Ser Gly Leu Ser Lys Glu Gln Lys Glu
            100                 105                 110

Lys Tyr Met Glu His Arg Gln Thr Tyr Gly Asn Thr Arg Glu Pro Leu
        115                 120                 125

Leu Glu Asn Leu Thr Ser Glu Tyr Asp Leu Asp Leu Phe Arg Arg Ala
    130                 135                 140

Gln Ala Arg Ala Ser Glu Asp Leu Glu Lys Leu Arg Leu Gln Gly Gln
145                 150                 155                 160

Ile Thr Glu Gly Ser Asn Met Ile Lys Thr Ile Ala Phe Gly Arg Tyr
                165                 170                 175

Glu Leu Asp Thr Trp Tyr His Ser Pro Tyr Pro Glu Glu Tyr Ala Arg
            180                 185                 190

Leu Gly Arg Leu Tyr Met Cys Glu Phe Cys Leu Lys Tyr Met Lys Ser
        195                 200                 205

Gln Thr Ile Leu Arg Arg His Met Ala Lys Cys Val Trp Lys His Pro
    210                 215                 220

Pro Gly Asp Glu Ile Tyr Arg Lys Gly Ser Ile Ser Val Phe Glu Val
225                 230                 235                 240

Asp Gly Lys Lys Asn Lys Ile Tyr Cys Gln Asn Leu Cys Leu Leu Ala

```
                     245                 250                 255
Lys Leu Phe Leu Asp His Lys Thr Leu Tyr Tyr Asp Val Glu Pro Phe
            260                 265                 270

Leu Phe Tyr Val Met Thr Glu Ala Asp Asn Thr Gly Cys His Leu Ile
        275                 280                 285

Gly Tyr Phe Ser Lys Glu Lys Asn Ser Phe Leu Asn Tyr Asn Val Ser
    290                 295                 300

Cys Ile Leu Thr Met Pro Gln Tyr Met Arg Gln Gly Tyr Gly Lys Met
305                 310                 315                 320

Leu Ile Asp Phe Ser Tyr Leu Leu Ser Lys Val Glu Glu Lys Val Gly
                325                 330                 335

Ser Pro Glu Arg Pro Leu Ser Asp Leu Gly Leu Ile Ser Tyr Arg Ser
            340                 345                 350

Tyr Trp Lys Glu Val Leu Leu Arg Tyr Leu His Asn Phe Gln Gly Lys
        355                 360                 365

Glu Ile Ser Ile Lys Glu Ile Ser Gln Glu Thr Ala Val Asn Pro Val
    370                 375                 380

Asp Ile Val Ser Thr Leu Gln Ala Leu Gln Met Leu Lys Tyr Trp Lys
385                 390                 395                 400

Gly Lys His Leu Val Leu Lys Arg Gln Asp Leu Ile Asp Glu Trp Ile
                405                 410                 415

Ala Lys Glu Ala Lys Arg Ser Asn Ser Asn Lys Thr Met Asp Pro Ser
            420                 425                 430

Cys Leu Lys Trp Thr Pro Pro Lys Gly Thr
        435                 440
```

<210> SEQ ID NO 6
<211> LENGTH: 531
<212> TYPE: PRT
<213> ORGANISM: Homo sapiens

<400> SEQUENCE: 6

```
Met Pro Arg Arg Lys Arg Asn Ala Gly Ser Ser Ser Asp Gly Thr Glu
1               5                   10                  15

Asp Ser Asp Phe Ser Thr Asp Leu Glu His Thr Asp Ser Ser Glu Ser
            20                  25                  30

Asp Gly Thr Ser Arg Arg Ser Ala Arg Val Thr Arg Ser Ser Ala Arg
        35                  40                  45

Leu Ser Gln Ser Ser Gln Asp Ser Ser Pro Val Arg Asn Leu Gln Ser
    50                  55                  60

Phe Gly Thr Glu Glu Pro Ala Tyr Ser Thr Arg Arg Val Thr Arg Ser
65                  70                  75                  80

Gln Gln Gln Pro Thr Pro Val Thr Pro Lys Lys Tyr Pro Leu Arg Gln
            85                  90                  95

Thr Arg Ser Ser Gly Ser Glu Thr Glu Gln Val Val Asp Phe Ser Asp
        100                 105                 110

Arg Gly His Leu Thr Gly Lys His Glu Arg His Phe Ser Ile Ser Gly
    115                 120                 125

Cys Pro Leu Tyr His Asn Leu Ser Ala Asp Glu Cys Lys Val Arg Ala
130                 135                 140

Gln Ser Arg Asp Lys Gln Ile Glu Glu Arg Met Leu Ser His Arg Gln
145                 150                 155                 160

Asp Asp Asn Asn Arg His Ala Thr Arg His Gln Ala Pro Thr Glu Arg
            165                 170                 175
```

```
Gln Leu Arg Tyr Lys Glu Lys Val Ala Glu Leu Arg Lys Lys Arg Asn
            180                 185                 190

Ser Gly Leu Ser Lys Glu Gln Lys Glu Lys Tyr Met Glu His Arg Gln
        195                 200                 205

Thr Tyr Gly Asn Thr Arg Glu Pro Leu Leu Glu Asn Leu Thr Ser Glu
    210                 215                 220

Tyr Asp Leu Asp Leu Phe Arg Arg Ala Gln Ala Arg Ala Ser Glu Asp
225                 230                 235                 240

Leu Glu Lys Leu Arg Leu Gln Gly Gln Ile Thr Glu Gly Ser Asn Met
                245                 250                 255

Ile Lys Thr Ile Ala Phe Gly Arg Tyr Glu Leu Asp Thr Trp Tyr His
            260                 265                 270

Ser Pro Tyr Pro Glu Glu Tyr Ala Arg Leu Gly Arg Leu Tyr Met Cys
        275                 280                 285

Glu Phe Cys Leu Lys Tyr Met Lys Ser Gln Thr Ile Leu Arg Arg His
    290                 295                 300

Met Ala Lys Cys Val Trp Lys His Pro Pro Gly Asp Glu Ile Tyr Arg
305                 310                 315                 320

Lys Gly Ser Ile Ser Val Phe Glu Val Asp Gly Lys Lys Asn Lys Ile
                325                 330                 335

Tyr Cys Gln Asn Leu Cys Leu Leu Ala Lys Leu Phe Leu Asp His Lys
            340                 345                 350

Thr Leu Tyr Tyr Asp Val Glu Pro Phe Leu Phe Tyr Val Met Thr Glu
        355                 360                 365

Ala Asp Asn Thr Gly Cys His Leu Ile Gly Tyr Phe Ser Lys Glu Lys
    370                 375                 380

Asn Ser Phe Leu Asn Tyr Asn Val Ser Cys Ile Leu Thr Met Pro Gln
385                 390                 395                 400

Tyr Met Arg Gln Gly Tyr Gly Lys Met Leu Ile Asp Phe Ser Tyr Leu
                405                 410                 415

Leu Ser Lys Val Glu Glu Lys Val Gly Ser Pro Glu Arg Pro Leu Ser
            420                 425                 430

Asp Leu Gly Leu Ile Ser Tyr Arg Ser Tyr Trp Lys Glu Val Leu Leu
        435                 440                 445

Arg Tyr Leu His Asn Phe Gln Gly Lys Glu Ile Ser Ile Lys Glu Ile
    450                 455                 460

Ser Gln Glu Thr Ala Val Asn Pro Val Asp Ile Val Ser Thr Leu Gln
465                 470                 475                 480

Ala Leu Gln Met Leu Lys Tyr Trp Lys Gly Lys His Leu Val Leu Lys
                485                 490                 495

Arg Gln Asp Leu Ile Asp Glu Trp Ile Ala Lys Glu Ala Lys Arg Ser
            500                 505                 510

Asn Ser Asn Lys Thr Met Asp Pro Ser Cys Leu Lys Trp Thr Pro Pro
        515                 520                 525

Lys Gly Thr
    530

<210> SEQ ID NO 7
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(20)
```

```
<223> OTHER INFORMATION: are modified by biotin and an amine group

<400> SEQUENCE: 7

Ser Gly Arg Gly Arg Gly Gly Arg Gly Leu Gly Lys Gly Gly Ala Arg
1               5                   10                  15

Arg His Arg Lys
            20

<210> SEQ ID NO 8
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(26)
<223> OTHER INFORMATION: are modified by biotin and an amine group
<220> FEATURE:
<221> NAME/KEY: MOD_RES
<222> LOCATION: (20)..(21)
<223> OTHER INFORMATION: METHYLATION

<400> SEQUENCE: 8

Ser Gly Arg Gly Lys Gly Gly Lys Gly Leu Gly Lys Gly Gly Ala Lys
1               5                   10                  15

Arg His Arg Lys Val Leu Arg Gly Gly Lys
            20                  25

<210> SEQ ID NO 9
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(26)
<223> OTHER INFORMATION: are modified by biotin and an amine group
<220> FEATURE:
<221> NAME/KEY: MOD_RES
<222> LOCATION: (20)..(21)
<223> OTHER INFORMATION: METHYLATION

<400> SEQUENCE: 9

Ser Gly Arg Gly Arg Gly Gly Arg Gly Leu Gly Lys Gly Gly Ala Arg
1               5                   10                  15

Arg His Arg Lys Val Leu Arg Gly Gly Lys
            20                  25

<210> SEQ ID NO 10
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(20)
<223> OTHER INFORMATION: are modified by biotin and an amine group

<400> SEQUENCE: 10

Ser Gly Arg Gly Arg Gly Gly Arg Gly Leu Gly Lys Gly Gly Ala Arg
1               5                   10                  15

Arg His Arg Lys
            20
```

```
<210> SEQ ID NO 11
<211> LENGTH: 545
<212> TYPE: PRT
<213> ORGANISM: Homo sapiens

<400> SEQUENCE: 11

Met His His His His His His Ser Ser Gly Val Asp Leu Gly Thr Glu
1               5                   10                  15

Asn Leu Tyr Phe Gln Ser Asn Ala Met Ala Glu Val Gly Glu Ile Ile
            20                  25                  30

Glu Gly Cys Arg Leu Pro Val Leu Arg Arg Asn Gln Asp Asn Glu Asp
        35                  40                  45

Glu Trp Pro Leu Ala Glu Ile Leu Ser Val Lys Asp Ile Ser Gly Arg
    50                  55                  60

Lys Leu Phe Tyr Val His Tyr Ile Asp Phe Asn Lys Arg Leu Asp Glu
65                  70                  75                  80

Trp Val Thr His Glu Arg Leu Asp Leu Lys Lys Ile Gln Phe Pro Lys
                85                  90                  95

Lys Glu Ala Lys Thr Pro Thr Lys Asn Gly Leu Pro Gly Ser Arg Pro
            100                 105                 110

Gly Ser Pro Glu Arg Glu Val Pro Ala Ser Ala Gln Ala Ser Gly Lys
        115                 120                 125

Thr Leu Pro Ile Pro Val Gln Ile Thr Leu Arg Phe Asn Leu Pro Lys
130                 135                 140

Glu Arg Glu Ala Ile Pro Gly Gly Glu Pro Asp Gln Pro Leu Ser Ser
145                 150                 155                 160

Ser Ser Cys Leu Gln Pro Asn His Arg Ser Thr Lys Arg Lys Val Glu
                165                 170                 175

Val Val Ser Pro Ala Thr Pro Val Pro Ser Glu Thr Ala Pro Ala Ser
            180                 185                 190

Val Phe Pro Gln Asn Gly Ala Ala Arg Arg Ala Val Ala Ala Gln Pro
        195                 200                 205

Gly Arg Lys Arg Lys Ser Asn Cys Leu Gly Thr Asp Glu Asp Ser Gln
210                 215                 220

Asp Ser Ser Asp Gly Ile Pro Ser Ala Pro Arg Met Thr Gly Ser Leu
225                 230                 235                 240

Val Ser Asp Arg Ser His Asp Asp Ile Val Thr Arg Met Lys Asn Ile
                245                 250                 255

Glu Cys Ile Glu Leu Gly Arg His Arg Leu Lys Pro Trp Tyr Phe Ser
            260                 265                 270

Pro Tyr Pro Gln Glu Leu Thr Thr Leu Pro Val Leu Tyr Leu Cys Glu
        275                 280                 285

Phe Cys Leu Lys Tyr Gly Arg Ser Leu Lys Cys Leu Gln Arg His Leu
290                 295                 300

Thr Lys Cys Asp Leu Arg His Pro Pro Gly Asn Glu Ile Tyr Arg Lys
305                 310                 315                 320

Gly Thr Ile Ser Phe Phe Glu Ile Asp Gly Arg Lys Asn Lys Ser Tyr
                325                 330                 335

Ser Gln Asn Leu Cys Leu Leu Ala Lys Cys Phe Leu Asp His Lys Thr
            340                 345                 350

Leu Tyr Tyr Asp Thr Asp Pro Phe Leu Phe Tyr Val Met Thr Glu Tyr
        355                 360                 365

Asp Cys Lys Gly Phe His Ile Val Gly Tyr Phe Ser Lys Glu Lys Glu
370                 375                 380
```

```
Ser Thr Glu Asp Tyr Asn Val Ala Cys Ile Leu Thr Leu Pro Pro Tyr
385                 390                 395                 400

Gln Arg Arg Gly Tyr Gly Lys Leu Leu Ile Glu Phe Ser Tyr Glu Leu
                405                 410                 415

Ser Lys Val Glu Gly Lys Thr Gly Thr Pro Glu Lys Pro Leu Ser Asp
            420                 425                 430

Leu Gly Leu Leu Ser Tyr Arg Ser Tyr Trp Ser Gln Thr Ile Leu Glu
        435                 440                 445

Ile Leu Met Gly Leu Lys Ser Glu Ser Gly Glu Arg Pro Gln Ile Thr
    450                 455                 460

Ile Asn Glu Ile Ser Glu Ile Thr Ser Ile Lys Lys Glu Asp Val Ile
465                 470                 475                 480

Ser Thr Leu Gln Tyr Leu Asn Leu Ile Asn Tyr Tyr Lys Gly Gln Tyr
                485                 490                 495

Ile Leu Thr Leu Ser Glu Asp Ile Val Asp Gly His Glu Arg Ala Met
            500                 505                 510

Leu Lys Arg Leu Leu Arg Ile Asp Ser Lys Cys Leu His Phe Thr Pro
        515                 520                 525

Lys Asp Trp Ser Lys Arg Gly Lys Trp Asp Tyr Lys Asp Asp Asp Asp
    530                 535                 540

Lys
545

<210> SEQ ID NO 12
<211> LENGTH: 524
<212> TYPE: PRT
<213> ORGANISM: Artificial Sequence
<220> FEATURE:
<223> OTHER INFORMATION: Synthetic Polypeptide

<400> SEQUENCE: 12

Ser Asn Ala Met Ala Glu Val Gly Glu Ile Ile Glu Gly Cys Arg Leu
1               5                   10                  15

Pro Val Leu Arg Arg Asn Gln Asp Asn Glu Asp Glu Trp Pro Leu Ala
            20                  25                  30

Glu Ile Leu Ser Val Lys Asp Ile Ser Gly Arg Lys Leu Phe Tyr Val
        35                  40                  45

His Tyr Ile Asp Phe Asn Lys Arg Leu Asp Glu Trp Val Thr His Glu
    50                  55                  60

Arg Leu Asp Leu Lys Lys Ile Gln Phe Pro Lys Lys Glu Ala Lys Thr
65                  70                  75                  80

Pro Thr Lys Asn Gly Leu Pro Gly Ser Arg Pro Gly Ser Pro Glu Arg
                85                  90                  95

Glu Val Pro Ala Ser Ala Gln Ala Ser Gly Lys Thr Leu Pro Ile Pro
            100                 105                 110

Val Gln Ile Thr Leu Arg Phe Asn Leu Pro Lys Glu Arg Glu Ala Ile
        115                 120                 125

Pro Gly Gly Glu Pro Asp Gln Pro Leu Ser Ser Ser Cys Leu Gln
    130                 135                 140

Pro Asn His Arg Ser Thr Lys Arg Lys Val Glu Val Val Ser Pro Ala
145                 150                 155                 160

Thr Pro Val Pro Ser Glu Thr Ala Pro Ala Ser Val Phe Pro Gln Asn
                165                 170                 175

Gly Ala Ala Arg Arg Ala Val Ala Ala Gln Pro Gly Arg Lys Arg Lys
            180                 185                 190
```

```
Ser Asn Cys Leu Gly Thr Asp Glu Asp Ser Gln Asp Ser Asp Gly
        195                 200                 205

Ile Pro Ser Ala Pro Arg Met Thr Gly Ser Leu Val Ser Asp Arg Ser
210                 215                 220

His Asp Asp Ile Val Thr Arg Met Lys Asn Ile Glu Cys Ile Glu Leu
225                 230                 235                 240

Gly Arg His Arg Leu Lys Pro Trp Tyr Phe Ser Pro Tyr Pro Gln Glu
                245                 250                 255

Leu Thr Thr Leu Pro Val Leu Tyr Leu Cys Glu Phe Cys Leu Lys Tyr
                260                 265                 270

Gly Arg Ser Leu Lys Cys Leu Gln Arg His Leu Thr Lys Cys Asp Leu
                275                 280                 285

Arg His Pro Pro Gly Asn Glu Ile Tyr Arg Lys Gly Thr Ile Ser Phe
290                 295                 300

Phe Glu Ile Asp Gly Arg Lys Asn Lys Ser Tyr Ser Gln Asn Leu Cys
305                 310                 315                 320

Leu Leu Ala Lys Cys Phe Leu Asp His Lys Thr Leu Tyr Tyr Asp Thr
                325                 330                 335

Asp Pro Phe Leu Phe Tyr Val Met Thr Glu Tyr Asp Cys Lys Gly Phe
                340                 345                 350

His Ile Val Gly Tyr Phe Ser Lys Glu Lys Glu Ser Thr Glu Asp Tyr
                355                 360                 365

Asn Val Ala Cys Ile Leu Thr Leu Pro Pro Tyr Gln Arg Arg Gly Tyr
370                 375                 380

Gly Lys Leu Leu Ile Glu Phe Ser Tyr Glu Leu Ser Lys Val Glu Gly
385                 390                 395                 400

Lys Thr Gly Thr Pro Glu Lys Pro Leu Ser Asp Leu Gly Leu Leu Ser
                405                 410                 415

Tyr Arg Ser Tyr Trp Ser Gln Thr Ile Leu Glu Ile Leu Met Gly Leu
                420                 425                 430

Lys Ser Glu Ser Gly Glu Arg Pro Gln Ile Thr Ile Asn Glu Ile Ser
                435                 440                 445

Glu Ile Thr Ser Ile Lys Lys Glu Asp Val Ile Ser Thr Leu Gln Tyr
450                 455                 460

Leu Asn Leu Ile Asn Tyr Tyr Lys Gly Gln Tyr Ile Leu Thr Leu Ser
465                 470                 475                 480

Glu Asp Ile Val Asp Gly His Glu Arg Ala Met Leu Lys Arg Leu Leu
                485                 490                 495

Arg Ile Asp Ser Lys Cys Leu His Phe Thr Pro Lys Asp Trp Ser Lys
                500                 505                 510

Arg Gly Lys Trp Asp Tyr Lys Asp Asp Asp Lys
                515                 520

<210> SEQ ID NO 13
<211> LENGTH: 308
<212> TYPE: PRT
<213> ORGANISM: Homo sapiens

<400> SEQUENCE: 13

Met His His His His His Ser Ser Gly Val Asp Leu Gly Thr Glu
1               5                   10                  15

Asn Leu Tyr Phe Gln Ser Asn Ala Pro Pro Asp Pro Gln Val Arg Cys
                20                  25                  30

Pro Ser Val Ile Glu Phe Gly Lys Tyr Glu Ile His Thr Trp Tyr Ser
                35                  40                  45
```

```
Ser Pro Tyr Pro Gln Glu Tyr Ser Arg Leu Pro Lys Leu Tyr Leu Cys
 50                  55                  60

Glu Phe Cys Leu Lys Tyr Met Lys Ser Arg Thr Ile Leu Gln Gln His
 65                  70                  75                  80

Met Lys Lys Cys Gly Trp Phe His Pro Pro Ala Asn Glu Ile Tyr Arg
                 85                  90                  95

Lys Asn Asn Ile Ser Val Phe Glu Val Asp Gly Asn Val Ser Thr Ile
                100                 105                 110

Tyr Cys Gln Asn Leu Cys Leu Leu Ala Lys Leu Phe Leu Asp His Lys
            115                 120                 125

Thr Leu Tyr Tyr Asp Val Glu Pro Phe Leu Phe Tyr Val Leu Thr Gln
130                 135                 140

Asn Asp Val Lys Gly Cys His Leu Val Gly Tyr Phe Ser Lys Glu Lys
145                 150                 155                 160

His Cys Gln Gln Lys Tyr Asn Val Ser Cys Ile Met Ile Leu Pro Gln
                165                 170                 175

Tyr Gln Arg Lys Gly Tyr Gly Arg Phe Leu Ile Asp Phe Ser Tyr Leu
            180                 185                 190

Leu Ser Lys Arg Glu Gly Gln Ala Gly Ser Pro Glu Lys Pro Leu Ser
            195                 200                 205

Asp Leu Gly Arg Leu Ser Tyr Met Ala Tyr Trp Lys Ser Val Ile Leu
210                 215                 220

Glu Cys Leu Tyr His Gln Asn Asp Lys Gln Ile Ser Ile Lys Lys Leu
225                 230                 235                 240

Ser Lys Leu Thr Gly Ile Cys Pro Gln Asp Ile Thr Ser Thr Leu His
                245                 250                 255

His Leu Arg Met Leu Asp Phe Arg Ser Asp Gln Phe Val Ile Ile Arg
            260                 265                 270

Arg Glu Lys Leu Ile Gln Asp His Met Ala Lys Leu Gln Leu Asn Leu
            275                 280                 285

Arg Pro Val Asp Val Asp Pro Glu Cys Leu Arg Trp Thr Pro Val Ile
            290                 295                 300

Val Ser Asn Ser
305

<210> SEQ ID NO 14
<211> LENGTH: 287
<212> TYPE: PRT
<213> ORGANISM: Artificial Sequence
<220> FEATURE:
<223> OTHER INFORMATION: Synthetic Polypeptide

<400> SEQUENCE: 14

Ser Asn Ala Pro Pro Asp Pro Gln Val Arg Cys Pro Ser Val Ile Glu
 1               5                  10                  15

Phe Gly Lys Tyr Glu Ile His Thr Trp Tyr Ser Ser Pro Tyr Pro Gln
                 20                  25                  30

Glu Tyr Ser Arg Leu Pro Lys Leu Tyr Leu Cys Glu Phe Cys Leu Lys
             35                  40                  45

Tyr Met Lys Ser Arg Thr Ile Leu Gln Gln His Met Lys Lys Cys Gly
 50                  55                  60

Trp Phe His Pro Pro Ala Asn Glu Ile Tyr Arg Lys Asn Asn Ile Ser
 65                  70                  75                  80

Val Phe Glu Val Asp Gly Asn Val Ser Thr Ile Tyr Cys Gln Asn Leu
                 85                  90                  95
```

```
Cys Leu Leu Ala Lys Leu Phe Leu Asp His Lys Thr Leu Tyr Tyr Asp
            100                 105                 110

Val Glu Pro Phe Leu Phe Tyr Val Leu Thr Gln Asn Asp Val Lys Gly
        115                 120                 125

Cys His Leu Val Gly Tyr Phe Ser Lys Glu Lys His Cys Gln Gln Lys
    130                 135                 140

Tyr Asn Val Ser Cys Ile Met Ile Leu Pro Gln Tyr Gln Arg Lys Gly
145                 150                 155                 160

Tyr Gly Arg Phe Leu Ile Asp Phe Ser Tyr Leu Leu Ser Lys Arg Glu
                165                 170                 175

Gly Gln Ala Gly Ser Pro Glu Lys Pro Leu Ser Asp Leu Gly Arg Leu
            180                 185                 190

Ser Tyr Met Ala Tyr Trp Lys Ser Val Ile Leu Glu Cys Leu Tyr His
        195                 200                 205

Gln Asn Asp Lys Gln Ile Ser Ile Lys Lys Leu Ser Lys Leu Thr Gly
    210                 215                 220

Ile Cys Pro Gln Asp Ile Thr Ser Thr Leu His His Leu Arg Met Leu
225                 230                 235                 240

Asp Phe Arg Ser Asp Gln Phe Val Ile Ile Arg Arg Glu Lys Leu Ile
                245                 250                 255

Gln Asp His Met Ala Lys Leu Gln Leu Asn Leu Arg Pro Val Asp Val
            260                 265                 270

Asp Pro Glu Cys Leu Arg Trp Thr Pro Val Ile Val Ser Asn Ser
        275                 280                 285

<210> SEQ ID NO 15
<211> LENGTH: 643
<212> TYPE: PRT
<213> ORGANISM: Homo sapiens

<400> SEQUENCE: 15

Met His His His His His Ser Ser Gly Val Asp Leu Gly Thr Glu
1               5                   10                  15

Asn Leu Tyr Phe Gln Ser Asn Ala Met Pro Arg Arg Lys Arg Asn Ala
            20                  25                  30

Gly Ser Ser Ser Asp Gly Thr Glu Asp Ser Asp Phe Ser Thr Asp Leu
        35                  40                  45

Glu His Thr Asp Ser Ser Glu Ser Asp Gly Thr Ser Arg Arg Ser Ala
    50                  55                  60

Arg Val Thr Arg Ser Ser Ala Arg Leu Ser Gln Ser Ser Gln Asp Ser
65                  70                  75                  80

Ser Pro Val Arg Asn Leu Gln Ser Phe Gly Thr Glu Glu Pro Ala Tyr
                85                  90                  95

Ser Thr Arg Arg Val Thr Arg Ser Gln Gln Gln Pro Thr Pro Val Thr
            100                 105                 110

Pro Lys Lys Tyr Pro Leu Arg Gln Thr Arg Ser Ser Gly Ser Glu Thr
        115                 120                 125

Glu Gln Val Val Asp Phe Ser Asp Arg Glu Thr Lys Asn Thr Ala Asp
    130                 135                 140

His Asp Glu Ser Pro Pro Arg Thr Pro Thr Gly Asn Ala Pro Ser Ser
145                 150                 155                 160

Glu Ser Asp Ile Asp Ile Ser Ser Pro Asn Val Ser His Asp Glu Ser
                165                 170                 175

Ile Ala Lys Asp Met Ser Leu Lys Asp Ser Gly Ser Asp Leu Ser His
```

```
            180                 185                 190
Arg Pro Lys Arg Arg Phe His Glu Ser Tyr Asn Phe Asn Met Lys
            195                 200                 205
Cys Pro Thr Pro Gly Cys Asn Ser Leu Gly His Leu Thr Gly Lys His
            210                 215                 220
Glu Arg His Phe Ser Ile Ser Gly Cys Pro Leu Tyr His Asn Leu Ser
225                 230                 235                 240
Ala Asp Glu Cys Lys Val Arg Ala Gln Ser Arg Asp Lys Gln Ile Glu
            245                 250                 255
Glu Arg Met Leu Ser His Arg Gln Asp Asp Asn Asn Arg His Ala Thr
            260                 265                 270
Arg His Gln Ala Pro Thr Glu Arg Gln Leu Arg Tyr Lys Glu Lys Val
            275                 280                 285
Ala Glu Leu Arg Lys Arg Asn Ser Gly Leu Ser Lys Glu Gln Lys
            290                 295                 300
Glu Lys Tyr Met Glu His Arg Gln Thr Tyr Gly Asn Thr Arg Glu Pro
305                 310                 315                 320
Leu Leu Glu Asn Leu Thr Ser Glu Tyr Asp Leu Asp Leu Phe Arg Arg
            325                 330                 335
Ala Gln Ala Arg Ala Ser Glu Asp Leu Glu Lys Leu Arg Leu Gln Gly
            340                 345                 350
Gln Ile Thr Glu Gly Ser Asn Met Ile Lys Thr Ile Ala Phe Gly Arg
            355                 360                 365
Tyr Glu Leu Asp Thr Trp Tyr His Ser Pro Tyr Pro Glu Glu Tyr Ala
            370                 375                 380
Arg Leu Gly Arg Leu Tyr Met Cys Glu Phe Cys Leu Lys Tyr Met Lys
385                 390                 395                 400
Ser Gln Thr Ile Leu Arg Arg His Met Ala Lys Cys Val Trp Lys His
            405                 410                 415
Pro Pro Gly Asp Glu Ile Tyr Arg Lys Gly Ser Ile Ser Val Phe Glu
            420                 425                 430
Val Asp Gly Lys Lys Asn Lys Ile Tyr Cys Gln Asn Leu Cys Leu Leu
            435                 440                 445
Ala Lys Leu Phe Leu Asp His Lys Thr Leu Tyr Tyr Asp Val Glu Pro
            450                 455                 460
Phe Leu Phe Tyr Val Met Thr Glu Ala Asp Asn Thr Gly Cys His Leu
465                 470                 475                 480
Ile Gly Tyr Phe Ser Lys Glu Lys Asn Ser Phe Leu Asn Tyr Asn Val
            485                 490                 495
Ser Cys Ile Leu Thr Met Pro Gln Tyr Met Arg Gln Gly Tyr Gly Lys
            500                 505                 510
Met Leu Ile Asp Phe Ser Tyr Leu Leu Ser Lys Val Glu Glu Lys Val
            515                 520                 525
Gly Ser Pro Glu Arg Pro Leu Ser Asp Leu Gly Leu Ile Ser Tyr Arg
            530                 535                 540
Ser Tyr Trp Lys Glu Val Leu Leu Arg Tyr Leu His Asn Phe Gln Gly
545                 550                 555                 560
Lys Glu Ile Ser Ile Lys Glu Ile Ser Gln Glu Thr Ala Val Asn Pro
            565                 570                 575
Val Asp Ile Val Ser Thr Leu Gln Ala Leu Gln Met Leu Lys Tyr Trp
            580                 585                 590
Lys Gly Lys His Leu Val Leu Lys Arg Gln Asp Leu Ile Asp Glu Trp
            595                 600                 605
```

```
Ile Ala Lys Glu Ala Lys Arg Ser Asn Ser Asn Lys Thr Met Asp Pro
        610                 615                 620

Ser Cys Leu Lys Trp Thr Pro Pro Lys Gly Thr Asp Tyr Lys Asp Asp
625                 630                 635                 640

Asp Asp Lys

<210> SEQ ID NO 16
<211> LENGTH: 622
<212> TYPE: PRT
<213> ORGANISM: Artificial Sequence
<220> FEATURE:
<223> OTHER INFORMATION: Synthetic Polypeptide

<400> SEQUENCE: 16

Ser Asn Ala Met Pro Arg Arg Lys Arg Asn Ala Gly Ser Ser Ser Asp
1               5                   10                  15

Gly Thr Glu Asp Ser Asp Phe Ser Thr Asp Leu Glu His Thr Asp Ser
                20                  25                  30

Ser Glu Ser Asp Gly Thr Ser Arg Arg Ser Ala Arg Val Thr Arg Ser
            35                  40                  45

Ser Ala Arg Leu Ser Gln Ser Ser Gln Asp Ser Ser Pro Val Arg Asn
    50                  55                  60

Leu Gln Ser Phe Gly Thr Glu Glu Pro Ala Tyr Ser Thr Arg Arg Val
65                  70                  75                  80

Thr Arg Ser Gln Gln Gln Pro Thr Pro Val Thr Pro Lys Lys Tyr Pro
                85                  90                  95

Leu Arg Gln Thr Arg Ser Ser Gly Ser Glu Thr Glu Gln Val Val Asp
            100                 105                 110

Phe Ser Asp Arg Glu Thr Lys Asn Thr Ala Asp His Asp Glu Ser Pro
        115                 120                 125

Pro Arg Thr Pro Thr Gly Asn Ala Pro Ser Ser Glu Ser Asp Ile Asp
    130                 135                 140

Ile Ser Ser Pro Asn Val Ser His Asp Glu Ser Ile Ala Lys Asp Met
145                 150                 155                 160

Ser Leu Lys Asp Ser Gly Ser Asp Leu Ser His Arg Pro Lys Arg Arg
                165                 170                 175

Arg Phe His Glu Ser Tyr Asn Phe Asn Met Lys Cys Pro Thr Pro Gly
            180                 185                 190

Cys Asn Ser Leu Gly His Leu Thr Gly Lys His Glu Arg His Phe Ser
        195                 200                 205

Ile Ser Gly Cys Pro Leu Tyr His Asn Leu Ser Ala Asp Glu Cys Lys
    210                 215                 220

Val Arg Ala Gln Ser Arg Asp Lys Gln Ile Glu Glu Arg Met Leu Ser
225                 230                 235                 240

His Arg Gln Asp Asp Asn Asn Arg His Ala Thr Arg His Gln Ala Pro
                245                 250                 255

Thr Glu Arg Gln Leu Arg Tyr Lys Glu Lys Val Ala Glu Leu Arg Lys
            260                 265                 270

Lys Arg Asn Ser Gly Leu Ser Lys Glu Gln Lys Glu Lys Tyr Met Glu
        275                 280                 285

His Arg Gln Thr Tyr Gly Asn Thr Arg Glu Pro Leu Leu Glu Asn Leu
    290                 295                 300

Thr Ser Glu Tyr Asp Leu Asp Leu Phe Arg Arg Ala Gln Ala Arg Ala
305                 310                 315                 320
```

```
Ser Glu Asp Leu Glu Lys Leu Arg Leu Gln Gly Gln Ile Thr Glu Gly
            325                 330                 335

Ser Asn Met Ile Lys Thr Ile Ala Phe Gly Arg Tyr Glu Leu Asp Thr
        340                 345                 350

Trp Tyr His Ser Pro Tyr Pro Glu Glu Tyr Ala Arg Leu Gly Arg Leu
            355                 360                 365

Tyr Met Cys Glu Phe Cys Leu Lys Tyr Met Lys Ser Gln Thr Ile Leu
370                 375                 380

Arg Arg His Met Ala Lys Cys Val Trp Lys His Pro Pro Gly Asp Glu
385                 390                 395                 400

Ile Tyr Arg Lys Gly Ser Ile Ser Val Phe Glu Val Asp Gly Lys Lys
            405                 410                 415

Asn Lys Ile Tyr Cys Gln Asn Leu Cys Leu Leu Ala Lys Leu Phe Leu
        420                 425                 430

Asp His Lys Thr Leu Tyr Tyr Asp Val Glu Pro Phe Leu Phe Tyr Val
            435                 440                 445

Met Thr Glu Ala Asp Asn Thr Gly Cys His Leu Ile Gly Tyr Phe Ser
450                 455                 460

Lys Glu Lys Asn Ser Phe Leu Asn Tyr Asn Val Ser Cys Ile Leu Thr
465                 470                 475                 480

Met Pro Gln Tyr Met Arg Gln Gly Tyr Gly Lys Met Leu Ile Asp Phe
            485                 490                 495

Ser Tyr Leu Leu Ser Lys Val Glu Glu Lys Val Gly Ser Pro Glu Arg
        500                 505                 510

Pro Leu Ser Asp Leu Gly Leu Ile Ser Tyr Arg Ser Tyr Trp Lys Glu
            515                 520                 525

Val Leu Leu Arg Tyr Leu His Asn Phe Gln Gly Lys Glu Ile Ser Ile
530                 535                 540

Lys Glu Ile Ser Gln Glu Thr Ala Val Asn Pro Val Asp Ile Val Ser
545                 550                 555                 560

Thr Leu Gln Ala Leu Gln Met Leu Lys Tyr Trp Lys Gly Lys His Leu
            565                 570                 575

Val Leu Lys Arg Gln Asp Leu Ile Asp Glu Trp Ile Ala Lys Glu Ala
        580                 585                 590

Lys Arg Ser Asn Ser Asn Lys Thr Met Asp Pro Ser Cys Leu Lys Trp
            595                 600                 605

Thr Pro Pro Lys Gly Thr Asp Tyr Lys Asp Asp Asp Asp Lys
610                 615                 620

<210> SEQ ID NO 17
<211> LENGTH: 473
<212> TYPE: PRT
<213> ORGANISM: Artificial Sequence
<220> FEATURE:
<223> OTHER INFORMATION: Synthetic Polypeptide

<400> SEQUENCE: 17

Met His His His His His His Met Ala Ala Gln Gly Ala Ala Ala Ala
1               5                   10                  15

Val Ala Ala Gly Thr Ser Gly Val Ala Gly Glu Gly Glu Pro Gly Pro
            20                  25                  30

Gly Glu Asn Ala Ala Ala Glu Gly Thr Ala Pro Ser Pro Gly Arg Val
        35                  40                  45

Ser Pro Pro Thr Pro Ala Arg Gly Glu Pro Glu Val Thr Val Glu Ile
    50                  55                  60
```

```
Gly Glu Thr Tyr Leu Cys Arg Arg Pro Asp Ser Thr Trp His Ser Ala
 65                  70                  75                  80

Glu Val Ile Gln Ser Arg Val Asn Asp Gln Glu Gly Arg Glu Glu Phe
                 85                  90                  95

Tyr Val His Tyr Val Gly Phe Asn Arg Arg Leu Asp Glu Trp Val Asp
            100                 105                 110

Lys Asn Arg Leu Ala Leu Thr Lys Thr Val Lys Asp Ala Val Gln Lys
        115                 120                 125

Asn Ser Glu Lys Tyr Leu Ser Glu Leu Ala Glu Gln Pro Glu Arg Lys
    130                 135                 140

Ile Thr Arg Asn Gln Lys Arg Lys His Asp Glu Ile Asn His Val Gln
145                 150                 155                 160

Lys Thr Tyr Ala Glu Met Asp Pro Thr Thr Ala Ala Leu Glu Lys Glu
                165                 170                 175

His Glu Ala Ile Thr Lys Val Lys Tyr Val Asp Lys Ile His Ile Gly
            180                 185                 190

Asn Tyr Glu Ile Asp Ala Trp Tyr Phe Ser Pro Phe Pro Glu Asp Tyr
        195                 200                 205

Gly Lys Gln Pro Lys Leu Trp Leu Cys Glu Tyr Cys Leu Lys Tyr Met
    210                 215                 220

Lys Tyr Glu Lys Ser Tyr Arg Phe His Leu Gly Gln Cys Gln Trp Arg
225                 230                 235                 240

Gln Pro Pro Gly Lys Glu Ile Tyr Arg Lys Ser Asn Ile Ser Val Tyr
                245                 250                 255

Glu Val Asp Gly Lys Asp His Lys Ile Tyr Cys Gln Asn Leu Cys Leu
            260                 265                 270

Leu Ala Lys Leu Phe Leu Asp His Lys Thr Leu Tyr Phe Asp Val Glu
        275                 280                 285

Pro Phe Val Phe Tyr Ile Leu Thr Glu Val Asp Arg Gln Gly Ala His
    290                 295                 300

Ile Val Gly Tyr Phe Ser Lys Glu Lys Glu Ser Pro Asp Gly Asn Asn
305                 310                 315                 320

Val Ala Cys Ile Leu Thr Leu Pro Pro Tyr Gln Arg Arg Gly Tyr Gly
                325                 330                 335

Lys Phe Leu Ile Ala Phe Ser Tyr Glu Leu Ser Lys Leu Glu Ser Thr
            340                 345                 350

Val Gly Ser Pro Glu Lys Pro Leu Ser Asp Leu Gly Lys Leu Ser Tyr
        355                 360                 365

Arg Ser Tyr Trp Ser Trp Val Leu Leu Glu Ile Leu Arg Asp Phe Arg
    370                 375                 380

Gly Thr Leu Ser Ile Lys Asp Leu Ser Gln Met Thr Ser Ile Thr Gln
385                 390                 395                 400

Asn Asp Ile Ile Ser Thr Leu Gln Ser Leu Asn Met Val Lys Tyr Trp
                405                 410                 415

Lys Gly Gln His Val Ile Cys Val Thr Pro Lys Leu Val Glu Glu His
            420                 425                 430

Leu Lys Ser Ala Gln Tyr Lys Lys Pro Pro Ile Thr Val Asp Ser Val
        435                 440                 445

Cys Leu Lys Trp Ala Pro Pro Lys His Lys Gln Val Lys Leu Ser Lys
    450                 455                 460

Lys Asp Tyr Lys Asp Asp Asp Lys
465                 470
```

MYST FAMILY HISTONE ACETYLTRANSFERASE INHIBITORS

CROSS REFERENCE TO RELATED APPLICATIONS

This application is a National Phase Application under 35 U.S.C. 371 of PCT International Application No. PCT/US2018/063110, filed Nov. 29, 2018, which claims priority to U.S. Provisional Application No. 62/592,215, filed Nov. 29, 2017, which applications are incorporated herein by reference in their entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Dec. 10, 2020, is named E050170036US01-SEQ-DFC and is 57.4 kilobytes in size.

SUMMARY

Protein acetylation is involved in several cellular processes. Lysine acetylation has been reported to modulate (e.g., inhibit) other protein modifications, such as methylation and ubiquitination, modify protein stability, alter subcellular localization, or change the spectrum of interacting proteins.

Some aspects of the present disclosure are based on the recognition of the importance of histone acetyl transferases, such as lysine acetyl transferases (KATs), and in particular MYST family histone acetyltransferases, in initiation and/or progression of some diseases and disorders, e.g., in cancer.

Some aspects of the present disclosure encompass the recognition that MYST family KATs represent a valuable target for modulating MYST family KAT activity, e.g., KAT-5, KAT-6A, KAT-7, and/or KAT-8 activity, in vitro and in vivo, including, for example, in a clinical context, such as cancer therapies. Some aspects of the present disclosure provide that MYST family KATs are therapeutic targets in diseases and conditions characterized by an aberrant activity of such KATs, e.g., an increased KAT-5, KAT-6A, KAT-7, and/or KAT-8 activity as compared to the respective activity observed in healthy cells, tissues, or under normal, non-pathological conditions.

Some aspects of the present disclosure provide that MYST family KATs, e.g., KAT-5, KAT-6A, KAT-7, and/or KAT-8, are therapeutic targets in various cancers. Some aspects of this disclosure are based on the recognition that MYST family KAT (e.g., KAT-5, KAT-6A, KAT-7, and/or KAT-8) activity in cancer cells is important for survival and/or proliferation of the cells. Some aspects of this disclosure provide methods and strategies for inhibiting the survival and/or proliferation of cells, e.g., of neoplastic or malignant cells, comprising contacting such cells with a MYST family KAT inhibitor, e.g., by contacting such cells with an inhibitor that inhibits KAT-5, KAT-6A, KAT-7, or KAT-8, or any combination thereof, in vitro, or in vivo, e.g., by administering the inhibitor to a subject harboring such cells or a tumor comprising such cells.

The present disclosure thus provides certain therapies useful for the treatment of diseases or conditions characterized by aberrant MYST family KAT (e.g., KAT-5, KAT-6A, KAT-7, and/or KAT-8) activity, such as various cancers. Methods and compositions provided by the present disclosure may be applicable, for example, to treatment of a wide range of solid tumors and/or to hematological malignancies.

Some aspects of this disclosure provide compounds, and pharmaceutically acceptable compositions thereof, that are inhibitors of MYST family lysine acetyl transferases (KATs). In some embodiments, the present disclosure provides inhibitors of MYST family KATs, e.g., of KAT-5, KAT-6A, KAT-7, and/or KAT-8. Such compounds have general formula I':

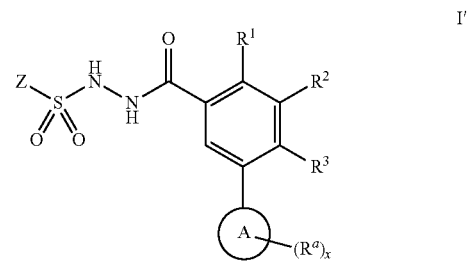

or a pharmaceutically acceptable salt thereof, wherein each of Ring A, Z, $R^1$, $R^2$, $R^3$, $R^a$, and x with respect to formula I' above, is as defined and described in embodiments herein. Such compounds also have general formula I:

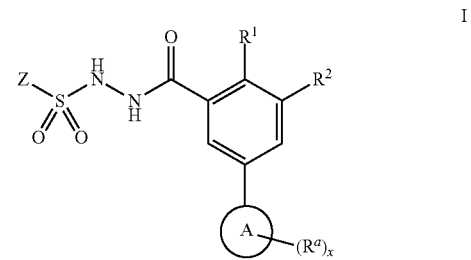

or a pharmaceutically acceptable salt thereof, wherein each of Ring A, Z, $R^1$, $R^2$, $R^a$, and x with respect to formula I above, is as defined and described in embodiments herein.

In some embodiments, compounds provided herein, and pharmaceutically acceptable compositions thereof, are useful for treating a variety of diseases, disorders, or conditions, characterized by, associated with, or mediated by KAT activity, e.g., by KAT-5, KAT-6A, KAT-7, and/or KAT-8 activity. Such diseases, disorders, or conditions include those described herein.

Compounds provided by this disclosure are also useful for the study of MYST family KATs in biological and pathological phenomena and the comparative evaluation of new KAT inhibitors.

BRIEF DESCRIPTION OF THE DRAWING

FIG. 1 presents a graph depicting the inhibition of acetylation of H3K23 in the human cell line CAL-120 by compound A-30.

DEFINITIONS

Compounds of this disclosure include those described generally above, and are further illustrated by the classes, subclasses, and species disclosed herein. As used herein, the following definitions shall apply unless otherwise indicated.

For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this disclosure. Such compounds are useful, for example, as analytical tools, as probes in biological assays, or as therapeutic agents in accordance with the present disclosure.

Combinations of substituents and variables envisioned by this disclosure are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be systemic or local. In some embodiments, administration may be enteral or parenteral. In some embodiments, administration may be by injection (e.g., intramuscular, intravenous, or subcutaneous injection). In some embodiments, injection may involve bolus injection, drip, perfusion, or infusion. In some embodiments administration may be topical. Those skilled in the art will be aware of appropriate administration routes for use with particular therapies described herein, for example from among those listed on www.fda.gov, which include auricular (otic), buccal, conjunctival, cutaneous, dental, endocervical, endosinusial, endotracheal, enteral, epidural, extra-amniotic, extracorporeal, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, intracorporus cavernosum, intradermal, intradiscal, intraductal, intraduodenal, intradural, intraepidermal, intraesophageal, intragastric, intragingival, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravitreal, laryngeal, nasal, nasogastric, ophthalmic, oral, oropharyngeal, parenteral, percutaneous, periarticular, peridural, perineural, periodontal, rectal, respiratory (e.g., inhalation), retrobulbar, soft tissue, subarachnoid, subconjunctival, subcutaneous, sublingual, submucosal, topical, transdermal, transmucosal, transplacental, transtracheal, ureteral, urethral, or vaginal. In some embodiments, administration may involve electro-osmosis, hemodialysis, infiltration, iontophoresis, irrigation, and/or occlusive dressing. In some embodiments, administration may involve dosing that is intermittent (e.g., a plurality of doses separated in time) and/or periodic (e.g., individual doses separated by a common period of time) dosing. In some embodiments, administration may involve continuous dosing.

Agent: As used herein, the term "agent", may refer to a compound, molecule, or entity of any chemical class including, for example, a small molecule, polypeptide, nucleic acid, saccharide, lipid, metal, or a combination or complex thereof. In some embodiments, the term "agent" may refer to a compound, molecule, or entity that comprises a polymer. In some embodiments, the term may refer to a compound or entity that comprises one or more polymeric moieties. In some embodiments, the term "agent" may refer to a compound, molecule, or entity that is substantially free of a particular polymer or polymeric moiety. In some embodiments, the term may refer to a compound, molecule, or entity that lacks or is substantially free of any polymer or polymeric moiety.

Aliphatic: The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic $C_3$-$C_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, or alkynyl groups and hybrids thereof such as (cycloalkyl) alkyl, (cycloalkenyl)alkyl or (cycloalkyl)alkenyl.

Alkylene: The term "alkylene" refers to a bivalent alkyl group. Exemplary alkylenes include —$CH_2$—, —CH$_2$CH$_2$—, —CH(CH$_3$)—, —CH$_2$CH(CH$_3$)—, —CH(CH$_3$)CH$_2$—, etc. In some embodiments, an "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a bivalent alkyl group in which one or more hydrogen atoms are replaced with a substituent. Suitable substituents include those described below for a substituted aliphatic group.

Allele: As used herein, the term "allele" refers to one of two or more existing genetic variants of a specific polymorphic genomic locus.

Amino acid: As used herein, the term "amino acid" refers to any compound and/or substance that can be incorporated into a polypeptide chain, e.g., through formation of one or more peptide bonds. In some embodiments, an amino acid has the general structure H$_2$N—C(H)(R)—COOH. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. As used herein, the term "standard amino acid" refers to any of the twenty L-amino acids commonly found in naturally occurring peptides. "Nonstandard amino acid" refers to any amino acid, other than the standard amino acids, regardless of whether it is or can be found in a natural source. In some embodiments, an amino acid, including a carboxy- and/or amino-terminal amino acid in a polypeptide, can contain a structural modification as compared to the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared to the general structure. In some embodiments, such modification may, for example, alter the stability or the circulating half-life of a polypeptide containing the modified amino acid as compared to one containing an otherwise identical unmodified amino acid. In some embodiments, such modification does not significantly alter a relevant activity of a polypeptide containing the modified amino acid, as compared to one containing an otherwise identical unmodified amino acid. As will be clear from context, in some embodiments, the term "amino acid" may be used to refer to a free amino acid; in some embodiments it may be used to refer to an amino acid residue of a polypeptide, e.g., an amino acid residue within a polypeptide.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in one or more certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog can be generated through performance of a synthetic process different from that used to generate the reference substance.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (for example when the one or more values of interest define a sufficiently narrow range that application of such a percentage variance would obviate the stated range).

Aryl: The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system and exemplary groups include phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Biological sample: The term "biological sample", as used herein, includes, without limitation, cell cultures or extracts thereof; biopsied material obtained from a mammal or extracts thereof; and blood, saliva, urine, feces, semen, tears, or other body fluids or extracts thereof. Inhibition of activity of a lysine acetyl transferase, for example, a MYST family KAT, such as, e.g., KAT-5, KAT-6A, KAT-7, and/or KAT-8, in a biological sample is useful for a variety of purposes that are known to one of skill in the art. Examples of such purposes include, but are not limited to, blood transfusion, organ transplantation, biological specimen storage, and biological assays.

Bridged bicyclic: As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

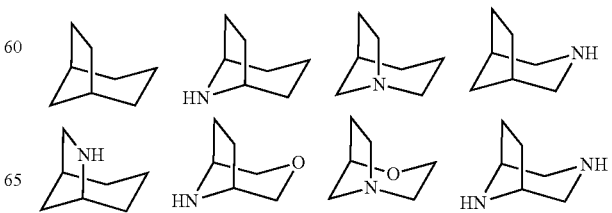

-continued

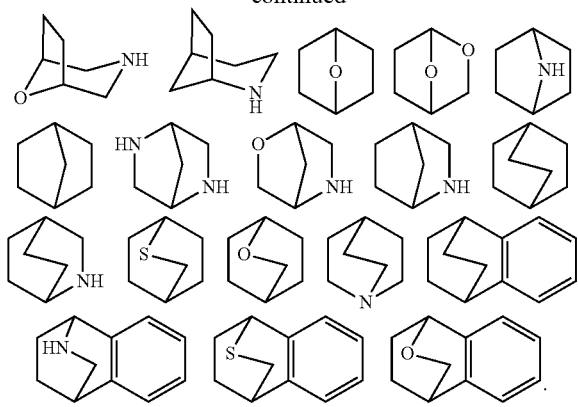

Cancer: As used herein, the term "cancer" refers to a disease, disorder, or condition in which cells exhibit relatively abnormal, uncontrolled, and/or autonomous growth, so that they display an abnormally elevated proliferation rate and/or aberrant growth phenotype characterized by a significant loss of control of cell proliferation. In some embodiments, a cancer may be characterized by one or more tumors. Those skilled in the art are aware of a variety of types of cancer including, for example, adrenocortical carcinoma, astrocytoma, basal cell carcinoma, carcinoid, cardiac, cholangiocarcinoma, chordoma, chronic myeloproliferative neoplasms, craniopharyngioma, ductal carcinoma in situ, ependymoma, intraocular melanoma, gastrointestinal carcinoid tumor, gastrointestinal stromal tumor (GIST), gestational trophoblastic disease, glioma, histiocytosis, leukemia (e.g., acute lymphoblastic leukemia (ALL), acute myeloid leukemia (AML), chronic lymphocytic leukemia (CLL), chronic myelogenous leukemia (CML), hairy cell leukemia, myelogenous leukemia, myeloid leukemia), lymphoma (e.g., Burkitt lymphoma [non-Hodgkin lymphoma], cutaneous T-cell lymphoma, Hodgkin lymphoma, mycosis fungoides, Sezary syndrome, AIDS-related lymphoma, follicular lymphoma, diffuse large B-cell lymphoma), melanoma, merkel cell carcinoma, mesothelioma, myeloma (e.g., multiple myeloma), myelodysplastic syndrome, papillomatosis, paraganglioma, pheochromacytoma, pleuropulmonary blastoma, retinoblastoma, sarcoma (e.g., Ewing sarcoma, Kaposi sarcoma, osteosarcoma, rhabdomyosarcoma, uterine sarcoma, vascular sarcoma), Wilms' tumor, and/or cancer of the adrenal cortex, anus, appendix, bile duct, bladder, bone, brain, breast, bronchus, central nervous system, cervix, colon, endometrium, esophagus, eye, fallopian tube, gall bladder, gastrointestinal tract, germ cell, head and neck, heart, intestine, kidney (e.g., Wilms' tumor), larynx, liver, lung (e.g., non-small cell lung cancer, small cell lung cancer), mouth, nasal cavity, oral cavity, ovary, pancreas, rectum, skin, stomach, testes, throat, thyroid, penis, pharynx, peritoneum, pituitary, prostate, rectum, salivary gland, ureter, urethra, uterus, vagina, or vulva.

Chromosome: As used herein, the term "chromosome" refers to a DNA molecule, optionally together with associated polypeptides and/or other entities, for example as found in the nucleus of eukaryotic cells. Typically, a chromosome carries genes and functions (e.g., origin of replication) that permit it to transmit hereditary information.

Combination therapy: As used herein, the term "combination therapy" refers to a clinical intervention in which a subject is simultaneously exposed to two or more therapeutic regimens (e.g. two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

Corresponding to: As used herein in the context of polypeptides, nucleic acids, and chemical compounds, the term "corresponding to", designates the position/identity of a structural element, e.g., of an amino acid residue, a nucleotide residue, or a chemical moiety, in a compound or composition through comparison with an appropriate reference compound or composition.

Disease or disorder associated with a MYST family KAT: As used herein, a "disease or disorder associated with a MYST family KAT" or, alternatively, "a MYST family KAT-mediated disease or disorder" means any disease or other deleterious condition in which a MYST family KAT (e.g., KAT-5, KAT-6A, KAT-7, or KAT-8), or a mutant of a MYST family KAT, is known or suspected to play a role. For example, as used herein, a "disease or disorder associated with KAT-7" or, alternatively, "a KAT-7-mediated disease or disorder" means any disease or other deleterious condition in which KAT-7, or a mutant thereof, is known or suspected to play a role.

Disease or disorder characterized by aberrant MYST-family KAT activity: As used herein, a "disease or disorder characterized by aberrant MYST family KAT activity" means any disease or other deleterious condition in which an aberrant activity of a MYST family KAT (e.g., KAT-5, KAT-6A, KAT-7, or KAT-8), or a mutant thereof, is known or suspected to play a role. An aberrant activity includes, for example, an increased level of a MYST family KAT (e.g., KAT-5, KAT-6A, KAT-7, and/or KAT-8) activity as compared to a control or reference level. In some embodiments, the control or reference level is an activity level of the MYST family KAT (e.g., KAT-5, KAT-6A, KAT-7, and/or KAT-8) observed, measured, or expected in the absence of the disease or condition, e.g., in a normal cell, tissue, or sample. For example, as used herein, a "disease or disorder characterized by aberrant KAT-7 activity" means any disease or other deleterious condition in which an aberrant activity of KAT-7, or a mutant thereof, is known or suspected to play a role. An aberrant activity includes, for example, an increased level of KAT-7 activity as compared to a control or reference level. In some embodiments, the control or reference level is an activity level of KAT-7 observed, measured, or expected in the absence of the disease or condition, e.g., in a normal cell, tissue, or sample.

Domain: As used herein the term "domain" refers to a section or portion of a polypeptide. In some embodiments, a "domain" is associated with a particular structural and/or functional feature of the polypeptide so that, when the domain is physically separated from the rest of its parent polypeptide, it substantially or entirely retains the particular structural and/or functional feature. In some embodiments, a domain may include a portion of a polypeptide that, when separated from that (parent) polypeptide and linked with a different (recipient) polypeptide, substantially retains and/or imparts on the recipient polypeptide one or more structural and/or functional features that characterized it in the parent polypeptide. In some embodiments, a domain is a section of a polypeptide. In some such embodiments, a domain is characterized by a particular structural element (e.g., a particular amino acid sequence or sequence motif, α-helix character, β-sheet character, coiled-coil character, random coil character), and/or by a particular functional feature (e.g., binding activity, enzymatic activity, folding activity, or signaling activity).

Epigenetic Mark: As used herein, the term "epigenetic mark" refers to a feature of a nucleic acid or polypeptide not directly governed by genetic code. For example, in some embodiments, an epigenetic mark may represent or result from a modification to the nucleic acid or polypeptide. In some embodiments, such modification can include, for example, methylation, acetylation, ubiquitiniation, phosphorylation, ribosylation, amidation, glycosylation or combinations thereof.

Expression: As used herein, the term "expression" of a nucleic acid sequence refers to the generation of any gene product from the nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Gene: As used herein, the term "gene" refers to a DNA sequence in a chromosome that encodes a gene product (e.g., an RNA product and/or a polypeptide product). In some embodiments, a gene includes a coding sequence (e.g., a sequence that encodes a particular gene product); in some embodiments, a gene includes a non-coding sequence. In some particular embodiments, a gene may include both coding (e.g., exonic) and non-coding (e.g., intronic) sequences. In some embodiments, a gene may include one or more regulatory elements (e.g. promoters, enhancers, silencers, termination signals) that, for example, may control or impact one or more aspects of gene expression (e.g., cell-type-specific expression, inducible expression).

Halogen: The term "halogen" means F, Cl, Br, or I.

Heteroatom: The term "heteroatom" means one or more of oxygen, sulfur, nitrogen, phosphorus, or silicon (including, any oxidized form of nitrogen, sulfur, phosphorus, or silicon; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

Heteroaryl: The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Exemplary heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Exemplary groups include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Heterocycle: As used herein, the terms "heterocycle," "heterocyclyl," "heterocyclic radical," and "heterocyclic ring" are used interchangeably and refer to a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl—

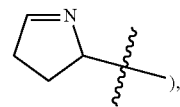

),

NH (as in pyrrolidinyl—

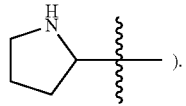

),

NR^ (as in N-substituted 2-pyrrolidinyl—

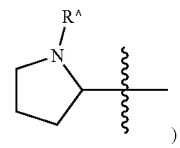

)

or $^+NR^\wedge$ (as in N-substituted 1-pyrrolidinyl—

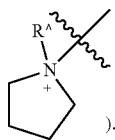

).

A heterocyclic ring can be attached to its pendant group at any heteroatom or carbon atom that results in a stable structure and any of the ring atoms can be optionally substituted. Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, isoindolinyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Inhibitor: As used herein, the term "inhibitor" is defined as a compound that binds to and/or inhibits a target protein, here a MYST family KAT, e.g., KAT-5, KAT-6A, KAT-7, and/or KAT-8, with measurable affinity. In certain embodiments, an inhibitor has an $IC_{50}$ and/or binding constant of less than about 50 µM, less than about 1 µM, less than about 500 nM, less than about 100 nM, or less than about 10 nM.

Lower alkyl: The term "lower alkyl" refers to a $C_1A$ straight or branched alkyl group. Exemplary lower alkyl groups are methyl, ethyl, propyl, isopropyl, butyl, isobutyl, and tert-butyl.

Lower haloalkyl: The term "lower haloalkyl" refers to a $C_{1-4}$ straight or branched alkyl group that is substituted with one or more halogen atoms.

Measurable affinity: The terms "measurable affinity" and "measurably inhibit," as used herein, means a measurable change in the activity of a target enzyme, here a MYST family KAT, e.g., KAT-5, KAT-6A, KAT-7, and/or KAT-8 between a sample comprising compounds of the present disclosure, or compositions thereof, and the target enzyme, and an equivalent sample comprising the target enzyme in the absence of said compound, or composition thereof.

Mutant: As used herein, the term "mutant" refers to an organism, a cell, or a biomolecule (e.g., a nucleic acid or a protein) that comprises a genetic variation as compared to a reference organism, cell, or biomolecule. For example, a mutant nucleic acid may, in some embodiments, comprise a mutation, e.g., a nucleobase substitution, a deletion of one or more nucleobases, an insertion of one or more nucleobases, an inversion of two or more nucleobases, or a truncation, as compared to a reference nucleic acid molecule. Similarly, a mutant protein may comprise an amino acid substitution, insertion, inversion, or truncation, as compared to a reference polypeptide. Additional mutations, e.g., fusions and indels, are known to those of skill in the art. An organism or cell comprising or expressing a mutant nucleic acid or polypeptide is also sometimes referred to herein as a "mutant." In some embodiments, a mutant comprises a genetic variant that is associated with a loss of function of a gene product. A loss of function may be a complete abolishment of function, e.g., an abolishment of the enzymatic activity of an enzyme, or a partial loss of function, e.g., a diminished enzymatic activity of an enzyme. In some embodiments, a mutant comprises a genetic variant that is associated with a gain of function, e.g., with a negative or undesirable alteration in a characteristic or activity in a gene product. In some embodiments, a mutant is characterized by a reduction or loss in a desirable level or activity as compared to a reference; in some embodiments, a mutant is characterized by an increase or gain of an undesirable level or activity as compared to a reference. In some embodiments, the reference organism, cell, or biomolecule is a wild-type organism, cell, or biomolecule.

Nucleic acid: As used herein, the term "nucleic acid" refers to a polymer of at least three nucleotides. In some embodiments, a nucleic acid comprises DNA. In some embodiments comprises RNA. In some embodiments, a nucleic acid is single stranded. In some embodiments, a nucleic acid is double stranded. In some embodiments, a nucleic acid comprises both single and double stranded portions. In some embodiments, a nucleic acid comprises a backbone that comprises one or more phosphodiester linkages. In some embodiments, a nucleic acid comprises a backbone that comprises both phosphodiester and non-phosphodiester linkages. For example, in some embodiments, a nucleic acid may comprise a backbone that comprises one or more phosphorothioate or 5'-N-phosphoramidite linkages and/or one or more peptide bonds, e.g., as in a "peptide nucleic acid". In some embodiments, a nucleic acid comprises one or more, or all, natural residues (e.g., adenine, cytosine, deoxyadenosine, deoxycytidine, deoxyguanosine, deoxythymidine, guanine, thymine, uracil). In some embodiments, a nucleic acid comprises one or more, or all, non-natural residues. In some embodiments, a non-natural residue comprises a nucleoside analog (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a non-natural residue comprises one or more modified sugars (e.g., 2'-fluororibose, ribose, 2'-deoxyribose, arabinose, and hexose) as compared to those in natural residues. In some embodiments, a nucleic acid has a nucleotide sequence that encodes a functional gene product such as an RNA or polypeptide. In some embodiments, a nucleic acid has a nucleotide sequence that comprises one or more introns. In some embodiments, a nucleic acid may be prepared by isolation from a natural source, enzymatic synthesis (e.g., by polymerization based on a complementary template, e.g., in vivo or in vitro, reproduction in a recombinant cell or system, or chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long.

Parenteral: The term "parenteral" as used herein includes subcutaneous, intravenous, intramuscular, intra-articular, intra-synovial, intrasternal, intrathecal, intrahepatic, intralesional and intracranial injection or infusion techniques.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Peptide: As used herein, the term "peptide" refers to a polypeptide that is typically relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids.

Pharmaceutical composition: As used herein, the term "pharmaceutical composition" refers to a composition that is suitable for administration to a human or animal subject. In some embodiments, a pharmaceutical composition comprises an active agent formulated together with one or more pharmaceutically acceptable carriers. In some embodiments, the active agent is present in a unit dose amount appropriate for administration in a therapeutic regimen. In some embodiments, a therapeutic regimen comprises one or more doses administered according to a schedule that has been determined to show a statistically significant probability of achieving a desired therapeutic effect when administered to a subject or population in need thereof. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. In some embodiments, a pharmaceutical composition is intended and suitable for administration to a human subject. In some embodiments, a pharmaceutical composition is sterile and substantially pyrogen-free.

Pharmaceutically acceptable salt: As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Pharmaceutically acceptable carrier, adjuvant, or vehicle: The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The amount of compounds of the present disclosure that may be combined with the carrier materials to produce a composition in a single dosage form will vary depending upon the host treated, the particular mode of administration, etc. Preferably, provided compositions are formulated so that a dosage of between 0.01 to about 100 mg/kg, or about 0.1 mg/kg to about 50 mg/kg, and preferably from about 1 mg/kg to about 25 mg/kg, of subject body weight/day of the inhibitor can be administered to a patient receiving these compositions to obtain the desired therapeutic effect. The amount of a compound of the present disclosure in the composition will also depend upon the particular compound in the composition.

Polypeptide: As used herein, the term "polypeptide," which is interchangeably used herein with the term "protein," refers to a polymer of at least three amino acid residues. In some embodiments, a polypeptide comprises one or more, or all, natural amino acids. In some embodiments, a polypeptide comprises one or more, or all non-natural amino acids. In some embodiments, a polypeptide comprises one or more, or all, D-amino acids. In some embodiments, a polypeptide comprises one or more, or all, L-amino acids. In some embodiments, a polypeptide comprises one or more pendant groups or other modifications, e.g., modifying or attached to one or more amino acid side chains, at the polypeptide's N-terminus, at the polypeptide's C-terminus, or any combination thereof. In some embodiments, a polypeptide comprises one or more modifications such as acetylation, amidation, aminoethylation, biotinylation, carbamylation, carbonylation, citrullination, deamidation, deimination, eliminylation, glycosylation, lipidation, methylation, pegylation, phosphorylation, sumoylation, or combinations thereof. In some embodiments, a polypeptide may participate in one or more intra- or inter-molecular disulfide bonds. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may comprise a stapled polypeptide. In some embodiments, a polypeptide participates in non-covalent complex formation by non-covalent or covalent association with one or more other polypeptides (e.g., as in an antibody). In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise a fragment of a parent polypeptide. In some embodiments, a useful polypeptide as may comprise a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Reference: As used herein, the term "reference" refers to a standard or control relative to which a comparison is performed. For example, in some embodiments, an agent, animal, individual, population, sample, sequence, or value of interest is compared to a reference or control agent, animal, individual, population, sample, sequence, or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Sample: As used herein, the term "sample" refers to a biological sample obtained or derived from a source of interest, as described herein. In some embodiments, a source of interest comprises an organism, such as a microbe, a plant, an animal or a human. In some embodiments, a biological sample comprises biological tissue or fluid. In some embodiments, a biological sample may comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom. In some embodiments, a biological sample comprises cells obtained from an individual, e.g., from a human or animal subject. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces). In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or polypeptides extracted from a sample or obtained by subjecting a primary sample to techniques such as amplification or reverse transcription of mRNA, isolation and/or purification of certain components.

Subject: As used herein, the term "subject" refers to an organism, for example, a mammal (e.g., a human, a non-human mammal, a non-human primate, a primate, a laboratory animal, a mouse, a rat, a hamster, a gerbil, a cat, or a dog). In some embodiments a human subject is an adult, adolescent, or pediatric subject. In some embodiments, a subject is suffering from a disease, disorder or condition, e.g., a disease, disorder or condition that can be treated as provided herein, e.g., a cancer or a tumor listed herein. In some embodiments, a subject is susceptible to a disease, disorder, or condition; in some embodiments, a susceptible subject is predisposed to and/or shows an increased risk (as compared to the average risk observed in a reference subject or population) of developing the disease, disorder or condition. In some embodiments, a subject displays one or more symptoms of a disease, disorder or condition. In some embodiments, a subject does not display a particular symptom (e.g., clinical manifestation of disease) or characteristic of a disease, disorder, or condition. In some embodiments, a subject does not display any symptom or characteristic of a disease, disorder, or condition. In some embodiments, a subject is a patient. In some embodiments, a subject is an individual to whom diagnosis and/or therapy is and/or has been administered.

Substituted or optionally substituted: As described herein, compounds of the disclosure may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

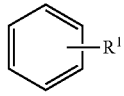

refers to at least

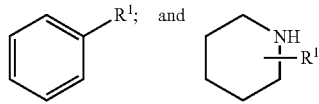

refers to at least

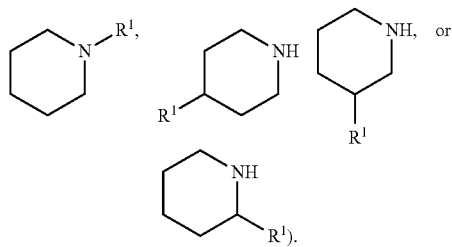

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —(CH$_2$)$_{0-4}$SC(O)R°; —(CH$_2$)$_{0-1}$C(O)NR°$_2$; —C(S)NR°$_2$; —C(S)SR°; —SC(S)SR°, —(CH$_2$)$_{0-1}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-1}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 3-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$, —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, —SSR$^\bullet$, or -Ph which may be substituted with R$^\bullet$, wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O ("oxo"), ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)NR†$_2$, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, $C_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Therapeutic agent: As used herein, the term "therapeutic agent" in general refers to any agent that elicits a desired effect (e.g., a desired biological, clinical, or pharmacological effect) when administered to a subject. In some embodiments, an agent is considered to be a therapeutic agent if it demonstrates a statistically significant effect across an appropriate population. In some embodiments, an appropriate population is a population of subjects suffering from and/or susceptible to a disease, disorder or condition. In some embodiments, an appropriate population is a population of model organisms. In some embodiments, an appropriate population may be defined by one or more criterion such as age group, gender, genetic background, preexisting clinical conditions, or prior exposure to therapy. In some embodiments, a therapeutic agent is a substance that alleviates, ameliorates, relieves, inhibits, prevents, delays onset of, reduces severity of, and/or reduces incidence of one or more symptoms or features of a disease, disorder, and/or condition in a subject when administered to the subject in an effective amount. In some embodiments, a "therapeutic agent" is an agent that has been or is required to be approved by a government agency before it can be marketed for administration to humans. In some embodiments, a "therapeutic agent" is an agent for which a medical prescription is required for administration to humans. In some embodiments, therapeutic agents may be MYST family KAT inhibitors, for example, KAT-5, KAT-6A, KAT-7, and/or KAT-8 inhibitors, as described herein.

Therapeutically effective amount: As used herein; the term "therapeutically effective amount" refers to an amount that produces a desired effect (e.g., a desired biological, clinical, or pharmacological effect) in a subject or population to which it is administered. In some embodiments, the term refers to an amount statistically likely to achieve the desired effect when administered to a subject in accordance with a particular dosing regimen (e.g., a therapeutic dosing regimen). In some embodiments, the term refers to an amount sufficient to produce the effect in at least a significant percentage (e.g., at least about 25%, about 30%, about 40%, about 50%, about 60%, about 70%, about 80%, about 90%, about 95%, or more) of a population that is suffering from and/or susceptible to a disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be an amount that provides a particular desired response in a significant number of subjects when administered to patients in need of such treatment, e.g., in at least about 25%, about 30%, about 40%, about 50%, about 60%, about 70%, about 80%, about 90%, about 95%, or more patients within a treated patient population. In some embodiments, reference to a therapeutically effective amount may be a reference to an amount sufficient to induce a desired effect as measured in one or more specific tissues (e.g., a tissue affected by the disease, disorder or condition) or fluids (e.g., blood, saliva, serum, sweat, tears, urine). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treat, treatment or treating: As used herein, the terms "treatment," "treat," and "treating" refer to partially or completely alleviating, inhibiting, delaying onset of, preventing, ameliorating and/or relieving a disorder or condition, or one or more symptoms of the disorder or condition, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

Tumor: As used herein, the term "tumor" refers to an abnormal growth of cells or tissue. In some embodiments, a tumor may comprise cells that are precancerous (e.g., benign), malignant, pre-metastatic, metastatic, and/or non-metastatic. In some embodiments, a tumor is associated with, or is a manifestation of, a cancer. In some embodiments, a tumor may be a disperse tumor or a liquid tumor. In some embodiments, a tumor may be a solid tumor.

Unit dosage form: The expression "unit dosage form" as used herein refers to a physically discrete unit of a provided compound and/or compositions thereof appropriate for the subject to be treated. It will be understood, however, that the total daily usage of the active agent (i.e., compounds and compositions of the present disclosure) will be decided by the attending physician within the scope of sound medical judgment. The specific effective dose level for any particular subject (i.e., patient) or organism will depend upon a variety of factors including the disorder being treated and the severity of the disorder; activity of specific active agent employed; specific composition employed; age, body weight, general health, sex and diet of the subject; time of administration, route of administration, and rate of excretion of the specific active agent employed; duration of the treatment; and like factors well known in the medical arts.

Unsaturated: The term "unsaturated," as used herein, means that a moiety has one or more units of unsaturation.

Wild-type: As used herein, the term "wild-type" refers to a form of an entity (e.g., a polypeptide or nucleic acid) that has a structure and/or activity as found in nature in a "normal" (as contrasted with mutant, diseased, altered) state or context. In some embodiments, more than one "wild type" form of a particular polypeptide or nucleic acid may exist in nature, for example as "alleles" of a particular gene or normal variants of a particular polypeptide. In some embodiments, that form (or those forms) of a particular polypeptide or nucleic acid that is most commonly observed in a population (e.g., in a human population) is the "wild type" form.

⁓ : As used herein, "⁓" represents a point of attachment between two atoms in a chemical structure.

DETAILED DESCRIPTION OF CERTAIN EMBODIMENTS

According to some aspects, the present disclosure provides a compound of formula I':

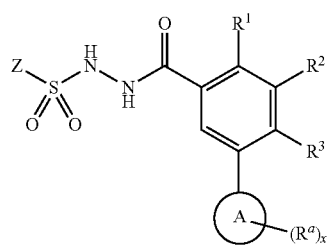

or a pharmaceutically acceptable salt thereof, wherein:
Z is selected from —Cy, —($C_{1-3}$ aliphatic)-Cy, or optionally substituted $C_{1-4}$ aliphatic;
Cy is an optionally substituted group selected from phenyl, a 3-10 membered saturated or partially unsaturated carbocyclic ring, a 6-10 membered bridged bicyclic carbocyclic ring, a 3-10 membered saturated or partially unsaturated heterocyclic ring having 1-2 heteroatoms independently selected from nitrogen, oxygen and sulfur, a 6-8 membered bridged bicyclic heterocyclic ring having 1-2 heteroatoms independently selected from nitrogen, oxygen and sulfur, a 5-6 membered heteroaryl ring having 1-3 heteroatoms independently selected from nitrogen, oxygen and sulfur, an 8-10 membered bicyclic aryl ring, and an 8-10 membered bicyclic heteroaryl ring having 1-3 heteroatoms independently selected from nitrogen oxygen and sulfur;
each of $R^1$ and $R^2$ is independently selected from halogen and $C_{1-4}$ aliphatic;

$R^3$ is selected from hydrogen, halogen, —CN, —$NR_2$, and optionally substituted $C_{1-4}$ aliphatic;
each R is independently selected from hydrogen, optionally substituted $C_{1-4}$ aliphatic, and —C(O)O($C_{1-4}$ aliphatic);
Ring A is an optionally substituted 5- or 6-membered heteroaryl ring having 1-4 heteroatoms independently selected from nitrogen, oxygen and sulfur;
each $R^a$ is selected from halogen and optionally substituted $C_{1-4}$ aliphatic; and
x is 0-3.

According to some aspects, the present disclosure provides a compound of formula I:

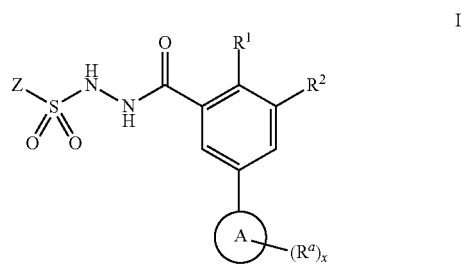

or a pharmaceutically acceptable salt thereof, wherein:
Z is selected from —Cy, —($C_{1-3}$ aliphatic)-Cy or optionally substituted Cia aliphatic;
Cy is an optionally substituted group selected from phenyl, a 3-10 membered saturated or partially unsaturated carbocyclic ring, a 3-10 membered saturated or partially unsaturated heterocyclic ring having 1-2 heteroatoms independently selected from nitrogen, oxygen and sulfur, a 6-8 membered bridged bicyclic heterocyclic ring having 1-2 heteroatoms independently selected from nitrogen, oxygen and sulfur, a 5-6 membered heteroaryl ring having 1-3 heteroatoms independently selected from nitrogen, oxygen and sulfur, an 8-10 membered bicyclic aryl ring, and an 8-10 membered bicyclic heteroaryl ring having 1-3 heteroatoms independently selected from nitrogen oxygen and sulfur;
each of $R^1$ and $R^2$ is independently selected from halogen and $C_{1-4}$ aliphatic;
Ring A is an optionally substituted 5- or 6-membered heteroaryl ring having 1-4 heteroatoms independently selected from nitrogen, oxygen and sulfur;
each $R^a$ is selected from halogen and optionally substituted $C_{1-4}$ aliphatic; and
x is 0-3.

In some embodiments, the compound of formula I' is not:

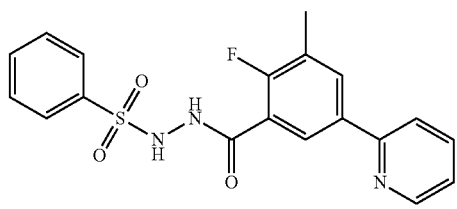

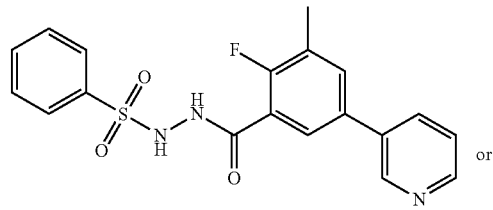

or

-continued

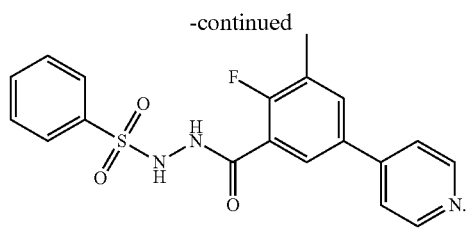

In some embodiments, the compound of formula I is not:

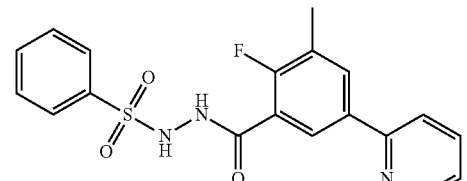

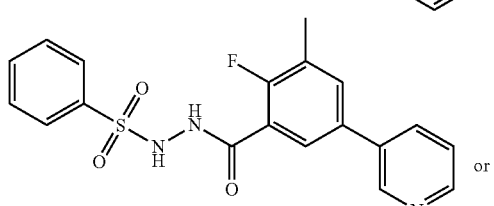

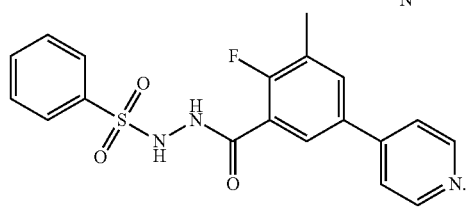

As defined above, Z is selected from —Cy, —(C$_{1-3}$ aliphatic)-Cy or optionally substituted C$_{1-4}$ aliphatic.

In some embodiments, Z is optionally substituted C$_{1-4}$ aliphatic. In some such embodiments, Z is methyl, ethyl, isopropyl, and tert-butyl.

In some embodiments, Z is —Cy. In some such embodiments, Z is selected from the group consisting of:

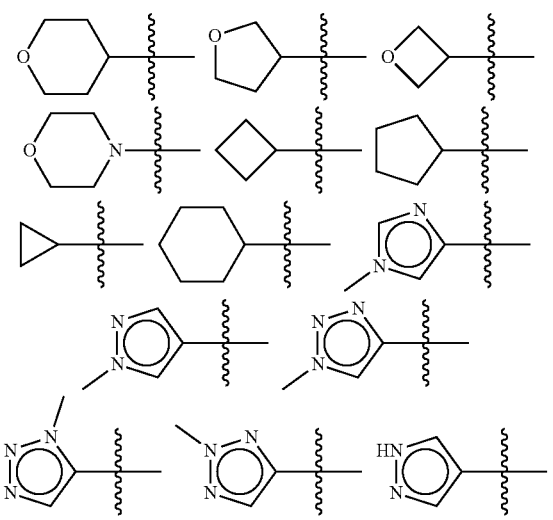

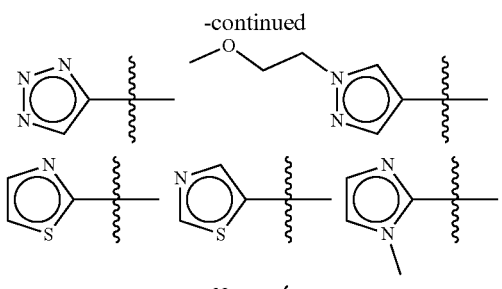

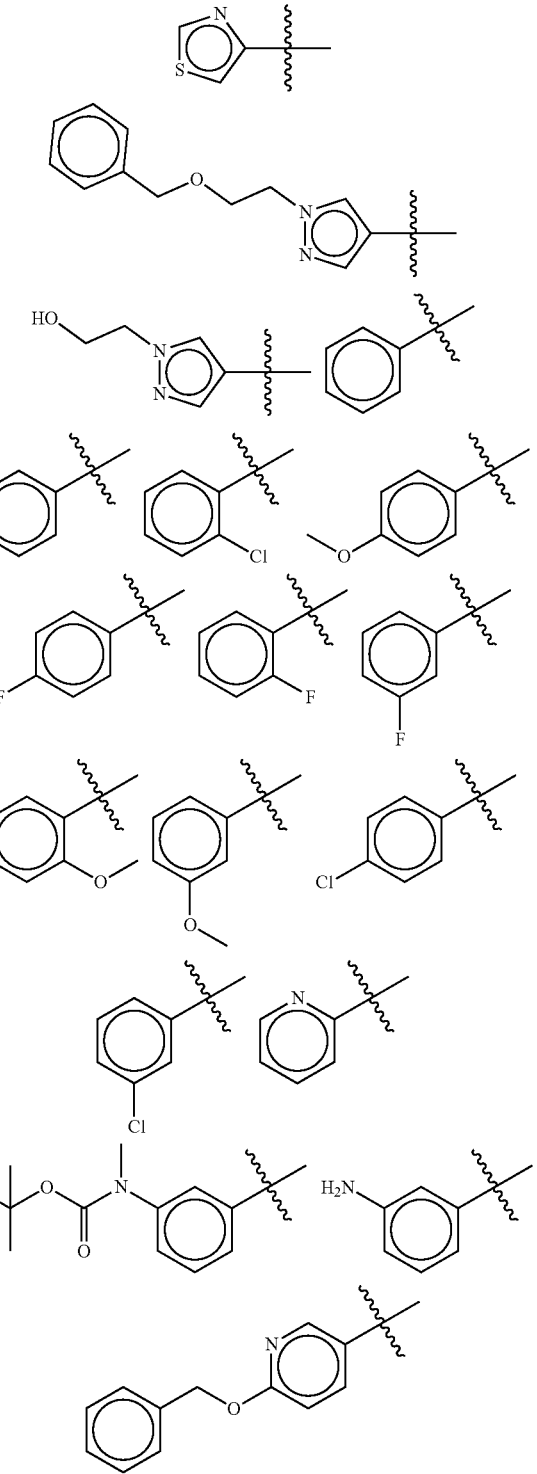

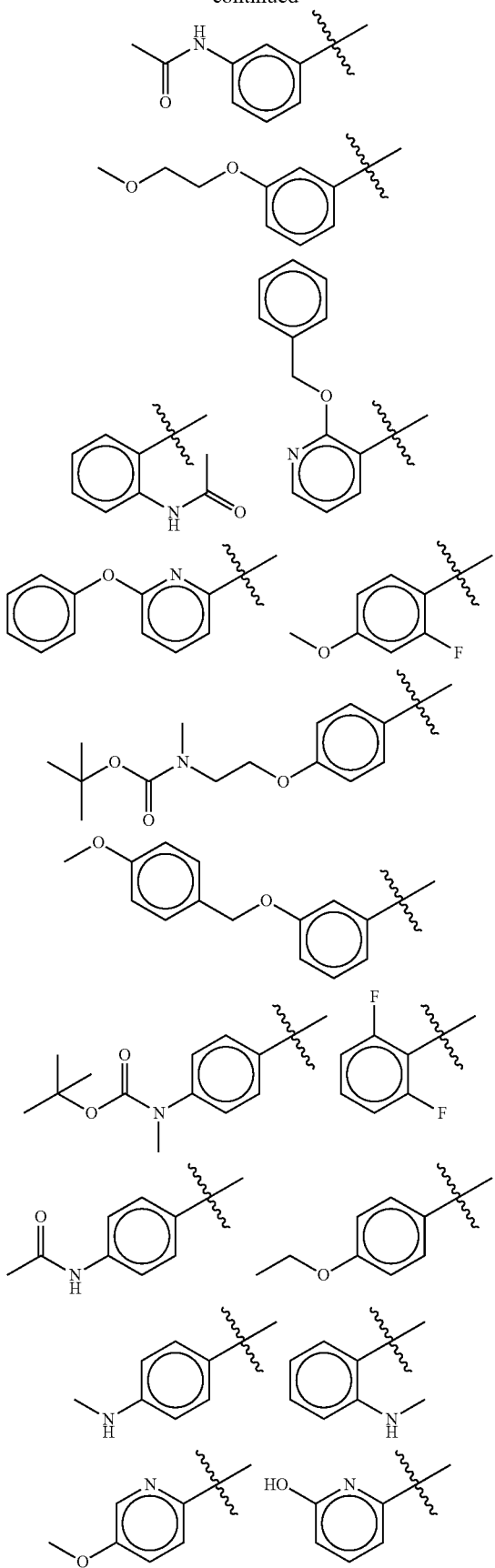
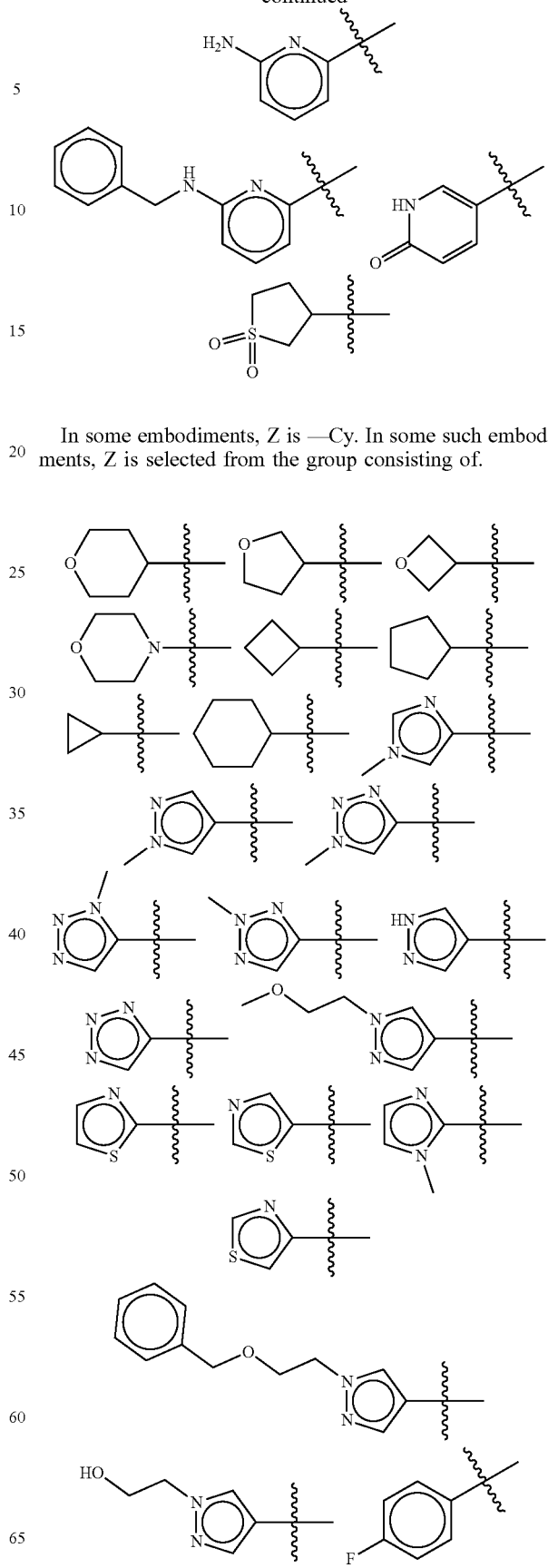
In some embodiments, Z is —Cy. In some such embodiments, Z is selected from the group consisting of.

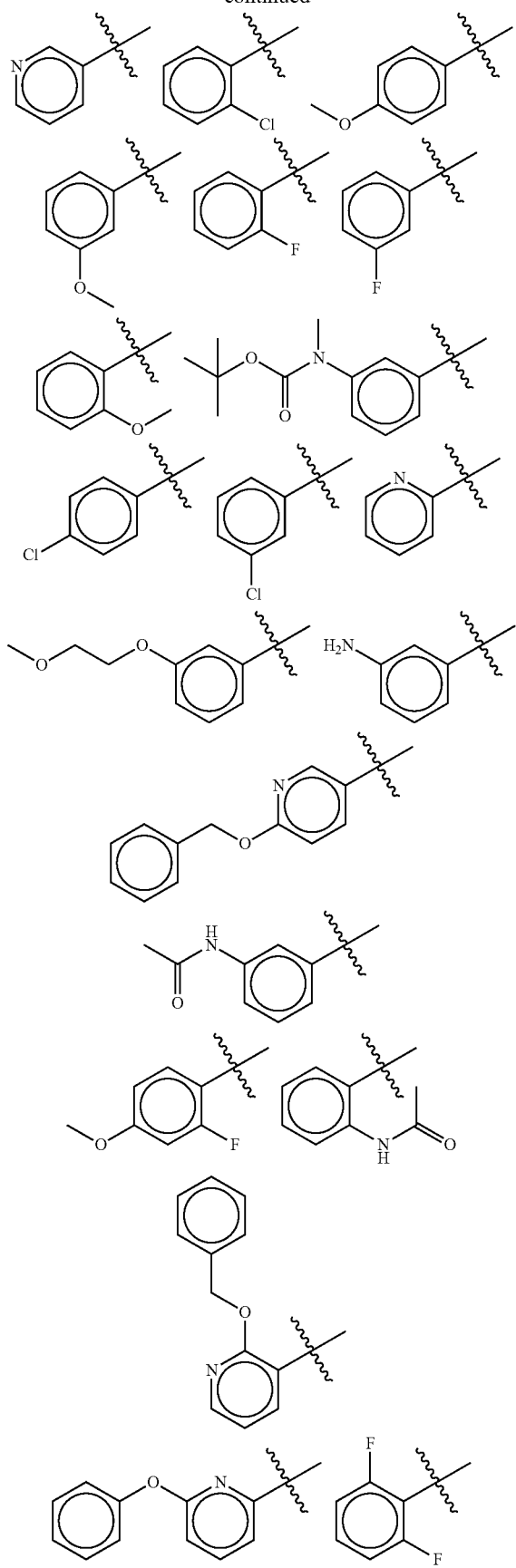
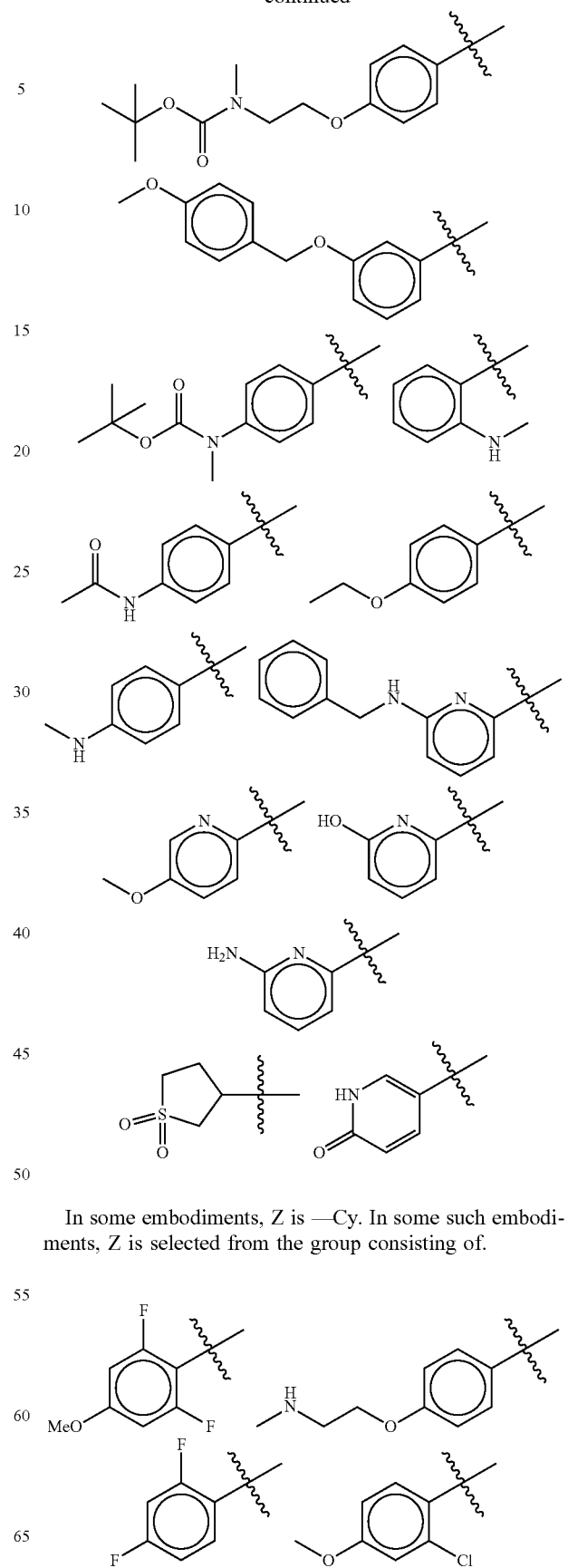
In some embodiments, Z is —Cy. In some such embodiments, Z is selected from the group consisting of:
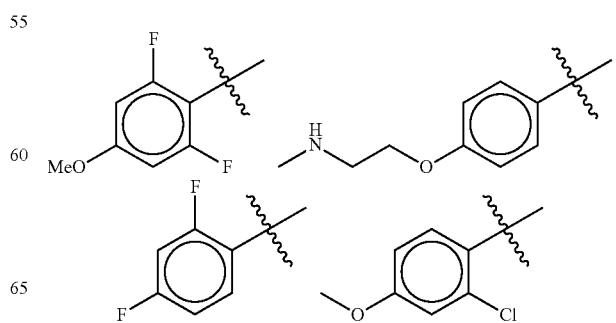

-continued
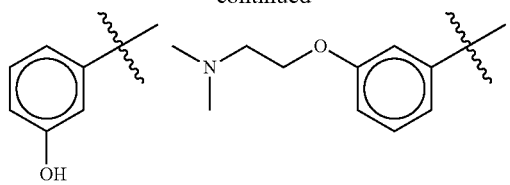
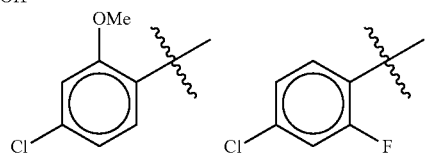
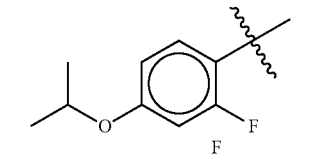
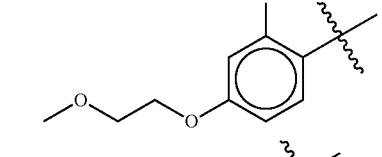
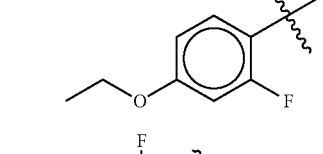
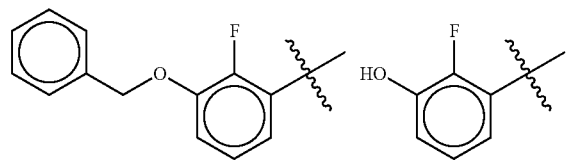
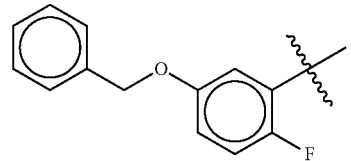
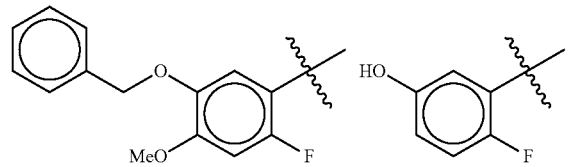
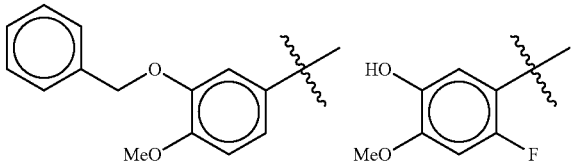
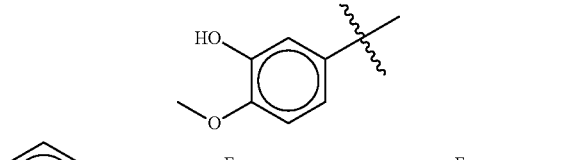
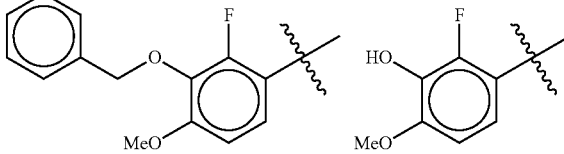
-continued
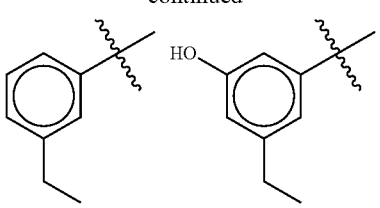
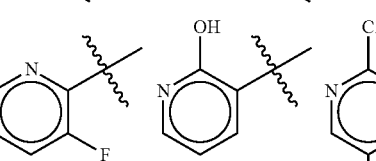
In some embodiments, Z is not:
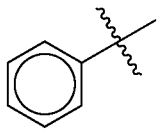
In some embodiments, Z is —(C$_{1-3}$ aliphatic)-Cy. In some such embodiments, Z is —CH$_2$—Cy. In some such embodiments, Z is selected from the group consisting of:
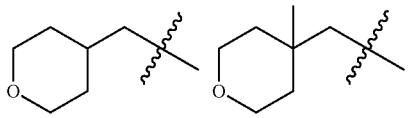
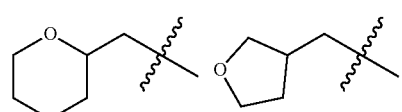
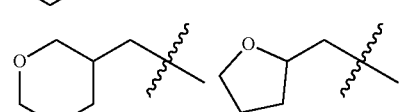
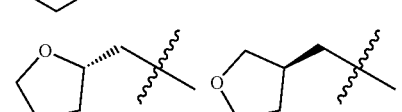
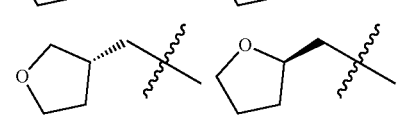

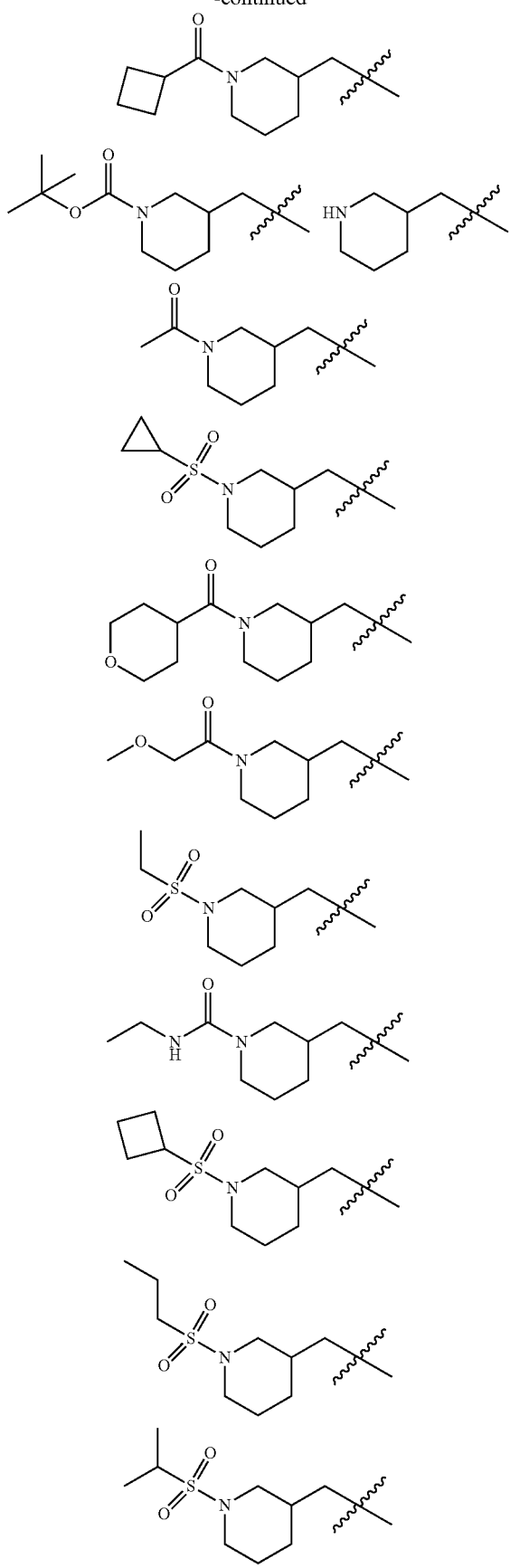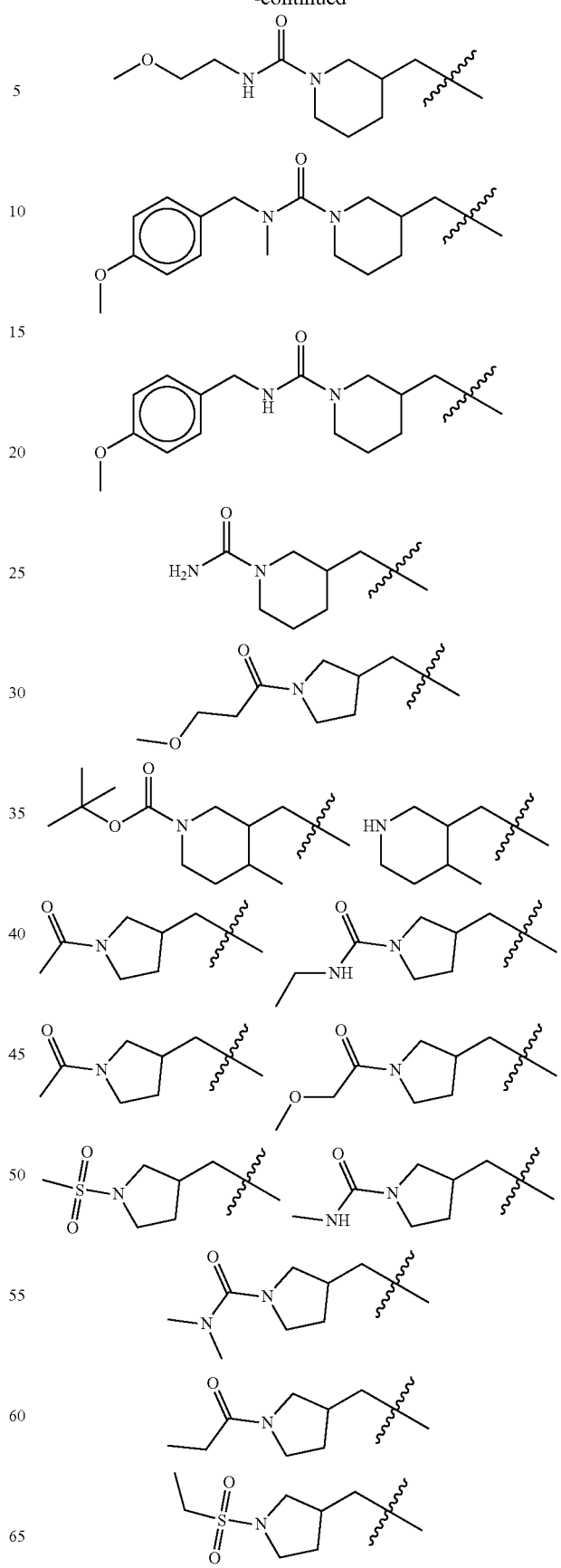

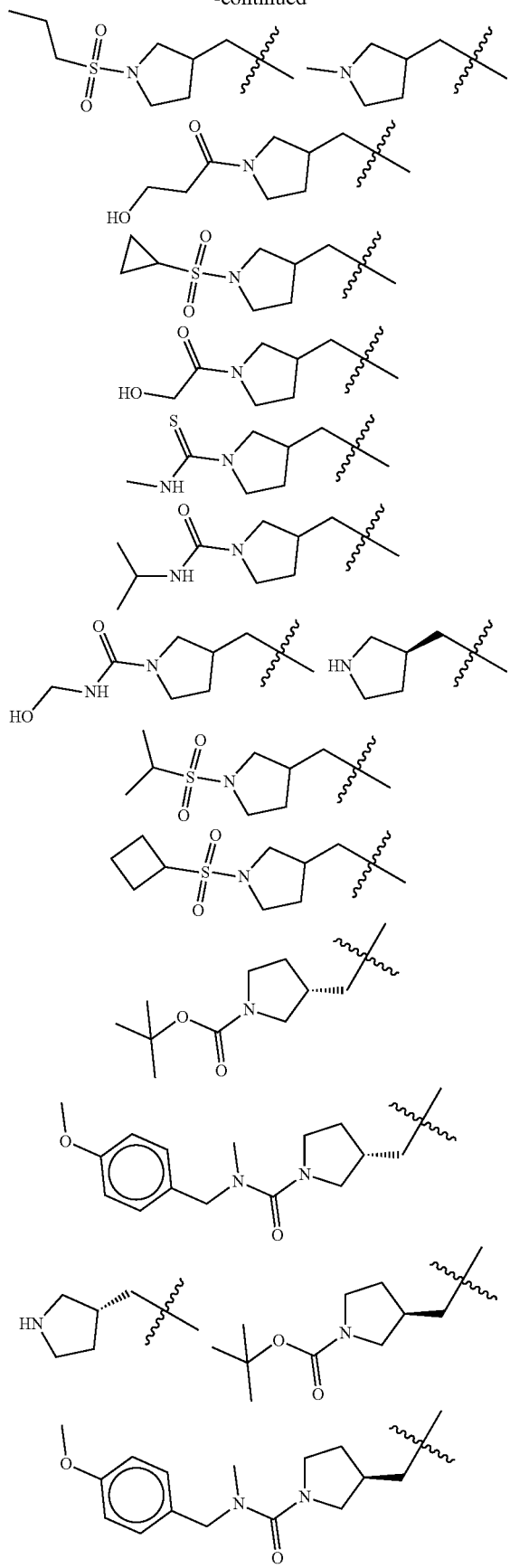
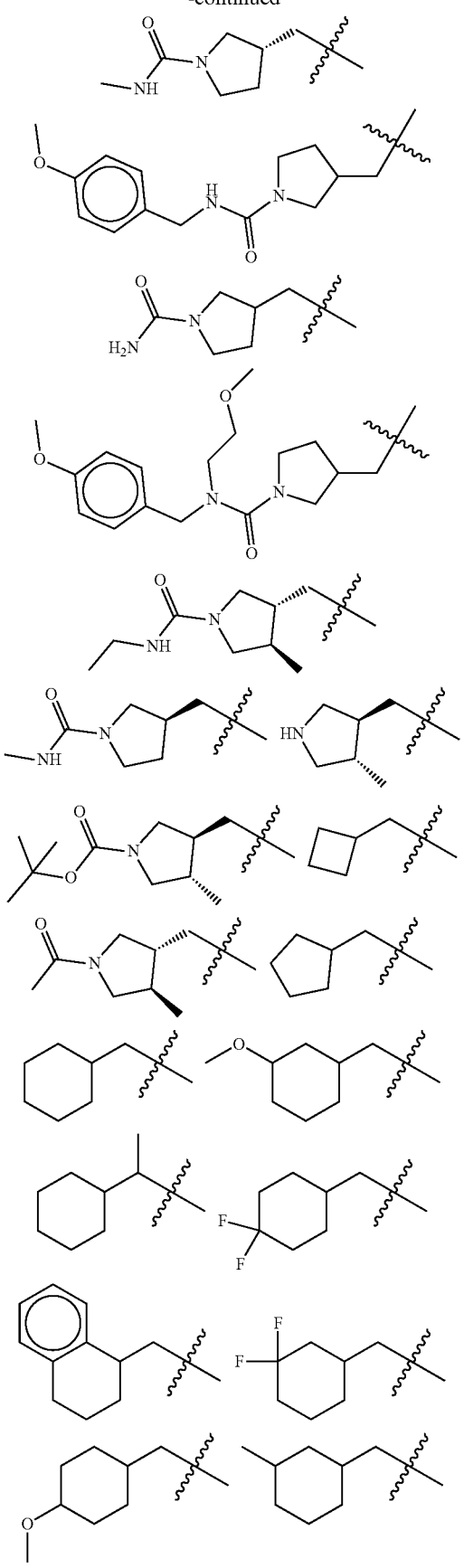

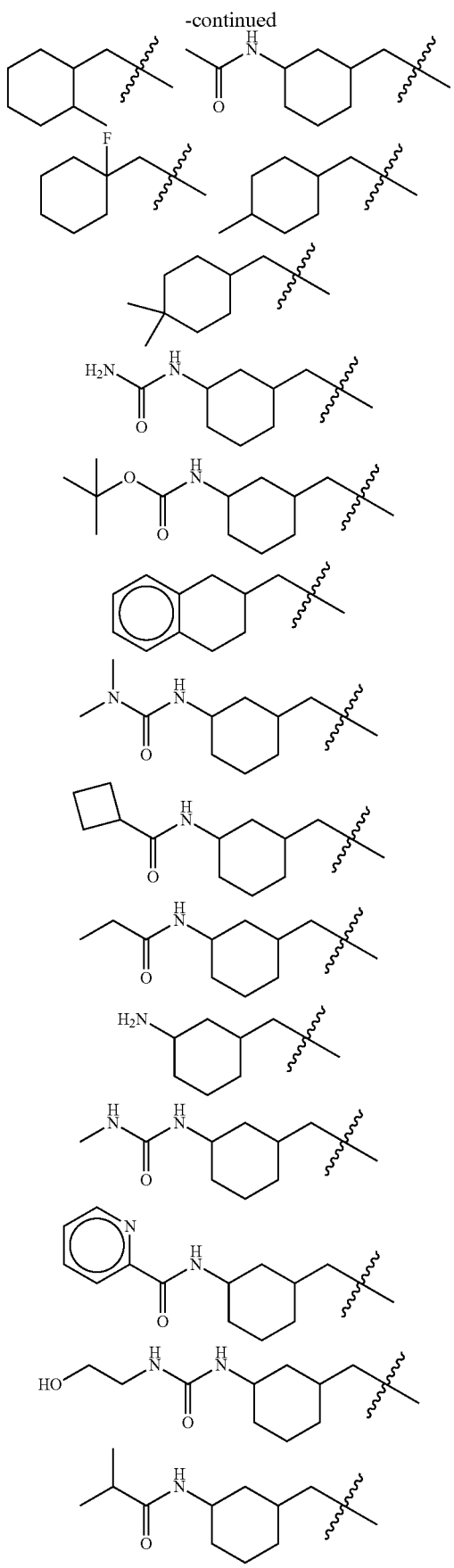
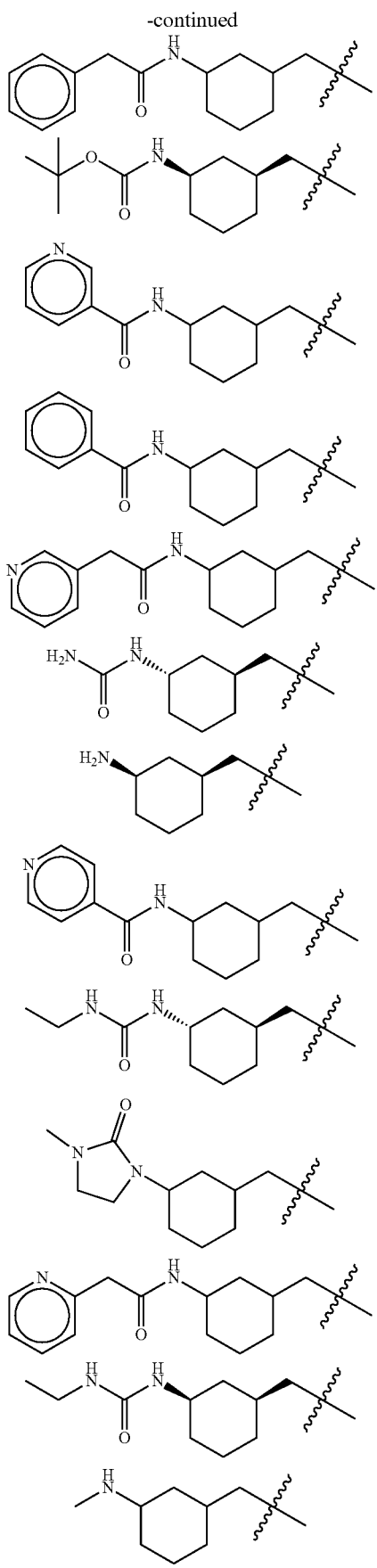

-continued
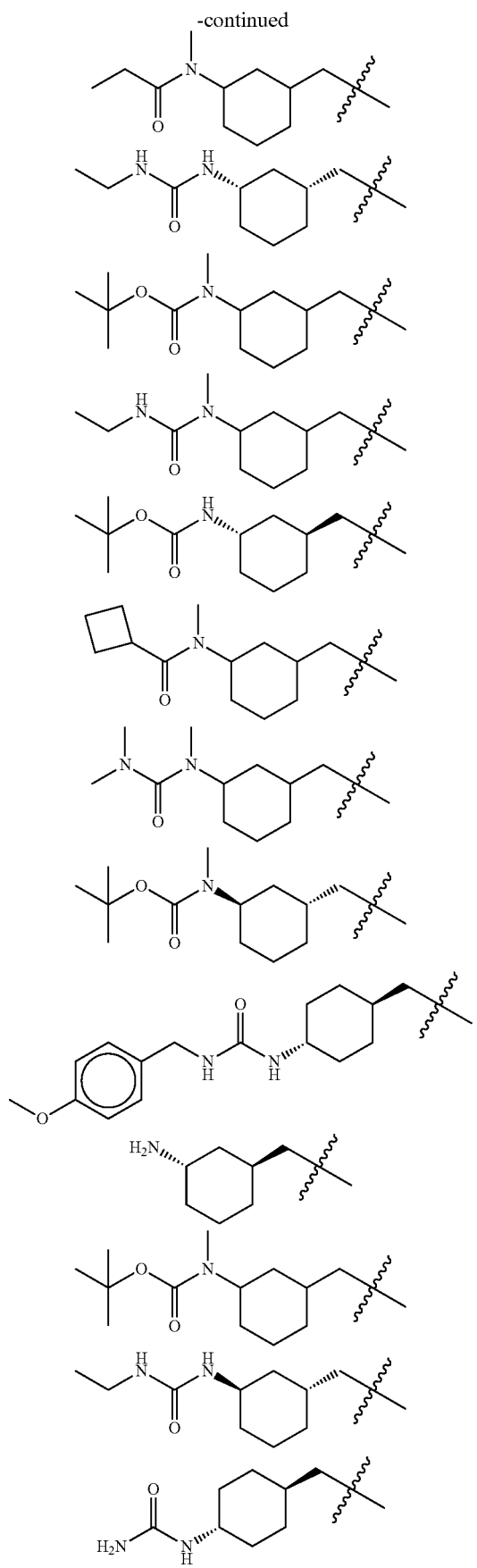
-continued
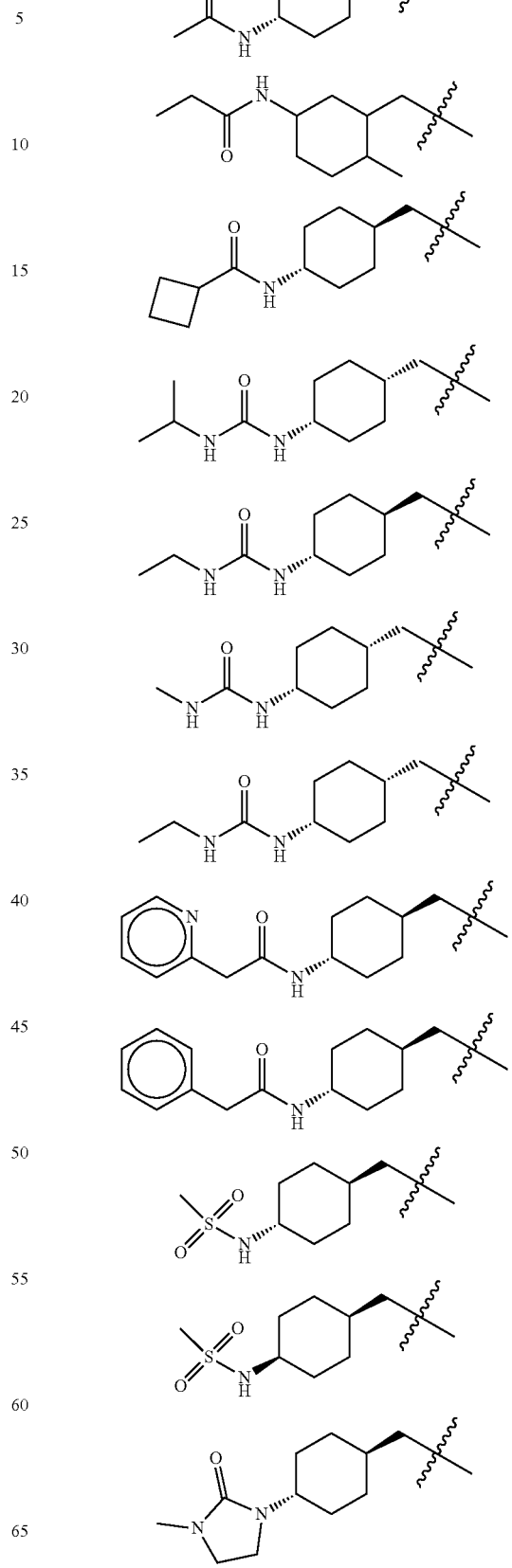

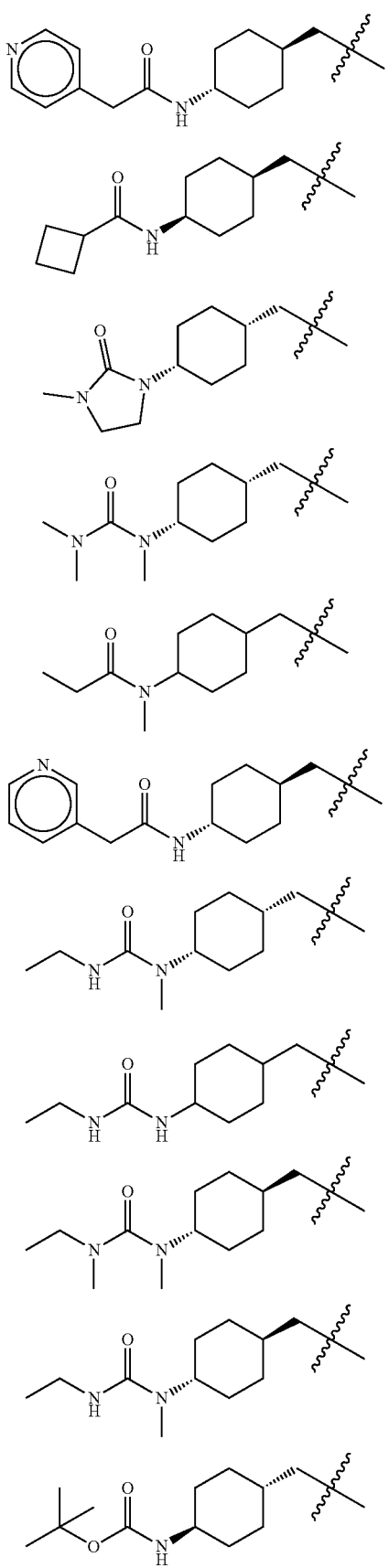
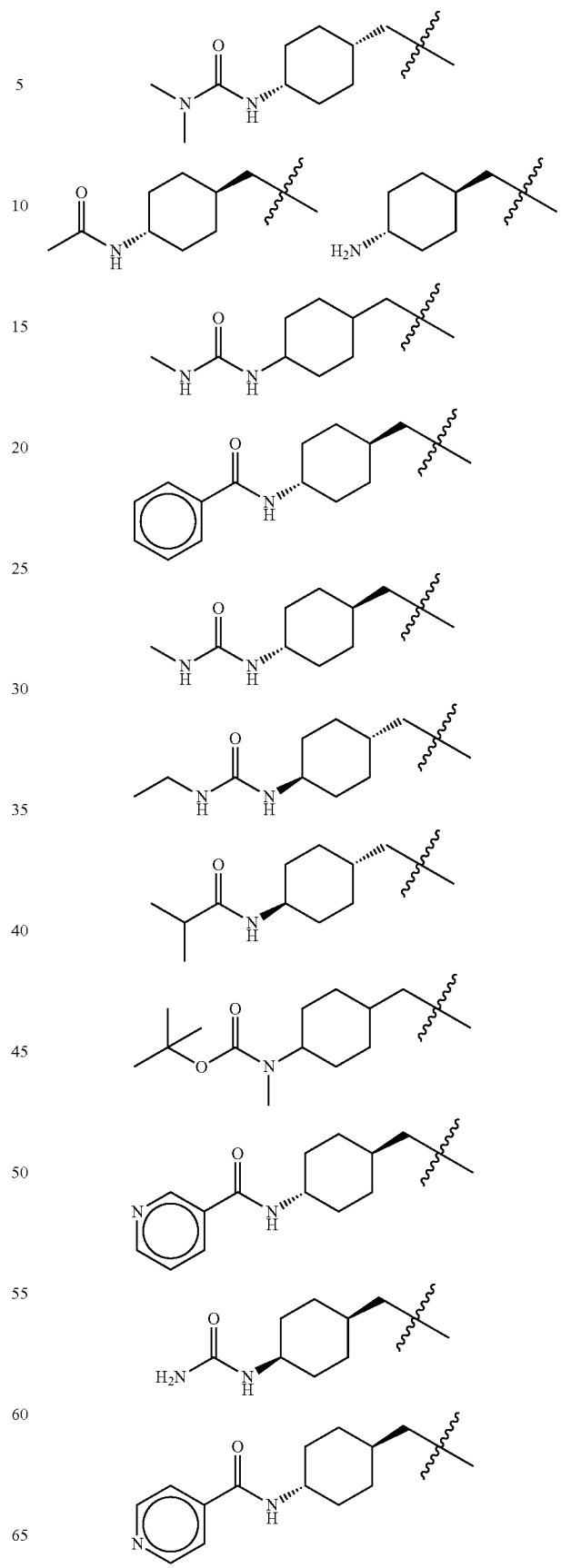

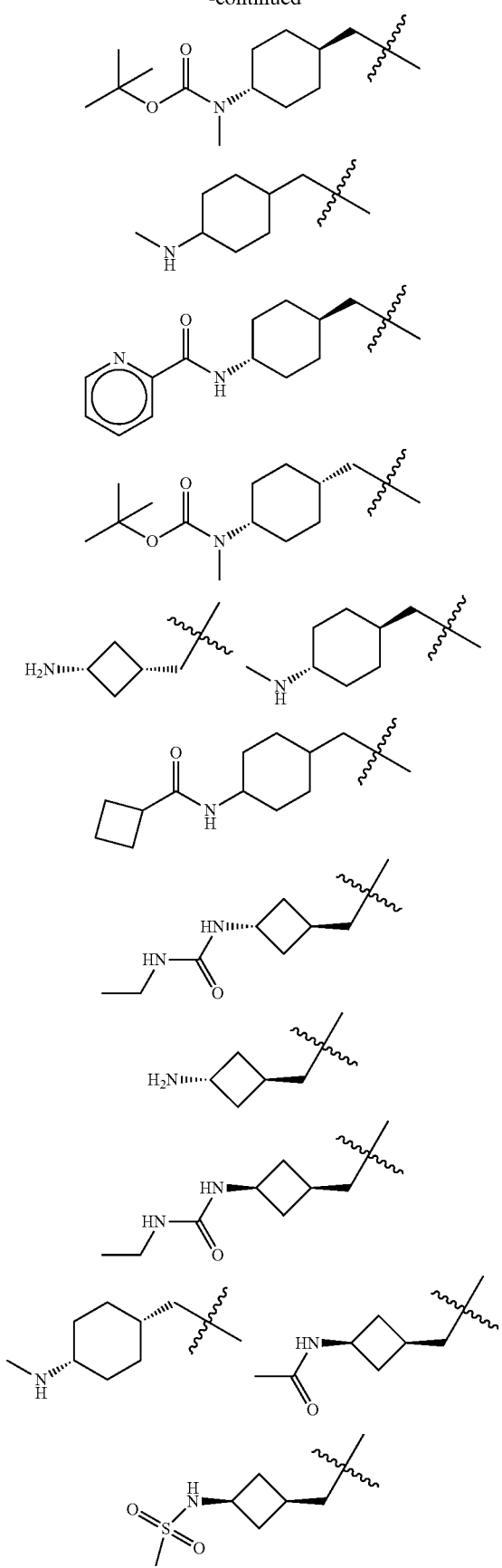
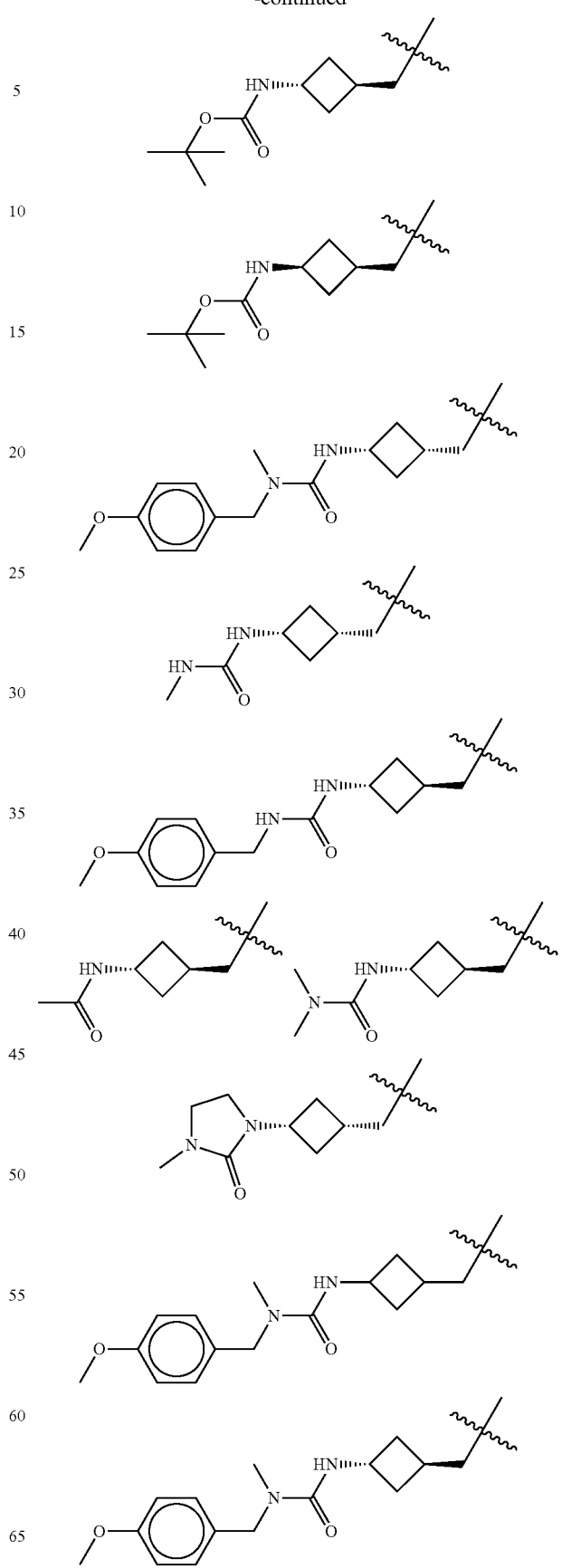

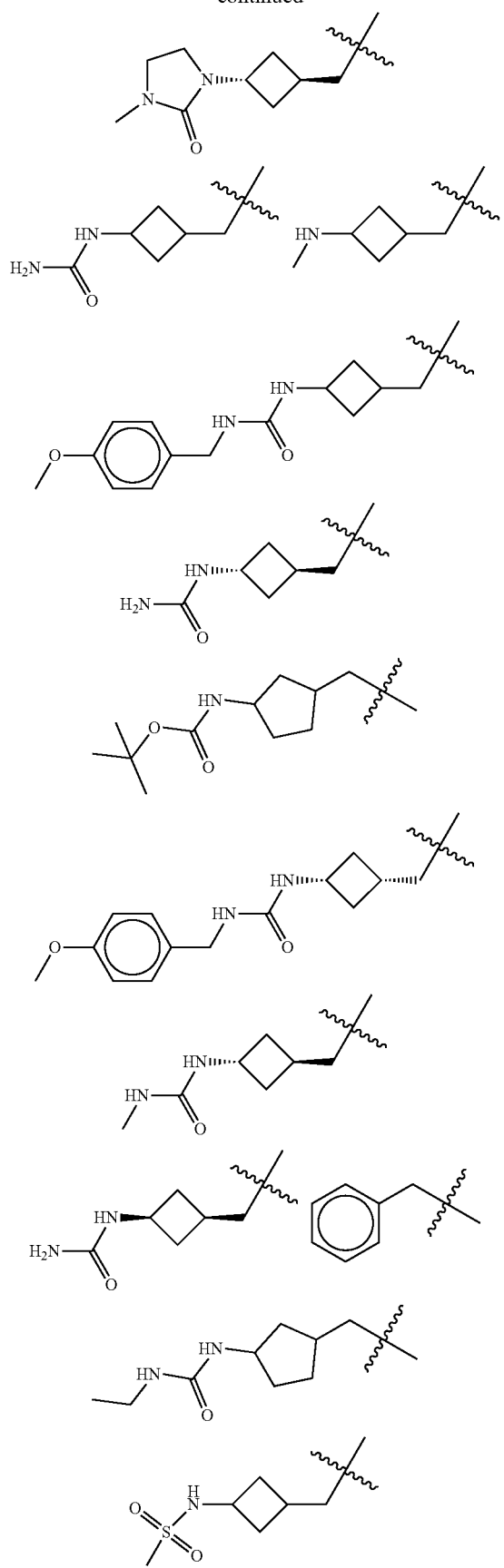
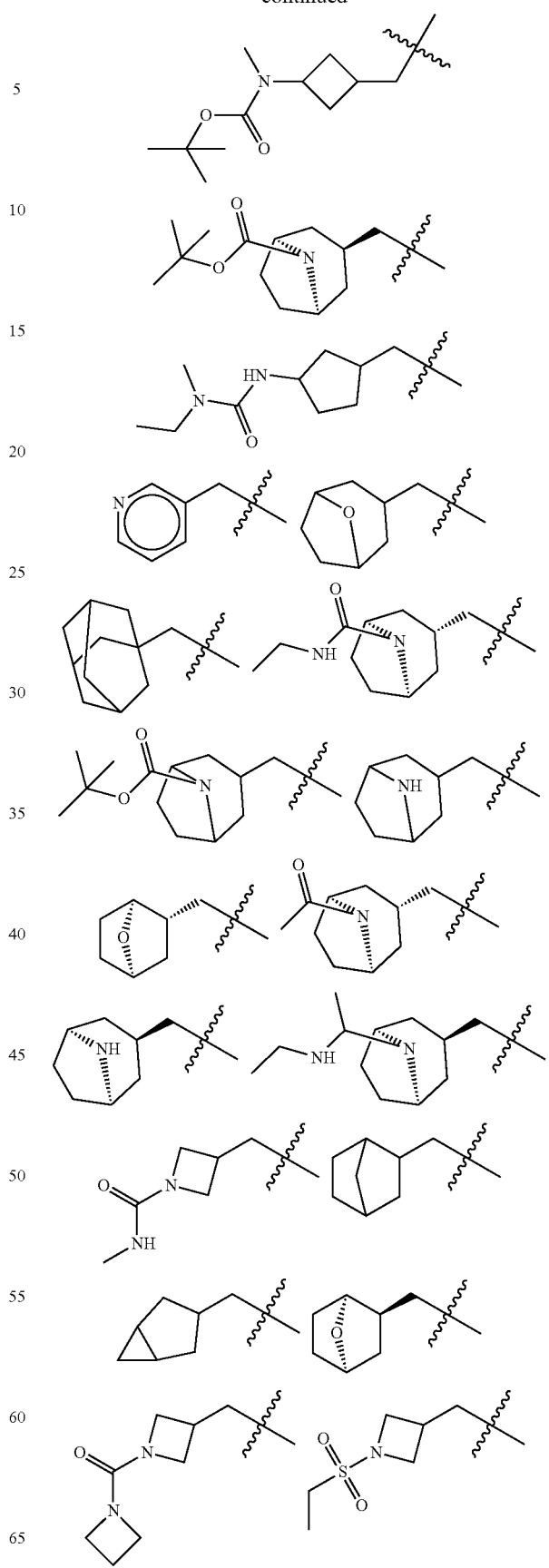

-continued
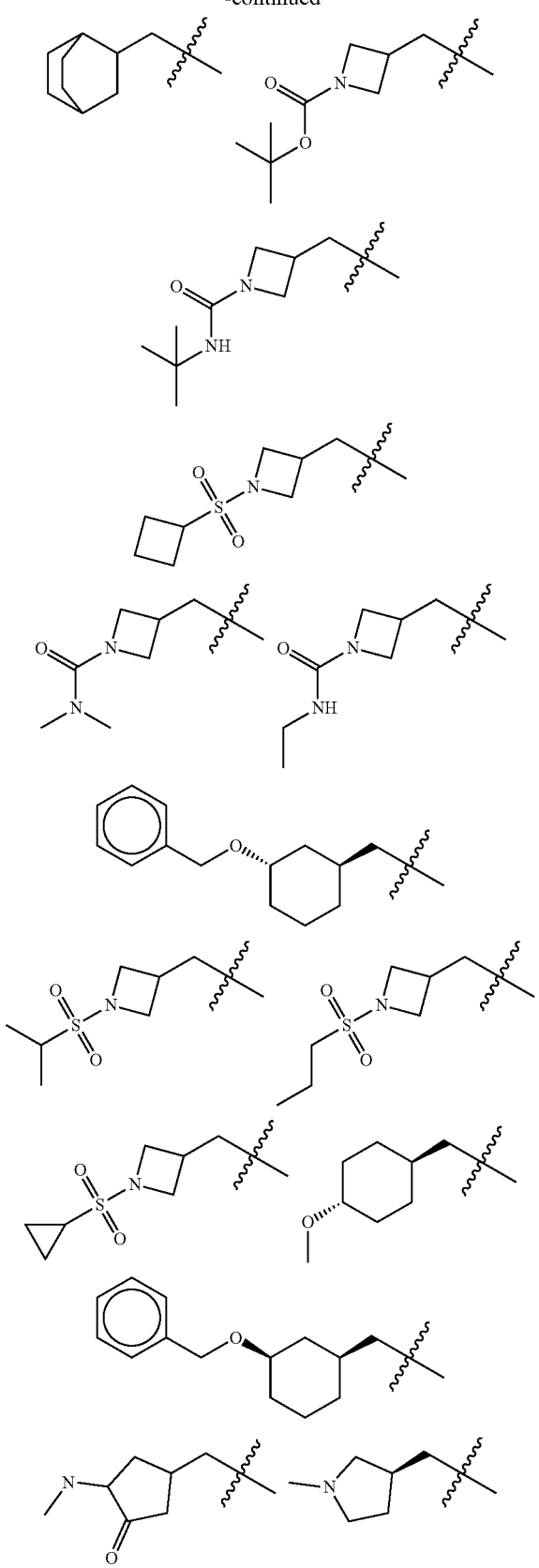
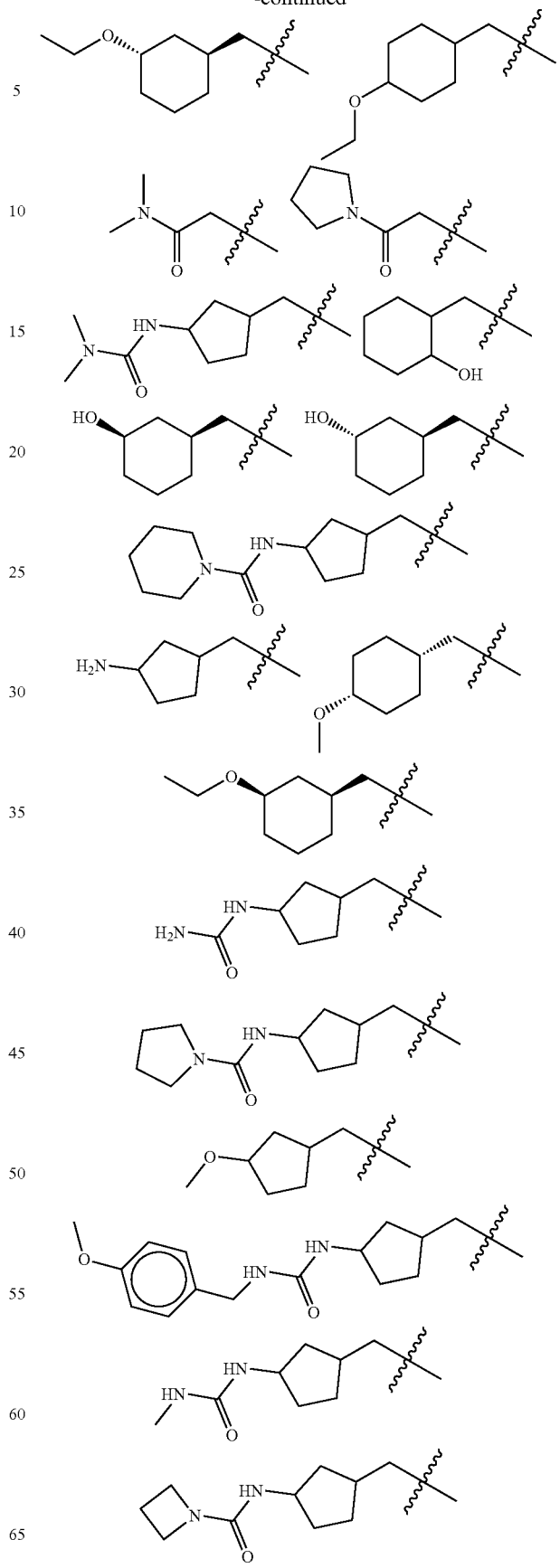

-continued
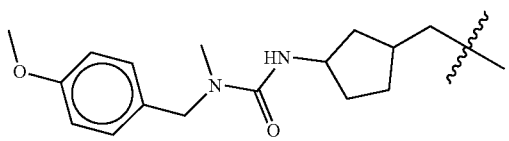
In some embodiments, Z is —(C$_{2-3}$ aliphatic)-Cy. In some such embodiments, Z is —CH$_2$—Cy. In some such embodiments, Z is selected from the group conssting of:
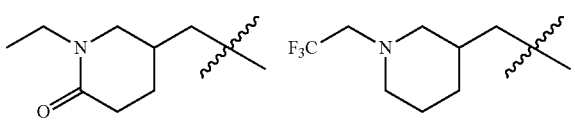
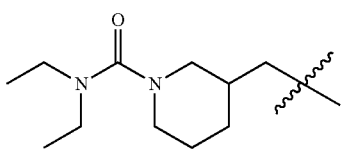
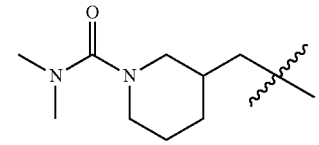
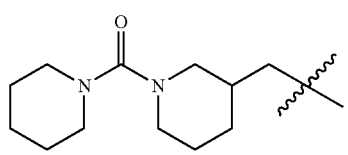
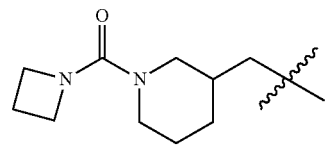
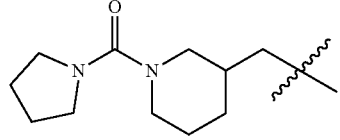
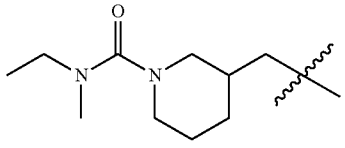
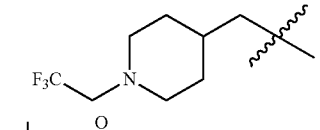
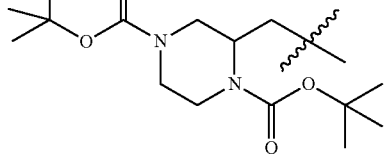
-continued
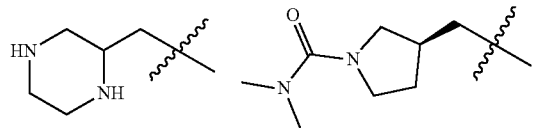
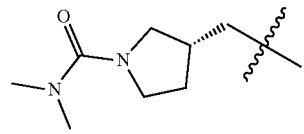
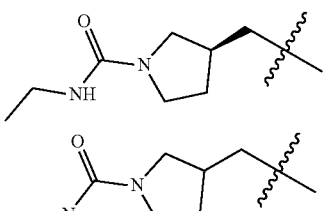
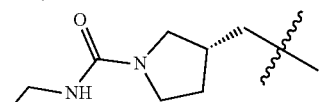
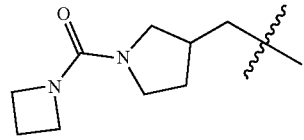
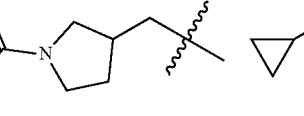
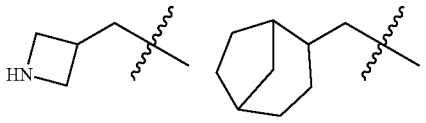
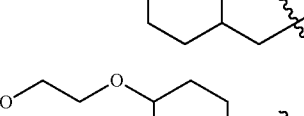
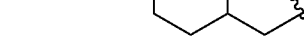

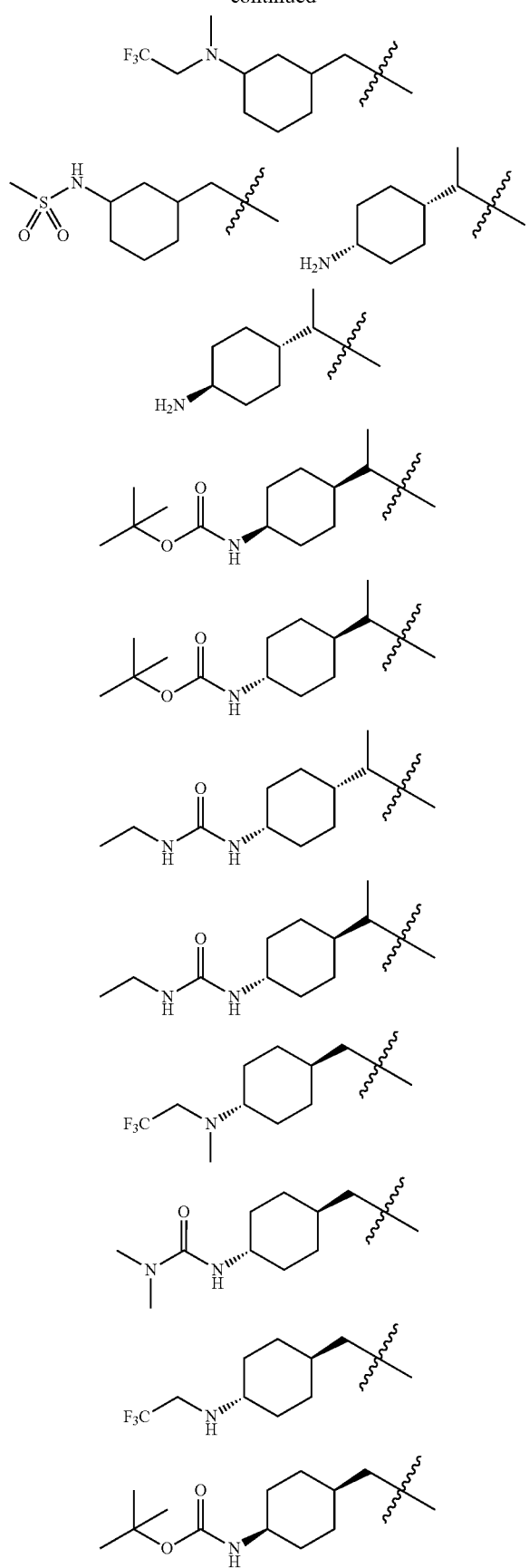
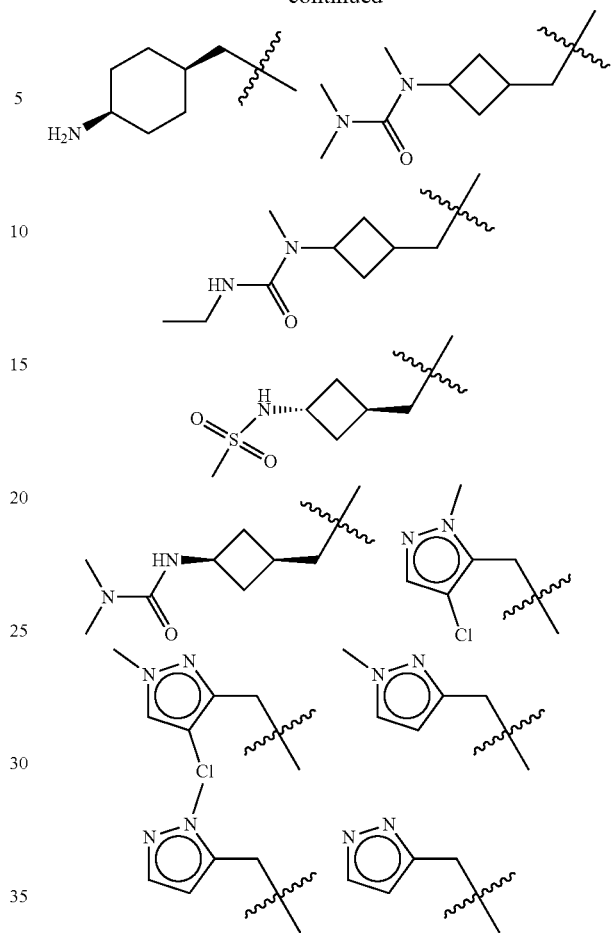

As defined above, Cy is an optionally substituted group selected from phenyl, a 3-10 membered saturated or partially unsaturated carbocyclic ring, a 6-10 membered bridged bicyclic carbocyclic ring, a 3-10 membered saturated or partially unsaturated heterocyclic ring having 1-2 heteroatoms independently selected from nitrogen, oxygen and sulfur, a 6-8 membered bridged bicyclic heterocyclic ring having 1-2 heteroatoms independently selected from nitrogen, oxygen and sulfur, a 5-6 membered heteroaryl ring having 1-2 heteroatoms independently selected from nitrogen, oxygen and sulfur, an 8-10 membered bicyclic aryl ring, and an 8-10 membered bicyclic heteroaryl ring having 1-3 heteroatoms independently selected from nitrogen oxygen and sulfur.

In some embodiments, Cy is phenyl.

In some embodiments, Cy is an optionally substituted 3-10 membered saturated or partially unsaturated carbocyclic ring. In some embodiments, Cy is an optionally substituted 3-10 membered saturated carbocyclic ring. In some such embodiments, Cy is an optionally substituted group selected from cyclopropyl, cyclobutyl, cyclopentyl, cyclohexyl, and cycloheptyl.

In some embodiments, Cy is an optionally substituted bicyclic carbocyclic ring. It will be appreciated that a bicyclic carbocyclic ring can be a bridged bicyclic ring. In some such embodiments, Cy is an optionally substituted group selected from:

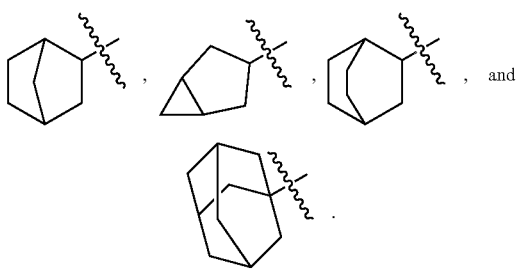

In some such embodiments, Cy is an optionally substituted group selected from:

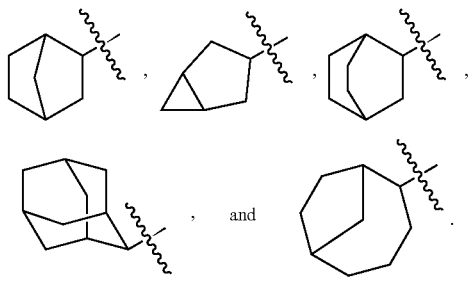

In some such embodiments, Cy is an optionally substituted group selected from:

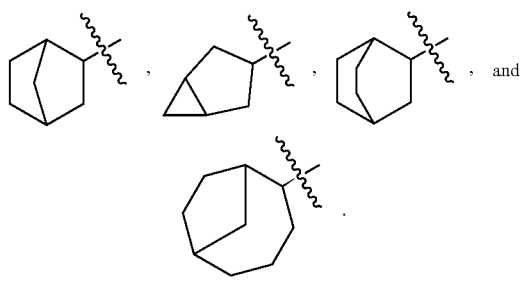

In some embodiments, Cy is an optionally substituted 5-6 membered heteroaryl ring having 1-3 heteroatoms independently selected from nitrogen, oxygen and sulfur. In some embodiments, Cy is a 5-membered heteroaryl ring having 1-3 heteroatoms independently selected from nitrogen, oxygen and sulfur. In some such embodiments, Cy is an optionally substituted group selected from pyrazolyl, imidazolyl, and triazolyl. In some embodiments, Cy is an optionally substituted group selected from:

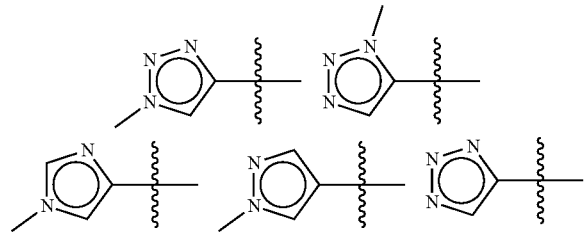

-continued

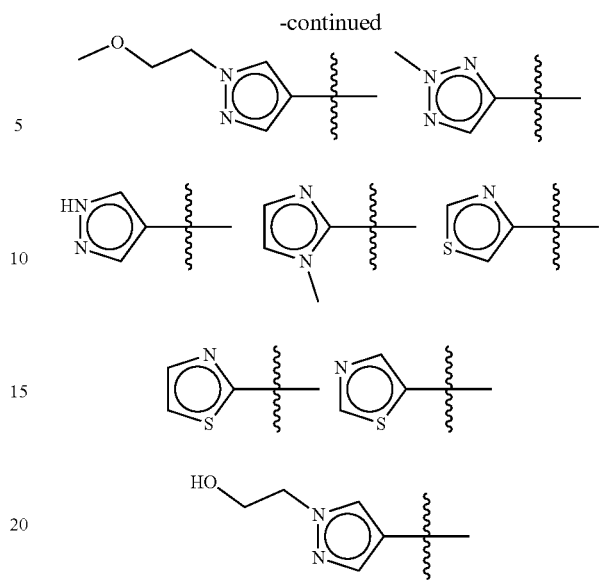

In some embodiments, Cy is an optionally substituted group selected from:

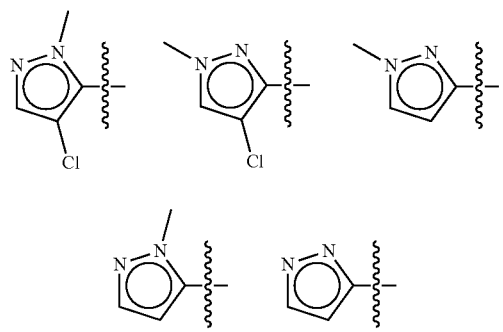

In some embodiments, Cy is an optionally substituted 5-6 membered heteroaryl ring having 1-3 heteroatoms independently selected from nitrogen, oxygen and sulfur. In some embodiments, Cy is a 6-membered heteroaryl ring having 1-3 heteroatoms independently selected from nitrogen, oxygen and sulfur. In some such embodiments, Cy is an optionally substituted group selected from pyridinyl. In some embodiments, Cy is an optionally substituted group selected from:

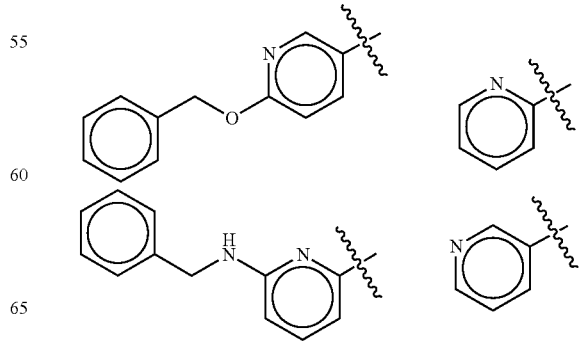

-continued

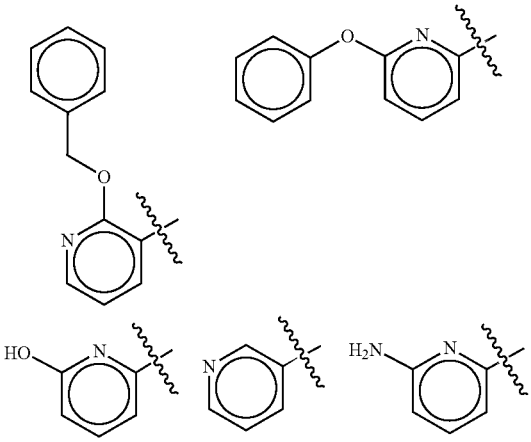

In some embodiments, Cy is an optionally substituted group selected from:

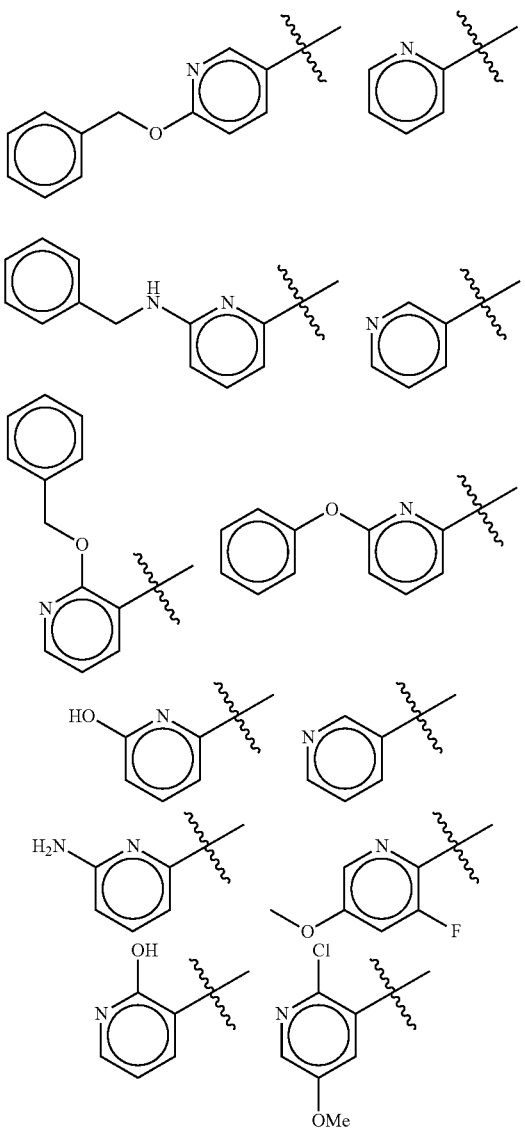

In some embodiments of formula I-a, Cy is an optionally substituted group selected from:

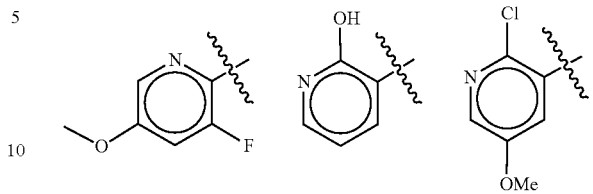

In some embodiments, Cy is an optionally substituted 3-10 membered saturated or partially unsaturated heterocyclic ring having 1-2 heteroatoms independently selected from nitrogen, oxygen and sulfur.

In some embodiments, Cy is an optionally substituted 4-membered saturated heterocyclic group having 1 heteroatom independently selected from nitrogen, oxygen and sulfur. In some such embodiments, Cy is optionally substituted oxetanyl. In some such embodiments, Cy is optionally substituted oxetanyl or azetidinyl.

In some embodiments, Cy is an optionally substituted 5-membered saturated heterocyclic group having 1-2 heteroatoms independently selected from nitrogen, oxygen and sulfur. In some such embodiments, Cy is an optionally substituted group selected from tetrahydrofuranyl and pyrrolidinyl.

In some embodiments, Cy is an optionally substituted 6-membered saturated heterocyclic group having 1-2 heteroatoms independently selected from nitrogen, oxygen and sulfur. In some such embodiments, Cy is an optionally substituted group selected from tetrahydropyranyl and piperidinyl. In some such embodiments, Cy is an optionally substituted group selected from tetrahydropyranyl, piperidinyl, and piperazinyl.

In some embodiments, Cy is an optionally substituted 7-membered saturated heterocyclic group having 1-2 heteroatoms independently selected from nitrogen, oxygen and sulfur. It will be appreciated that a 7-membered saturated heterocyclic ring can be a bridged bicyclic ring. In some such embodiments, Cy is an optionally substituted group selected from:

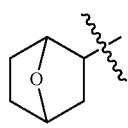

In some embodiments, Cy is an optionally substituted 8-membered saturated heterocyclic group having 1-2 heteroatoms independently selected from nitrogen, oxygen and sulfur. It will be appreciated that an 8-membered saturated heterocyclic ring can be a bridged bicyclic ring. In some such embodiments, Cy is an optionally substituted group selected from:

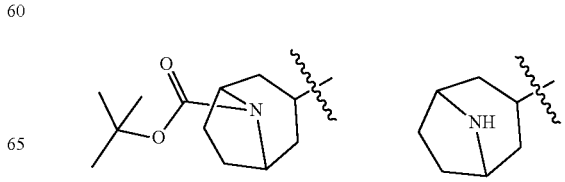

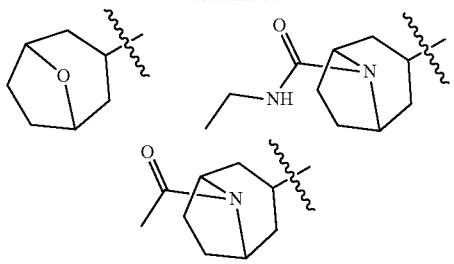

As defined above, each of $R^1$ and $R^2$ is independently selected from halogen and $C_{1-4}$ aliphatic. In some embodiments, $R^1$ is fluoro. In some embodiments, $R^1$ is chloro. In some embodiments, $R^1$ is methyl. In some embodiments, $R^2$ is fluoro. In some embodiments, $R^2$ is chloro. In some embodiments, $R^2$ is methyl. In some embodiments, $R^1$ is fluoro and $R^2$ is chloro. In some embodiments, $R^1$ is fluoro and $R^2$ is methyl. In some embodiments, $R^1$ is fluoro and $R^2$ is fluoro. In some embodiments, $R^1$ is chloro and $R^2$ is chloro. In some embodiments, $R^1$ is methyl and $R^2$ is methyl.

As defined above, $R^3$ is selected from hydrogen, halogen, —CN, —NR$_2$, and optionally substituted $C_{1-4}$ aliphatic. In some embodiments, $R^3$ is hydrogen. In some embodiments, $R^3$ is halogen. In some embodiments, $R^3$ is —CN. In some embodiments, $R^3$ is —NR$_2$. In some embodiments, $R^3$ is —NH$_2$. In some embodiments, $R^3$ is —N(C(O)O$^t$Bu)$_2$. In some embodiments, $R^3$ is optionally substituted $C_{1-4}$ aliphatic.

As defined above, each R is independently selected from hydrogen, optionally substituted $C_{1-4}$ aliphatic, and —C(O)O($C_{1-4}$ aliphatic). In some embodiments, each R is hydrogen. In some embodiments, each R is —C(O)O($C_{1-4}$ aliphatic). In some embodiments, each R is —C(O)O$^t$Bu.

As defined above, Ring A is an optionally substituted 5- or 6-membered heteroaryl ring having 1-4 heteroatoms independently selected from nitrogen, oxygen and sulfur.

In some embodiments, Ring A is an optionally substituted 5-membered heteroaryl ring having 1-4 heteroatoms independently selected from nitrogen, oxygen and sulfur. In some embodiments, Ring A is an optionally substituted 5-membered heteroaryl ring having 2-3 nitrogen atoms. In some such embodiments, Ring A is selected from pyrazolyl, imidazolyl, and triazolyl.

In some embodiments, Ring A is an optionally substituted 5-membered heteroaryl ring having 4 nitrogen atoms. In some embodiments, Ring A is tetrazol-5-yl.

In some embodiments, Ring A is an optionally substituted 5-membered heteroaryl ring having 1 nitrogen atom and 1 additional heteroatom selected from oxygen and sulfur. In some such embodiments, Ring A is selected from oxazolyl and thiazolyl.

In some embodiments, Ring A is selected from:

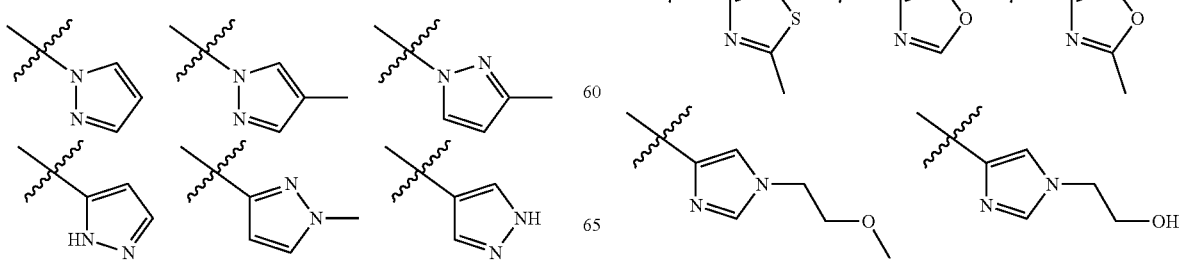

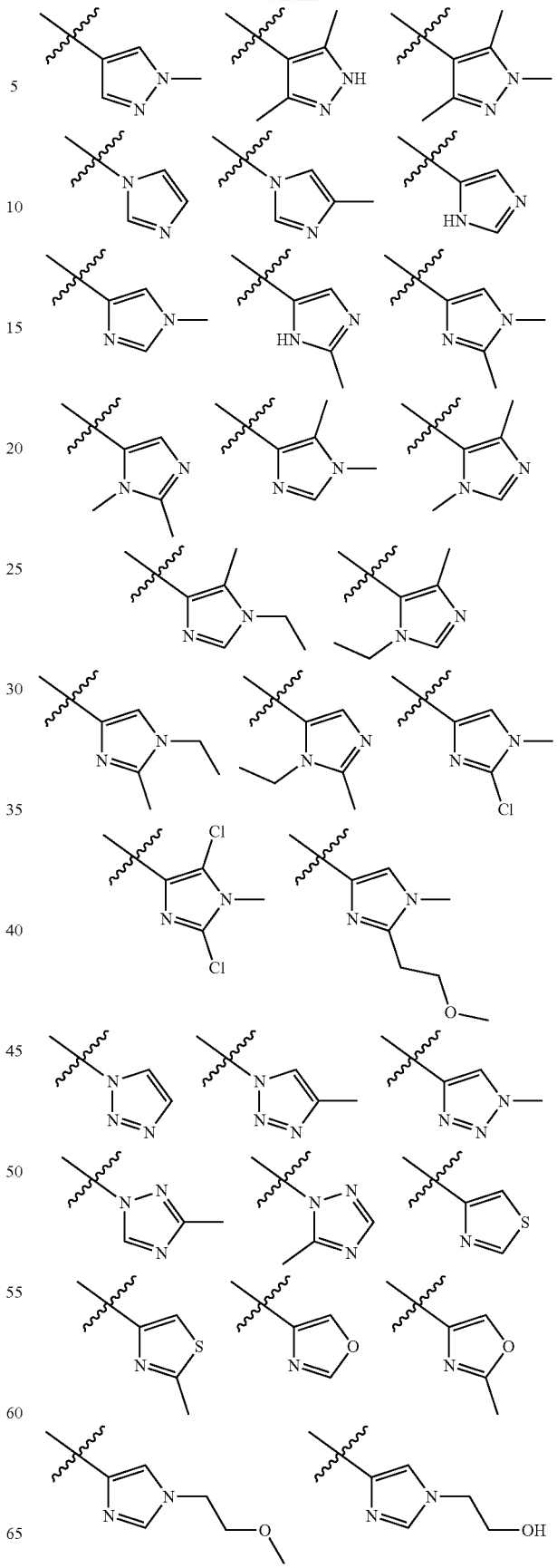

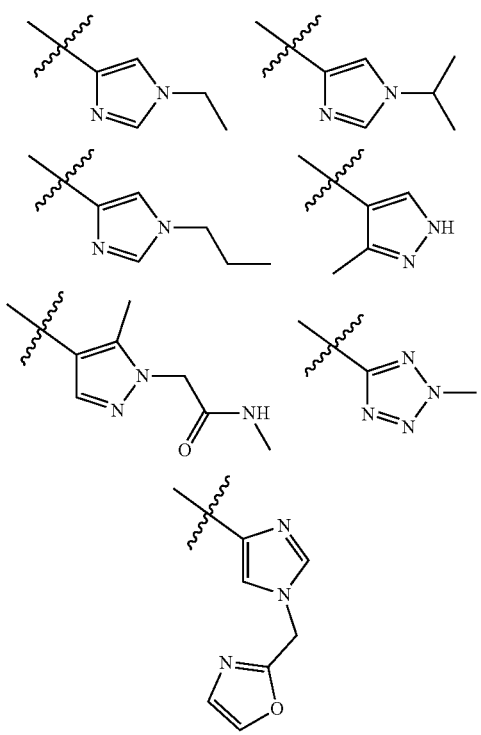
In some embodiments, Ring A is selected from:
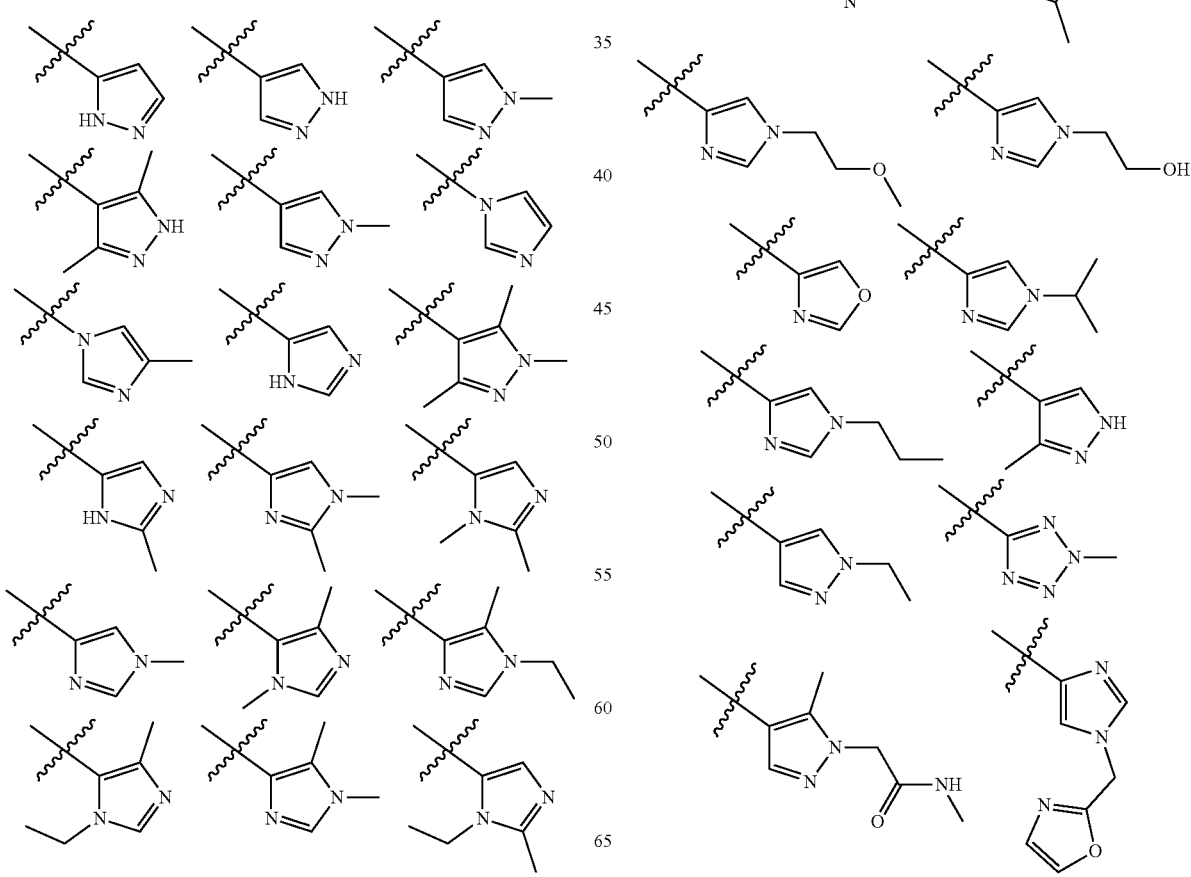

In some embodiments, Ring A is

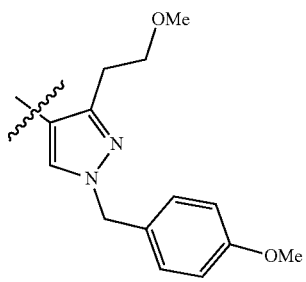

In some embodiments, Ring A is not:

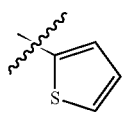

In some embodiments, Ring A is an optionally substituted 6-membered heteroaryl ring having 1-4 heteroatoms independently selected nitrogen, oxygen and sulfur. In some such embodiments, Ring A is selected from 2-pyridyl, 3-pyridyl and 4-pyridyl.

As defined above, x is 0-3. In some embodiments, x is 0. In some embodiments, x is 1. In some embodiments, x is 2. In some embodiments, x is 3. In some embodiments, x is 0-1. In some embodiments, x is 1-2.

In some embodiments,

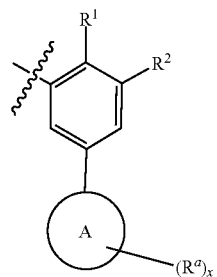

is selected from the group consisting of:

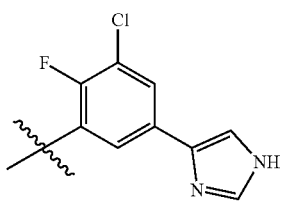

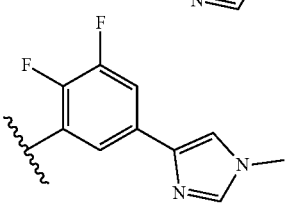

-continued

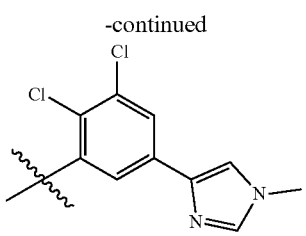

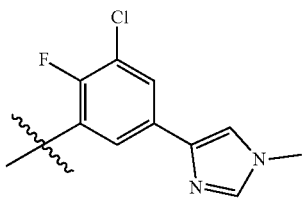

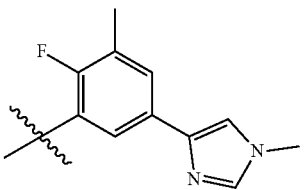

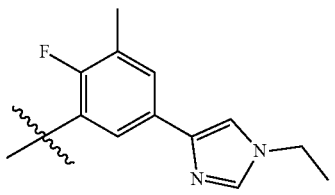

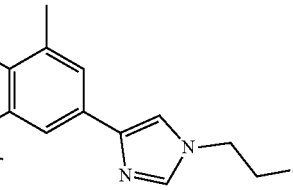

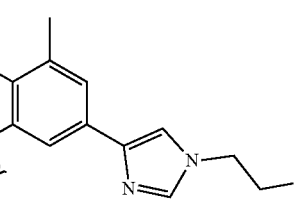

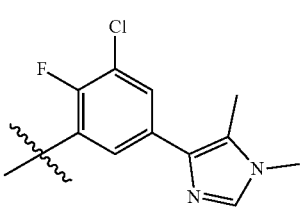

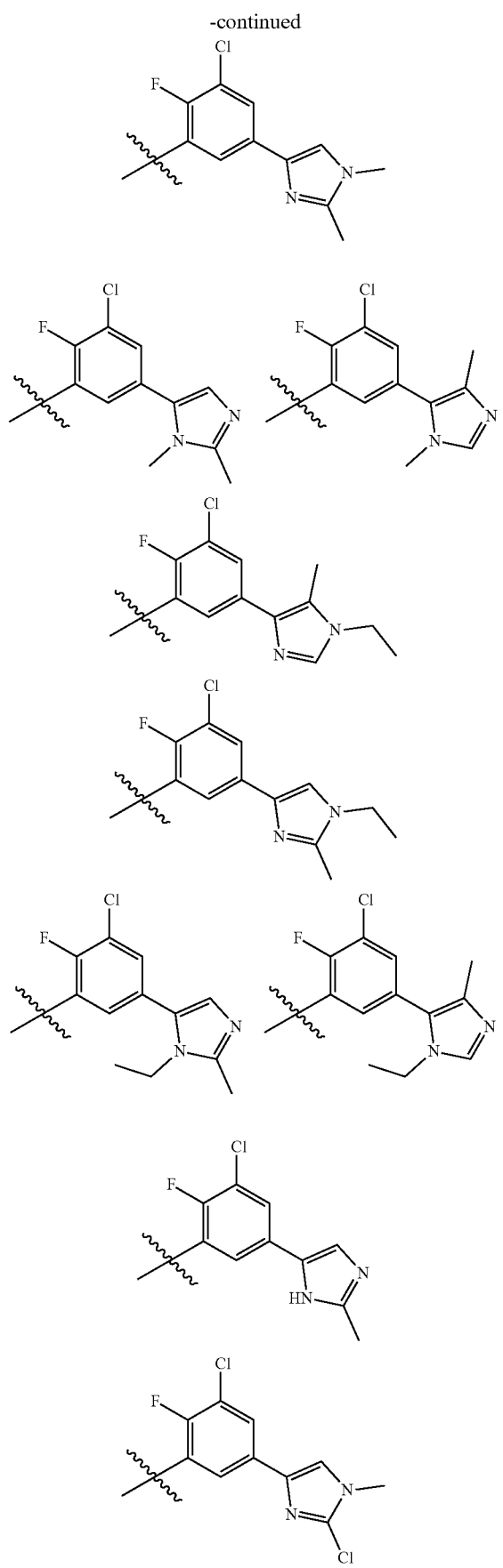
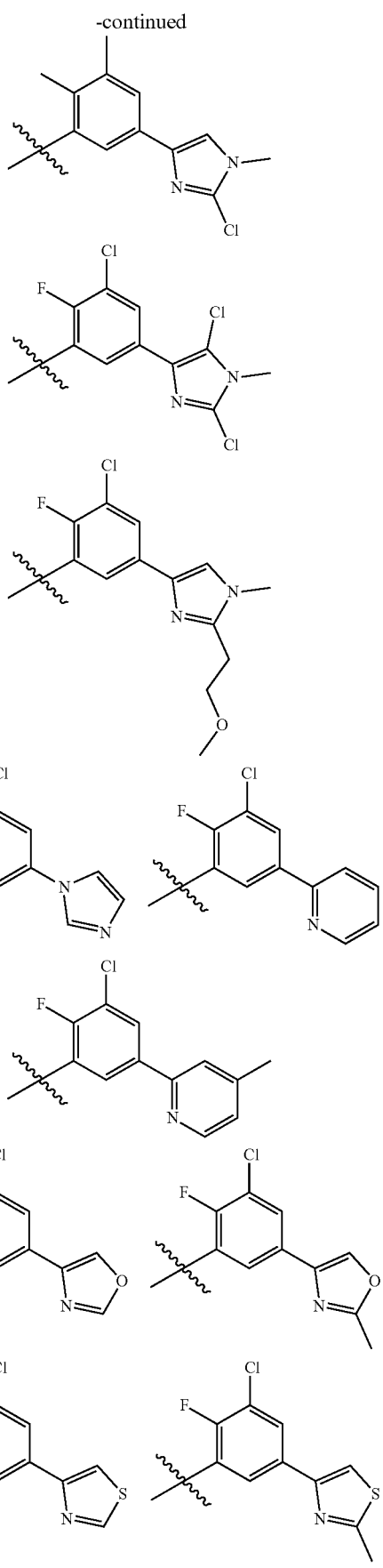

-continued
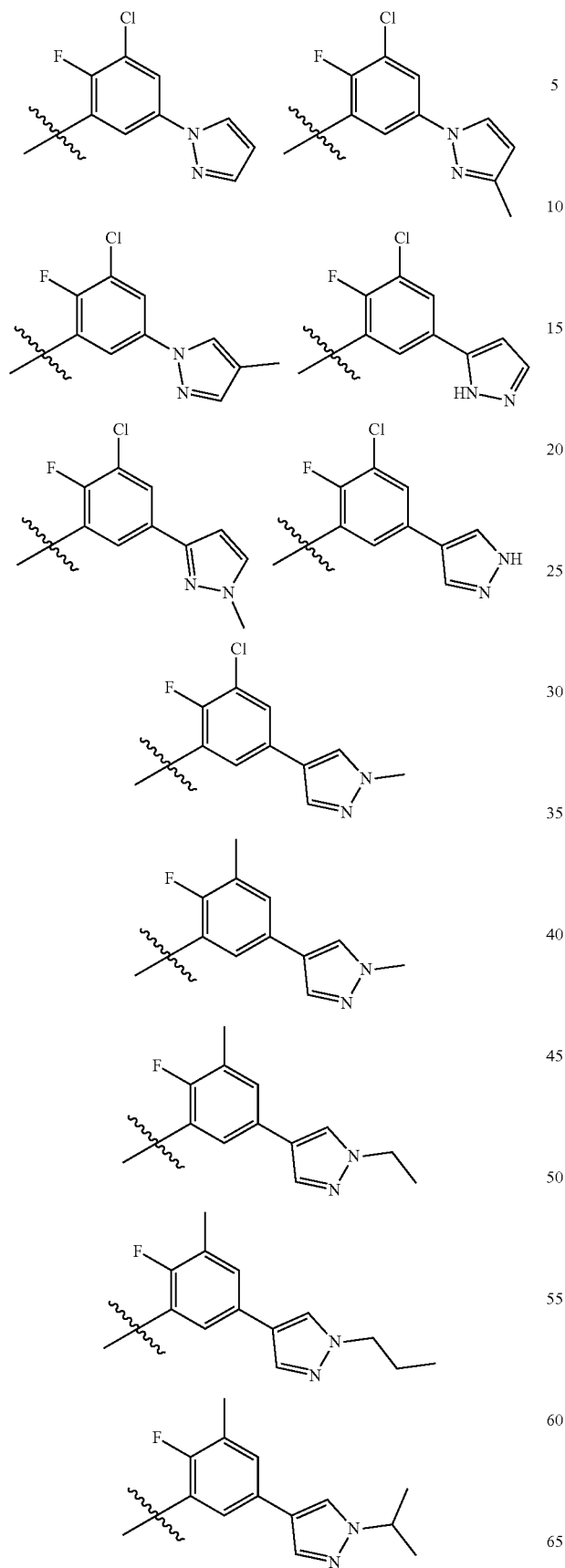
-continued
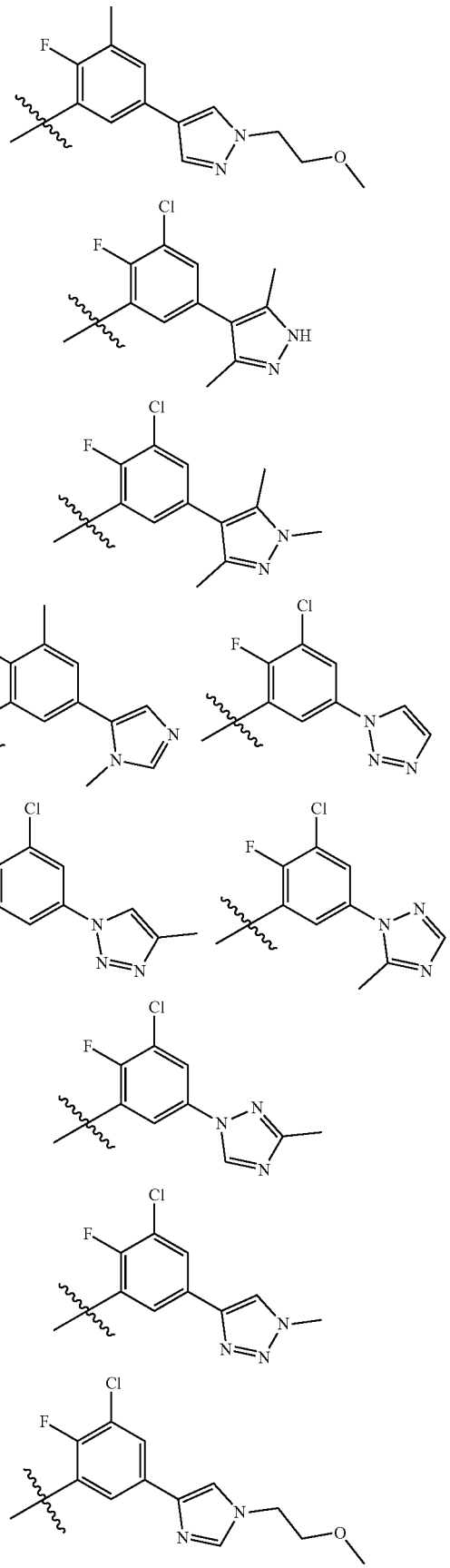

-continued
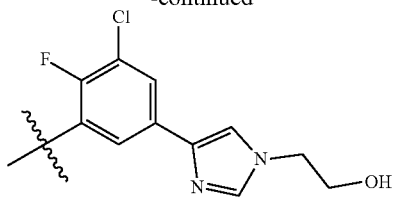
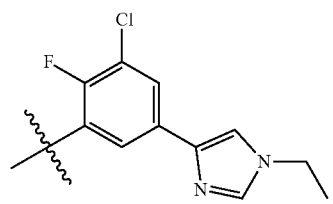
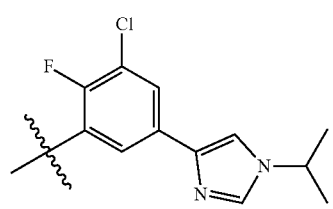
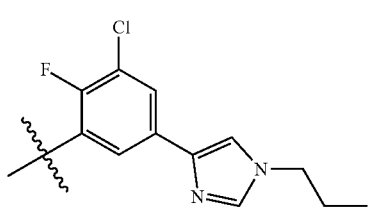
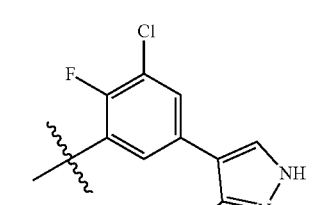
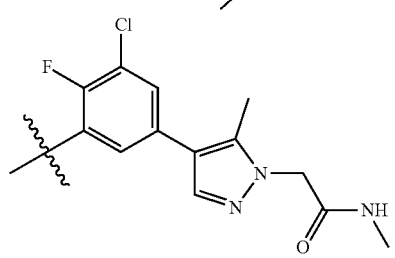
-continued
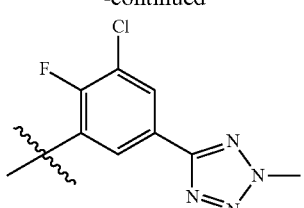
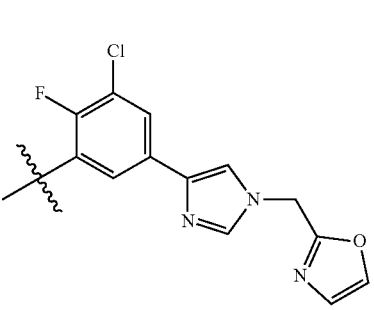
In some embodiments,
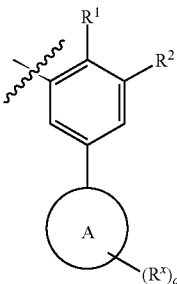 is
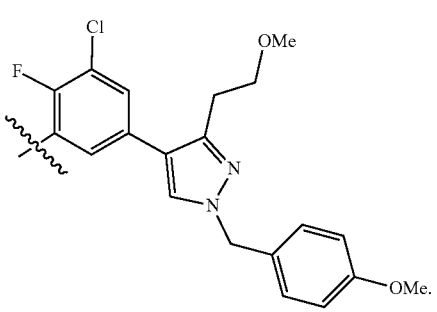
In some embodiments, a compound of formula I is selected from the group consisting of those listed in Table 1:
| Cmpd No | Compound Structure |
|---|---|
| I-1 | 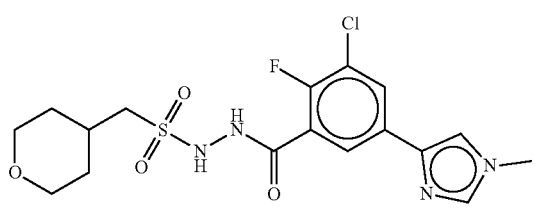 |

-continued
| Cmpd No | Compound Structure |
|---|---|
| I-2 | 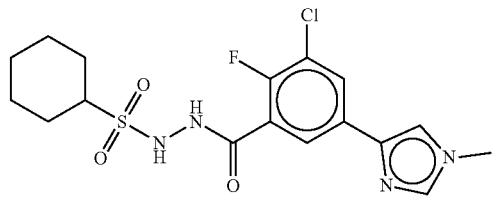 |
| I-3 | 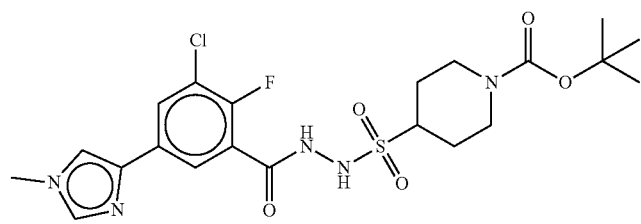 |
| I-6 | 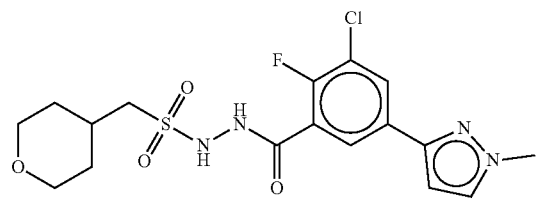 |
| I-7 | 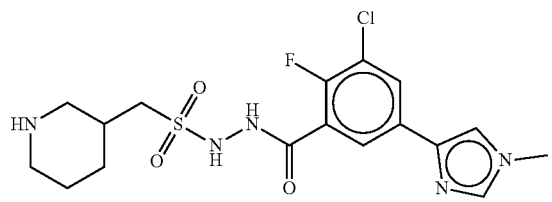 |
| I-8 | 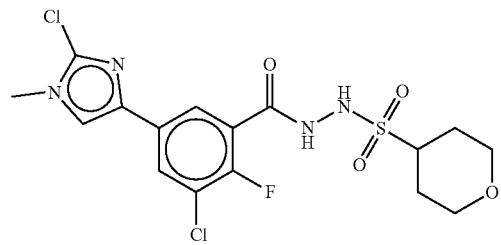 |
| I-4 | 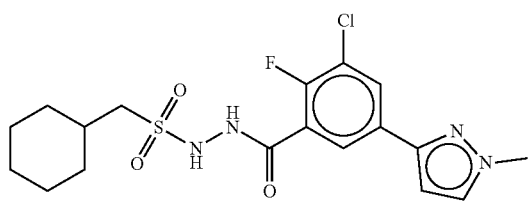 |
| I-5 | 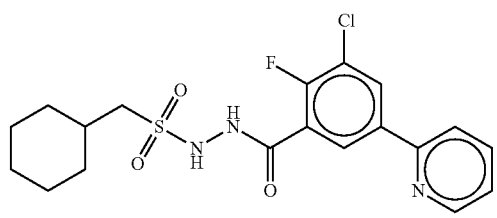 |

| Cmpd No | Compound Structure |
|---|---|
| I-11 | 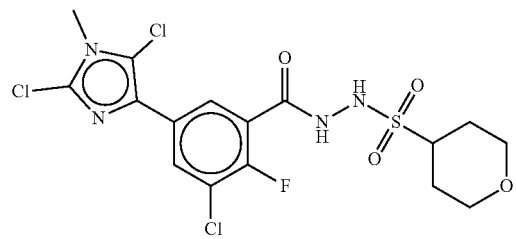 |
| I-12 | 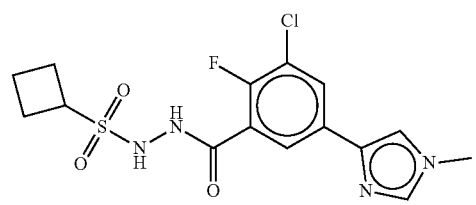 |
| I-13 | 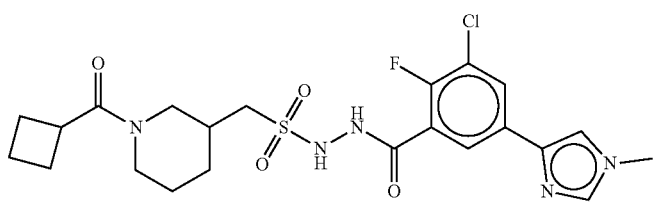 |
| I-9 | 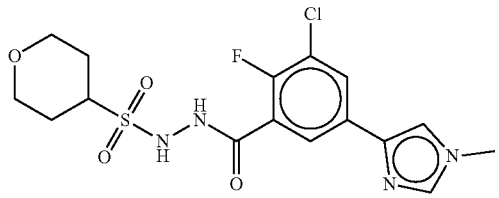 |
| I-10 | 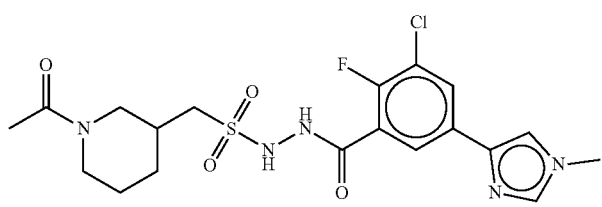 |
| I-16 | 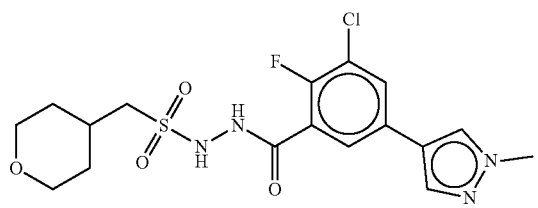 |
| I-17 | 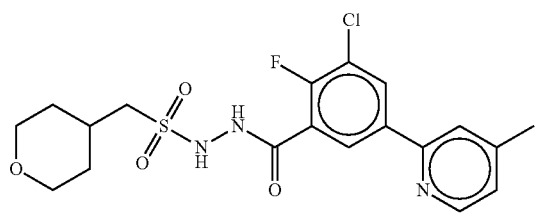 |

-continued
| Cmpd No | Compound Structure |
|---|---|
| I-18 | 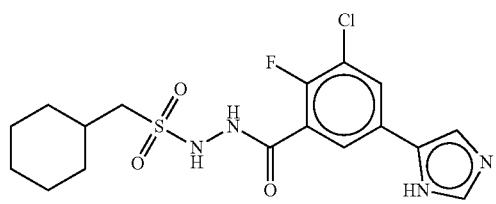 |
| I-14 | 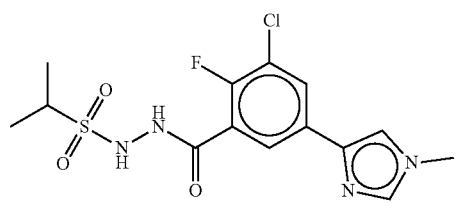 |
| I-15 | 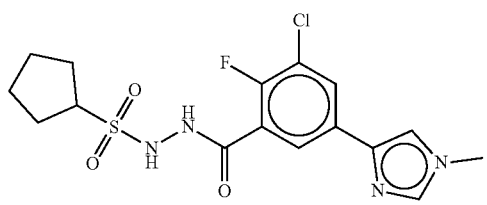 |
| I-21 | 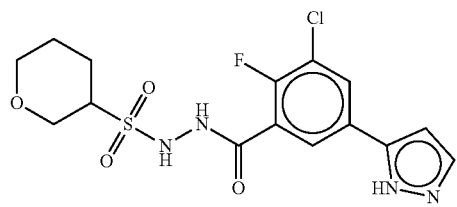 |
| I-22 | 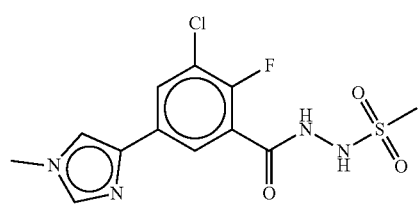 |
| I-23 | 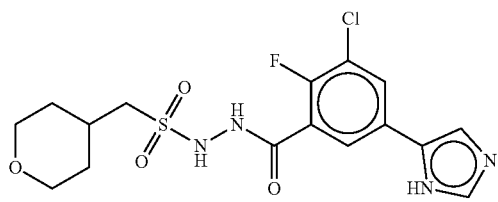 |
| I-19 | 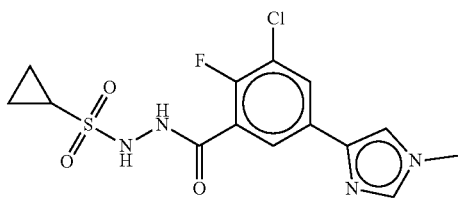 |

-continued
| Cmpd No | Compound Structure |
|---|---|
| I-20 | 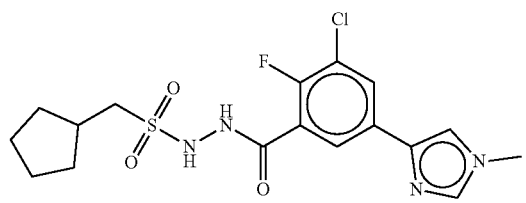 |
| I-26 | 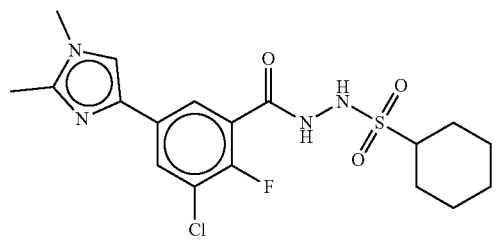 |
| I-27 | 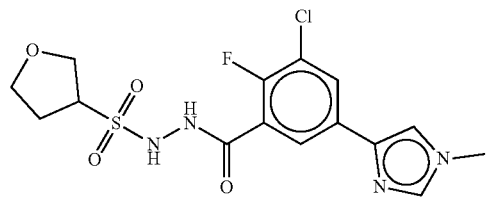 |
| I-28 | 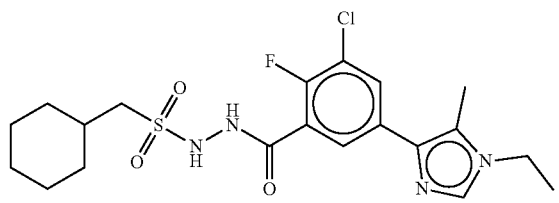 |
| I-24 | 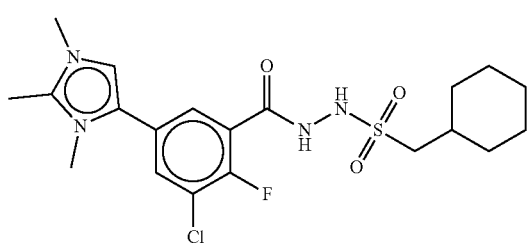 |
| I-25 | 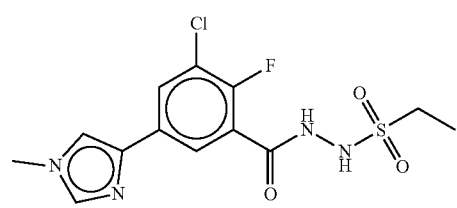 |
| I-31 | 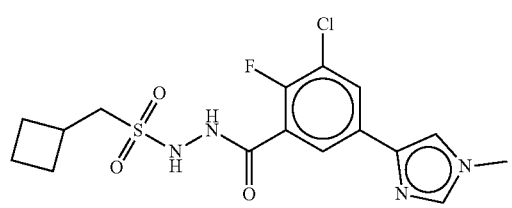 |

-continued

| Cmpd No | Compound Structure |
|---|---|
| I-32 | (structure) |
| I-33 | (structure) |
| I-29 | (structure) |
| I-30 | (structure) |
| I-36 | (structure) |
| I-37 | (structure) |
| I-38 | (structure) |

-continued
| Cmpd No | Compound Structure |
|---|---|
| I-34 | 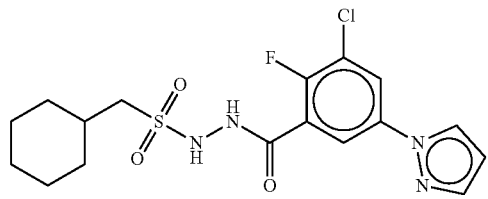 |
| I-35 | 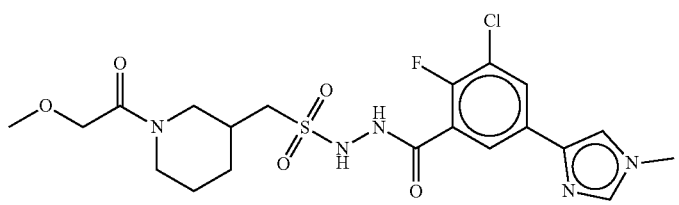 |
| I-41 | 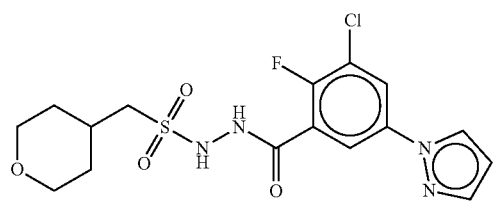 |
| I-42 | 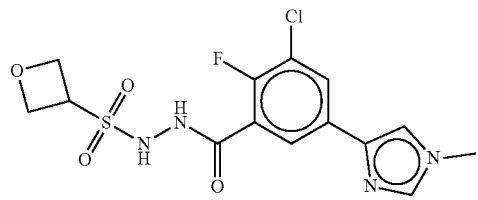 |
| I-43 | 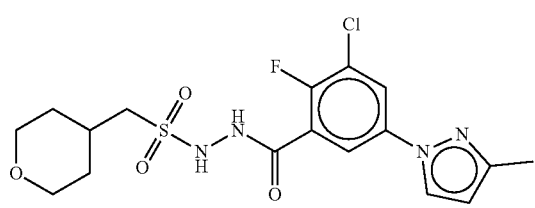 |
| I-39 | 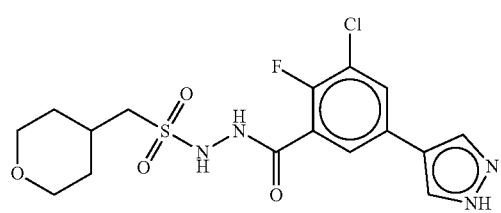 |
| I-40 | 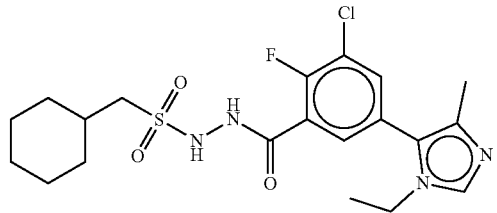 |

| Cmpd No | Compound Structure |
|---|---|
| I-46 | 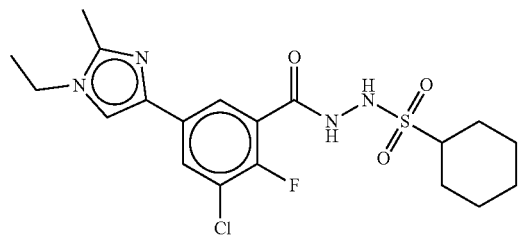 |
| I-47 | 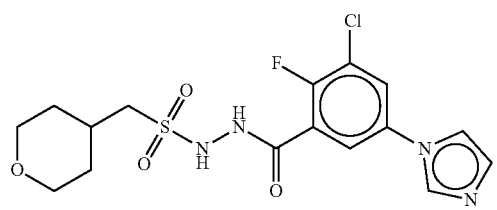 |
| I-48 | 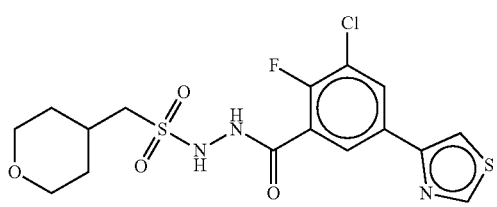 |
| I-44 | 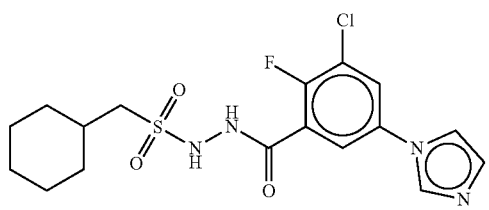 |
| I-45 | 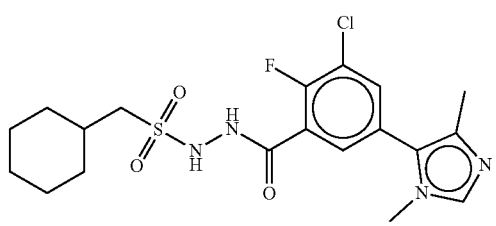 |
| I-51 | 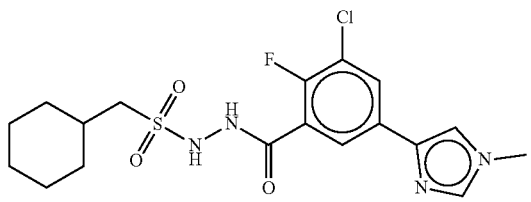 |
| I-52 | 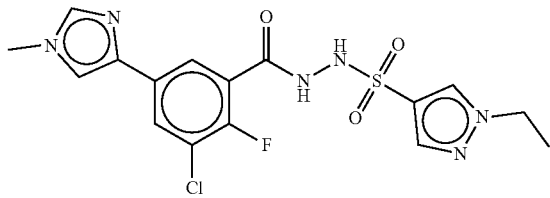 |

| Cmpd No | Compound Structure |
|---|---|
| I-53 | 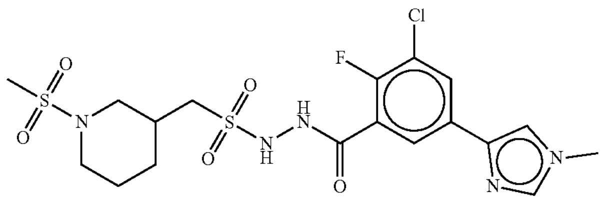 |
| I-49 | 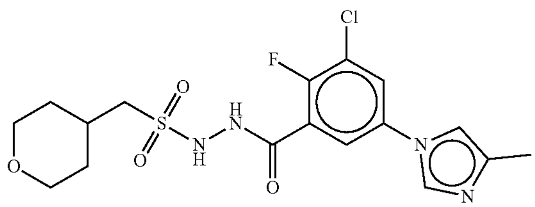 |
| I-50 | 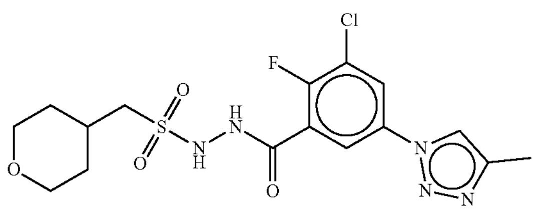 |
| I-56 | 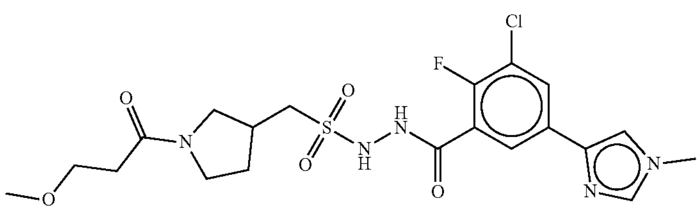 |
| I-57 | 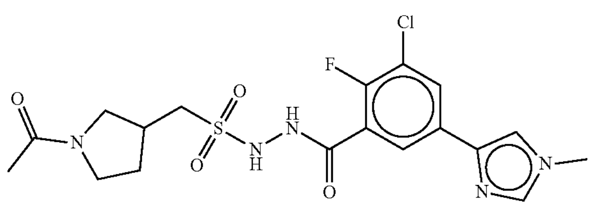 |
| I-58 | 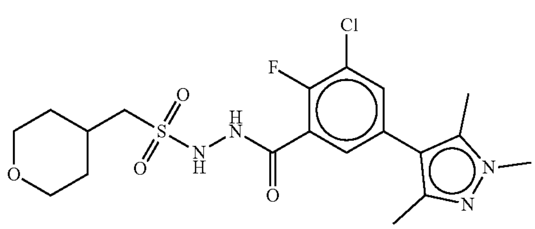 |
| I-54 | 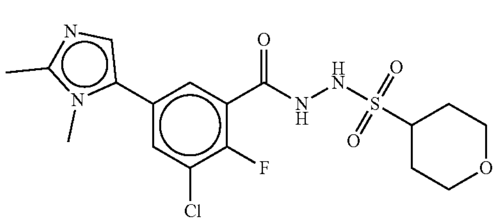 |

-continued
| Cmpd No | Compound Structure |
|---|---|
| I-55 | 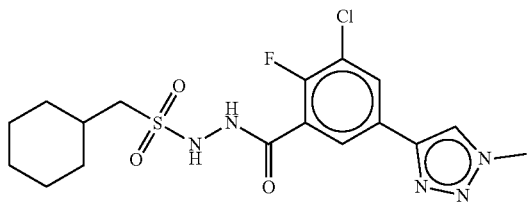 |
| I-61 | 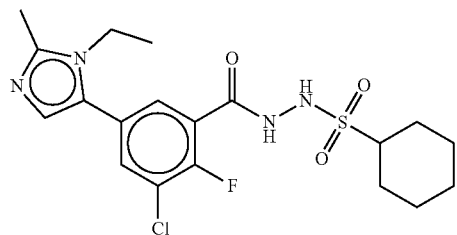 |
| I-62 | 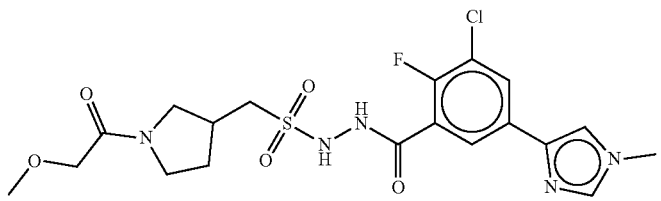 |
| I-63 | 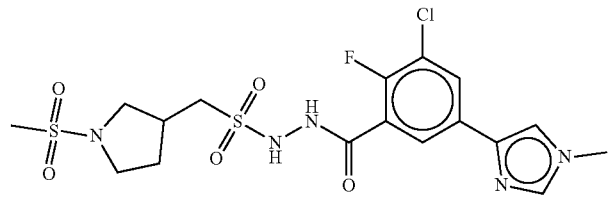 |
| I-59 | 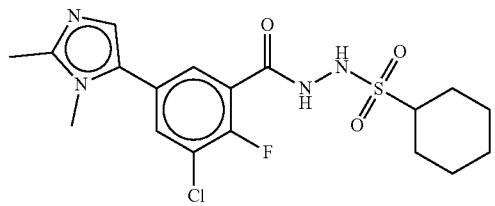 |
| I-60 | 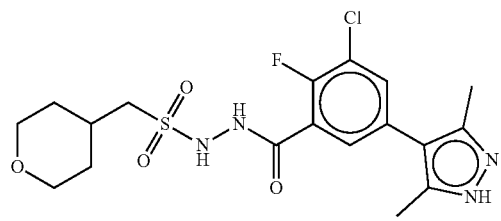 |
| I-66 | 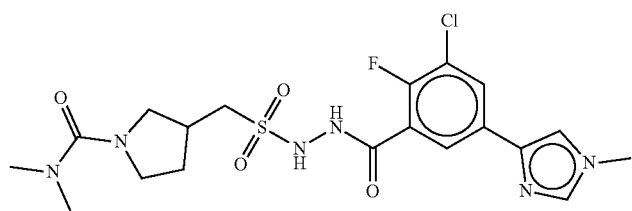 |

| Cmpd No | Compound Structure |
|---|---|
| I-67 | 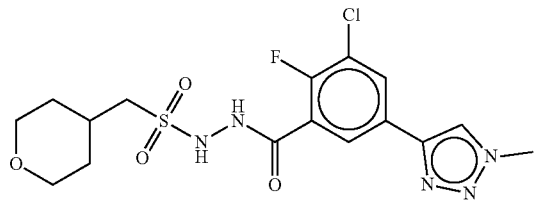 |
| I-68 | 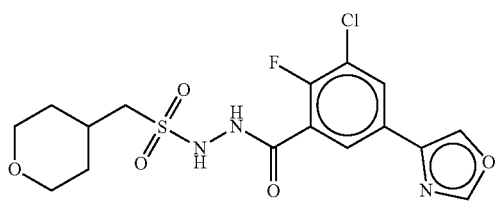 |
| I-64 | 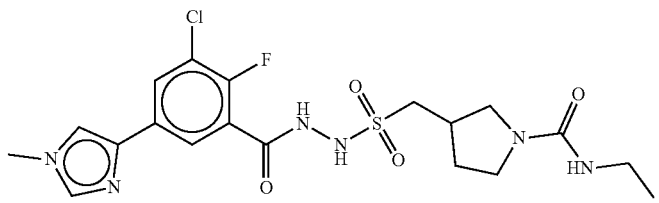 |
| I-65 | 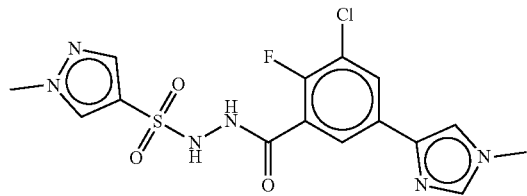 |
| I-71 | 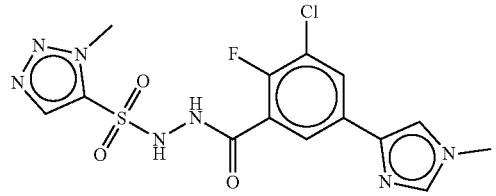 |
| I-72 | 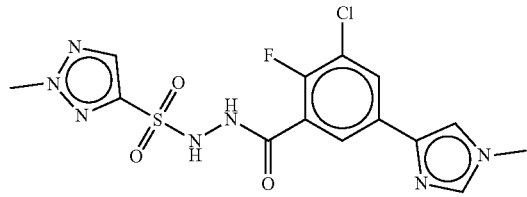 |
| I-73 | 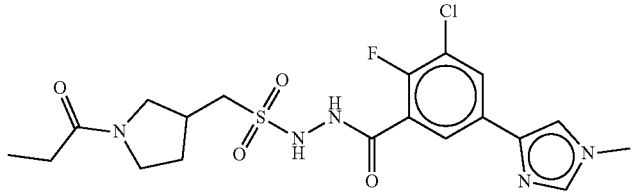 |

| Cmpd No | Compound Structure |
|---|---|
| I-69 | 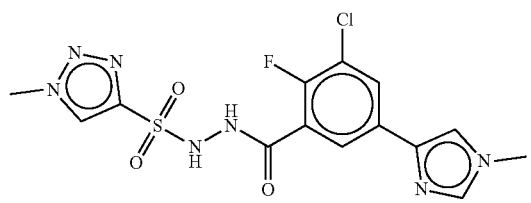 |
| I-70 | 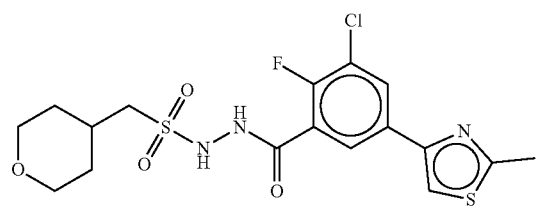 |
| I-76 | 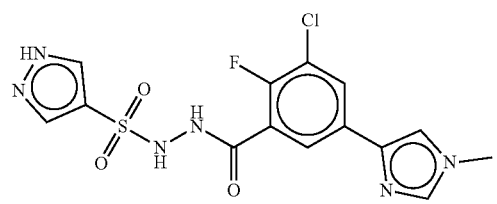 |
| I-77 | 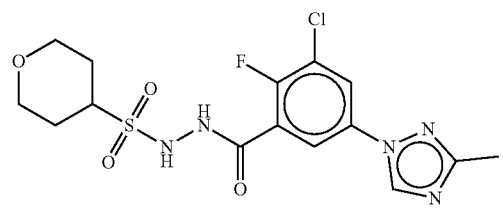 |
| I-78 | 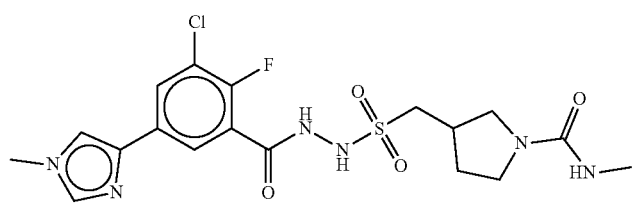 |
| I-74 | 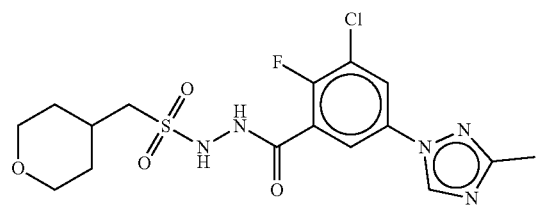 |
| I-75 | 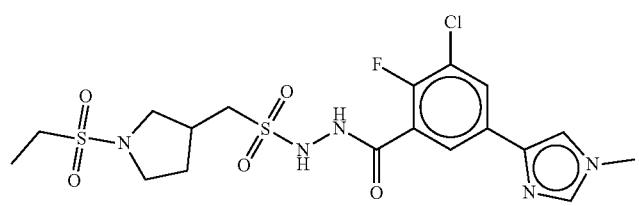 |

-continued

| Cmpd No | Compound Structure |
|---|---|
| I-81 | 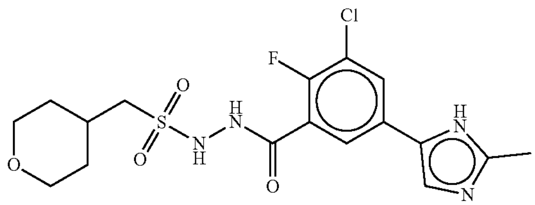 |
| I-82 | 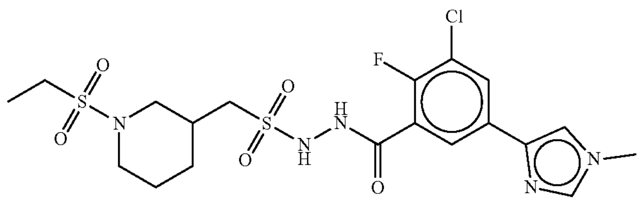 |
| I-83 | 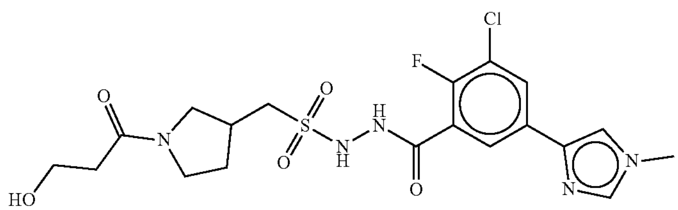 |
| I-79 | 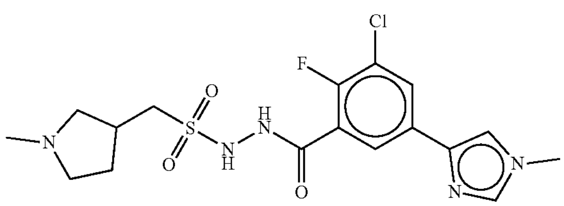 |
| I-80 | 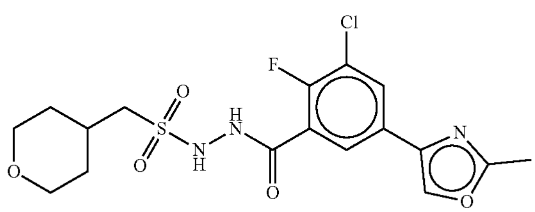 |
| I-86 | 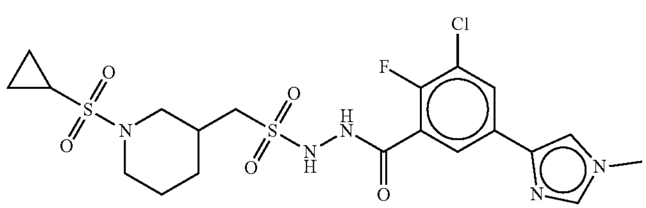 |
| I-87 | 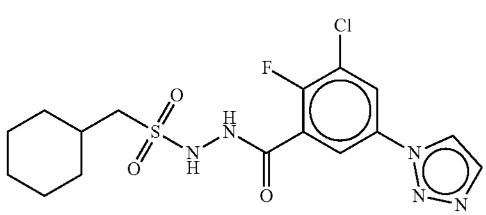 |

| Cmpd No | Compound Structure |
|---|---|
| I-88 | 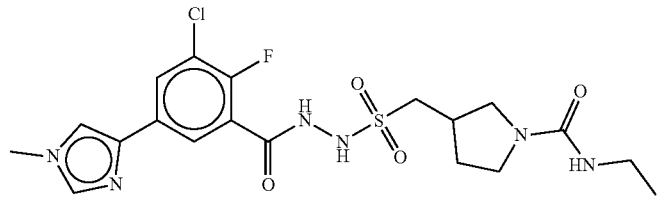 |
| I-84 | 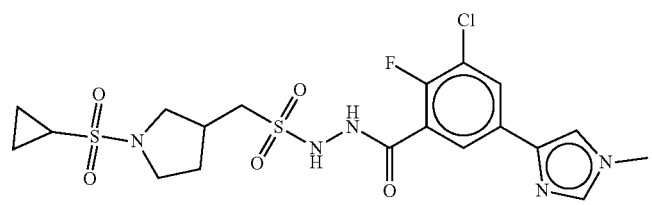 |
| I-85 | 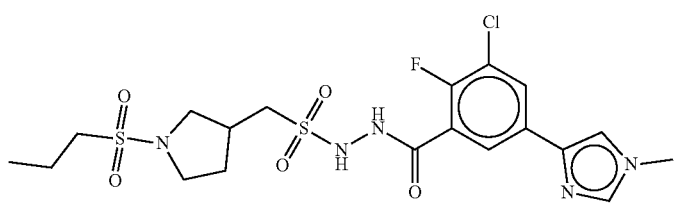 |
| I-91 | 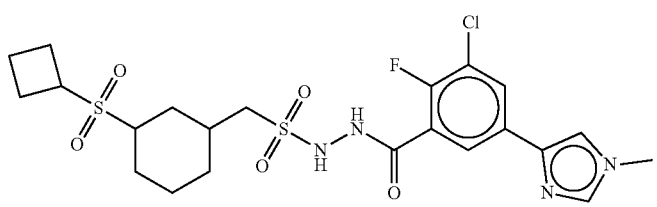 |
| I-92 | 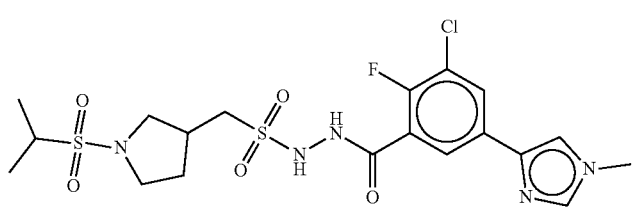 |
| I-93 | 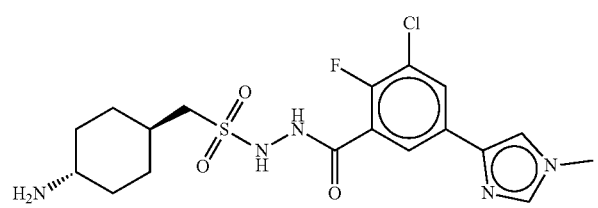 |
| I-89 | 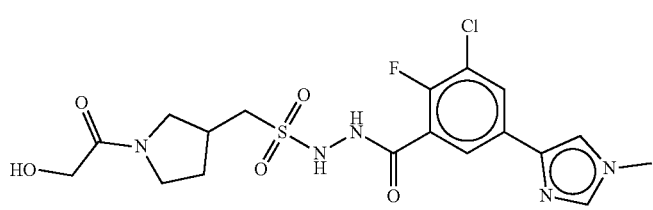 |

-continued
| Cmpd No | Compound Structure |
|---|---|
| I-90 | 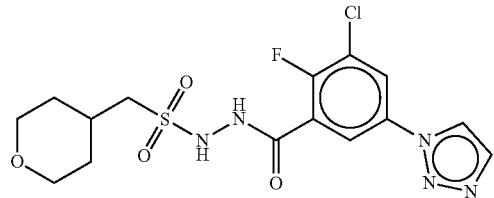 |
| I-96 | 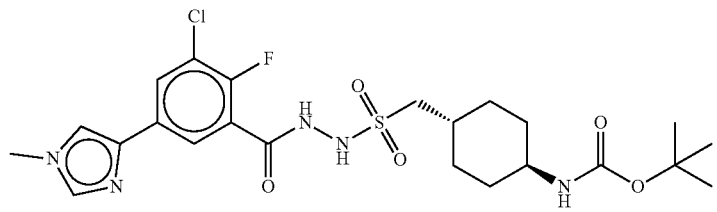 |
| I-97 | 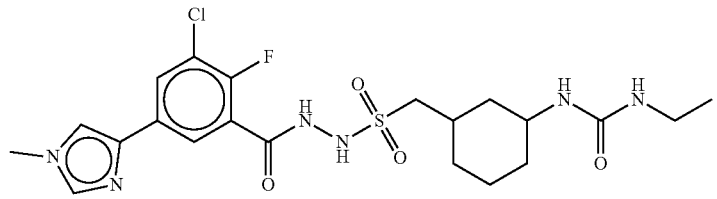 |
| I-98 | 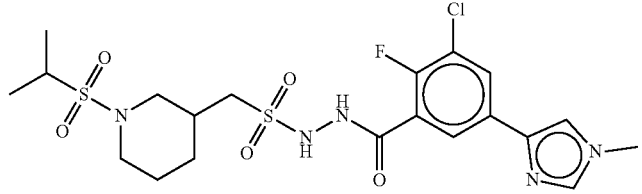 |
| I-94 | 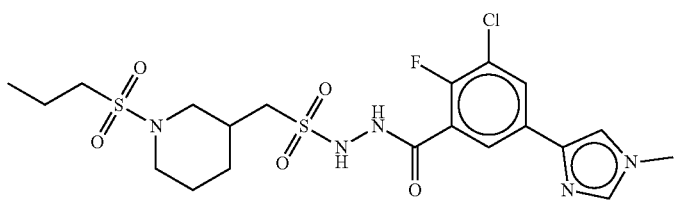 |
| I-95 | 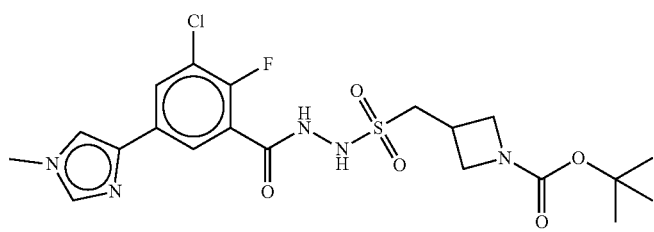 |
| I-101 | 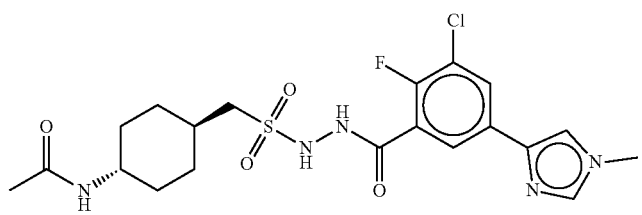 |

-continued
| Cmpd No | Compound Structure |
|---|---|
| I-102 | 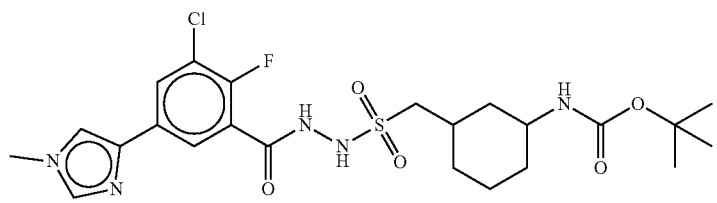 |
| I-103 | 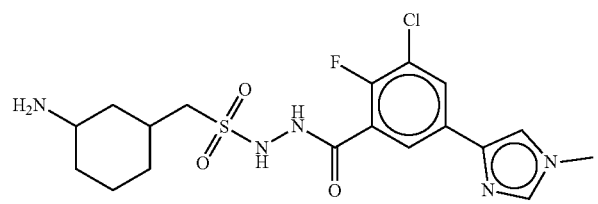 |
| I-99 | 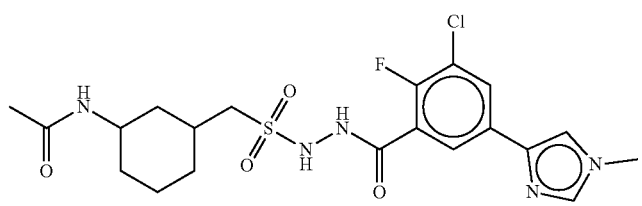 |
| I-100 | 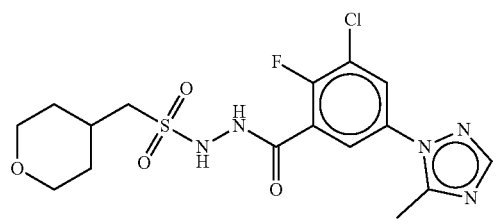 |
| I-106 | 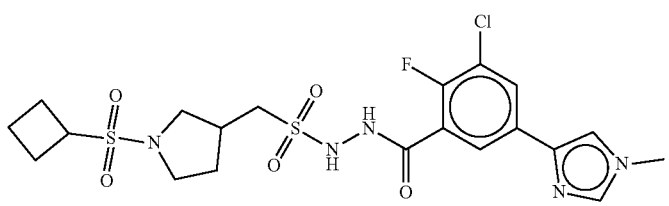 |
| I-107 | 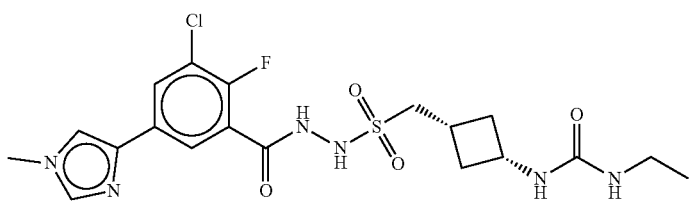 |
| I-108 | 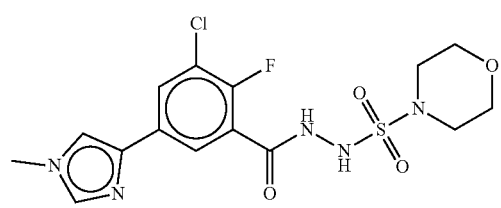 |

-continued
| Cmpd No | Compound Structure |
|---|---|
| I-104 | 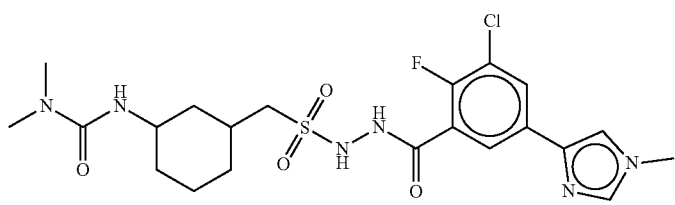 |
| I-105 | 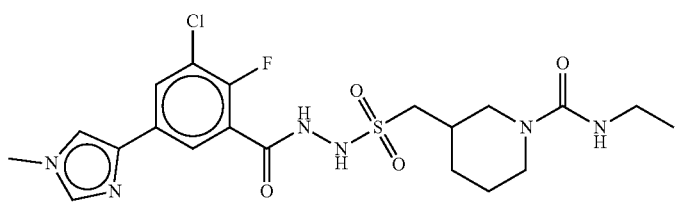 |
| I-111 | 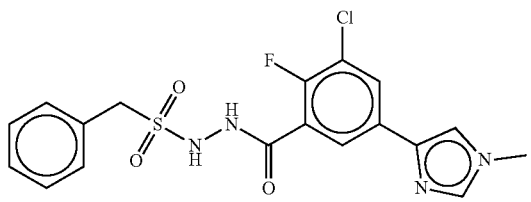 |
| I-112 | 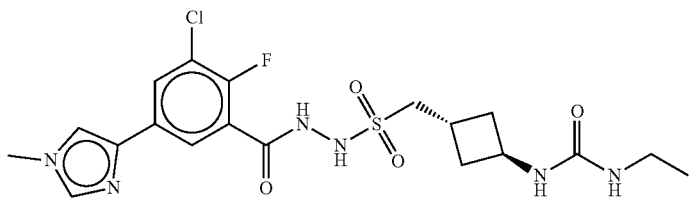 |
| I-113 | 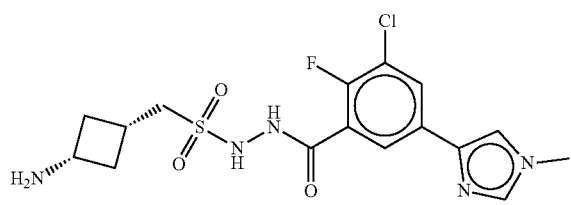 |
| I-109 | 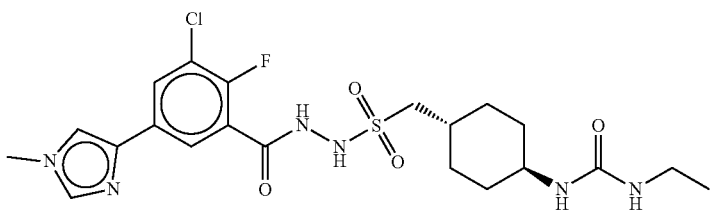 |
| I-110 | 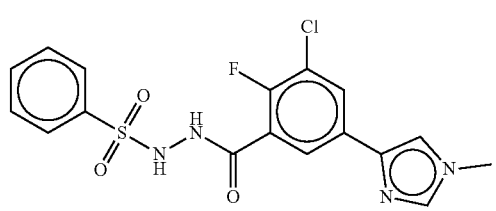 |

| Cmpd No | Compound Structure |
|---|---|
| I-116 | 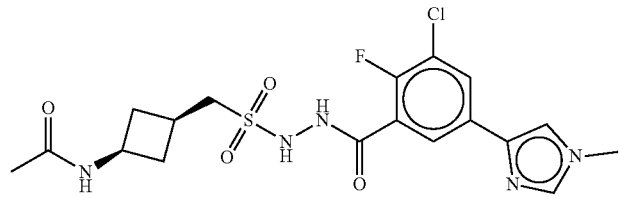 |
| I-117 | 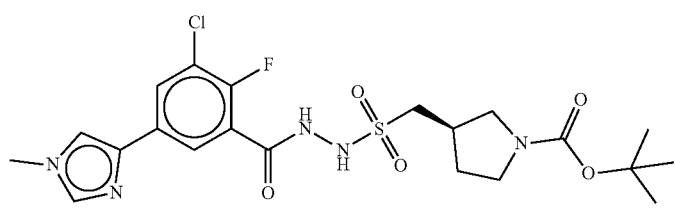 |
| I-118 | 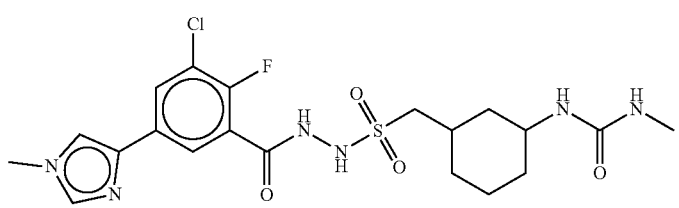 |
| I-114 | 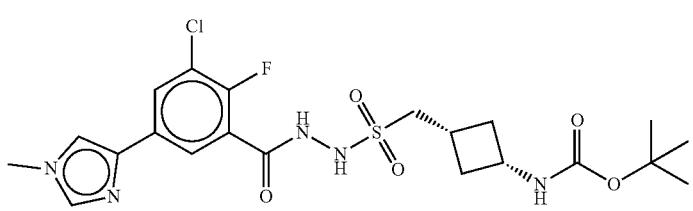 |
| I-115 | 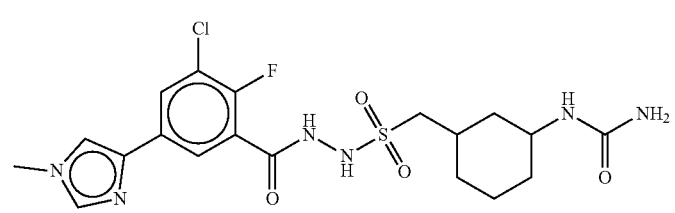 |
| I-121 | 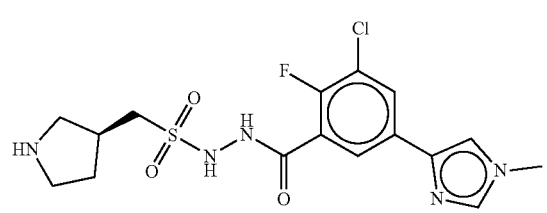 |
| I-122 | 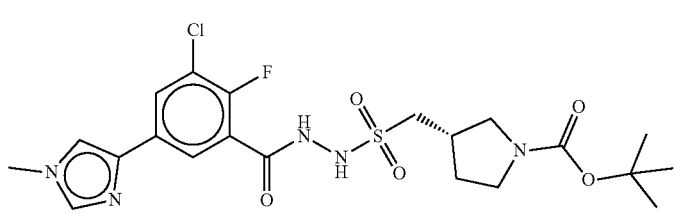 |

| Cmpd No | Compound Structure |
|---|---|
| I-123 | 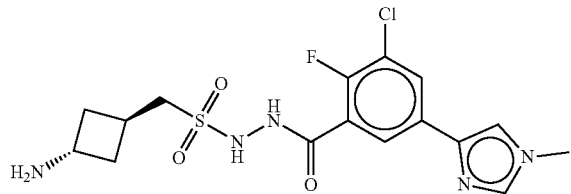 |
| I-119 | 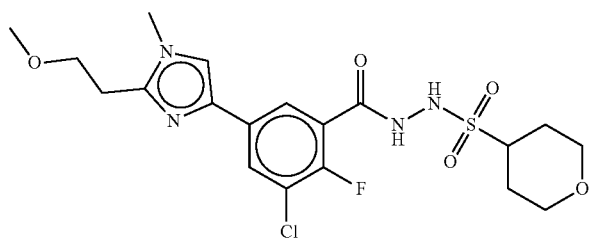 |
| I-120 | 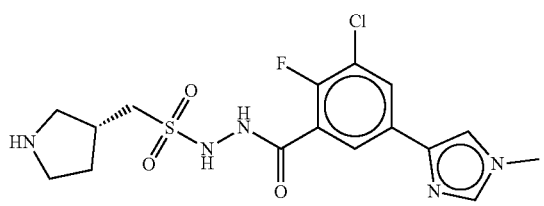 |
| I-126 | 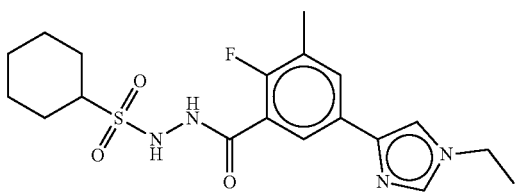 |
| I-127 | 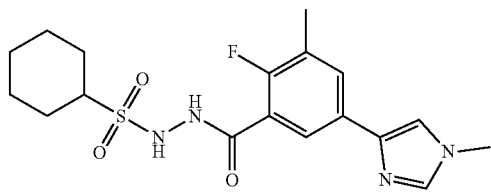 |
| I-128 | 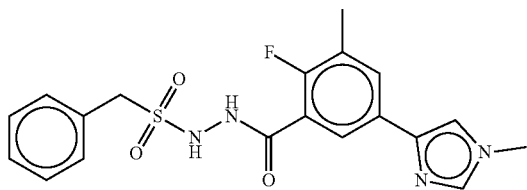 |
| I-124 | 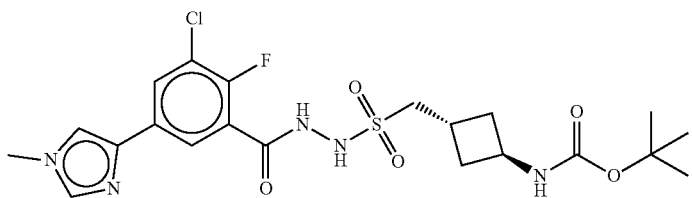 |

| Cmpd No | Compound Structure |
|---|---|
| I-125 | 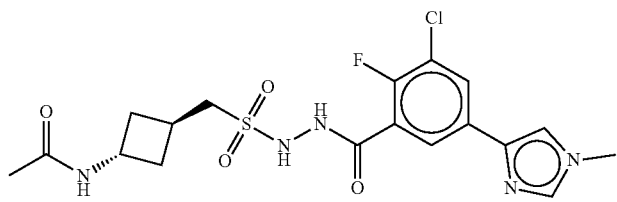 |
| I-131 | 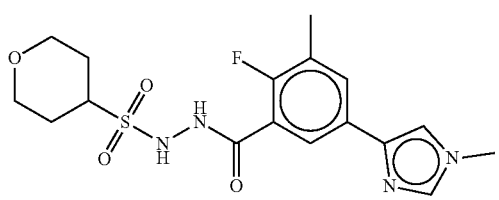 |
| I-132 | 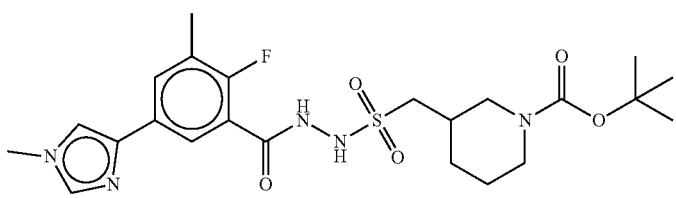 |
| I-133 | 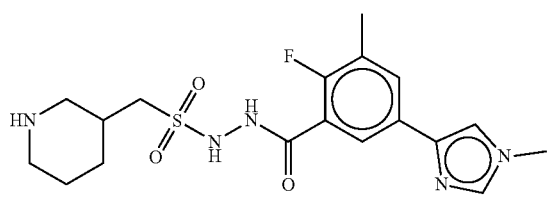 |
| I-129 | 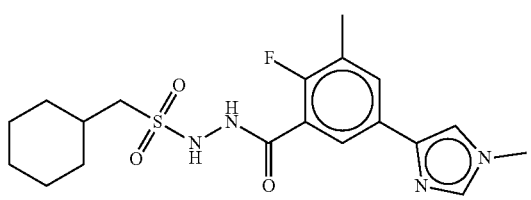 |
| I-130 | 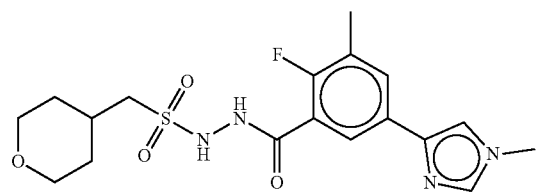 |
| I-136 | 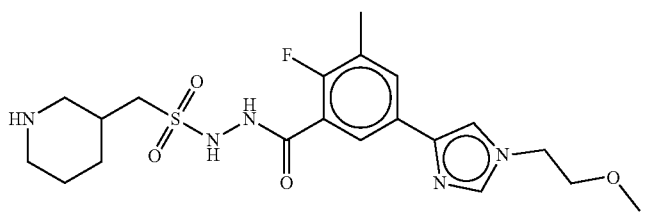 |

| Cmpd No | Compound Structure |
|---|---|
| I-137 | 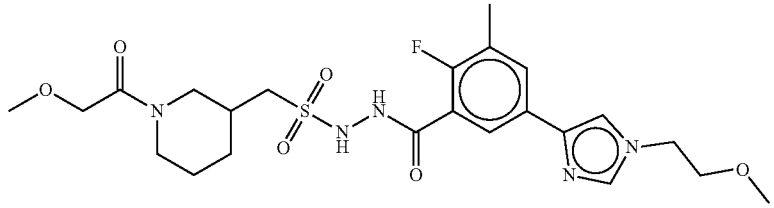 |
| I-138 | 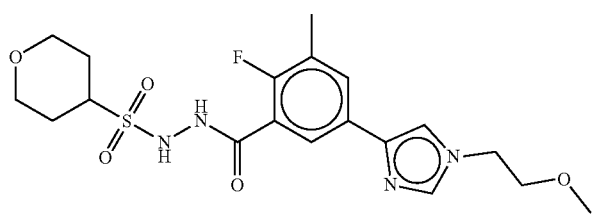 |
| I-134 | 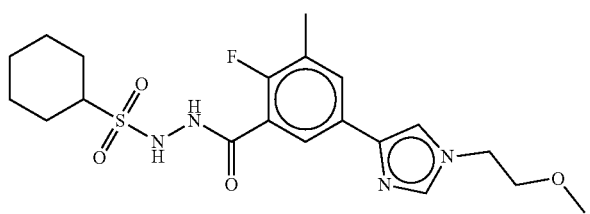 |
| I-135 | 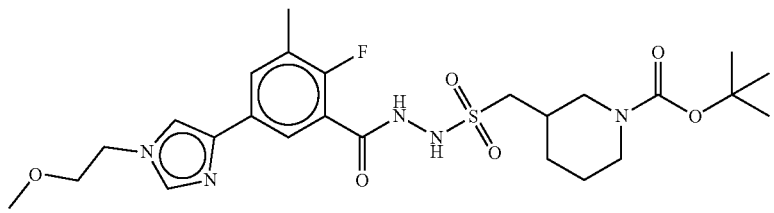 |
| I-141 | 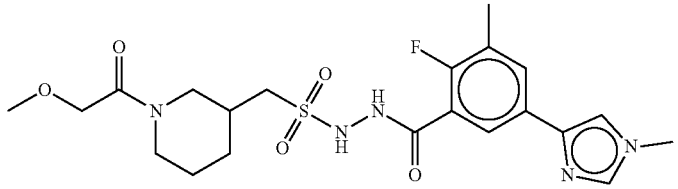 |
| I-142 | 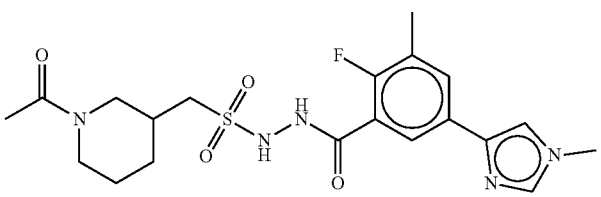 |
| I-143 | 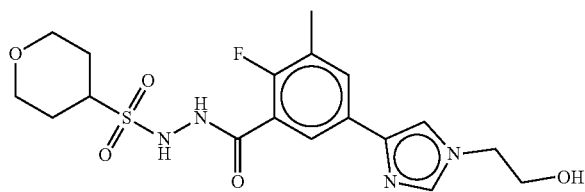 |

-continued
| Cmpd No | Compound Structure |
|---|---|
| I-139 | 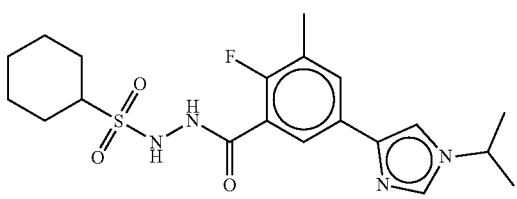 |
| I-140 | 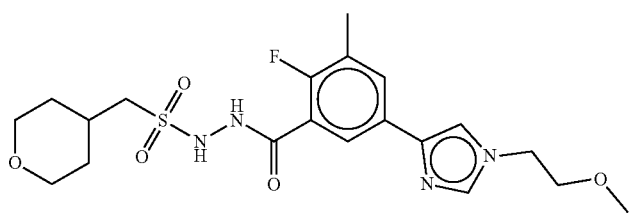 |
| I-146 | 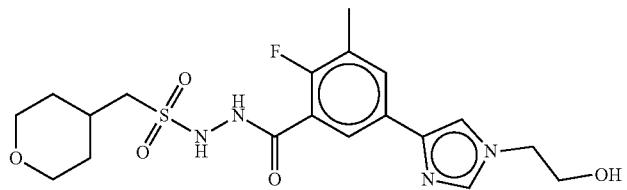 |
| I-147 | 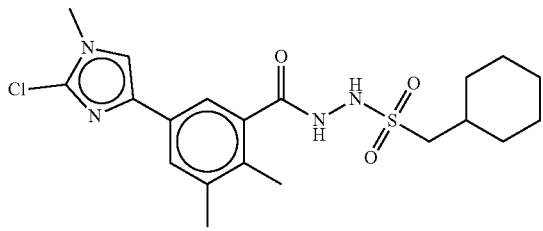 |
| I-148 | 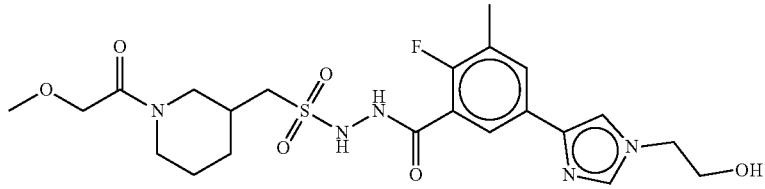 |
| I-144 | 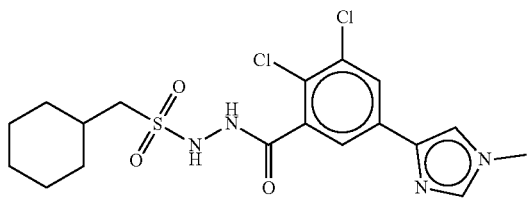 |
| I-145 | 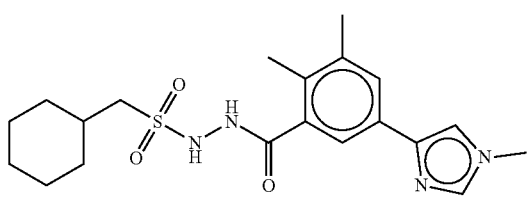 |

| Cmpd No | Compound Structure |
|---|---|
| I-151 | 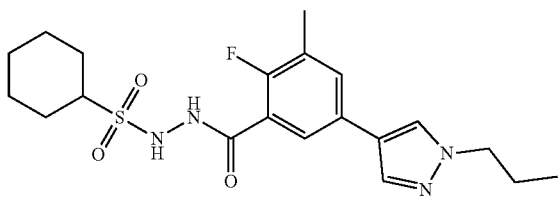 |
| I-152 | 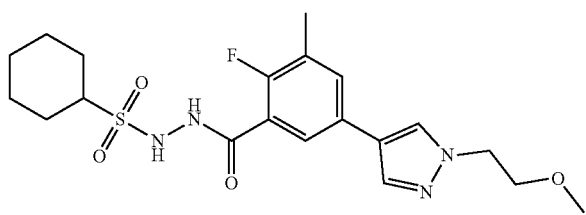 |
| I-153 | 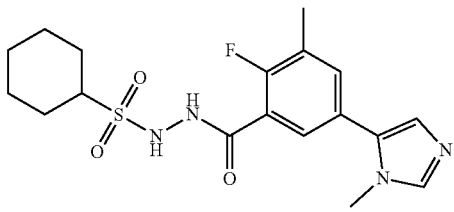 |
| I-149 | 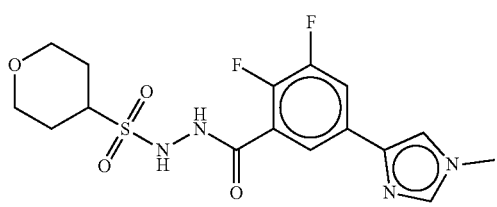 |
| I-150 | 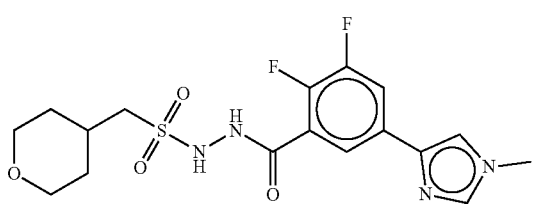 |
| I-156 | 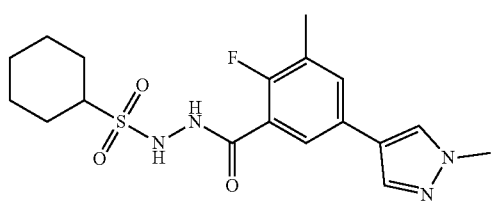 |
| I-157 | 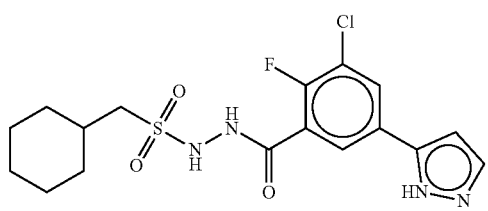 |

| Cmpd No | Compound Structure |
|---|---|
| I-158 | 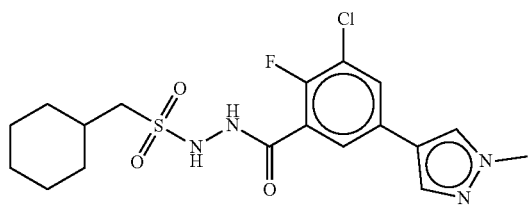 |
| I-154 | 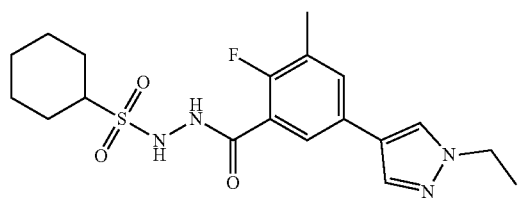 |
| I-155 | 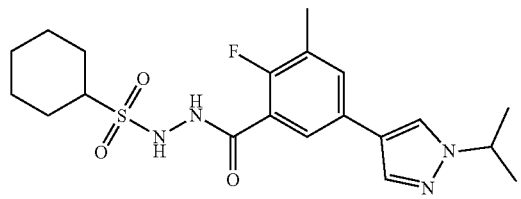 |
| I-161 | 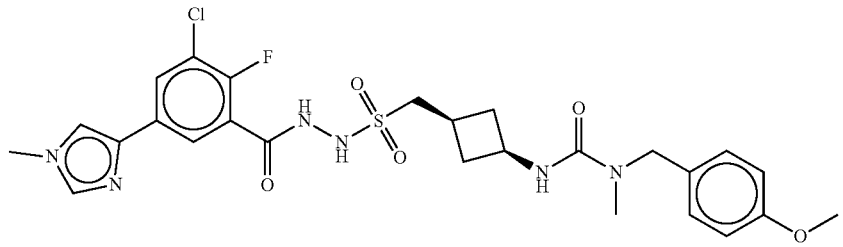 |
| I-162 | 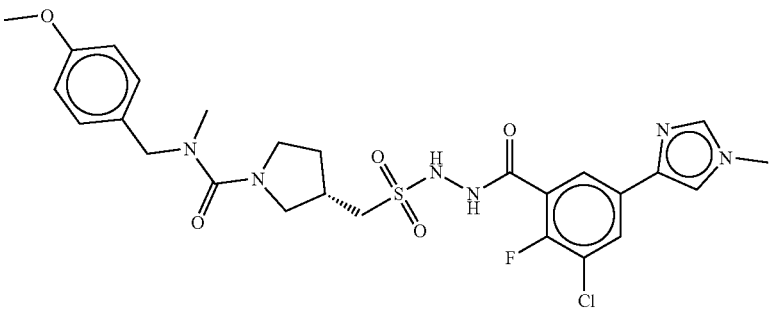 |
| I-163 | 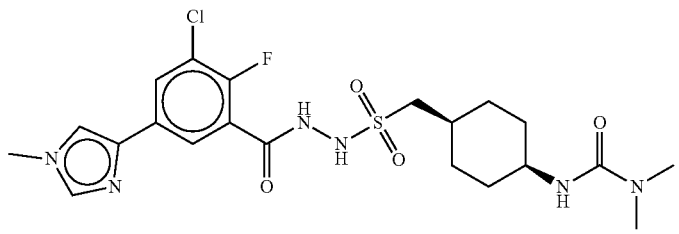 |

-continued
| Cmpd No | Compound Structure |
|---|---|
| I-159 | 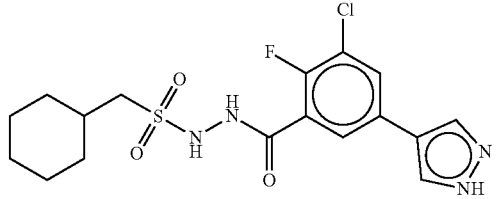 |
| I-160 | 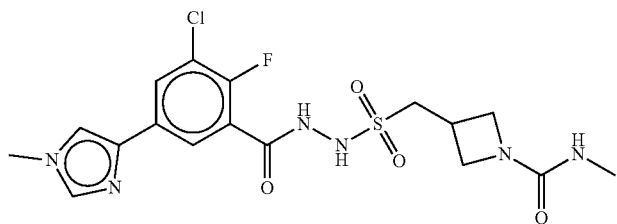 |
| I-166 | 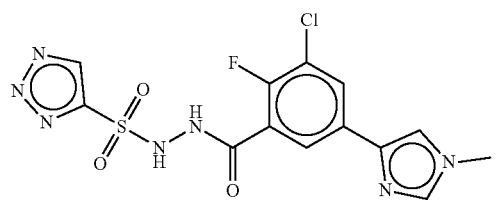 |
| I-167 | 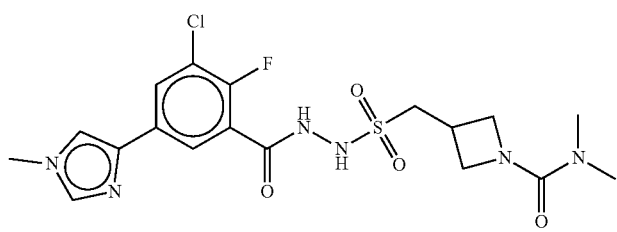 |
| I-168 | 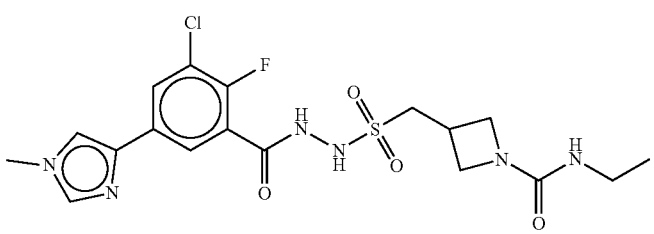 |
| I-164 | 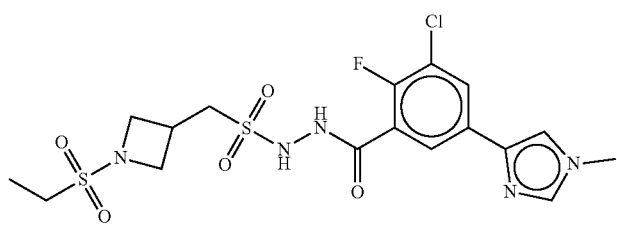 |
| I-165 | 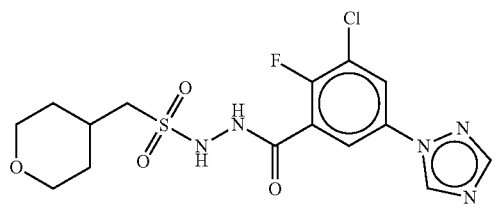 |

| Cmpd No | Compound Structure |
|---|---|
| I-171 | 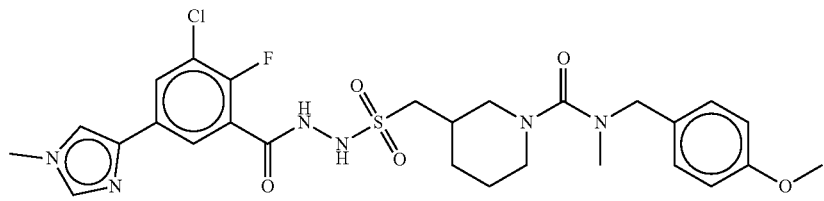 |
| I-172 | 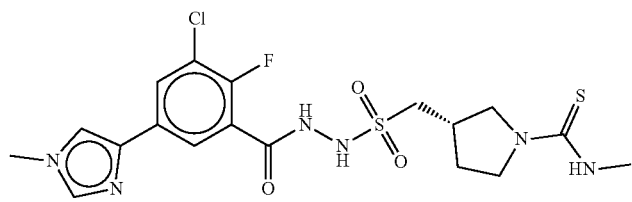 |
| I-173 | 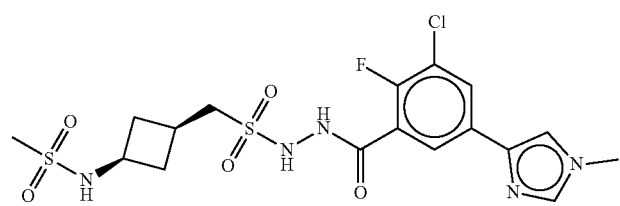 |
| I-169 | 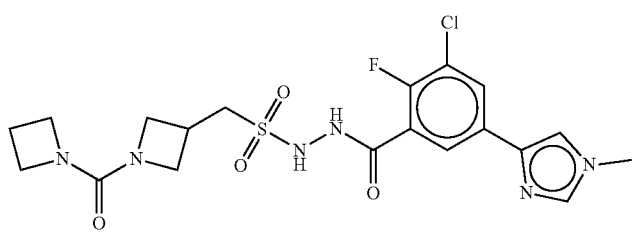 |
| I-170 | 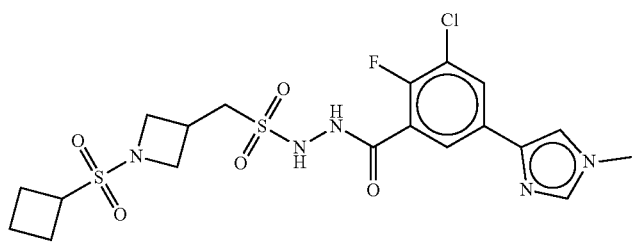 |
| I-176 | 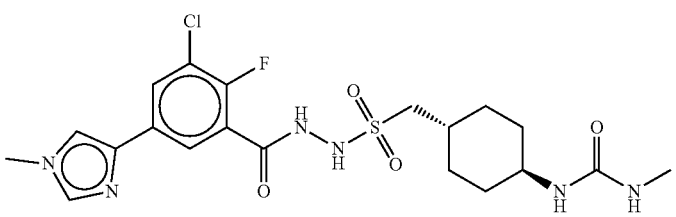 |
| I-177 | 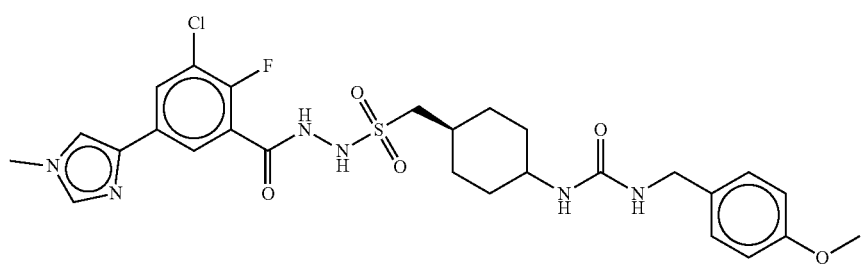 |

| Cmpd No | Compound Structure |
|---|---|
| I-178 | 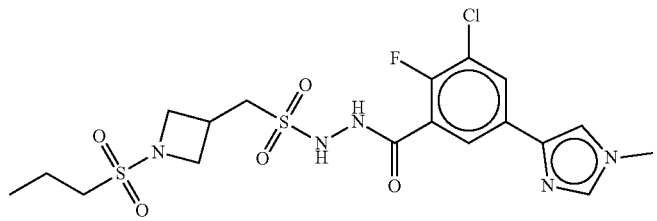 |
| I-174 | 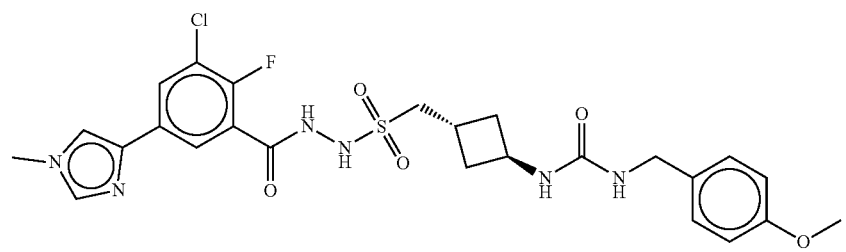 |
| I-175 | 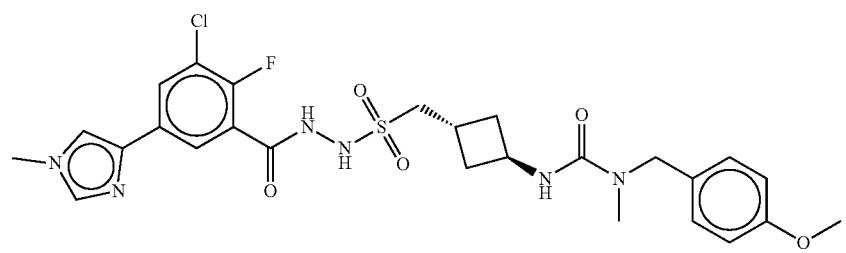 |
| I-181 | 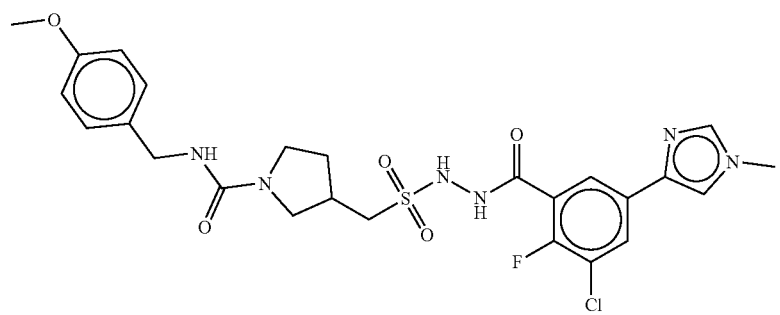 |
| I-182 | 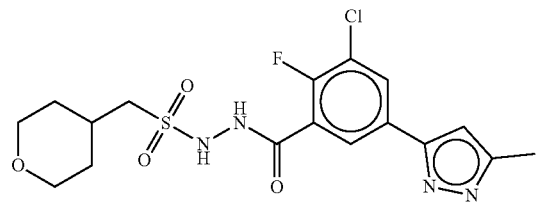 |
| I-183 | 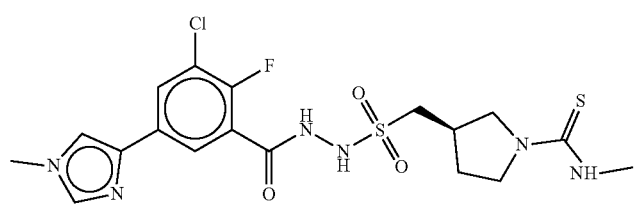 |

| Cmpd No | Compound Structure |
|---|---|
| I-179 | 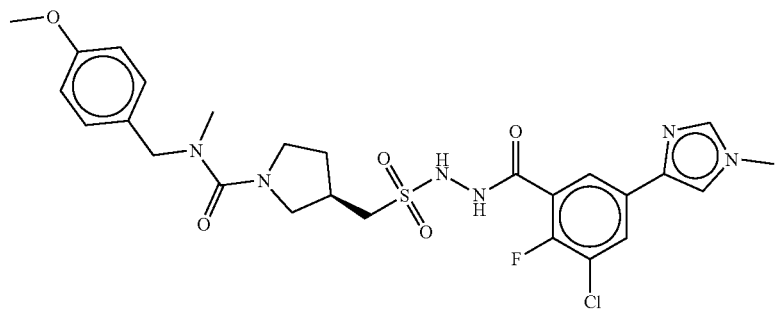 |
| I-180 | 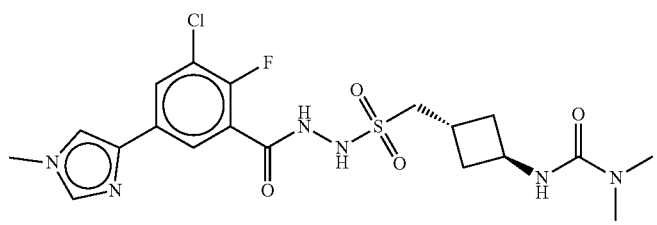 |
| I-186 | 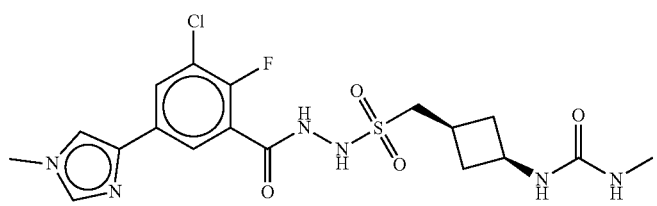 |
| I-187 | 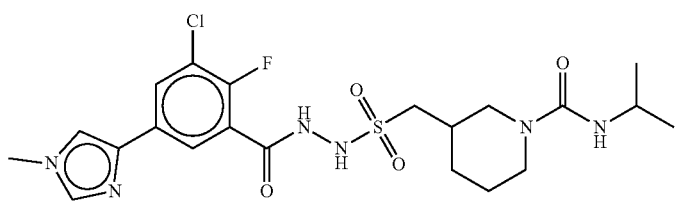 |
| I-188 | 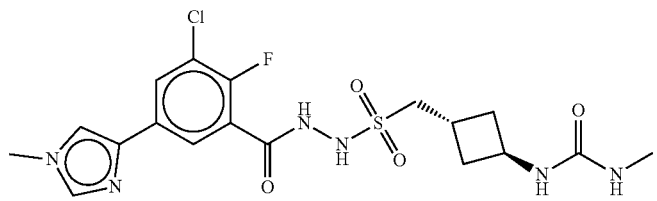 |
| I-184 | 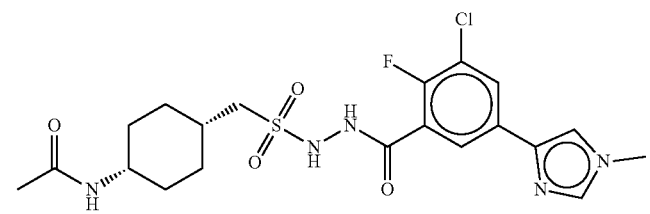 |

-continued
| Cmpd No | Compound Structure |
|---|---|
| I-185 | 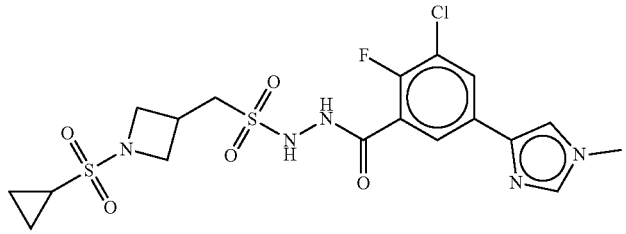 |
| I-191 | 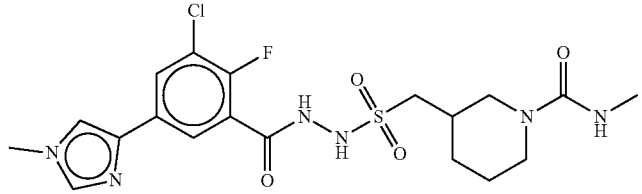 |
| I-192 | 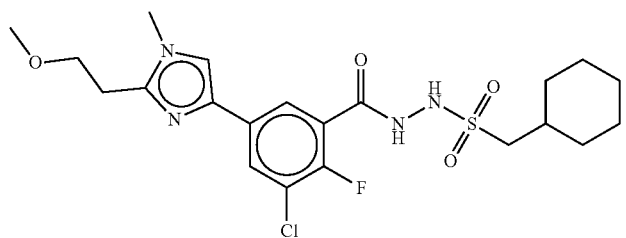 |
| I-193 | 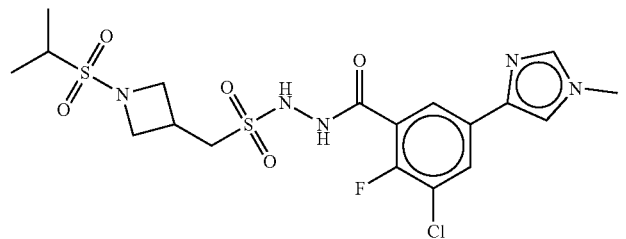 |
| I-189 | 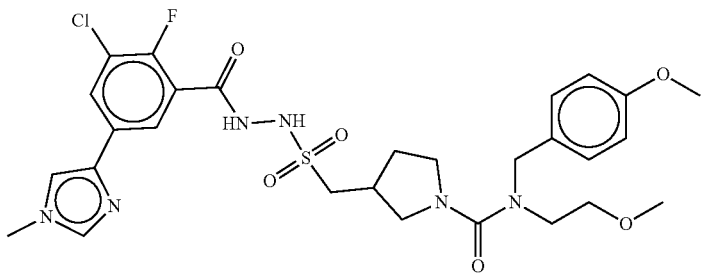 |
| I-190 | 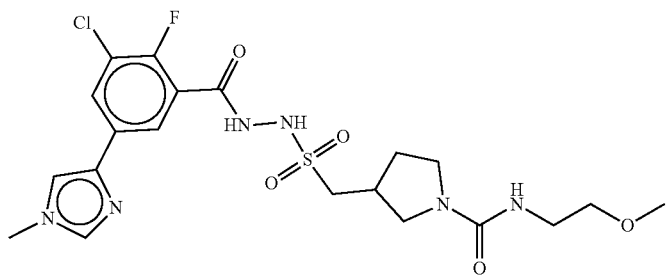 |

-continued
| Cmpd No | Compound Structure |
|---|---|
| I-196 | 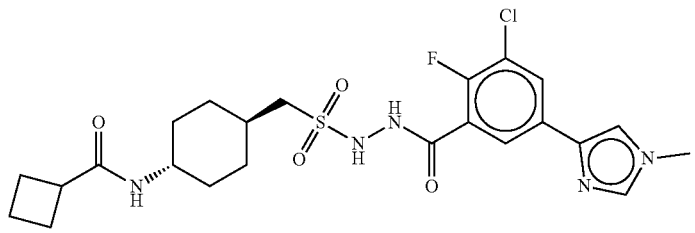 |
| I-197 | 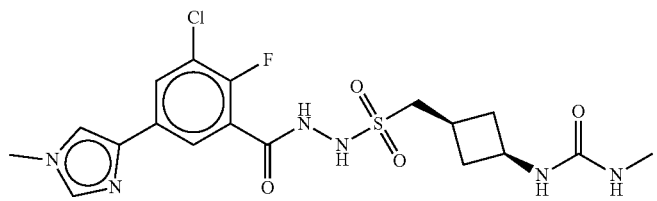 |
| I-198 | 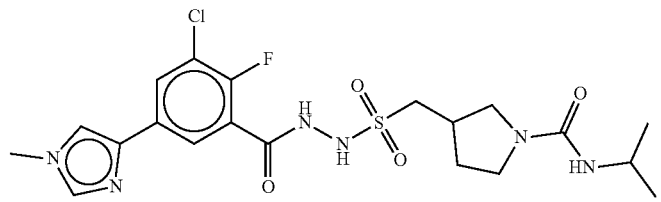 |
| I-194 | 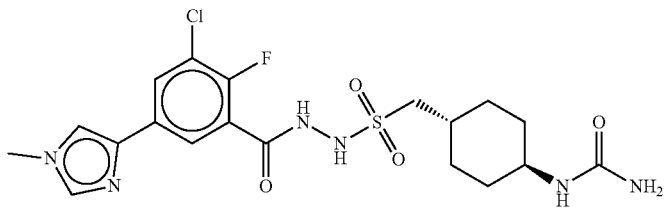 |
| I-195 | 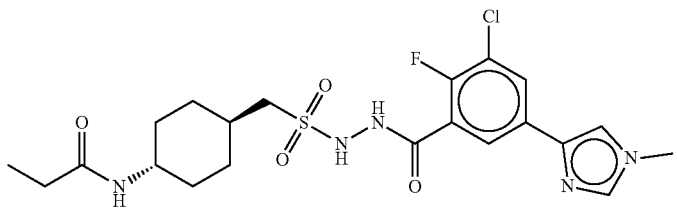 |
| I-201 | 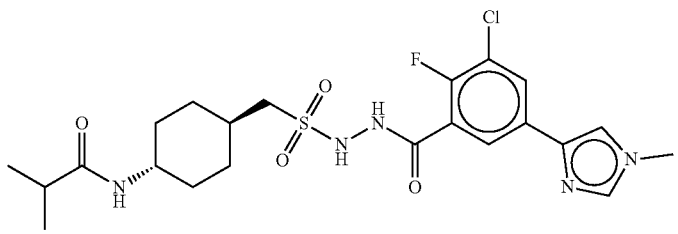 |
| I-202 | 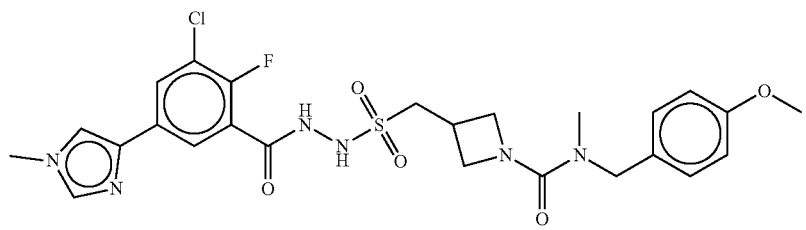 |

| Cmpd No | Compound Structure |
|---|---|
| I-203 | 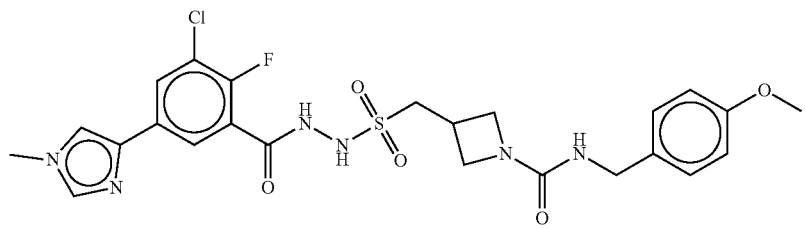 |
| I-199 | 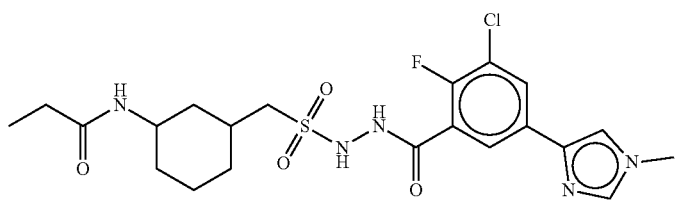 |
| I-200 | 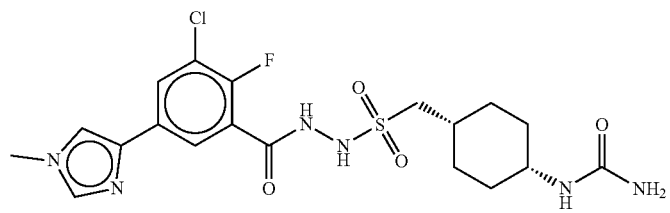 |
| I-206 | 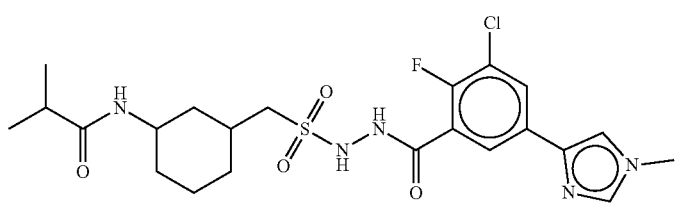 |
| I-207 | 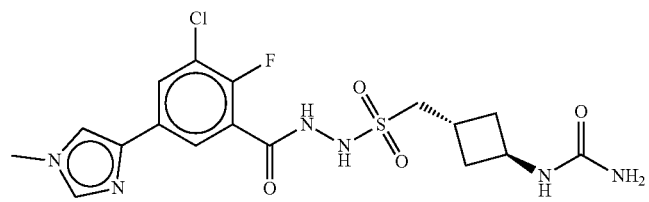 |
| I-208 | 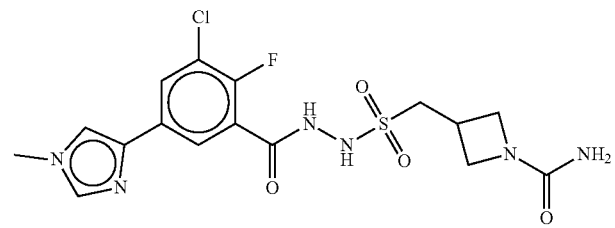 |
| I-204 | 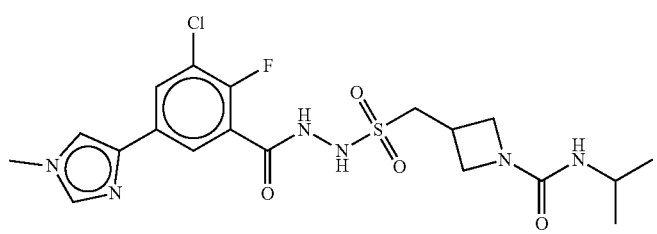 |

-continued
| Cmpd No | Compound Structure |
|---|---|
| I-205 | 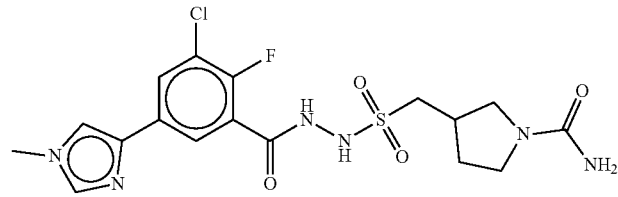 |
| I-211 | 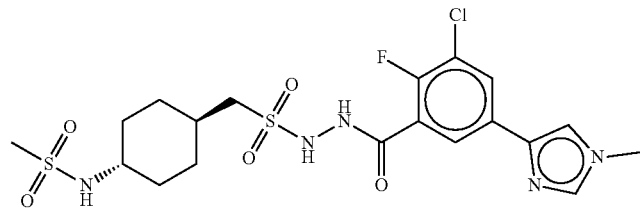 |
| I-212 | 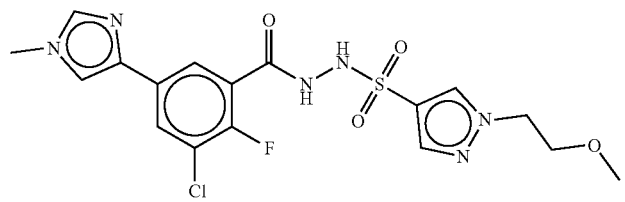 |
| I-213 | 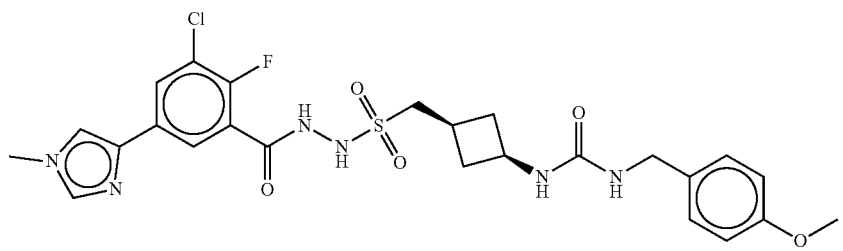 |
| I-209 | 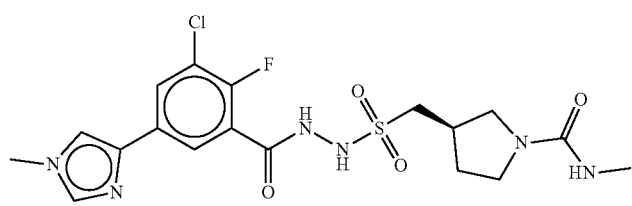 |
| I-210 | 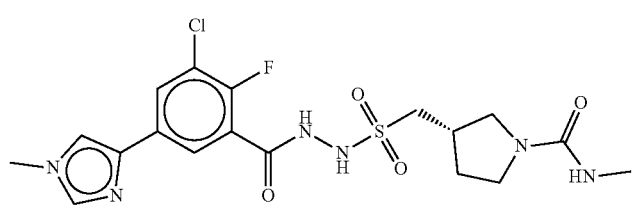 |
| I-216 | 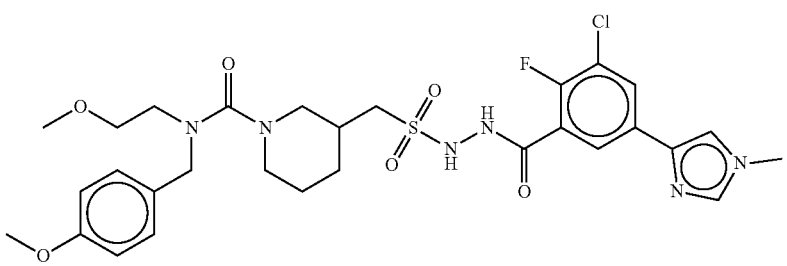 |

-continued
| Cmpd No | Compound Structure |
|---|---|
| I-217 | 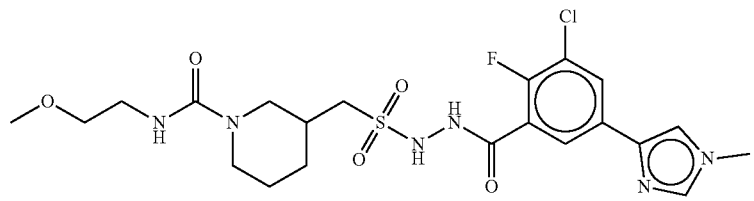 |
| I-218 | 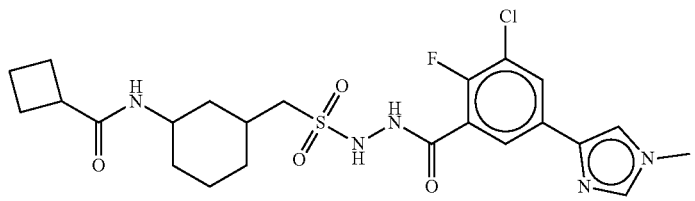 |
| I-214 | 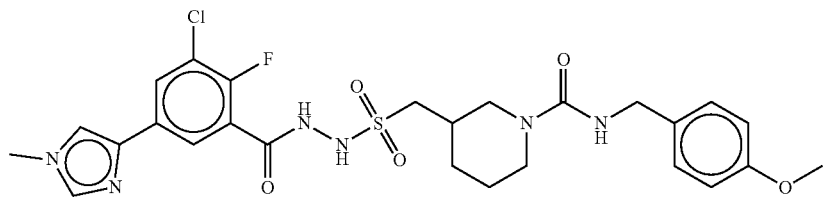 |
| I-215 | 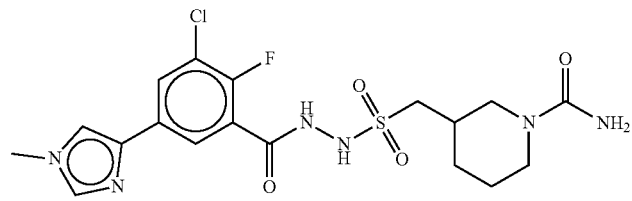 |
| I-221 | 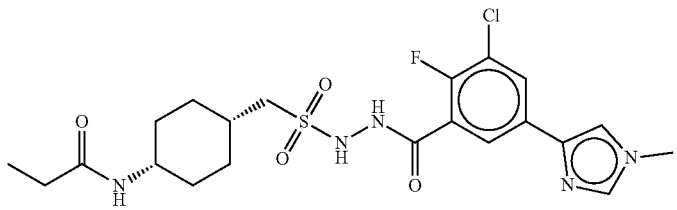 |
| I-222 | 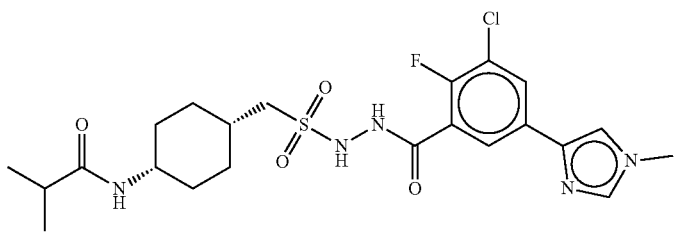 |
| I-223 | 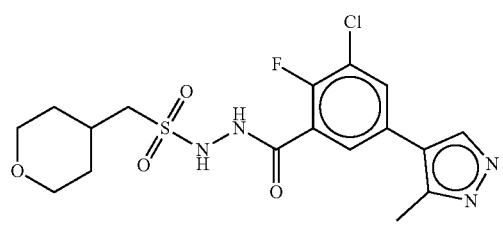 |

-continued
| Cmpd No | Compound Structure |
|---|---|
| I-219 | 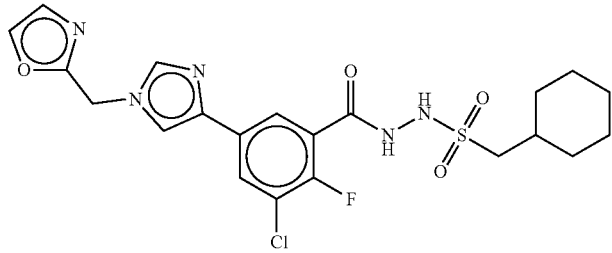 |
| I-220 | 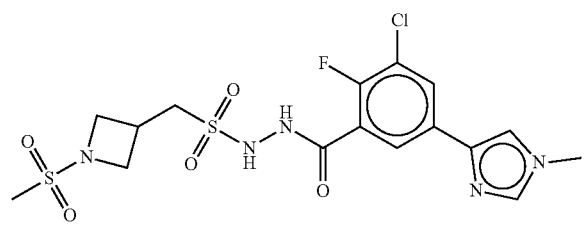 |
| I-226 | 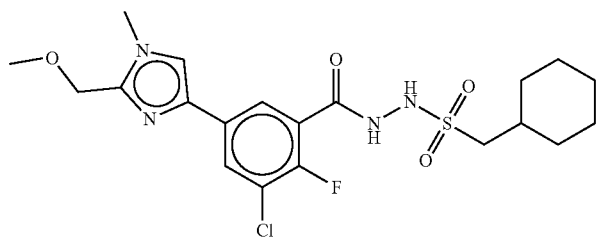 |
| I-227 | 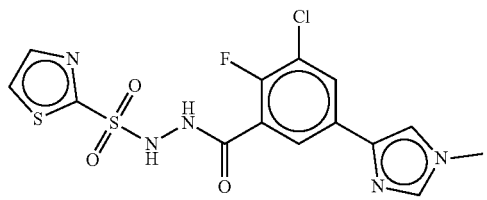 |
| I-228 | 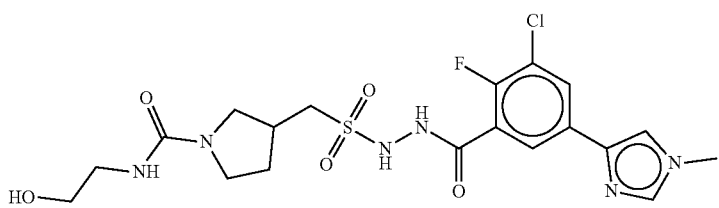 |
| I-224 | 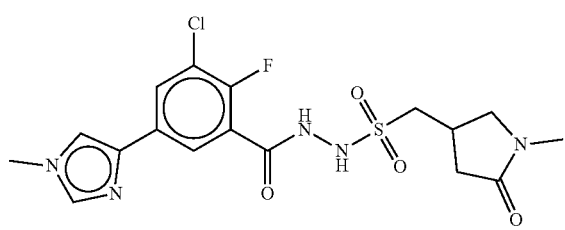 |
| I-225 | 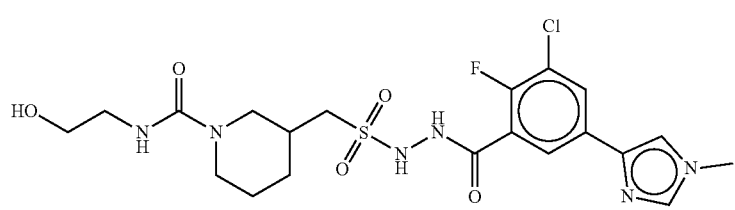 |

| Cmpd No | Compound Structure |
|---|---|
| I-231 | 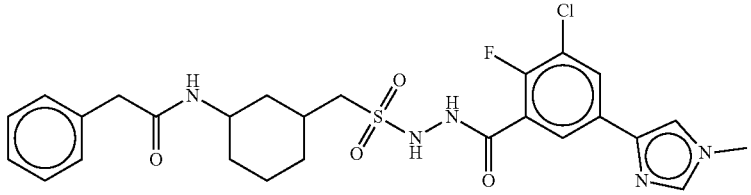 |
| I-232 | 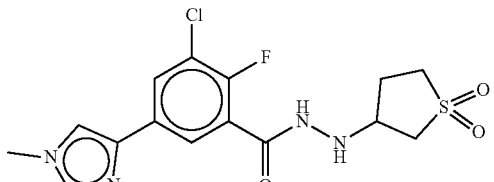 |
| I-233 | 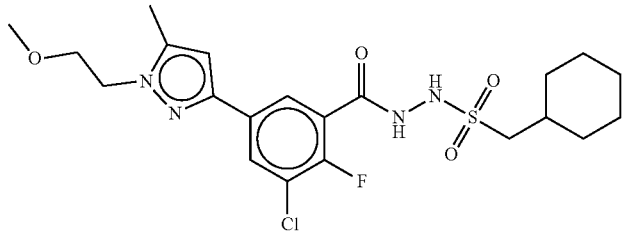 |
| I-229 | 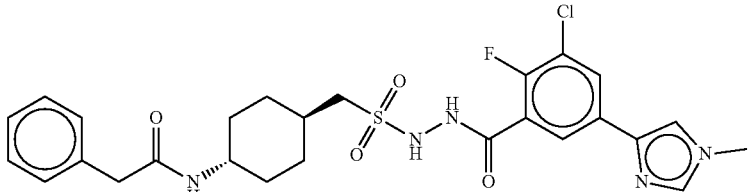 |
| I-230 | 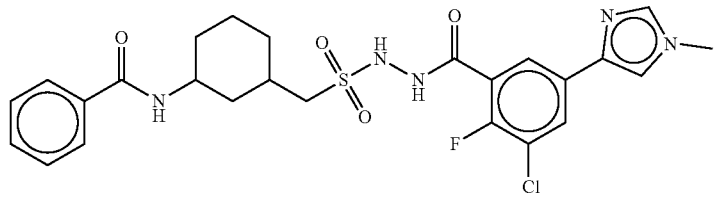 |
| I-236 | 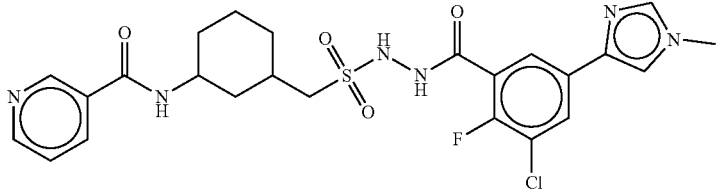 |
| I-237 | 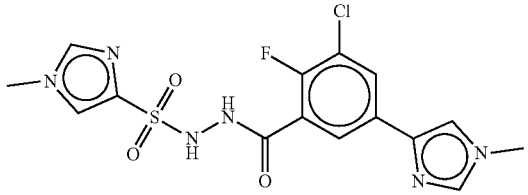 |

| Cmpd No | Compound Structure |
|---|---|
| I-238 | 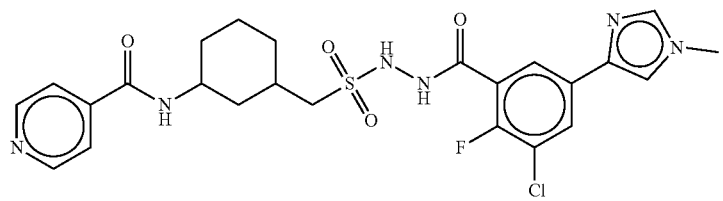 |
| I-234 | 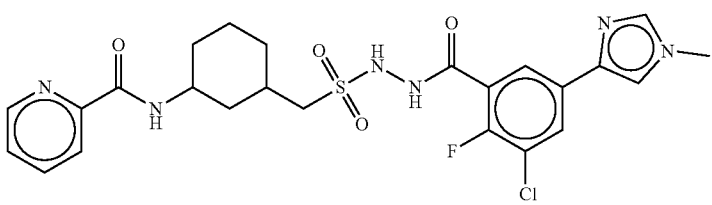 |
| I-235 | 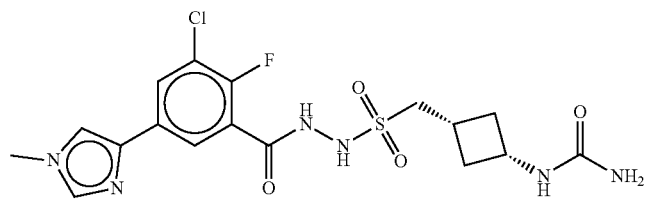 |
| I-241 | 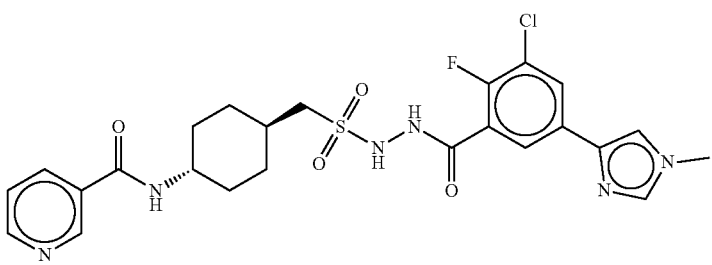 |
| I-242 | 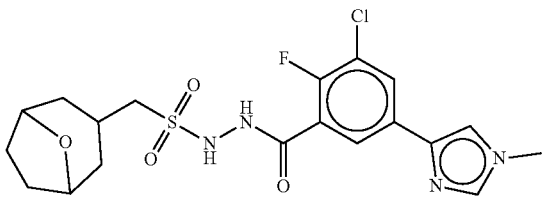 |
| I-243 | 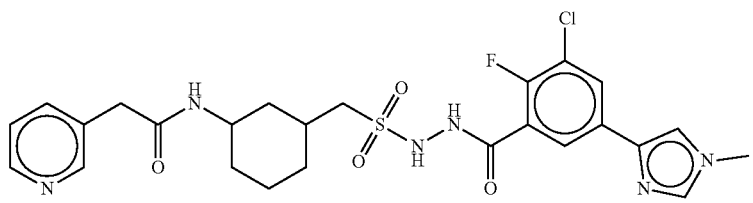 |
| I-239 | 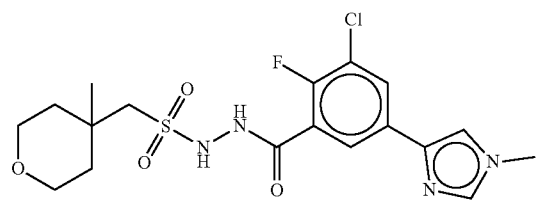 |

| Cmpd No | Compound Structure |
|---|---|
| I-240 | 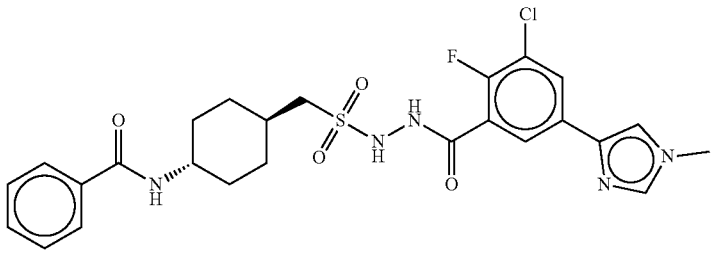 |
| I-246 | 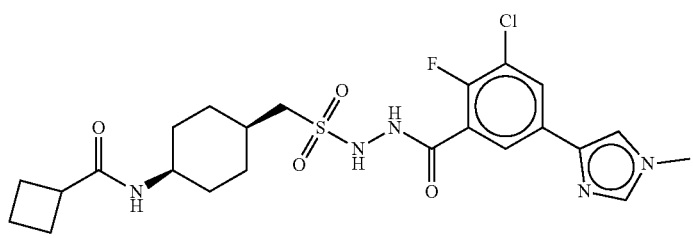 |
| I-247 | 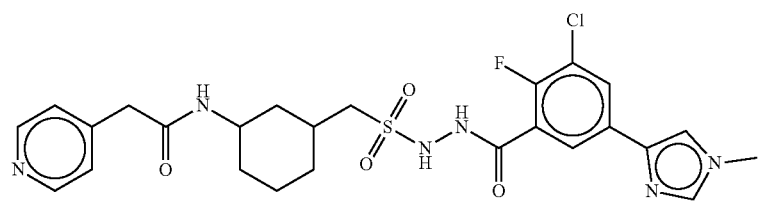 |
| I-248 | 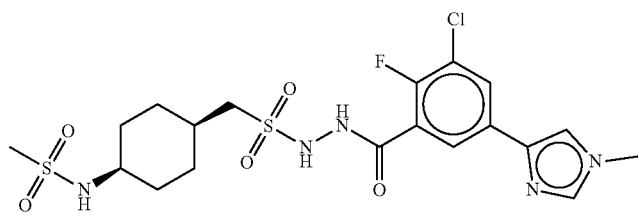 |
| I-244 | 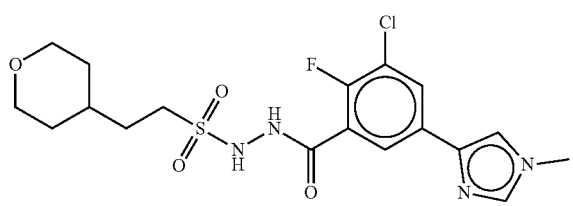 |
| I-245 | 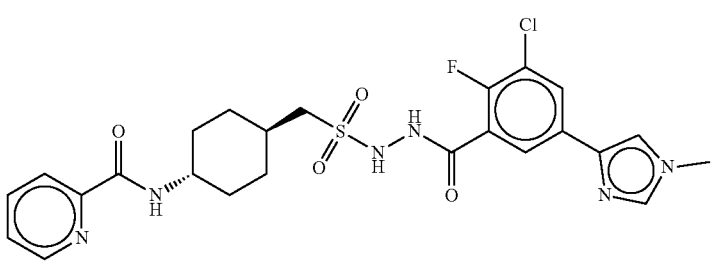 |

| Cmpd No | Compound Structure |
|---|---|
| I-251 | 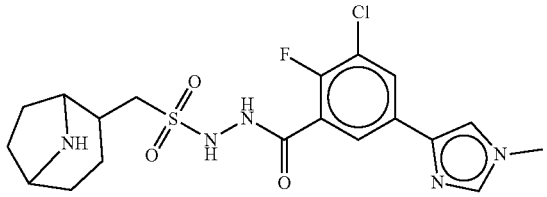 |
| I-252 | 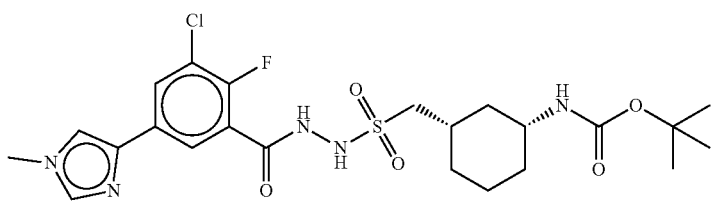 |
| I-253 | 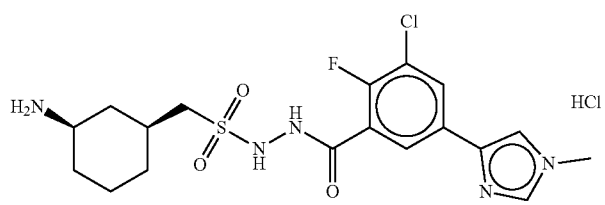 |
| I-249 | 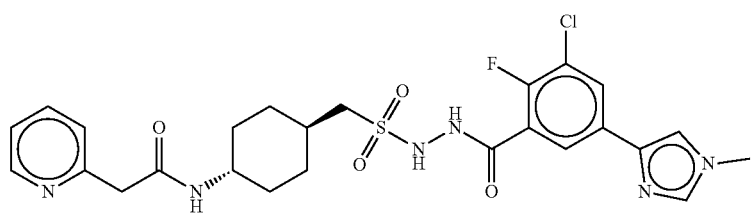 |
| I-250 | 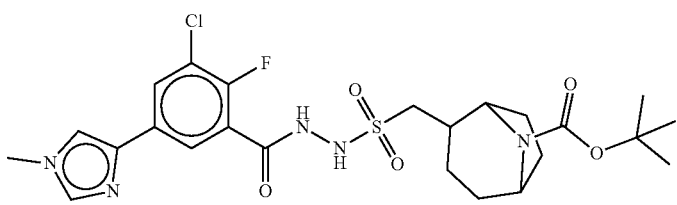 |
| I-256 | 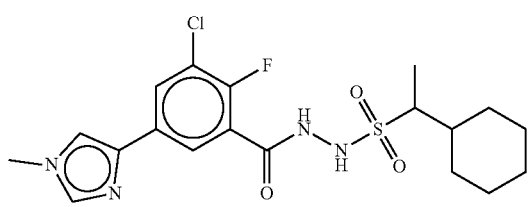 |
| I-257 | 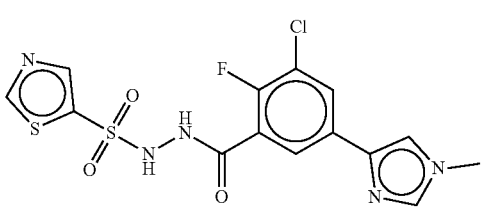 |

-continued
| Cmpd No | Compound Structure |
|---|---|
| I-258 | 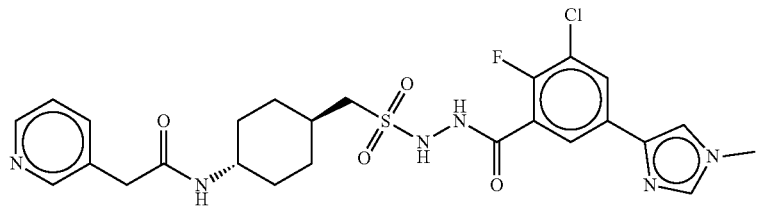 |
| I-254 | 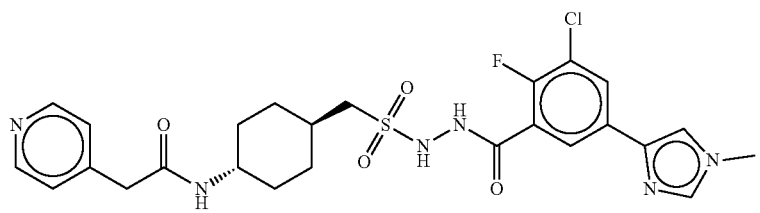 |
| I-255 | 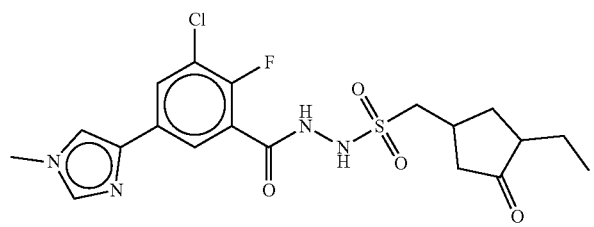 |
| I-261 | 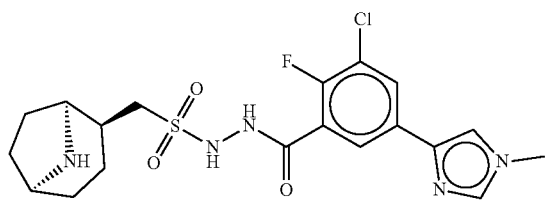 |
| I-262 | 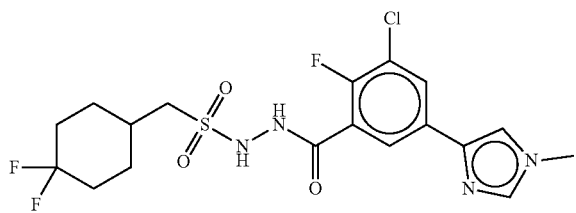 |
| I-263 | 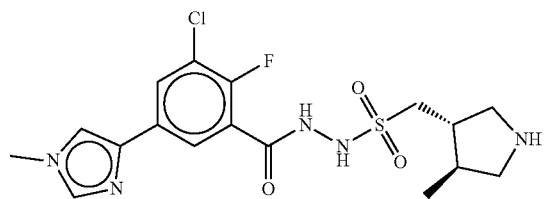 |
| I-259 | 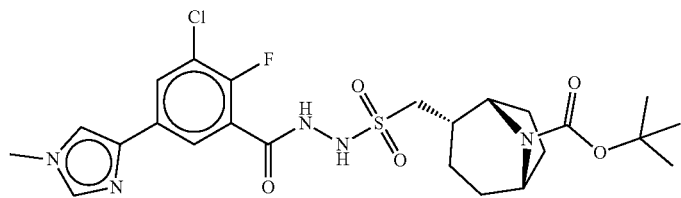 |

| Cmpd No | Compound Structure |
|---|---|
| I-260 | 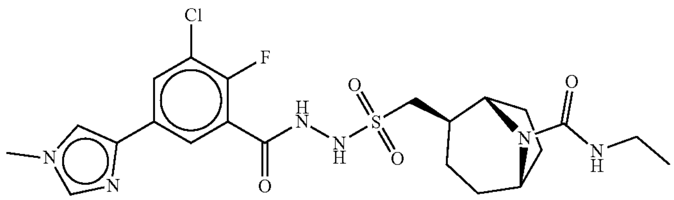 |
| I-266 | 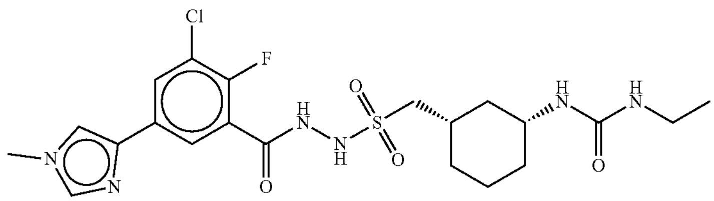 |
| I-267 | 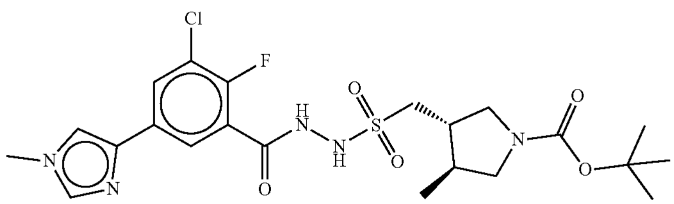 |
| I-268 | 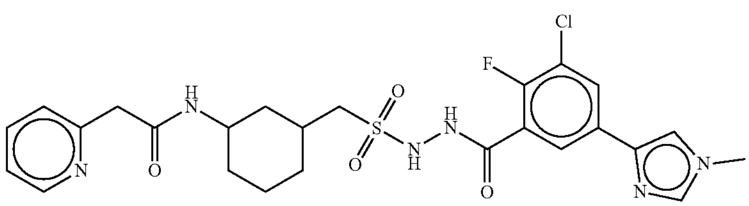 |
| I-264 | 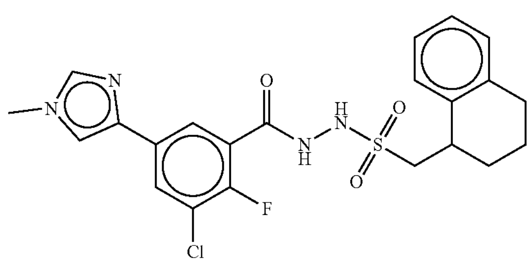 |
| I-265 | 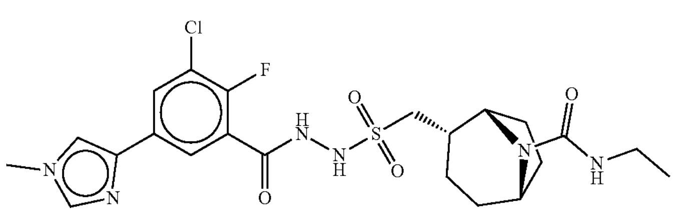 |
| I-271 | 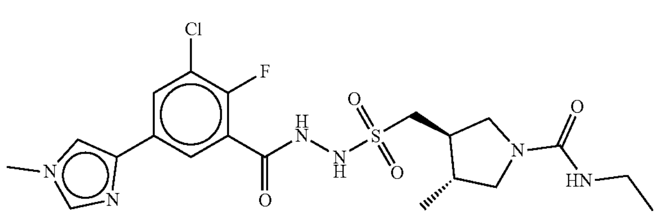 |

| Cmpd No | Compound Structure |
|---|---|
| I-272 | 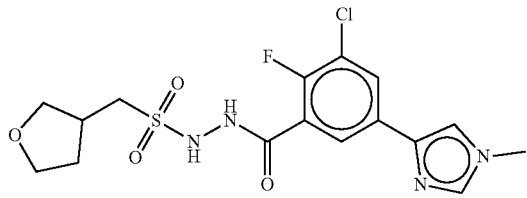 |
| I-273 | 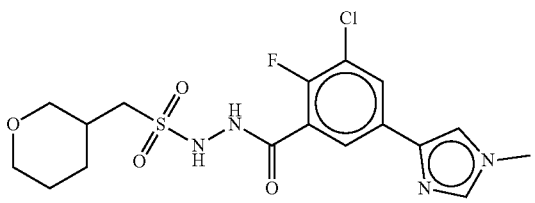 |
| I-269 | 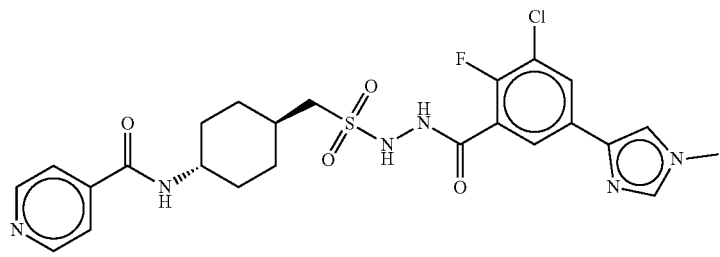 |
| I-270 | 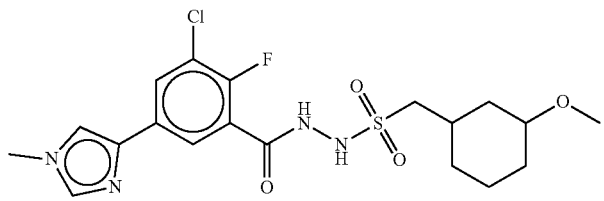 |
| I-276 | 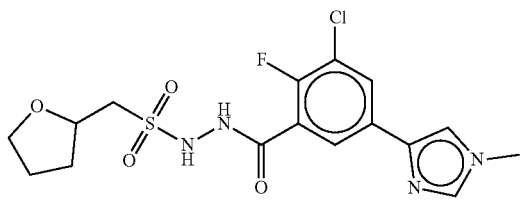 |
| I-277 | 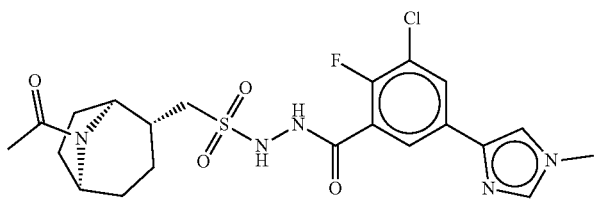 |
| I-278 | 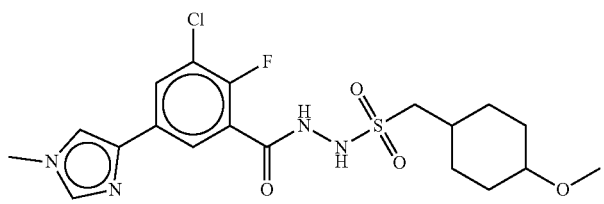 |

-continued
| Cmpd No | Compound Structure |
|---|---|
| I-274 | 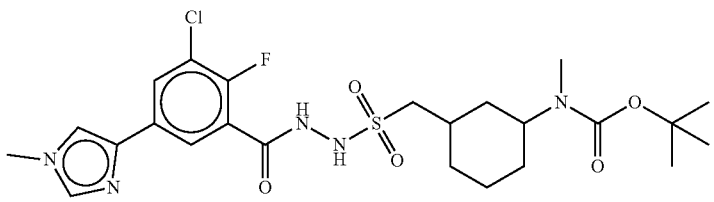 |
| I-275 | 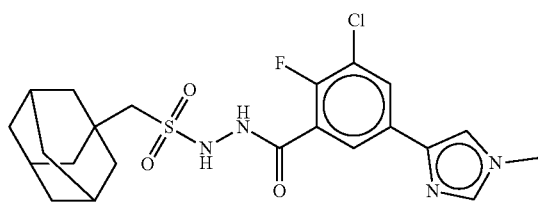 |
| I-281 | 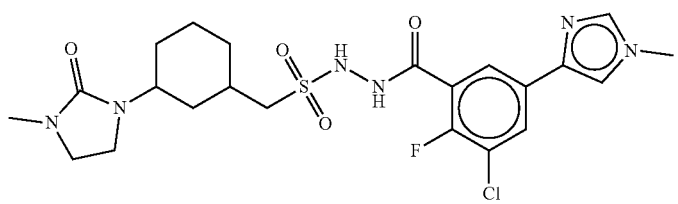 |
| I-282 | 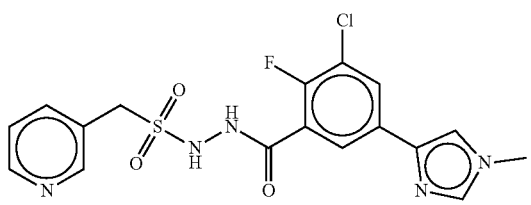 |
| I-283 | 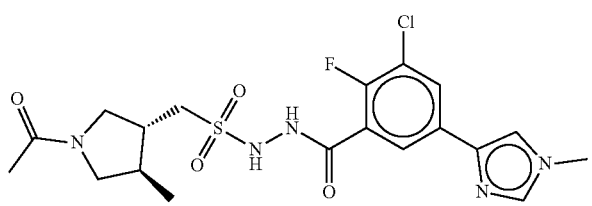 |
| I-279 | 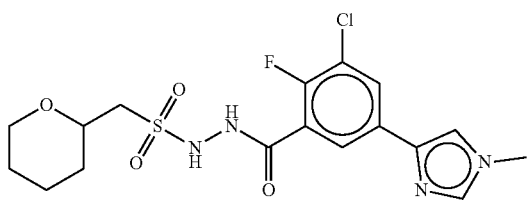 |
| I-280 | 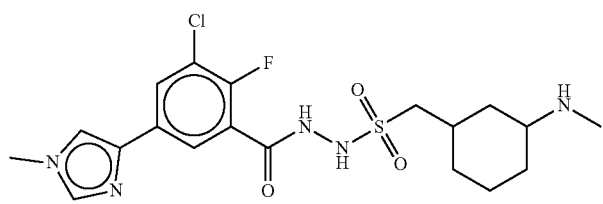 |

-continued
| Cmpd No | Compound Structure |
|---|---|
| I-286 | 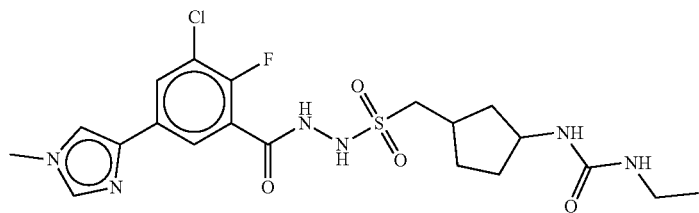 |
| I-287 | 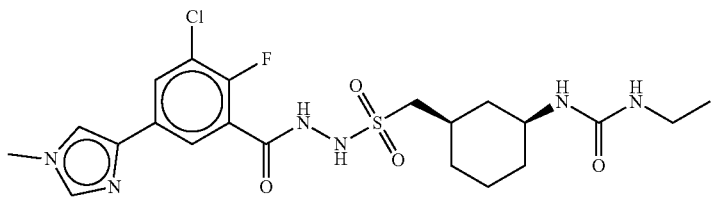 |
| I-288 | 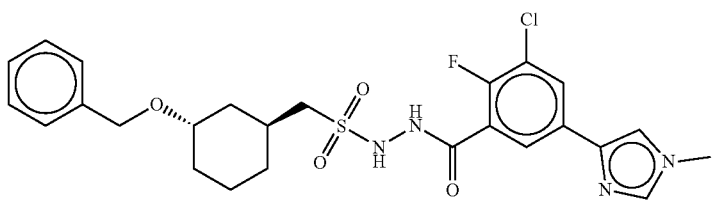 |
| I-284 | 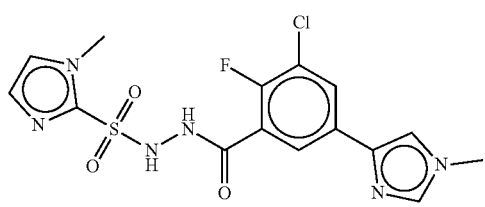 |
| I-285 | 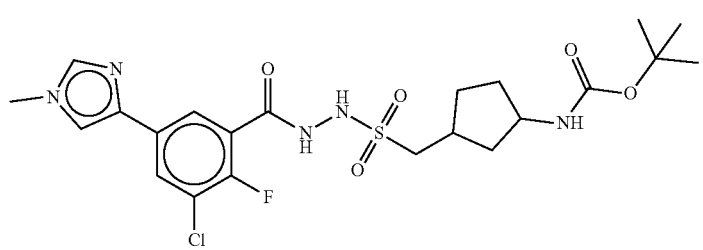 |
| I-291 | 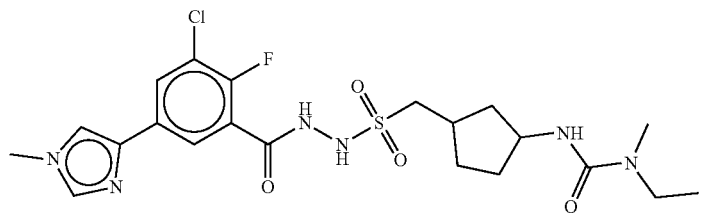 |
| I-292 | 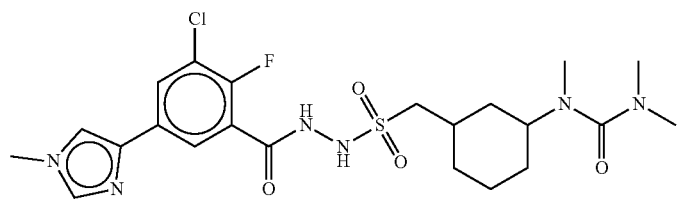 |

| Cmpd No | Compound Structure |
|---|---|
| I-293 | 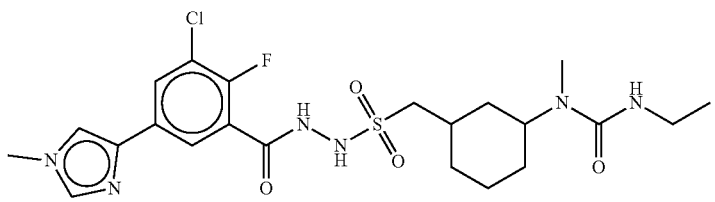 |
| I-289 | 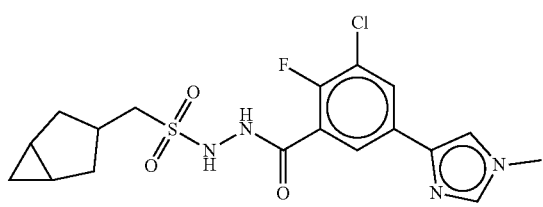 |
| I-290 | 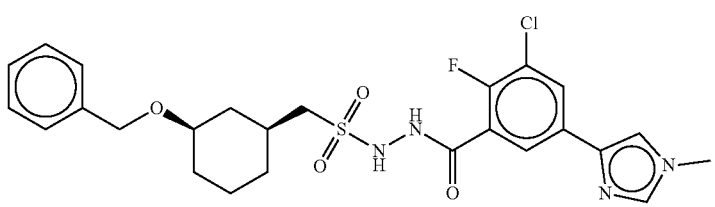 |
| I-296 | 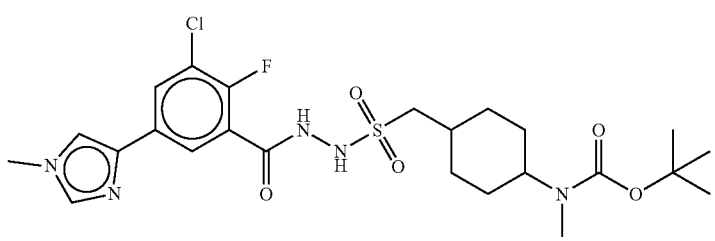 |
| I-297 | 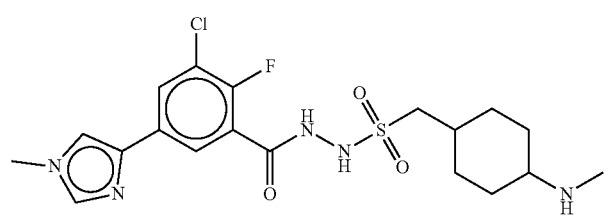 |
| I-298 | 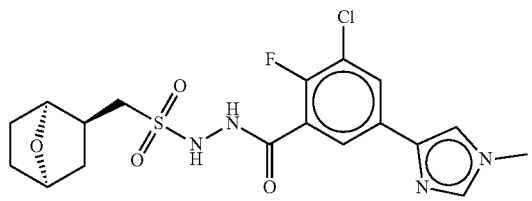 |
| I-294 | 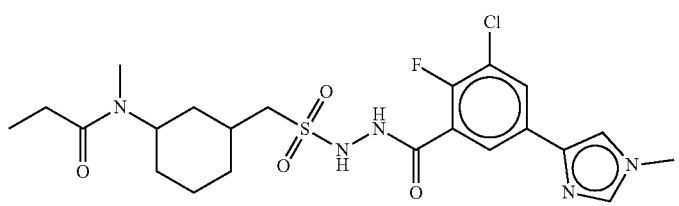 |

| Cmpd No | Compound Structure |
|---|---|
| I-295 | 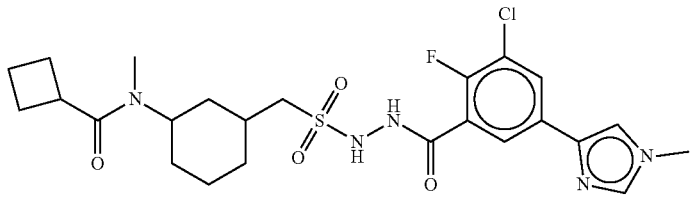 |
| I-301 | 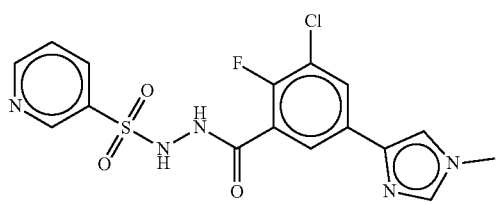 |
| I-302 | 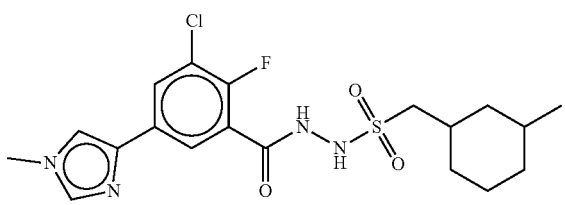 |
| I-303 | 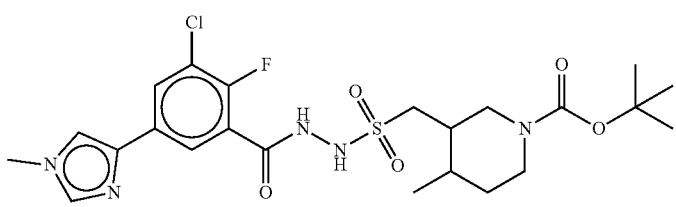 |
| I-299 | 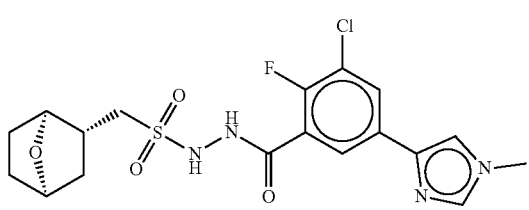 |
| I-300 | 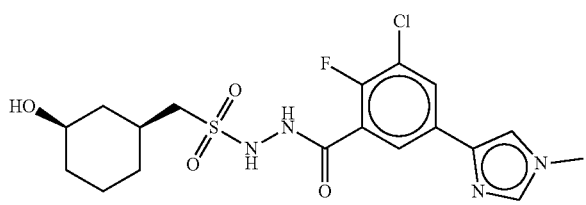 |
| I-306 | 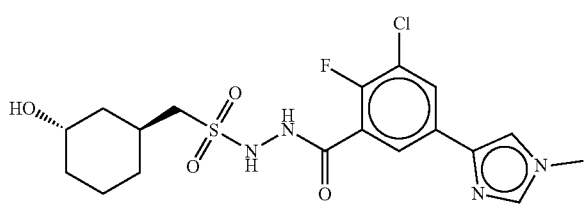 |

| Cmpd No | Compound Structure |
|---|---|
| I-307 | 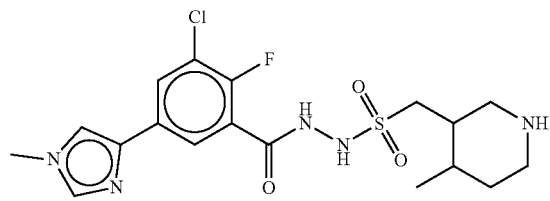 |
| I-308 | 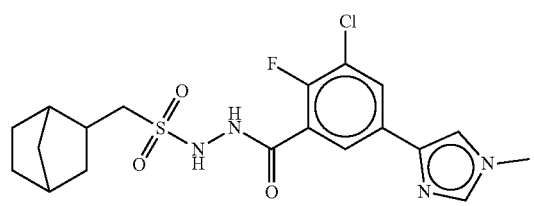 |
| I-304 | 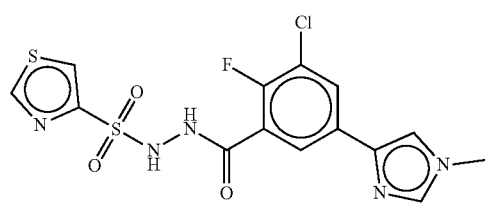 |
| I-305 | 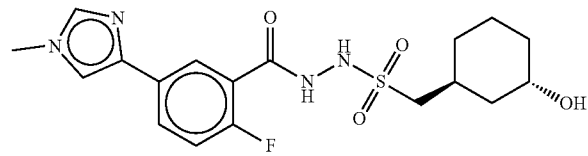 |
| I-311 | 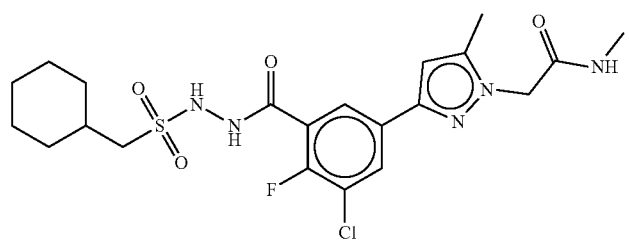 |
| I-312 | 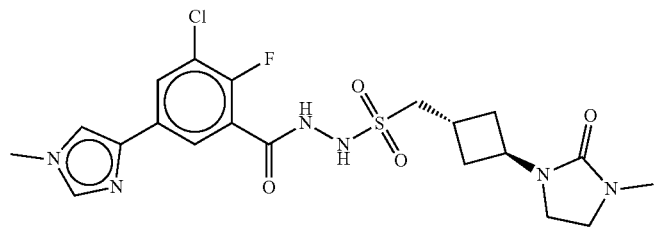 |
| I-313 | 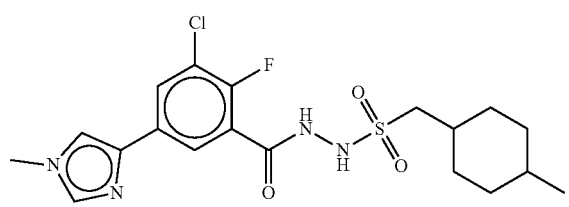 |

| Cmpd No | Compound Structure |
|---|---|
| I-309 | 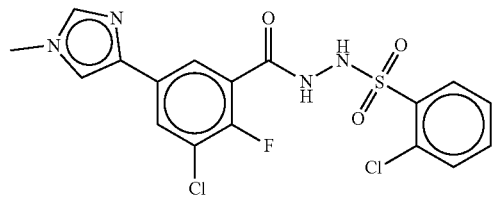 |
| I-310 | 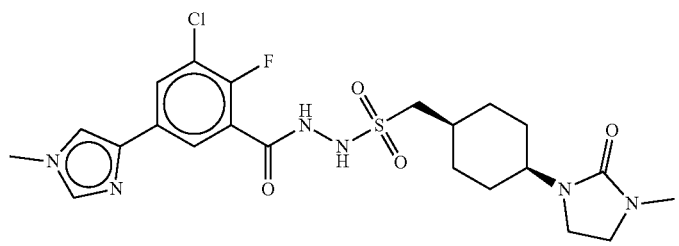 |
| I-316 | 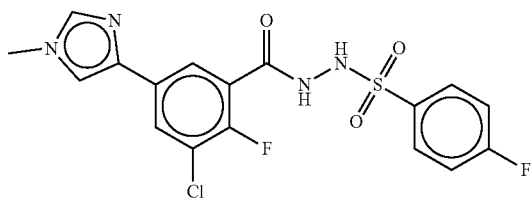 |
| I-317 | 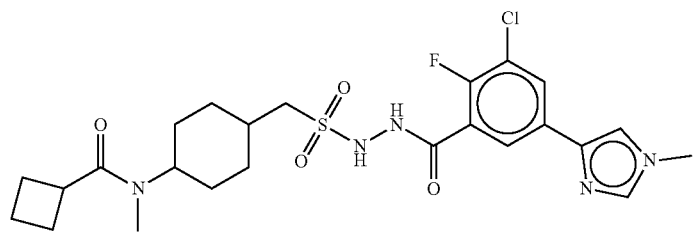 |
| I-318 | 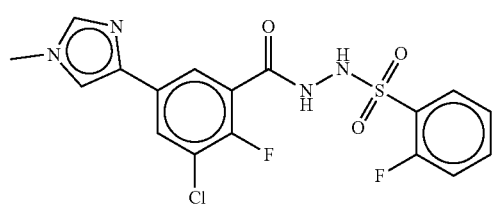 |
| I-314 | 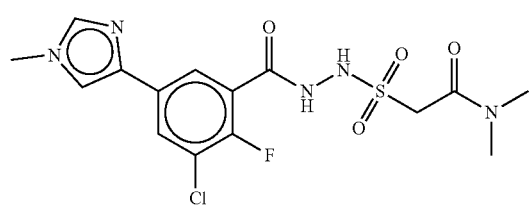 |
| I-315 | 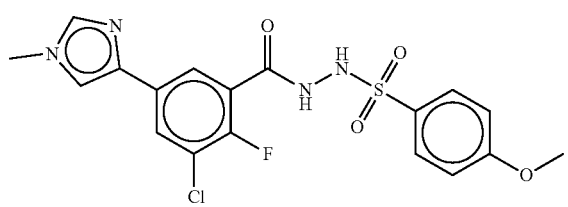 |

-continued

| Cmpd No | Compound Structure |
|---|---|
| I-321 | 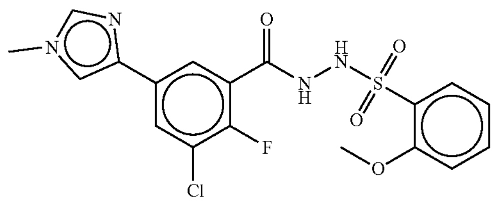 |
| I-322 | 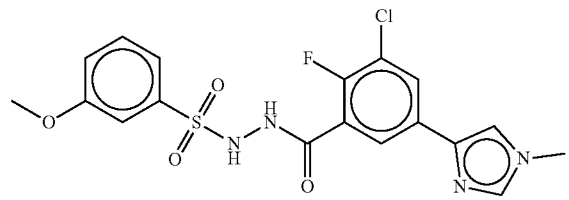 |
| I-323 | 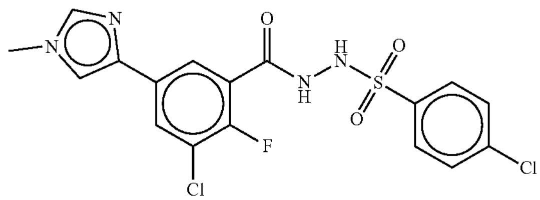 |
| I-319 | 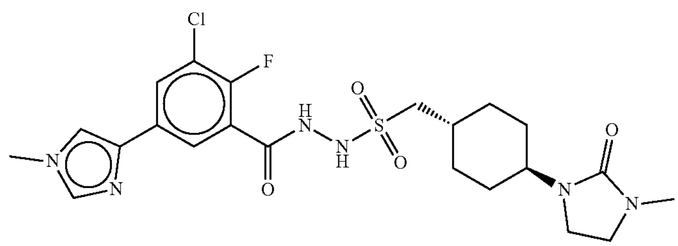 |
| I-320 | 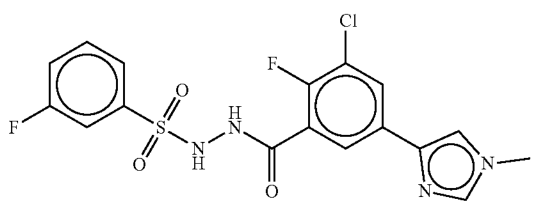 |
| I-326 | 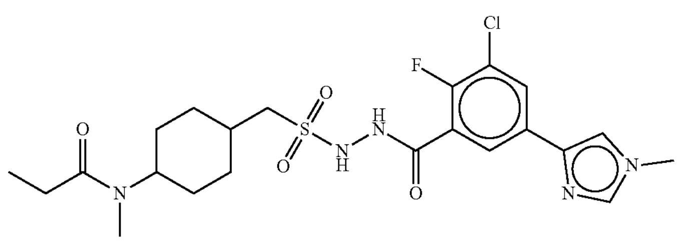 |
| I-327 | 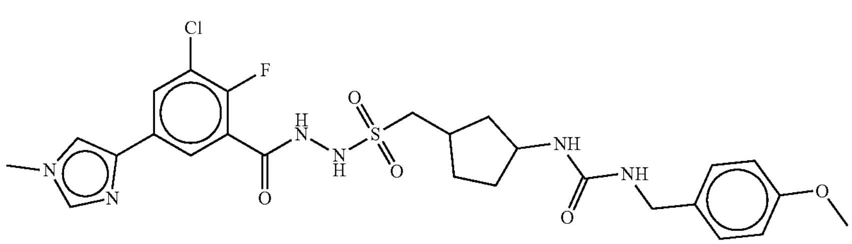 |

| Cmpd No | Compound Structure |
|---|---|
| I-328 | 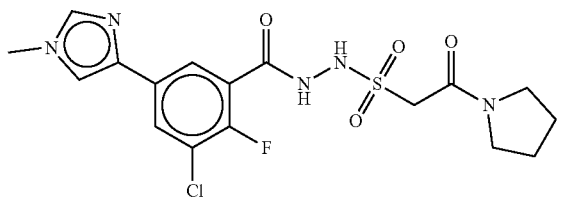 |
| I-324 | 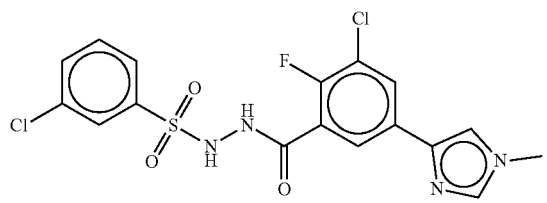 |
| I-325 | 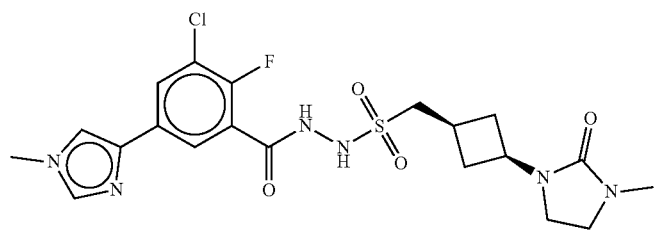 |
| I-331 | 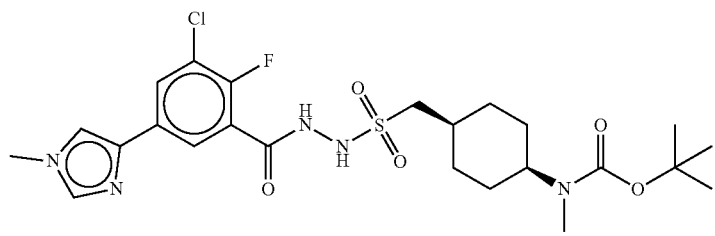 |
| I-332 | 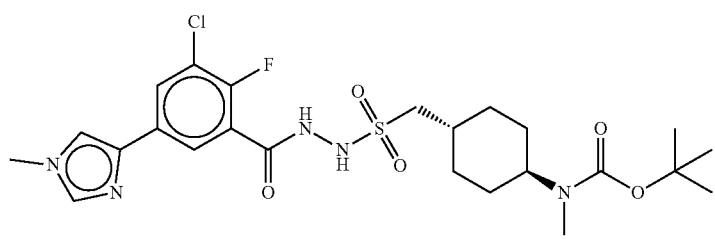 |
| I-333 | 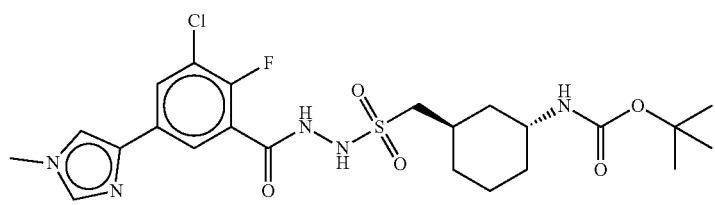 |
| I-329 | 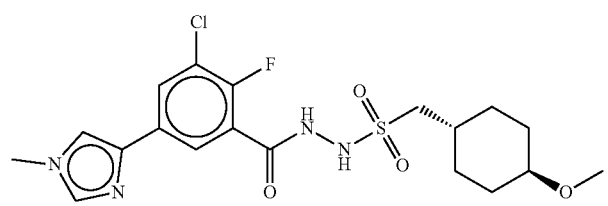 |

-continued
| Cmpd No | Compound Structure |
|---|---|
| I-330 | 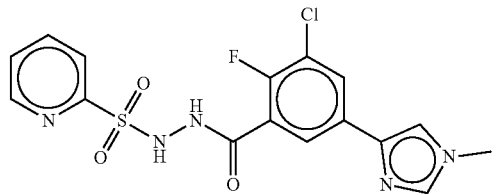 |
| I-336 | 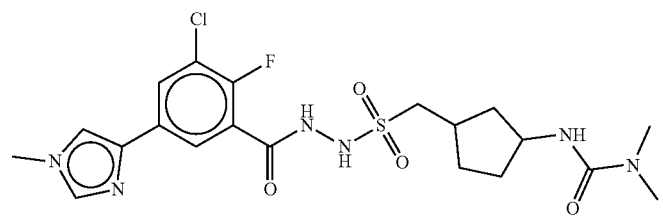 |
| I-337 | 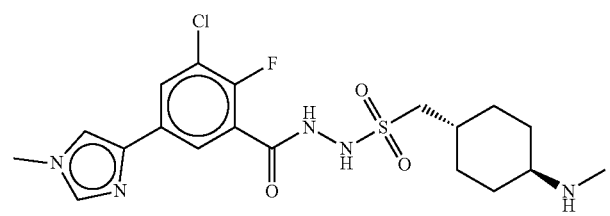 |
| I-338 | 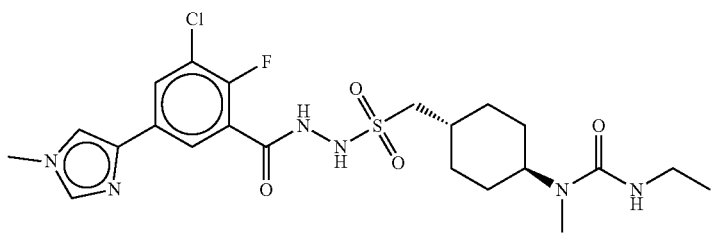 |
| I-334 | 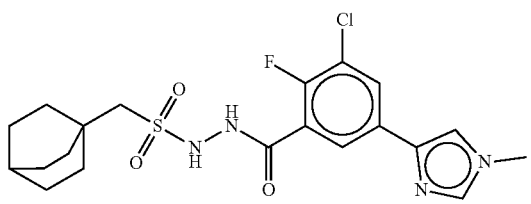 |
| I-335 | 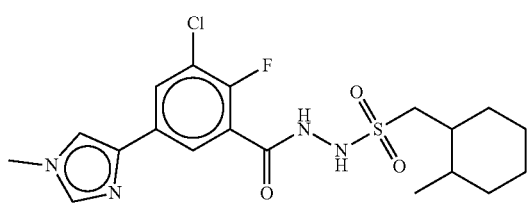 |
| I-341 | 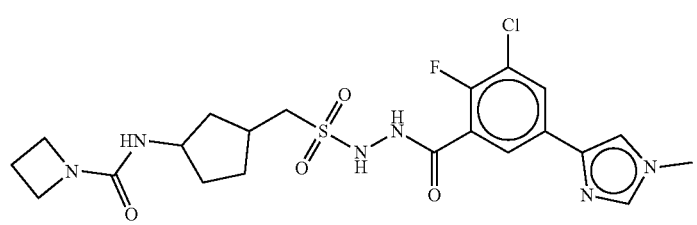 |

-continued
| Cmpd No | Compound Structure |
|---|---|
| I-342 | 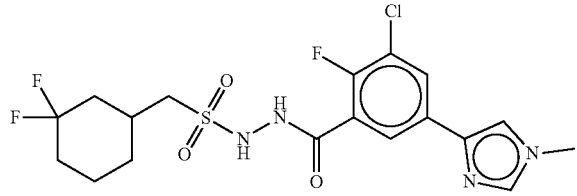 |
| I-343 | 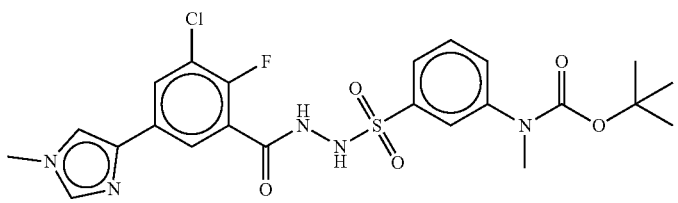 |
| I-339 | 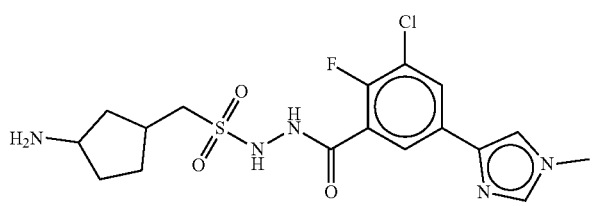 |
| I-340 | 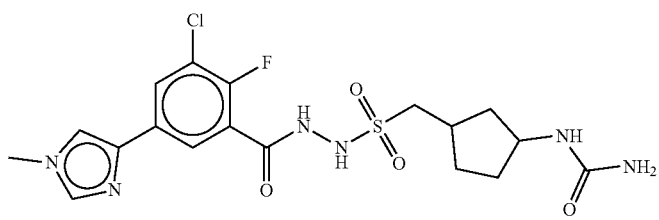 |
| I-346 | 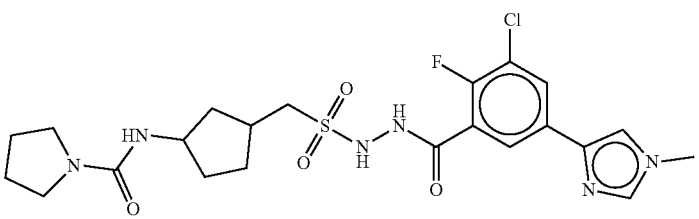 |
| I-347 | 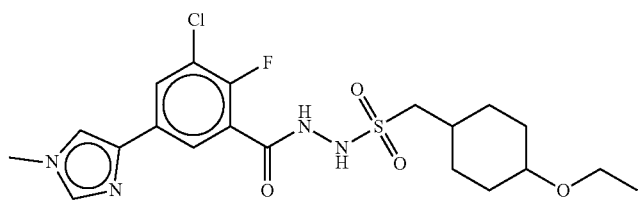 |
| I-348 | 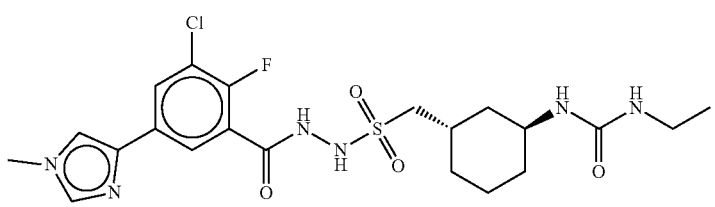 |

-continued
| Cmpd No | Compound Structure |
|---|---|
| I-344 | 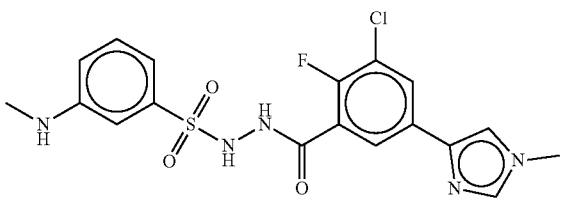 |
| I-345 | 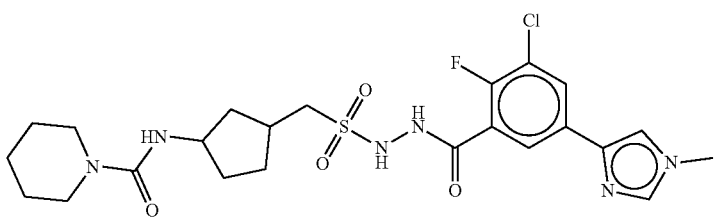 |
| I-351 | 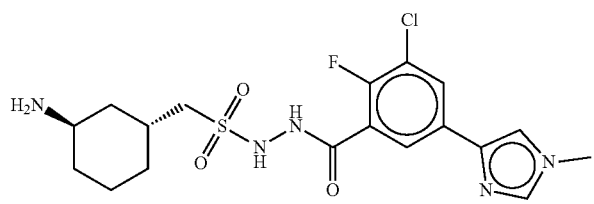 |
| I-352 | 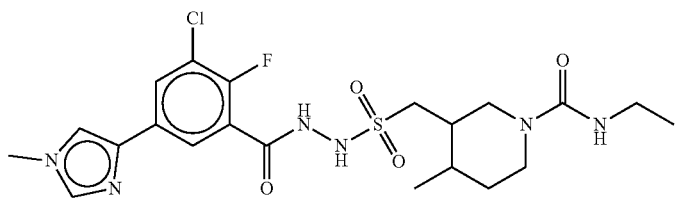 |
| I-353 | 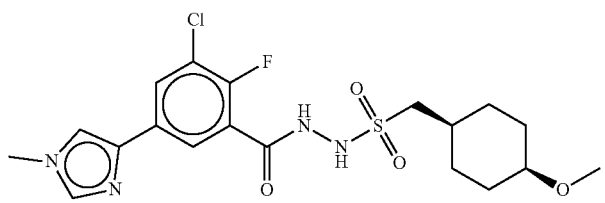 |
| I-349 | 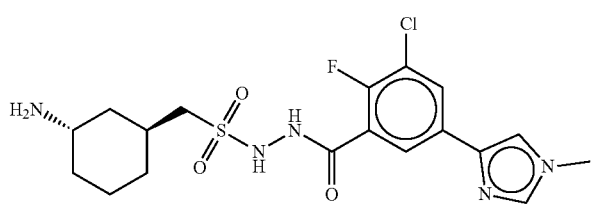 |
| I-350 | 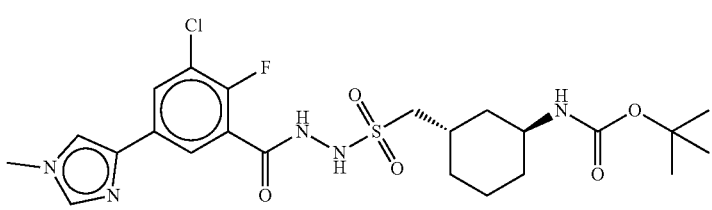 |

| Cmpd No | Compound Structure |
|---|---|
| I-356 | 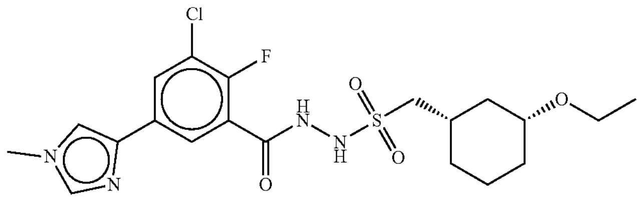 |
| I-357 | 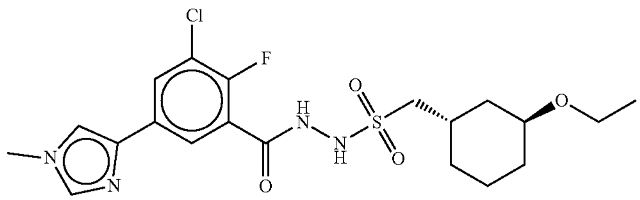 |
| I-358 | 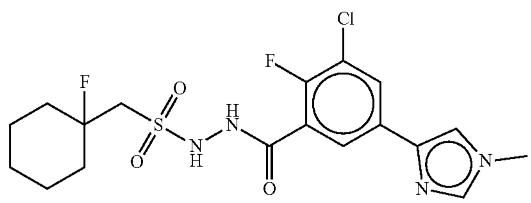 |
| I-354 | 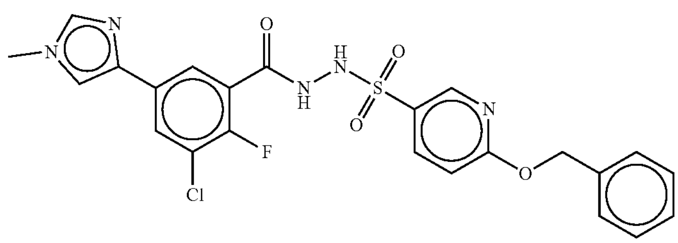 |
| I-355 | 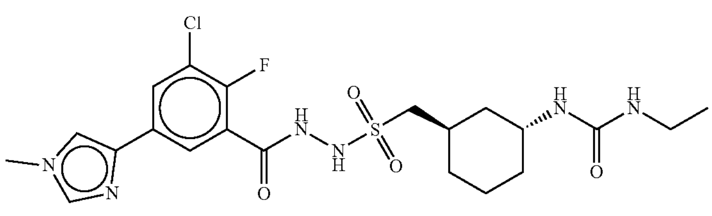 |
| I-361 | 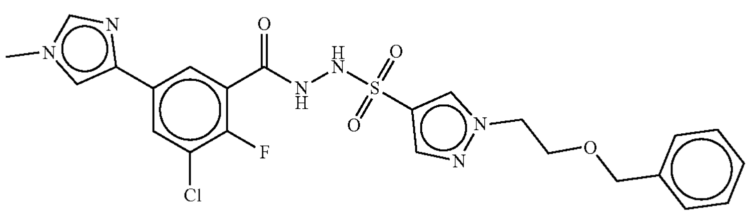 |
| I-362 | 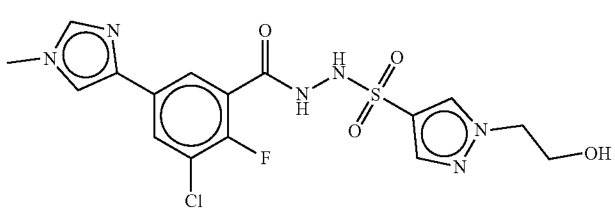 |

| Cmpd No | Compound Structure |
|---|---|
| I-363 | 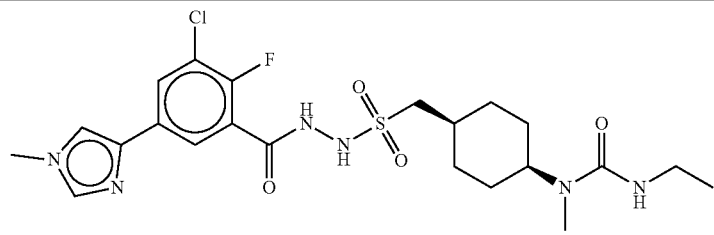 |
| I-359 | 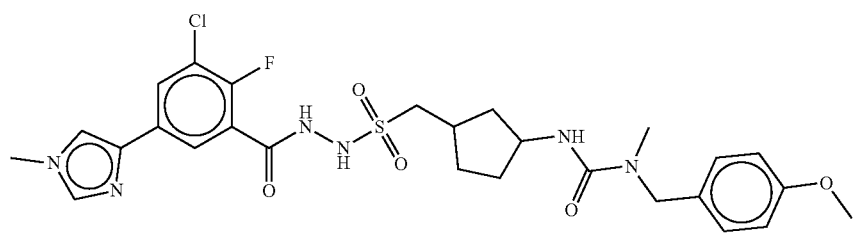 |
| I-360 | 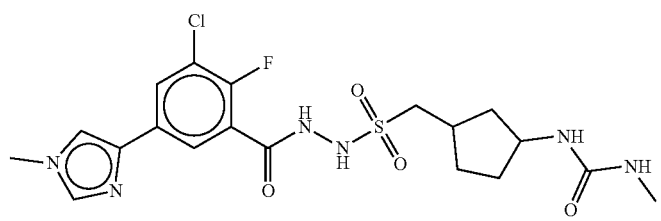 |
| I-366 | 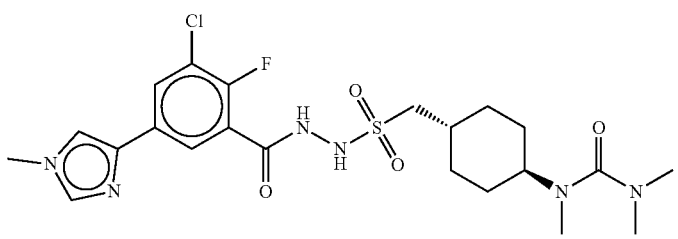 |
| I-367 | 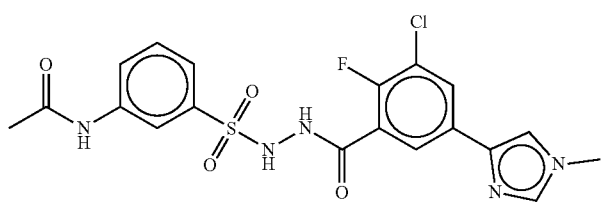 |
| I-368 | 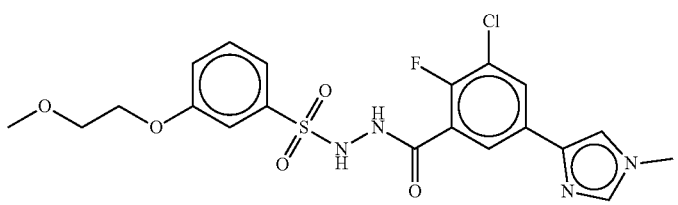 |
| I-364 | 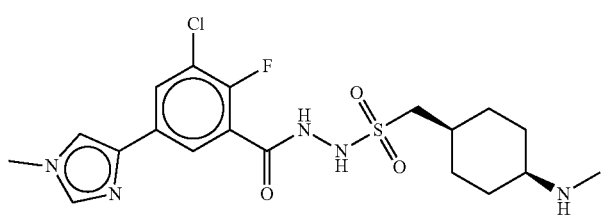 |

| Cmpd No | Compound Structure |
|---|---|
| I-365 | 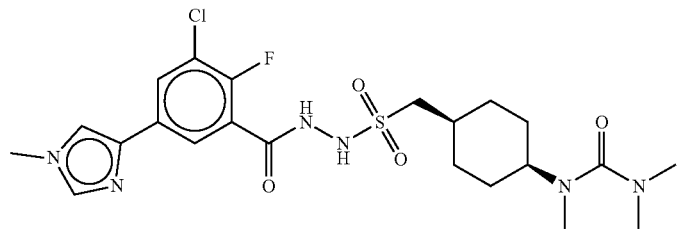 |
| I-371 | 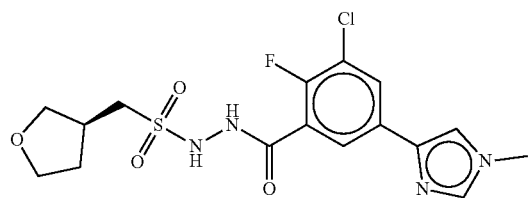 |
| I-372 | 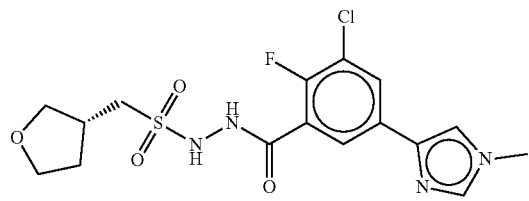 |
| I-373 | 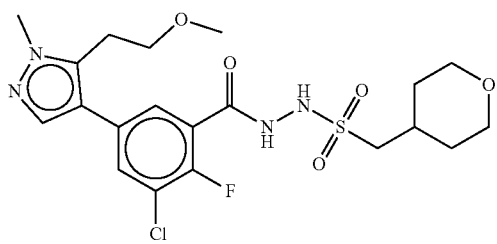 |
| I-369 | 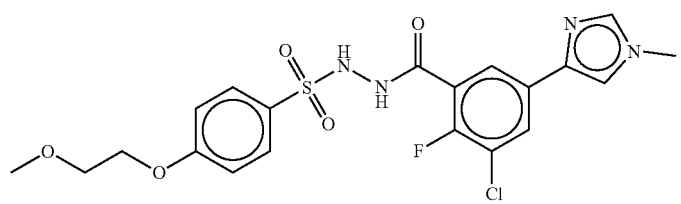 |
| I-370 | 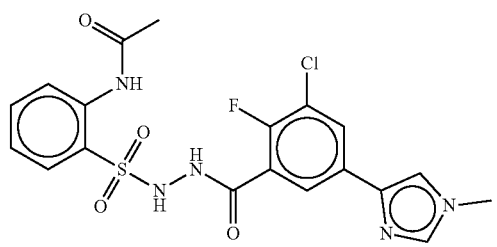 |
| I-376 | 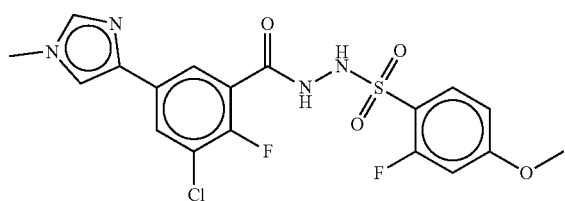 |

-continued
| Cmpd No | Compound Structure |
|---|---|
| I-377 | 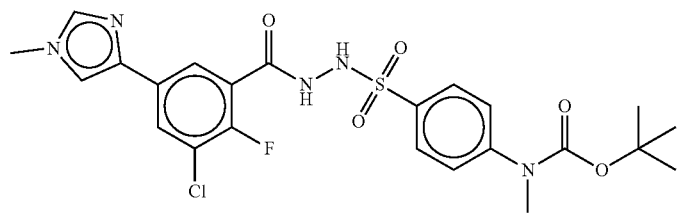 |
| I-378 | 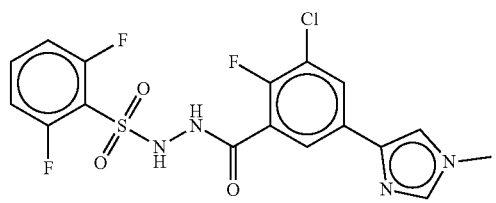 |
| I-374 | 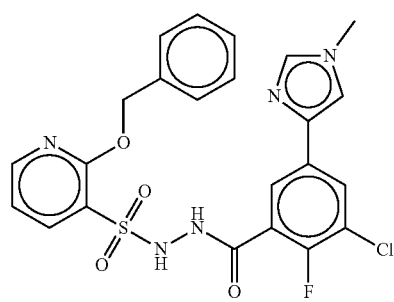 |
| I-375 | 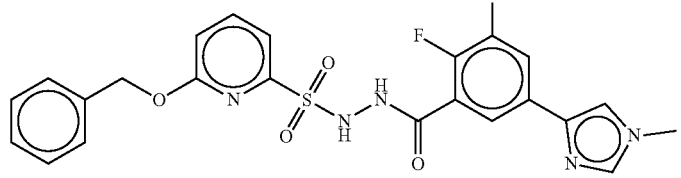 |
| I-381 | 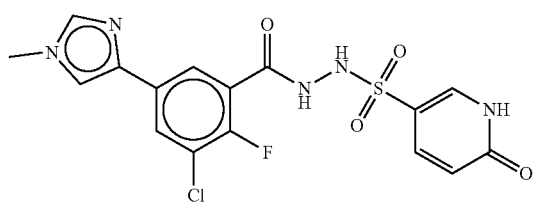 |
| I-382 | 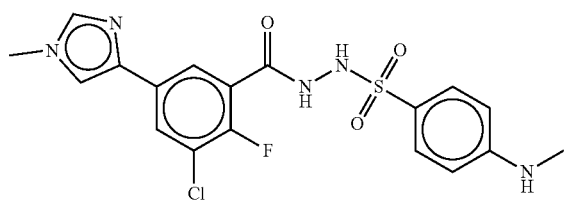 |
| I-383 | 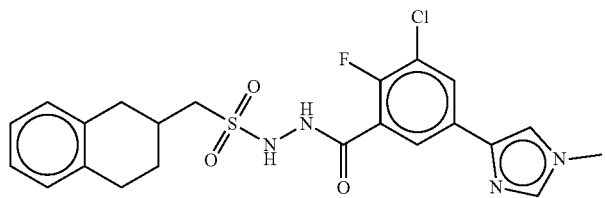 |

-continued
| Cmpd No | Compound Structure |
|---|---|
| I-379 | 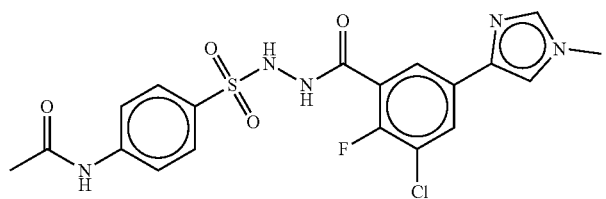 |
| I-380 | 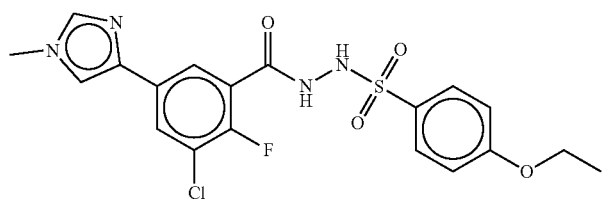 |
| I-386 | 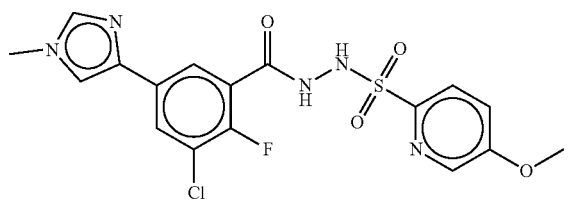 |
| I-387 | 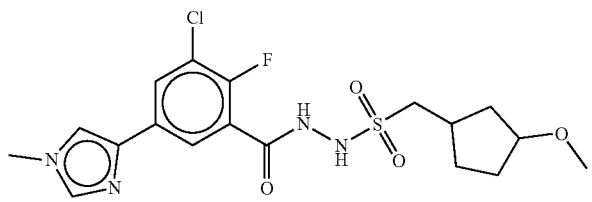 |
| I-388 | 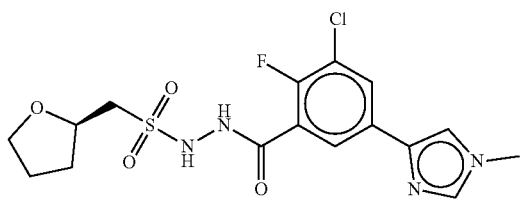 |
| I-384 | 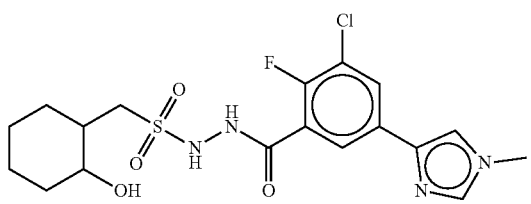 |
| I-385 | 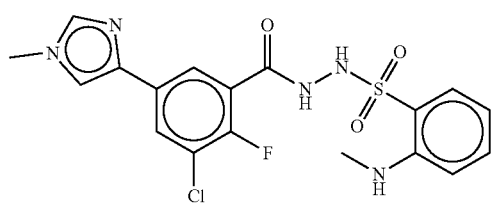 |

| Cmpd No | Compound Structure |
|---------|-------------------|
| I-391 | 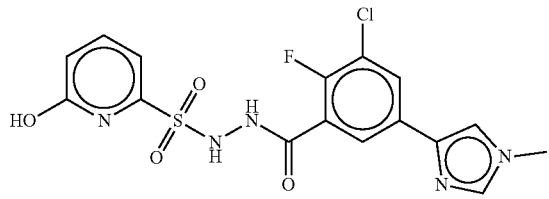 |
| I-392 | 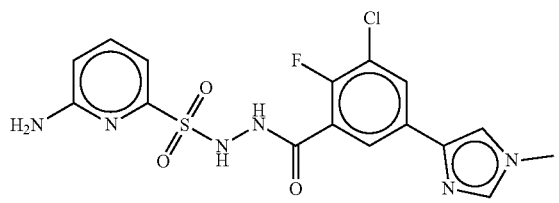 |
| I-393 | 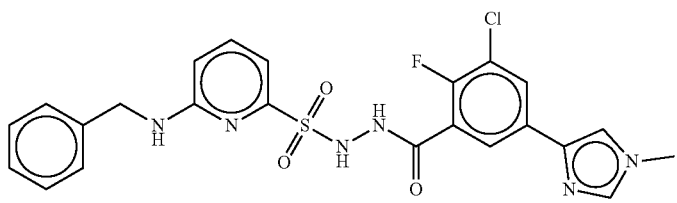 |
| I-389 | 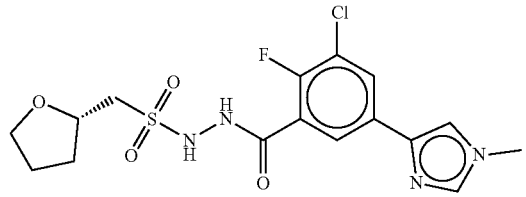 |
| I-390 | 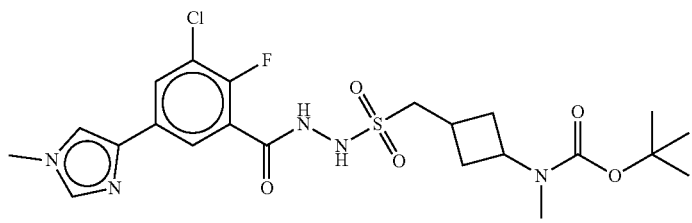 |
| I-396 | 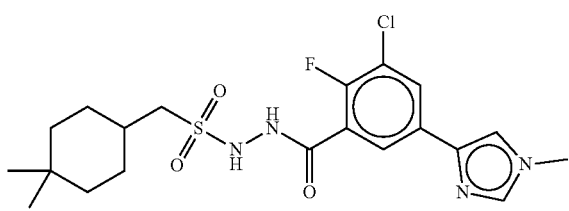 |
| I-397 | 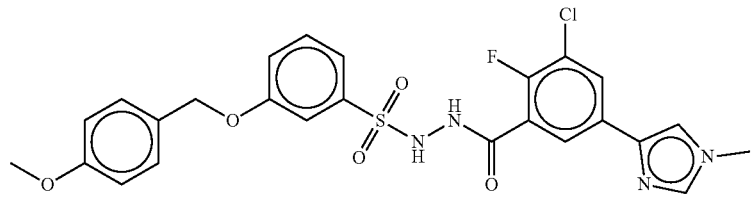 |

| Cmpd No | Compound Structure |
|---|---|
| I-398 | 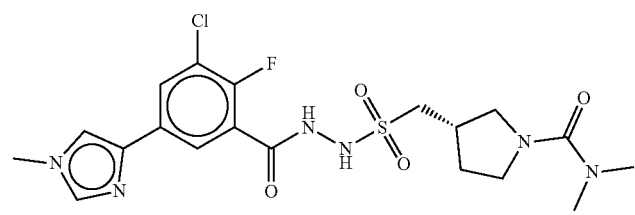 |
| I-394 | 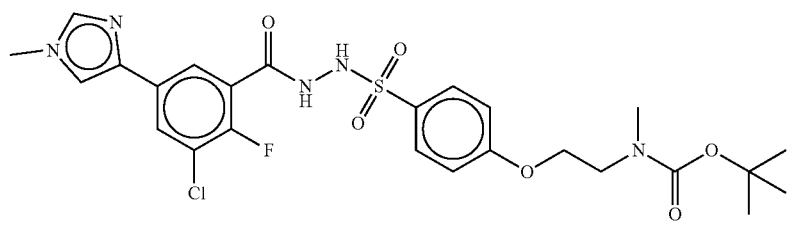 |
| I-395 | 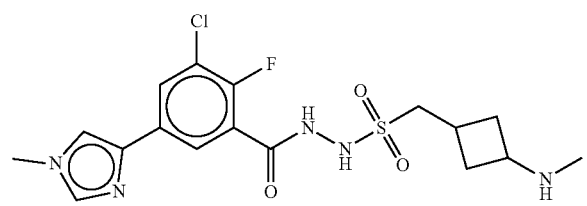 |
| I-401 | 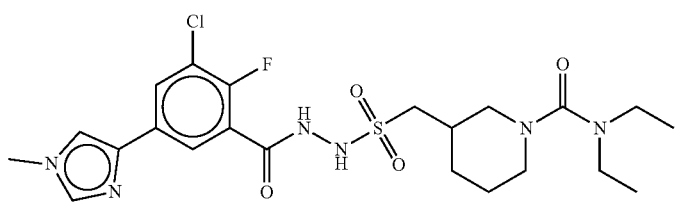 |
| I-402 | 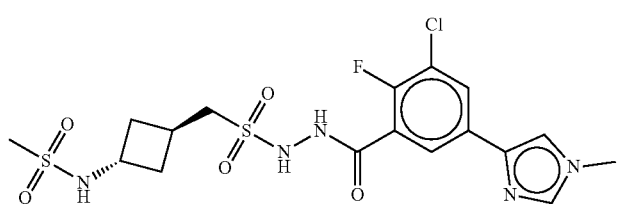 |
| I-403 | 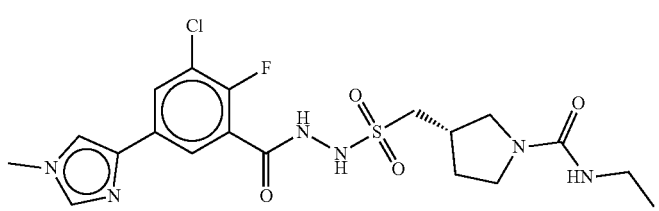 |
| I-399 | 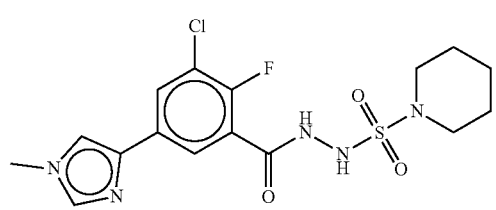 |

| Cmpd No | Compound Structure |
|---|---|
| I-400 | 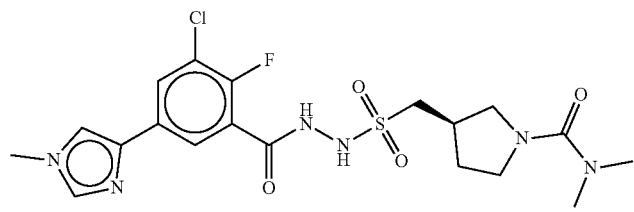 |
| I-406 | 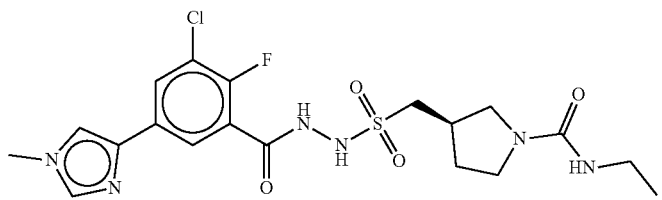 |
| I-407 | 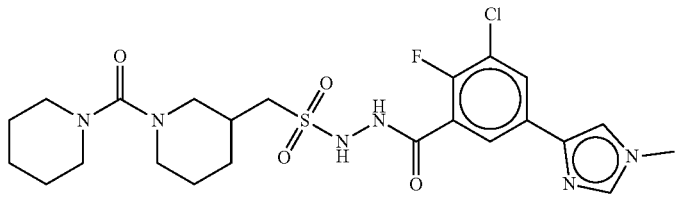 |
| I-408 | 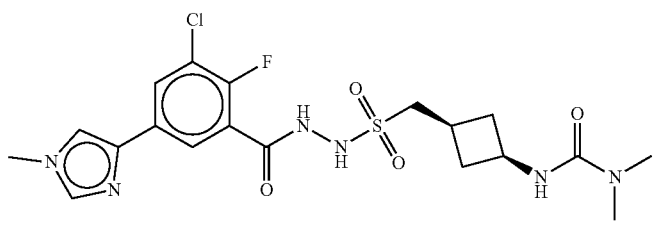 |
| I-404 | 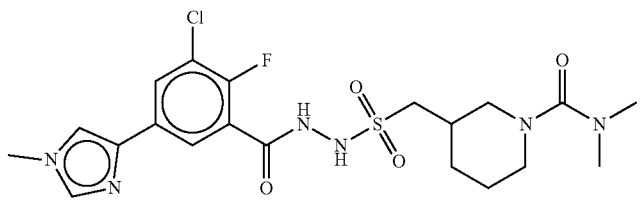 |
| I-405 | 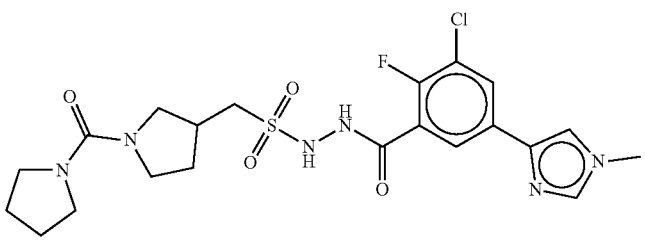 |
| I-411 | 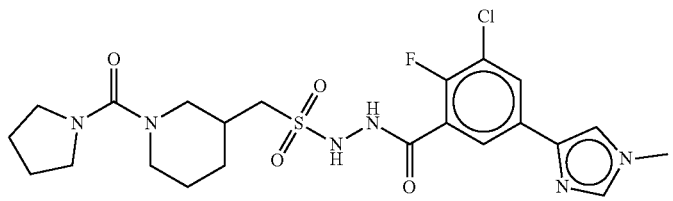 |

-continued
| Cmpd No | Compound Structure |
|---|---|
| I-412 | 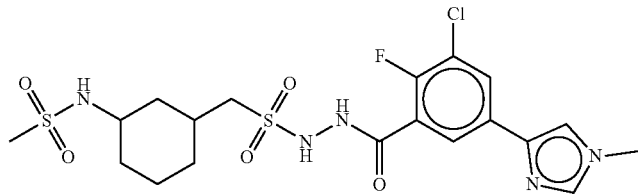 |
| I-413 | 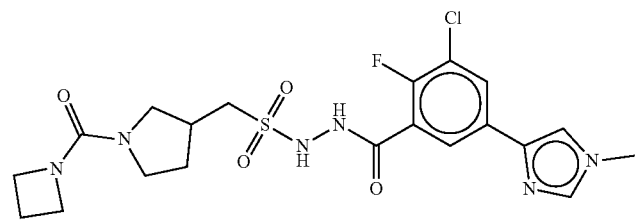 |
| I-409 | 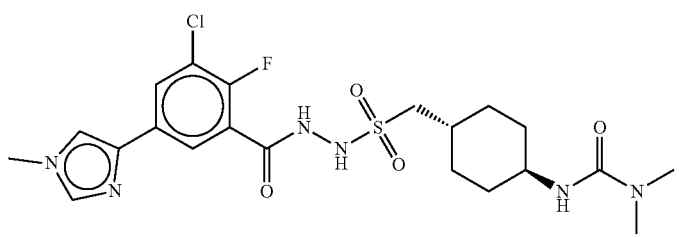 |
| I-410 | 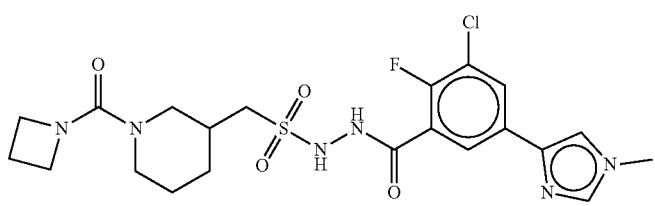 |
| I-416 | 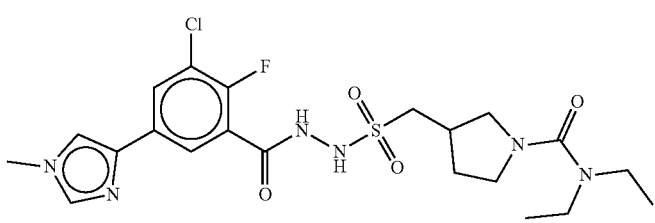 |
| I-417 | 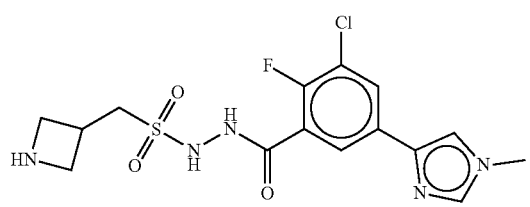 |
| I-418 | 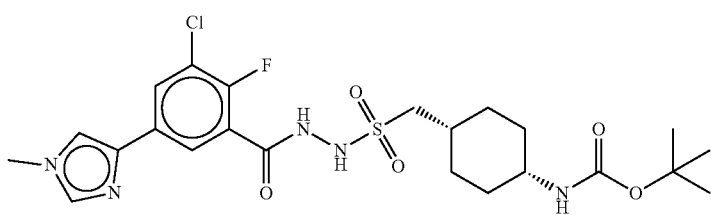 |

| Cmpd No | Compound Structure |
|---|---|
| I-414 | 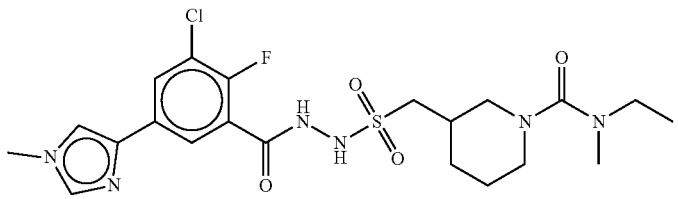 |
| I-415 | 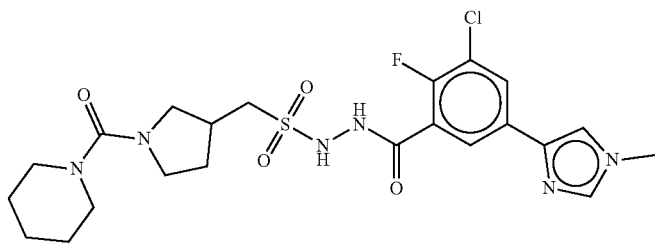 |
| I-421 | 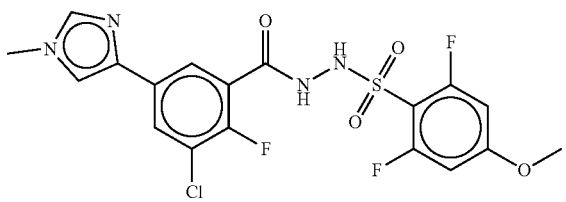 |
| I-422 | 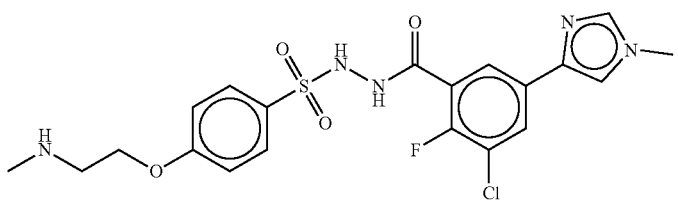 |
| I-423 | 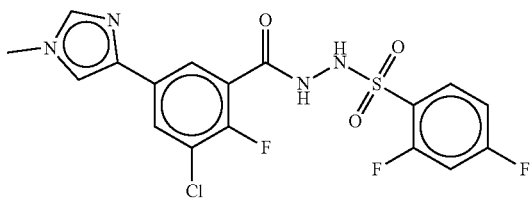 |
| I-419 | 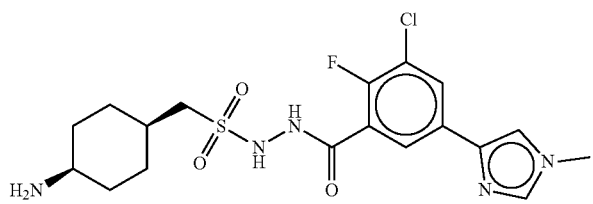 |
| I-420 | 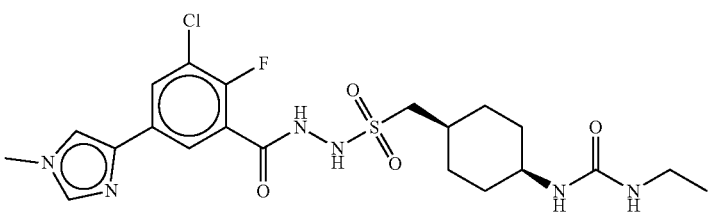 |

| Cmpd No | Compound Structure |
|---|---|
| I-426 | 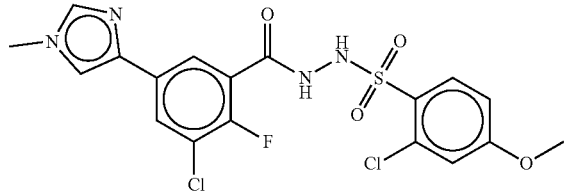 |
| I-427 | 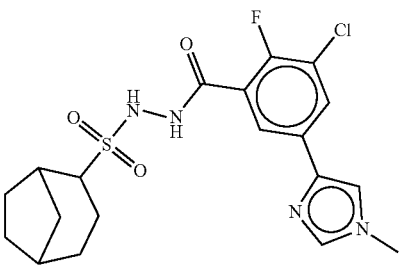 |
| I-428 | 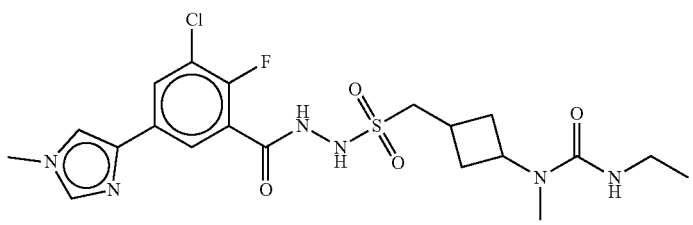 |
| I-424 | 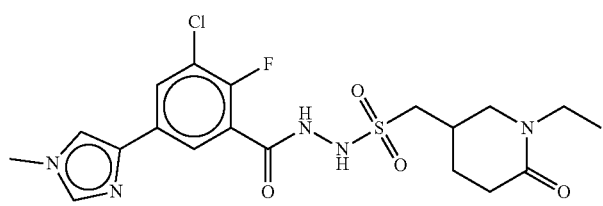 |
| I-425 | 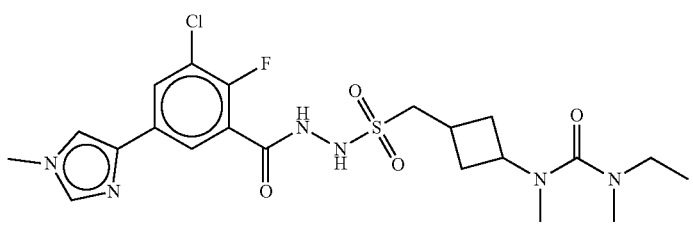 |
| I-431 | 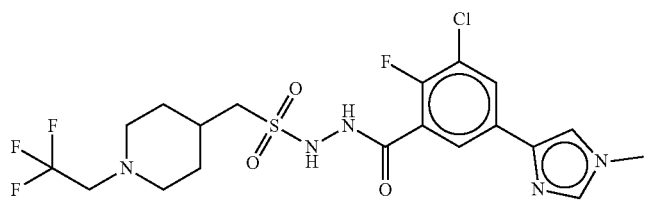 |
| I-432 | 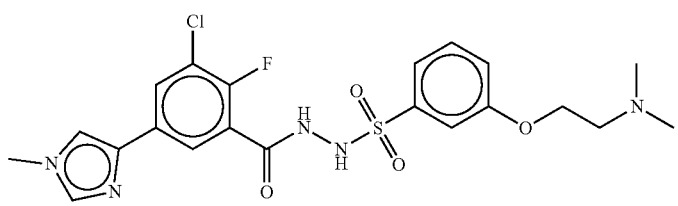 |

-continued
| Cmpd No | Compound Structure |
|---|---|
| I-433 | 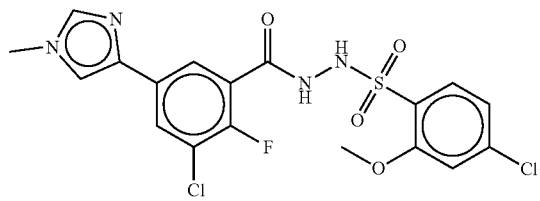 |
| I-429 | 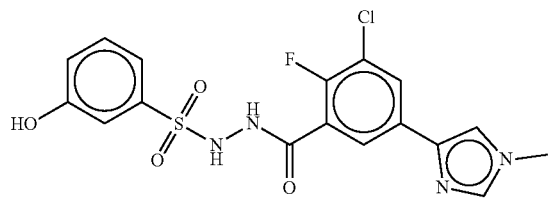 |
| I-430 | 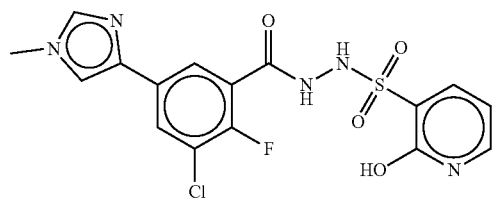 |
| I-436 | 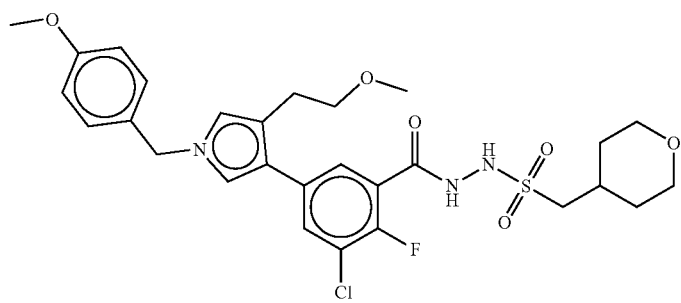 |
| I-437 | 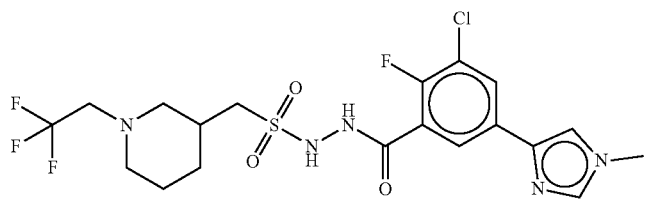 |
| I-438 | 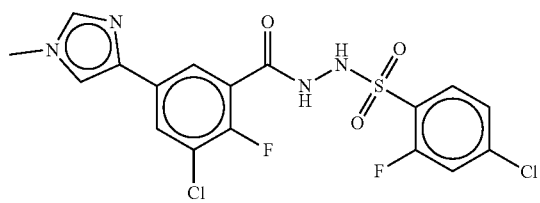 |
| I-434 | 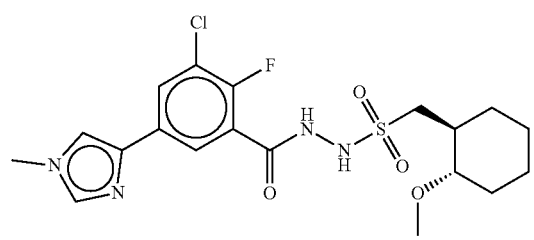 |

| Cmpd No | Compound Structure |
|---|---|
| I-435 | 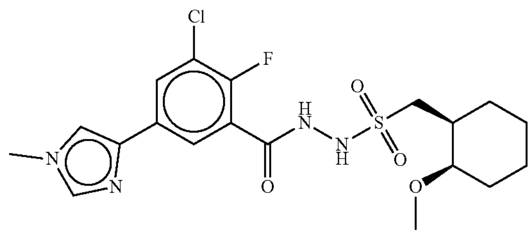 |
| I-441 | 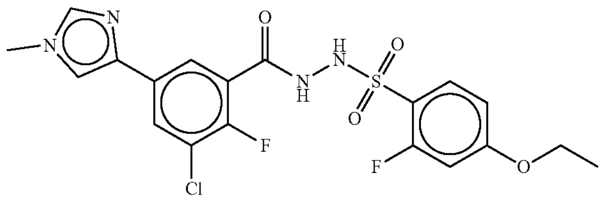 |
| I-442 | 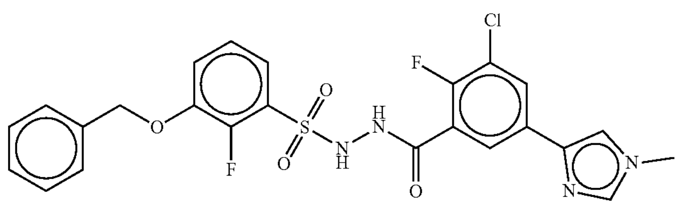 |
| I-443 | 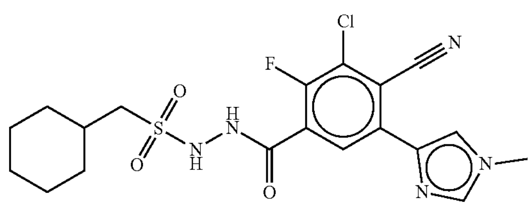 |
| I-439 | 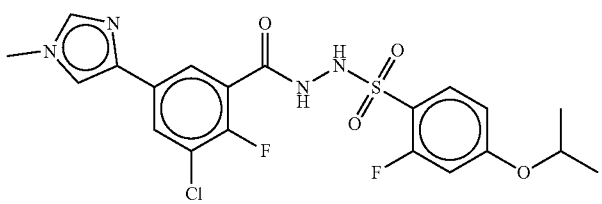 |
| I-440 | 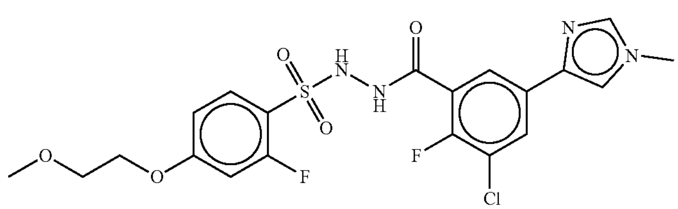 |
| I-446 | 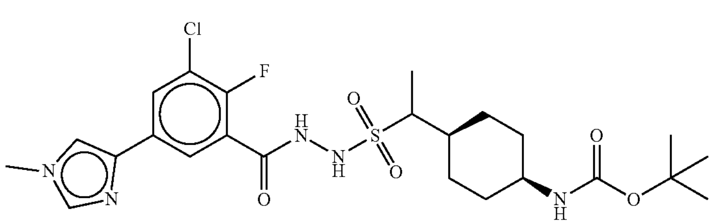 |

| Cmpd No | Compound Structure |
|---|---|
| I-447 | 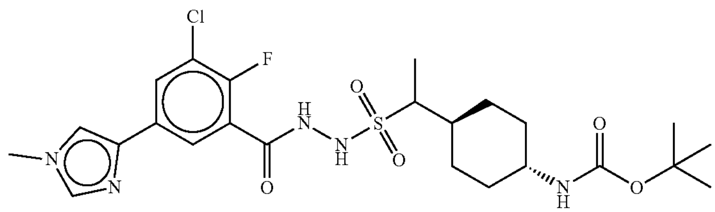 |
| I-448 | 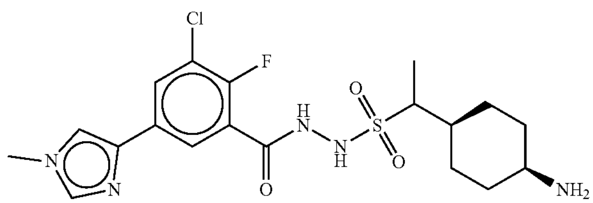 |
| I-444 | 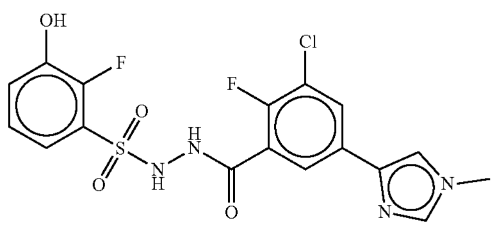 |
| I-445 | 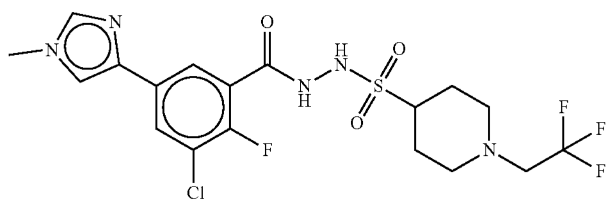 |
| I-451 | 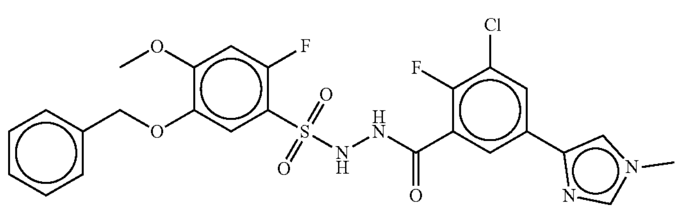 |
| I-452 | 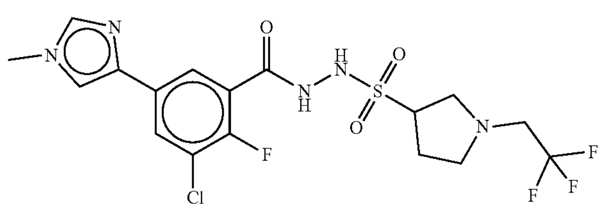 |
| I-453 | 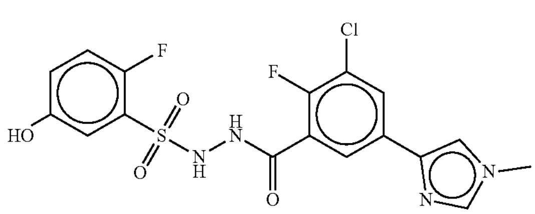 |

| Cmpd No | Compound Structure |
|---|---|
| I-449 | 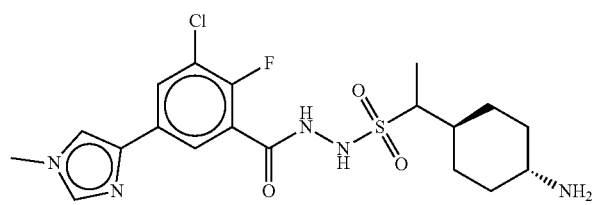 |
| I-450 | 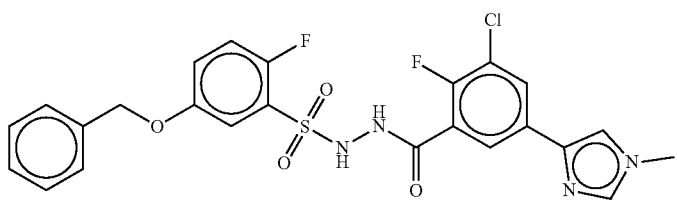 |
| I-456 | 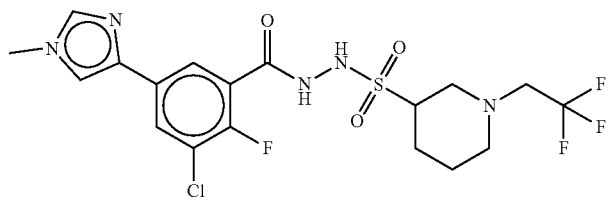 |
| I-457 | 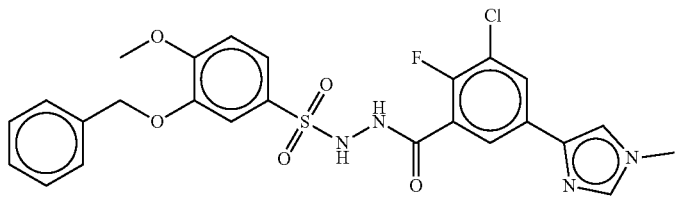 |
| I-458 | 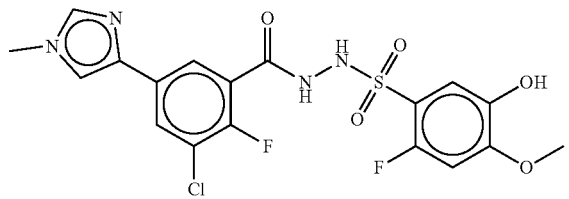 |
| I-454 | 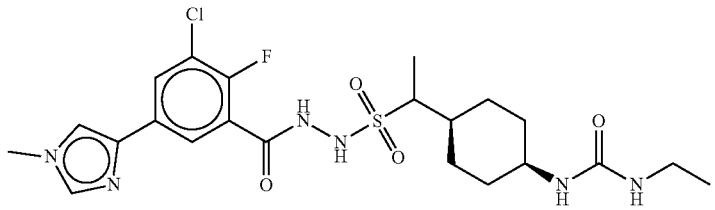 |
| I-455 | 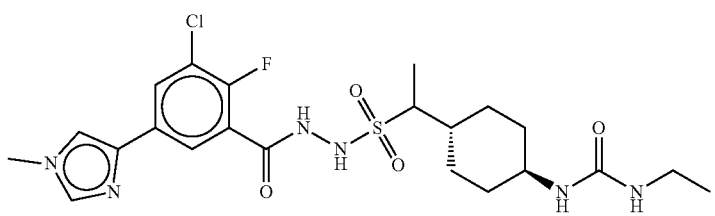 |

-continued

| Cmpd No | Compound Structure |
|---|---|
| I-461 | 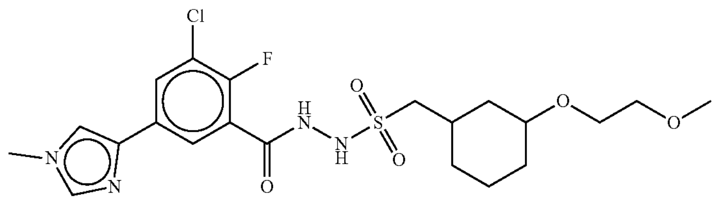 |
| I-462 | 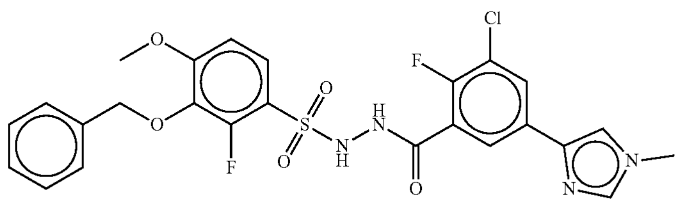 |
| I-463 | 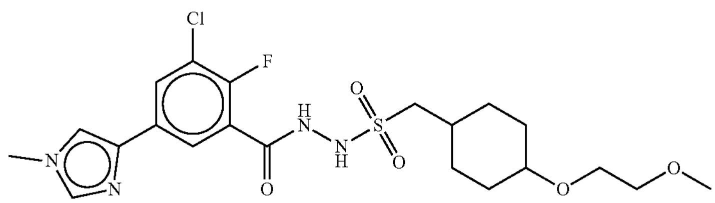 |
| I-459 | 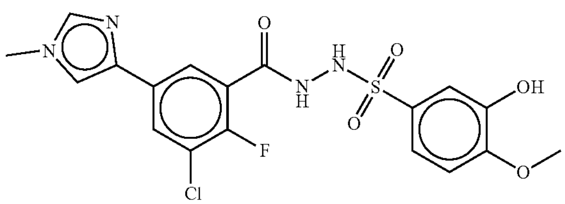 |
| I-460 | 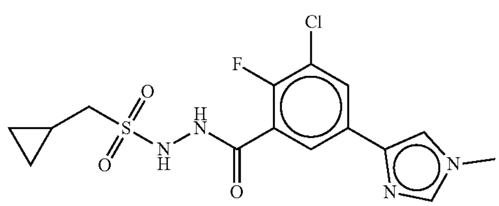 |
| I-466 | 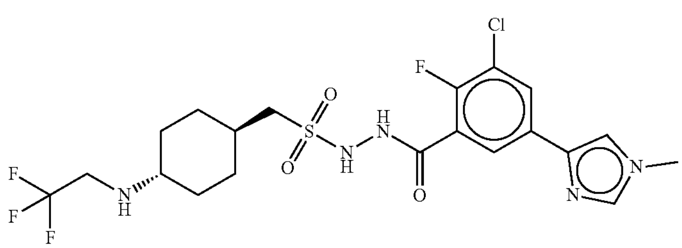 |
| I-467 | 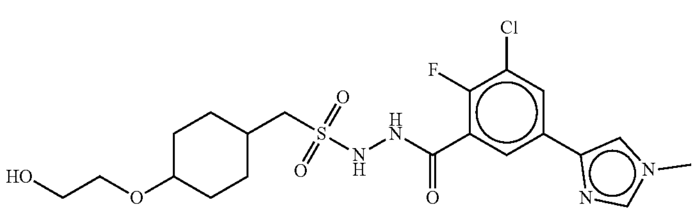 |

| Cmpd No | Compound Structure |
|---|---|
| I-468 | 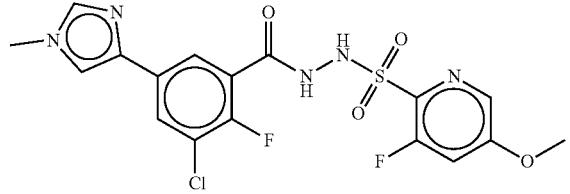 |
| I-464 | 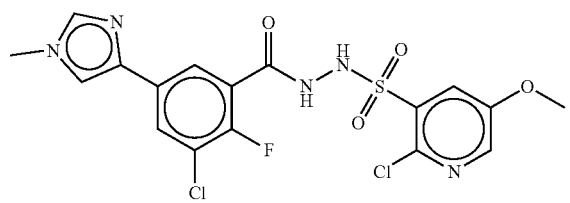 |
| I-465 | 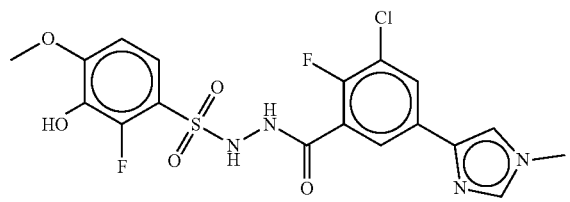 |
| I-471 | 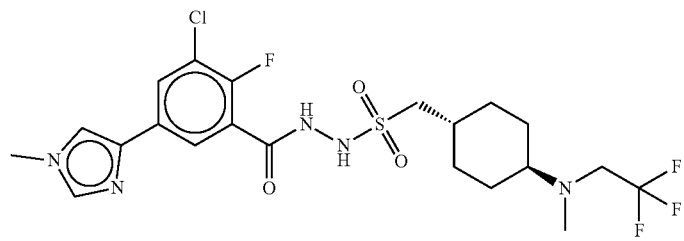 |
| I-472 | 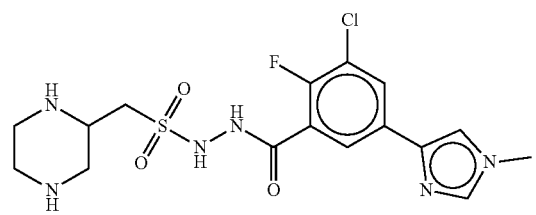 |
| I-473 | 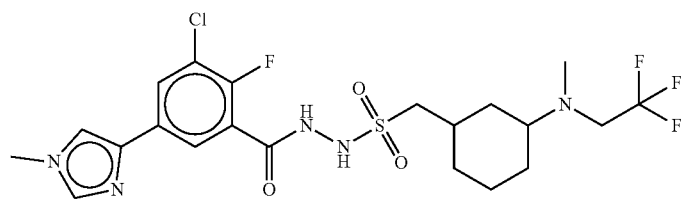 |

| Cmpd No | Compound Structure |
|---|---|
| I-469 | 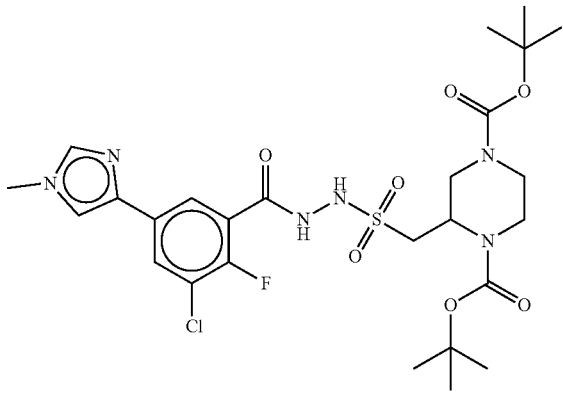 |
| I-470 | 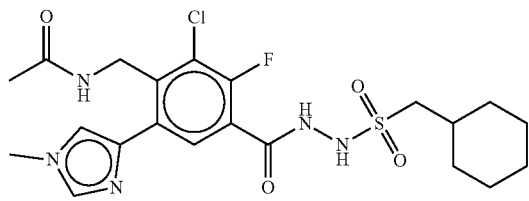 |
| I-476 | 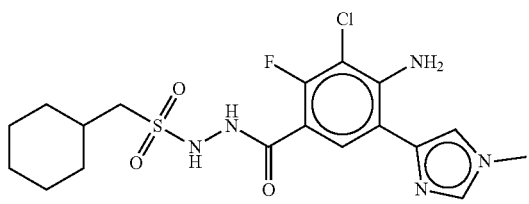 |
| I-477 | 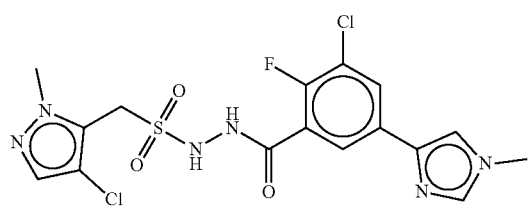 |
| I-478 | 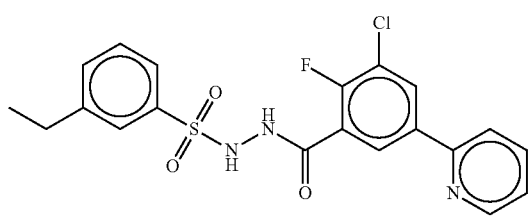 |
| I-474 | 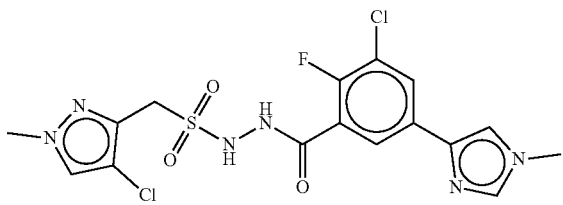 |

| Cmpd No | Compound Structure |
|---|---|
| I-475 | 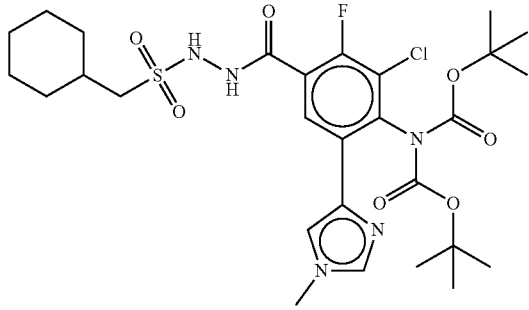 |
| I-481 | 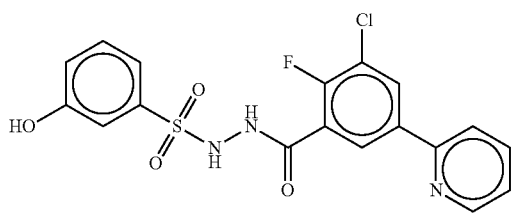 |
| I-482 | 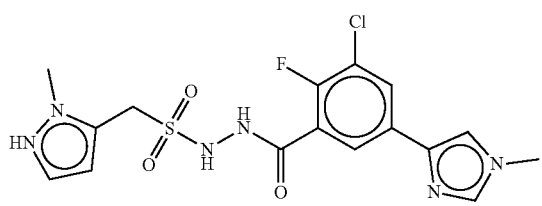 |
| I-479 | 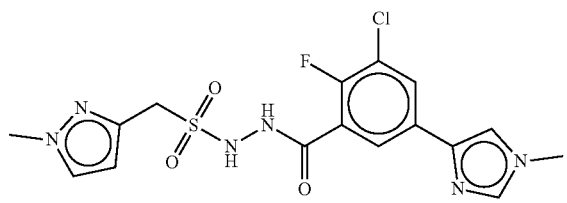 |
| I-480 | 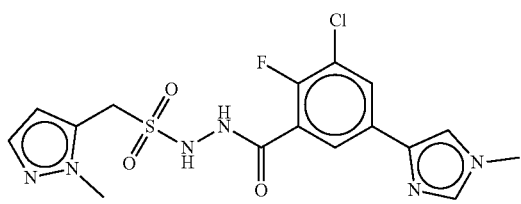 |
| I-483 | 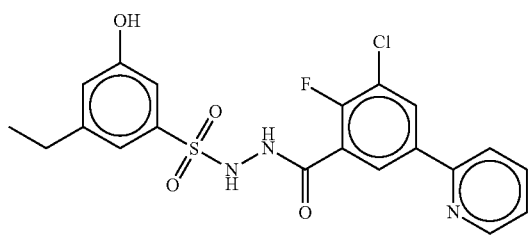 |

In some embodiments of formula I, $R^1$ is fluoro and $R^2$ is chloro, thus forming a compound of formula I-a:

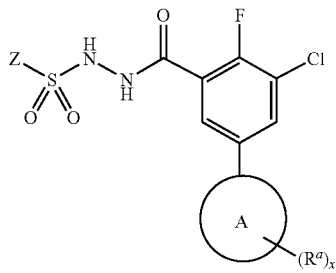

I-a or a pharmaceutically acceptable salt thereof, wherein each of Z, Ring A, $R^a$ and x is as defined above and described in classes and subclasses herein.

As defined above, Z is selected from —Cy, —($C_{1-3}$ aliphatic)-Cy or optionally substituted $C_{1-3}$ aliphatic.

In some embodiments of formula I-a, Z is optionally substituted $C_{1-4}$ aliphatic. In some such embodiments of formula I-a, Z is methyl, ethyl, isopropyl, and tert-butyl.

In some embodiments of formula I-a, Z is —Cy. In some such embodiments of formula I-a, Z is selected from the group consisting of:

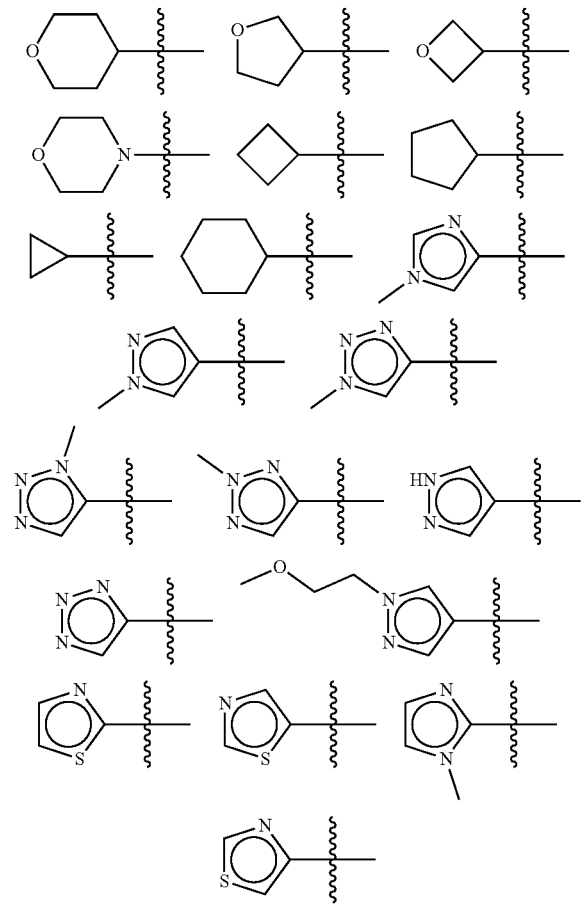

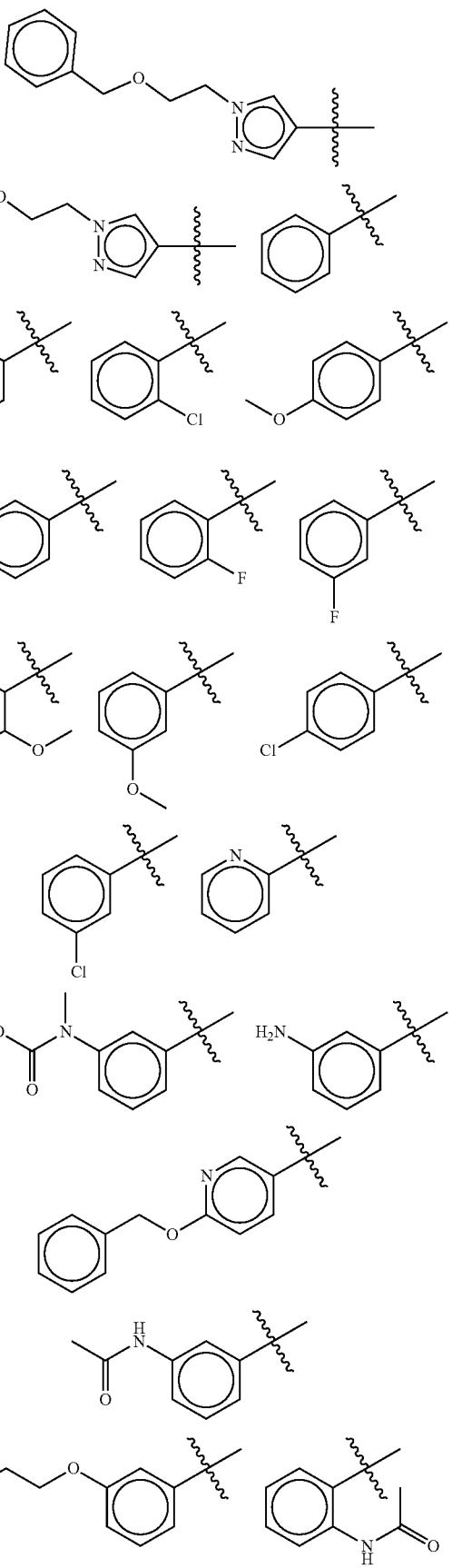

-continued
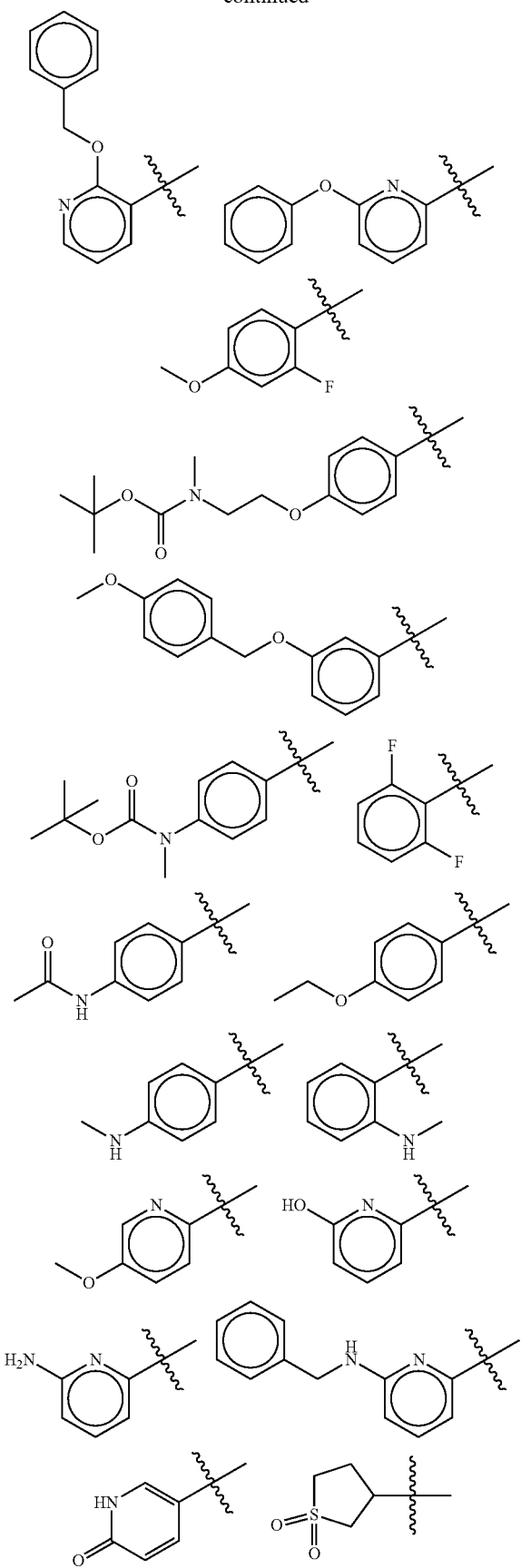
In some embodiments of formula I-a, Z is —Cy. In some such embodiments of formula I-a, Z is selected from the group consisting of:
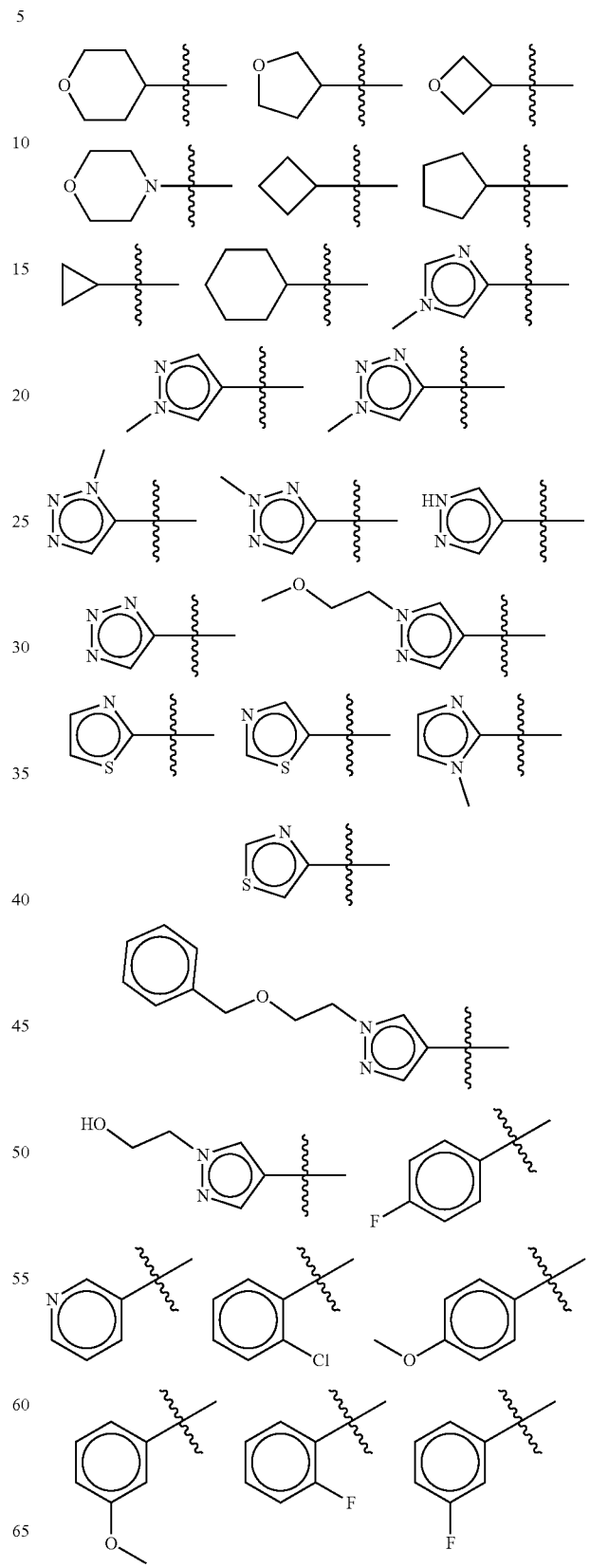

-continued
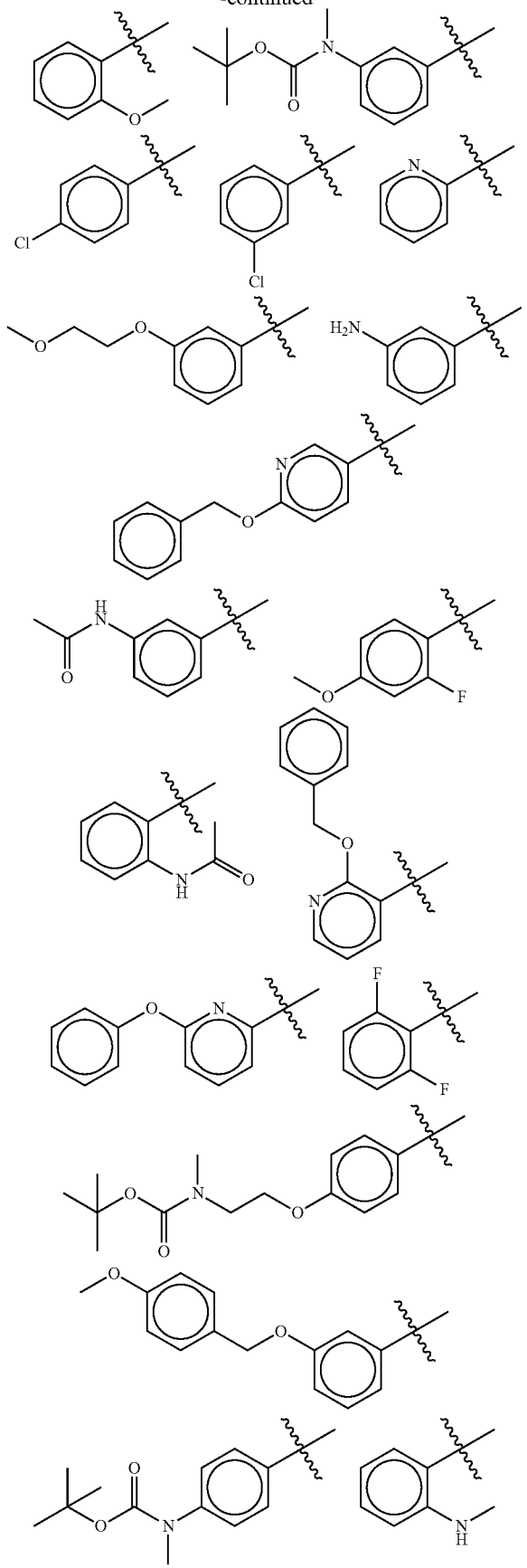
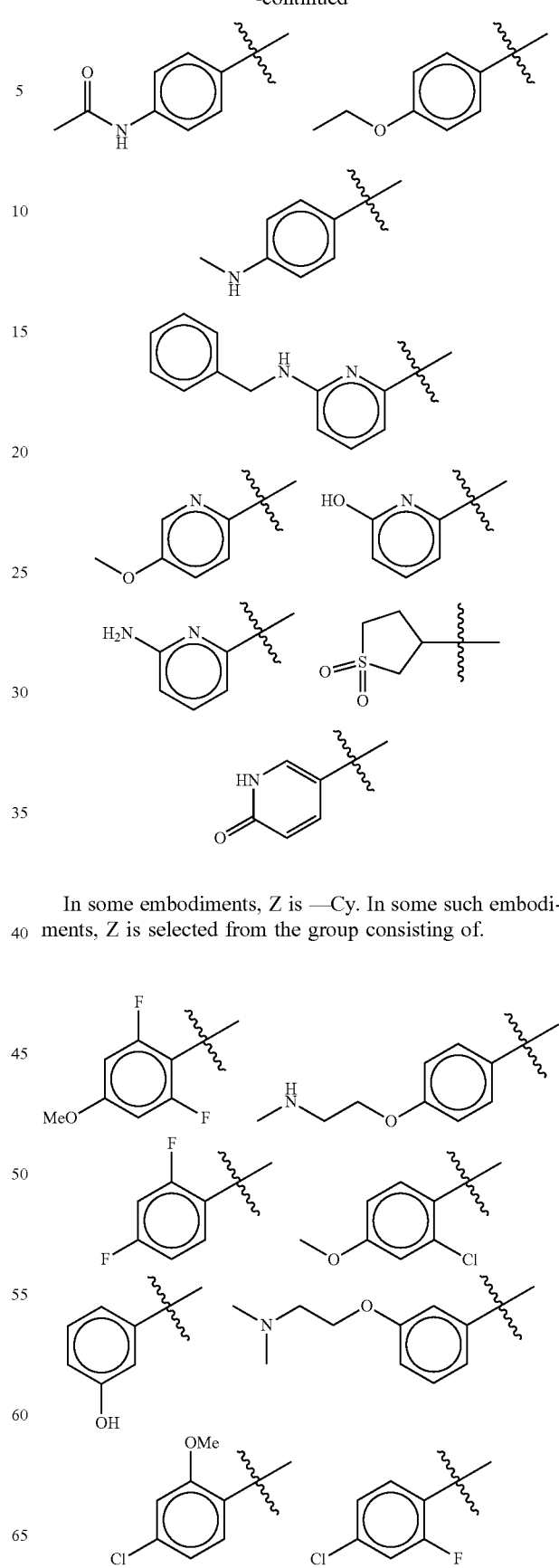
-continued
In some embodiments, Z is —Cy. In some such embodiments, Z is selected from the group consisting of.

-continued
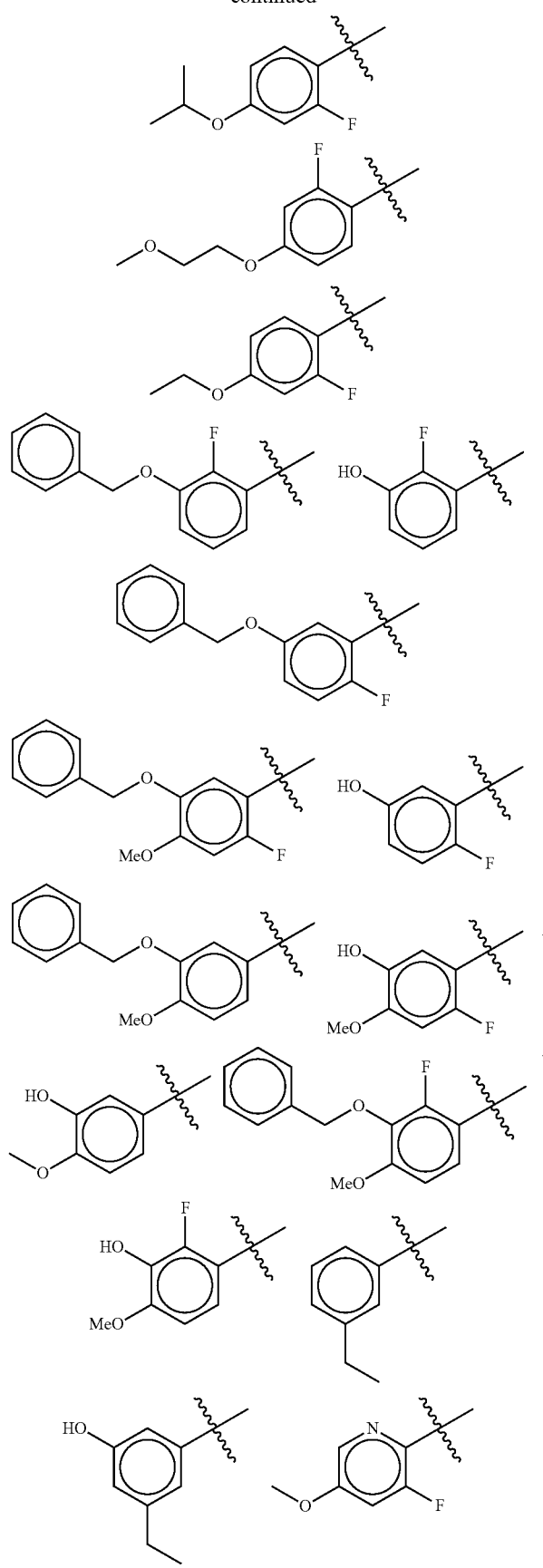
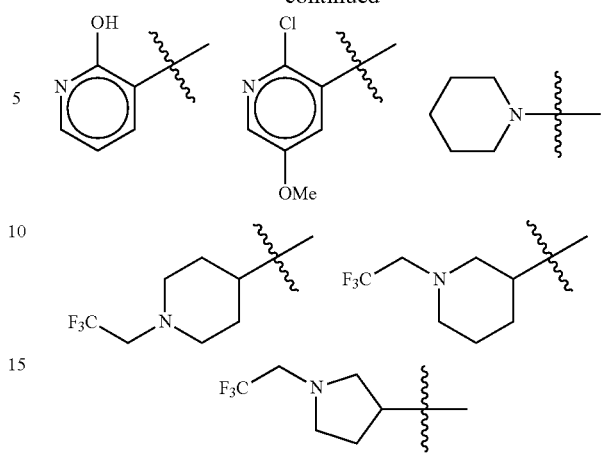
In some embodiments of formula I-a, Z is not:
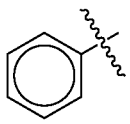
In some embodiments of formula I-a, Z is —(C$_{1-3}$ aliphatic)-Cy. In some such embodiments of formula I-a, Z is —CH$_2$—Cy. In some such embodiments of formula I-a, Z is selected from the group consisting of:
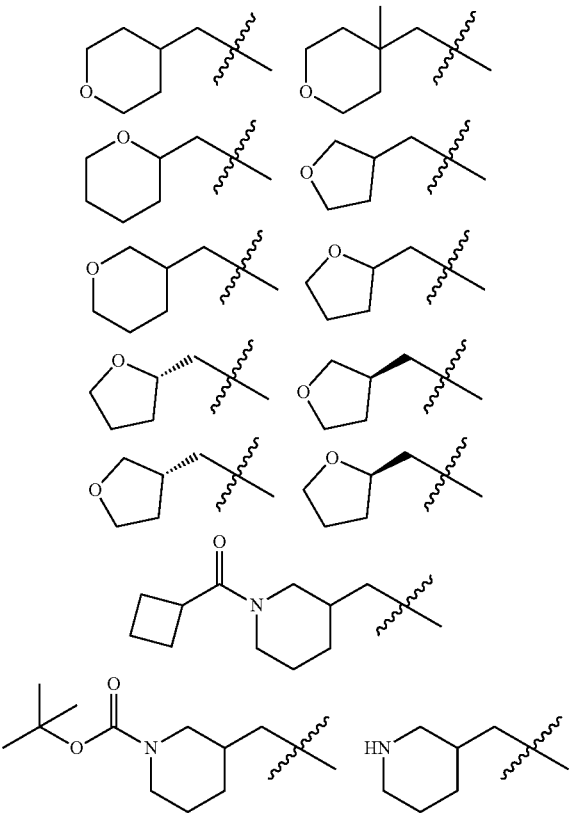

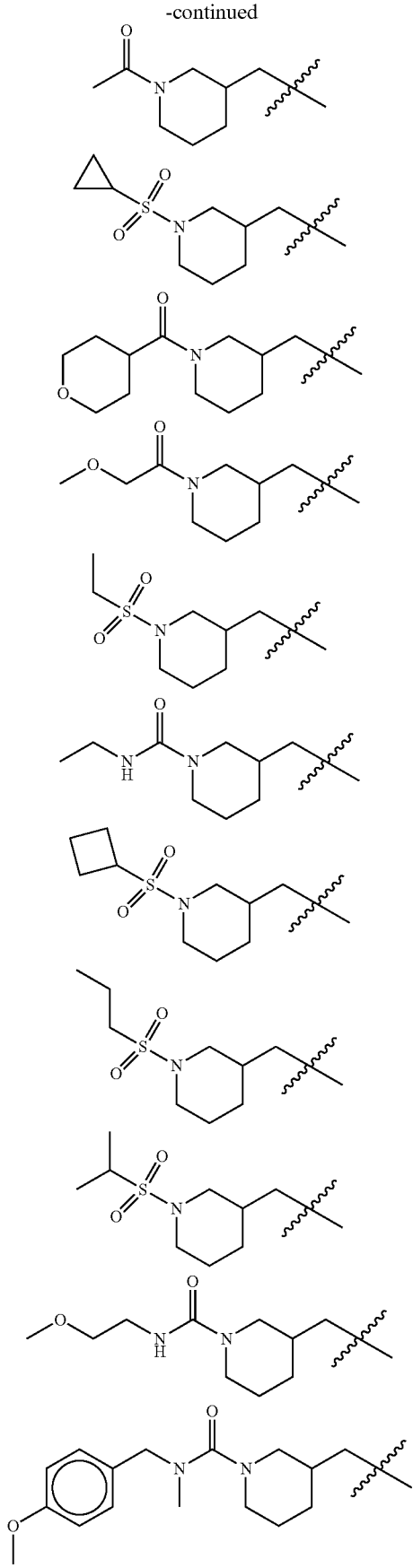
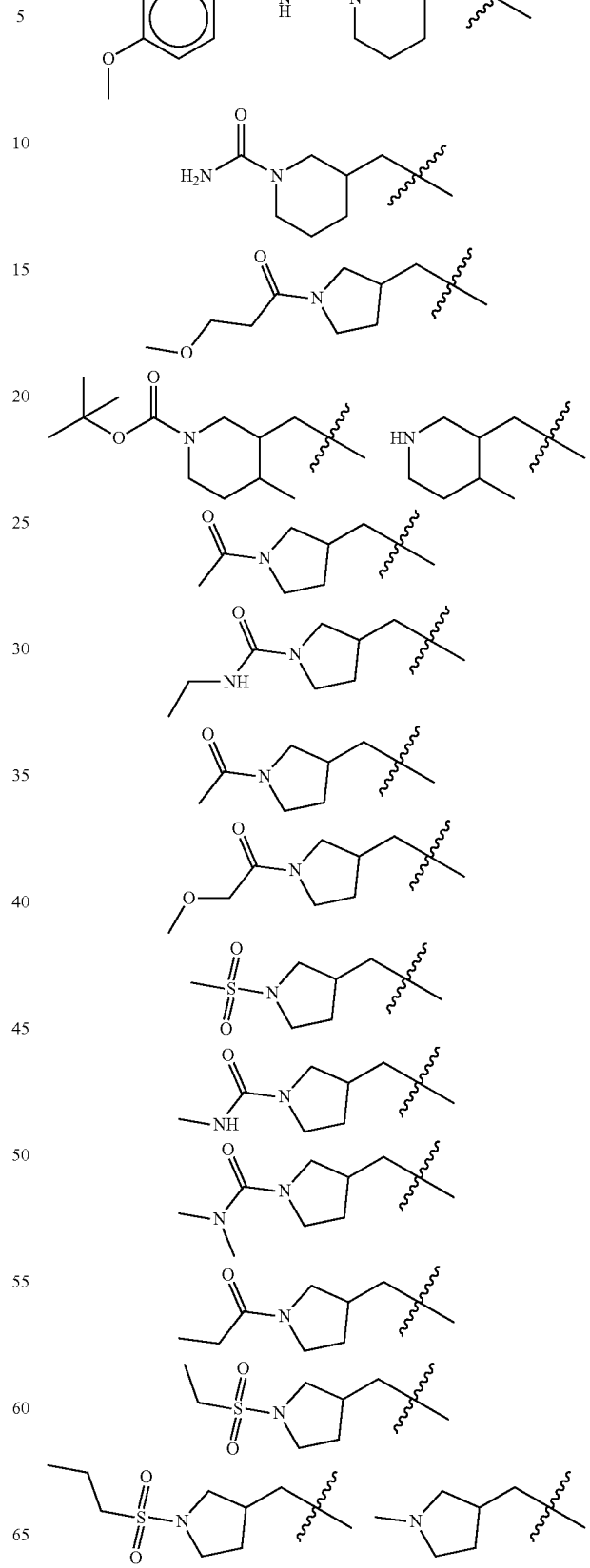

-continued
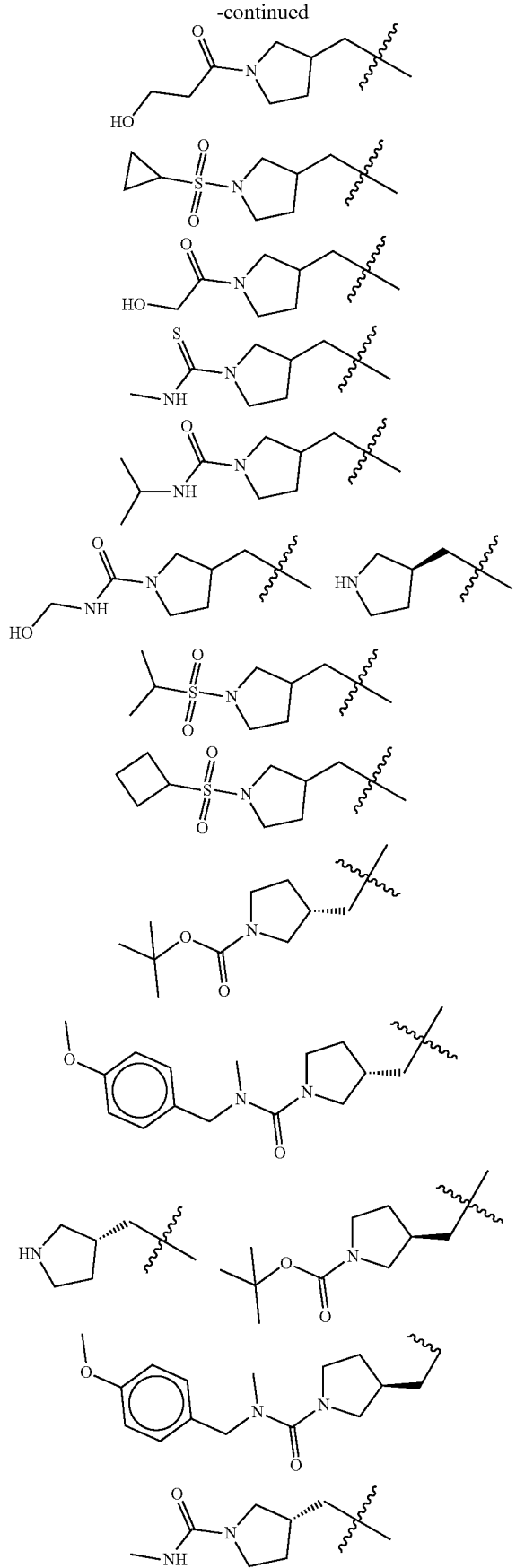
-continued
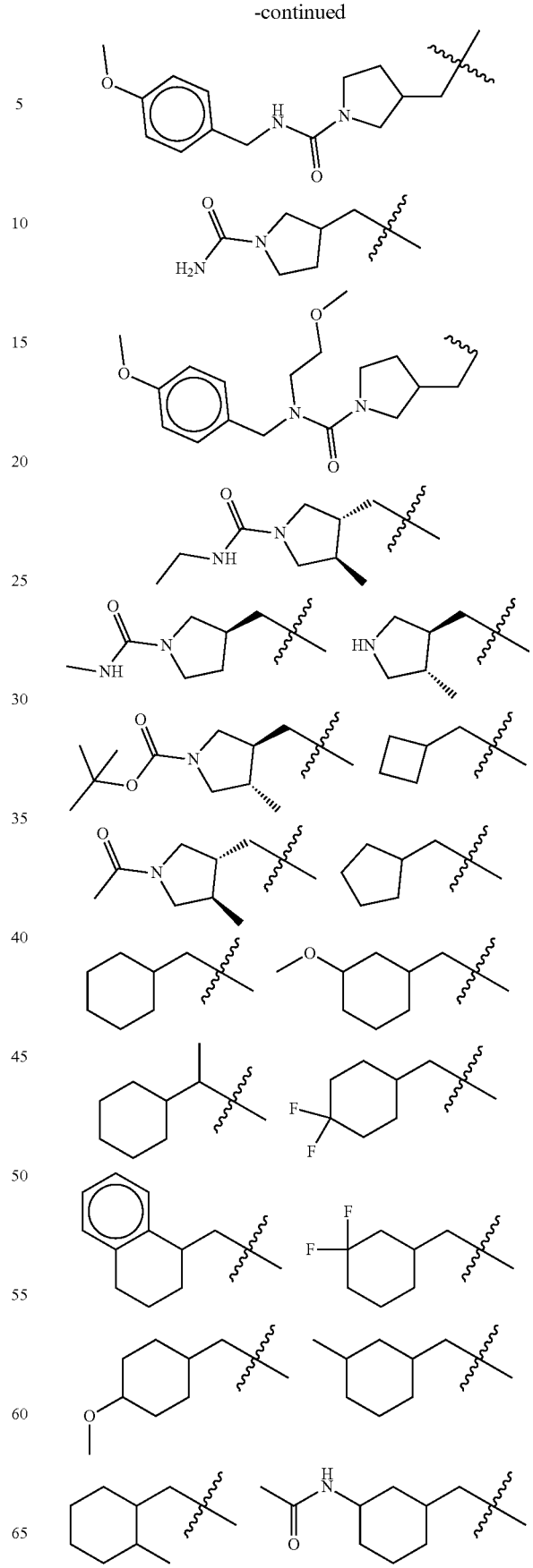

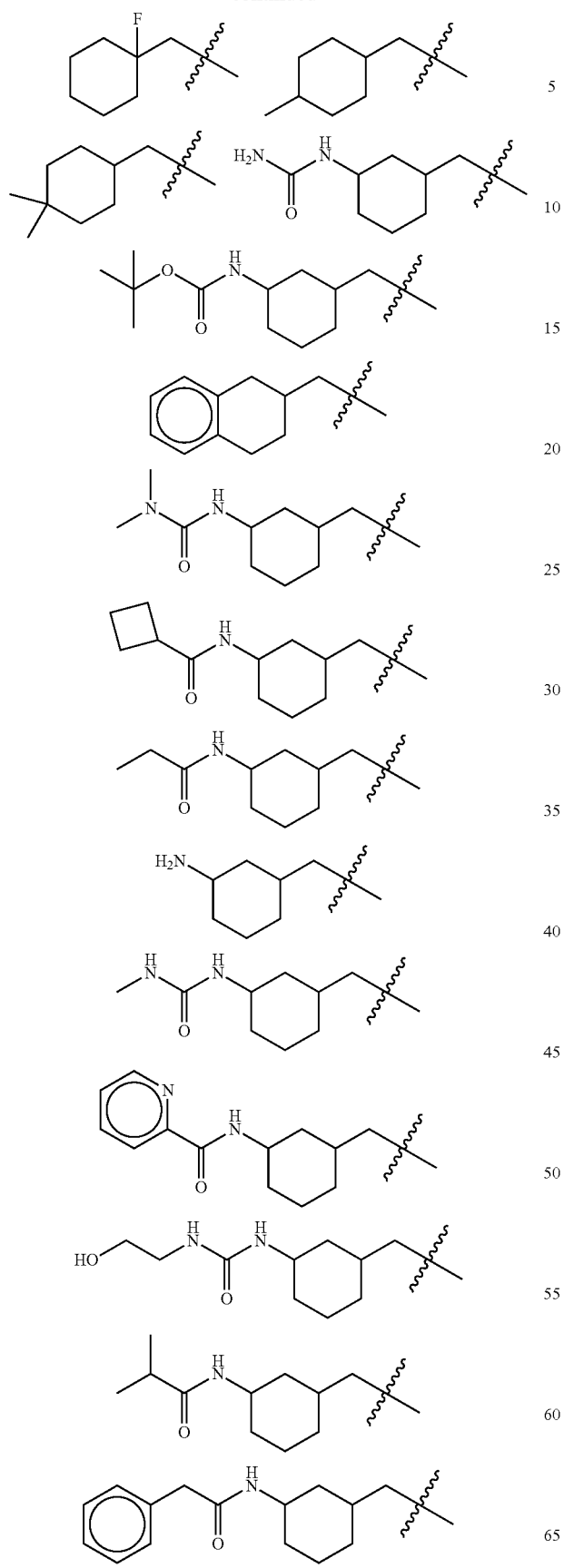
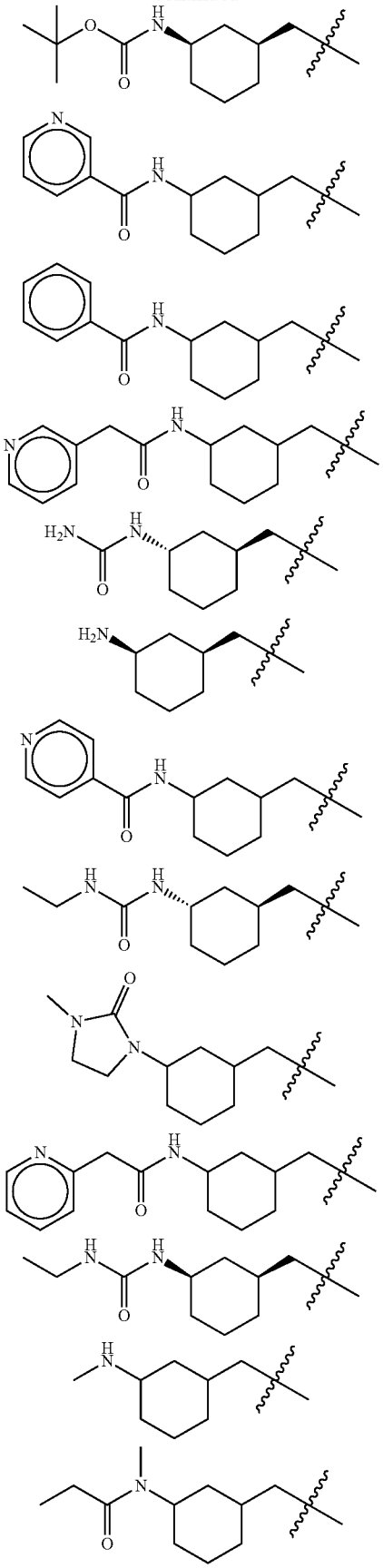

221
-continued
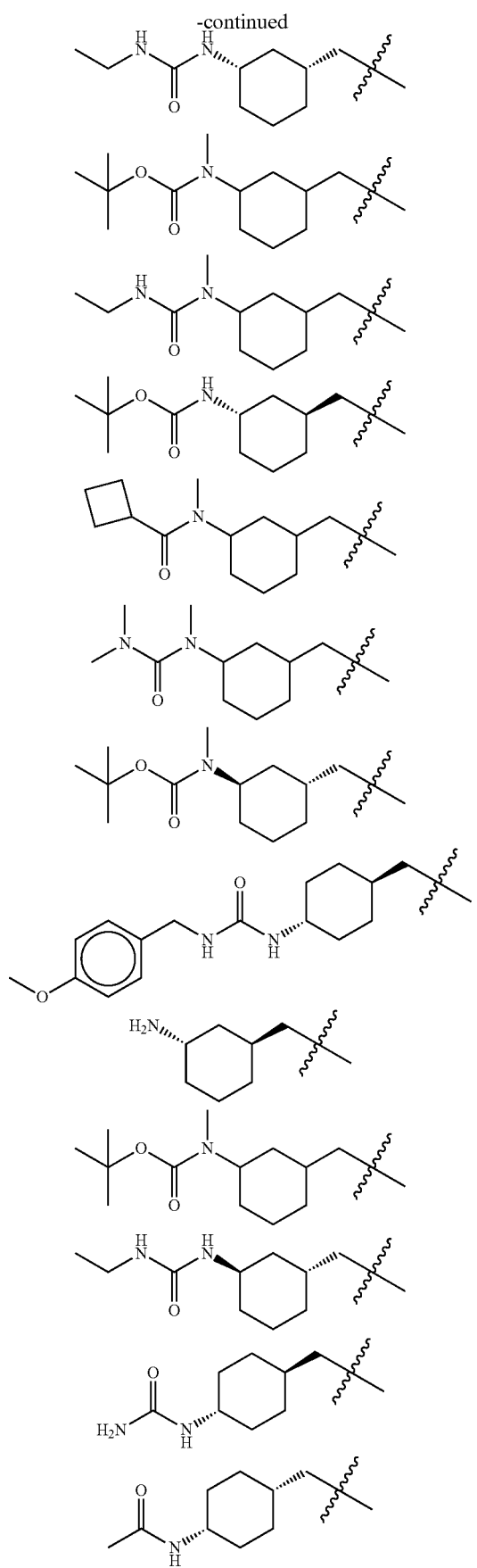
222
-continued
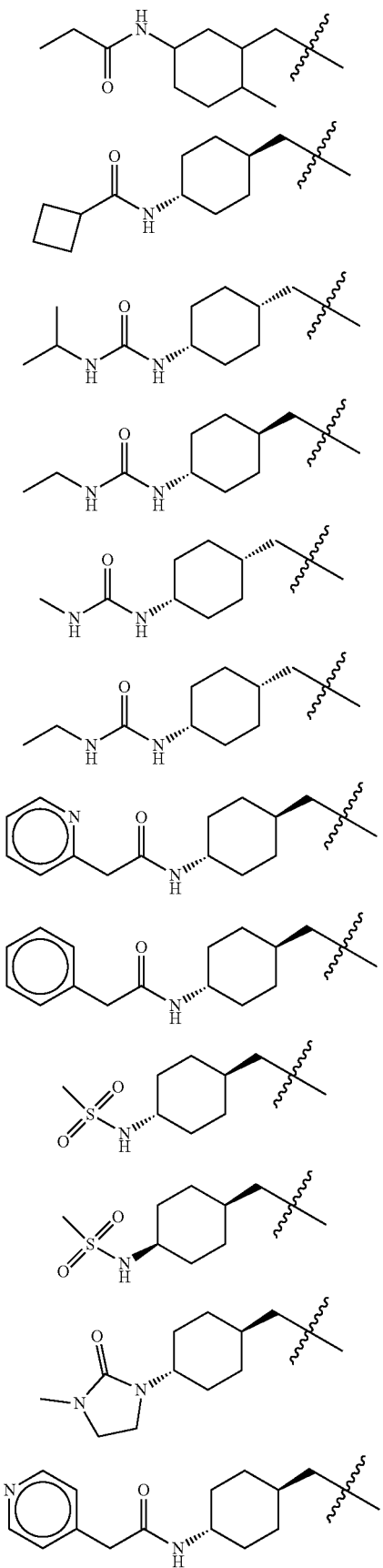

223
-continued
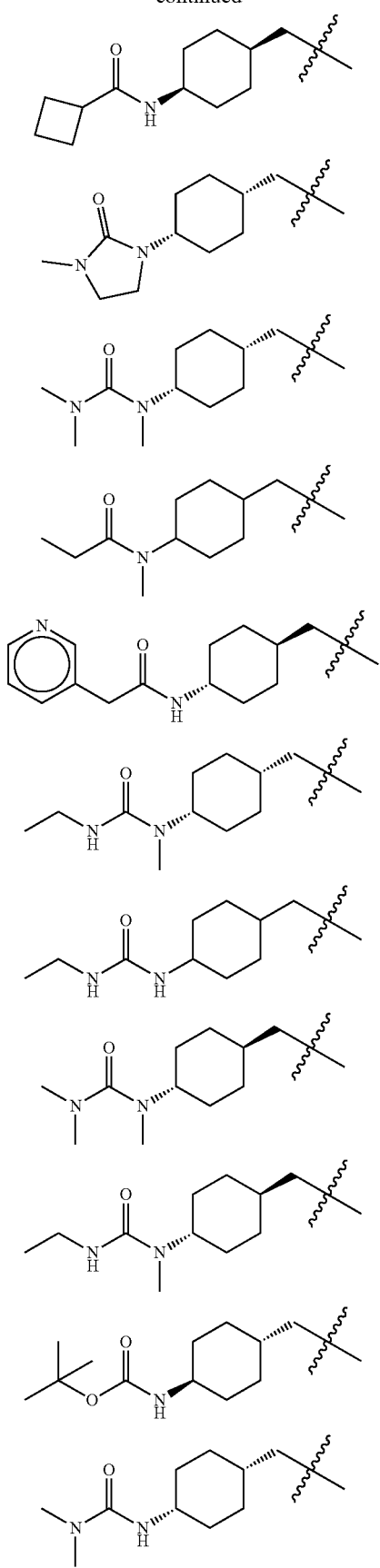
224
-continued
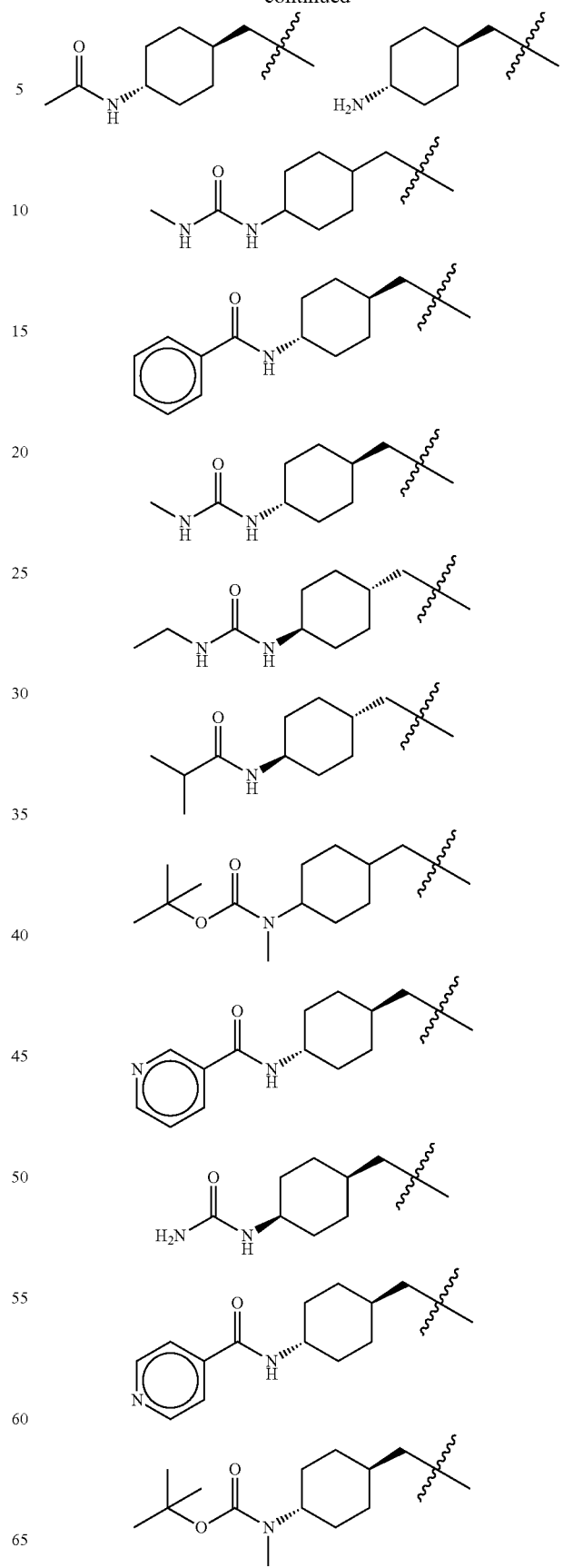

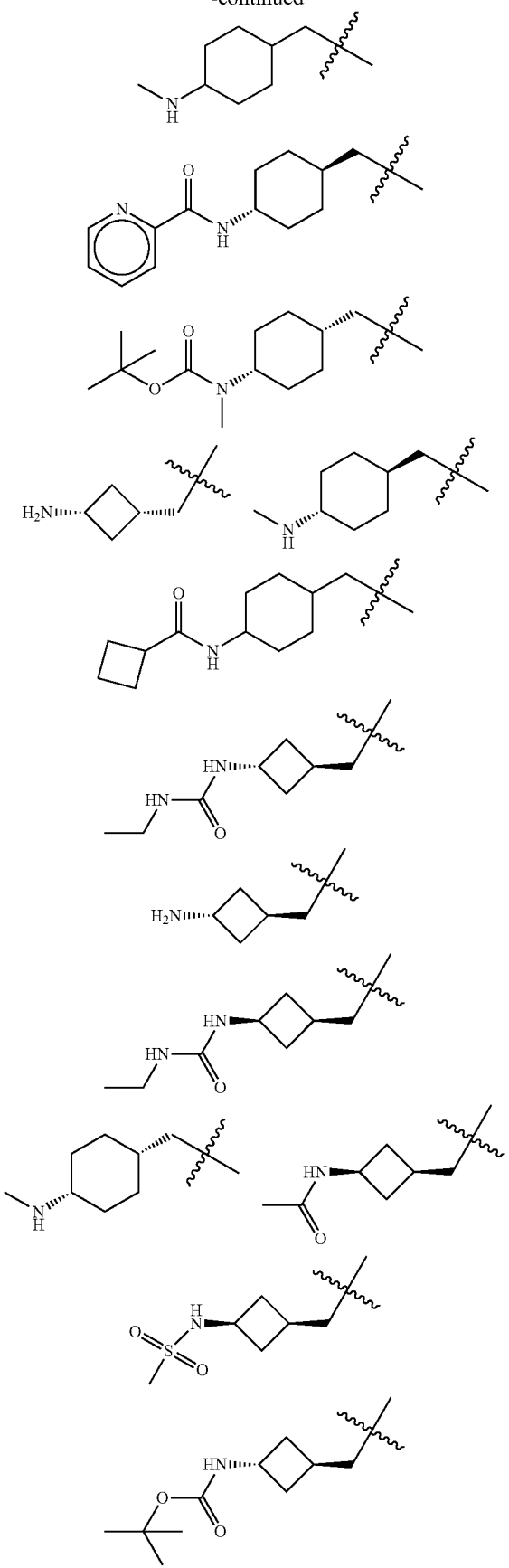
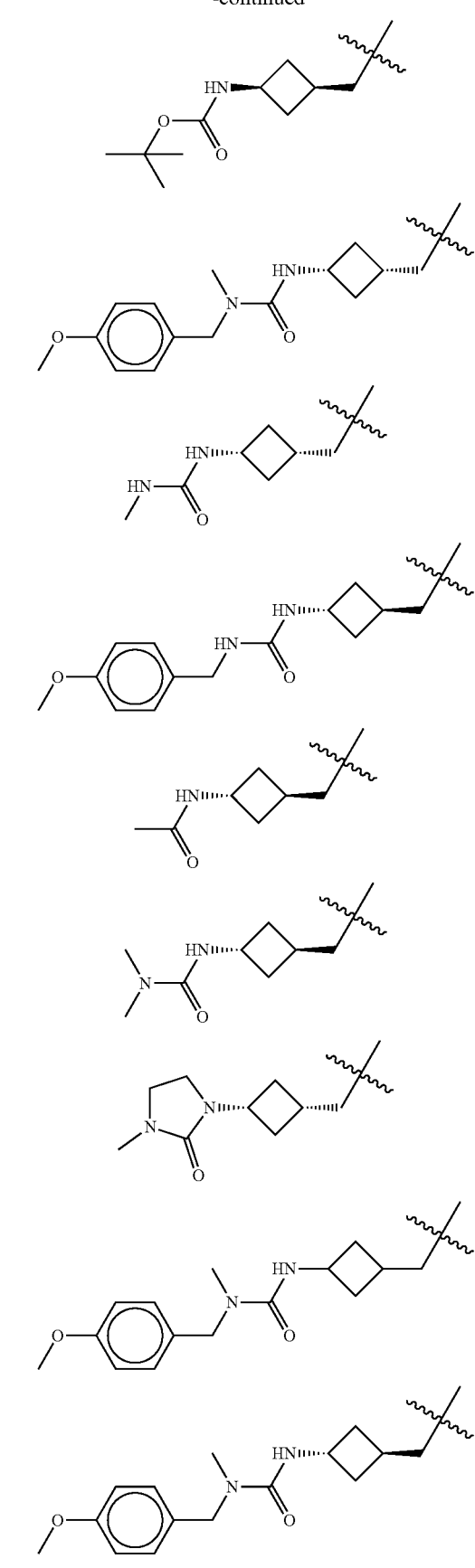

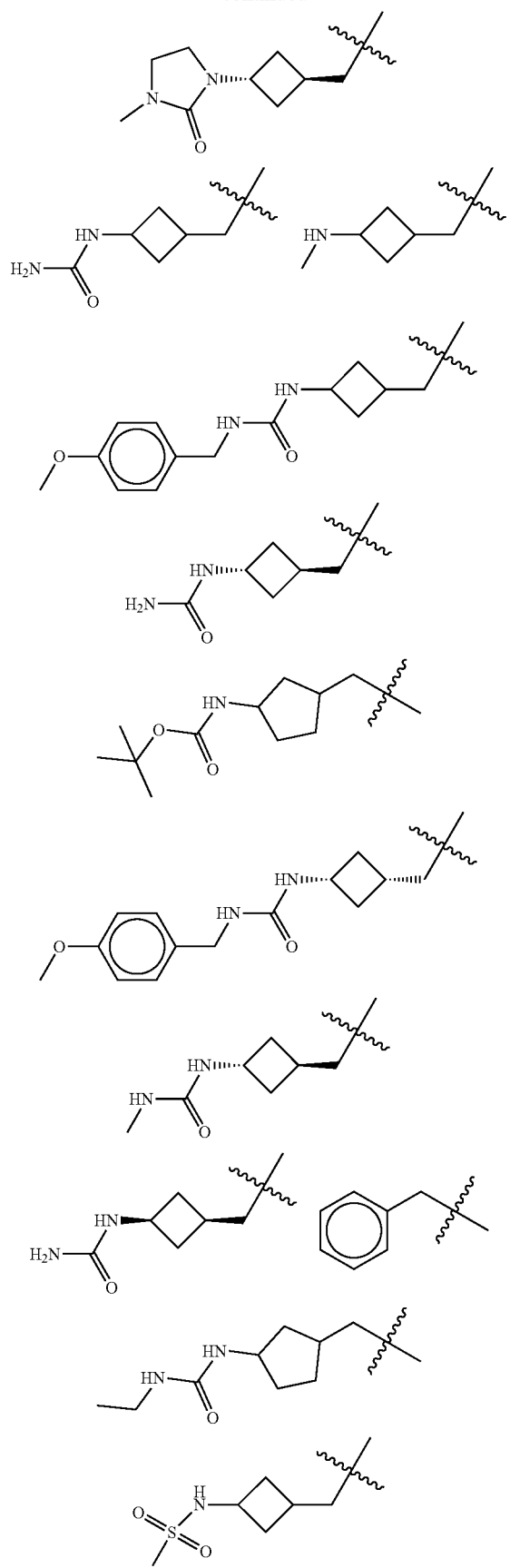
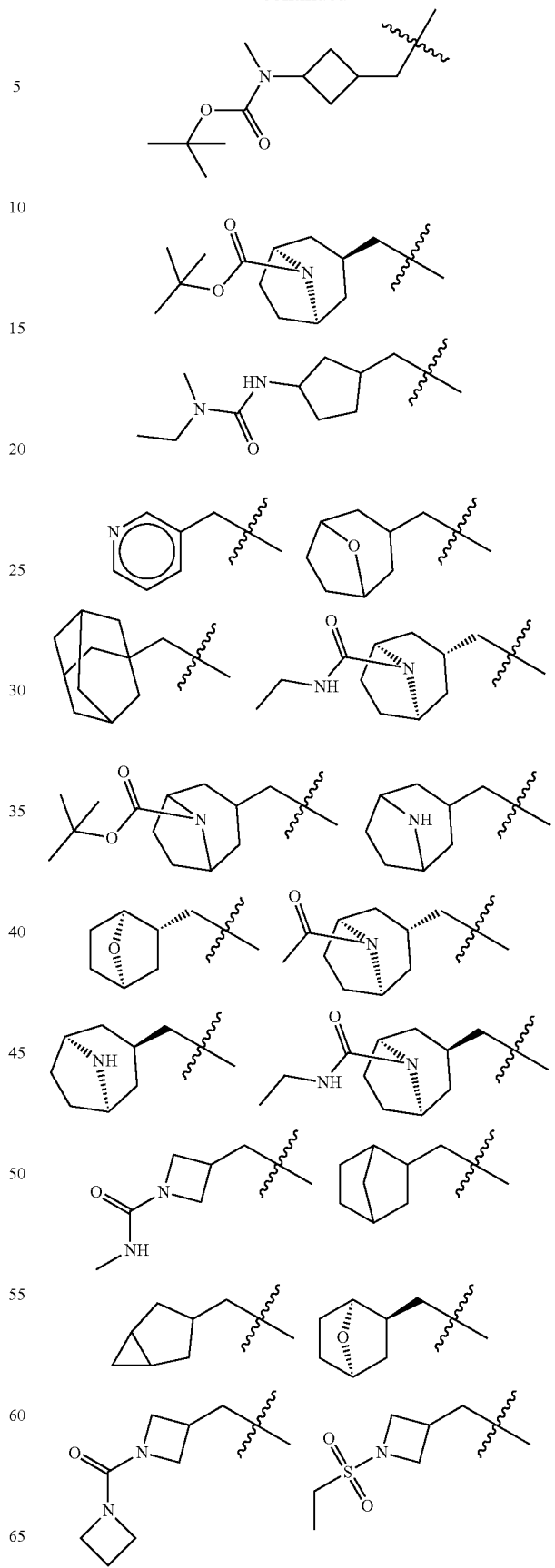

229
-continued
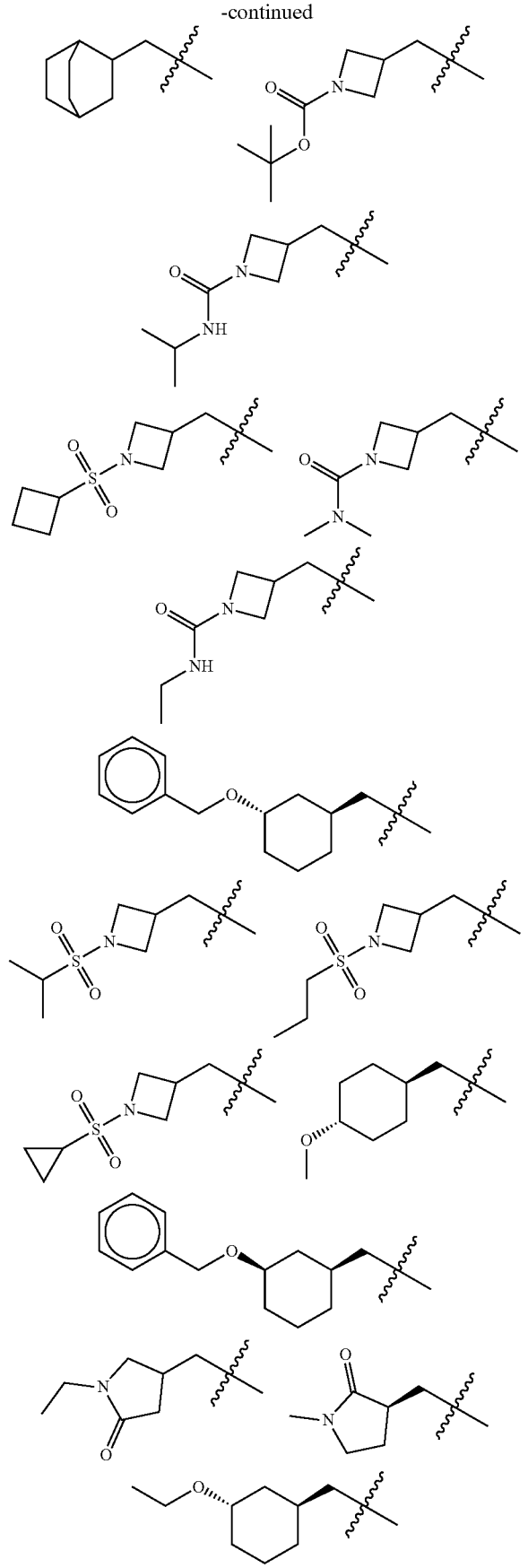
230
-continued
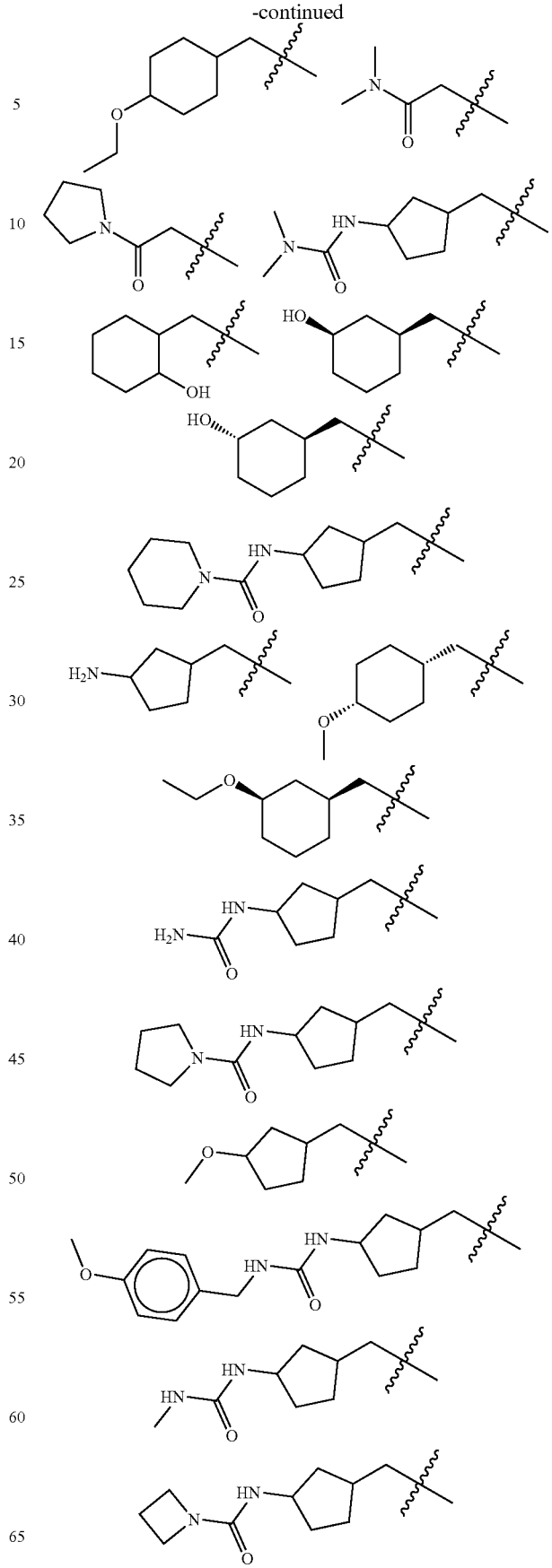

-continued
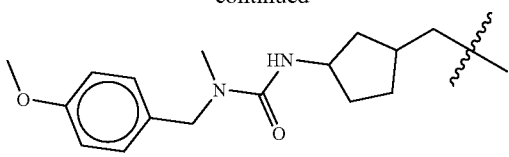
In some embodiments, Z is —(C$_{1-3}$ aliphatic)-Cy. In some such embodiments, Z is —CH$_2$—Cy. In some such embodiments, Z is selected from the group consisting of:
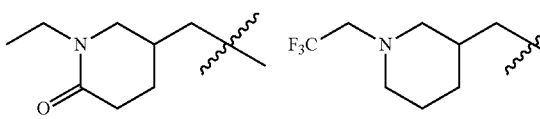
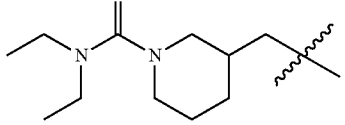
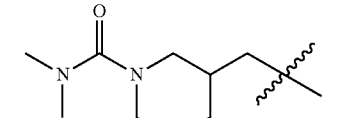
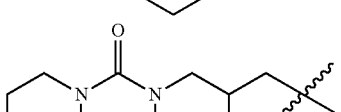

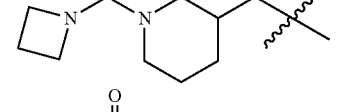

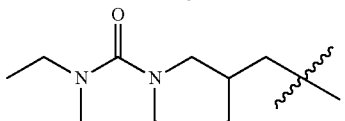

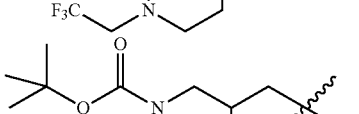
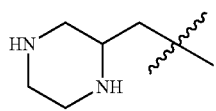 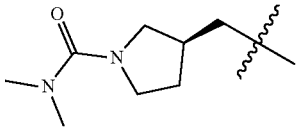
-continued
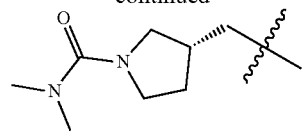
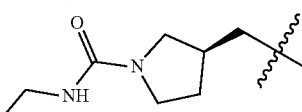
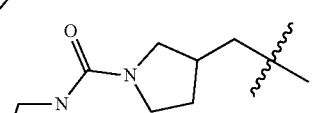
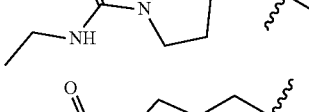
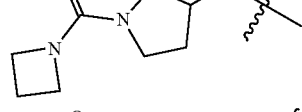
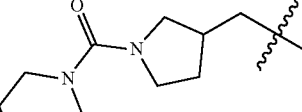
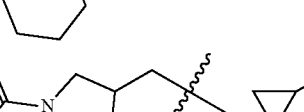
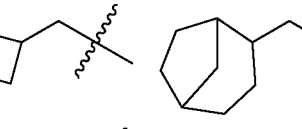
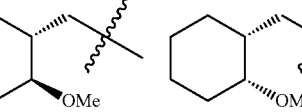
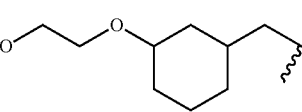
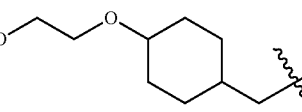
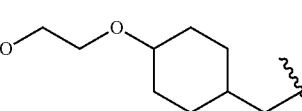
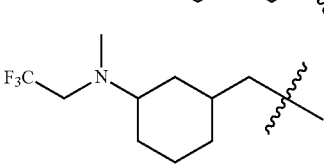

-continued

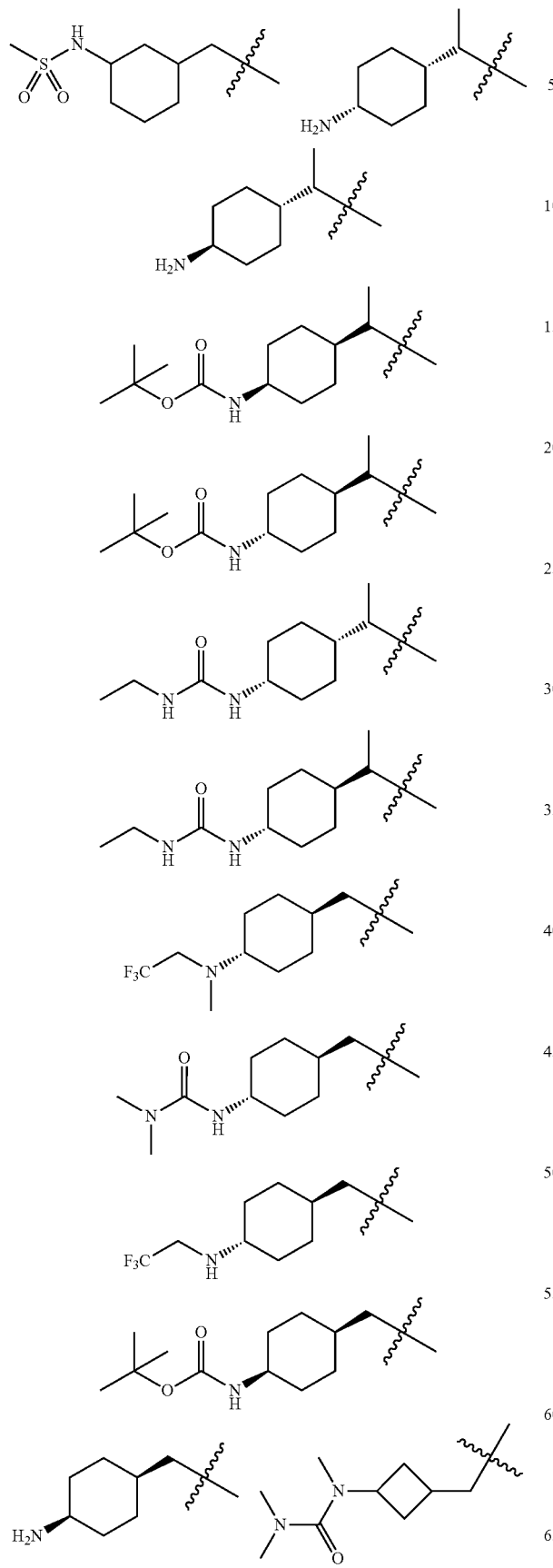

-continued

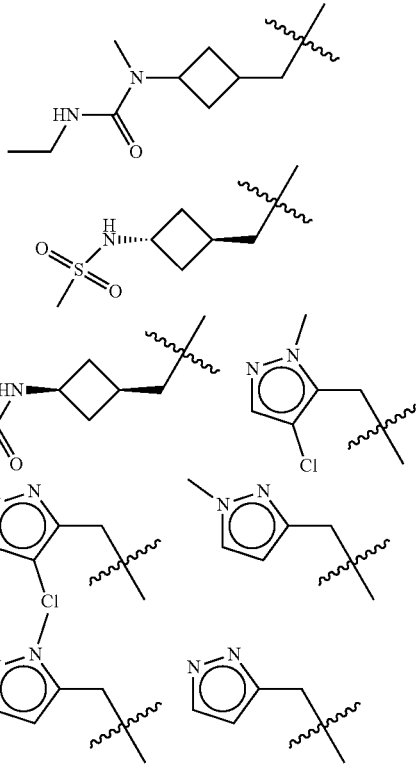

As defined above, Cy is an optionally substituted group selected from phenyl, a 3-10 membered saturated or partially unsaturated carbocyclic ring, a 3-10 membered saturated or partially unsaturated heterocyclic ring having 1-2 heteroatoms independently selected from nitrogen, oxygen and sulfur, a 6-8 membered bridged bicyclic heterocyclic ring having 1-2 heteroatoms independently selected from nitrogen, oxygen and sulfur, a 5-6 membered heteroaryl ring having 1-2 heteroatoms independently selected from nitrogen, oxygen and sulfur, an 8-10 membered bicyclic aryl ring, and an 8-10 membered bicyclic heteroaryl ring having 1-3 heteroatoms independently selected from nitrogen oxygen and sulfur.

In some embodiments of formula I-a, Cy is phenyl.

In some embodiments of formula I-a, Cy is an optionally substituted 3-10 membered saturated or partially unsaturated carbocyclic ring. In some embodiments, Cy is an optionally substituted 3-10 membered saturated carbocyclic ring. In some such embodiments, Cy is an optionally substituted group selected from cyclopropyl, cyclobutyl, cyclopentyl, cyclohexyl, cycloheptyl.

In some embodiments of formula I-a, Cy is an optionally substituted bicyclic carbocyclic ring. It will be appreciated that a bicyclic carbocyclic ring can be a bridged bicyclic ring. In some such embodiments of formula I-a, Cy is an optionally substituted group selected from:

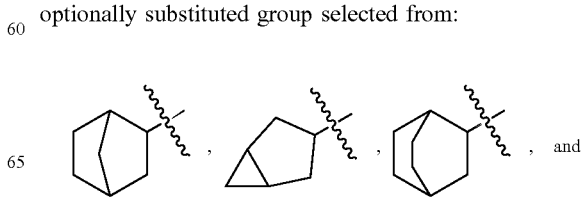

, and

-continued

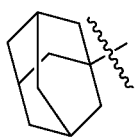

In some such embodiments, Cy is an optionally substituted group selected from:

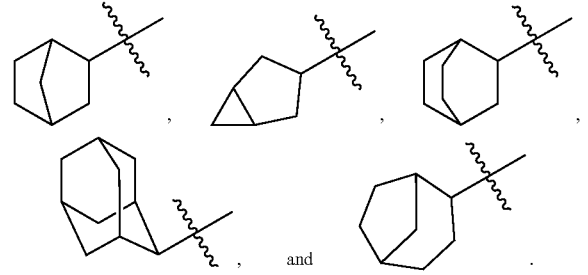

In some such embodiments Cy is an optionally substituted group selected from:

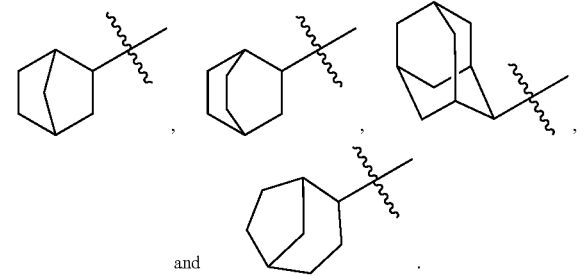

In some embodiments of formula I-a, Cy is an optionally substituted 5-6 membered heteroaryl ring having 1-3 heteroatoms independently selected from nitrogen, oxygen and sulfur. In some embodiments of formula I-a, Cy is a 5-membered heteroaryl ring having 1-3 heteroatoms independently selected from nitrogen, oxygen and sulfur. In some such embodiments of formula I-a, Cy is an optionally substituted group selected from pyrazolyl, imidazolyl, and triazolyl. In some embodiments of formula I-a, Cy is an optionally substituted group selected from:

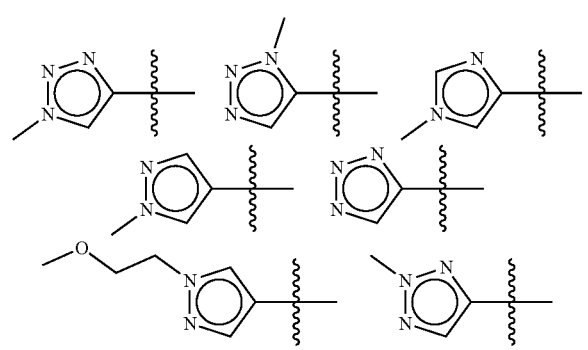

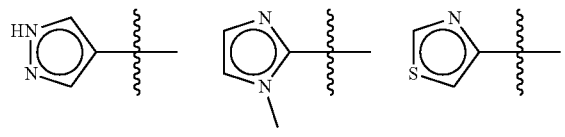

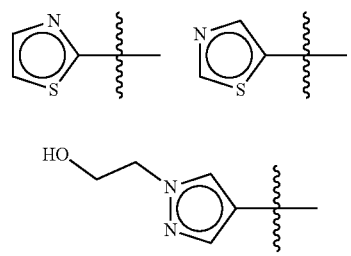

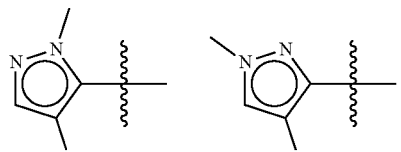

In some embodiments of formula I-a, Cy is an optionally substituted group selected from:

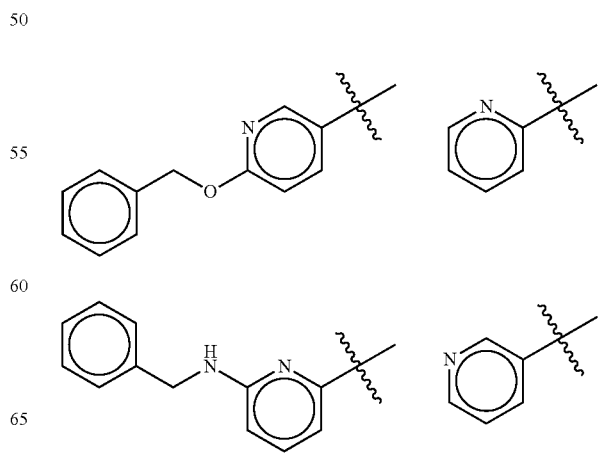

In some embodiments of formula I-a, Cy is an optionally substituted 5-6 membered heteroaryl ring having 1-3 heteroatoms independently selected from nitrogen, oxygen and sulfur. In some embodiments of formula I-a, Cy is a 6-membered heteroaryl ring having 1-3 heteroatoms independently selected from nitrogen, oxygen and sulfur. In some such embodiments of formula I-a, Cy is an optionally substituted group selected from pyridinyl. In some embodiments of formula I-a, Cy is an optionally substituted group selected from:

-continued

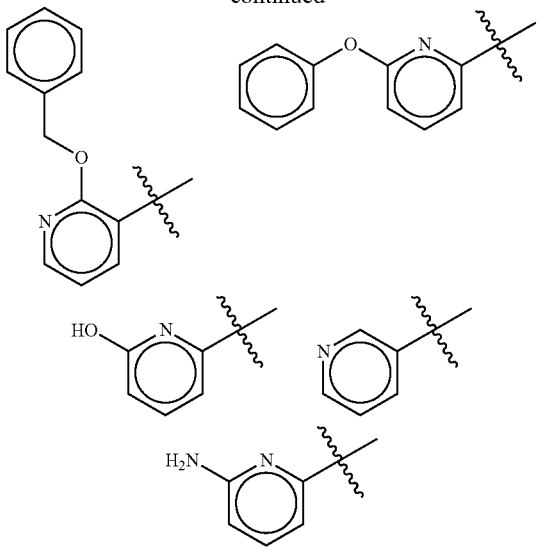

In some embodiments of formula I-a, Cy is an optionally substituted group selected from:

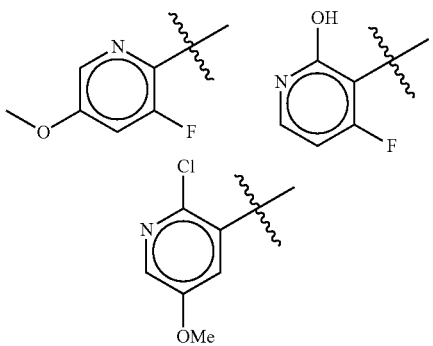

In some embodiments of formula I-a, Cy is an optionally substituted 3-10 membered saturated or partially unsaturated heterocyclic ring having 1-2 heteroatoms independently selected from nitrogen, oxygen and sulfur.

In some embodiments of formula I-a, Cy is an optionally substituted 4-membered saturated heterocyclic group having 1 heteroatom independently selected from nitrogen, oxygen and sulfur. In some such embodiments of formula I-a, Cy is optionally substituted oxetanyl. In some such embodiments, Cy is optionally substituted oxetanyl or azetidinyl.

In some embodiments of formula I-a, Cy is an optionally substituted 5-membered saturated heterocyclic group having 1-2 heteroatoms independently selected from nitrogen, oxygen and sulfur. In some such embodiments of formula I-a, Cy is an optionally substituted group selected from tetrahydrofuranyl and pyrrolidinyl.

In some embodiments of formula I-a, Cy is an optionally substituted 6-membered saturated heterocyclic group having 1-2 heteroatoms independently selected from nitrogen, oxygen and sulfur. In some such embodiments of formula I-a, Cy is an optionally substituted group selected from tetrahydropyranyl and piperidinyl. In some such embodiments, Cy is an optionally substituted group selected from tetrahydropyranyl, piperidinyl, and piperazinyl.

In some embodiments of formula I-a, Cy is an optionally substituted 7-membered saturated heterocyclic group having 1-2 heteroatoms independently selected from nitrogen, oxygen and sulfur. It will be appreciated that a 7-membered saturated heterocyclic ring can be a bridged bicyclic ring. In some such embodiments of formula I-a, Cy is an optionally substituted group selected from:

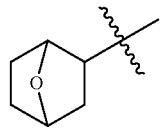

In some embodiments of formula I-a, Cy is an optionally substituted 8-membered saturated heterocyclic group having 1-2 heteroatoms independently selected from nitrogen, oxygen and sulfur. It will be appreciated that an 8-membered saturated heterocyclic ring can be a bridged bicyclic ring. In some such embodiments of formula I-a, Cy is an optionally substituted group selected from:

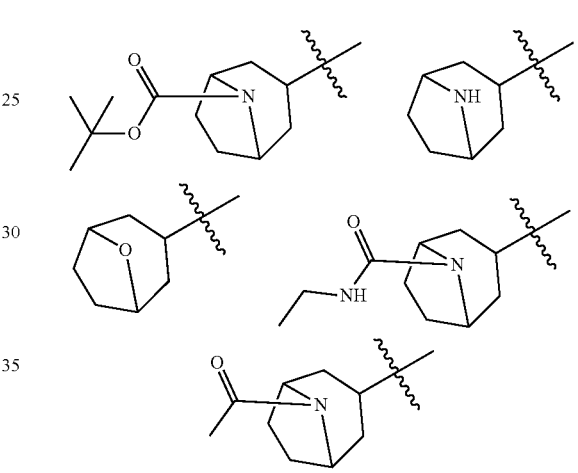

As defined above, each of $R^1$ and $R^2$ is independently selected from halogen and $C_{1-4}$ aliphatic. In some embodiments of formula I-a, $R^1$ is fluoro. In some embodiments of formula I-a, $R^1$ is chloro. In some embodiments of formula I-a, $R^1$ is methyl. In some embodiments of formula I-a, $R^2$ is fluoro. In some embodiments of formula I-a, $R^2$ is chloro. In some embodiments of formula I-a, $R^2$ is methyl. In some embodiments of formula I-a, $R^1$ is fluoro and $R^2$ is chloro. In some embodiments of formula I-a, $R^1$ is fluoro and $R^2$ is methyl. In some embodiments of formula I-a, $R^1$ is fluoro and $R^2$ is fluoro. In some embodiments of formula I-a, $R^1$ is chloro and $R^2$ is chloro. In some embodiments of formula I-a, $R^1$ is methyl and $R^2$ is methyl.

As defined above, Ring A is an optionally substituted 5- or 6-membered heteroaryl ring having 1-4 heteroatoms independently selected from nitrogen, oxygen and sulfur.

In some embodiments of formula I-a, Ring A is an optionally substituted 5-membered heteroaryl ring having 1-4 heteroatoms independently selected from nitrogen, oxygen and sulfur. In some embodiments of formula I-a, Ring A is an optionally substituted 5-membered heteroaryl ring having 2-3 nitrogen atoms. In some such embodiments of formula I-a, Ring A is selected from pyrazolyl, imidazolyl, and triazolyl.

In some embodiments of formula I, Ring A is an optionally substituted 5-membered heteroaryl ring having 4 nitrogen atoms. In some embodiments of formula I-a, Ring A is tetrazol-5-yl.

In some embodiments of formula I-a, Ring A is an optionally substituted 5-membered heteroaryl ring having 1 nitrogen atom and 1 additional heteroatom selected from oxygen and sulfur. In some such embodiments of formula I-a, Ring A is selected from oxazolyl and thiazolyl.

In some embodiments of formula I-a, Ring A is selected from:

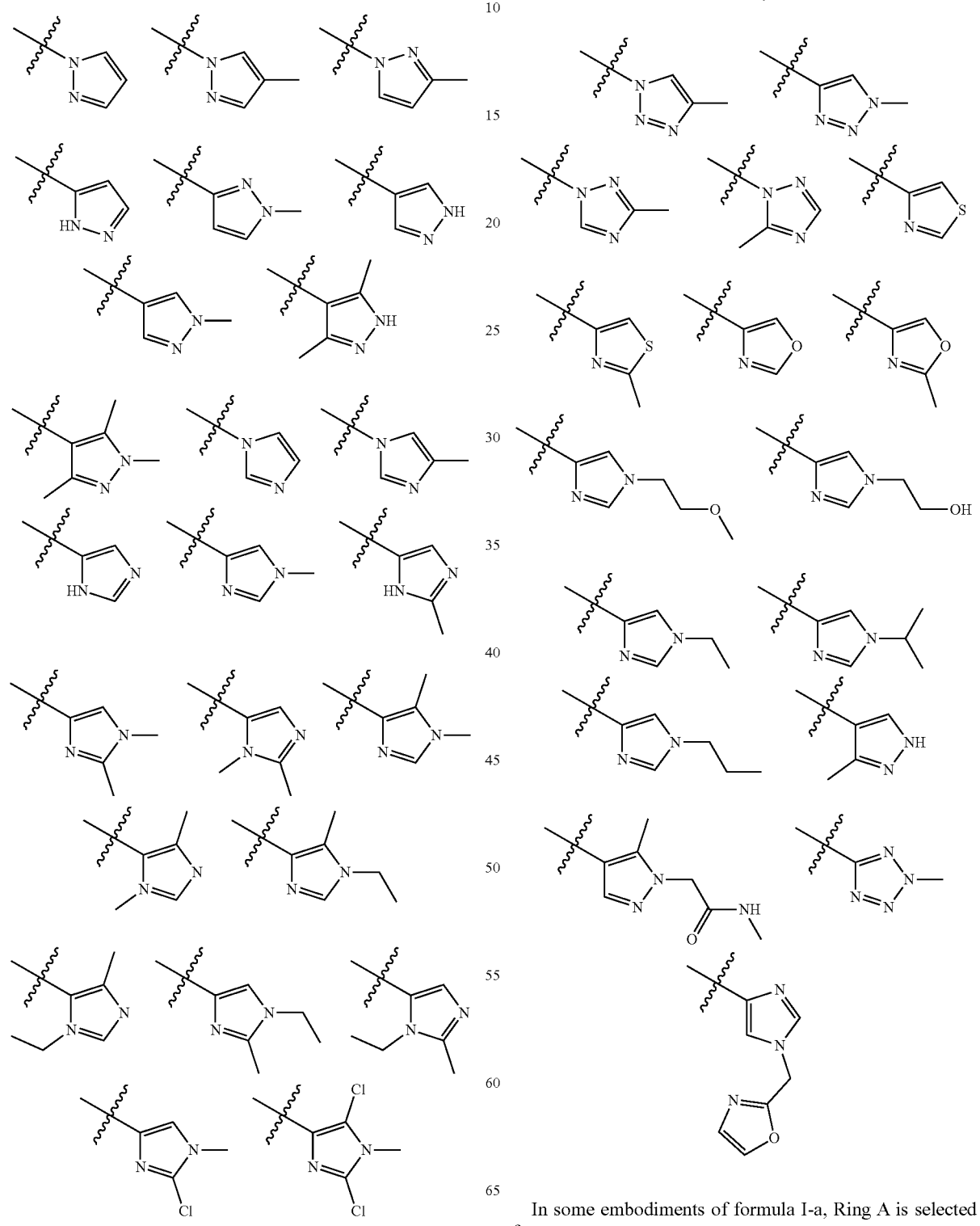

In some embodiments of formula I-a, Ring A is selected from:

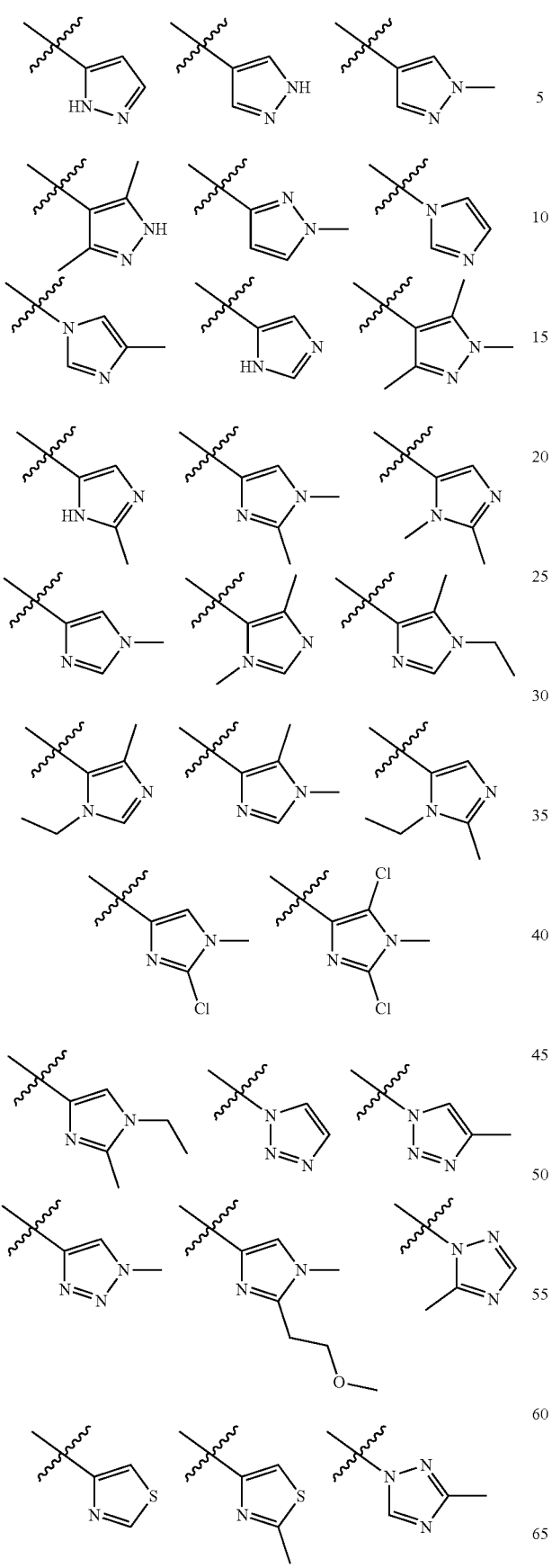

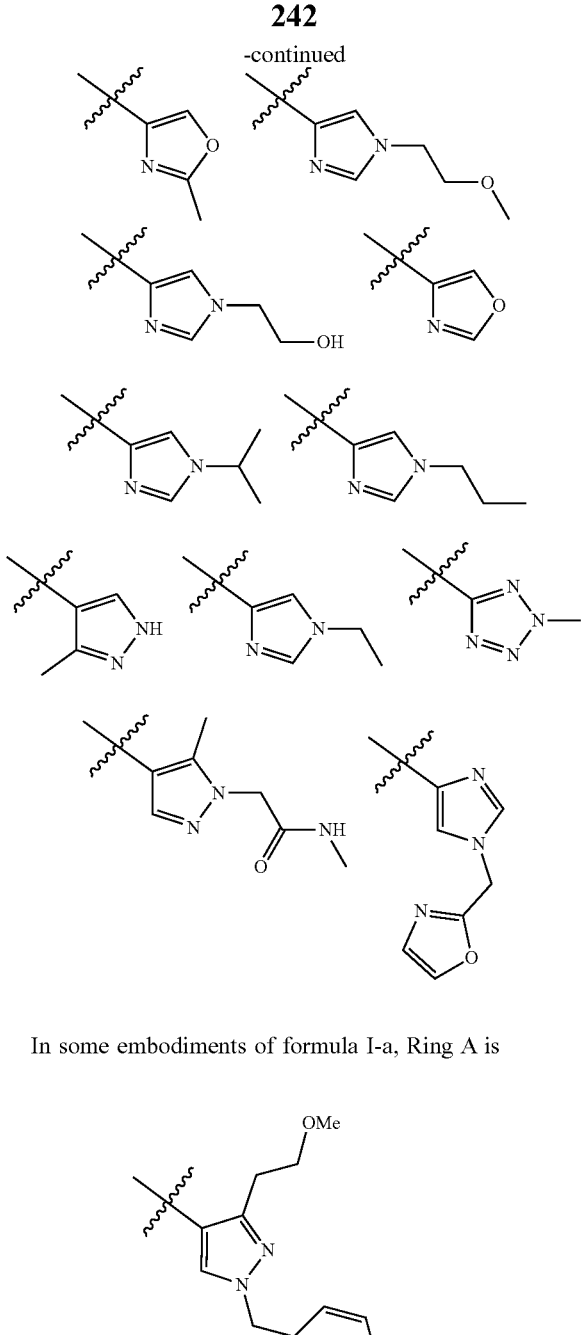

In some embodiments of formula I-a, Ring A is

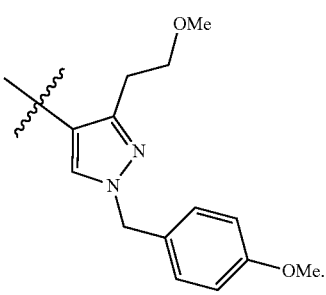

In some embodiments of formula I-a, Ring A is an optionally substituted 6-membered heteroaryl ring having 1-4 heteroatoms independently selected nitrogen, oxygen and sulfur. In some such embodiments of formula I-a, Ring A is selected from 2-pyridyl. 3-pyridyl and 4-pyridyl.

As defined above, x is 0-3. In some embodiments of formula I-a, x is 0. In some embodiments of formula I-a, x is 1. In some embodiments of formula I-a, x is 2. In some embodiments of formula I-a, x is 3. In some embodiments of formula I-a, x is 0-1. In some embodiments of formula I-a, x is 1-2.

According to some aspects, the present disclosure provides a compound of formula II:

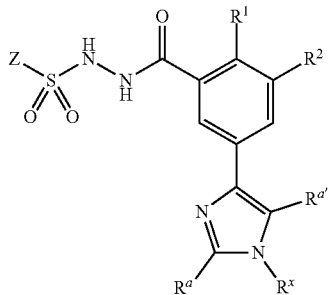

or a pharmaceutically acceptable salt thereof, wherein:
Z is selected from —Cy, —($C_{1-3}$ aliphatic)-Cy or optionally substituted $C_{1-4}$ aliphatic;
Cy is an optionally substituted group selected from phenyl, a 3-10 membered saturated or partially unsaturated carbocyclic ring, a 3-10 membered saturated or partially unsaturated heterocyclic ring having 1-2 heteroatoms independently selected from nitrogen, oxygen and sulfur, a 6-8 membered bridged bicyclic heterocyclic ring having 1-2 heteroatoms independently selected from nitrogen, oxygen and sulfur, a 5-6 membered heteroaryl ring having 1-2 heteroatoms independently selected from nitrogen, oxygen and sulfur, an 8-10 membered bicyclic aryl ring, and an 8-10 membered bicyclic heteroaryl ring having 1-3 heteroatoms independently selected from nitrogen oxygen and sulfur;
each of $R^1$ and $R^2$ is independently selected from halogen and CIA aliphatic;
$R^x$ is optionally substituted $C_{1-4}$ aliphatic; and
each of $R^a$ and $R^{a'}$ is independently selected from hydrogen, halogen and optionally substituted $C_{1-4}$ aliphatic.

As defined above for formula II, Z is selected from —Cy, —($C_{1-3}$ aliphatic)-Cy or optionally substituted Cia aliphatic.

As defined above for formula II, Cy is an optionally substituted group selected from phenyl, a 3-10 membered saturated or partially unsaturated carbocyclic ring, a 3-10 membered saturated or partially unsaturated heterocyclic ring having 1-2 heteroatoms independently selected from nitrogen, oxygen and sulfur, a 6-8 membered bridged bicyclic heterocyclic ring having 1-2 heteroatoms independently selected from nitrogen, oxygen and sulfur, a 5-6 membered heteroaryl ring having 1-2 heteroatoms independently selected from nitrogen, oxygen and sulfur, an 8-10 membered bicyclic aryl ring, and an 8-10 membered bicyclic heteroaryl ring having 1-3 heteroatoms independently selected from nitrogen oxygen and sulfur.

As defined above for formula II, each of $R^1$ and $R^2$ is independently selected from halogen and $C_{1-4}$ aliphatic. In some embodiments of formula II, $R^1$ is fluoro. In some embodiments of formula II, $R^1$ is chloro. In some embodiments of formula II, $R^1$ is methyl. In some embodiments of formula II, $R^2$ is fluoro. In some embodiments of formula II, $R^2$ is chloro. In some embodiments of formula II, $R^2$ is methyl. In some embodiments of formula II, $R^1$ is fluoro and $R^2$ is chloro. In some embodiments of formula II, $R^1$ is fluoro and $R^2$ is methyl. In some embodiments of formula II, $R^1$ is fluoro and $R^2$ is fluoro. In some embodiments of formula II, $R^1$ is chloro and $R^2$ is chloro. In some embodiments, $R^1$ is methyl and $R^2$ is methyl.

As defined above for formula II, $R^x$ is optionally substituted $C_{1-4}$ aliphatic. In some embodiments of formula II, $R^x$ is methyl. In some embodiments of formula II, $R^x$ is ethyl.

In some embodiments of formula II, $R^x$ is isopropyl. In some embodiments of formula II, $R^x$ is $C_{1-4}$ aliphatic optionally substituted with —$(CH_2)_{0-4}OR°$, wherein $R°$ is hydrogen or $C_{1-6}$ aliphatic.

As defined above for formula II, each of $R^a$ and $R^{a'}$ is independently selected from hydrogen, halogen and optionally substituted $C_{1-4}$ aliphatic. In some embodiments of formula II, $R^a$ is hydrogen. In some embodiments of formula II, $R^a$ is optionally substituted Cia aliphatic. In some embodiments of formula II, $R^a$ is $C_{1-4}$ aliphatic optionally substituted with —$(CH_2)_{0-4}OR°$, wherein $R°$ is hydrogen or $C_{1-6}$ aliphatic. In some such embodiments, $R^a$ is —$CH_2CH_2OCH_3$. In some embodiments of formula II, $R^a$ is methyl. In some embodiments of formula II, $R^a$ is halogen. In some such embodiments of formula II, $R^a$ is chloro.

In some embodiments of formula II, $R^{a'}$ is hydrogen. In some embodiments of formula II, $R^a$ is methyl. In some embodiments of formula II, $R^a$ is halogen. In some such embodiments of formula II, $R^{a'}$ is chloro.

As defined above for formula II, Z is selected from —Cy, —($C_{1-3}$ aliphatic)-Cy or optionally substituted $C_{1-4}$ aliphatic.

In some embodiments of formula II, Z is optionally substituted $C_{1-4}$ aliphatic. In some such embodiments, Z is methyl, ethyl, isopropyl, and tert-butyl.

In some embodiments of formula II, Z is —Cy. In some such embodiments, Z is selected from the group consisting of:

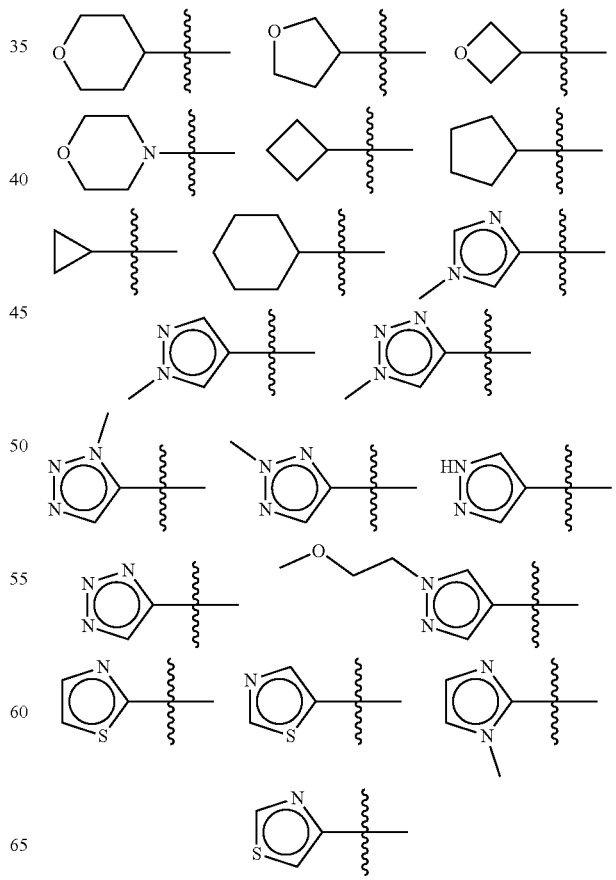

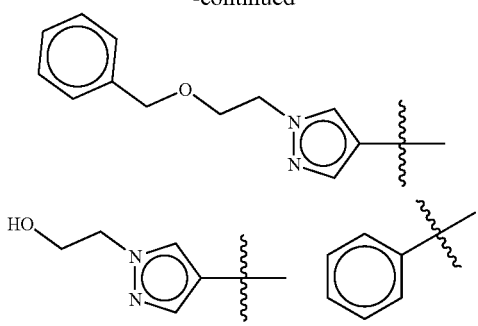
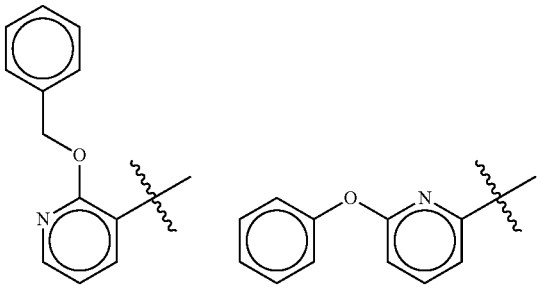
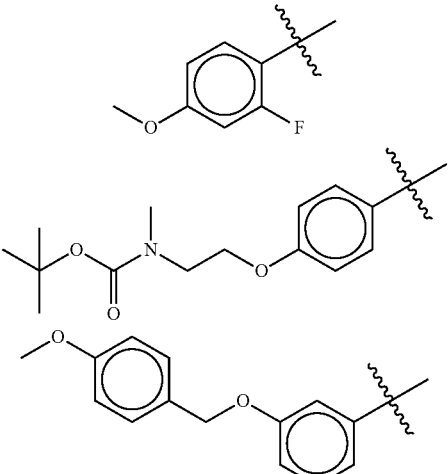
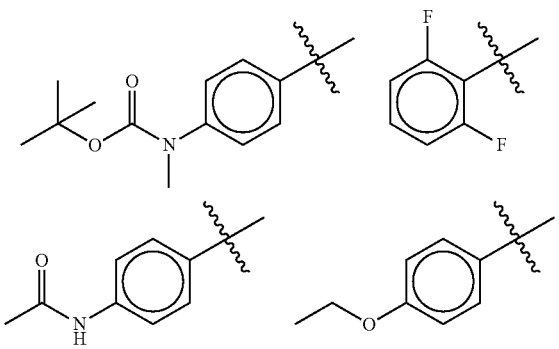
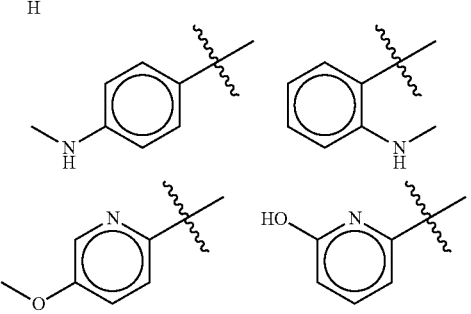
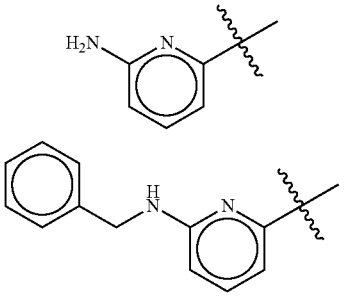

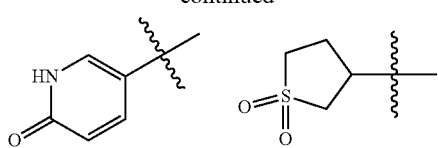
In some embodiments of formula II, Z is —Cy. In some such embodiments, Z is selected from the group consisting of:
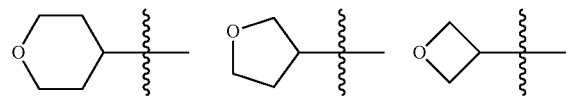
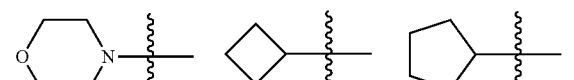
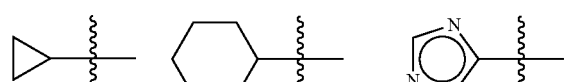
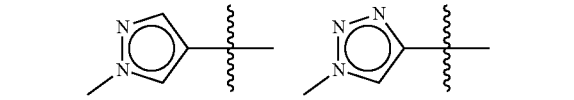
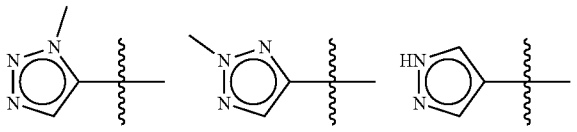
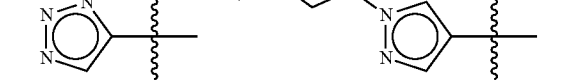
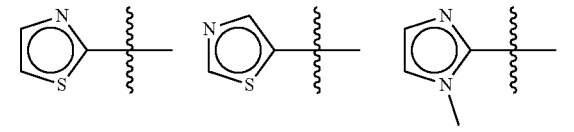
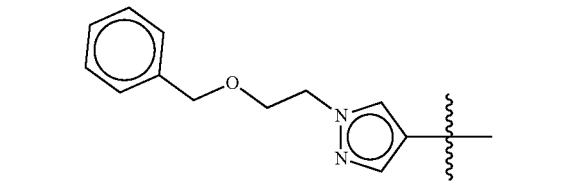
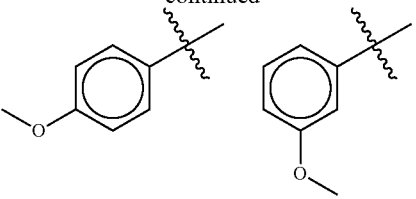
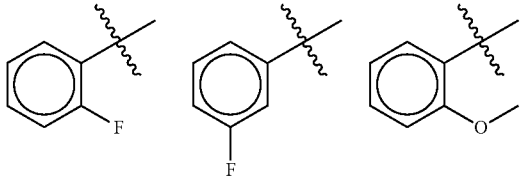
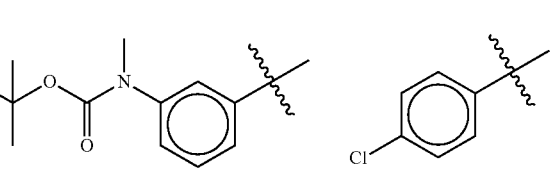
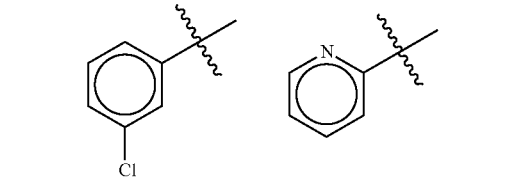
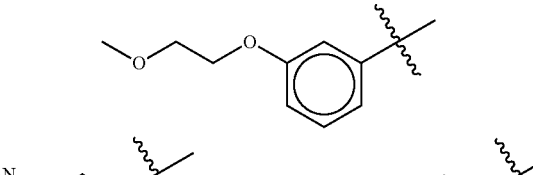
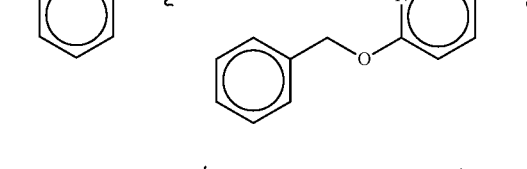
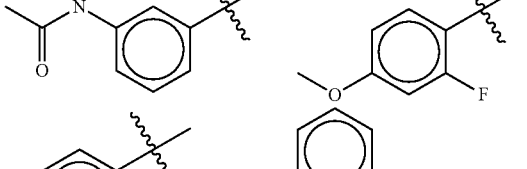
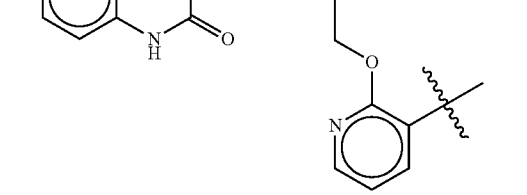
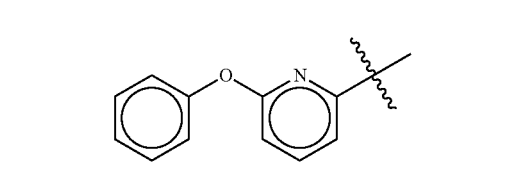

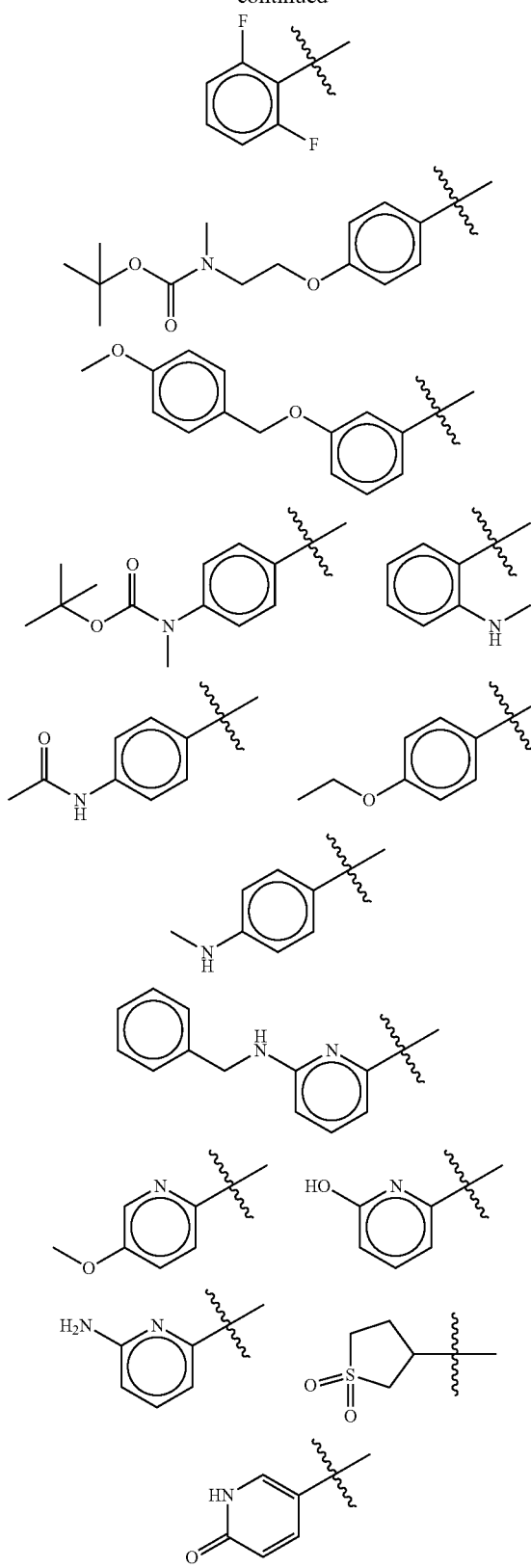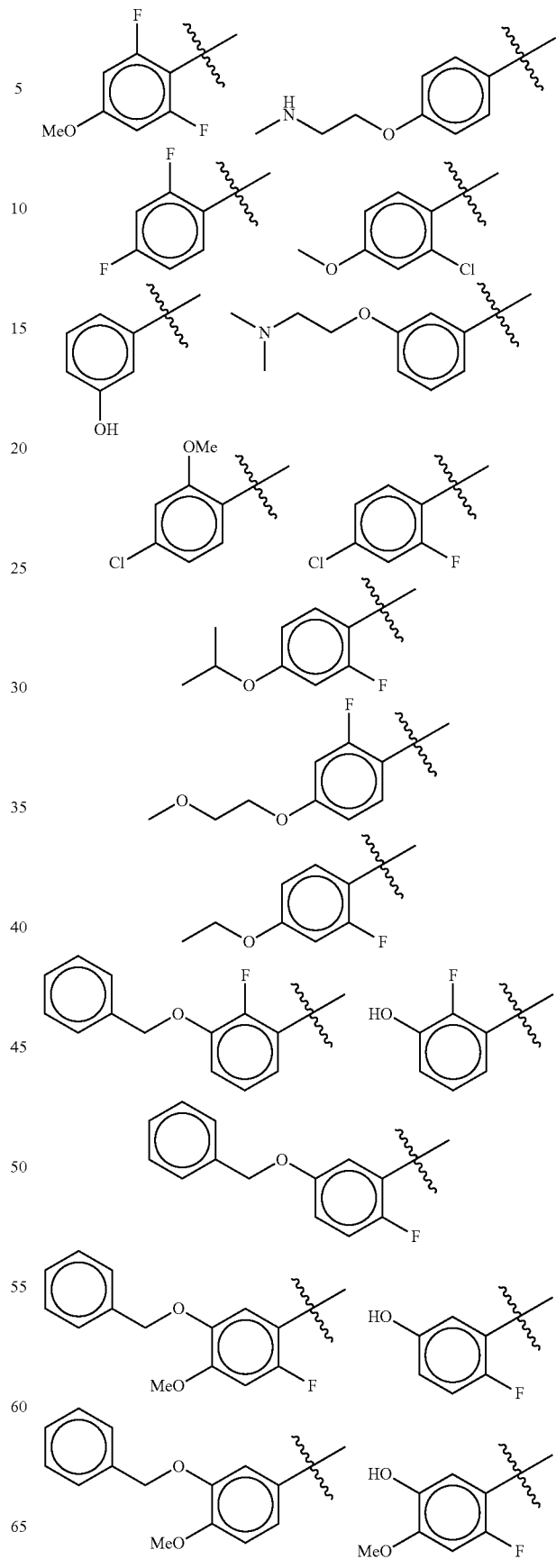
In some embodiments of formula II, Z is —Cy. In some such embodiments, Z is selected from the group consisting of:

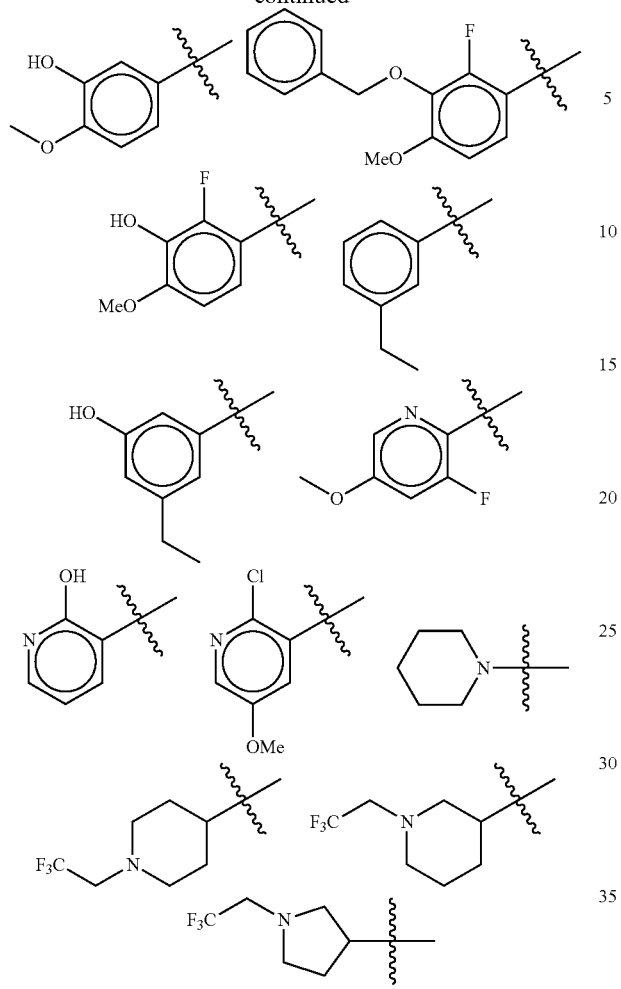
In some embodiments of formula II, Z is —(C$_{1-3}$ aliphatic)-Cy. In some such embodiments, Z is —CH$_2$—Cy. In some such embodiments, Z is selected from the group consisting of:
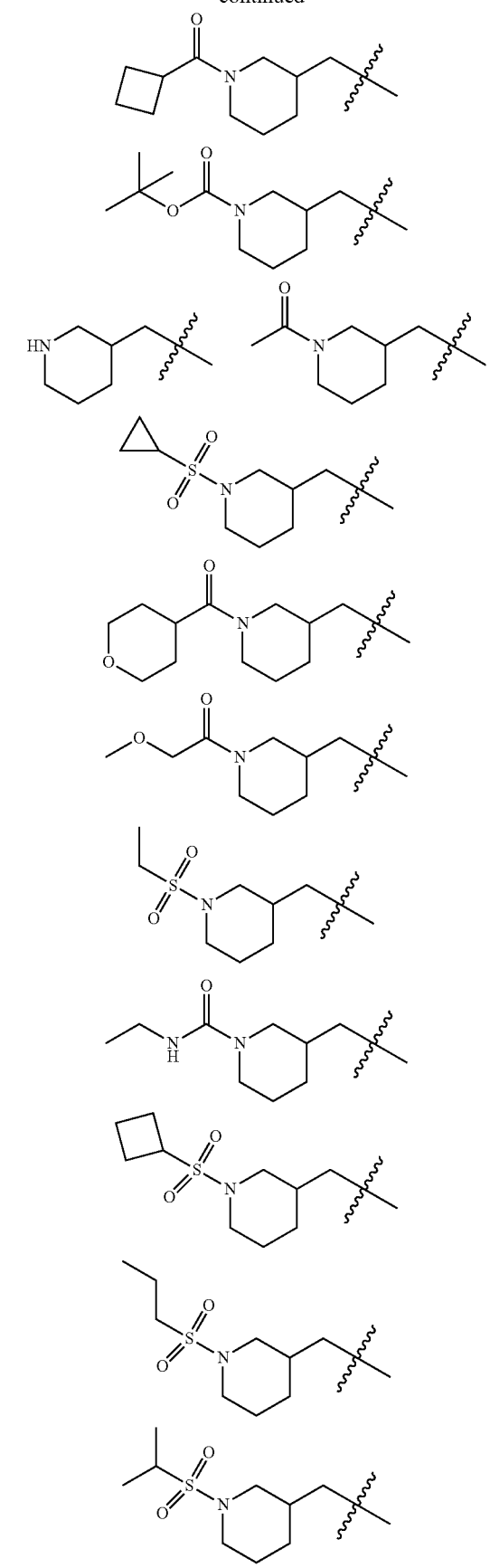

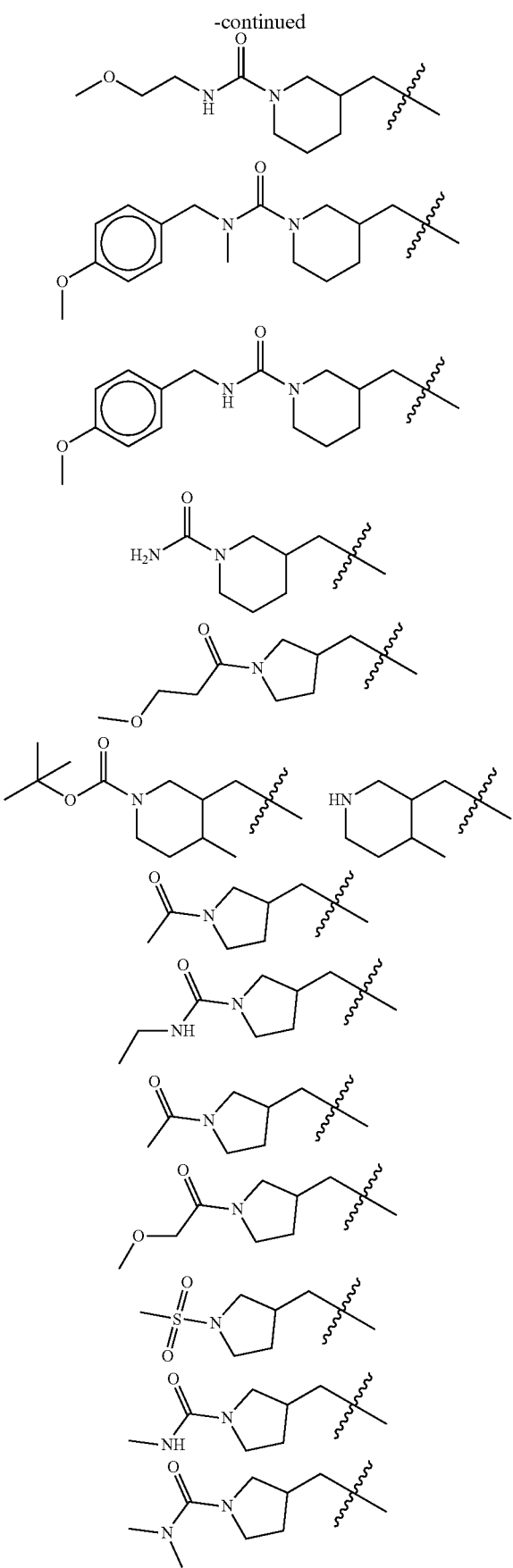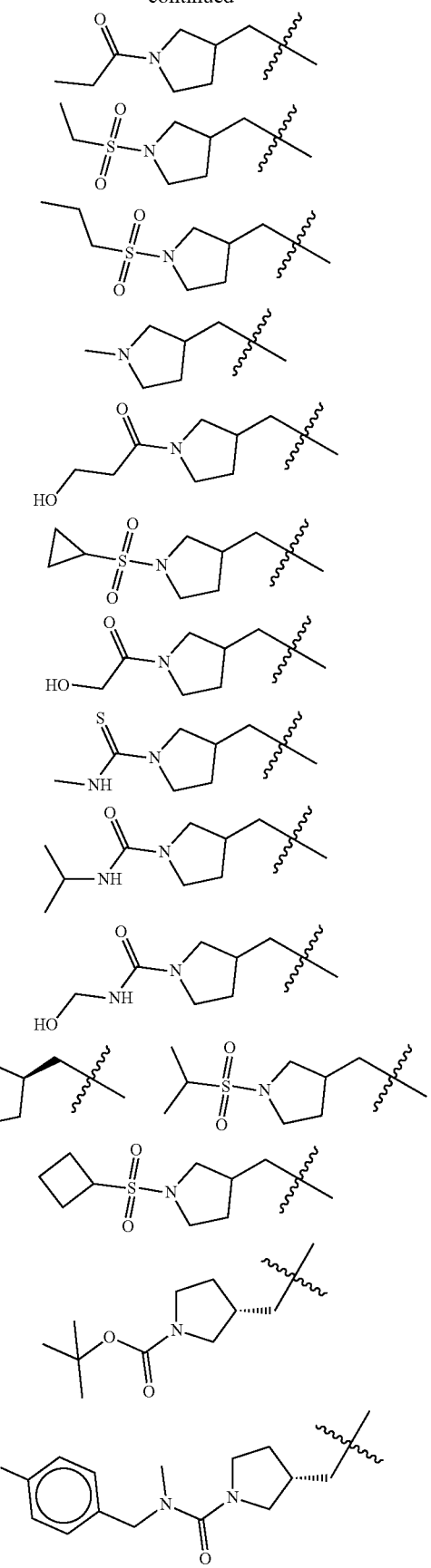

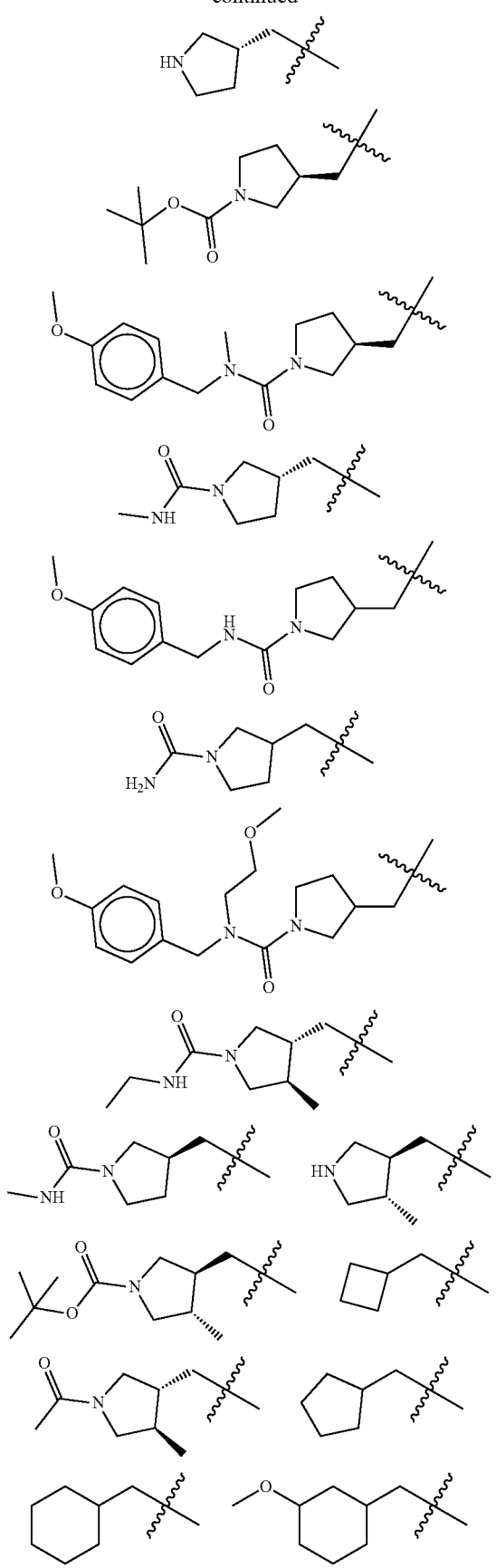
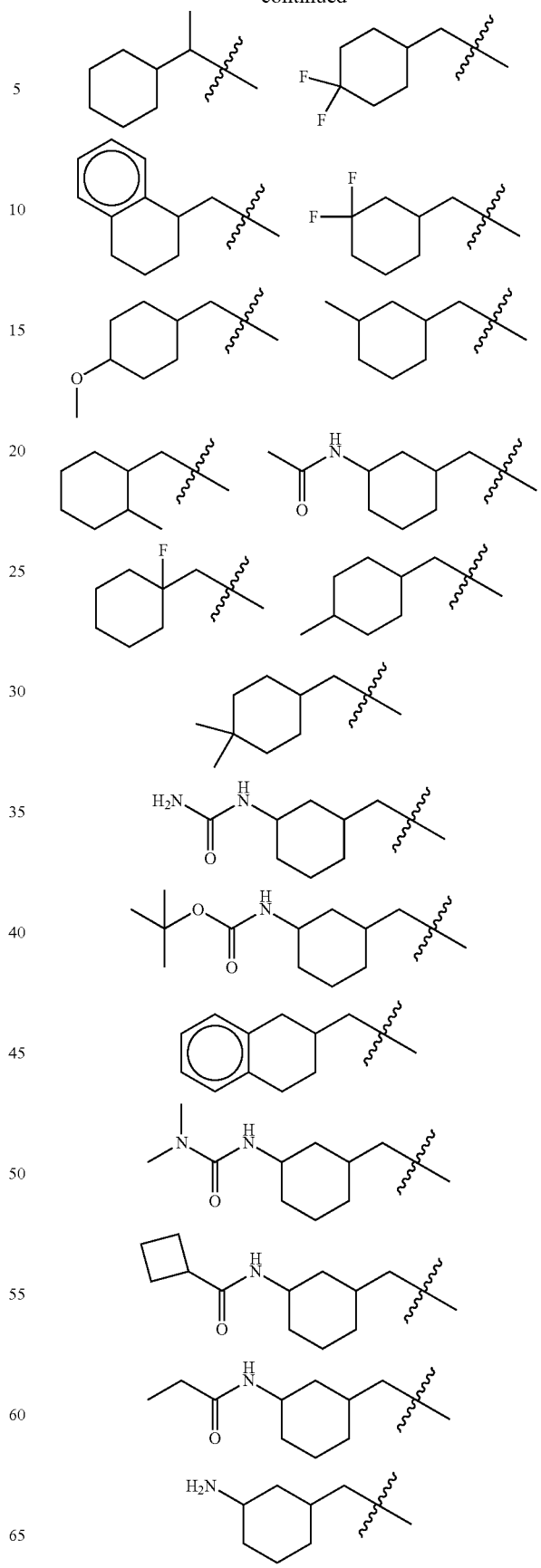

257
-continued
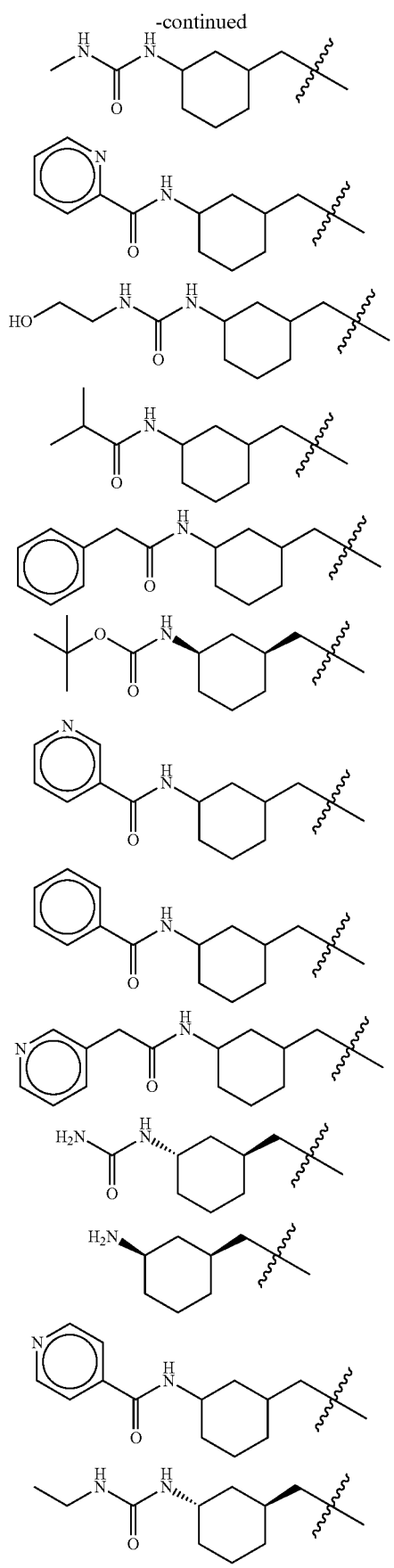
258
-continued
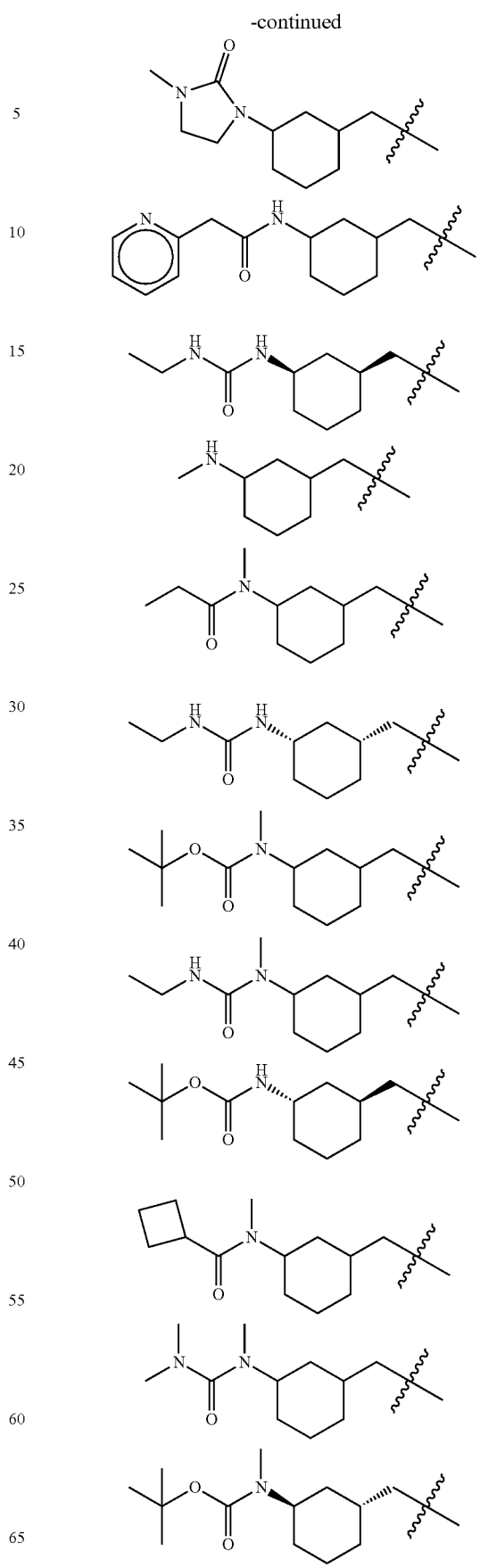

259
-continued
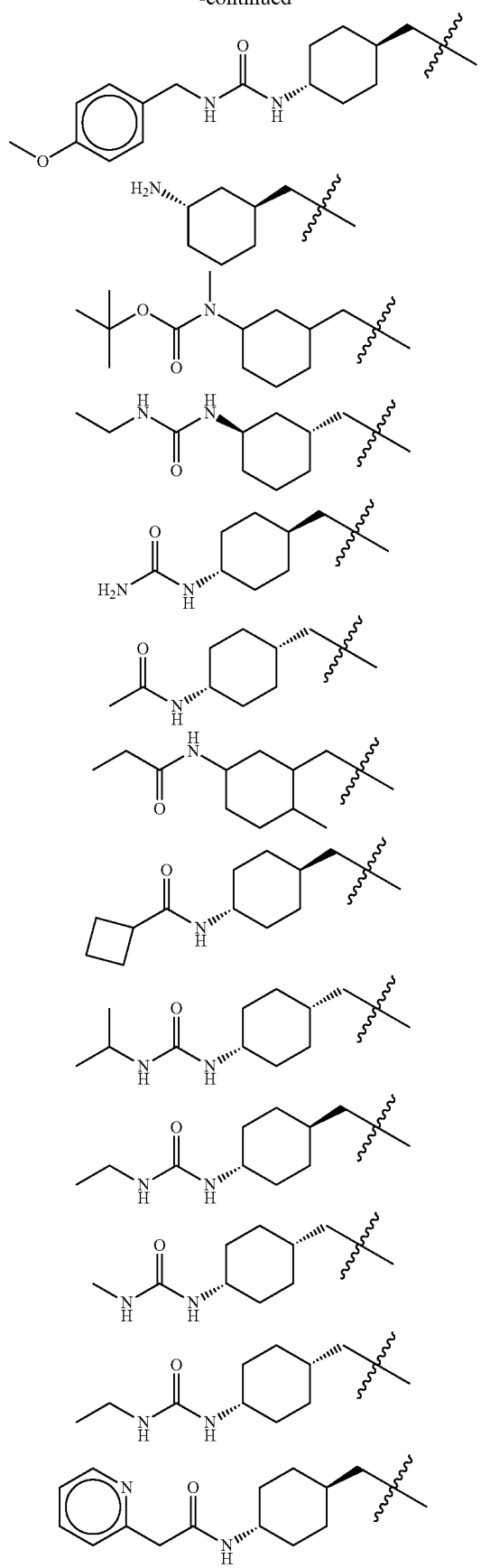
260
-continued
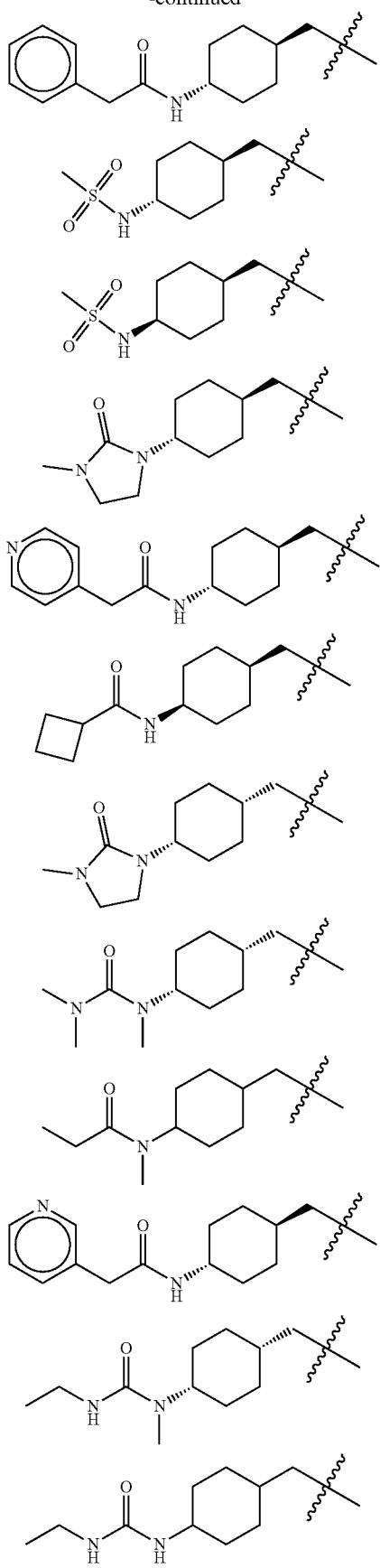

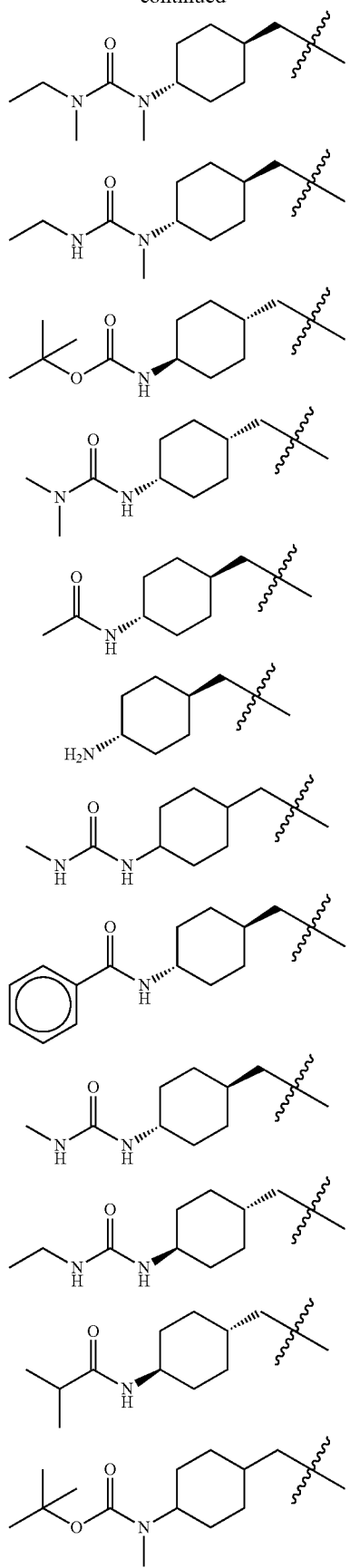
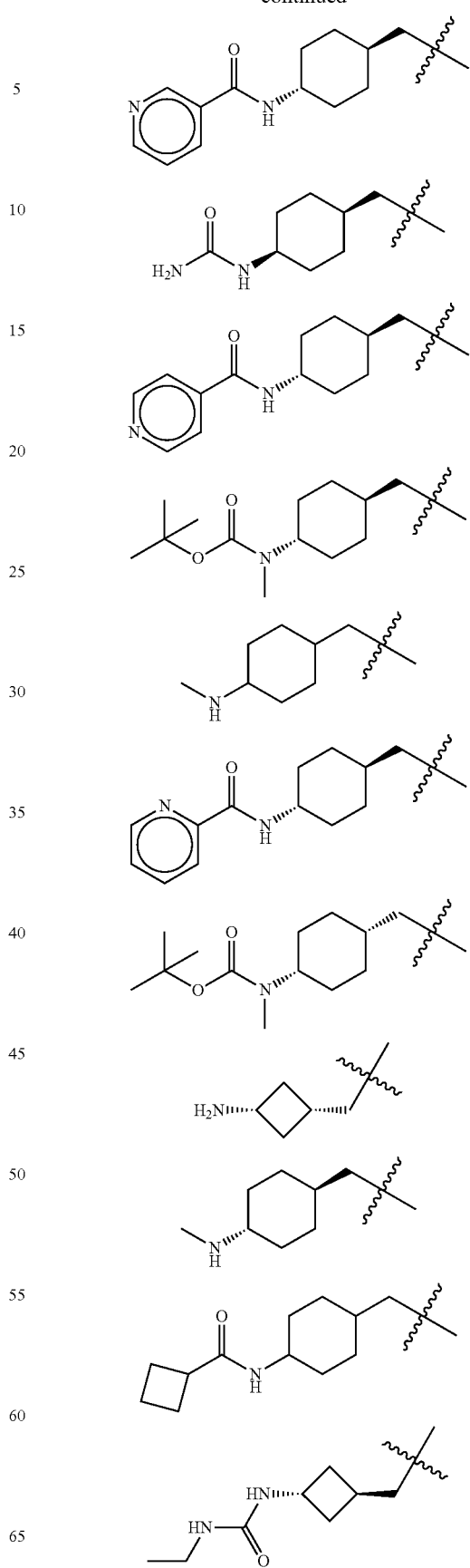

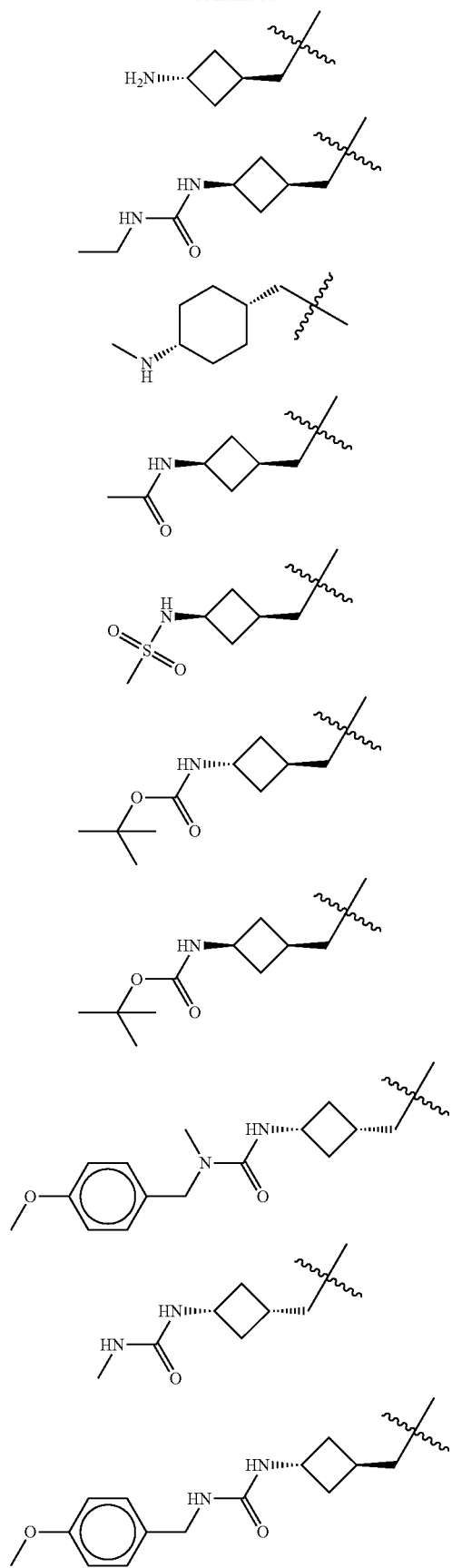
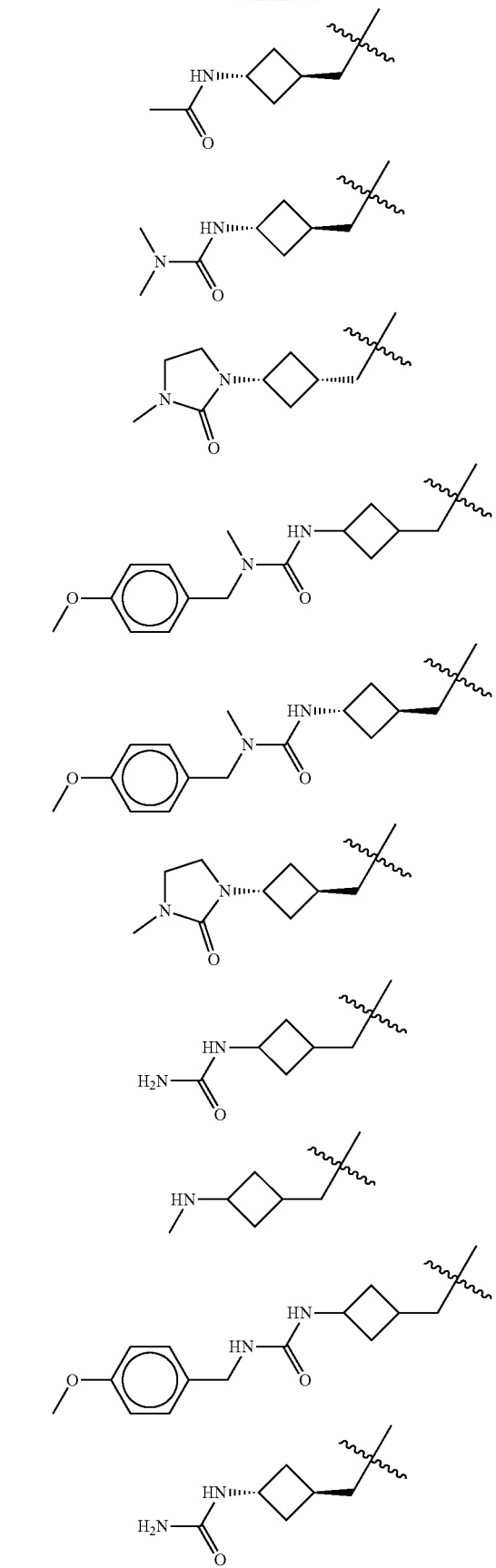

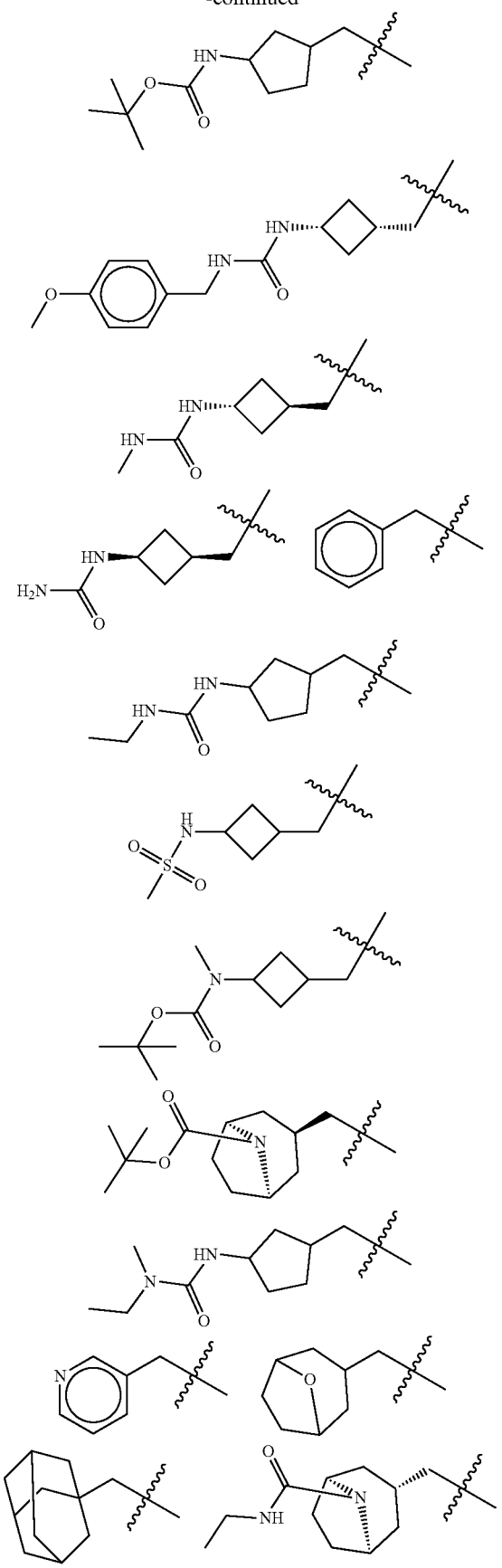
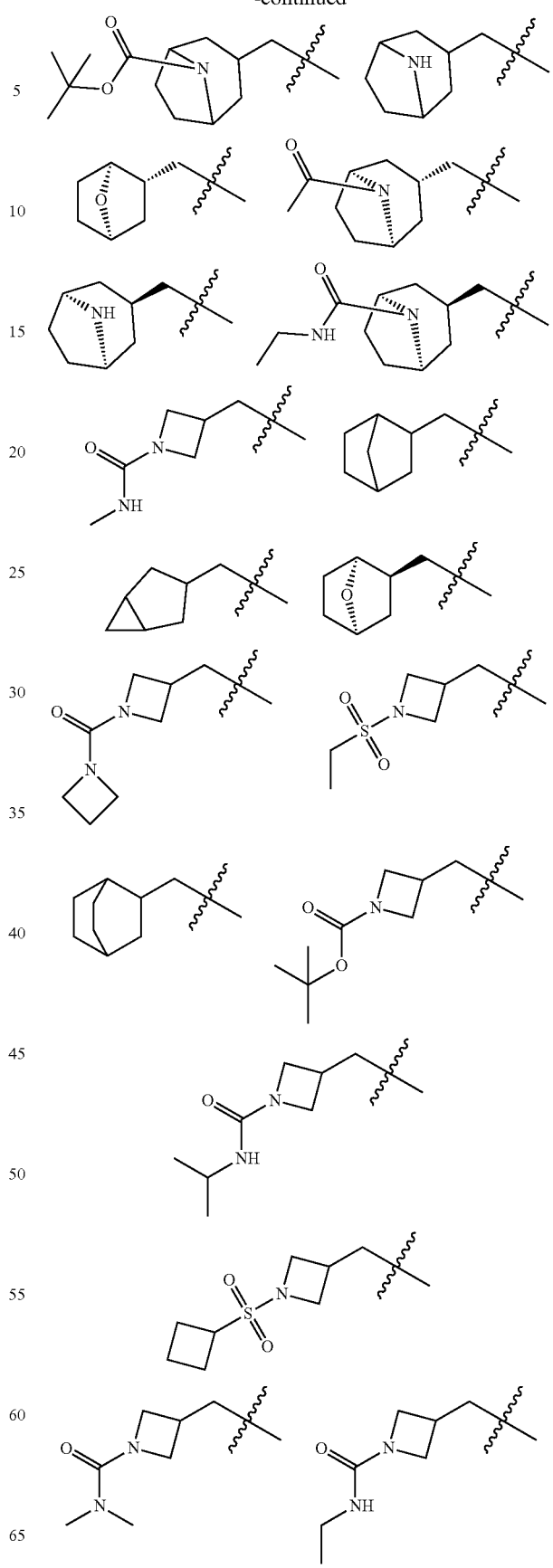

267
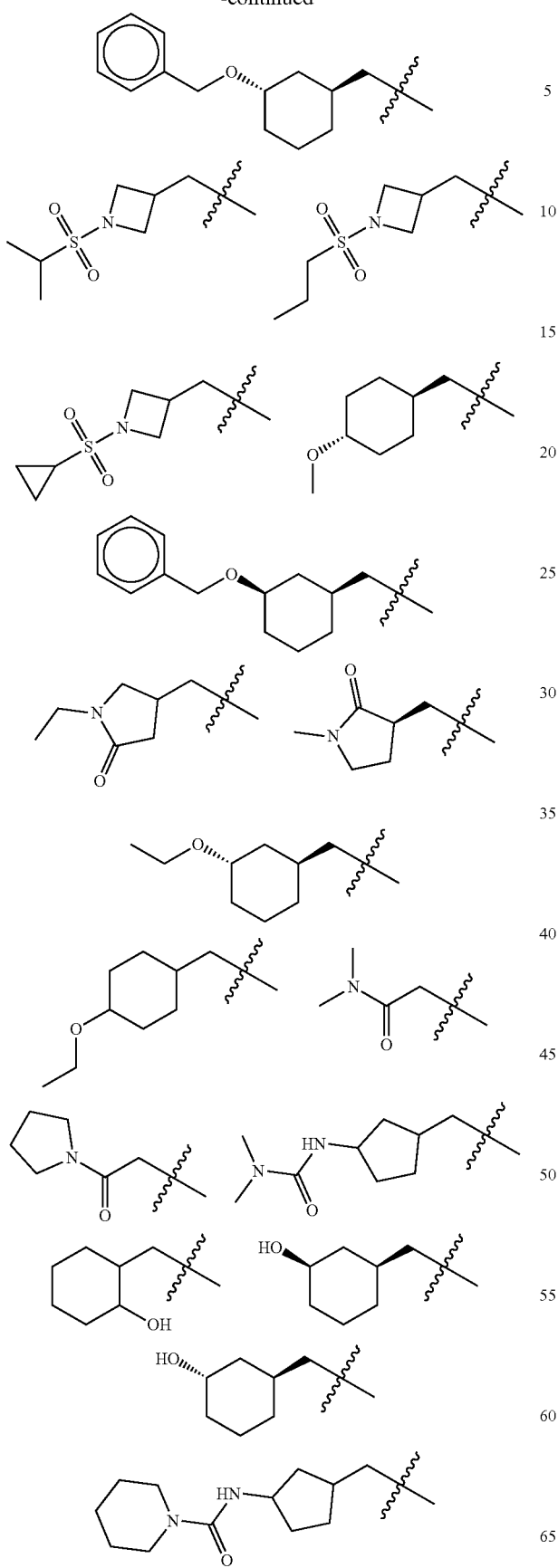
268
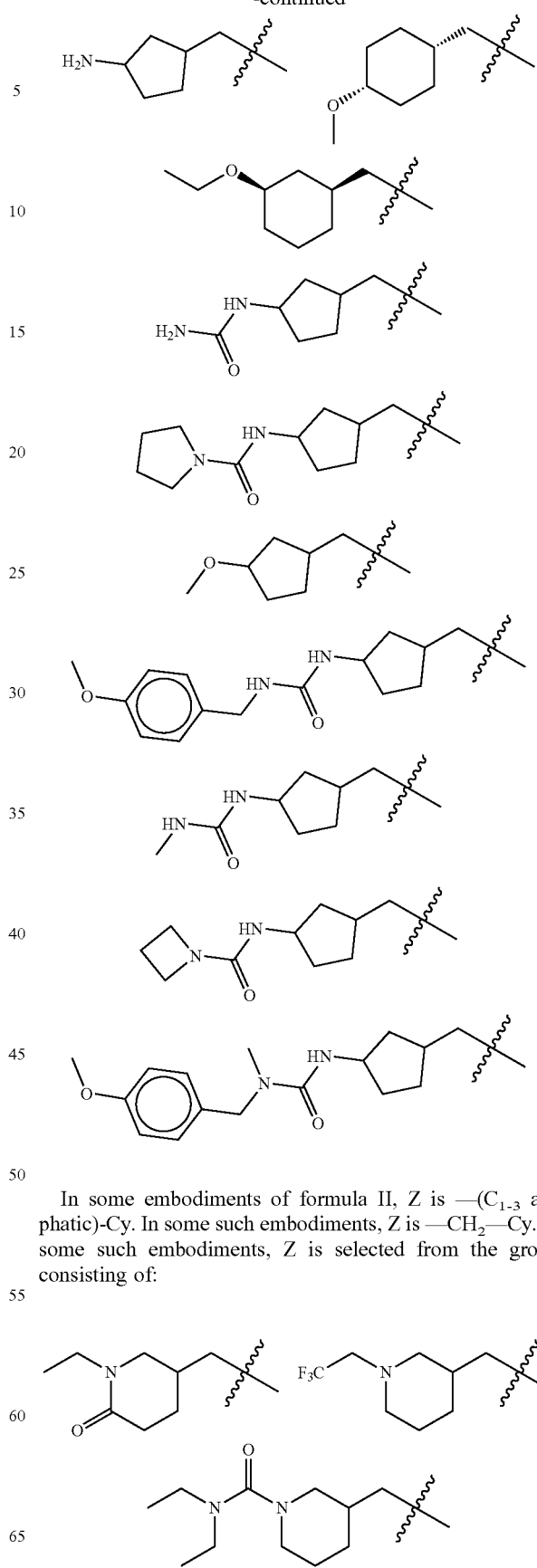
In some embodiments of formula II, Z is —($C_{1-3}$ aliphatic)-Cy. In some such embodiments, Z is —$CH_2$—Cy. In some such embodiments, Z is selected from the group consisting of:

269
-continued
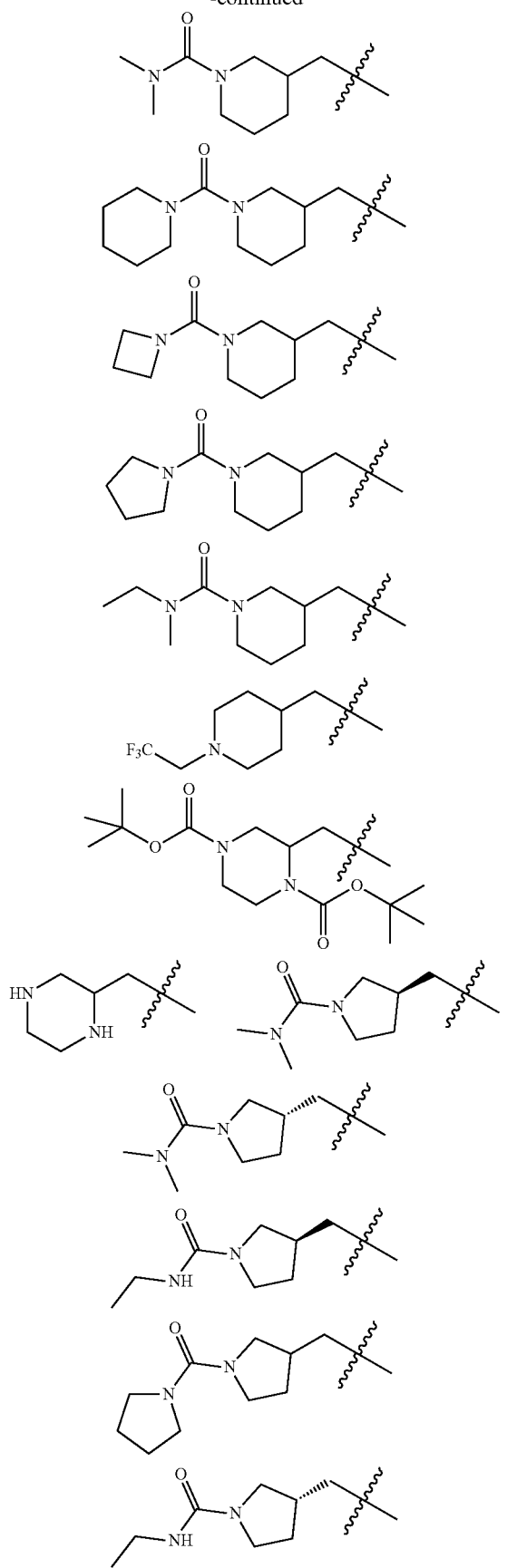
270
-continued
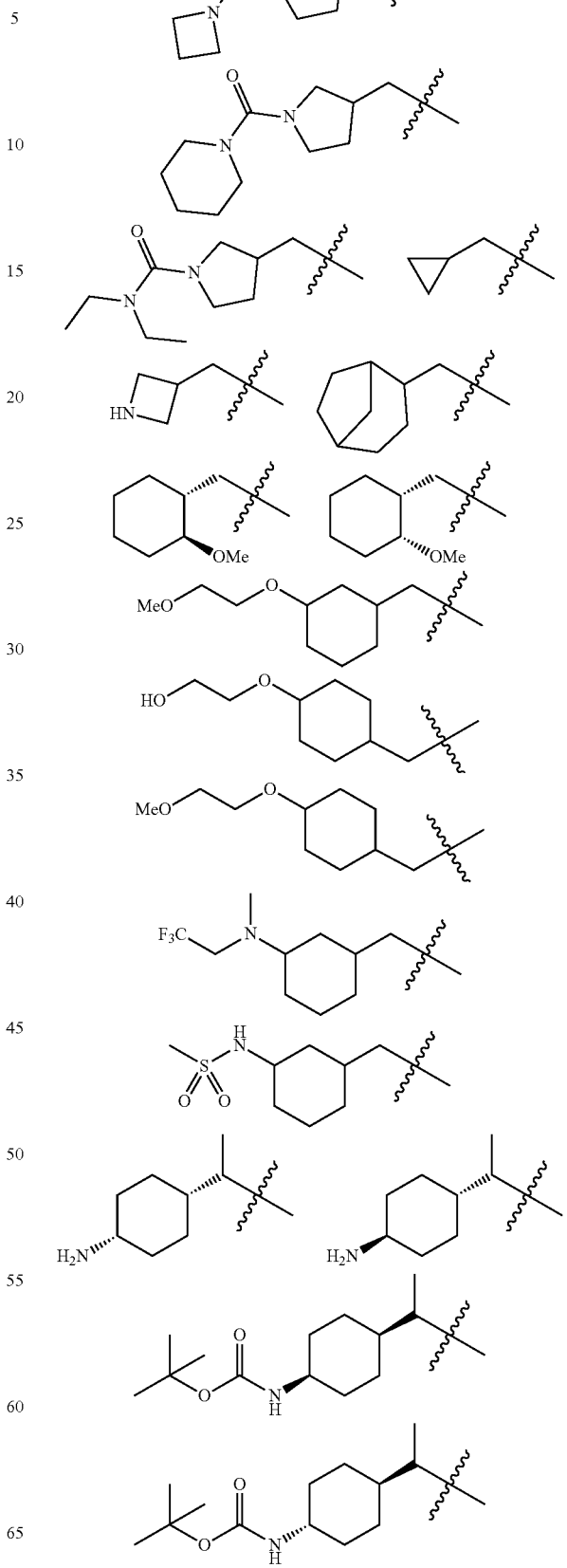

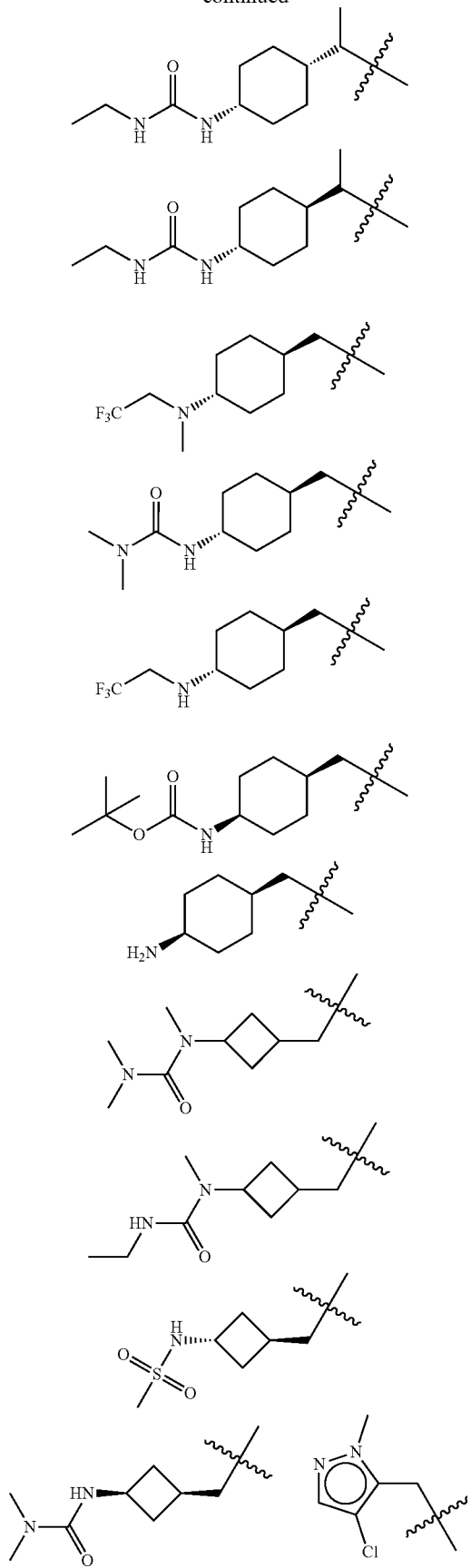

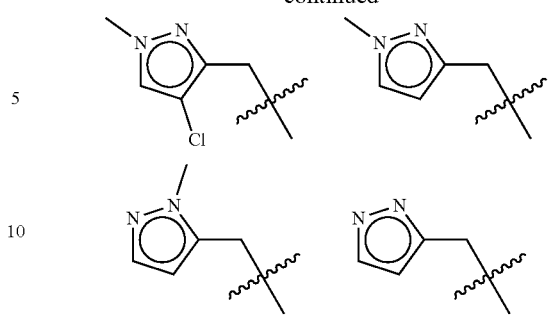

As defined above for formula II, Cy is an optionally substituted group selected from phenyl, a 3-10 membered saturated or partially unsaturated carbocyclic ring, a 3-10 membered saturated or partially unsaturated heterocyclic ring having 1-2 heteroatoms independently selected from nitrogen, oxygen and sulfur, a 6-8 membered bridged bicyclic heterocyclic ring having 1-2 heteroatoms independently selected from nitrogen, oxygen and sulfur, a 5-6 membered heteroaryl ring having 1-2 heteroatoms independently selected from nitrogen, oxygen and sulfur, an 8-10 membered bicyclic aryl ring, and an 8-10 membered bicyclic heteroaryl ring having 1-3 heteroatoms independently selected from nitrogen oxygen and sulfur.

In some embodiments of formula II, Cy is phenyl.

In some embodiments of formula II, Cy is an optionally substituted 3-10 membered saturated or partially unsaturated carbocyclic ring. In some embodiments of formula II, Cy is an optionally substituted 3-10 membered saturated carbocyclic ring. In some such embodiments, Cy is an optionally substituted group selected from cyclopropyl, cyclobutyl, cyclopentyl, and cyclohexyl.

In some embodiments of formula II, Cy is an optionally substituted bicyclic carbocyclic ring. It will be appreciated that a bicyclic carbocyclic ring can be a bridged bicyclic ring. In some such embodiments, Cy is an optionally substituted group selected from:

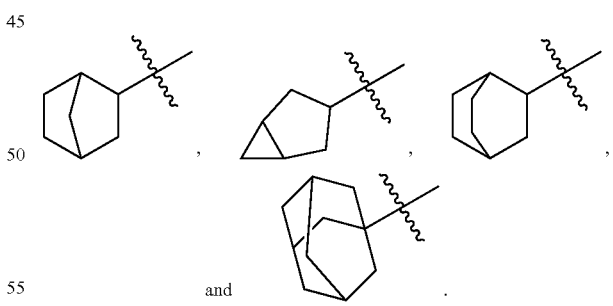

In some such embodiments, Cy is an optionally substituted group selected from:

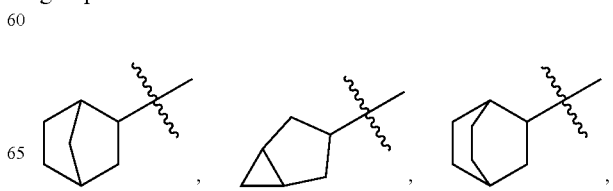

-continued

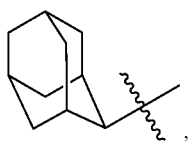, and 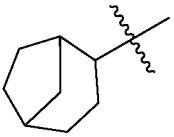.

In some such embodiments, Cy is an optionally substituted group selected from:

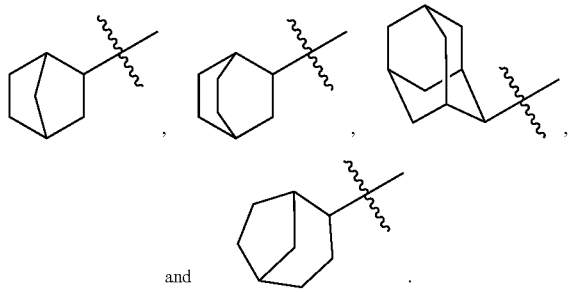

and 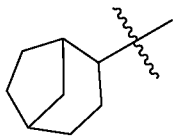.

In some embodiments of formula II, Cy is an optionally substituted 5-6 membered heteroaryl ring having 1-3 heteroatoms independently selected from nitrogen, oxygen and sulfur. In some embodiments of formula II, Cy is a 5-membered heteroaryl ring having 1-3 heteroatoms independently selected from nitrogen, oxygen and sulfur. In some such embodiments, Cy is an optionally substituted group selected from pyrazolyl, imidazolyl, and triazolyl.

In some embodiments of formula II, Cy is selected from:

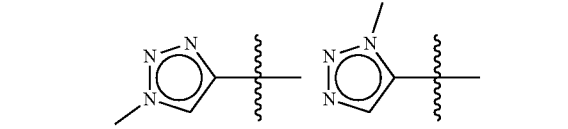
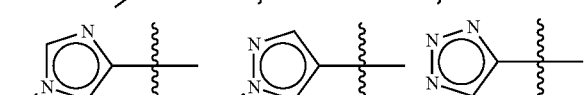

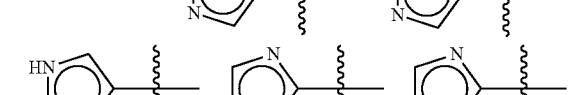
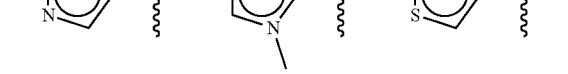

In some embodiments of formula II, Cy is an optionally substituted group selected from:

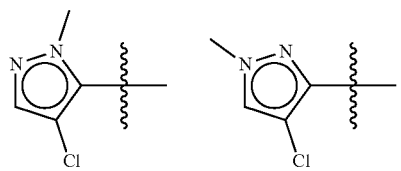

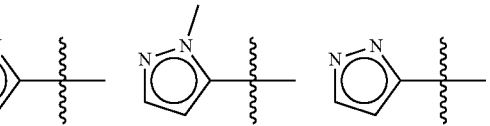

In some embodiments of formula II, Cy is an optionally substituted 5-6 membered heteroaryl ring having 1-3 heteroatoms independently selected from nitrogen, oxygen and sulfur. In some embodiments, Cy is a 6-membered heteroaryl ring having 1-3 heteroatoms independently selected from nitrogen, oxygen and sulfur. In some such embodiments, Cy is an optionally substituted group selected from pyridinyl. In some embodiments, Cy is an optionally substituted group selected from:

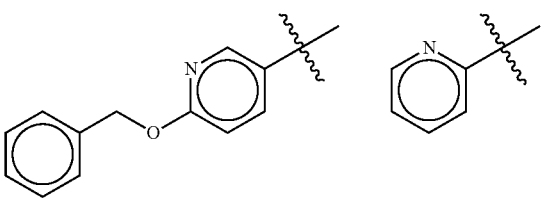

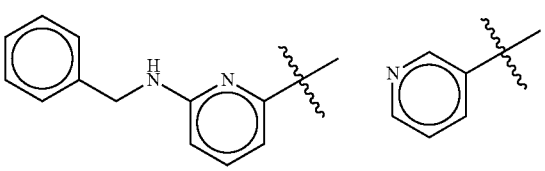

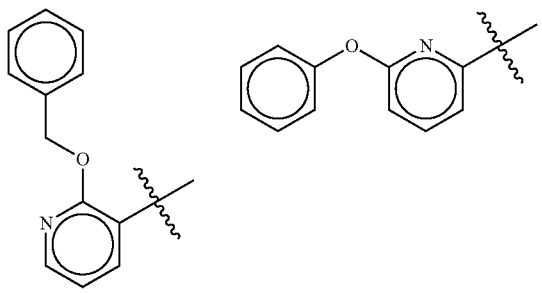

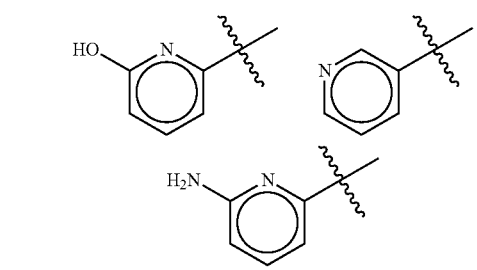

In some embodiments of formula II, Cy is an optionally substituted group selected from:

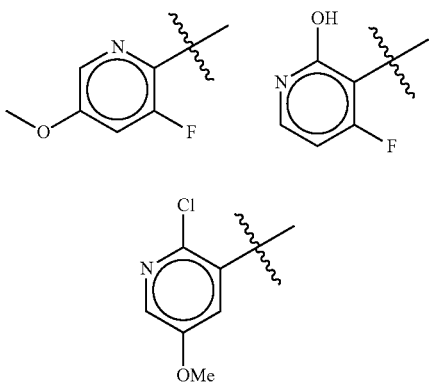

In some embodiments of formula II, Cy is an optionally substituted 3-10 membered saturated or partially unsaturated heterocyclic ring having 1-2 heteroatoms independently selected from nitrogen, oxygen and sulfur.

In some embodiments of formula II, Cy is an optionally substituted 4-membered saturated heterocyclic group having 1 heteroatom independently selected from nitrogen, oxygen and sulfur. In some such embodiments, Cy is optionally substituted oxetanyl. In some such embodiments, Cy is optionally substituted oxetanyl or azetidinyl.

In some embodiments of formula II, Cy is an optionally substituted 5-membered saturated heterocyclic group having 1-2 heteroatoms independently selected from nitrogen, oxygen and sulfur. In some such embodiments, Cy is an optionally substituted group selected from tetrahydrofuranyl and pyrrolidinyl.

In some embodiments of formula II, Cy is an optionally substituted 6-membered saturated heterocyclic group having 1-2 heteroatoms independently selected from nitrogen, oxygen and sulfur. In some such embodiments, Cy is an optionally substituted group selected from tetrahydropyranyl and piperidinyl. In some such embodiments, Cy is an optionally substituted group selected from tetrahydropyranyl, piperidinyl, and piperazinyl.

In some embodiments of formula II, Cy is an optionally substituted 7-membered saturated heterocyclic group having 1-2 heteroatoms independently selected from nitrogen, oxygen and sulfur. It will be appreciated that a 7-membered saturated heterocyclic ring can be a bridged bicyclic ring. In some such embodiments, Cy is an optionally substituted group selected from:

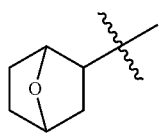

In some embodiments of formula II, Cy is an optionally substituted 8-membered saturated heterocyclic group having 1-2 heteroatoms independently selected from nitrogen, oxygen and sulfur. It will be appreciated that an 8-membered saturated heterocyclic ring can be a bridged bicyclic ring. In some such embodiments, Cy is an optionally substituted group selected from:

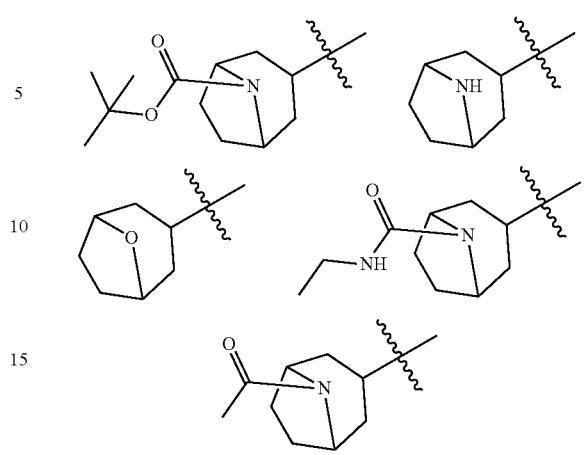

In some embodiments of formula II, $R^1$ is fluoro and $R^2$ is chloro, thus forming a compound of formula II-a:

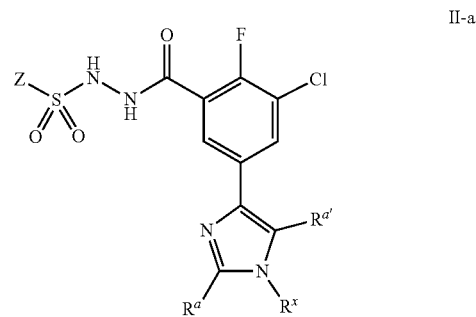

II-a or a pharmaceutically acceptable salt thereof, wherein each of Z, $R^x$, $R^a$ and x is as defined above and described in classes and subclasses herein.

In some embodiments of formula II, $R^1$ is fluoro, $R^2$ is chloro, and $R^x$ is methyl, thus forming a compound of formula II-b:

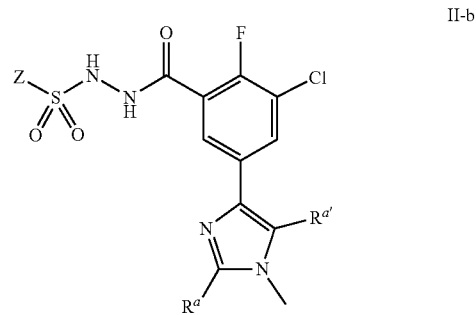

II-b or a pharmaceutically acceptable salt thereof, wherein each of Z, $R^a$ and $R^{a'}$ is as defined above and described in classes and subclasses herein.

In some embodiments of formula II, $R^1$ is fluoro, $R^2$ is chloro, $R^x$ is methyl, $R^a$ is hydrogen and $R^{a'}$ is hydrogen, thus forming a compound of formula II-c:

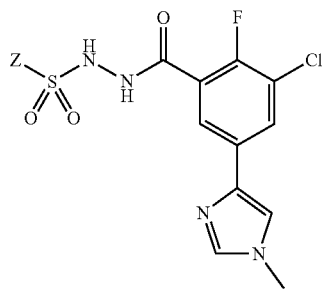

II-c or a pharmaceutically acceptable salt thereof, wherein Z is as defined above and described in classes and subclasses herein.

According to some aspects, the present disclosure provides a compound of formula III:

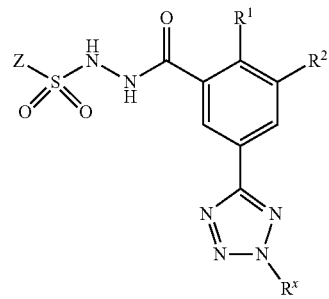

III or a pharmaceutically acceptable salt thereof, wherein:
Z is selected from —Cy, —($C_{1-3}$ aliphatic)-Cy or optionally substituted $C_{1-4}$ aliphatic;
Cy is an optionally substituted group selected from phenyl, a 3-10 membered saturated or partially unsaturated carbocyclic ring, a 3-10 membered saturated or partially unsaturated heterocyclic ring having 1-2 heteroatoms independently selected from nitrogen, oxygen and sulfur, a 6-8 membered bridged bicyclic heterocyclic ring having 1-2 heteroatoms independently selected from nitrogen, oxygen and sulfur, and a 5-6 membered heteroaryl ring having 1-2 heteroatoms independently selected from nitrogen, oxygen and sulfur, an 8-10 membered bicyclic aryl ring, and an 8-10 membered bicyclic heteroaryl ring having 1-3 heteroatoms independently selected from nitrogen oxygen and sulfur;
each of $R^1$ and $R^2$ is independently selected from halogen and $C_{1-4}$ aliphatic; and
$R^x$ is optionally substituted $C_{1-4}$ aliphatic.

As defined above for formula III, Z is selected from —Cy, —($C_{1-3}$ aliphatic)-Cy or optionally substituted $C_{1-4}$ aliphatic.

As defined above for formula III, Cy is an optionally substituted group selected from phenyl, a 3-10 membered saturated or partially unsaturated carbocyclic ring, a 3-10 membered saturated or partially unsaturated heterocyclic ring having 1-2 heteroatoms independently selected from nitrogen, oxygen and sulfur, a 6-8 membered bridged bicyclic heterocyclic ring having 1-2 heteroatoms independently selected from nitrogen, oxygen and sulfur, a 5-6 membered heteroaryl ring having 1-2 heteroatoms independently selected from nitrogen, oxygen and sulfur, an 8-10 membered bicyclic aryl ring, and an 8-10 membered bicyclic heteroaryl ring having 1-3 heteroatoms independently selected from nitrogen oxygen and sulfur.

As defined above for formula III, each of $R^1$ and $R^2$ is independently selected from halogen and $C_{1-4}$ aliphatic. In some embodiments of formula III, $R^1$ is fluoro. In some embodiments of formula III, $R^1$ is chloro. In some embodiments of formula III, $R^1$ is methyl. In some embodiments of formula III, $R^2$ is fluoro. In some embodiments of formula II, $R^2$ is chloro. In some embodiments of formula III, $R^2$ is methyl. In some embodiments of formula III, $R^1$ is fluoro and $R^2$ is chloro. In some embodiments of formula III, $R^1$ is fluoro and $R^2$ is methyl. In some embodiments of formula III, $R^1$ is fluoro and $R^2$ is fluoro. In some embodiments of formula III, $R^1$ is chloro and $R^2$ is chloro. In some embodiments, $R^1$ is methyl and $R^2$ is methyl.

As defined above for formula III, $R^x$ is optionally substituted $C_{1-4}$ aliphatic. In some embodiments of formula III, $R^x$ is methyl. In some embodiments of formula III, $R^x$ is ethyl. In some embodiments of formula III, $R^x$ is isopropyl. In some embodiments of formula III, $R^x$ is $C_{1-4}$ aliphatic optionally substituted with —$(CH_2)_{0-4}OR°$, wherein $R°$ is hydrogen or $C_{1-6}$ aliphatic.

As defined above for formula III, Z is selected from —Cy, —($C_{1-3}$ aliphatic)-Cy or optionally substituted $C_{1-4}$ aliphatic.

In some embodiments of formula III, Z is optionally substituted $C_{1-4}$ aliphatic. In some such embodiments, Z is methyl, ethyl, isopropyl, and tert-butyl.

In some embodiments of formula III, Z is —Cy.

In some embodiments of formula III, Z is —($C_{1-3}$ aliphatic)-Cy. In some such embodiments, Z is —$CH_2$—Cy. In some such embodiments, Z is selected from the group consisting of:

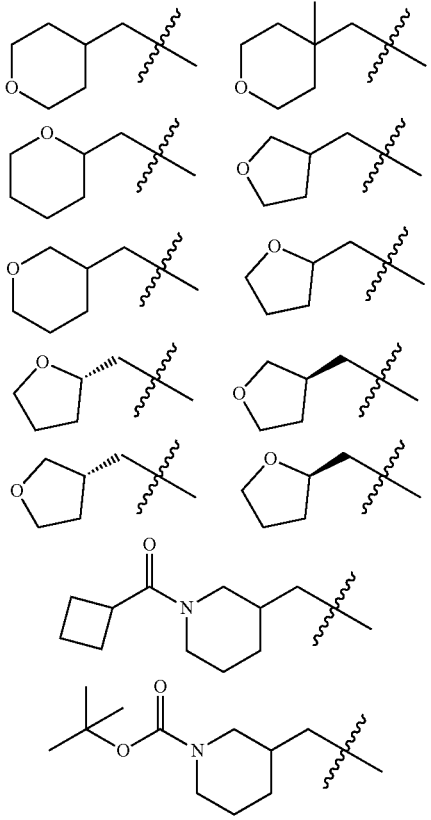

279
-continued
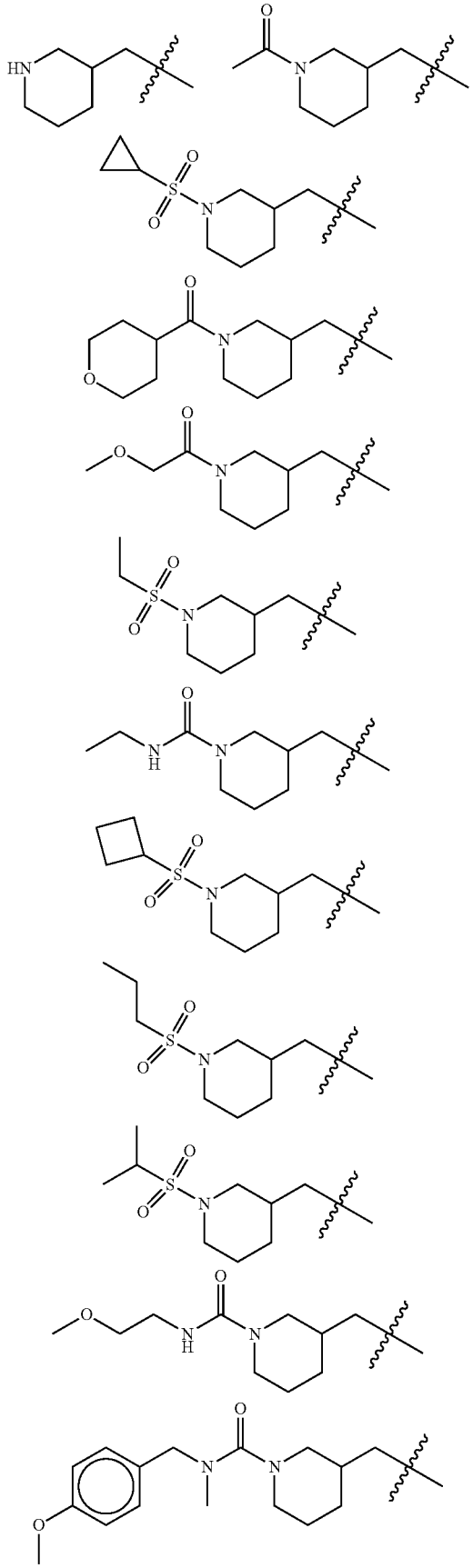
280
-continued
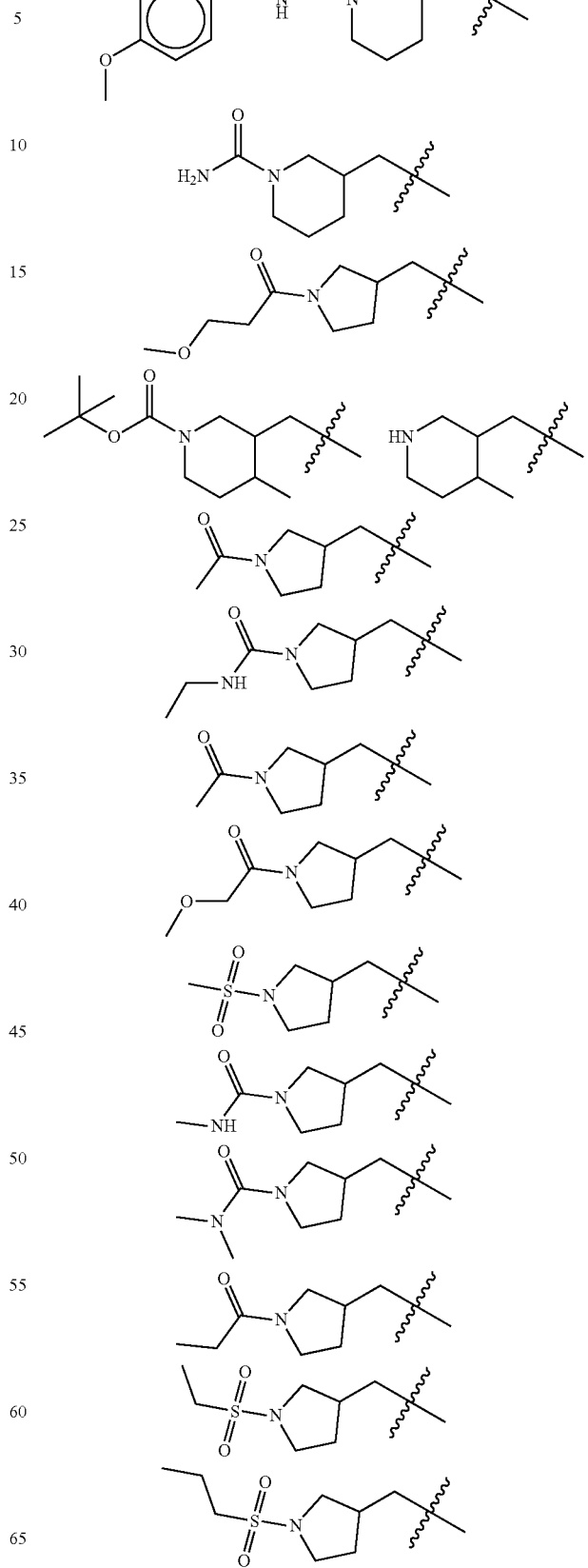

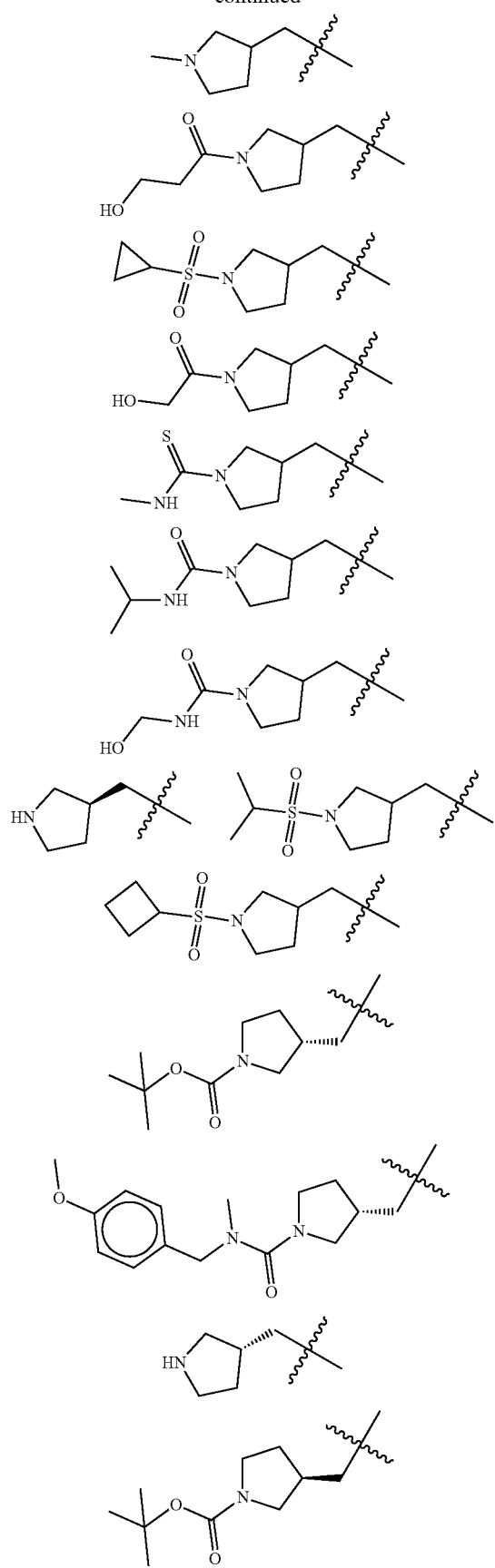
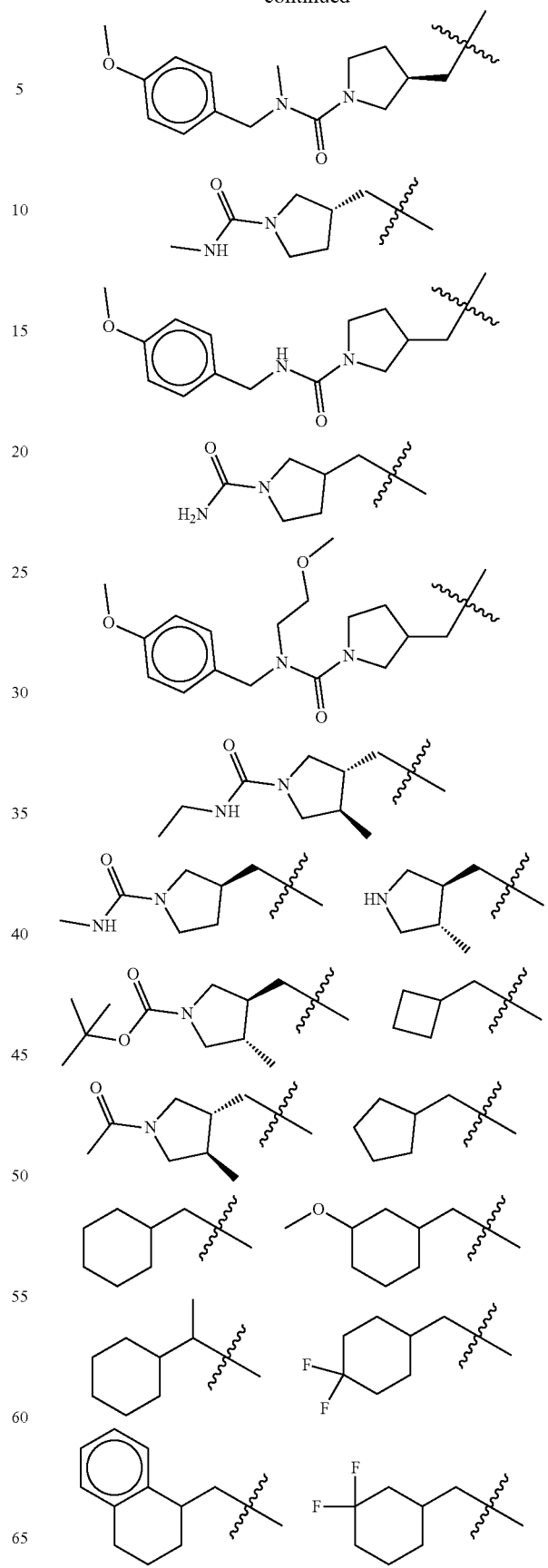

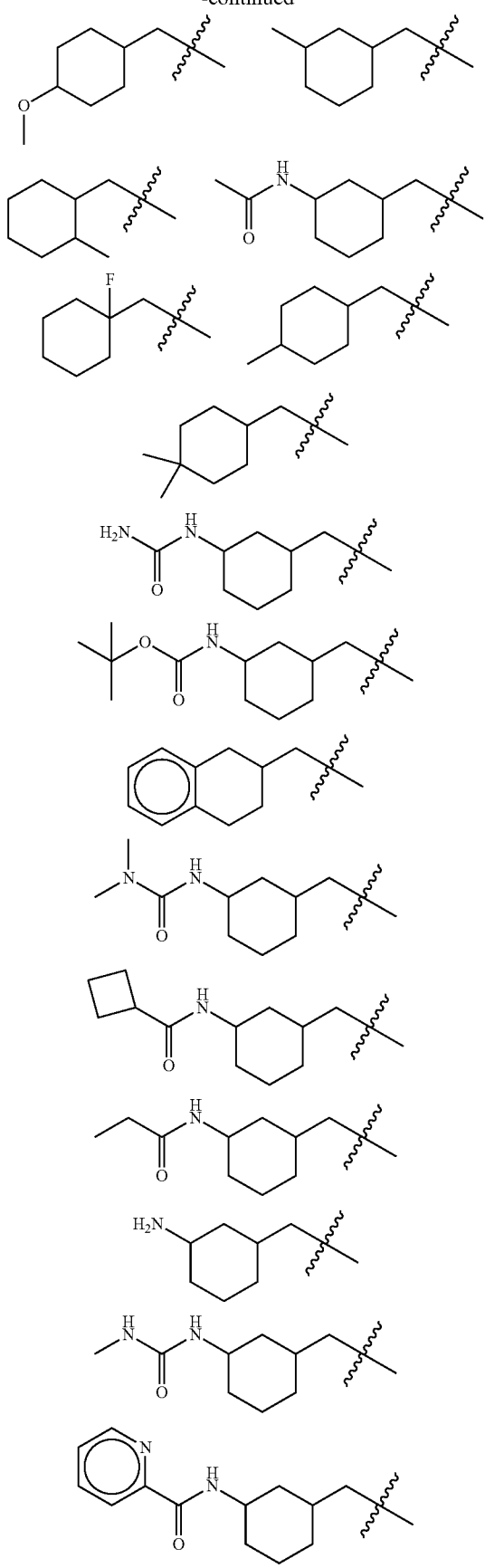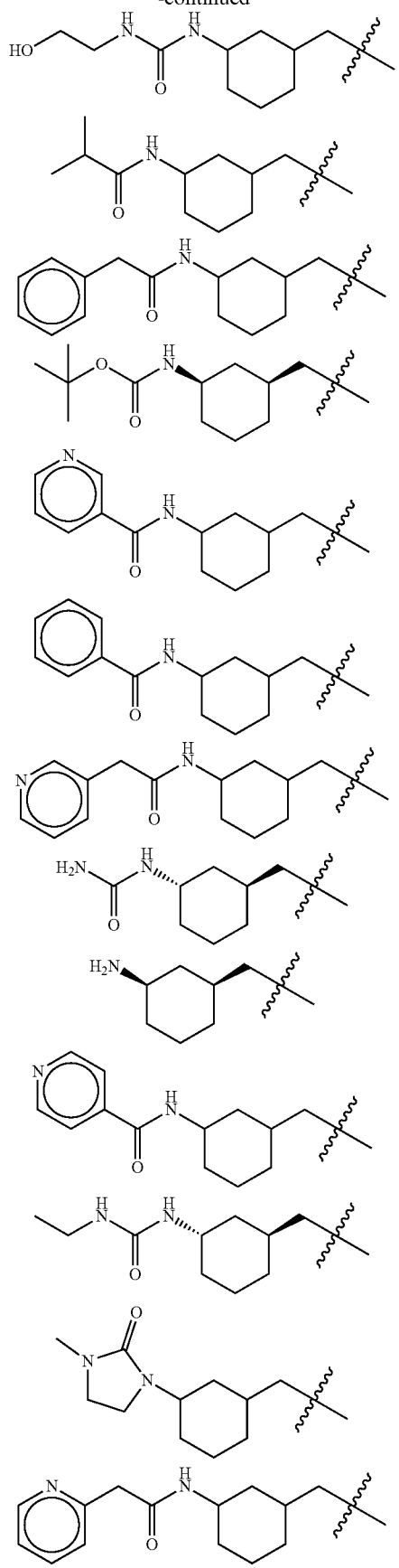

285
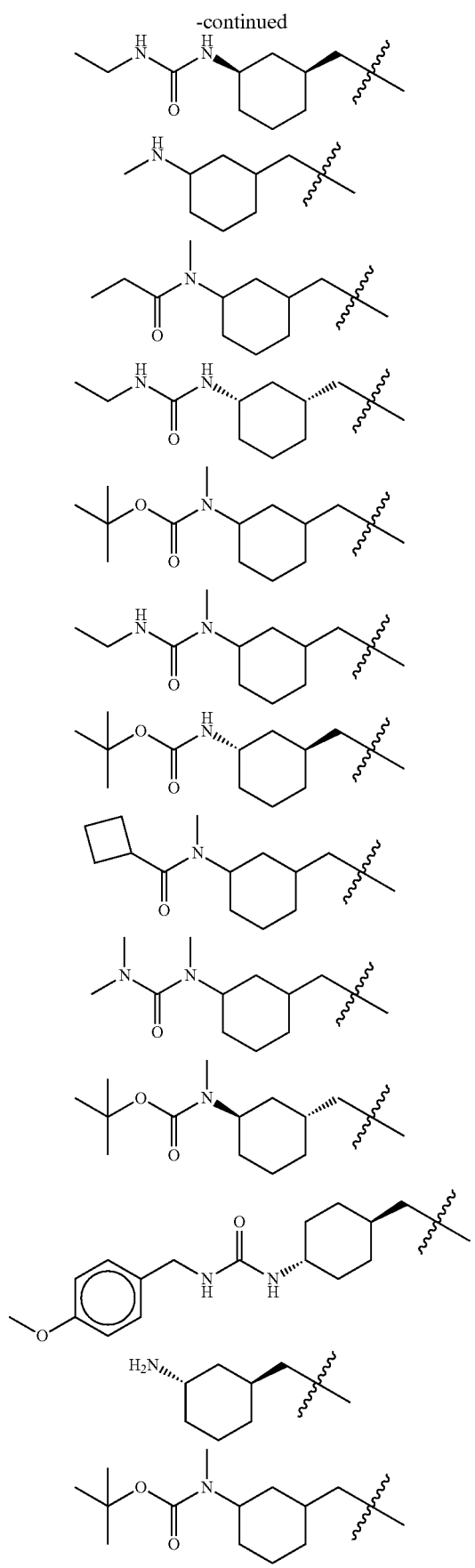
286
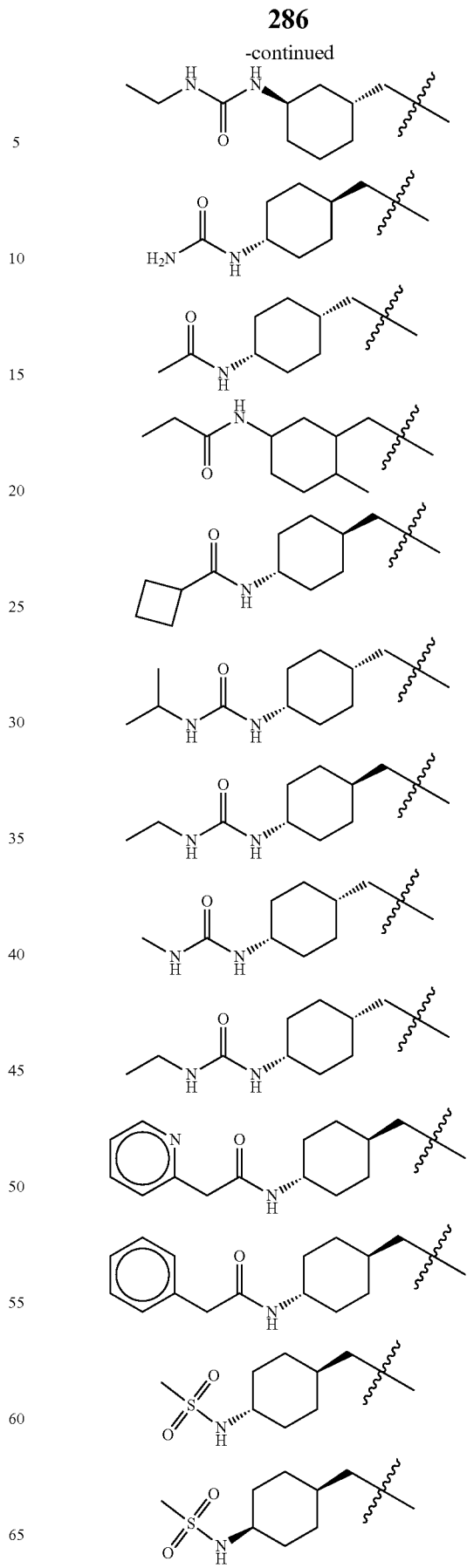

287
-continued
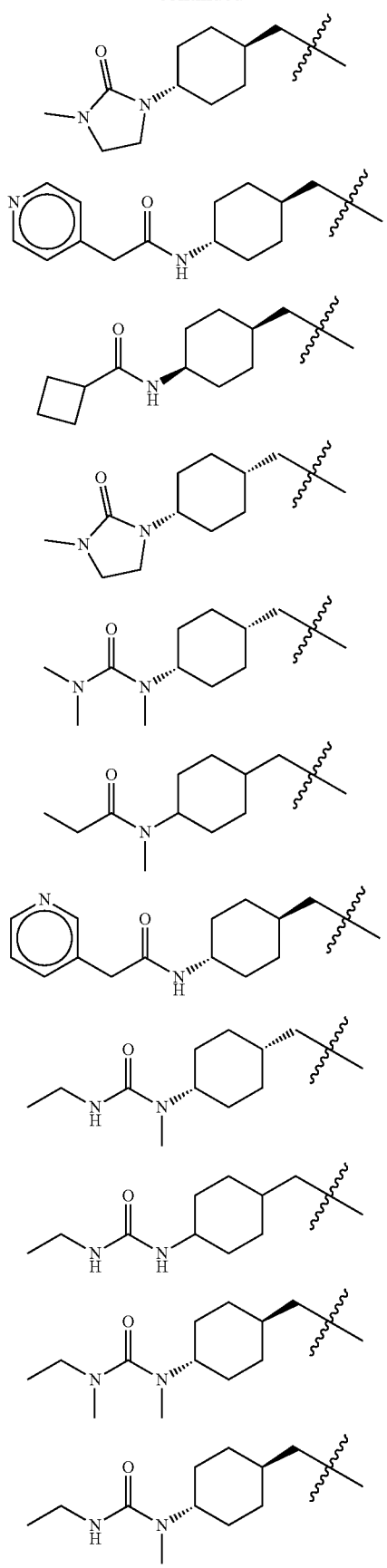
288
-continued
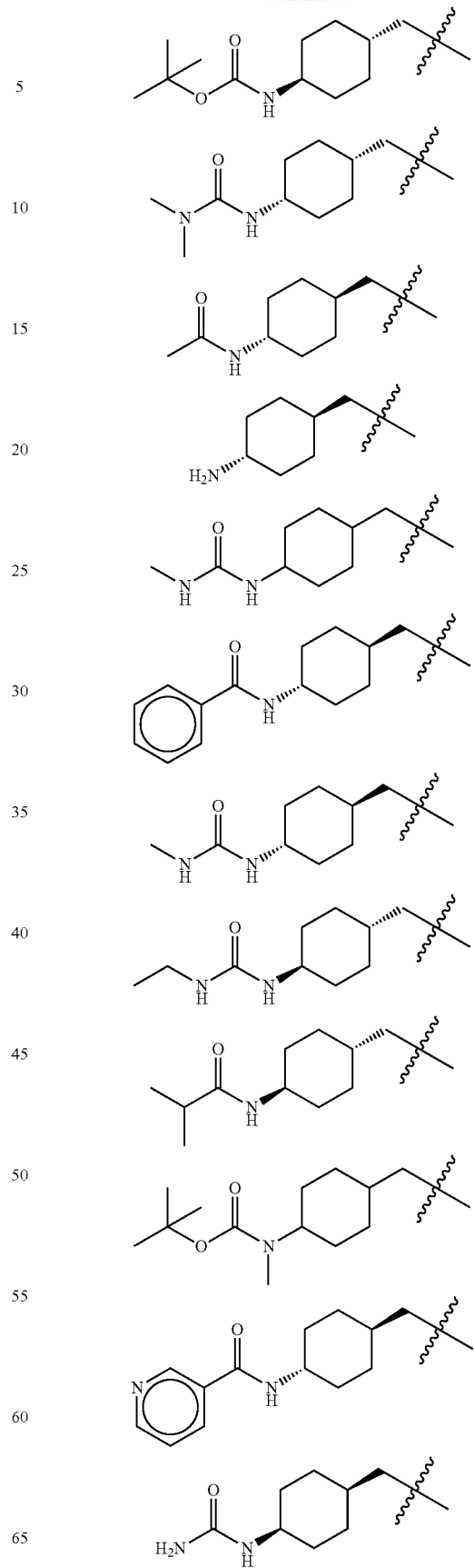

289
-continued
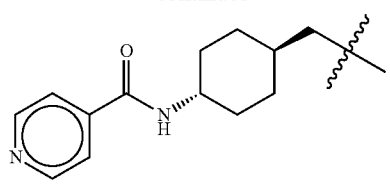
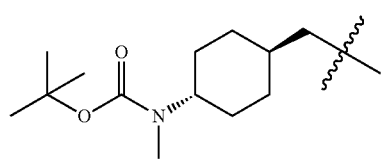
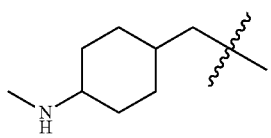
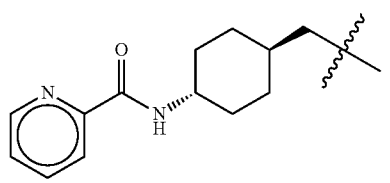
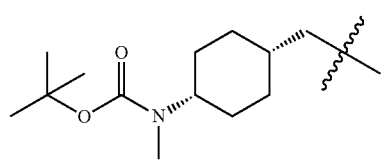
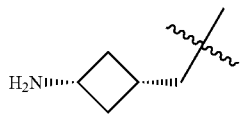
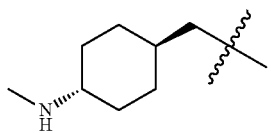
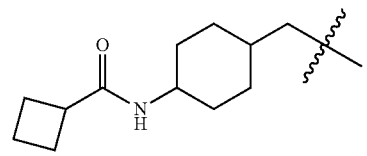
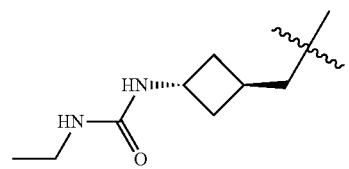
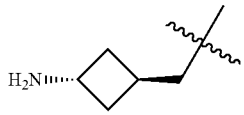
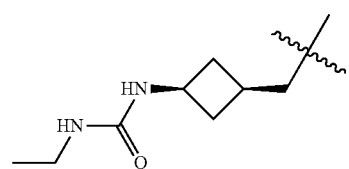
290
-continued
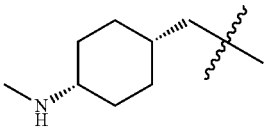
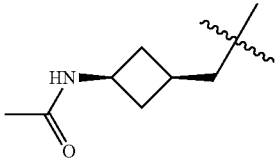
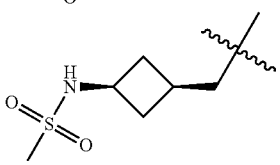
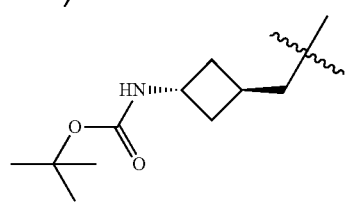
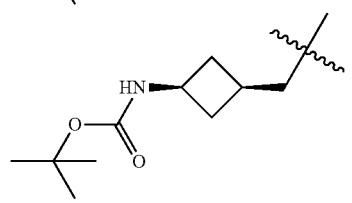
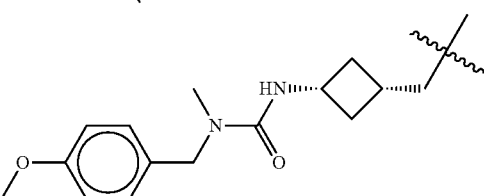
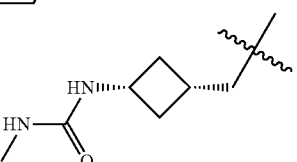
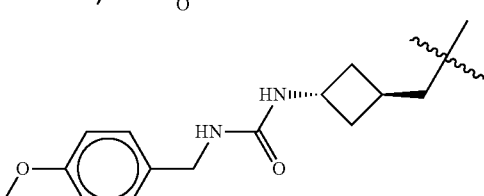
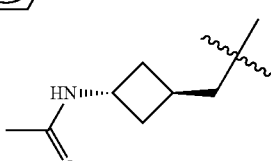
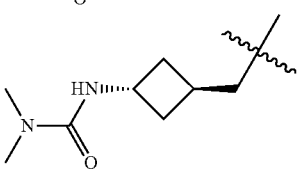

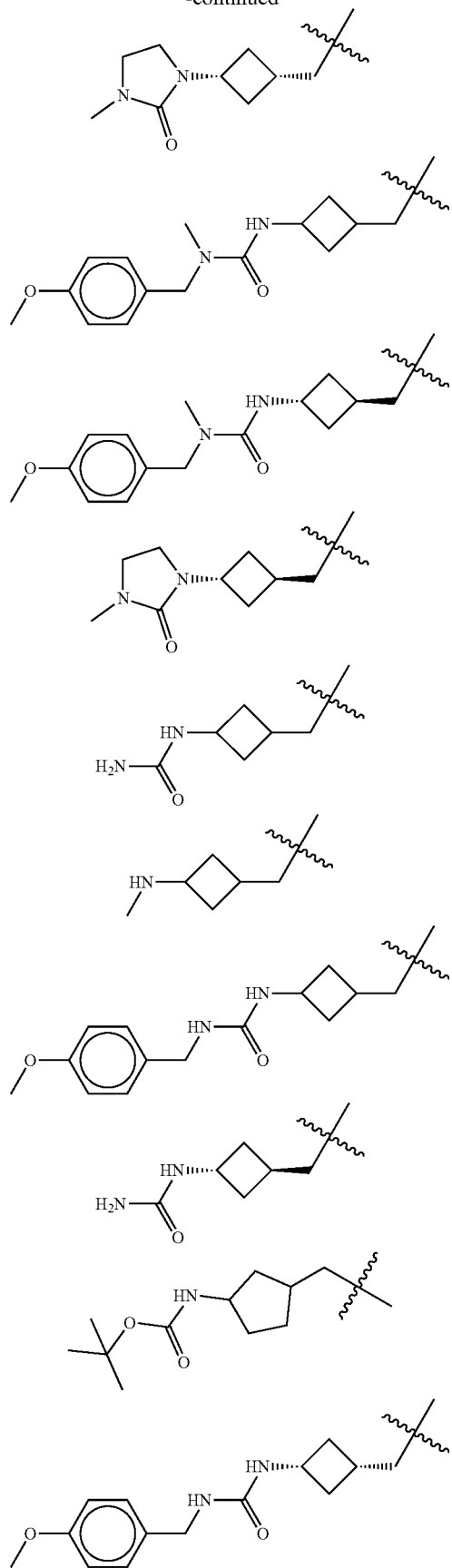
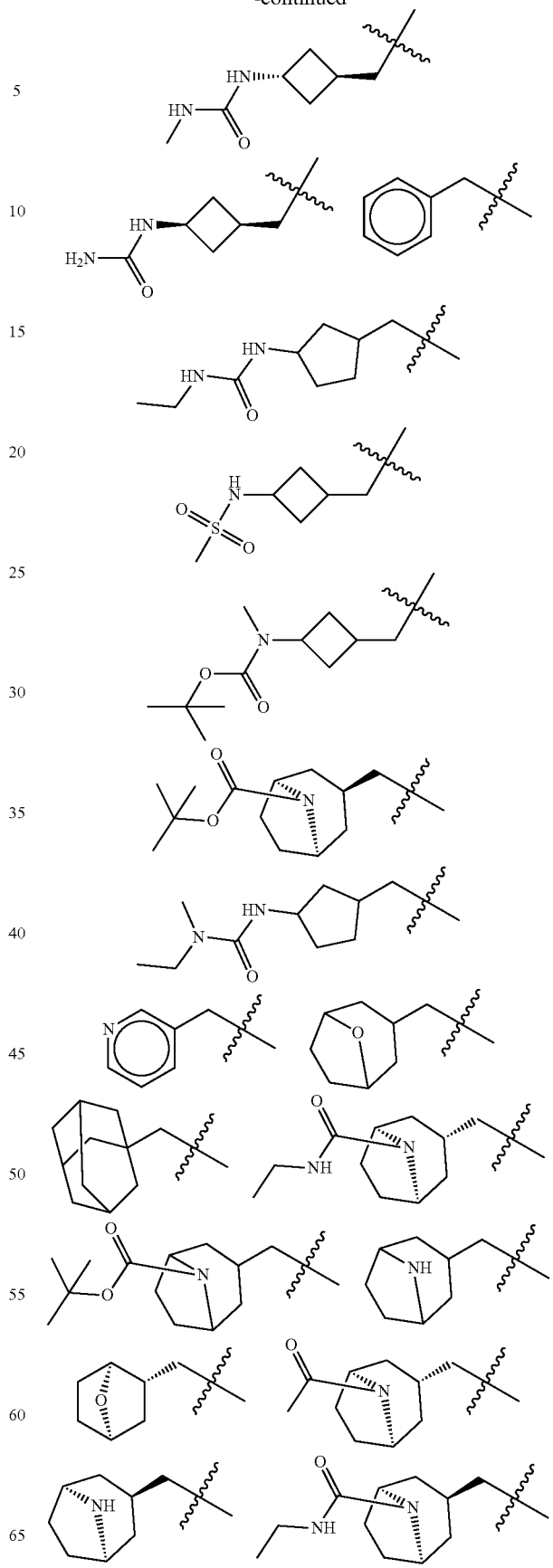

293
-continued
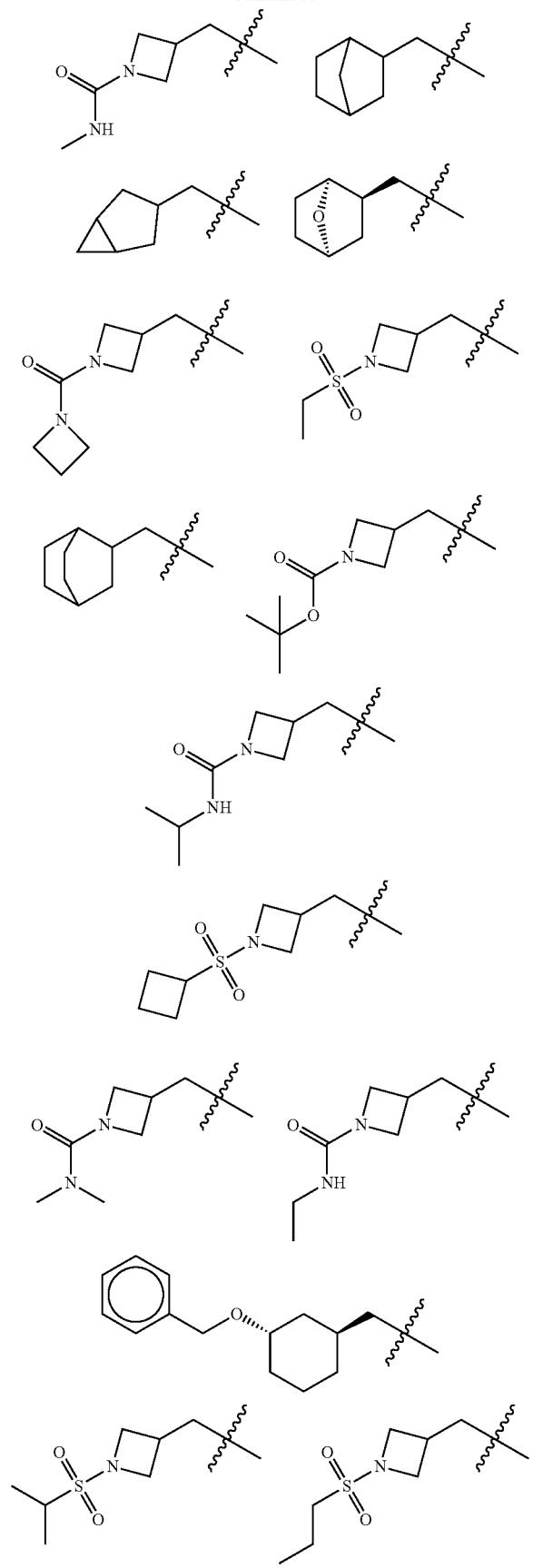
294
-continued
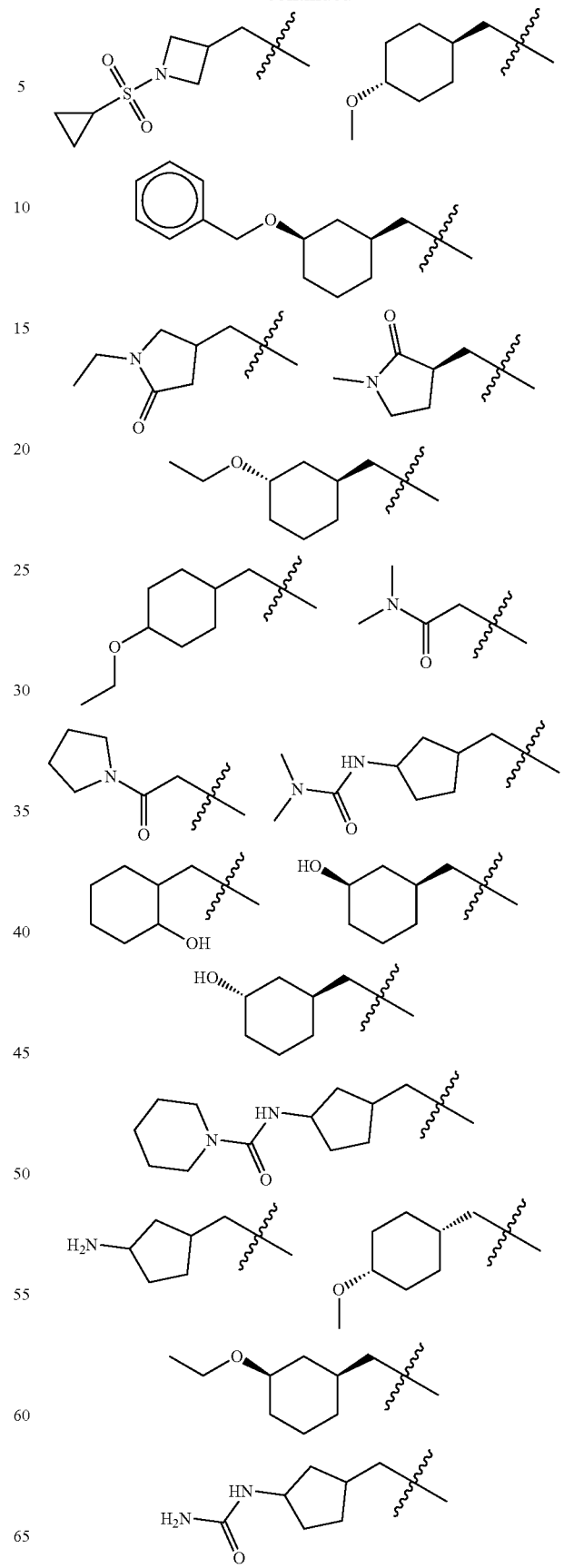

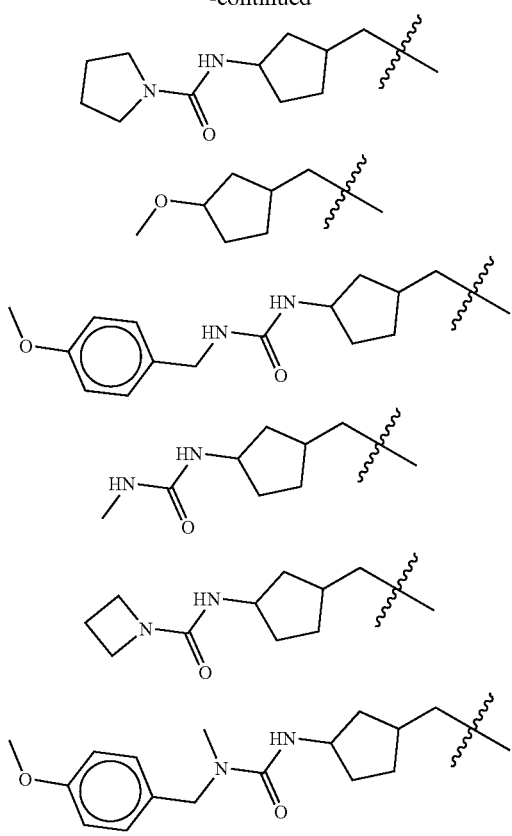
In some embodiments of formula III, Z is —(C$_{1-3}$ aliphatic)-Cy. In some such embodiments, Z is —CH$_2$—Cy. In some such embodiments, Z is selected from the group consisting of:
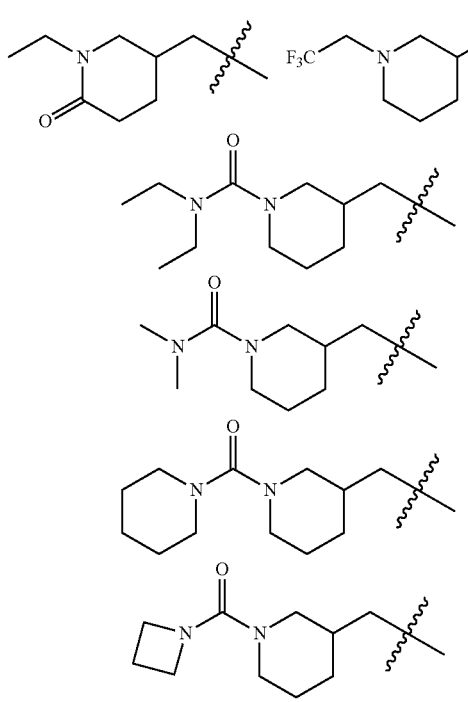
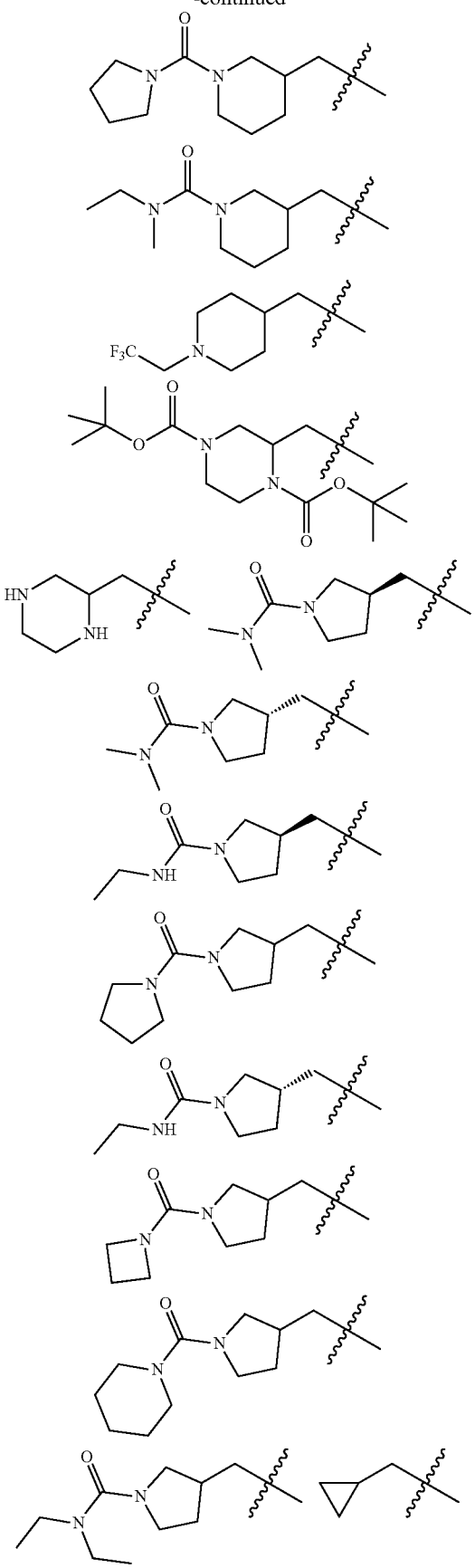

297
-continued

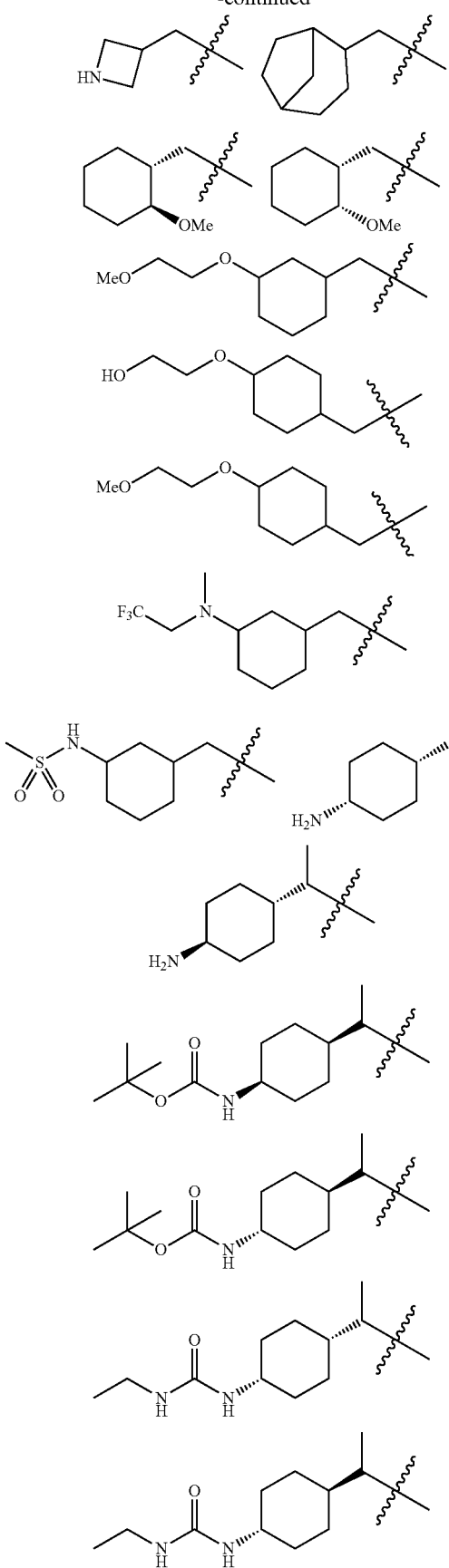

298
-continued

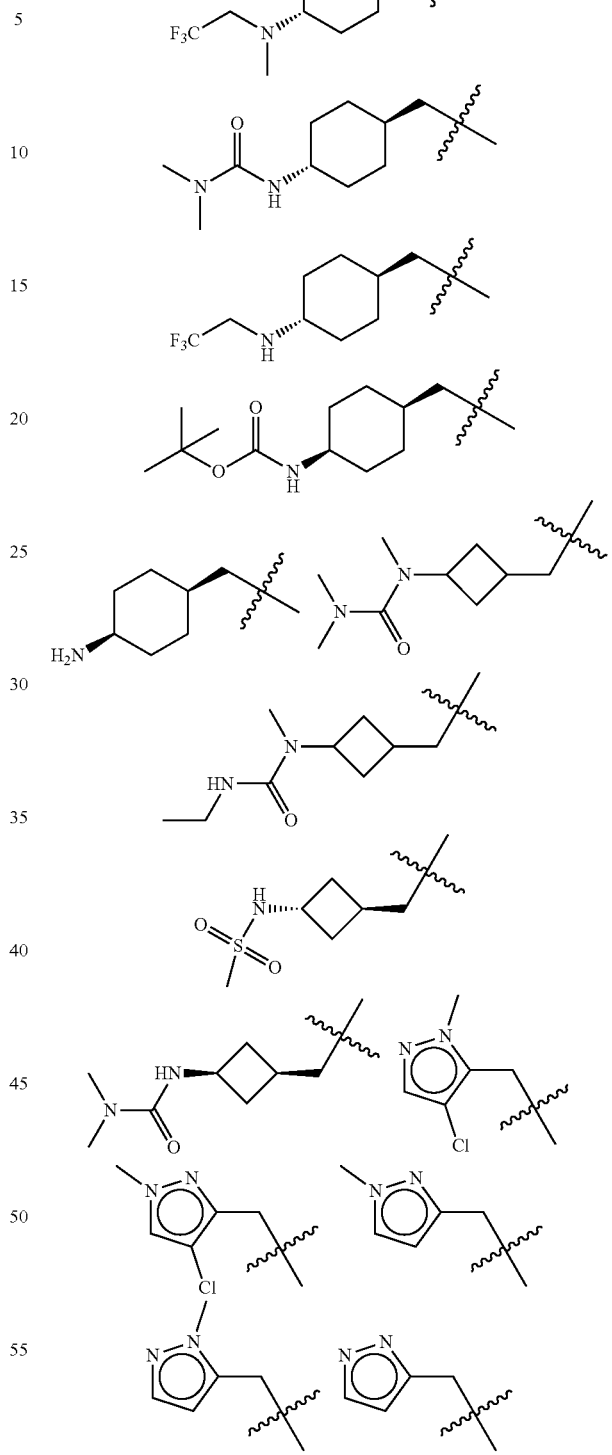

As defined above for formula III, Cy is an optionally substituted group selected from phenyl, a 3-10 membered saturated or partially unsaturated carbocyclic ring, a 3-10 membered saturated or partially unsaturated heterocyclic ring having 1-2 heteroatoms independently selected from nitrogen, oxygen and sulfur, a 6-8 membered bridged bicyclic heterocyclic ring having 1-2 heteroatoms independently selected from nitrogen, oxygen and sulfur, a 5-6 membered heteroaryl ring having 1-2 heteroatoms independently selected from nitrogen, oxygen and sulfur, an 8-10 membered bicyclic aryl ring, and an 8-10 membered bicyclic heteroaryl ring having 1-3 heteroatoms independently selected from nitrogen oxygen and sulfur.

In some embodiments of formula III, Cy is phenyl.

In some embodiments of formula III, Cy is an optionally substituted 3-10 membered saturated or partially unsaturated carbocyclic ring. In some embodiments of formula III, Cy is an optionally substituted 3-10 membered saturated carbocyclic ring. In some such embodiments, Cy is an optionally substituted group selected from cyclopropyl, cyclobutyl, cyclopentyl, and cyclohexyl.

In some embodiments of formula III, Cy is an optionally substituted bicyclic carbocyclic ring. It will be appreciated that a bicyclic carbocyclic ring can be a bridged bicyclic ring. In some such embodiments, Cy is an optionally substituted group selected from:

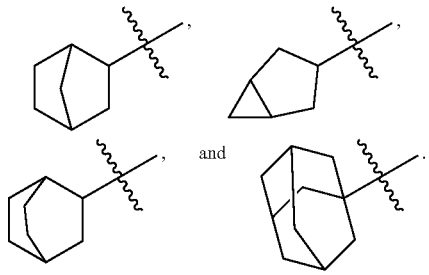

In some such embodiments, Cy is an optionally substituted group selected from:

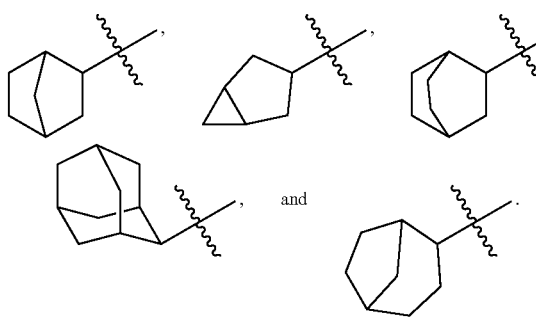

In some such embodiments, Cy is an optionally substituted group selected from:

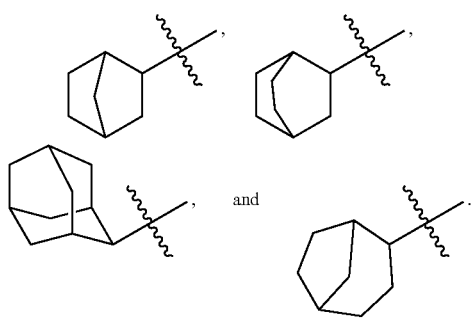

In some embodiments of formula III, Cy is an optionally substituted 5-6 membered heteroaryl ring having 1-3 heteroatoms independently selected from nitrogen, oxygen and sulfur. In some embodiments of formula III, Cy is a 5-membered heteroaryl ring having 1-3 heteroatoms independently selected from nitrogen, oxygen and sulfur. In some such embodiments, Cy is an optionally substituted group selected from pyrazolyl, imidazolyl, and triazolyl.

In some embodiments of formula III, Cy is selected from:

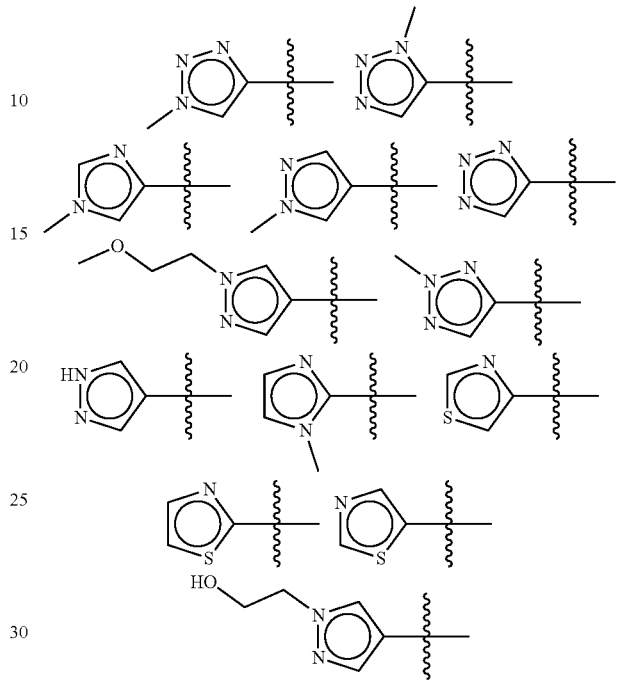

In some embodiments of formula III, Cy is an optionally substituted group selected from:

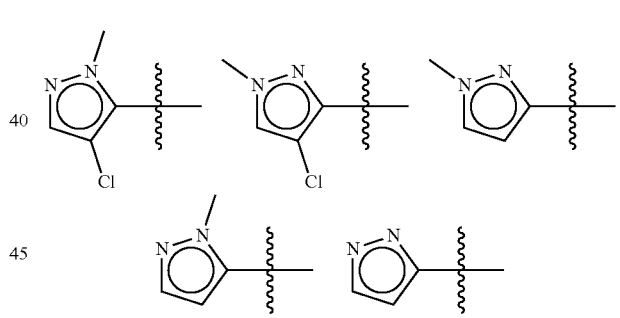

In some embodiments of formula III, Cy is an optionally substituted 5-6 membered heteroaryl ring having 1-3 heteroatoms independently selected from nitrogen, oxygen and sulfur. In some embodiments, Cy is a 6-membered heteroaryl ring having 1-3 heteroatoms independently selected from nitrogen, oxygen and sulfur. In some such embodiments, Cy is an optionally substituted group selected from pyridinyl. In some embodiments, Cy is an optionally substituted group selected from:

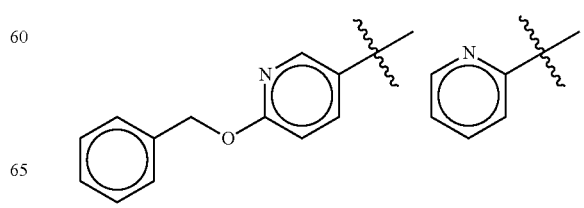

-continued

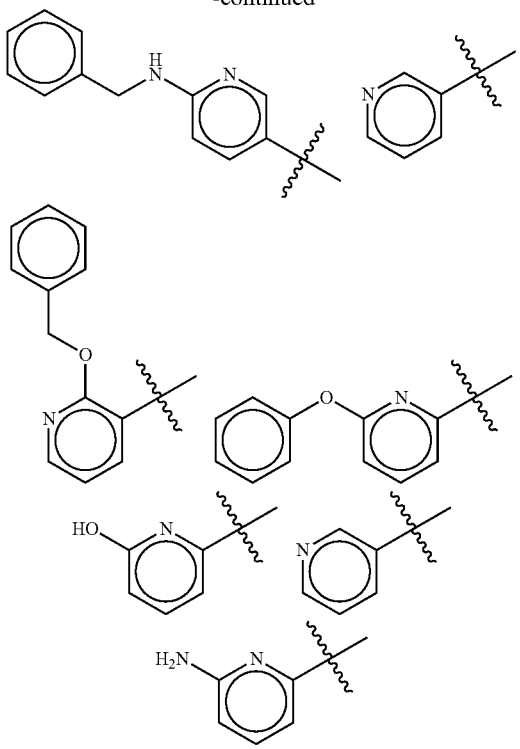

In some embodiments of formula III, Cy is an optionally substituted group selected from:

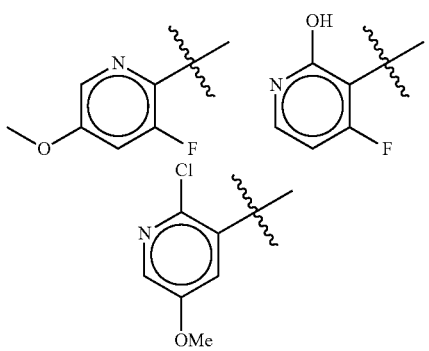

In some embodiments of formula III, Cy is an optionally substituted 3-10 membered saturated or partially unsaturated heterocyclic ring having 1-2 heteroatoms independently selected from nitrogen, oxygen and sulfur.

In some embodiments of formula III, Cy is an optionally substituted 4-membered saturated heterocyclic group having 1 heteroatom independently selected from nitrogen, oxygen and sulfur. In some such embodiments, Cy is optionally substituted oxetanyl. In some such embodiments, Cy is optionally substituted oxetanyl or azetidinyl.

In some embodiments of formula III, Cy is an optionally substituted 5-membered saturated heterocyclic group having 1-2 heteroatoms independently selected from nitrogen, oxygen and sulfur. In some such embodiments, Cy is an optionally substituted group selected from tetrahydrofuranyl and pyrrolidinyl.

In some embodiments of formula III, Cy is an optionally substituted 6-membered saturated heterocyclic group having 1-2 heteroatoms independently selected from nitrogen, oxygen and sulfur. In some such embodiments, Cy is an optionally substituted group selected from tetrahydropyranyl and piperidinyl. In some such embodiments, Cy is an optionally substituted group selected from tetrahydropyranyl, piperidinyl, and piperazinyl.

In some embodiments of formula III, Cy is an optionally substituted 7-membered saturated heterocyclic group having 1-2 heteroatoms independently selected from nitrogen, oxygen and sulfur. It will be appreciated that a 7-membered saturated heterocyclic ring can be a bridged bicyclic ring. In some such embodiments, Cy is an optionally substituted group selected from:

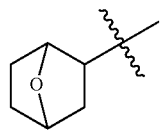

In some embodiments of formula III, Cy is an optionally substituted 8-membered saturated heterocyclic group having 1-2 heteroatoms independently selected from nitrogen, oxygen and sulfur. It will be appreciated that an 8-membered saturated heterocyclic ring can be a bridged bicyclic ring. In some such embodiments, Cy is an optionally substituted group selected from:

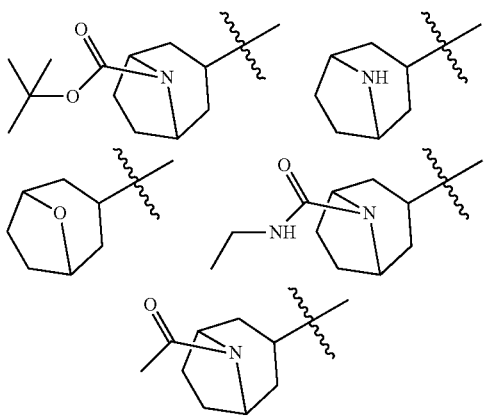

In some embodiments of formula III, $R^1$ is fluoro, $R^2$ is chloro, and $R^x$ is methyl, thus forming a compound of formula III-a:

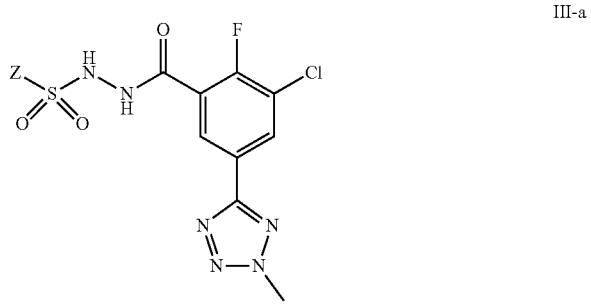

III-a or a pharmaceutically acceptable salt thereof, wherein Z is as defined above and described in classes and subclasses herein.

In some embodiments, the present disclosure provides a compound, or a pharmaceutically acceptable salt thereof, selected from the compounds listed in Table 2:

TABLE 2

| Cmpd No | Compound Structure |
|---|---|
| A-1 | 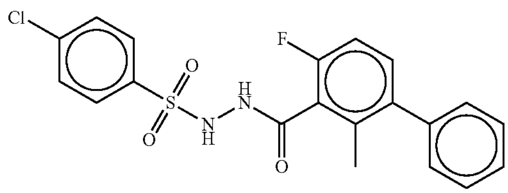 |
| A-2 | 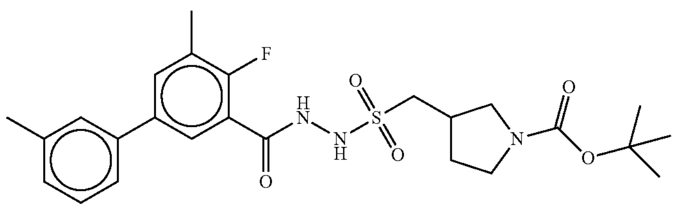 |
| A-3 | 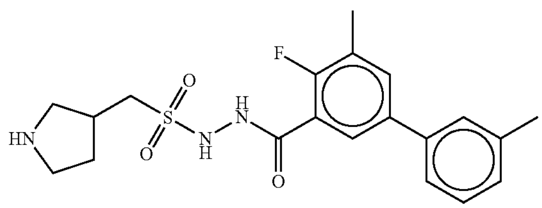 |
| A-4 | 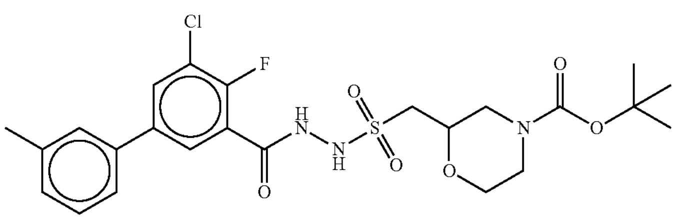 |
| A-5 | 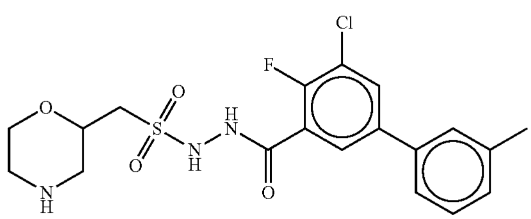 |
| A-6 | 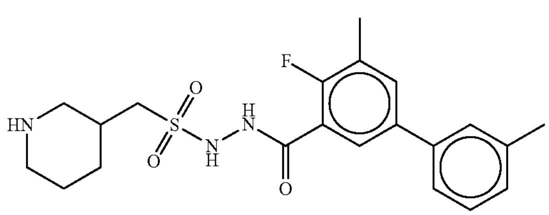 |
| A-7 | 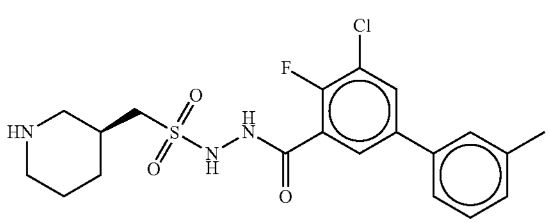 |

TABLE 2-continued

| Cmpd No | Compound Structure |
|---|---|
| A-8 | 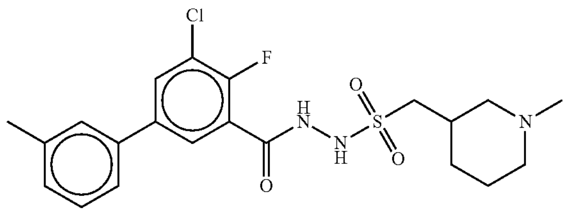 |
| A-9 | 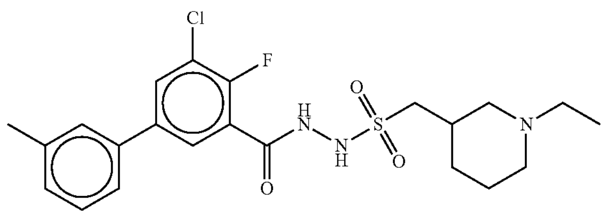 |
| A-10 | 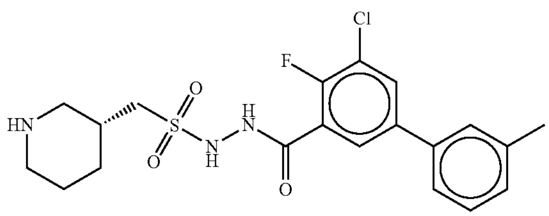 |
| A-11 | 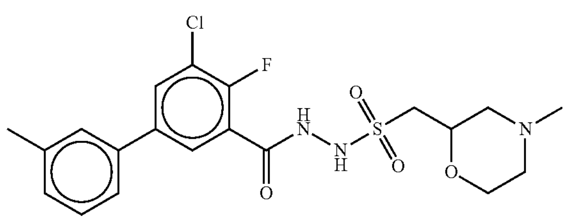 |
| A-12 | 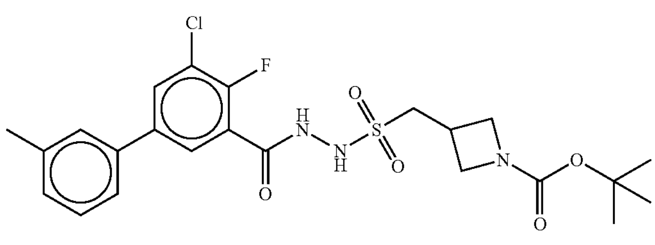 |
| A-13 | 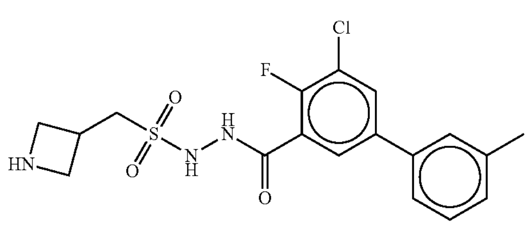 |

TABLE 2-continued

| Cmpd No | Compound Structure |
|---|---|
| A-14 | 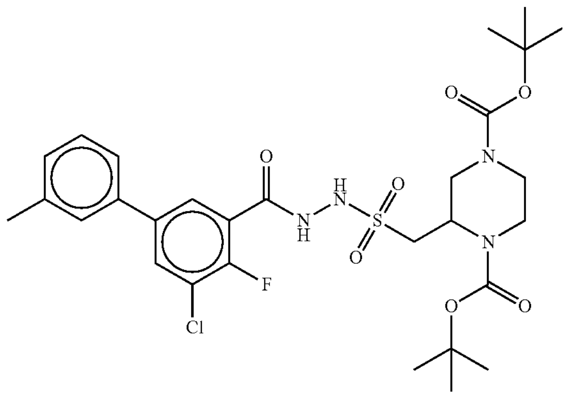 |
| A-15 | 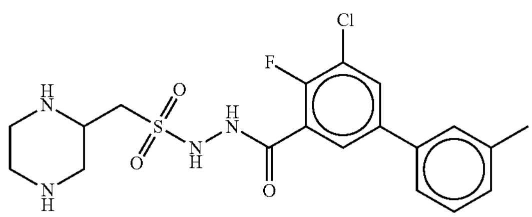 |
| A-16 | 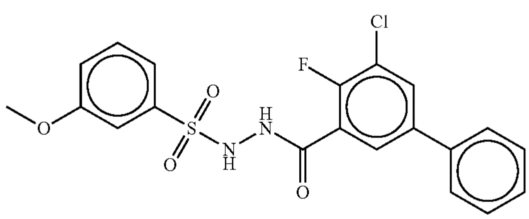 |
| A-17 | 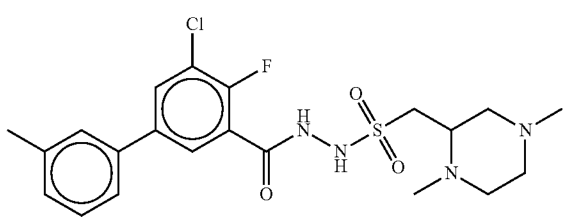 |
| A-18 | 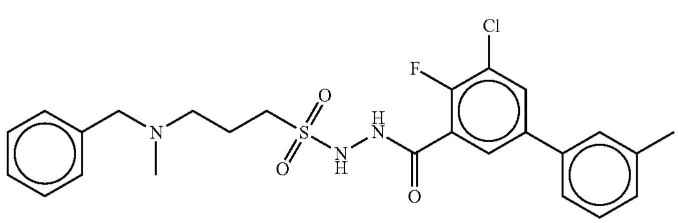 |
| A-19 | 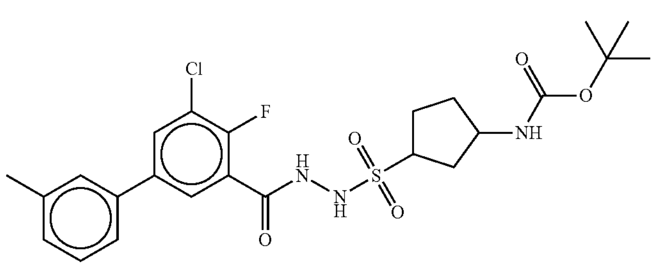 |

TABLE 2-continued
| Cmpd No | Compound Structure |
|---|---|
| A-20 | 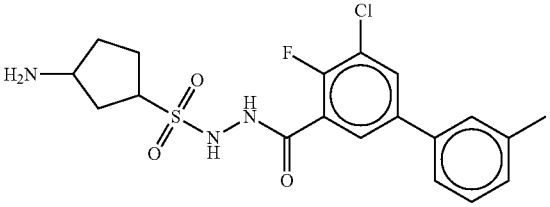 |
| A-21 | 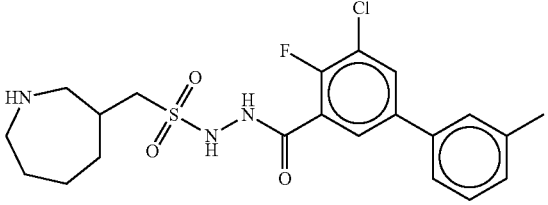 |
| A-22 | 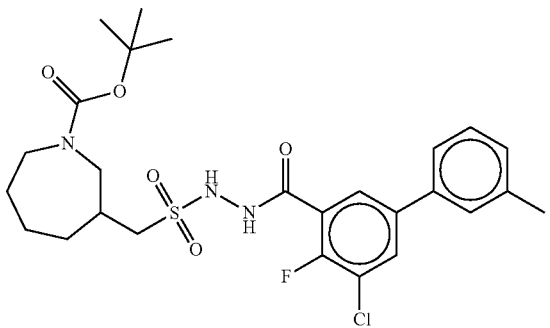 |
| A-23 | 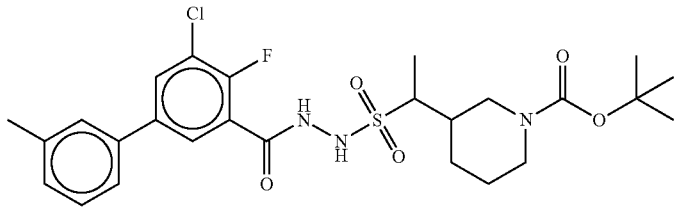 |
| A-24 | 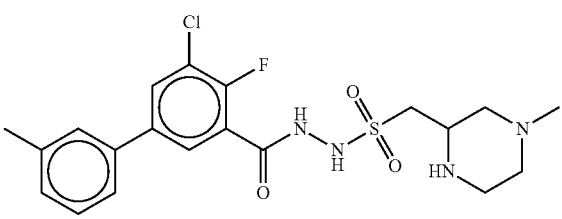 |
| A-25 | 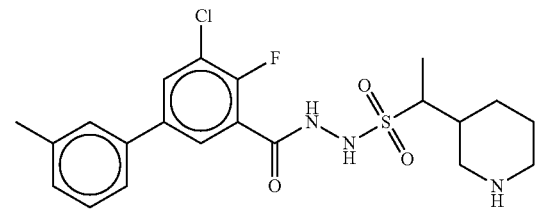 |

TABLE 2-continued
| Cmpd No | Compound Structure |
|---|---|
| A-26 | 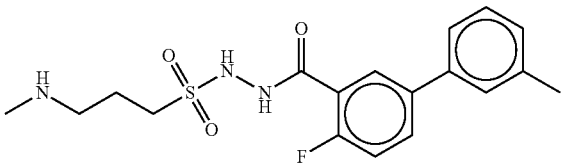 |
| A-27 | 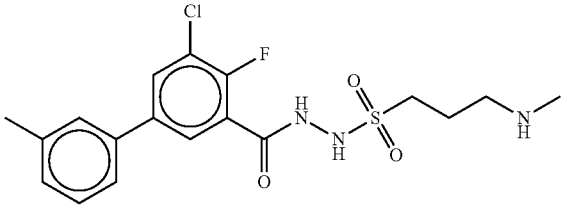 |
| A-28 | 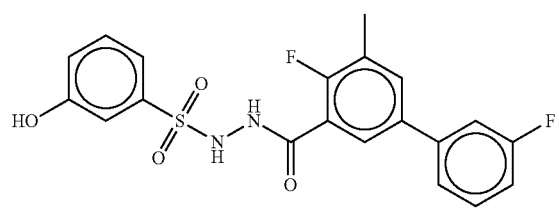 |
| A-29 | 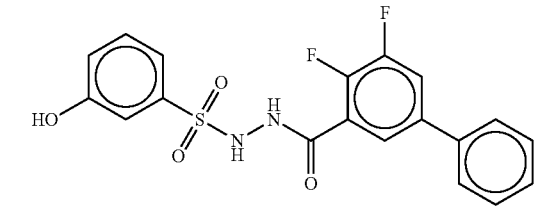 |
| A-30 | 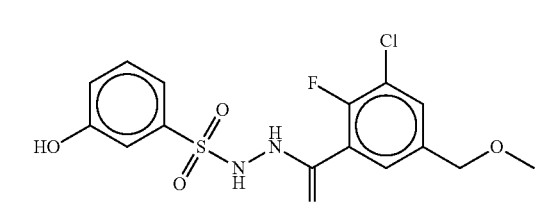 |
| A-31 | 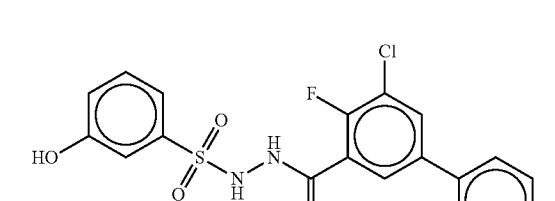 |
| A-32 | 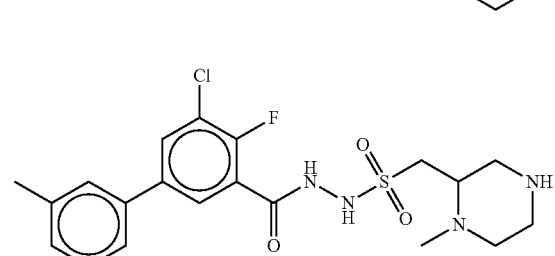 |

Acetyl Transferases

Histone acetylation and deacetylation are processes by which lysine residues within the N-terminal tail protruding from histone cores of the nucleosome are acetylated and deacetylated. Without wishing to be bound by any particular theory, it is believed that histone acetylation is a part of gene regulation. Histone Acetyltransferases, also known as HATs, are a family of enzymes that acetylate the histone tails of the nucleosome among other nuclear and cytoplasmic non-histone targets. Some HATs acetylate a lysine residue, and such Lysine Acetyltransferases are also referred to as KATs.

KATs can be divided into families based on their structure and sequence similarity. KAT families include, for example, the Gcn5-related N-acetyltransferase (GNAT) family, which includes GCN5 and PCAF, the CREBBP/EP300 family and the MYST (MOZ, Ybf2/Sas3, Sas2, Tip60) family. The MYST family of HATs is named after its four founding members MOZ, Ybf2 (Sas3), Sas2, and Tip60. Other members include Esa1, MOF, MORF, and HBO1. Members of the MYST family are characterized by the presence of the MYST catalytic domain, and have been reported to acetylate lysine residues on histones, e.g., on histone 2A (H2A), histone 3 (H3), and histone 4 (H4). Lysine acetyltransferases are also referred to as KATs, and members of the MYST family of histone acetyltransferases include, for example, KAT-5 (also sometimes referred to as Tip60), KAT-6A (also sometimes referred to as MOZ, MYST3, RUNXBP2, or ZNF220), KAT-6B (also sometimes referred to as MORF, MYST4, or MOZ2), KAT-7 (also sometimes referred to as (HBO1, HBOa, or MYST2), and KAT-8 (also sometimes referred to as MOF, YBF2, SAS3, or MYST1).

Different KATs may contain various other domains in addition to the HAT domain which facilitate interactions with other proteins, including reader domains for acetylation and other modifications. See, e.g., Farria et al. Oncogene (2015) 34, 4901-4913, incorporated herein by reference. Some KATs, for example those in the GNAT and CREBBP/EP300 families, contain bromodomains. Bromodomains help KATs recognize and bind to acetylated lysine residues on histone substrates. Together these domains allow for specificity and diversity in KAT substrates. All KATs examined to date have important functions in cellular differentiation and embryo development. Several KATs have also been associated with oncogenesis. For example, CREBBP/EP300, have been implicated in cancer development and progression. See, e.g., Farria et al. Oncogene (2015) 34, 4901-4913; Lee et al. Nat. Rev. Mol. Cell Biol. 8 (4): 284-95; and Avvakumov et al. Oncogene (2007) 26, 5395-5407, the entire contents of each of which are incorporated herein by reference.

Inhibitors of KATs and histone deacetylase inhibitors (HDACs) have potential as anti-cancer therapies. As noted, KATs within the MYST family are grouped together on the basis of their close sequence similarities and their possession of a particular acetyl transferase homology region. The name is derived from the first four members identified: MOZ (KAT-6A), Ybf2/Sas3, Sas2, Tip60 (KAT-5). Additional KATs have also been identified, including MOF (KAT-8) and HBO-1 (KAT-7). The MYST catalytic domain that defines the family has a C2HC zinc finger and an acetyl-CoA binding site. These enzymes are involved in transcription regulation, DNA replication, recombination, and repair. They are directly implicated in the development of a variety of diseases, including cancer.

One MYST family HAT of particular interest, KAT-7, also known as Lysine Acetyltransferase 7, HBO1, HBOA, MYST2, and ZC2HC7, belongs to the MYST family of histone acetyl transferases and plays an essential role in DNA replication. The KAT-7 coding region has been identified as a common retroviral integration site, and KAT-7 has been linked to numerous disease binding partners, including AR, the von Hippel-Lindau tumour suppressor, and ING4 and -5. Specific cancers that have been identified as being linked to KAT-7 inhibition include, for example, breast cancer, prostate cancer, and leukemia.

The protein sequences of exemplary KAT-7 proteins have been reported. Exemplary human KAT-7 protein sequences include, for example, and without limitation, the sequences provided below. Additional KAT-7 sequences, including KAT-7 sequences from other species and additional human KAT-7 sequences will be apparent to those of ordinary skill in the art, and include, for example, and without limitation, those KAT-7 sequences listed in the NCBI and ENSEMBL gene databases.

NP_008998.1 histone acetyltransferase KAT-7
isoform 1 [Homo sapiens]
(SEQ ID NO: 1)
MPRRKRNAGSSSDGTEDSDFSTDLEHTDSSESDGTSRRSARVTRSSA

RLSQSSQDSSPVRNLQSFGTEEPAYSTRRVTRSQQQPTPVTPKKYPL

RQTRSSGSETEQVVDFSDRETKNTADHDESPPRTPTGNAPSSESDID

ISSPNVSHDESIAKDMSLKDSGSDLSHRPKRRRFHESYNFNMKCPTP

GCNSLGHLTGKHERHFSISGCPLYHNLSADECKVRAQSRDKQIEERM

LSHRQDDNNRHATRHQAPTERQLRYKEKVAELRKKRNSGLSKEQKEK

YMEHRQTYGNTREPLLENLTSEYDLDLFRRAQARASEDLEKLRLQGQ

ITEGSNMIKTIAFGRYELDTWYHSPYPEEYARLGRLYMCEFCLKYMK

SQTILRRHMAKCVWKHPPGDEIYRKGSISVFEVDGKKNKIYCQNLCL

LAKLFLDHKTLYYDVEPFLFYVMTEADNTGCHLIGYFSKEKNSFLNY

NVSCILTMPQYMRQGYGKMLIDFSYLLSKVEEKVGSPERPLSDLGLI

SYRSYWKEVLLRYLHNFQGKEISIKEISQETAVNPVDIVSTLQALQM

LKYWKGKHLVLKRQDLIDEWIAKEAKRSNSNKTMDPSCLKWTPPKGT

NP_001186084.1 histone acetyltransferase KAT-7
isoform 2 [Homo sapiens]
(SEQ ID NO: 2)
MPRRKRNAGSSSDGTEDSDFSTDLEHTDSSESDGTSRRSARVTRSSA

RLSQSSQDSSPVRNLQSFGTEEPAYSTRRVTRSQQQPTPVTPKKYPL

RQTRSSGSETEQVVDFSDRETKNTADHDESPPRTPTGNAPSSESDID

ISSPNVSHDESIAKDMSLKDSGSDLSHRPKRRRFHESYNFNMKCPTP

GCNSLGHLTGKHERHFSISGCPLYHNLSADECKAPTERQLRYKEKVA

ELRKKRNSGLSKEQKEKYMEHRQTYGNTREPLLENLTSEYDLDLFRR

AQARASEDLEKLRLQGQITEGSNMIKTIAFGRYELDTWYHSPYPEEY

ARLGRLYMCEFCLKYMKSQTILRRHMAKCVWKHPPGDEIYRKGSISV

FEVDGKKNKIYCQNLCLLAKLFLDHKTLYYDVEPFLFYVMTEADNTG

CHLIGYFSKEKNSFLNYNVSCILTMPQYMRQGYGKMLIDFSYLLSKV

EEKVGSPERPLSDLGLISYR SYWKEVLLRY LHNFQGKEIS

IKEISQETAV NPVDIVSTLQALQMLKYWKGKHLVLKRQDL

IDEWIAKEAK RSNSNKTMDP SCLKWTPPKGT

```
NP_001186085.1 histone acetyltransferase KAT-7
isoform 3 [Homo sapiens]
                                    (SEQ ID NO: 3)
MPRRKRNAGSSSDGTEDSDFSTDLEHTDSSESDGTSRRSARVTRSSA

RLSQSSQGHLTGKHERHFSISGCPLYHNLSADECKVRAQSRDKQIEE

RMLSHRQDDNNRHATRHQAPTERQLRYKEKVAELRKKRNSGLSKEQK

EKYMEHRQTYGNTREPLLENLTSEYDLDLFRRAQARASEDLEKLRLQ

GQITEGSNMIKTIAFGRYELDTWYHSPYPEEYARLGRLYMCEFCLKY

MKSQTILRRHMAKCVWKHPPGDEIYRKGSISVFEVDGKKNKIYCQNL

CLLAKLFLDHKTLYYDVEPFLFYVMTEADNTGCHLIGYFSKEKNSFL

NYNVSCILTMPQYMRQGYGKMLIDFSYLLSKVEEKVGSPERPLSDLG

LISYRSYWKEVLLRYLHNFQGKEISIKEISQETAVNPVDIVSTLQAL

QMLKYWKGKHLVLKRQDLIDEWIAKEAKRSNSNKTMDPSCLKWTPPK

GT

NP_001186086.1 histone acetyltransferase KAT-7
isoform 4 [Homo sapiens]
                                    (SEQ ID NO: 4)
MPRRKRNAGSSSDGTEDSDFSTDLEHTDSSESDGTSRRSARVTRSSA

RLSQSSQDSSPVRNLQSFGTEEPAYSTRRVTRSQQQPTPVTPKKYPL

RQTRSSGSETEQVVDFSDRGHLTGKHERHFSISGCPLYHNLSADECK

APTERQLRYKEKVAELRKKRNSGLSKEQKEKYMEHRQTYGNTREPLL

ENLTSEYDLDLFRRAQARASEDLEKLRLQGQITEGSNMIKTIAFGRY

ELDTWYHSPYPEEYARLGRLYMCEFCLKYMKSQTILRRHMAKCVWKH

PPGDEIYRKGSISVFEVDGKKNKIYCQNLCLLAKLFLDHKTLYYDVE

PFLFYVMTEADNTGCHLIGYFSKEKNSFLNYNVSCILTMPQYMRQGY

GKMLIDFSYLLSKVEEKVGSPERPLSDLGLISYRSYWKEVLLRYLHN

FQGKEISIKEISQETAVNPVDIVSTLQALQMLKYWKGKHLVLKRQDL

IDEWIAKEAKRSNSNKTMDPSCLKWTPPKGT

NP_001186087.1 histone acetyltransferase KAT-7
isoform 5 [Homo sapiens]
                                    (SEQ ID NO: 5)
MPRRKRNAGSSSDGTEDSDFSTDLEHTDSSESDGTSRRSARVTRSSA

RLSQSSQGHLTGKHERHFSISGCPLYHNLSADECKAPTERQLRYKEK

VAELRKKRNSGLSKEQKEKYMEHRQTYGNTREPLLENLTSEYDLDLF

RRAQARASEDLEKLRLQGQITEGSNMIKTIAFGRYELDTWYHSPYPE

EYARLGRLYMCEFCLKYMKSQTILRRHMAKCVWKHPPGDEIYRKGSI

SVFEVDGKKNKIYCQNLCLLAKLFLDHKTLYYDVEPFLFYVMTEADN

TGCHLIGYFSKEKNSFLNYNVSCILTMPQYMRQGYGKMLIDFSYLLS

KVEEKVGSPERPLSDLGLISYRSYWKEVLLRYLHNFQGKEISIKEIS

QETAVNPVDIVSTLQALQMLKYWKGKHLVLKRQDLIDEWIAKEAKRS

NSNKTMDPSCLKWTPPKGT

NP_001333635.1 histone acetyltransferase KAT-7
isoform 6 [Homo sapiens]
                                    (SEQ ID NO: 6)
MPRRKRNAGSSSDGTEDSDFSTDLEHTDSSESDGTSRRSARVTRSSA

RLSQSSQDSSPVRNLQSFGTEEPAYSTRRVTRSQQQPTPVTPKKYPL

RQTRSSGSETEQVVDFSDRGHLTGKHERHFSISGCPLYHNLSADECK

VRAQSRDKQIEERMLSHRQDDNNRHATRHQAPTERQLRYKEKVAELR

KKRNSGLSKEQKEKYMEHRQTYGNTREPLLENLTSEYDLDLFRRAQA

RASEDLEKLRLQGQITEGSNMIKTIAFGRYELDTWYHSPYPEEYARL

GRLYMCEFCLKYMKSQTILRRHMAKCVWKHPPGDEIYRKGSISVFEV

DGKKNKIYCQNLCLLAKLFLDHKTLYYDVEPFLFYVMTEADNTGCHL

IGYFSKEKNSFLNYNVSCILTMPQYMRQGYGKMLIDFSYLLSKVEEK

VGSPERPLSDLGLISYRSYWKEVLLRYLHNFQGKEISIKEISQETAV

NPVDIVSTLQALQMLKYWKGKHLVLKRQDLIDEWIAKEAKRSNSNKT

MDPSCLKWTPPKGT
```

In some embodiments, the present disclosure provides inhibitors of MYST family KATs, e.g., of KAT-5, KAT-6A, KAT-7, and/or KAT-8, for use as histone acetyltransferase inhibitors, e.g., in vitro or in vivo. In certain embodiments, the present disclosure provides inhibitors of MYST family KATs, e.g., KAT-5, KAT-6A, KAT-7, and/or KAT-8, for use in treating diseases or disorders that are characterized by an abnormal MYST family KAT activity, e.g., certain cancers.

Some aspects of this disclosure provide methods for modulating protein acetylation, e.g., histone acetylation, e.g., in a cell or tissue, by contacting a histone acetylase, e.g., KAT-5, KAT-6A, KAT-7, and/or KAT-8, or a cell or tissue expressing such a histone acetylase, with compounds of the present disclosure in an amount sufficient to modulate the activity of the histone acetylase, e.g., of KAT-5, KAT-6A, KAT-7, and/or KAT-8, e.g., as measured by a reduction in the acetylation of a target protein of the histone acetyltransferase, e.g., a histone acetylated by KAT-5, KAT-6A, KAT-7, and/or KAT-8 activity. In some embodiments, the contacting is in vitro. In some embodiments, the contacting is in vivo, e.g., by administering the compounds of the present disclosure, or a pharmaceutically acceptable salt thereof, to a subject, e.g., a human subject. In some embodiments, the subject is a subject having or diagnosed with a cancer or a precancerous condition.

Some aspects of this disclosure provide methods for selectively inhibiting at least one KAT. For example, in some embodiments, it is beneficial to be able to selectively inhibit a specific MYST family KAT or a combination of two or more MYST family KATs, while not inhibiting one or more different KATs, or while inhibiting one or more different KATs to a lesser extent. As used herein, the term "selectively inhibiting" refers to inhibiting of a particular MYST family KAT, or a group of MYST family KATs, while inhibiting a different KAT or a group of KATs to a different extent.

For example, in some embodiments, selectively inhibiting a MYST family KAT, refers to inhibiting the activity of the MYST family KAT at a potency that is at least 2-fold, at least 5-fold, at least 10-fold, at least 15-fold, at least 20-fold, at least 25-fold, at least 50-fold, at least 75-fold, at least 100-fold, at least 200-fold, at least 250-fold, at least 500-fold, at least 750-fold, at least 1000-fold, at least 2000-fold, at least 2500-fold, at least 5000-fold, at least 7500-fold, or at least 10000-fold the potency at which a different KAT, e.g., a different MYST family KAT is inhibited.

The potency of inhibition of a given KAT inhibitor can be determined, e.g., measured, by methods well known to those of skill in the art. Some exemplary methods are provided herein, and other suitable methods will be apparent to the skilled artisan based on the present disclosure and the general knowledge in the art. One exemplary suitable measure of inhibition potency is the $IC_{50}$ value of a given KAT inhibitory compound with regard to a specific KAT enzyme, e.g., as exemplified for some compounds and some MYST family KATs elsewhere herein. Since the $IC_{50}$ value is a measure of the concentration of a given inhibitor to achieve a certain level of inhibition, it will be understood that a lower $IC_{50}$ value indicates a more potent inhibition. To provide a non-limiting example, a KAT-7 inhibitor would be said to inhibit KAT-7 at a potency that is 10-fold the potency at which it inhibits KAT-5, if the $IC_{50}$ of that inhibitor with regard to KAT-7 is 10-fold lower than the $IC_{50}$ of the inhibitor with regard to KAT-5.

Other measures of inhibition potency are also suitable, e.g., the level of inhibition of activity of a specific KAT at a given inhibitor concentration, e.g., as compared to the activity of the KAT in the absence of the inhibitor. To provide a non-limiting example, a KAT-7 inhibitor would be said to inhibit KAT-7 at a potency that is 10-fold the potency at which it inhibits KAT-5, if exposure of KAT-7 to the inhibitor results in a 10-fold greater inhibition of KAT-7 activity than the inhibition of KAT-5 activity that is achieved by exposure of KAT-5 to the inhibitor at the same concentration in the same assay.

Some exemplary, non-limiting suitable measures to compare inhibition potency of a given inhibitor amongst different KATs are provided herein, as are suitable assays (e.g., biochemical or cellular assays) for determining inhibition potency of a given KAT inhibitor, and additional suitable measures and assays will be apparent to the person of ordinary skill in the art in view of the present disclosure and the knowledge in the art. The disclosure is not limited in this respect.

In some embodiments, the present disclosure provides compounds (e.g., compounds of formula I, formula I-a, formula II, formula II-a, formula II-b, formula II-b, formula III, and/or formula III-a) and methods for selectively inhibiting a specific MYST family KAT, e.g., KAT-5, KAT-6A, KAT-7, or KAT-8, as compared to a different KAT, e.g., a different MYST family KAT. In some embodiments, the present disclosure provides compounds (e.g., compounds of formula I', formula I, formula I-a, formula II, formula II-a, formula II-b, formula II-c, formula III, and/or formula III-a) and methods for selectively inhibiting a specific MYST family KAT, e.g., KAT-5, KAT-6A, KAT-7, or KAT-8, as compared to a different KAT, e.g., a different MYST family KAT. For example, in some embodiments, the present disclosure provides compounds and methods for selectively inhibiting KAT-7 as compared to KAT-5. In some embodiments, the present disclosure provides compounds and methods for selectively inhibiting a group of MYST family KATs, e.g., KAT-7 and KAT-6A, as compared to a different KAT, e.g., a MYST family KAT, e.g., as compared to KAT-5. In some embodiments, the present disclosure provides compounds and methods for selectively inhibiting KAT-7 and KAT-8 as compared to KAT-5. In some embodiments, the present disclosure provides compounds and methods for selectively inhibiting KAT-7, KAT-6A, and KAT-8 as compared to KAT-5. In some embodiments, the present disclosure provides compounds and methods for selectively inhibiting KAT-7 as compared to KAT-5 and KAT-6A. In some embodiments, the present disclosure provides compounds and methods for selectively inhibiting KAT-7 as compared to KAT-5 and KAT-8. In some embodiments, the present disclosure provides compounds and methods for selectively inhibiting KAT-7 as compared to KAT-5, KAT-6A, and KAT-8.

In some embodiments, the present disclosure provides compounds and methods for selectively inhibiting KAT-7 and KAT-6A as compared to KAT-5 and KAT-8. In some embodiments, the present disclosure provides compounds and methods for selectively inhibiting KAT-7 and KAT-8 as compared to KAT-5 and KAT-6A.

In some embodiments, the present disclosure provides compounds that selectively inhibit a single MYST-family KAT, e.g., KAT-7. In some embodiments, the present disclosure provides compounds that selectively inhibit two MYST-family KATs (dual inhibitors), e.g., KAT-7 and KAT-6A, or KAT-7 and KAT-8. In some embodiments, the present disclosure provides compounds that selectively inhibit three MYST family KATs (triple inhibitors), e.g., KAT-7, KAT-6A, and KAT-8. It will be appreciated that the assays and experiments described below facilitate the characterization and/or identification of compounds that inhibit one or more MYST family KATs. Persons skilled in the art performing and/or using the assays and experiments described herein can readily identify other inhibitors of MYST family KATs, and therefore can determine which compounds selectively inhibit certain MYST family KATs compared to other MYST family KATs.

Cancers and Tumors

The present disclosure provides, inter alia, compounds and compositions useful in the treatment of cancer, e.g., for the treatment of a tumor in a subject.

In some embodiments, the present disclosure provides a method of treating a disease or disorder associated with a MYST family KAT, e.g., with KAT-5, KAT-6A, KAT-7, and/or KAT-8. In certain embodiments, the disease or disorder is a KAT-7-mediated disorder. In certain embodiments, the disease or disorder is a KAT-6A-mediated disorder. In certain embodiments, the disease or disorder is a KAT-8-mediated disorder. In certain embodiments, the disease or disorder is a KAT-5-mediated disorder.

Cancers that can be treated with the methods and compositions provided herein, e.g., include, for example, adrenocortical carcinoma, astrocytoma, basal cell carcinoma, carcinoid, cardiac, cholangiocarcinoma, chordoma, chronic myeloproliferative neoplasms, craniopharyngioma, ductal carcinoma in situ, ependymoma, intraocular melanoma, gastrointestinal carcinoid tumor, gastrointestinal stromal tumor (GIST), gestational trophoblastic disease, glioma, histiocytosis, leukemia (e.g., acute lymphoblastic leukemia (ALL), acute myeloid leukemia (AML), chronic lymphocytic leukemia (CLL), chronic myelogenous leukemia (CML), hairy cell leukemia, myelogenous leukemia, and myeloid leukemia), lymphoma (e.g., Burkitt lymphoma (non-Hodgkin lymphoma), cutaneous T-cell lymphoma, Hodgkin lymphoma, mycosis fungoides, Sezary syndrome, AIDS-related lymphoma, follicular lymphoma, diffuse large B-cell lymphoma), melanoma, merkel cell carcinoma, mesothelioma, myeloma (e.g., multiple myeloma), myelodysplastic syndrome, papillomatosis, paraganglioma, pheochromacytoma, pleuropulmonary blastoma, retinoblastoma, sarcoma (e.g., Ewing sarcoma, Kaposi sarcoma, osteosarcoma, rhabdomyosarcoma, uterine sarcoma, vascular sarcoma), Wilms' tumor, and/or cancer of the adrenal cortex, anus, appendix, bile duct, bladder, bone, brain, breast, bronchus, central nervous system, cervix, colon, endometrium, esophagus, eye, fallopian tube, gall bladder, gastrointestinal tract, germ cell, head and neck, heart, intestine, kidney (e.g., Wilms' tumor), larynx, liver, lung (e.g., non-small cell lung cancer, small cell lung cancer), mouth, nasal cavity, oral cavity, ovary, pancreas, rectum, skin, stomach, testes, throat, thyroid, penis, pharynx, peritoneum, pituitary, prostate, rectum, salivary gland, ureter, urethra, uterus, vagina, or vulva.

In some embodiments, the present disclosure provides methods and compositions for treating a tumor in a subject. In some embodiments, the tumor is a solid tumor. In some embodiments, the tumor is a liquid or disperse tumor. In some embodiments, the tumor is associated with a hematologic malignancy, including but not limited to, acute lymphoblastic leukemia, acute myeloid leukemia, chronic lymphocytic leukemia, chronic myelogenous leukemia, hairy cell leukemia, AIDS-related lymphoma, Hodgkin lymphoma, non-Hodgkin lymphoma, follicular lymphoma, diffuse large B-cell lymphoma, Langerhans cell histiocytosis, multiple myeloma, or myeloproliferative neoplasms.

In some embodiments, a tumor comprises a solid tumor. In some embodiments, solid tumors include but are not limited to tumors of the bladder, breast, central nervous system, cervix, colon, esophagus, endometrium, head and neck, kidney, liver, lung, ovary, pancreas, skin, stomach, uterus, or upper respiratory tract. In some embodiments, a tumor that may be treated by the compositions and methods of the present disclosure is a breast tumor. In some embodiments, a tumor that may be treated by the compositions and methods of the present disclosure is not a lung tumor.

In some embodiments, a tumor or cancer suitable for treatment with the methods and compositions provided herein includes, for example, acute lymphoblastic leukemia (ALL), acute myeloid leukemia (AML), adrenal cortex cancer, adrenocortical carcinoma, AIDS-related cancer (e.g., Kaposi sarcoma, AIDS-related lymphoma, primary CNS lymphoma), anal cancer, appendix cancer, astrocytoma, atypical rhabdoid tumor, basal cell carcinoma, bile duct cancer, bladder cancer, bone cancer, brain tumor, breast cancer, bronchial tumor, Burkitt lymphoma, carcinoid tumor, carcinoma, cardiac (heart) tumor, central nervous system tumor, cervical cancer, cholangiocarcinoma, chordoma, chronic lymphocytic leukemia (CLL), chronic myelogenous leukemia (CML), chronic myeloproliferative neoplasm, colorectal cancer, craniopharyngioma, cutaneous T-cell lymphoma, ductal carcinoma in situ (DCIS), embryonal tumor, endometrial cancer, endometrial sarcoma, ependymoma, esophageal, esthesioneuroblastoma, Ewing sarcoma, extracranial germ cell tumor, extragonadal germ cell tumor, eye cancer, fallopian tube cancer, gallbladder cancer, gastric (stomach) cancer, gastrointestinal carcinoid tumor, gastrointestinal stromal tumor (GIST), germ cell tumor, gestational trophoblastic disease, glioma, hairy cell leukemia, head and neck cancer, hepatocellular (liver) cancer, Hodgkin lymphoma, hypopharyngeal cancer, intraocular melanoma, islet cell tumor, Kaposi sarcoma, kidney tumor, Langerhans cell histiocytosis, laryngeal cancer, leukemia, lip and oral cavity cancer, liver cancer, lung cancer, lymphoma, male breast cancer, malignant fibrous histiocytoma, melanoma, Merkel cell carcinoma, mesothelioma, mouth cancer, multiple endocrine neoplasia syndrome, multiple myeloma, plasma cell neoplasm, mycosis fungoides, myelodysplastic syndrome, myelodysplastic/myeloproliferative neoplasm, nasal cavity cancer, nasopharyngeal cancer, neuroblastoma, non-Hodgkin lymphoma, non-small cell lung cancer, oral cancer, oral cavity cancer, oropharyngeal cancer, osteosarcoma, ovarian cancer, pancreatic cancer, pancreatic neuroendocrine tumor (islet cell tumor), paraganglioma, paranasal sinus cancer, parathyroid cancer, penile cancer, pharyngeal cancer, pheochromocytoma, pituitary tumor, pleuropulmonary blastoma, primary central nervous system (CNS) lymphoma, primary peritoneal cancer, prostate cancer, rectal cancer, renal cell (kidney) cancer, retinoblastoma, rhabdomyosarcoma, salivary gland cancer, sarcoma, Sézary syndrome, skin cancer, small intestine cancer, soft tissue sarcoma, squamous cell carcinoma, squamous neck cancer, stomach (gastric) cancer, T-cell lymphoma, testicular cancer, throat cancer, thymic carcinoma, thymoma, thyroid cancer, urethral cancer, uterine sarcoma, vaginal cancer, vascular tumor, vulvar cancer, Waldenström macroglobulinemia, or Wilms' tumor.

Pharmaceutical Compositions

In some embodiments, the present disclosure provides a pharmaceutical composition comprising an inhibitor of a MYST family KAT, e.g., of KAT-5, KAT-6, KAT-7, and/or KAT-8, as described herein. In some embodiments, the compounds of the present disclosure (e.g., compounds of formula I, formula I-a, formula II, formula II-a, formula II-b, formula II-c, formula III, and/or formula III-a), can be administered to a subject, e.g., to a human patient, alone, e.g., in the form of a pharmaceutically acceptable salt, a solvated or hydrated form of compounds of the present disclosure, and any polymorph or crystal form thereof. In some embodiments, the compounds of the present disclosure (e.g., compounds of formula I', formula I, formula I-a, formula II, formula II-a, formula II-b, formula II-c, formula III, and/or formula III-a), can be administered to a subject, e.g., to a human patient, alone, e.g., in the form of a pharmaceutically acceptable salt, a solvated or hydrated form of compounds of the present disclosure, and any polymorph or crystal form thereof. In some embodiments, the compounds of the present disclosure, can be administered in the form of a pharmaceutical composition, e.g., where the compounds of the present disclosure are admixed with a suitable carrier or excipient. A pharmaceutical composition typically comprises or can be administered at a dose sufficient to treat or ameliorate a disease or condition in the recipient subject, e.g., to treat or ameliorate a cancer as described herein. Accordingly, a pharmaceutical composition is formulated in a manner suitable for administration to a subject, e.g., in that it is free from pathogens and formulated according to the applicable regulatory standards for administration to a subject, e.g., for administration to a human subject. As an example, a formulation for injection is typically sterile and essentially pyrogen-free.

Compounds of the present disclosure can also be administered to a subject as a mixture with other agents, e.g., with one or more additional therapeutic agent(s), e.g., in a suitably formulated pharmaceutical composition. For example, some aspects of the present disclosure relate to pharmaceutical compositions comprising a therapeutically effective dose of compounds of the present disclosure, or a pharmaceutically acceptable salt, hydrate, enantiomer or stereoisomer thereof; and a pharmaceutically acceptable diluent or carrier.

Techniques for formulation and administration of compounds of the present disclosure may be found in references well known to one of ordinary skill in the art, such as Remington's "*The Science and Practice of Pharmacy,*" 21st ed., Lippincott Williams & Wilkins 2005, the entire contents of which are incorporated herein by reference.

Pharmaceutical compositions as provided herein are typically formulated for a suitable route of administration. Suitable routes of administration may, for example, include enteral administration, e.g., oral, rectal, or intestinal administration; parenteral administration, e.g., intravenous, intramuscular, intraperitoneal, subcutaneous, or intramedullary injection, as well as intrathecal, direct intraventricular, or intraocular injections; topical delivery, including eyedrop and transdermal; and intranasal and other transmucosal delivery, or any suitable route provided herein or otherwise apparent to those of ordinary skill in the art.

The pharmaceutical compositions provided herein may be manufactured, e.g., by mixing, dissolving, granulating, dragee-making, levigating, emulsifying, encapsulating, entrapping, or lyophilizing processes, or by any other suitable processes known to those of ordinary skill in the art.

Pharmaceutical compositions for use in accordance with the present disclosure may be formulated using one or more physiologically acceptable carriers comprising excipients and auxiliaries which facilitate processing of compounds of the present disclosure into preparations which can be used pharmaceutically. Proper formulation is dependent upon the route of administration chosen.

For injection, the agents of the disclosure may be formulated in aqueous solutions, preferably in physiologically compatible buffers such as Hanks' solution, Ringer's solution, or physiological saline buffer. For transmucosal administration, penetrants are used in the formulation appropriate to the barrier to be permeated. Such penetrants are generally known in the art.

For oral administration, compounds of the present disclosure can be formulated readily by combining the compound with pharmaceutically acceptable carriers known in the art. Such carriers enable compounds of the present disclosure to be formulated as tablets, pills, dragees, capsules, liquids, gels, syrups, slurries, suspensions and the like, for oral ingestion by a patient to be treated. Pharmaceutical preparations for oral use can be obtained by combining the compounds of the present disclosure with a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredient(s), e.g., compounds of the present disclosure, in admixture with filler such as lactose, binders such as starches, and/or lubricants such as talc or magnesium stearate and, optionally, stabilizers. In soft capsules, the compounds of the present disclosure may be dissolved or suspended in suitable liquids, such as fatty oils, liquid paraffin, or liquid polyethylene glycols. In addition, stabilizers may be added.

For buccal administration, the compositions may take the form of tablets or lozenges formulated in conventional manner.

For administration by inhalation, compounds of the present disclosure for use according to the present disclosure is conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the compounds of the present disclosure and a suitable powder base such as lactose or starch.

Suitable compound(s) of the present disclosure can be formulated for parenteral administration by injection, e.g., bolus injection or continuous infusion. Formulations for injection may be presented in unit dosage form, e.g., in ampoules, or in multi-dose containers, and, in some embodiments, may contain an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of compound(s) of the present disclosure in water-soluble form. Additionally, suspensions of compound(s) of the present disclosure may be prepared as appropriate injection suspensions, e.g., aqueous or oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of compound(s) of the present disclosure to allow for the preparation of highly concentrated solutions.

Alternatively, the active ingredient(s), e.g., compound(s) of the present disclosure, may be in powder form for reconstitution before use with a suitable vehicle, e.g., sterile pyrogen-free water.

Compound(s) of the present disclosure may also be formulated in rectal compositions such as suppositories or retention enemas, e.g., containing conventional suppository bases, such as cocoa butter or other glycerides.

In addition to the formulations described previously, compounds of the present disclosure may also be formulated as a depot preparation. Such long acting formulations may be administered by implantation (for example, subcutaneously or intramuscularly or by intramuscular injection). Thus, for example, compounds of the present disclosure may be formulated with suitable polymeric or hydrophobic materials (for example as an emulsion in an acceptable oil) or ion exchange resins, or as sparingly soluble derivatives (for example, as a sparingly soluble salt).

Alternatively, other delivery systems for hydrophobic pharmaceutical compound(s) of the present disclosure may be employed. Liposomes and emulsions are examples of delivery vehicles or carriers for hydrophobic drugs. Certain organic solvents such as dimethysulfoxide also may be employed. Additionally, compounds of the present disclosure may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compound(s) of the present disclosure for a few hours, a few days, a few weeks, or a few months, e.g., up to over 100 days.

The pharmaceutical compositions may also comprise suitable solid or gel phase carriers or excipients. Examples of such carriers or excipients include but are not limited to calcium carbonate, calcium phosphate, various sugars, starches, cellulose derivatives, gelatin, and polymers, such as polyethylene glycols.

Additional suitable pharmaceutical compositions and processes and strategies for formulating a suitable compound of the present disclosure will be apparent to the skilled artisan based on the present disclosure. The disclosure is not limited in this respect.

Methods of Treatment

Some aspects of this disclosure provide methods for modulating protein acetylation, e.g., histone acetylation, in a subject in need thereof by administering compounds of the present disclosure to the subject in an amount sufficient to modulate acetylation of a target protein, e.g., a histone acetylated by a MYST family KAT, e.g., by KAT-5, KAT-6, KAT-7, and/or KAT-8, activity. In some embodiments, the subject is a subject having or diagnosed with a cancer or a precancerous condition.

Provided herein are methods of treating, preventing or alleviating a symptom of conditions and diseases, such as cancers and precancerous conditions, the course of which can be influenced by modulating the acetylation status of histones or other proteins that are acetylated by a MYST family KAT, e.g., by KAT-5, KAT-6, KAT-7, and/or KAT-8, wherein said acetylation status is mediated at least in part by the activity of CREBBP. Modulation of the acetylation status of histones can in turn influence the level of expression of target genes activated by acetylation, and/or target genes suppressed by acetylation.

For example, some aspects of the disclosure provide methods for treating or alleviating a symptom of cancer or precancerous condition. In some embodiments, the method comprises the step of administering to a subject having a cancer or a precancerous condition compounds of the present disclosure, e.g., in the form of a pharmaceutical composition, at a therapeutically effective amount.

In some embodiments, compounds of the present disclosure inhibit histone acetyltransferase activity of a MYST family KAT, e.g., of KAT-5, KAT-6, KAT-7, and/or KAT-8. In some embodiments, compounds of the present disclosure selectively inhibit histone acetyltransferase activity of a MYST family KAT, e.g., of KAT-5, KAT-6, KAT-7, and/or KAT-8.

In some embodiments, the subject is diagnosed with a disease or disorder known to be associated with a dysregulation of histone acetylation, e.g., with a dysfunction of a MYST family KAT, e.g., of KAT-5, KAT-6, KAT-7, and/or KAT-8. In some embodiments, the subject is diagnosed with a disease or disorder mediated by a MYST family KAT, e.g., by KAT-5, KAT-6, KAT-7, and/or KAT-8. In some embodiments, the subject has been diagnosed with a cancer.

Dysregulated histone acetylation has been reported to be involved in aberrant expression of certain genes in cancers and other diseases. Compounds described herein can be used to treat such histone acetylation-associated diseases, e.g., to inhibit histone acetylation mediated by a MYST family KAT, e.g., KAT-5-, KAT-6-, KAT-7-, and/or KAT-8-mediated histone acetylation in affected cells, tissues, or subjects.

Modulators of histone acetylation can be used for modulating cell proliferation, e.g., of cells harboring a mutation resulting in aberrant histone acetylation, or for inducing cell death in cells depending on histone acetylation by a MYST family KAT, e.g., by KAT-5, KAT-6, KAT-7, and/or KAT-8, histone acetylation for survival or proliferation. Accordingly, diseases that may be treated with compound(s) of the present disclosure include hyperproliferative diseases, such as benign cell growth and malignant cell growth (cancer).

Exemplary cancers that may be treated with a compound provided herein include, without limitation, lymphomas, including non-Hodgkin lymphoma, follicular lymphoma (FL) and diffuse large B-cell lymphoma (DLBCL); melanoma; leukemia, including CML; acute lymphoblastic leukemia; acute myeloid leukemia; adrenocortical carcinoma; AIDS-related cancers; AIDS-related lymphoma; anal cancer; astrocytoma, childhood cerebellar; basal cell carcinoma, see skin cancer (non-melanoma); bile duct cancer, extrahepatic; bladder cancer; bone cancer, osteosarcoma/malignant fibrous histiocytoma; brain stem glioma; brain tumor; brain tumor, cerebellar astrocytoma; brain tumor, cerebral astrocytoma/malignant glioma; brain tumor, ependymoma; brain tumor, medulloblastoma; brain tumor, supratentorial primitive neuroectodermal tumors; brain tumor, visual pathway and hypothalamic glioma; breast cancer; bronchial adenomas/carcinoids; Burkitt's lymphoma; carcinoid tumor; carcinoid tumor, gastrointestinal; carcinoma of unknown primary; central nervous system lymphoma, primary; cerebellar astrocytoma; cervical cancer; childhood cancers; chronic lymphocytic leukemia; chronic myelogenous leukemia; chronic myelogenous leukemia, hairy cell; chronic myeloproliferative disorders; colon cancer; colorectal cancer; cutaneous T-cell lymphoma, see mycosis fungoides and Sezary syndrome; endometrial cancer; esophageal cancer; Ewing's family of tumors; extrahepatic bile duct cancer; eye cancer, intraocular melanoma; eye cancer, retinoblastoma; gallbladder cancer; gastric (stomach) cancer; gastrointestinal carcinoid tumor; germ cell tumor, extracranial; germ cell tumor, extragonadal; germ cell tumor, ovarian; gestational trophoblastic tumor; glioma; glioma, childhood brain stem; glioma, childhood cerebral astrocytoma; glioma, childhood visual pathway and hypothalamic; hairy cell leukemia; head and neck cancer; hepatocellular (liver) cancer, adult (primary); hepatocellular (liver) cancer, childhood (primary); Hodgkin's lymphoma; Hodgkin's lymphoma during pregnancy; hypopharyngeal cancer; hypothalamic and visual pathway glioma; intraocular melanoma; islet cell carcinoma (endocrine pancreas); Kaposi's sarcoma; kidney (renal cell) cancer; kidney cancer; laryngeal cancer; leukemia; lip and oral cavity cancer; liver cancer, adult (primary); liver cancer, childhood (primary); lung cancer, non-small cell; lung cancer, small cell; lymphoma, primary central nervous system; macroglobulinemia, Waldenstrom's; malignant fibrous histiocytoma of bone/osteosarcoma; medulloblastoma; melanoma; Merkel cell carcinoma; mesothelioma; mesothelioma, adult malignant; metastatic squamous neck cancer with occult primary; multiple endocrine neoplasia syndrome; multiple myeloma; multiple myeloma/plasma cell neoplasm mycosis fungoides; myelodysplastic syndromes; myelodysplastic/myeloproliferative diseases; myeloid leukemia, adult acute; myeloid leukemia, childhood acute; myeloproliferative disorders, chronic; nasal cavity and paranasal sinus cancer; nasopharyngeal cancer; neuroblastoma; non-Hodgkin's lymphoma; non-Hodgkin's lymphoma during pregnancy; oral cancer; oral cavity cancer, lip and; oropharyngeal cancer; osteosarcoma/malignant fibrous histiocytoma of bone; ovarian cancer; ovarian epithelial cancer; ovarian low malignant potential tumor; pancreatic cancer; pancreatic cancer, islet cell; paranasal sinus and nasal cavity cancer; parathyroid cancer; penile cancer; pheochromocytoma; pineoblastoma and supratentorial primitive neuroectodermal tumors; pituitary tumor; plasma cell neoplasm/multiple myeloma; pleuropulmonary blastoma; pregnancy and breast cancer; prostate cancer; rectal cancer; retinoblastoma; rhabdomyosarcoma; salivary gland cancer; sarcoma, Ewing's family of tumors; sarcoma, soft tissue; sarcoma, uterine; Sezary syndrome; skin cancer; skin cancer (non-melanoma); small intestine cancer; soft tissue sarcoma; squamous cell carcinoma, see skin cancer (non-melanoma); squamous neck cancer with occult primary, metastatic; stomach (gastric) cancer; testicular cancer; thymoma; thymoma and thymic carcinoma; thyroid cancer; transitional cell cancer of the renal pelvis and ureter; trophoblastic tumor, gestational; unknown primary site, cancer of; unusual cancers of childhood; urethral cancer; uterine cancer, endometrial; uterine sarcoma; vaginal cancer; visual pathway and hypothalamic glioma; vulvar cancer; Waldenstrom's macroglobulinemia; Wilms' tumor; and women's cancers. Exemplary precancerous conditions that can be treated with compound(s) of the present disclosure include myelodisplastic syndrome (MDS; formerly known as preleukemia).

Any other disease in which histone acetylation mediated by a MYST family KAT, e.g., by KAT-5, KAT-6, KAT-7, and/or KAT-8, plays a role may be treatable or preventable using compounds and methods described herein.

Administration

In some embodiments, an active agent for use in accordance with the present disclosure is formulated, dosed, and/or administered in a therapeutically effective amount using pharmaceutical compositions and dosing regimens that are consistent with good medical practice and appropriate for the relevant agent(s) and subject(s). In principle, therapeutic compositions can be administered by any appropriate method known in the art, including, without limitation, oral, mucosal, by-inhalation, topical, buccal, nasal, rectal, or parenteral (e.g. intravenous, infusion, intratumoral, intranodal, subcutaneous, intraperitoneal, intramuscular, intradermal, transdermal, or other kinds of administration involving physical breaching of a tissue of a subject and administration of the therapeutic composition through the breach in the tissue).

In some embodiments, a dosing regimen for a particular active agent may involve intermittent or continuous (e.g., by perfusion or other slow release system) administration, for example to achieve a particular desired pharmacokinetic profile or other pattern of exposure in one or more tissues or fluids of interest in the subject receiving therapy.

In some embodiments, different agents administered in combination may be administered via different routes of delivery and/or according to different schedules. Alternatively or additionally, in some embodiments, one or more doses of a first active agent is administered substantially simultaneously with, and in some embodiments via a common route and/or as part of a single composition with, one or more other active agents.

Factors to be considered when optimizing routes and/or dosing schedule for a given therapeutic regimen may include, for example, the particular indication being treated, the clinical condition of a subject (e.g., age, overall health, prior therapy received and/or response thereto) the site of delivery of the agent, the nature of the agent (e.g. small molecule, an antibody or other polypeptide-based compound), the mode and/or route of administration of the agent, the presence or absence of combination therapy, and other factors known to medical practitioners. For example, in the treatment of cancer, relevant features of the indication being treated may include, for example, one or more of cancer type, stage, and location.

In some embodiments, one or more features of a particular pharmaceutical composition and/or of a utilized dosing regimen may be modified over time (e.g., increasing or decreasing the amount of active agent in any individual dose, increasing or decreasing time intervals between doses), for example in order to optimize a desired therapeutic effect or response.

In general, type, amount, and frequency of dosing of active agents in accordance with the present disclosure are governed by safety and efficacy requirements that apply when one or more relevant agent(s) is/are administered to a mammal, preferably a human. In general, such features of dosing are selected to provide a particular, and typically detectable, therapeutic response as compared to what is observed absent therapy.

In the context of the present disclosure, an exemplary desirable therapeutic response may involve, but is not limited to, inhibition of and/or decreased tumor growth, tumor size, metastasis, one or more of the symptoms and side effects that are associated with a tumor, as well as increased apoptosis of cancer cells, therapeutically relevant decrease or increase of one or more cell marker or circulating markers. Such criteria can be readily assessed by any of a variety of immunological, cytological, and other methods that are disclosed in the literature.

In some embodiments, an effective dose (and/or a unit dose) of an active agent, may be at least about 0.01 µg/kg body weight, at least about 0.05 µg/kg body weight, at least about 0.1 µg/kg body weight, at least about 1 µg/kg body weight, at least about 2.5 µg/kg body weight, at least about 5 µg/kg body weight, and not more than about 100 µg/kg body weight. It will be understood by one of skill in the art that in some embodiments such guidelines may be adjusted for the molecular weight of the active agent. The dosage may also be varied for route of administration, the cycle of treatment, or consequently to dose escalation protocol that can be used to determine the maximum tolerated dose and dose limiting toxicity (if any) in connection to the administration of compounds of the present disclosure and/or an additional therapeutic agent at increasing doses. Consequently, the relative amounts of the each agent within a pharmaceutical composition may also vary, for example, each composition may comprise between 0.001% and 100% (w/w) of the corresponding agent.

In some embodiments, a "therapeutically effective amount" or "therapeutically effective dose" is an amount of a compound of the present disclosure, or a combination of two or more compounds of the present disclosure, or a combination of compounds of the present disclosure with one or more additional therapeutic agent(s), which inhibits, totally or partially, the progression of the condition or alleviates, at least partially, one or more symptoms of the condition. In some embodiments, a therapeutically effective amount can be an amount which is prophylactically effective. In some embodiments, an amount which is therapeutically effective may depend upon a patient's size and/or gender, the condition to be treated, severity of the condition and/or the result sought. In some embodiments, a therapeutically effective amount refers to that amount of a compound of the present disclosure that results in amelioration of at least one symptom in a patient. In some embodiments, for a given patient, a therapeutically effective amount may be determined by methods known to those of skill in the art.

In some embodiments, toxicity and/or therapeutic efficacy of compounds of the present disclosure can be determined by standard pharmaceutical procedures in cell cultures or experimental animals, e.g., for determining the maximum tolerated dose (MTD) and the $ED_{50}$ (effective dose for 50% maximal response). Typically, the dose ratio between toxic and therapeutic effects is the therapeutic index; in some embodiments, this ratio can be expressed as the ratio between MTD and $ED_{50}$. Data obtained from such cell culture assays and animal studies can be used in formulating a range of dosage for use in humans.

In some embodiments, dosage may be guided by monitoring the effect of compounds of the present disclosure on one or more pharmacodynamic markers of enzyme inhibition (e.g., histone acetylation or target gene expression) in diseased or surrogate tissue. For example, cell culture or animal experiments can be used to determine the relationship between doses required for changes in pharmacodynamic markers and doses required for therapeutic efficacy can be determined in cell culture or animal experiments or early stage clinical trials. In some embodiments, dosage of compounds of the present disclosure lies preferably within a range of circulating concentrations that include the $ED_{50}$ with little or no toxicity. In some embodiments, dosage may vary within such a range, for example depending upon the dosage form employed and/or the route of administration utilized. The exact formulation, route of administration and dosage can be chosen by the individual physician in view of the patient's condition. In the treatment of crises or severe conditions, administration of a dosage approaching the MTD may be required to obtain a rapid response.

In some embodiments, dosage amount and/or interval may be adjusted individually, for example to provide plasma levels of an active moiety which are sufficient to maintain, for example a desired effect, or a minimal effective concentration (MEC) for a period of time required to achieve therapeutic efficacy. In some embodiments, MEC for particular compounds of the present disclosure can be estimated, for example, from in vitro data and/or animal experiments. Dosages necessary to achieve the MEC will depend on individual characteristics and route of administration. In some embodiments, high pressure liquid chromatography (HPLC) assays or bioassays can be used to determine plasma concentrations.

In some embodiments, dosage intervals can be determined using the MEC value. In certain embodiments, compound(s) of the present disclosure should be administered using a regimen which maintains plasma levels above the MEC for 10-90% of the time, preferably between 30-90% and most preferably between 50-90% until the desired amelioration of a symptom is achieved. In other embodiments, different MEC plasma levels will be maintained for differing amounts of time. In cases of local administration or selective uptake, the effective local concentration of the drug may not be related to plasma concentration.

One of skill in the art can select from a variety of administration regimens and will understand that an effective amount of particular compounds of the present disclosure may be dependent on the subject being treated, on the subject's weight, the severity of the affliction, the manner of administration and/or the judgment of the prescribing physician.

Combination Therapy

In some embodiments, compounds of the present disclosure can be used in combination with another therapeutic agent to treat diseases such as cancer. In some embodiments, compounds of the present disclosure, or a pharmaceutical composition thereof, can optionally be administered in combination with one or more additional therapeutic agents, such as a cancer therapeutic agent, e.g., a chemotherapeutic agent or a biological agent. An additional agent can be, for example, a therapeutic agent that is art-recognized as being useful to treat the disease or condition being treated by compounds of the present disclosure, e.g., an anti-cancer agent, or an agent that ameliorates a symptom associated with the disease or condition being treated. The additional agent also can be an agent that imparts a beneficial attribute to the therapeutic composition (e.g., an agent that affects the viscosity of the composition). For example, in some embodiments, compounds of the present disclosure are administered to a subject who has received, is receiving, and/or will receive therapy with another therapeutic agent or modality (e.g., with a chemotherapeutic agent, surgery, radiation, or a combination thereof).

Some embodiments of combination therapy modalities provided by the present disclosure provide, for example, administration of compounds of the present disclosure and additional agent(s) in a single pharmaceutical formulation. Some embodiments provide administration of compounds of the present disclosure and administration of an additional therapeutic agent in separate pharmaceutical formulations.

Examples of chemotherapeutic agents that can be used in combination with compounds of the present disclosure described herein include platinum compounds (e.g., cisplatin, carboplatin, and oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, and bendamustine), antitumor antibiotics (e.g., daunorubicin, doxorubicin, idarubicin, epirubicin, mitoxantrone, bleomycin, mytomycin C, plicamycin, and dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, and nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vicristine, vindesine, vinorelbine, and vinblastine), tyrosine kinase inhibitors (e.g., imatinib, dasatinib, nilotinib, sorafenib, and sunitinib), nitrosoureas (e.g., carmustine, fotemustine, and lomustine), hexamethylmelamine, mitotane, angiogenesis inhibitors (e.g., thalidomide and lenalidomide), steroids (e.g., prednisone, dexamethasone, and prednisolone), hormonal agents (e.g., tamoxifen, raloxifene, leuprolide, bicaluatmide, granisetron, and flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, and oxaprozin), selective cyclooxygenase-2 (COX-2) inhibitors, or any combination thereof.

Examples of biological agents that can be used in the compositions and methods described herein include monoclonal antibodies (e.g., rituximab, cetuximab, panetumumab, tositumomab, trastuzumab, alemtuzumab, gemtuzumab ozogamicin, bevacizumab, catumaxomab, denosumab, obinutuzumab, ofatumumab, ramucirumab, pertuzumab, ipilimumab, nivolumab, nimotuzumab, lambrolizumab, pidilizumab, siltuximab, BMS-936559, RG7446/MPDL3280A, MEDI4736, tremelimumab, or others known in the art), enzymes (e.g., L-asparaginase), cytokines (e.g., interferons and interleukins), growth factors (e.g., colony stimulating factors and erythropoietin), cancer vaccines, gene therapy vectors, or any combination thereof.

In some embodiments, compounds of the present disclosure is administered to a subject in need thereof in combination with another agent for the treatment of cancer, either in the same or in different pharmaceutical compositions. In some embodiments, the additional agent is an anticancer agent. In some embodiments, the additional agent affects (e.g., inhibits) histone modifications, such as histone acetylation or histone methylation. In certain embodiments, an additional anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®); biologics (such as Alpha Interferon, Bacillus Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Velcade® and Zevalin™); small molecules (such as Tykerb®); corticosteroids (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

The additional agents that can be used in combination with compounds of the present disclosure as set forth above are for illustrative purposes and not intended to be limiting. The combinations embraced by this disclosure, include, without limitation, one or more compounds of the present disclosure as provided herein and at least one additional agent selected from the lists above or otherwise provided herein. Compounds of the present disclosure can also be used in combination with one or with more than one additional agent, e.g., with two, three, four, five, or six, or more, additional agents.

In some embodiments, treatment methods described herein are performed on subjects for which other treatments of the medical condition have failed or have had less success in treatment through other means, e.g., in subjects having a cancer refractory to standard-of-care treatment. Additionally, the treatment methods described herein can be performed in conjunction with one or more additional treatments of the medical condition, e.g., in addition to or in combination with standard-of-care treatment. For instance, the method can comprise administering a cancer-therapeutic regimen, e.g., nonmyeloablative chemotherapy, surgery, hormone therapy, and/or radiation, prior to, substantially simultaneously with, or after the administration of compounds of the present disclosure described herein, or composition thereof. In certain embodiments, a subject to which compounds of the present disclosure described herein is administered can also be treated with antibiotics and/or one or more additional pharmaceutical agents.

EXAMPLES

Synthetic Procedures

Materials and Methods

Equipment: $^1$H NMR Spectra were recorded at 400 MHz using a Bruker AVANCE 400 MHz spectrometer. LC-MS equipment and conditions are as follows:

LC-MS (Agilent):

LC: Agilent Technologies 1290 series, Binary Pump, Diode Array Detector. Agilent Poroshell 120 EC-C18, 2.7 μm, 4.6×50 mm column. Mobile phase: A: 0.05% Formic acid in water (v/v), B: 0.05% Formic acid in ACN (v/v). Flow Rate: 1 mL/min at 25° C. Detector: 214 nm, 254 nm. Gradient stop time, 5 min. Timetable:

| T (min) | A(%) | B(%) |
|---------|------|------|
| 0.0 | 90 | 10 |
| 0.5 | 90 | 10 |
| 4.5 | 0 | 100 |
| 4.51 | 90 | 10 |
| 5.0 | 90 | 10 |

MS: G6120A, Quadrupole LC/MS, Ion Source: ES-API, TIC: 70-1000 m/z, Fragmentor: 60, Drying gas flow: 10 L/min, Nebulizer pressure: 35 psi, Drying gas temperature: 350° C., Vcap: 3000V.

Sample preparation: samples were dissolved in ACN or methanol at ~100 μg/mL, then filtered through a 0.22 μm filter membrane. Injection volume: 1~10 μL.

Definitions: Boc (tert-butoxycarbonyl); CDCl$_3$ (deuterated chloroform); DCM (dichloromethane); DMF (N,N-dimethylformamide); DMSO (dimethylsulfoxide); DMSO-d$_6$ (deuterated dimethylsulfoxide); EDCI (1-ethyl-3-(3-dimethylaminopropyl) carbodiimide); eq (equivalent); ES-API (electrospray atmospheric pressure ionization); Et$_3$N (triethylamine); Et$_2$O (diethyl ether); EtOAc (ethyl acetate); g (gram); h (hour); HATU (2-(7-aza-1H-benzotriazole-1-yl)-1,1,3,3-tetramethyluronium hexafluorophosphate); $^1$H NMR (proton nuclear magnetic resonance); HOBt (hydroxybenzotriazole); Hz (hertz); L (litre); LC-MS (liquid chromatography-mass spectrometry); M (molar); MeOH (methanol); mg (milligrams); MHz (megahertz); min (minutes); mL (millilitres); mmol (millimoles); Pet. ether (petroleum ether); ppm (parts per million); psi (pounds per square inch); R$_t$ (retention time); RT (room temperature); THF (tetrahydrofuran); TLC (thin layer chromatography); v/v (volume/volume).

Common Intermediate

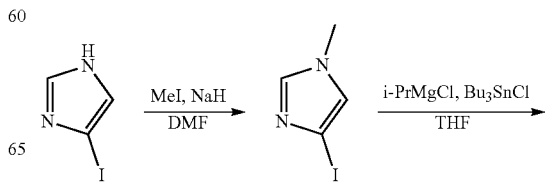

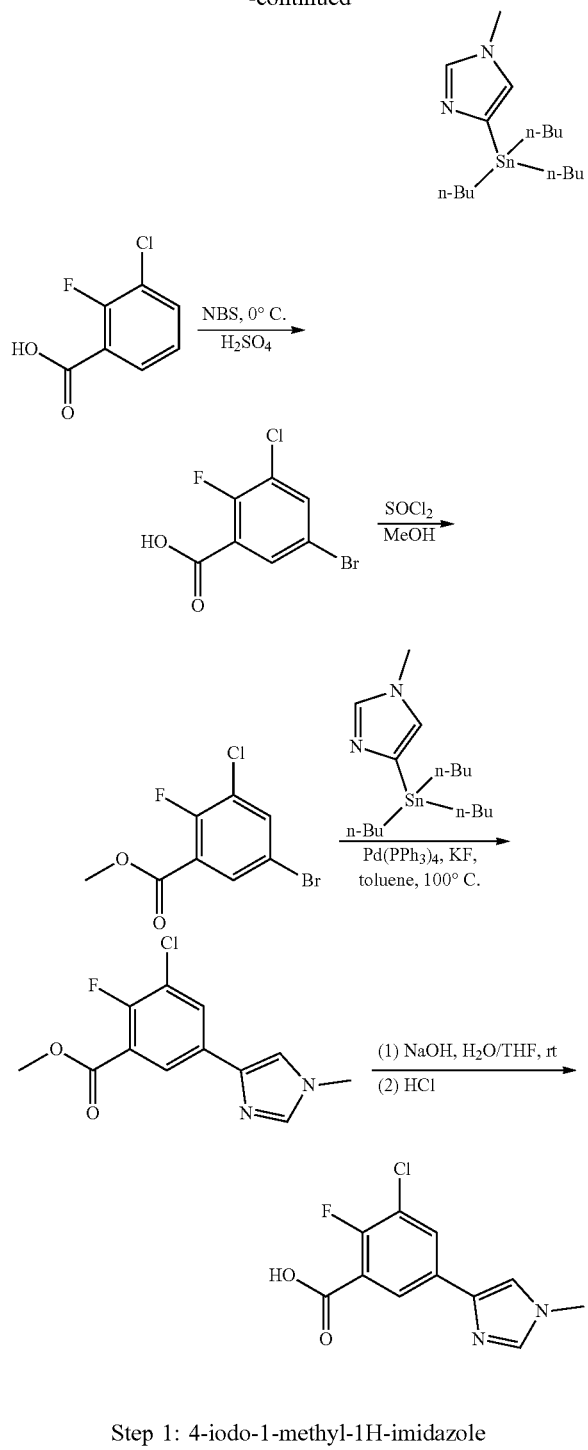

Step 1: 4-iodo-1-methyl-1H-imidazole

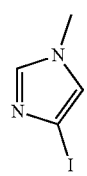

Sodium hydride (15.3 g, 385 mmol) was added to a mixture of 4-iodo-1H-imidazole (50 g, 257 mmol) in THF (150 mL) at 0° C. After stirring for 0.5 h, iodomethane (40.0 g, 282 mmol) was added to the solution and the resulting mixture was stirred at room temperature overnight under $N_2$. TLC (DCM/EtOAc=2/1, v/v) indicated that starting material was consumed and two new spots were formed. The reaction was quenched with MeOH (50 mL), then concentrated to dryness, the residue was purified by silica gel column (DCM/EtOAc=10/1, v/v) to afford the desired product (higher Rf) (28 g, 52%) as a yellow solid.

$^1$H NMR (400 MHz, CDCl$_3$) δ (ppm): 7.32 (s, 1H), 6.96 (d, J=1.2 Hz, 1H), 3.68 (s, 3H).

Step 2: 1-methyl-4-(tributylstannyl)-1H-imidazole

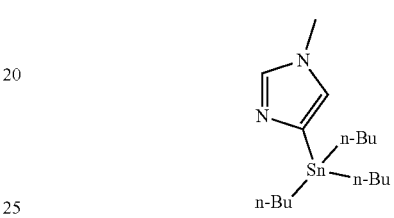

To a solution of 4-iodo-1-methyl-1H-imidazole (34.0 g, 163 mmol) in THF (300 mL) at −10° C. was added isopropylmagnesium chloride (25.0 g, 244 mmol) dropwise under $N_2$. The mixture was stirred for 1 h at this temperature, and then tributylchlorostannane (55.6 g, 171 mmol) was added drop-wise. The reaction was stirred at room temperature overnight under $N_2$. The reaction mixture was diluted with saturated aqueous NH$_4$Cl (400 mL) and extracted with EtOAc (200 mL×3). The combined organic phases were washed with water (200 mL×2) and brine (200 mL), dried over Na$_2$SO$_4$, and concentrated to dryness, to afford the desired product (65.0 g, 100%) as colourless oil, which was used in the next step directly.

LC-MS (Agilent): $R_t$ 2.84 min; m/z calculated for $C_{16}H_{32}N_2Sn$ [M+H]$^+$ 373.2. found 373.2.

Step 3: 5-bromo-3-chloro-2-fluorobenzoic Acid

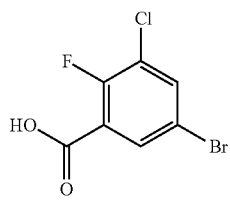

To a solution of 3-chloro-2-fluorobenzoic acid (80 g, 458 mmol) in 98% conc. H$_2$SO$_4$ (400 mL) was added 1-bromopyrrolidine-2,5-dione (85.4 g, 480 mmol) at 0° C. The mixture was stirred at 0° C. for 3 h under $N_2$, then warmed to room temperature and stirred for 28 h. The mixture was poured into ice-water (1000 mL), and the solid was collected by filtration, washed with water and dried to afford the desired product (110 g, 91%) as a white solid.

$^1$H NMR (400 MHz, DMSO-d6) δ (ppm): 8.11-8.05 (m, 1H), 7.90-7.87 (m, 1H).

333

Step 4: methyl 5-bromo-3-chloro-2-fluorobenzoate

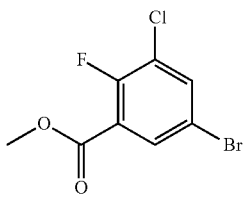

To a solution of 5-bromo-3-chloro-2-fluorobenzoic acid (50.4 g, 198 mmol) in MeOH (400 mL) was added SOCl$_2$ (40 mL) slowly at 0° C. The reaction solution was heated at reflux for 4 h under N$_2$. The reaction mixture was concentrated in vacuo to give a white solid. The solid was diluted with EtOAc (500 mL) and the solution was washed with water (250 mL), Sat. NaHCO$_3$ (200 mL, aq), and brine (250 mL) and concentrated in vacuo to afford the desired product (51 g, 96%) as a light yellow solid.

$^1$H NMR (400 MHz, DMSO-d6) δ (ppm): 8.21-8.18 (m, 1H), 7.96-7.93 (m, 1H), 3.88 (s, 3H).

Step 5: methyl 3-chloro-2-fluoro-5-(1-methyl-1H-imidazol-4-yl)benzoate

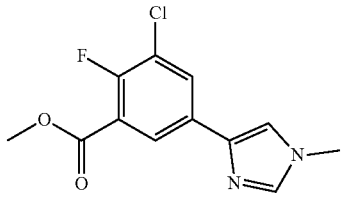

A mixture of 1-methyl-4-(tributylstannyl)-1H-imidazole (60.6 g, 163 mmol), methyl 5-bromo-3-chloro-2-fluorobenzoate (33.4 g, 125 mmol) and potassium fluoride (28.4 g, 489 mmol) in toluene (600 mL) was degassed with N$_2$ and tetrakis(triphenylphosphane) palladium (2.81 g, 2.44 mmol) was added quickly. The reaction mixture was heated to 100° C. and stirring continued overnight. The reaction mixture was cooled to room temperature, potassium fluoride (28.4 g, 489 mmol) and water (300 mL) were added and the mixture stirred for a further 30 min. The mixture was diluted with EtOAc (500 mL) and filtered. The organic layer was separated and the aqueous layer extracted with EtOAc (200 mL×2). The organic phases were combined and dried over Na$_2$SO$_4$, concentrated to dryness, to afford the crude product, which was triturated with (Petroleum/EtOAc=10/1, v/v) to afford the desired product (33.5 g, 77%) as an off-white solid.

$^1$H NMR (400 MHz, CDCl$_3$) δ (ppm): 8.12 (dd, J=6.0, 2.3 Hz, 1H), 8.04 (dd, J=6.4, 2.3 Hz, 1H), 7.57 (s, 1H), 7.22 (s, 1H), 3.95 (s, 3H), 3.75 (s, 3H).

334

Step 6: 3-chloro-2-fluoro-5-(1-methyl-1H-imidazol-4-yl)benzoic acid

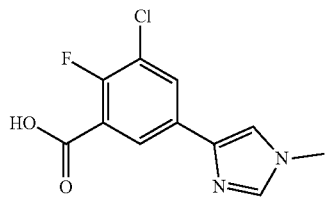

To a solution of sodium hydroxide (19.9 g, 500 mmol) in water (200 mL) was added a solution of methyl 3-chloro-2-fluoro-5-(1-methyl-1H-imidazol-4-yl)benzoate (33.8 g, 125 mmol) in THF (250 mL) drop-wise. After the addition was complete, the reaction was stirred for further 2 h at room temperature. Most of the solvent was removed by evaporation, and the residue was adjusted pH to 5.0 with HCL (6.0 M, aq). The mixture was stirred for 30 min and the solid was collected by filtration, washed with small amount of DCM (20 mL×2) and dried in vacuo to afford the desired product (29.2 g, 92%) as an off-white solid.

$^1$H NMR (400 MHz, DMSO-d6) δ (ppm): 8.14 (dd, J=6.4, 2.3 Hz, 1H), 8.07 (dd, J=6.5, 2.3 Hz, 1H), 7.79 (s, 1H), 7.68 (s, 11H), 3.68 (s, 3H).

Compound I-51

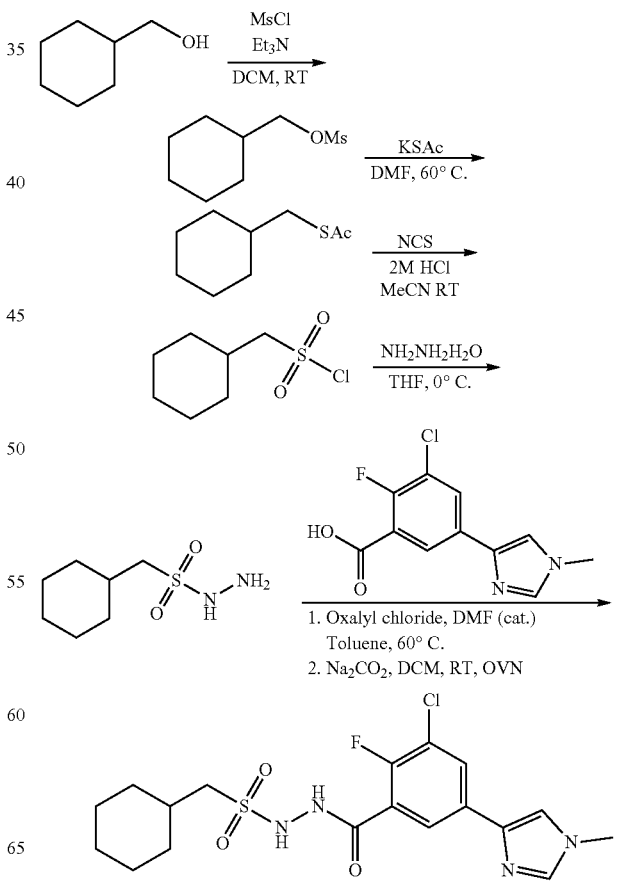

Step 1: cyclohexylmethyl methanesulfonate

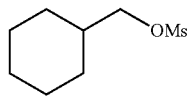

Methanesulfonyl chloride (65.0 g, 568 mmol) was added to a solution of cyclohexylmethanol (50 g, 437 mmol) and triethylamine (66.2 g, 655 mmol) in DCM (600 mL) at 0° C. under $N_2$. After stirring at room temperature for 6 h, the reaction mixture was washed with 1 M HCl (150 mL) and the aqueous layer was extracted with DCM (200 mL×2). The combined organic layers were dried over $Na_2SO_4$ and concentrated to afford the desired product (84 g, 99%) as a yellow oil.

$^1$H NMR (400 MHz, CDCl$_3$) δ (ppm): 4.01 (d, J=6.0 Hz, 2H), 2.99 (s, 3H), 1.76-1.65 (m, 6H), 1.30-1.14 (m, 3H), 1.04-0.98 (m, 2H)

Step 2: S-(cyclohexylmethyl) ethanethioate

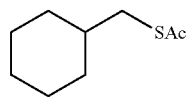

Potassium thioacetate (59.7 g, 523 mmol) was added to a solution of cyclohexylmethyl methanesulfonate (84 g, 436 mmol) in DMF (800 mL) under $N_2$. After heating at 60° C. for 5 h, the reaction mixture was diluted with $H_2O$ (6 L) and extracted with EtOAc (2 L×2). The combined organic layers were washed with brine (1 L), dried over $Na_2SO_4$ and concentrated. The residue was purified by silica gel column (PE/EtOAc=15/1, v/v) to afford the desired product (57 g, 76%) as a yellow oil.

$^1$H NMR (400 MHz, CDCl$_3$) δ (ppm): 2.78 (d, J=6.8 Hz, 2H), 2.32 (s, 3H), 1.78-1.62 (m, 5H), 1.45-1.41 (m, 1H), 1.30-1.20 (m, 3H), 0.98-0.92 (m, 2H)

Step 3: cyclohexylmethanesulfonyl chloride

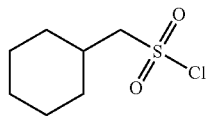

2 M Hydrochloric acid (178 mL, 357 mmol) was added to a solution of N-chlorosuccinimide (173 g, 1300 mmol) in acetonitrile (1 L) at 0° C. under $N_2$, S-(cyclohexylmethyl) ethanethioate (56 g, 325 mmol) was added and the reaction was stirred at room temperature overnight. The reaction mixture was concentrated in vacuo and the residue was extracted with EtOAc (500 mL×2). The combined organic layers were dried over $Na_2SO_4$ and concentrated to afford the desired product (63.9 g, 100%) as colourless oil, which was used to the next step directly.

Step 4: cyclohexylmethanesulfonohydrazide

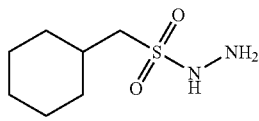

80% hydrazine hydrate (46.5 g, 745 mmol) was added to a solution of cyclohexylmethanesulfonyl chloride (63.9 g, 324 mmol) in THF (1 L) at 0° C. After stirring at room temperature for 1 hour, the reaction mixture was concentrated and the residue purified by silica gel column (DCM/MeOH=20/1, v/v) to afford the desired product (17 g, 27%) as a white solid.

$^1$H NMR (400 MHz, DMSO-d$_6$) δ (ppm): 7.78 (s, 1H), 4.31 (s, 2H), 2.93 (d, J=5.2 Hz, 2H), 1.87-1.77 (m, 3H), 1.66-1.57 (m, 3H), 1.24-1.02 (m, 5H)

Step 5: N'-(3-chloro-2-fluoro-5-(1-methyl-1H-imidazol-4-yl)benzoyl)-1-cyclohexyl methanesulfonohydrazide

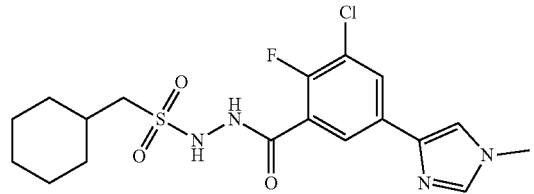

To a solution of 3-chloro-2-fluoro-5-(1-methyl-1H-imidazol-4-yl)benzoic acid (250.0 mg, 0.98 mmol) in toluene (10 mL) was added oxalyl chloride (374.0 mg, 2.95 mmol) and DMF (cat.) at room temperature under $N_2$. The reaction was heated at 60° C. for 1 h, then concentrated under reduced pressure and the residue dissolved in dichloromethane (15 mL). To this solution was added sodium carbonate (312.3 mg, 2.95 mmol) and cyclohexylmethanesulfonohydrazide (188.8 mg, 0.98 mmol). The resulting mixture was stirred at room temperature overnight. Methanol (5 mL) was added and the mixture concentrated under reduced pressure. The residue was purified by silica gel column (DCM/MeOH=20/1, v/v) to afford the desired product (140 mg, 31%) as a white solid.

LC-MS (Agilent): R$_t$ 2.73 min; m/z calculated for $C_{18}H_{22}ClFN_4O_3S$ [M+H]$^+$ 429.0/431.1. found 429.0/431.1.

$^1$H NMR (400 MHz, d$_6$-DMSO) δ (ppm): 10.71 (brs, 1H), 9.73 (brs, 1H), 8.03 (dd, J=6.4, 1.6 Hz 1H), 7.84 (dd, J=5.6, 2.0 Hz 1H), 7.78 (s, 1H), 7.69 (s, 1H), 3.69 (s, 3H), 3.03 (d, J=6.4 Hz, 2H), 2.02-1.94 (m, 1H), 1.91-1.88 (m, 2H), 1.68-1.58 (m, 3H), 1.29-1.02 (m, 5H).

Compound I-315

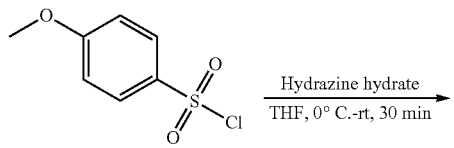

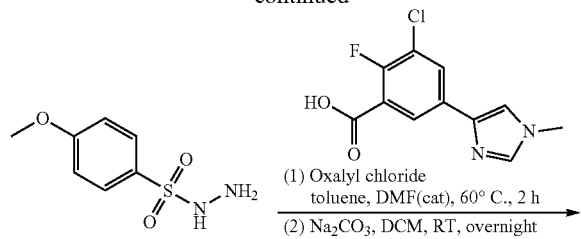

Step 1: 4-methoxybenzene-1-sulfonohydrazide

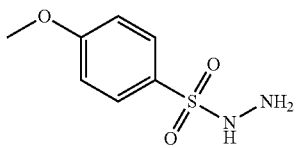

80% Hydrazine hydrate (693 mg, 11.1 mmol) was added into a solution of 4-methoxybenzene-1-sulfonyl chloride (1 g, 4.83 mmol) in THF (20 mL) at 0° C. under $N_2$, then the mixture stirred at room temperature for 30 min. The reaction solution was filtered, the filtrate was concentrated under reduced pressure. The residue was purified by silica gel column (DCM/MeOH=20/1, v/v) to afford the desired product (825 mg, 84%) as a white solid.

LC-MS (Agilent): $R_t$ 1.82 min; m/z calculated for $C_7H_{10}N_2O_3S$ [M+1]$^+$ =203.1. found 203.1.

$^1$H NMR (400 MHz, DMSO-$d_6$) δ (ppm): 8.19 (t, J=3 Hz, 1H), 7.72 (d, J=8.8 Hz, 2H), 7.11 (d, J=8.8 Hz, 2H), 4.01 (d, J=3.2 Hz, 3H), 3.84 (s, 3H).

Step 2: N'-(3-chloro-2-fluoro-5-(1-methyl-1H-imidazol-4-yl)benzoyl)-4-methoxybenzenesulfonohydrazide

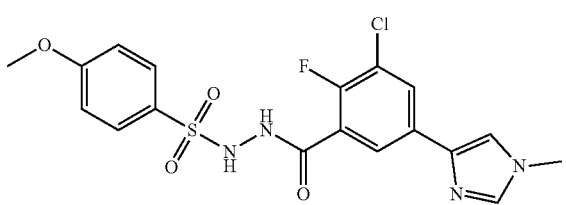

To a solution of 3-chloro-2-fluoro-5-(1-methyl-1H-imidazol-4-yl)benzoic acid (100 mg, 395 μmol) in toluene (20 mL) were added oxalyl chloride (200 mg, 1.58 mmol) and DMF (Cat.). After stirring at 60° C. for 2 h, the reaction mixture was concentrated in vacuo. The residue obtained was dissolved in dichloromethane (20 mL) and to this solution were added 4-methoxybenzene-1-sulfonohydrazide (80 mg, 395 μmol) and sodium carbonate (146 mg, 1.38 mmol). The reaction was stirred at room temperature for 16 h under $N_2$. The reaction solution was filtered and the filtrate concentrated under reduced pressure. The residue was purified by column (DCM/MeOH=20/1, v/v) to afford the desired product (80 mg, 46%) as a white solid.

LC-MS (Agilent): $R_t$ 2.24 min; m/z calculated for $C_{18}H_{26}ClFN_4O_4S$ [M+1]$^+$=439.1/441.1. found 439.1/441.1.

$^1$H NMR: (400 MHz, DMSO-$d_6$) δ (ppm): 10.69 (d, J=3.2 Hz, 1H), 10.02 (d, J=3.6 Hz, 1H), 7.98 (dd, J=6.4, 1.6 Hz, 1H), 7.80 (d, J=8.8 Hz, 2H), 7.75 (s, 1H), 7.68-7.65 (m, 2H), 7.10 (d, J=8.8 Hz, 2H), 3.83 (s, 3H), 3.69 (s, 3H).

Compound I-344

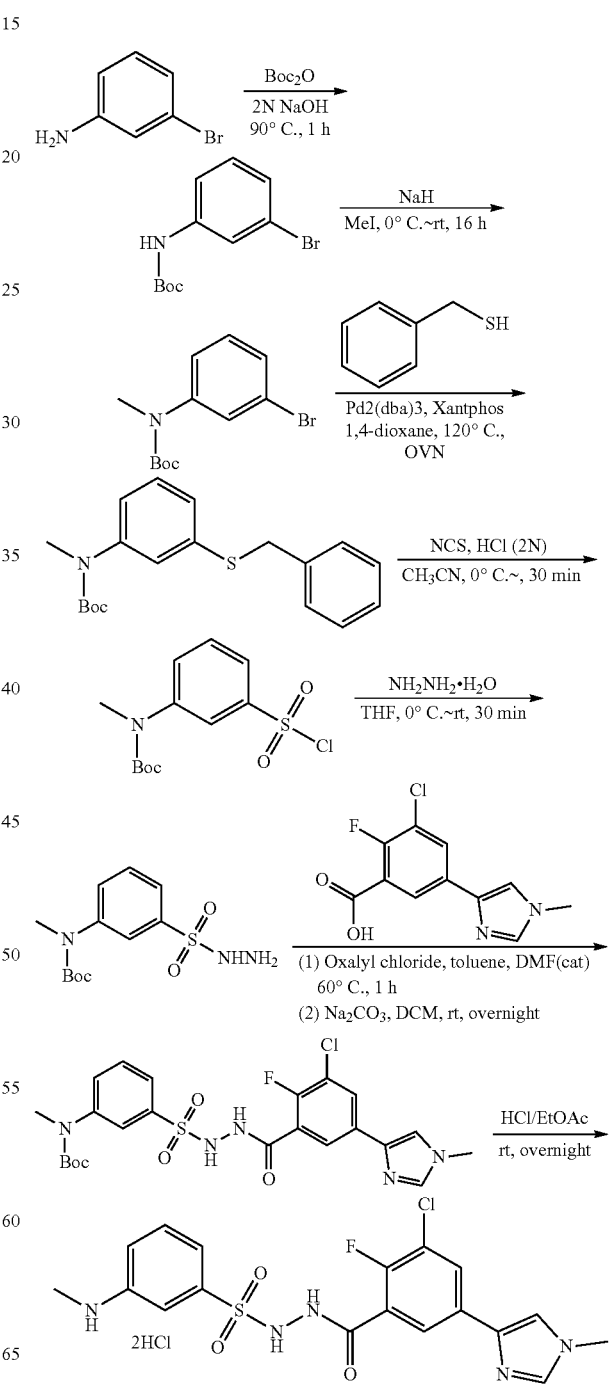

Step 1: tert-butyl (3-bromophenyl)carbamate

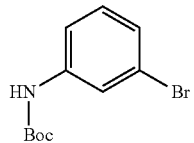

A solution of 3-bromoaniline (5.0 g, 29.0 mmol) and di-tert-butyl dicarbonate (9.49 g, 43.5 mmol) in sodium hydroxide solution (2 M, 100 mL) was stirred at 90° C. for 1 h. After cooling to room temperature, the reaction was diluted with water (100 mL) and extracted with EtOAc (50 mL×2). The combined organic phases were washed with brine (100 mL), dried over $Na_2SO_4$ and concentrated to afford the desired product (7.89 g, 100%) as a white solid.

LC-MS (Agilent): $R_t$ 4.00 min; m/z calculated for $C_{11}H_{14}BrNO_2$ [M−56+H]$^+$ 216.0. found 216.0.

$^1$H NMR (400 MHz, CDCl$_3$) δ (ppm): 7.66 (s, 1H), 7.21-7.19 (m, 1H), 7.17-7.11 (m, 2H), 6.48 (brs, 1H), 1.52 (s, 9H).

Step 2: tert-butyl (3-bromophenyl)(methyl)carbamate

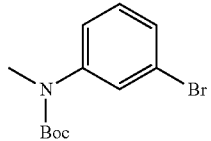

Sodium hydride (806 mg, 20.2 mmol) was added to a solution of tert-butyl N-(3-bromophenyl)carbamate (3.7 g, 13.5 mmol) in DMF (80 mL) at 0° C. After stirring for 0.5 h under N$_2$, iodomethane (2.10 g, 14.8 mmol) was added and the resulting reaction was stirred at room temperature overnight under N$_2$. The mixture was poured into water (100 mL) and extracted with EtOAc (50 mL×2). The combined organic phases were washed with water (100 mL×3), brine (100 mL), dried over Na$_2$SO$_4$ and concentrated to afford the desired product (3.86 g, 100%) as a yellow oil.

LC-MS (Agilent): $R_t$ 4.18 min; m/z calculated for $C_{12}H_{16}BrNO_2$ [M−56+H]+230.0. found 230.0.

$^1$H NMR (400 MHz, CDCl$_3$) δ (ppm): 7.42 (s, 1H), 7.30-7.27 (m, 1H), 7.18 (d, J=4.8 Hz, 2H), 3.24 (s, 3H), 1.46 (s, 9H).

Step 3: tert-butyl (3-(benzylthio)phenyl)(methyl)carbamate

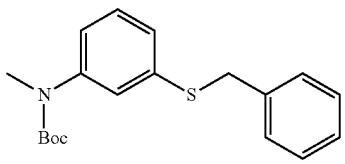

To a mixture of tert-butyl N-(3-bromophenyl)-N-methylcarbamate (1.5 g, 5.24 mmol) in dioxane (50.0 mL) were added Pd$_2$(dba)$_3$ (479 mg, 524 umol), Xantphos (601 mg, 1.04 mmol), phenylmethanethiol (976 mg, 7.86 mmol) and DIEA (1.34 g, 10.4 mmol). The mixture was stirred at reflux under a N$_2$ atmosphere overnight. The reaction mixture was diluted with water (100 mL) and extracted with EtOAc (60 mL×3). The combined organic layers were dried over Na$_2$SO$_4$ and concentrated under reduced pressure. The residue was purified by silica gel column (Pet.ether/EtOAc=50/1, v/v) to afford the desired product (1.7 g, 99%) as a red oil.

LC-MS (Agilent): $R_t$ 4.45 min; m/z calculated for $C_{19}H_{23}NO_2S$ [M−56+H]$^+$ 274.1. found 274.1.

$^1$H NMR (400 MHz, d$_6$-DMSO) δ (ppm): 7.36-7.34 (m, 2H), 7.29 (s, 1H), 7.27-7.26 (m, 1H), 7.24 (s, 1H) 7.22-7.21 (m, 2H), 7.13-7.11 (m, 1H), 7.08-7.06 (m, 1H), 4.24 (s, 2H), 3.12 (s, 3H), 1.37 (s, 9H).

Step 4: tert-butyl (3-(chlorosulfonyl)phenyl)(methyl)carbamate

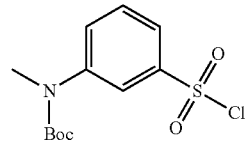

2 M Hydrochloric acid (235 mg, 6.46 mmol) was added to a solution of N-chlorosuccinimide (3.13 g, 23.5 mmol) in acetonitrile (10.0 mL) at 0° C. After stirring 10 min at 0° C. under N$_2$, tert-butyl (3-(benzylthio)phenyl)(methyl)carbamate (1.94 g, 5.88 mmol) was added and the mixture was stirred at room temperature for 20 min. The reaction mixture was concentrated in vacuo, the residue was diluted with water (50 mL) and extracted with EtOAc (50 mL×3). The combined organic layers were dried over Na$_2$SO$_4$ and concentrated to give the crude product (1.79 g, 100%) as a yellow oil, which was used for the next step directly.

Step 5: tert-butyl (3-(hydrazinylsulfonyl)phenyl)(methyl)carbamate

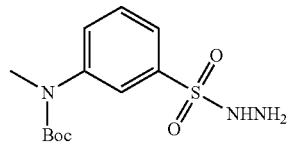

80% Hydrazine hydrate (837 mg, 13.4 mmol) was added to a solution of tert-butyl N-[3-(chlorosulfonyl)phenyl]-N-methylcarbamate (1.79 g, 5.85 mmol) in THF (25 mL) at 0° C. under N$_2$ atmosphere, then the mixture was stirred at room temperature for 20 min. The mixture was concentrated and the residue was purified by column (DCM:MeOH=80:1) to give the desired product (1.12 g, ~60% purity by LCMS, 64%) as a yellow oil.

LC-MS (Agilent): $R_t$ 2.76 min; m/z calculated for $C_{12}H_{19}N_3O_4S$ [M−56+H]$^+$ 246.1. found 246.1.

Step 6: tert-butyl(3-((2-(3-chloro-2-fluoro-5-(1-methyl-1H-imidazol-4-yl)benzoyl) hydrazinyl)sulfonyl)phenyl)(methyl)carbamate

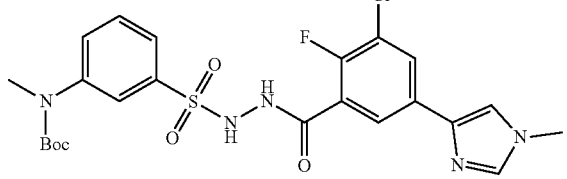

To a solution of 3-chloro-2-fluoro-5-(1-methyl-1H-imidazol-4-yl)benzoic acid (211 mg, 0.8295 mmol) in toluene (20 mL) were added oxalyl chloride (314 mg, 2.48 mmol) and DMF (Cat.). After stirring at 60° C. for 2 h, the reaction mixture was concentrated in vacuo. The residue obtained was dissolved in dichloromethane (20 mL) and to this solution were added tert-butyl N-[3-(hydrazinesulfonyl)phenyl]-N-methylcarbamate (250 mg, 0.83 mmol) and sodium carbonate (262 mg, 2.48 mmol). The reaction was stirred at room temperature for 12 h under $N_2$. The reaction solution was filtered and the filtrate concentrated in vacuo. The residue was purified by silica gel column (DCM/MeOH=40/1, v/v) then reverse phase column (C18 column, 40 g, 45% ACN in water) to afford the desired product (110 mg, 25%) as a white solid.

LC-MS (Agilent): $R_t$ 2.72 min; m/z calculated for $C_{23}H_{25}ClFN_5O_5S$ [M−56+H]$^+$ 538.1/540.1. found 538.1/540.1.

$^1$H NMR (400 MHz, $d_6$-DMSO) δ (ppm): 10.74 (s, 1H), 10.26 (s, 1H), 7.99 (dd, J=6.8, 2.0 Hz, 1H), 7.82 (s, 1H), 7.74 (s, 1H), 7.70-7.66 (m, 3H), 7.58-7.54 (m, 2H), 3.68 (s, 3H), 3.19 (s, 3H), 1.37 (s, 9H).

Step 7: N'-(3-chloro-2-fluoro-5-(1-methyl-1H-imidazol-4-yl)benzoyl)-3-(methylamino) benzenesulfonohydrazide Hydrochloride

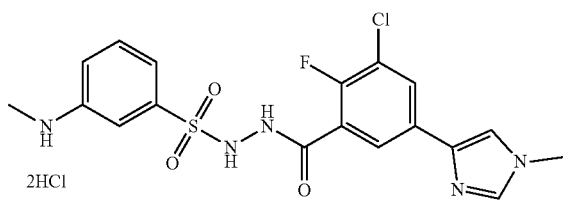

A solution of tert-butyl N-[3-({[3-chloro-2-fluoro-5-(1-methyl-1H-imidazol-4-yl)phenyl]formohydrazido}sulfonyl)phenyl]-N-methylcarbamate (95 mg, 0.18 mmol) in 1 M HCl/EtOAc (642 mg, 17.6 mmol) was stirred at room temperature overnight under $N_2$. The mixture was filtered, and the filter cake was washed with EtOAc (2 mL) to give the desired product (78 mg, 87%) as a white solid.

LC-MS (Agilent): $R_t$ 2.14 min; m/z calculated for $C_{18}H_{17}ClFN_5O_3S$ [M+H]$^+$ 438.1/440.1. found 438.1/440.1.

$^1$H NMR (400 MHz, $d_6$-DMSO) δ (ppm): 10.70 (s, 1H), 10.11 (s, 1H), 9.22 (s, 1H), 8.33 (dd, J=6.4, 2.0 Hz, 1H), 8.30 (s, 1H), 7.86-7.84 (dd, J=5.2, 2.0 Hz, 1H), 7.31 (t, J=8.2 Hz, 1H), 7.16 (s, 2H), 6.90 (d, J=7.6 Hz, 1H), 3.89 (s, 3H), 2.71 (s, 3H).

Compound I-318

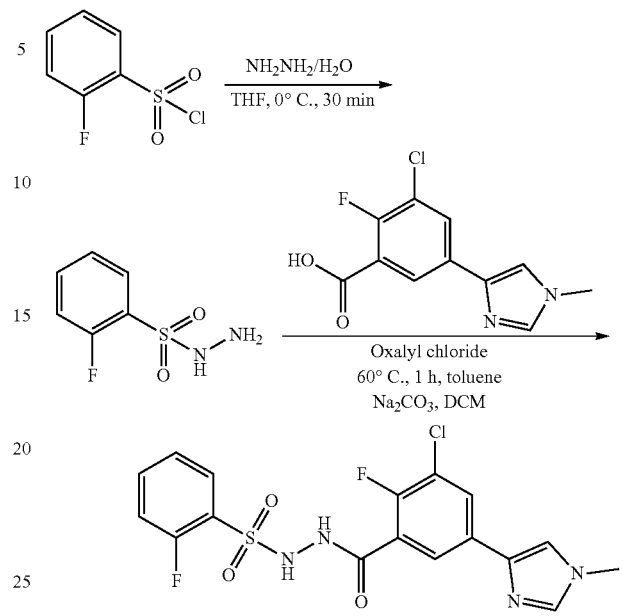

Step 1: 2-fluorobenzenesulfonohydrazide

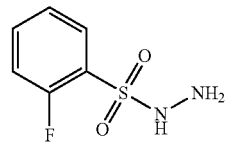

To a solution of 2-fluorobenzenesulfonohydrazide (2.0 g, 10.3 mmol) in THF (40 mL) was added dropwise 80% hydrazine hydrate (1.48 g, 23.7 mmol) at 0° C. under a nitrogen atmosphere. The resulting mixture was stirred at 0° C. for 30 min. The reaction mixture was concentrated in vacuo and the residue purified by silica gel column (DCM/MeOH=50/1, v/v) to afford the desired product (1.5 g, 77%) as a white solid.

$^1$H NMR (400 MHz, DMSO-$d_6$) δ (ppm): 8.63 (s, 1H), 7.80 (td, J=7.6 Hz, 1.6 Hz, 1H), 7.74-7.68 (m, 1H), 7.44-7.36 (m, 2H), 4.29 (brs, 2H).

Step 2: N'-(3-chloro-2-fluoro-5-(1-methyl-1H-imidazol-4-yl)benzoyl)-2-fluorobenzene sulfonohydrazide

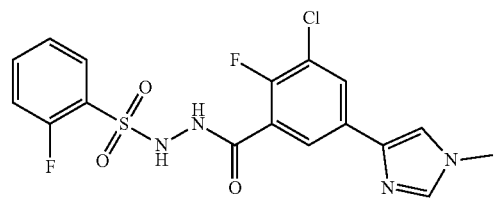

3-chloro-2-fluoro-5-(1-methyl-1H-imidazol-4-yl) benzoic acid (100 mg, 0.39 mmol) was dissolved in toluene (5 mL), oxalyl chloride (125 mg. 0.98 mmol) and DMF (cat) were added. After stirring at 60° C. for 1 h under nitrogen atmosphere, toluene was removed under reduced pressure. The residue was dissolved in DCM (5 mL) and this solution was added to a suspension of 2-fluorobenzenesulfonohydrazide (74 mg, 0.39 mmol) and sodium carbonate (124 mg, 1.17 mmol) in DCM (5 mL). After stirring at room temperature overnight under a nitrogen atmosphere, the reaction mixture was concentrated and the residue was purified by silica gel column (DCM/MeOH=40/1, v/v) to give the desired product (60 mg, 36%) as a white solid.

LC-MS (Agilent): R, 2.20 min; m/z calculated for $C_{17}H_{13}ClF_2N_4O_3S$ $[M+H]^+$ 427. found 427.0.

$^1$H NMR (400 MHz, DMSO-$d_6$) δ (ppm): 10.78 (d, J=2.8 Hz, 1H), 10.48 (d, J=2.8 Hz, 1H), 7.99 (dd, J=6.8, 2.4 Hz, 1H), 7.85 (td, J=7.6 Hz, 1.2 Hz, 1H), 7.74-7.66 (m, 4H), 7.41 (t, J=10.4 Hz, 1H), 7.35 (t, J=7.6 Hz, 1H), 3.69 (s, 3H).

Compound I-386

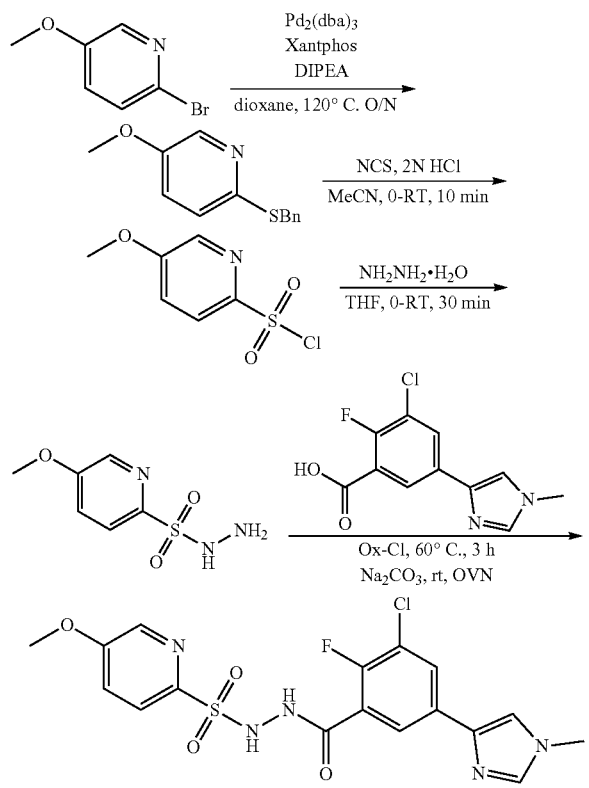

Step 1: 2-bromo-5-methoxypyridine

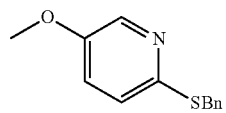

A mixture of 2-bromo-5-methoxypyridine (1 g, 5.31 mmol), BnSH (988 mg, 7.96 mmol), DIEA (1.36 g, 10.6 mmol), Pd$_2$(dba)$_3$ (243 mg, 0.266 mmol) and Xantphos (307 mg, 0.531 mmol) in 1,4-Dioxane (10 mL) was heated at reflux overnight. The reaction solution was concentrated and the residue was purified by silica gel column (PE:EtOAc=20:1) to afford the desired product (1.17 g, 96%) as a yellow solid.

$^1$H NMR (400 MHz, DMSO-$d_6$) δ (ppm): 8.22 (d, J=2.8 Hz, 1H), 7.37-7.33 (m, 2H), 7.32-7.21 (m, 5H), 4.35 (s, 2H), 3.79 (s, 3H).

Step 2: 5-methoxypyridine-2-sulfonyl chloride

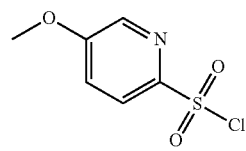

To a solution of NCS (1.15 g, 8.64 mmol) in MeCN (10 mL) was added HCl (84.1 mg, 2.37 mmol) at 0° C. and the solution was stirred for 10 min. 2-(benzylsulfanyl)-5-methoxypyridine (500 mg, 2.16 mmol) was added and the resulting mixture was stirred for 30 min. The reaction solution was diluted with water (60 mL) and extracted with EtOAc (20 mL×3). The combined organic phases were dried over Na$_2$SO$_4$ and concentrated to give 5-methoxypyridine-2-sulfonyl chloride (1.5 g) as a brown oil, which was used in the next step directly.

Step 3: 5-methoxypyridine-2-sulfonohydrazide

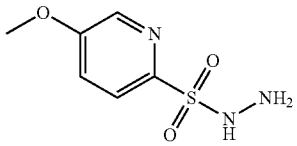

To a solution of 5-methoxypyridine-2-sulfonyl chloride (448 mg, 2.15 mmol) in THF (10 mL) was added hydrazine hydrate (308 mg, 4.94 mmol) at 0° C. and the resulting mixture was stirred for 1 h. The mixture was concentrated under reduced pressure and the residue purified by silica gel column (DCM:MeOH=20:1, v/v) to afford the desired product (165 mg, 38%) as a yellow solid.

$^1$H NMR (400 MHz, DMSO-$d_6$) δ (ppm): 8.56 (s, 1H), 8.41 (d, J=2.81 Hz, 1H), 7.91 (d, J=8.8 Hz, 1H), 7.61 (dd, J=6.0, 2.8 Hz, 1H), 4.14 (s, 2H), 3.92 (s, 3H).

Step 4: N'-(3-chloro-2-fluoro-5-(1-methyl-1H-imidazol-4-yl)benzoyl)-5-methoxy pyridine-2-sulfonohydrazide

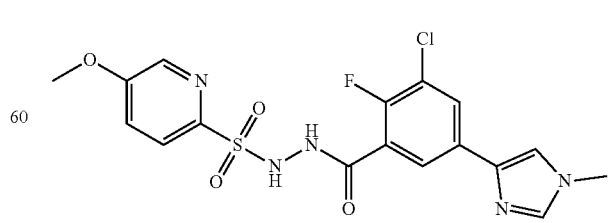

To a solution of 3-chloro-2-fluoro-5-(1-methyl-1H-imidazol-4-yl)benzoic acid (150 mg, 0.59 mmol) in toluene (5 mL) were added oxalyl chloride (223 mg, 1.76 mmol) and DMF (cat.), the mixture was stirred at 60° C. for 1 h. The reaction mixture was concentrated in vacuo and the residue obtained was dissolved in DCM (5.0 mL). This solution was added into a suspension of 5-methoxypyridine-2-sulfonohydrazide (119 mg, 0.589 mmol) and sodium carbonate (124 mg, 1.17 mmol) in DCM (5.0 mL). The reaction mixture was stirred at room temperature overnight and then concentrated in vacuo. The residue was purified by silica gel column (DCM/MeOH=20/1, v/v) to afford the desired product (150 mg, 54%) as a white solid.

LC-MS (Agilent): $R_t$ 1.94 min; m/z calculated for $C_{17}H_{15}ClFN_5O_4S$ [M+1]+=439.85. found 440.1/442.1.

$^1$H NMR: (400 MHz, DMSO-$d_6$) δ (ppm): 10.65 (s, 1H), 10.24 (s, 1H), 8.41 (d, J=2.8 Hz, 1H), 7.98 (dd, J=6.8, 2.0 Hz, 1H), 7.94 (d, J=8.8 Hz, 1H), 7.76 (s, 1H), 7.71-7.69 (m, 2H), 7.59 (dd, J=8.4, 2.8 Hz, 1H), 3.91 (s, 3H), 3.68 (s, 3H).

Compound I-376

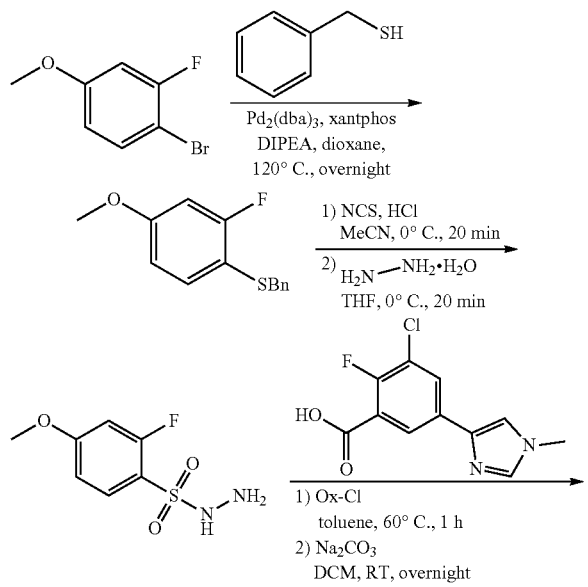

Step 1: benzyl(2-fluoro-4-methoxyphenyl)sulfane

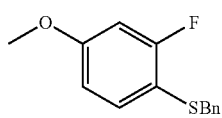

To a solution of 1-bromo-2-fluoro-4-methoxybenzene (1.0 g, 4.88 mmol) and phenylmethanethiol (909 mg, 7.32 mmol) in 1,4-dioxane (30 mL) were added Pd$_2$(dba)$_3$ (445 mg, 0.49 mmol), Xantphos (564 mg, 0.97 mmol) and DIPEA (1.25 g, 9.74 mmol), the resulting mixture was stirred at reflux under N$_2$ atmosphere overnight. The mixture was diluted with EtOAc (50 mL) and washed with water. The organic layer was dried and concentrated, the residue was purified by column (pet.ether) to afford the desired product (1.1 g, 92%) as a yellow oil.

LC-MS (Agilent): $R_t$ 3.00 min; m/z calculated for $C_{14}H_{13}FOS$ [M+1]+ 249.1. found 249.1.

$^1$H NMR (400 MHz, CDCl$_3$) δ (ppm): 7.27 (s, 1H), 7.25-7.14 (m, 5H), 6.65 (dd, J=10.8, 2.4 Hz, 1H), 6.57 (dd, J=8.8, 2.4 Hz, 1H), 3.98 (s, 2H), 3.79 (s, 3H)

Step 2: 2-fluoro-4-methoxybenzenesulfonohydrazide

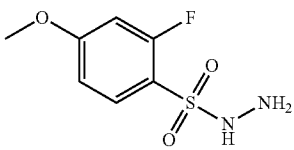

To a solution of N-chlorosuccinimide (1.07 g, 8.04 mmol) in MeCN (5 mL) was added hydrochloric acid (2 M, 80.5 mg, 2.21 mmol) at 0° C., the mixture was stirred at 0° C. for 20 min. 1-(benzylsulfanyl)-2-fluoro-4-methoxybenzene (500 mg, 2.01 mmol) in MeCN (2 mL) was added and the mixture was stirred at room temperature for 0.5 h. The mixture was concentrated to afford the crude product. The crude product dissolved in THF was added into a solution of hydrazine hydrate (333 mg, 5.34 mmol) in THF (8 mL) slowly at 0° C. and the resulting mixture was stirred at RT for 1 h. The mixture was concentrated and the residue was purified by silica gel column (DCM:MeOH=20:1) to afford the desired product (210 mg, 47%) as a colourless oil.

$^1$H NMR (400 MHz, DMSO-$d_6$) δ (ppm): 8.44 (s, 1H), 7.69 (t, J=8.4 MHz, 1H), 7.03 (d, J=12.4 Hz, 1H), 6.93 (d, J=8.8 Hz, 1H), 4.19 (s, 2H), 3.85 (s, 3H).

Step 3: N'-(3-chloro-2-fluoro-5-(1-methyl-1H-imidazol-4-yl)benzoyl)-2-fluoro-4-methoxybenzenesulfonohydrazide

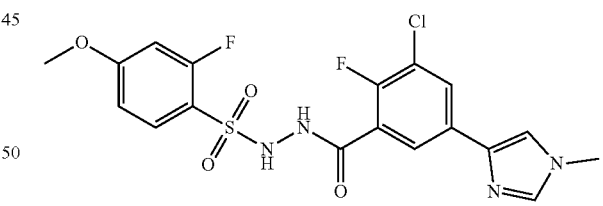

To a solution of 3-chloro-2-fluoro-5-(1-methyl-1H-imidazol-4-yl)benzoic acid (115 mg, 0.454 mmol) in toluene (5 mL) were added oxalyl chloride (172 mg, 1.36 mmol) and DMF (cat.). The mixture was stirred at 60° C. for 1 h then concentrated and the residue was added to a mixture of 2-fluoro-4-methoxybenzene-1-sulfonohydrazide (100 mg, 0.454 mmol) and sodium carbonate (96.2 mg, 0.908 mmol) in DCM (5 mL). The resulting mixture was stirred at room temperature overnight. The mixture was concentrated and the residue was purified by reverse phase column (C18 column, 40 g, 60% ACN in water) to afford the desired product (45 mg, 22%) as a light yellow solid.

LC-MS (Agilent): $R_t$ 2.29 min; m/z calculated for $C_{18}H_{15}ClF_2N_4O_4S$ [M+1]+ 457.1/459.1. found 457.1/459.1.

¹H NMR: (400 MHz, DMSO-d6) δ (ppm): 10.72 (s, 1H), 10.29 (s, 1H), 7.98 (s, 1H), 7.80-7.60 (m, 4H), 7.06-6.97 (m, 1H), 6.92-6.88 (m, 1H), 3.83 (s, 3H), 3.68 (s, 3H).

Biochemical Assays

KAT-5. Enzyme assay buffer was 50 mM Tris pH 8.0, 0.002% Tween20, 0.005% bovine skin gelatin, and 1 mM dithiothreitol (DTT). For determination of $IC_{50}$ values, compounds were serially diluted with 2% (v/v) DMSO in the final reaction, pre-incubating each dilution of each compound with 40 μL of assay buffer containing KAT-5 enzyme (9 nM final concentration). 10 μL of assay buffer containing 1 μM peptide substrate and 0.5 μM acetyl coenzyme A (final concentrations) was added. Reactions (50 μL total) were then carried out at 25° C. for 90 minutes. Reactions were terminated by the addition of 0.5% formic acid (final concentration), and a sample of each reaction was analyzed by SAMDI Tech, Inc. (Chicago, Ill.) using self-assembled monolayer desorption/ionization time-of-flight mass spectrometry (Mrksich, M. (2008) Mass spectrometry of self-assembled monolayers: a new tool for molecular surface science. ACS Nano 2, 7-18).

KAT-6A. Enzyme assay buffer was 50 mM Tris pH 8.0, 0.002% Tween20, 0.005% bovine skin gelatin, and 1 mM dithiothreitol (DTT). For determination of $IC_{50}$ values, compounds were serially diluted with 2% (v/v) DMSO in the final reaction, pre-incubating each dilution of each compound with 40 μL of assay buffer containing KAT-6A enzyme (12.5 nM final concentration). 10 μL of assay buffer containing 1 μM peptide substrate and 1 μM acetyl coenzyme A (final concentrations) was added. Reactions (50 μL total) were then carried out at 25° C. for 90 minutes. Reactions were terminated by the addition of 0.5% formic acid (final concentration), and a sample of each reaction was analyzed by SAMDI Tech, Inc. (Chicago, Ill.) using self-assembled monolayer desorption/ionization time-of-flight mass spectrometry (Mrksich, M. (2008) Mass spectrometry of self-assembled monolayers: a new tool for molecular surface science. ACS Nano 2, 7-18).

KAT-7. Enzyme assay buffer was 50 mM Tris pH 8.0, 0.002% Tween20, 0.005% bovine skin gelatin, and 1 mM dithiothreitol (DTT). For determination of $IC_{50}$ values, compounds were serially diluted with 2% (v/v) DMSO in the final reaction, pre-incubating each dilution of each compound with 40 μL of assay buffer containing KAT-7 enzyme (6 nM final concentration). 10 μL of assay buffer containing 1 μM peptide substrate and 2 μM acetyl coenzyme A (final concentrations) was added. Reactions (50 μL total) were then carried out at 25° C. for 120 minutes. Reactions were terminated by the addition of 0.5% formic acid (final concentration), and a sample of each reaction was analyzed by SAMDI Tech, Inc. (Chicago, Ill.) using self-assembled monolayer desorption/ionization time-of-flight mass spectrometry (Mrksich, M. (2008) Mass spectrometry of self-assembled monolayers: a new tool for molecular surface science. ACS Nano 2, 7-18).

KAT-8. Enzyme assay buffer was 50 mM Tris pH 8.0, 0.002% Tween20, 0.005% bovine skin gelatin, and 1 mM dithiothreitol (DTT). For determination of $IC_{50}$ values, compounds were serially diluted with 2% (v/v) DMSO in the final reaction, pre-incubating each dilution of each compound with 40 μL of assay buffer containing KAT-8 enzyme (12.5 nM final concentration). 10 μL of assay buffer containing 1 μM peptide substrate and 5 μM acetyl coenzyme A (final concentrations) was added. Reactions (50 μL total) were then carried out at 25° C. for 90 minutes. Reactions were terminated by the addition of 0.5% formic acid (final concentration), and a sample of each reaction was analyzed by SAMDI Tech, Inc. (Chicago, Ill.) using self-assembled monolayer desorption/ionization time-of-flight mass spectrometry (Mrksich, M. (2008) Mass spectrometry of self-assembled monolayers: a new tool for molecular surface science. ACS Nano 2, 7-18).

Biochemical assay parameters are summarized in Table 3.

TABLE 3

| Enzyme | Construct/ amino acids | Assay [Enz] (nM) | Peptide substrate | Assay [Peptide] (μM) | Assay [Acetyl CoA] (μM) | Reaction Time (min) |
|---|---|---|---|---|---|---|
| KAT-5 | Full length | 9 | H4 1-20 K5R K8R K16R SGRGRGGRGLGKGG ARRHRK(Biotin)-NH₂ | 1 | 0.5 | 90 |
| KAT-6A | 501-784 | 12.5 | H4 1-26 K20Me1 SGRGKGGKGLGKGG AKRHRK(Me1)VLRG GK(Biotin)-NH₂ | 1 | 1 | 90 |
| KAT-7 | Full length | 6 | H4 1-26 K20Me1 K5R K8R K16R SGRGRGGRGLGKGG ARRHRK(Me)VLRGG K(Biotin)-NH2 | 1 | 2 | 120 |
| KAT-8 | Full length | 12.5 | H4 1-20 K5R K8R K16R SGRGRGGRGLGKGG ARRHRK(Biotin)-NH₂ | 1 | 5 | 90 |

Enzyme Constructs

KAT5FL:
Original protein before affinity tag cleavage:
MHHHHHHSSGVDLGTENLYFQSNAMAEVGEIIEGCRLPVLRRNQDNEDEW
PLAEILSVKDISGRKLFYVHYIDFNKRLDEWVTHERLDLKKIQFPKKEAK
TPTKNGLPGSRPGSPEREVPASAQASGKTLPIPVQITLRFNLPKEREAIP
GGEPDQPLSSSSCLQPNHRSTKRKVEVVSPATPVPSETAPASVFPQNGAA
RRAVAAQPGRKRKSNCLGTDEDSQDSSDGIPSAPRMTGSLVSDRSHDDIV
TRMKNIECIELGRHRLKPWYFSPYPQELTTLPVLYLCEFCLKYGRSLKCL
QRHLTKCDLRHPPGNEIYRKGTISFFEIDGRKNKSYSQNLCLLAKCFLDH
KTLYYDTDPPFLFYVMTEYDCKGFHIVGYFSKEKESTEDYNVACILTLPPY
QRRGYGKLLIEFSYELSKVEGKTGTPEKPLSDLGLLSYRSYWSQTILEIL
MGLKSESGERPQITINEISEITSIKKEDVISTLQYLNLINYYKGQYILTL
SEDIVDGHERAMLKRLLRIDSKCLHFTPKDWSKRGKW*DYKDDDDK*

Final protein after affinity tag cleavage:
SNAMAEVGEIIEGCRLPVLRRNQDNEDEWPLAEILSVKDISGRKLFYVHY
IDFNKRLDEWVTHERLDLKKIQFPKKEAKTPTKNGLPGSRPGSPEREVPA
SAQASGKTLPIPVQITLRFNLPKEREAIPGGEPDQPLSSSSCLQPNHRST
KRKVEVVSPATPVPSETAPASVFPQNGAARRAVAAQPGRKRKSNCLGTDE
DSQDSSDGIPSAPRMTGSLVSDRSHDDIVTRMKNIECIELGRHRLKPWYF
SPYPQELTTLPVLYLCEFCLKYGRSLKCLQRHLTKCDLRHPPGNEIYRKG
TISFFEIDGRKNKSYSQNLCLLAKCFLDHKTLYYDTDPPFLFYVMTEYDCK
GFHIVGYFSKEKESTEDYNVACILTLPPYQRRGYGKLLIEFSYELSKVEG
KTGTPEKPLSDLGLLSYRSYWSQTILEILMGLKSESGERPQITINEISEI
TSIKKEDVISTLQYLNLINYYKGQYILTLSEDIVDGHERAMLKRLLRIDS
KCLHFTPKDWSKRGKW*DYKDDDDK*

KAT6A 501-784:
Original protein before affinity tag cleavage:
MHHHHHHSSGVDLGTENLYFQSNAPPDPQVRCPSVIEFGKYEIHTWYSSP
YPQEYSRLPKLYLCEFCLKYMKSRTILQQHMKKCGWFHPPANEIYRKNNI
SVFEVDGNVSTIYCQNLCLLAKLFLDHKTLYYDVEPFLFYVLTQNDVKGC
HLVGYFSKEKHCQQKYNVSCIMILPQYQRKGYGRFLIDFSYLLSKREGQA
GSPEKPLSDLGRLSYMAYWKSVILECLYHQNDKQISIKKLSKLTGICPQD
ITSTLHHLRMLDFRSDQFVIIRREKLIQDHMAKLQLNLRPVDVDPECLRW
TPVIVSNS Final protein after affinity tag cleavage:
SNAPPDPQVRCPSVIEFGKYEIHTWYSSPYPQEYSRLPKLYLCEFCLKYM
KSRTILQQHMKKCGWFHPPANEIYRKNNISVFEVDGNVSTIYCQNLCLLA
KLFLDHKTLYYDVEPFLFYVLTQNDVKGCHLVGYFSKEKHCQQKYNVSCI
MILPQYQRKGYGRFLIDFSYLLSKREGQAGSPEKPLSDLGRLSYMAYWKS
VILECLYHQNDKQISIKKLSKLTGICPQDITSTLHHLRMLDFRSDQFVII
RREKLIQDHMAKLQLNLRPVDVDPECLRWTPVIVSNS KAT7: KAT7-1-611-FLAG
Original protein before affinity tag cleavage:
MHHHHHHSSGVDLGTENLYFQSNAMPRRKRNAGSSSDGTEDSDFSTDLEH
TDSSESDGTSRRSARVTRSSARLSQSSQDSSPVRNLQSFGTEEPAYSTRR
VTRSQQQPTPVTPKKYPLRQTRSSGSETEQVVDFSDRETKNTADHDESPP
RTPTGNAPSSESDIDISSPNVSHDESIAKDMSLKDSGSDLSHRPKRRRFH
ESYNFNMKCPTPGCNSLGHLTGKHERHFSISGCPLYHNLSADECKVRAQS
RDKQIEERMLSHRQDDNNRHATRHQAPTERQLRYKEKVAELRKKRNSGLS
KEQKEKYMEHRQTYGNTREPLLENLTSEYDLDLFRRAQARASEDLEKLRL
QGQITEGSNMIKTIAFGRYELDTWYHSPYPEEYARLGRLYMCEFCLKYMK
SQTILRRHMAKCVWKHPPGDEIYRKGSISVFEVDGKKNKIYCQNLCLLAK
LFLDHKTLYYDVEPPFLFYVMTEADNTGCHLIGYFSKEKNSFLNYNVSCIL
TMPQYMRQGYGKMLIDFSYLLSKVEEKVGSPERPLSDLGLISYRSYWKEV
LLRYLHNFQGKEISIKEISQETAVNPVDIVSTLQALQMLKYWKGKHLVLK
RQDLIDEWIAKEAKRSNSNKTMDPSCLKWTPPKGT*DYKDDDDK*

Final protein after affinity tag cleavage:
SNAMPRRKRNAGSSSDGTEDSDFSTDLEHTDSSESDGTSRRSARVTRSSA
RLSQSSQDSSPVRNLQSFGTEEPAYSTRRVTRSQQQPTPVTPKKYPLRQT
RSSGSETEQVVDFSDRETKNTADHDESPPRTPTGNAPSSESDIDISSPNV
SHDESIAKDMSLKDSGSDLSHRPKRRRFHESYNFNMKCPTPGCNSLGHLT
GKHERHFSISGCPLYHNLSADECKVRAQSRDKQIEERMLSHRQDDNNRHA
TRHQAPTERQLRYKEKVAELRKKRNSGLSKEQKEKYMEHRQTYGNTREPL
LENLTSEYDLDLFRRAQARASEDLEKLRLQGQITEGSNMIKTIAFGRYEL
DTWYHSPYPEEYARLGRLYMCEFCLKYMKSQTILRRHMAKCVWKHPPGDE
IYRKGSISVFEVDGKKNKIYCQNLCLLAKLFLDHKTLYYDVEPFLFYVMT
EADNTGCHLIGYFSKEKNSFLNYNVSCILTMPQYMRQGYGKMLIDFSYLL
SKVEEKVGSPERPLSDLGLISYRSYWKEVLLRYLHNFQGKEISIKEISQE
TAVNPVDIVSTLQALQMLKYWKGKHLVLKRQDLIDEWIAKEAKRSNSNKT
MDPSCLKWTPPKGT*DYKDDDDK*

KAT-8: His-KAT-8-1-458-FLAG
Final protein (no cleavage):
*MHHHHHH*MAAQGAAAAVAAGTSGVAGEGEPGPGENAAAEGTAPSPGRVSP
PTPARGEPEVTVEIGETYLCRRPDSTWHSAEVIQSRVNDQEGREEFYVHY
VGFNRRLDEWVDKNRLALTKTVKDAVQKNSEKYLSELAEQPERKITRNQK
RKHDEINHVQKTYAEMDPTTAALEKEHEAITKVKYVDKIHIGNYEIDAWY
FSPFPEDYGKQPKLWLCEYCLKYMKYEKSYRFHLGQCQWRQPPGKEIYRK
SNISVYEVDGKDHKIYCQNLCLLAKLFLDHKTLYFDVEPFVFYILTEVDR
QGAHIVGYFSKEKESPDGNNVACILTLPPYQRRGYGKFLIAFSYELSKLE
STVGSPEKPLSDLGKLSYRSYWSWVLLEILRDFRGTLSIKDLSQMTSITQ
NDIISTLQSLNMVKYWKGQHVICVTPKLVEEHLKSAQYKKPPITVDSVCL
KWAPPKHKQVKLSKK*DYKDDDDK* underlined residues: His-TEV tag
italicized residues: Flag tag
underlined and italicized residues: His Tag Table 4 shows the activity of selected compounds of this disclosure in KAT-5, KAT-6A, KAT-7, and KAT-8 inhibition assays. The compound numbers correspond to the compound numbers above. Compounds having an activity designated as "A" provided an IC$_{50}$ of 10 μM; compounds having an activity designated as "B" provided an IC$_{50}$ of 10.01-50 μM; compounds having an activity designated as "C" provided an IC$_{50}$ of 50.01-100 μM; and compounds having an activity designated as "D" provided an IC$_{50}$ of >100 PM.

TABLE 4

| Compound | KAT-5 IC$_{50}$ (μM) | KAT-6A IC$_{50}$ (μM) | KAT-7 IC$_{50}$ (μM) | KAT-8 IC$_{50}$ (μM) |
|---|---|---|---|---|
| I-1 | A | A | A | D |
| I-2 | A | A | A | B |
| I-3 | A | A | A | D |
| I-4 | A | A | A | C |
| I-5 | A | A | A | D |
| I-6 | B | A | B | D |
| I-7 | B | C | A | D |
| I-8 | D | B | B | D |
| I-9 | B | B | A | D |
| I-10 | A | A | A | D |
| I-11 | C | B | C | D |
| I-12 | C | C | A | D |
| I-13 | A | A | A | D |
| I-14 | C | D | B | D |
| I-15 | B | C | A | D |
| I-16 | B | D | A | D |
| I-17 | A | A | A | D |
| I-18 | A | A | A | B |
| I-19 | D | D | B | D |
| I-20 | A | A | A | C |
| I-21 | A | A | A | D |
| I-22 | D | B | A | D |
| I-23 | A | A | A | D |
| I-24 | A | A | A | B |
| I-25 | B | C | A | D |
| I-26 | A | B | A | D |
| I-27 | B | C | A | D |
| I-28 | B | D | A | D |
| I-29 | B | D | C | D |
| I-30 | D | D | D | D |
| I-31 | A | A | A | B |
| I-32 | A | A | A | D |
| I-33 | B | B | A | D |
| I-34 | A | A | B | D |
| I-35 | A | A | A | B |
| I-36 | B | A | A | D |
| I-37 | C | B | B | D |
| I-38 | A | — | A | D |
| I-39 | B | B | C | D |
| I-40 | D | D | D | D |
| I-41 | B | A | C | D |
| I-42 | D | D | A | D |
| I-43 | B | A | C | D |
| I-44 | C | D | D | D |
| I-45 | D | D | C | D |
| I-46 | B | C | A | D |
| I-47 | A | C | D | D |
| I-48 | A | A | A | D |
| I-49 | D | D | D | D |
| I-50 | A | A | B | D |
| I-51 | A | A | A | B |
| I-52 | B | B | A | D |
| I-53 | A | A | A | C |
| I-54 | C | D | D | D |
| I-55 | A | A | A | B |
| I-56 | B | B | A | B |
| I-57 | B | B | A | B |
| I-58 | D | D | D | D |
| I-59 | B | D | D | D |
| I-60 | D | D | D | D |
| I-61 | D | D | B | D |
| I-62 | B | B | A | B |
| I-63 | A | A | A | B |
| I-64 | A | A | A | B |
| I-65 | C | B | A | D |
| I-66 | A | A | A | B |

TABLE 4-continued

| Compound | KAT-5 IC$_{50}$ (μM) | KAT-6A IC$_{50}$ (μM) | KAT-7 IC$_{50}$ (μM) | KAT-8 IC$_{50}$ (μM) |
|---|---|---|---|---|
| I-67 | B | B | B | D |
| I-68 | A | B | B | B |
| I-69 | B | B | A | B |
| I-70 | B | B | B | B |
| I-71 | B | B | A | B |
| I-72 | B | A | A | B |
| I-73 | A | B | A | B |
| I-74 | B | B | B | B |
| I-75 | A | A | A | B |
| I-76 | B | B | A | B |
| I-77 | B | B | B | B |
| I-78 | A | B | A | B |
| I-79 | B | B | A | B |
| I-80 | B | A | B | B |
| I-81 | A | A | B | B |
| I-82 | A | A | A | B |
| I-83 | B | B | A | B |
| I-84 | A | A | A | B |
| I-85 | A | A | A | B |
| I-86 | A | A | A | B |
| I-87 | B | A | B | B |
| I-88 | A | B | A | B |
| I-89 | B | B | A | B |
| I-90 | B | B | B | B |
| I-91 | A | A | A | B |
| I-92 | A | A | A | B |
| I-93 | B | B | A | B |
| I-94 | A | A | A | B |
| I-95 | B | A | A | B |
| I-96 | A | A | A | B |
| I-97 | A | A | A | B |
| I-98 | A | — | A | B |
| I-99 | A | — | A | B |
| I-100 | B | B | B | B |
| I-101 | A | A | A | B |
| I-102 | A | A | A | B |
| I-103 | B | B | A | B |
| I-104 | A | A | A | B |
| I-105 | A | A | A | B |
| I-106 | A | A | A | B |
| I-107 | A | A | A | B |
| I-108 | B | B | A | B |
| I-109 | A | A | A | B |
| I-110 | A | A | A | B |
| I-111 | A | A | A | B |
| I-112 | A | B | A | B |
| I-113 | B | B | A | B |
| I-114 | A | A | A | B |
| I-115 | A | A | A | B |
| I-116 | A | A | A | B |
| I-117 | A | A | A | B |
| I-118 | A | A | A | B |
| I-119 | B | B | B | B |
| I-120 | B | B | A | B |
| I-121 | B | B | A | B |
| I-122 | B | B | A | B |
| I-123 | B | B | A | B |
| I-124 | A | A | A | B |
| I-125 | B | B | B | B |
| I-126 | A | B | A | D |
| I-127 | A | B | A | D |
| I-128 | B | B | A | D |
| I-129 | A | A | A | D |
| I-130 | A | B | A | D |
| I-131 | B | B | A | D |
| I-132 | A | A | A | D |
| I-133 | D | D | A | D |
| I-134 | B | D | A | D |
| I-135 | A | C | B | D |
| I-136 | D | D | D | D |
| I-137 | B | C | B | D |
| I-138 | B | D | C | D |
| I-139 | B | D | A | D |
| I-140 | B | B | A | D |
| I-141 | A | A | A | D |
| I-142 | A | A | A | D |
| I-143 | C | C | C | D |

TABLE 4-continued

| Compound | KAT-5 IC$_{50}$ (μM) | KAT-6A IC$_{50}$ (μM) | KAT-7 IC$_{50}$ (μM) | KAT-8 IC$_{50}$ (μM) |
|---|---|---|---|---|
| I-144 | D | D | A | D |
| I-145 | D | D | B | D |
| I-146 | B | B | B | D |
| I-147 | D | D | D | D |
| I-148 | B | B | B | B |
| I-149 | B | B | A | B |
| I-150 | B | B | A | B |
| I-151 | C | D | B | D |
| I-152 | B | D | D | D |
| I-153 | D | D | D | D |
| I-154 | B | D | A | D |
| I-155 | D | D | B | D |
| I-156 | B | D | A | D |
| I-157 | A | A | A | B |
| I-158 | A | B | A | D |
| I-159 | A | B | A | C |
| I-160 | B | B | A | B |
| I-161 | A | A | A | B |
| I-162 | A | B | A | B |
| I-163 | A | A | A | B |
| I-164 | B | A | A | B |
| I-165 | B | B | B | B |
| I-166 | A | A | A | B |
| I-167 | B | A | A | B |
| I-168 | B | B | A | B |
| I-169 | B | A | A | B |
| I-170 | B | A | A | B |
| I-171 | A | A | A | B |
| I-172 | A | A | A | B |
| I-173 | A | A | A | B |
| I-174 | A | A | A | B |
| I-175 | A | A | A | B |
| I-176 | A | A | A | B |
| I-177 | A | A | A | A |
| I-178 | B | A | A | B |
| I-179 | A | A | A | B |
| I-180 | A | A | A | B |
| I-181 | A | A | A | B |
| I-182 | A | A | A | B |
| I-183 | A | A | A | B |
| I-184 | A | A | A | B |
| I-185 | B | A | A | B |
| I-186 | A | A | A | B |
| I-187 | A | A | A | B |
| I-188 | B | B | A | B |
| I-189 | A | A | A | B |
| I-190 | A | A | A | B |
| I-191 | A | A | A | B |
| I-192 | B | B | A | B |
| I-193 | B | A | A | B |
| I-194 | A | A | A | B |
| I-195 | A | A | A | B |
| I-196 | A | A | A | B |
| I-197 | A | A | A | B |
| I-198 | A | A | A | B |
| I-199 | A | A | A | B |
| I-200 | A | A | A | A |
| I-201 | A | A | A | B |
| I-202 | A | A | A | B |
| I-203 | A | A | A | B |
| I-204 | B | B | A | B |
| I-205 | A | A | A | B |
| I-206 | A | A | A | B |
| I-207 | B | A | A | B |
| I-208 | B | B | A | B |
| I-209 | A | B | A | B |
| I-210 | A | B | A | B |
| I-211 | A | A | A | B |
| I-212 | B | B | A | B |
| I-213 | A | A | A | B |
| I-214 | A | A | A | B |
| I-215 | A | A | A | B |
| I-216 | A | B | A | B |
| I-217 | A | A | A | B |
| I-218 | A | A | A | B |
| I-219 | A | A | A | B |
| I-220 | B | B | A | B |
| I-221 | A | A | A | B |
| I-222 | A | B | A | B |
| I-223 | B | B | B | B |
| I-224 | B | B | A | B |
| I-225 | A | A | A | B |
| I-226 | A | B | A | B |
| I-227 | A | A | A | B |
| I-228 | A | B | A | B |
| I-229 | A | A | A | B |
| I-230 | A | A | A | B |
| I-231 | A | A | A | B |
| I-232 | B | B | B | B |
| I-233 | B | B | A | B |
| I-234 | A | A | A | B |
| I-235 | A | A | A | B |
| I-236 | A | A | A | B |
| I-237 | B | A | A | B |
| I-238 | A | A | A | B |
| I-239 | A | B | A | B |
| I-240 | A | A | A | B |
| I-241 | A | A | A | B |
| I-242 | A | A | A | B |
| I-243 | A | A | A | B |
| I-244 | A | A | A | B |
| I-245 | A | A | A | B |
| I-246 | A | A | A | B |
| I-247 | A | A | A | B |
| I-248 | A | A | A | B |
| I-249 | A | A | A | B |
| I-250 | A | B | A | B |
| I-251 | B | B | A | B |
| I-252 | A | A | A | B |
| I-253 | B | B | A | B |
| I-254 | A | A | A | B |
| I-255 | B | B | A | B |
| I-256 | A | A | A | B |
| I-257 | B | B | B | B |
| I-258 | A | A | A | B |
| I-259 | A | B | — | B |
| I-260 | A | A | — | B |
| I-261 | B | B | B | B |
| I-262 | A | A | A | B |
| I-263 | B | B | — | B |
| I-264 | A | A | A | B |
| I-265 | A | A | A | B |
| I-266 | A | A | A | B |
| I-267 | A | B | A | B |
| I-268 | A | A | — | B |
| I-269 | A | A | — | B |
| I-270 | A | A | — | B |
| I-271 | B | B | — | B |
| I-272 | A | A | — | B |
| I-273 | A | A | — | B |
| I-274 | A | A | — | B |
| I-275 | A | A | — | B |
| I-276 | A | A | — | B |
| I-277 | A | A | — | B |
| I-278 | A | A | — | B |
| I-279 | A | A | — | B |
| I-280 | B | B | A | B |
| I-281 | A | A | A | B |
| I-282 | A | B | A | B |
| I-283 | B | B | A | B |
| I-284 | B | A | A | B |
| I-285 | A | A | A | B |
| I-286 | A | A | A | B |
| I-287 | A | A | A | B |
| I-288 | A | A | A | B |
| I-289 | A | A | A | B |
| I-290 | A | B | A | B |
| I-291 | A | B | A | B |
| I-292 | A | A | A | B |
| I-293 | A | A | A | B |
| I-294 | A | A | A | B |
| I-295 | A | A | A | B |
| I-296 | A | A | A | B |
| I-297 | B | B | A | B |

TABLE 4-continued

| Compound | KAT-5 IC$_{50}$ (µM) | KAT-6A IC$_{50}$ (µM) | KAT-7 IC$_{50}$ (µM) | KAT-8 IC$_{50}$ (µM) |
|---|---|---|---|---|
| I-298 | A | A | A | B |
| I-299 | A | A | A | B |
| I-300 | A | A | A | B |
| I-301 | B | A | A | B |
| I-302 | A | A | A | B |
| I-303 | A | B | A | B |
| I-304 | A | A | A | B |
| I-305 | B | B | A | B |
| I-306 | A | A | A | B |
| I-307 | B | B | B | B |
| I-308 | A | A | A | A |
| I-309 | A | A | A | B |
| I-310 | A | A | A | B |
| I-311 | A | B | A | B |
| I-312 | A | A | A | B |
| I-313 | A | A | A | B |
| I-314 | B | B | A | B |
| I-315 | A | A | A | B |
| I-316 | A | A | A | B |
| I-317 | A | A | A | B |
| I-318 | A | A | A | B |
| I-319 | A | A | A | B |
| I-320 | A | A | A | B |
| I-321 | A | A | A | B |
| I-322 | A | A | A | B |
| I-323 | A | A | A | B |
| I-324 | A | A | A | B |
| I-325 | A | A | A | B |
| I-326 | A | A | A | B |
| I-327 | A | A | A | B |
| I-328 | B | B | A | B |
| I-329 | A | A | A | B |
| I-330 | A | A | A | B |
| I-331 | A | B | A | B |
| I-332 | A | A | A | B |
| I-333 | A | A | A | B |
| I-334 | A | A | A | B |
| I-335 | A | A | A | B |
| I-336 | A | A | A | B |
| I-337 | B | B | A | B |
| I-338 | A | A | A | B |
| I-339 | B | B | A | B |
| I-340 | A | A | A | B |
| I-341 | A | A | A | B |
| I-342 | A | A | A | B |
| I-343 | A | A | A | B |
| I-344 | A | A | A | B |
| I-345 | A | A | A | B |
| I-346 | A | A | A | B |
| I-347 | A | A | A | B |
| I-348 | A | A | A | B |
| I-349 | B | B | A | B |
| I-350 | A | A | A | B |
| I-351 | B | B | B | B |
| I-352 | A | B | A | B |
| I-353 | A | A | A | B |
| I-354 | A | B | A | B |
| I-355 | A | A | A | B |
| I-356 | A | B | A | B |
| I-357 | A | A | A | B |
| I-358 | A | A | A | B |
| I-359 | A | A | A | B |
| I-360 | A | A | A | B |
| I-361 | B | B | A | B |
| I-362 | A | B | A | B |
| I-363 | A | B | A | B |
| I-364 | B | B | A | B |
| I-365 | A | A | A | B |
| I-366 | A | A | A | B |
| I-367 | A | A | A | B |
| I-368 | A | A | A | B |
| I-369 | A | B | A | B |
| I-370 | B | A | A | B |
| I-371 | A | A | A | B |
| I-372 | A | B | A | B |
| I-373 | B | B | B | B |
| I-374 | A | A | A | B |
| I-375 | A | A | A | B |
| I-376 | A | A | A | B |
| I-377 | B | B | A | B |
| I-378 | A | A | A | B |
| I-379 | B | B | A | B |
| I-380 | A | A | A | B |
| I-381 | B | A | A | B |
| I-382 | B | A | A | D |
| I-383 | A | A | A | B |
| I-384 | A | B | A | C |
| I-385 | A | A | A | D |
| I-386 | A | A | A | B |
| I-387 | A | A | A | C |
| I-388 | A | A | A | D |
| I-389 | A | A | A | D |
| I-390 | A | B | — | D |
| I-391 | A | A | — | C |
| I-392 | A | A | — | D |
| I-393 | A | A | — | D |
| I-394 | B | B | — | D |
| I-395 | B | B | — | D |
| I-396 | A | A | — | B |
| I-397 | — | — | — | D |
| I-421 | — | A | — | — |
| I-422 | — | D | — | — |
| I-423 | — | A | — | — |
| I-424 | — | B | — | — |
| I-425 | — | C | — | — |
| I-426 | — | B | — | — |
| I-427 | — | B | — | — |
| I-428 | — | A | — | — |
| I-429 | — | A | — | — |
| I-430 | — | B | — | — |
| I-431 | — | B | — | — |
| I-432 | — | A | — | — |
| I-434 | — | A | — | — |
| I-435 | — | A | — | — |
| I-436 | — | D | — | — |
| I-437 | — | B | — | — |
| I-438 | — | A | — | — |
| I-439 | — | A | — | — |
| I-440 | — | A | — | — |
| I-441 | — | A | — | — |
| I-442 | — | A | — | — |
| I-443 | — | D | — | — |
| I-444 | — | A | — | — |
| I-445 | — | B | — | — |
| I-446 | — | A | — | — |
| I-447 | — | A | — | — |
| I-448 | — | D | — | — |
| I-449 | — | D | — | — |
| I-450 | — | A | — | — |
| I-451 | — | B | — | — |
| I-452 | — | B | — | — |
| I-453 | — | A | — | — |
| I-454 | — | A | — | — |
| I-455 | — | B | — | — |
| I-456 | — | B | — | — |
| I-457 | — | B | — | — |
| I-458 | — | A | — | — |
| I-459 | — | A | — | — |
| I-460 | — | B | — | — |
| I-461 | — | A | — | — |
| I-462 | B | B | — | — |
| I-463 | — | A | — | — |
| I-464 | — | A | — | — |
| I-465 | — | A | — | — |
| I-466 | — | A | — | — |
| I-467 | A | A | A | — |
| I-468 | A | A | — | — |
| I-469 | D | D | — | — |
| I-470 | D | B | — | — |
| I-471 | A | A | A | — |
| I-472 | D | D | — | — |
| I-473 | A | B | A | — |
| I-474 | A | A | A | — |
| I-475 | D | D | C | — |

TABLE 4-continued

| Compound | KAT-5 IC$_{50}$ (μM) | KAT-6A IC$_{50}$ (μM) | KAT-7 IC$_{50}$ (μM) | KAT-8 IC$_{50}$ (μM) |
|---|---|---|---|---|
| I-476 | A | A | A | — |
| I-477 | A | B | — | — |
| I-478 | A | A | A | — |
| I-479 | A | A | A | — |
| I-480 | B | B | A | — |
| I-481 | A | A | A | — |
| I-482 | B | B | A | — |
| I-483 | A | A | A | — |

Table 5 shows the activity of selected compounds of this disclosure in KAT-5, KAT-6A, KAT-7, and KAT-8 inhibition assays. The compound numbers correspond to the compound numbers above. Compounds having an activity designated as "A" provided an IC of ≤10 μM; compounds having an activity designated as "B" provided an IC$_{50}$ of 10.01-50 μM; compounds having an activity designated as "C" provided an IC$_{50}$ of 50.01-100 μM; compounds having an activity designated as "D" provided an IC$_{50}$ of >100 μM; and compounds having an activity designated as "E" provided an IC$_{50}$ of ≤1 μM.

TABLE 5

| Compound | KAT-5 IC$_{50}$ (μM) | KAT-6A IC$_{50}$ (μM) | KAT-7 IC$_{50}$ (μM) |
|---|---|---|---|
| A-1 | — | B | — |
| A-2 | — | D | — |
| A-3 | — | D | — |
| A-4 | — | A | — |
| A-5 | — | B | — |
| A-6 | — | D | — |
| A-7 | — | D | — |
| A-8 | — | D | — |
| A-9 | — | D | — |
| A-10 | — | D | — |
| A-11 | A | A | — |
| A-12 | B | B | A |
| A-13 | D | D | B |
| A-14 | D | D | B |
| A-15 | D | D | A |
| A-16 | A | E | E |
| A-17 | D | B | A |
| A-18 | D | D | — |
| A-19 | B | C | A |
| A-20 | D | D | B |
| A-21 | D | D | A |
| A-22 | B | B | E |
| A-23 | D | D | E |
| A-24 | C | B | A |
| A-25 | D | D | B |
| A-26 | D | D | D |
| A-27 | D | D | D |
| A-28 | E | E | E |
| A-29 | A | E | E |
| A-30 | A | E | A |
| A-31 | E | E | E |
| A-32 | D | D | B |

Table 6 provides data for certain comparative compounds A-D, in particular, the biochemical assay data for KAT-5, KAT-6A, KAT-7, and KAT-8 inhibition assays. Compounds having an activity designated as "A" provided an IC$_{50}$ of ≤10 μM; compounds having an activity designated as "B" provided an IC$_{50}$ 10.01-50 μM; compounds having an activity designated as "C" provided an IC$_{50}$ of 50.01-100 μM; and compounds having an activity designated as "D" provided an IC$_{50}$ of >100 μM.

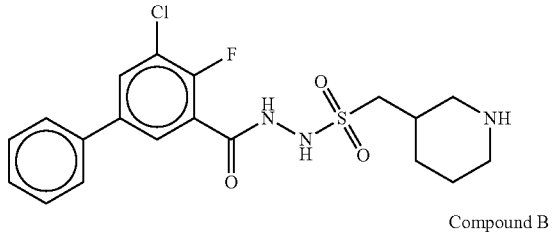

Compound A

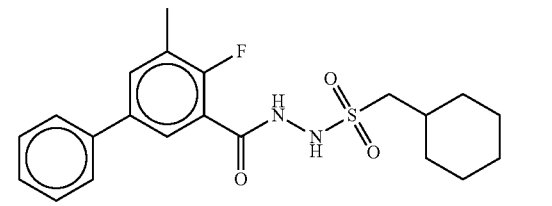

Compound B

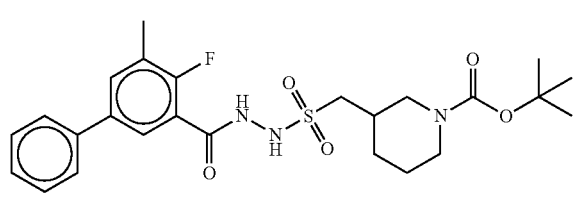

Compound C

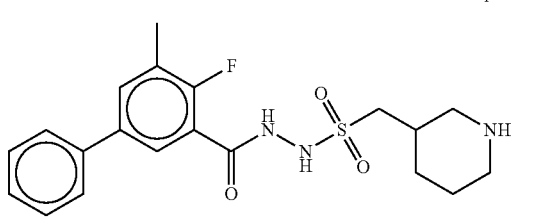

Compound D

TABLE 6

| Compound Name | KAT-5 IC$_{50}$ (μM) | KAT-6A IC$_{50}$ (μM) | KAT-7 IC$_{50}$ (μM) | KAT-8 IC$_{50}$ (μM) |
|---|---|---|---|---|
| A | B | B | C | D |
| B | A | A | A | C |
| C | A | A | B | D |
| D | B | D | D | D |

Cellular Assays

Inhibition of acetylation of H3K23 in Human cell line CAL-120. Cell line CAL-120 was plated in eleven 10 cm tissue culture dishes at a cell density of 4×10$^5$ cells/cm$^2$ and treated with ten 2-fold serial dilutions of compound A-30 starting at 10 μM and one dish with DMSO (vehicle control) for 3 hours. Cells were tripsinized, washed twice with ice cold PBS and snap-frozen. Histones were extracted from cell pellets. Protein concentration was assessed and 60 ng of protein sample from histone extraction was prepared in triplicate in 100 μl coating buffer (0.05% w/v BSA in PBS) and added directly to high binding 96 well plates. Plates were left at 4° C. overnight to allow protein to adhere. Coating buffer with histones was discarded and plates blotted, and 100 μL per well of primary antibody solution of rabbit anti-H3K23ac antibody (Millipore 07-355) (1:600) and mouse anti-total H3 antibody (CST-14269) (1:500) in Odyssey buffer with 0.1% Tween 20 (v/v) was added to the wells of the plate and incubated for 1 hour. Plates were transferred to a Biotek plate washer and washed 3 times with 100 µL per well of wash buffer (1×PBS with 0.05% Tween 20 (v/v)). Next 100 µL per well of secondary antibody solution were added. The secondary antibody solution consisted of a 1:100 dilution of goat-Anti-rabbit IgG (H+L) Alexa Fluor 680 (Life Technologies catalog A21076; Lot: 1655809) and 1:1000 dilution of Donkey anti-mouse IgG (H+L) IRDye 800CW (Odyssey Catalog 926-32212) in Odyssey buffer with 0.1% Tween 20 (v/v) and incubated for 1 hour in the dark at room temperature. The plates were washed 3 times with 100 µL per well wash buffer (1×PBS with 0.05% Tween 20 (v/v)) and then filled with 100 µL per well of 1×PBS. Plates were imaged on the Licor Odyssey instrument which measures integrated intensity at 680 nm and 800 nm wavelength. Both 680 nm and 800 nm channels were scanned.

Calculations were performed as follows: First, the ratio for each well was determined by:

$$\left(\frac{\text{anti} - \text{histone } H3K23 \text{ Acetyl 700 nm value}}{\text{anti} - \text{histone total } H3 \text{ 800 nm value}}\right)$$

Then, the average of the ratio values for each test well was calculated and used to determine the percent of H3K23Ac from vehicle for each test well in the plate:

$$\text{Percent of } H3K23Ac \text{ from vehicle} = \left(\left(\frac{\text{(Individual Test Sample Ratio)}}{\text{(Minimum Inhibition Ratio)}}\right) * 100\right)$$

Lastly, dose response curves were plotted as percent of control vs log of concentration, and relative $IC_{50}$ values were generated using triplicate wells per concentration of compound with the Graphpad Prism software. FIG. 1 depicts a representative inhibition of acetylation of H3 K23 cells by compound A-30 in the CAL-120 cell line.

Long term proliferation assay. A panel of multiple myeloma (MM) and acute myeloid leukemia (AML) cell lines were tested in 14-day proliferation assays. Exponentially growing cells were plated, in triplicate, in 96-well plates at the appropriate cell density in a final volume of 150 µL. Cells were incubated in the presence of increasing concentrations of compound A-30. Viable cell number was determined at 0, 4, 7, 11, and 14 days using Calcein staining and using an Accumen instrument to enumerate the number of cells. On days of cell counts, growth media and compound A-30 were replaced, and cells split back to initial density. Total cell number is expressed as split-adjusted viable cells per well.

Calculations were performed as follows:
First, the inhibition of proliferation was calculated for each well at each treatment concentration at each timepoint with the following formula:

$$\text{Percent Inhibition} = 100 - \left(\left(\frac{\text{(Individual Test Sample viable cells per well)}}{\text{(DMSO viable cells per well)}}\right) * 100\right)$$

Then, for each cell line, concentration response curves were plotted as average and standard deviation from triplicate determinations as percent inhibition vs log of concentration of compound A-30. Absolute $IC_{50}$ values (concentration of compound at which 50% inhibition occurs) were determined from the curve at each timepoint using Graphpad Prism software. Results for the 14-day timepoint are shown in Table 7. An $IC_{50}$ value of ≤10 µM is designated as "A"; an $IC_{50}$ value of >10 µM is designated as "B".

TABLE 7

| Cell line | Indication | $IC_{50}$ (µM) |
|---|---|---|
| KMS34 | MM | A |
| RPMI8226 | MM | A |
| NOMO1 | AML | A |
| OCIAML3 | AML | A |
| KMS11 | MM | A |
| LP1 | MM | A |
| OCIAML2 | AML | B |
| MOLM13 | AML | B |
| SEM | AML | B |
| THP1 | AML | B |

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

Acetyl Transferases

Histone acetylation and deacetylation are processes by which lysine residues within the N-terminal tail protruding from histone cores of the nucleosome are acetylated and deacetylated. Without wishing to be bound by any particular theory, it is believed that histone acetylation is a part of gene regulation. Histone Acetyltransferases, also known as HATs, are a family of enzymes that acetylate the histone tails of the nucleosome among other nuclear and cytoplasmic non-histone targets. Some HATs acetylate a lysine residue, and such Lysine Acetyltransferases are also referred to as KATs.

KATs can be divided into families based on their structure and sequence similarity. KAT families include, for example, the Gcn5-related N-acetyltransferase (GNAT) family, which includes GCN5 and PCAF, the CREBBP/EP300 family and the MYST (MOZ, Ybf2/Sas3, Sas2, Tip60) family. The MYST family of HATs is named after its four founding members MOZ, Ybf2 (Sas3), Sas2, and Tip60. Other members include Esa1, MOF, MORF, and HBO1. Members of the MYST family are characterized by the presence of the MYST catalytic domain, and have been reported to acetylate lysine residues on histones, e.g., on histone 2A (H2A), histone 3 (H3), and histone 4 (H4). Lysine acetyltransferases are also referred to as KATs, and members of the MYST family of histone acetyltransferases include, for example, KAT-5 (also sometimes referred to as Tip60), KAT-6A (also sometimes referred to as MOZ, MYST3, RUNXBP2, or ZNF220), KAT-6B (also sometimes referred to as MORF, MYST4, or MOZ2), KAT-7 (also sometimes referred to as (HBO1, HBOa, or MYST2), and KAT-8 (also sometimes referred to as MOF, YBF2, SAS3, or MYST1).

We claim:
1. A compound of formula I':
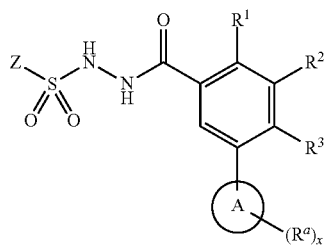
or a pharmaceutically acceptable salt thereof, wherein:
Z is selected from
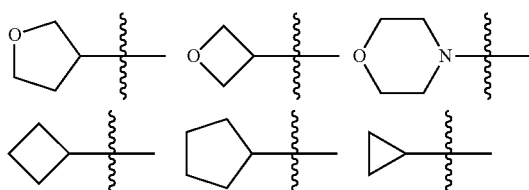
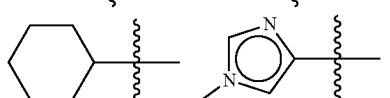
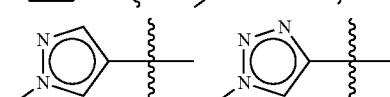
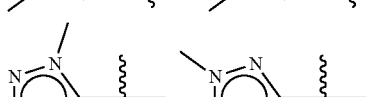
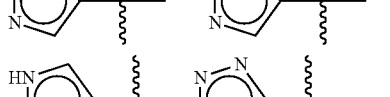
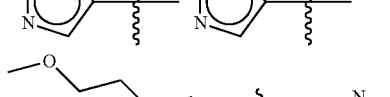
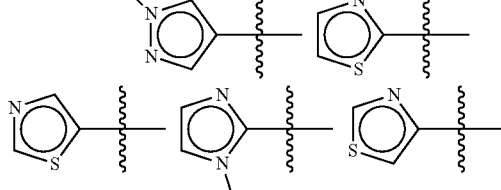
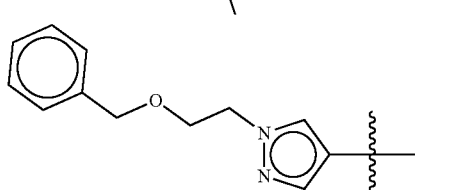
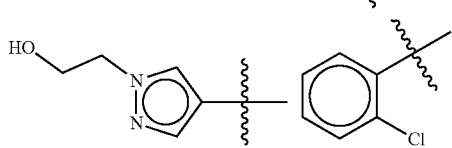
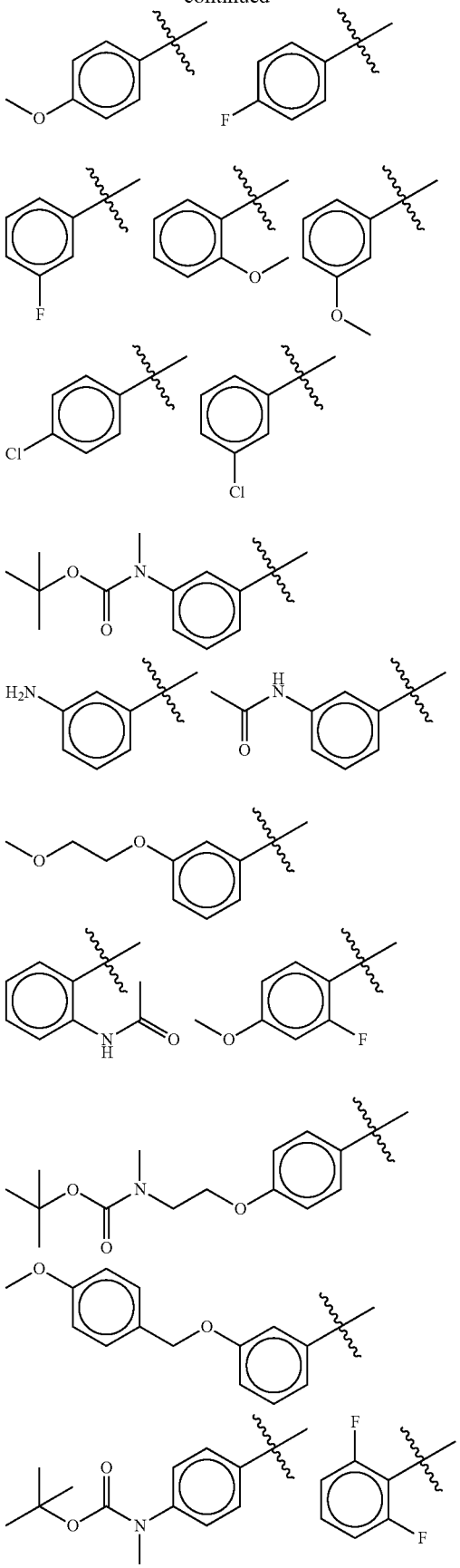

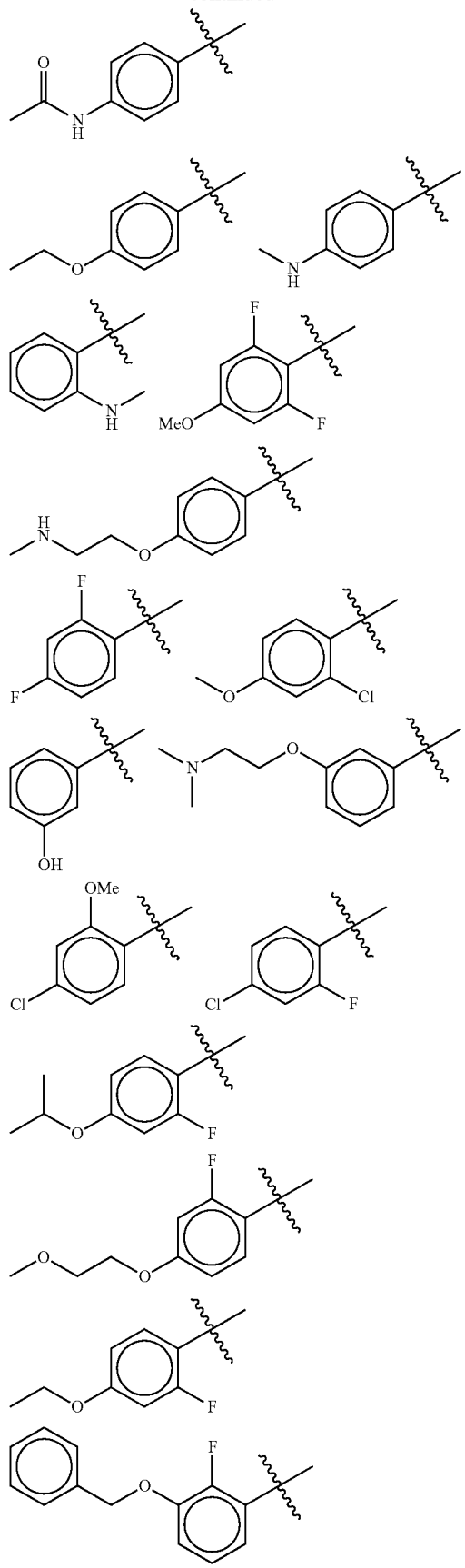
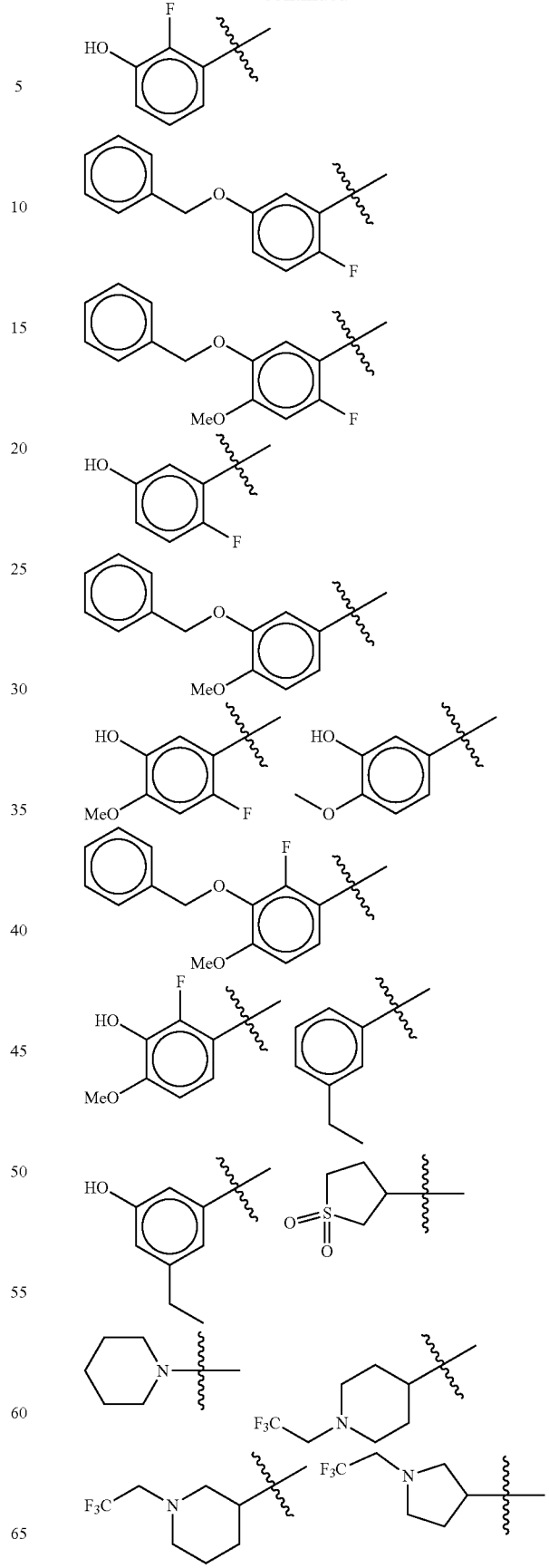

403
-continued
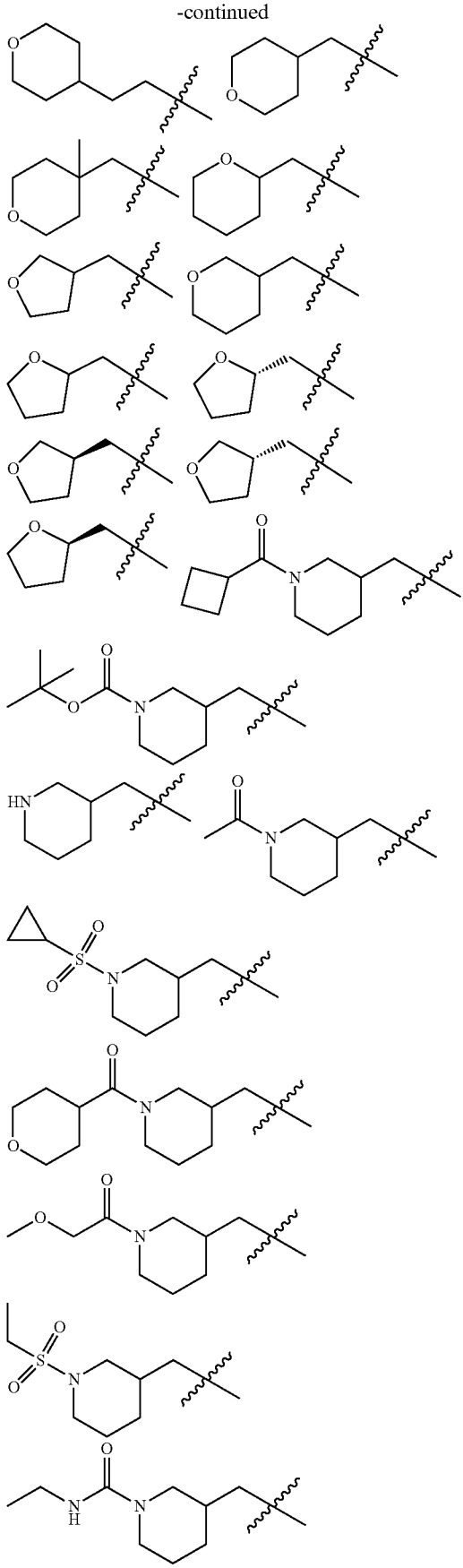
404
-continued
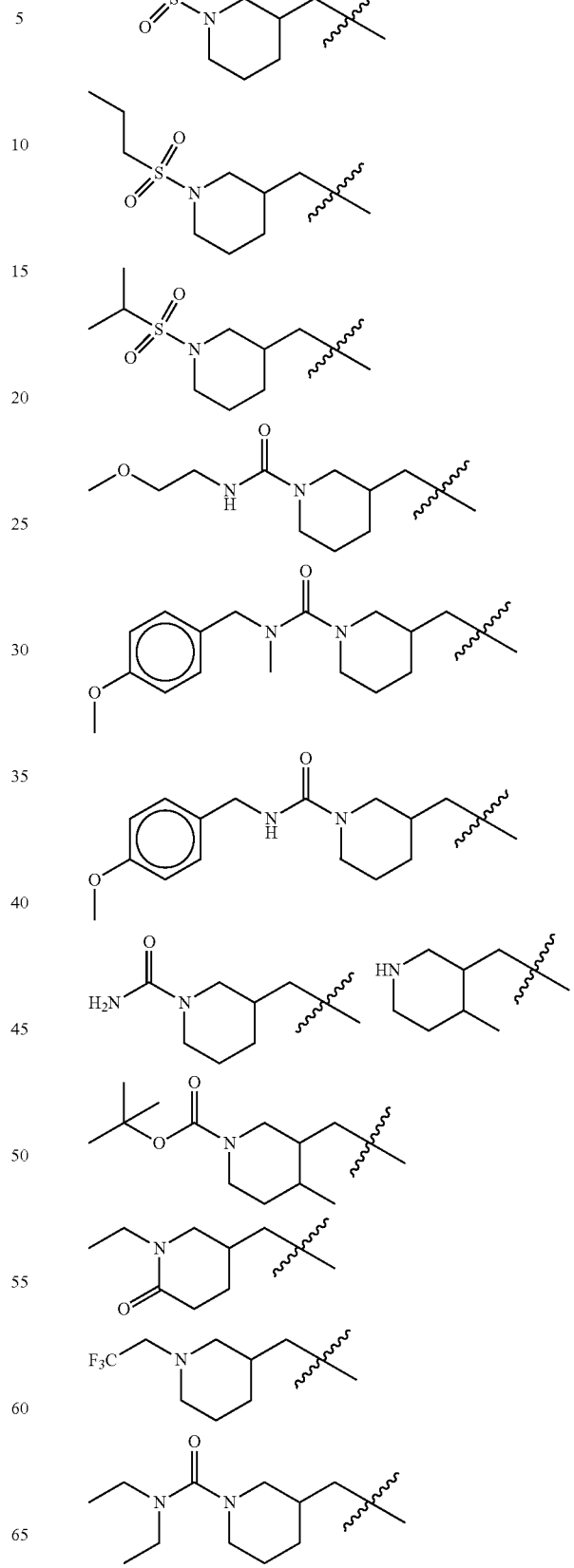

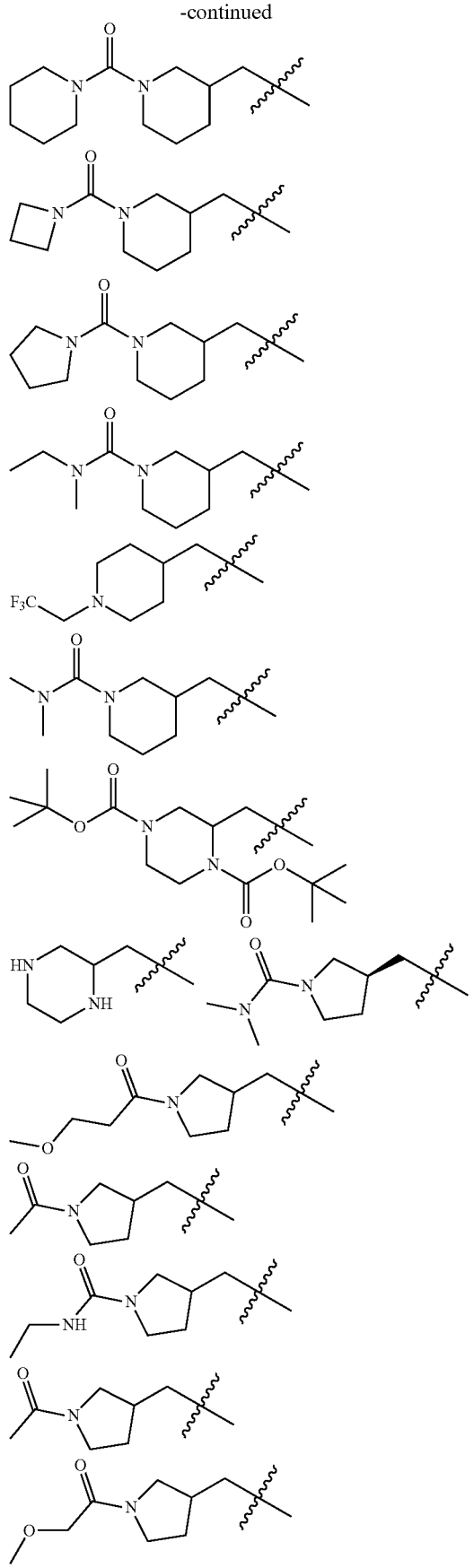
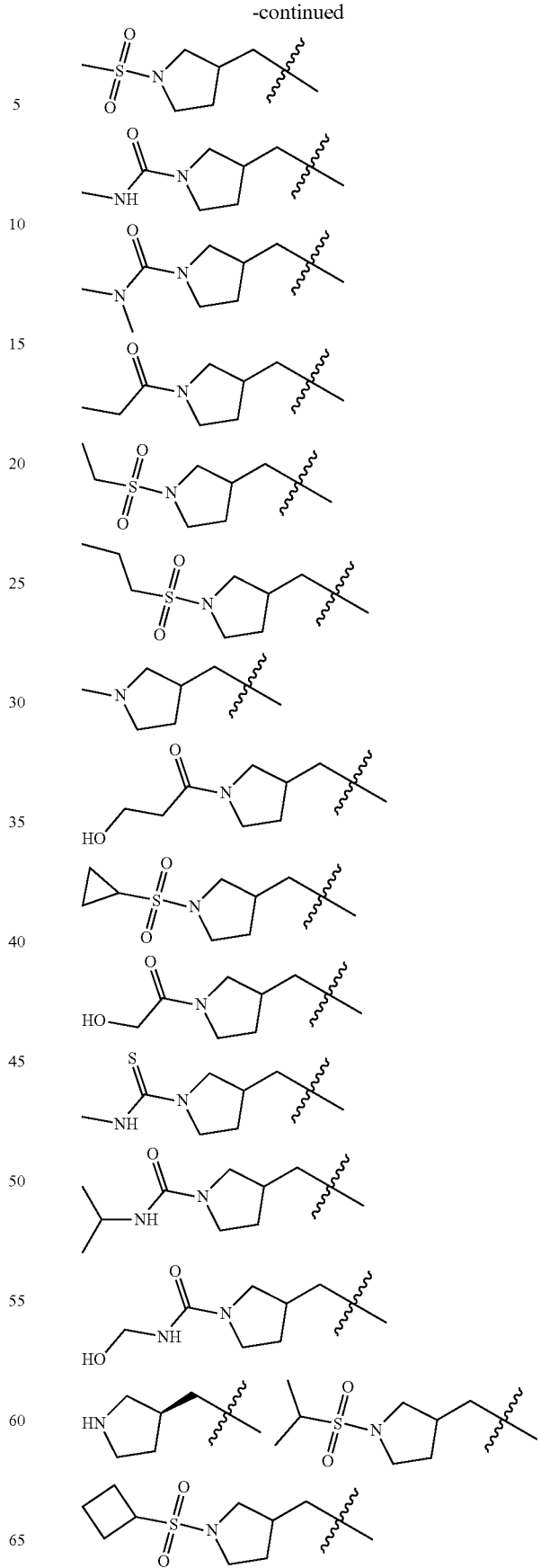

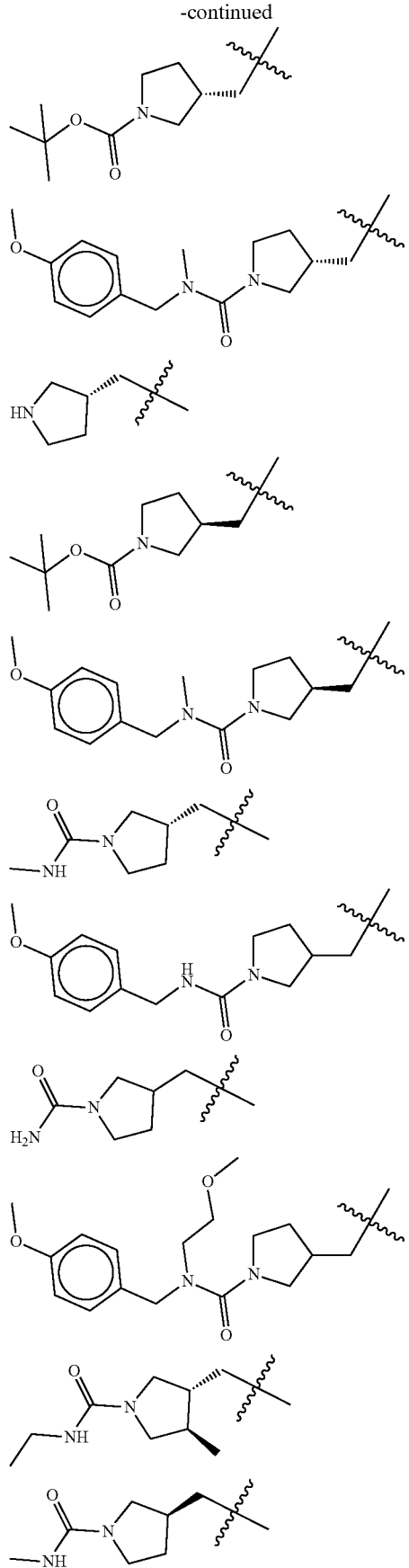
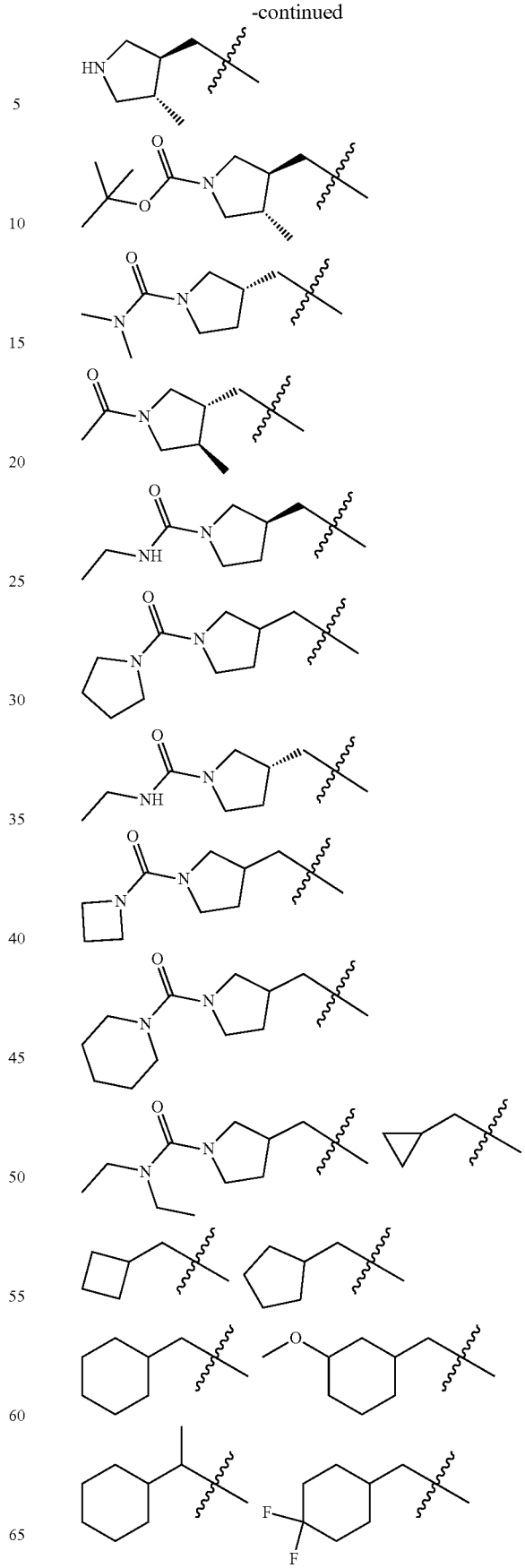

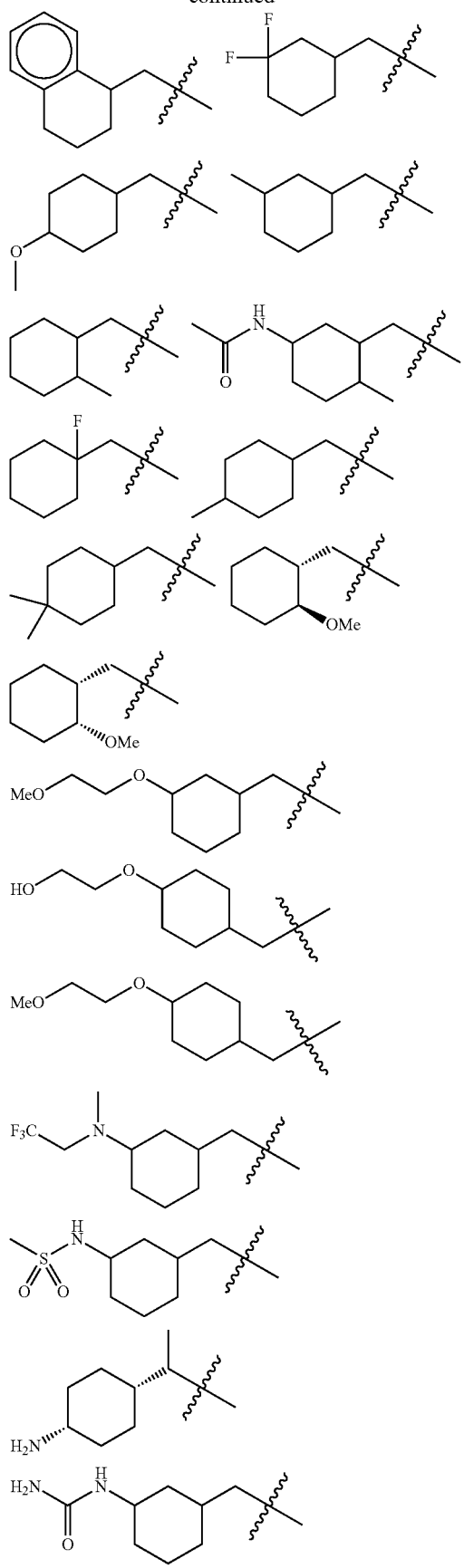
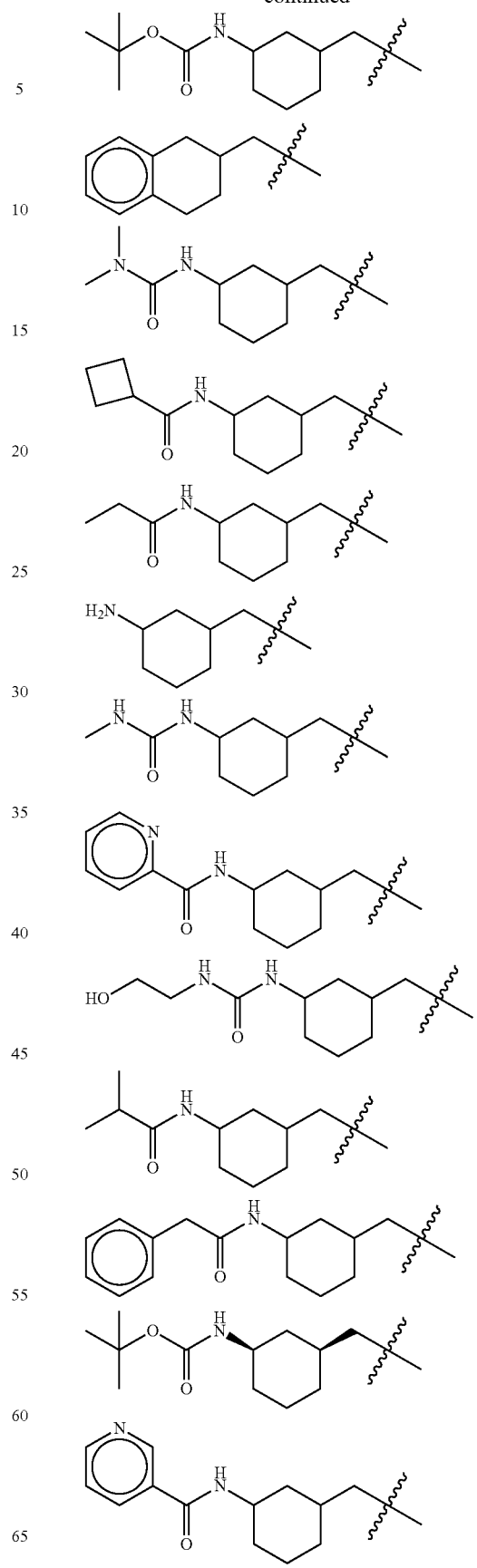

411
-continued
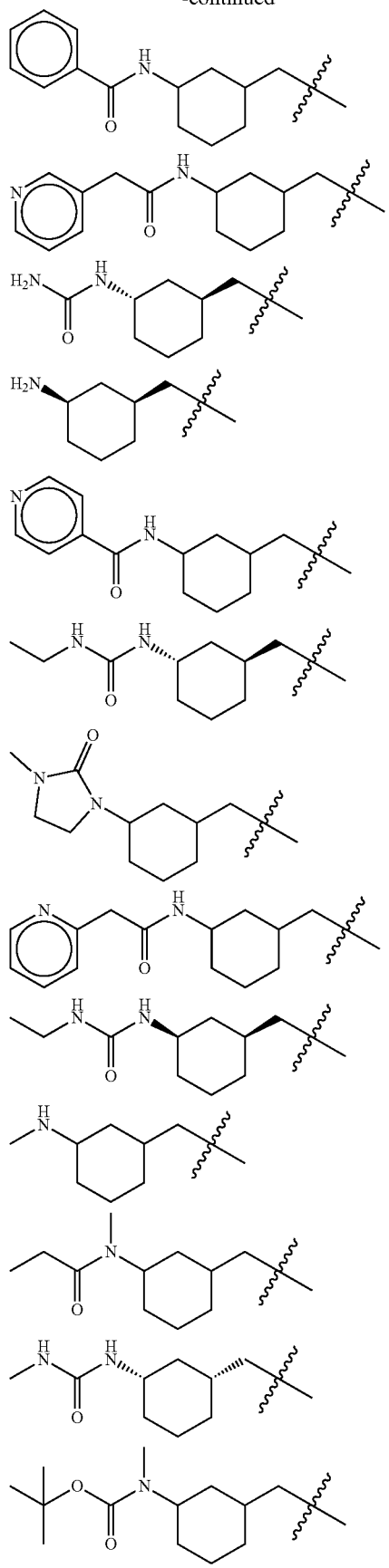
412
-continued
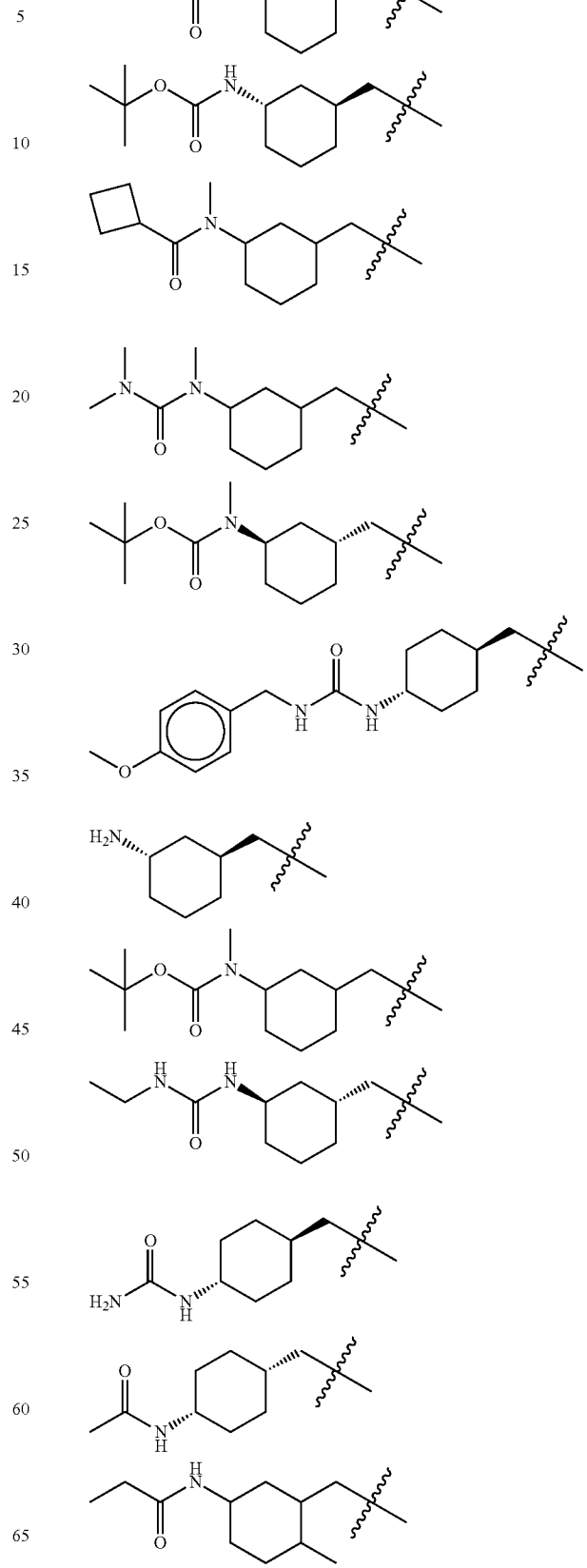

413
-continued
414
-continued
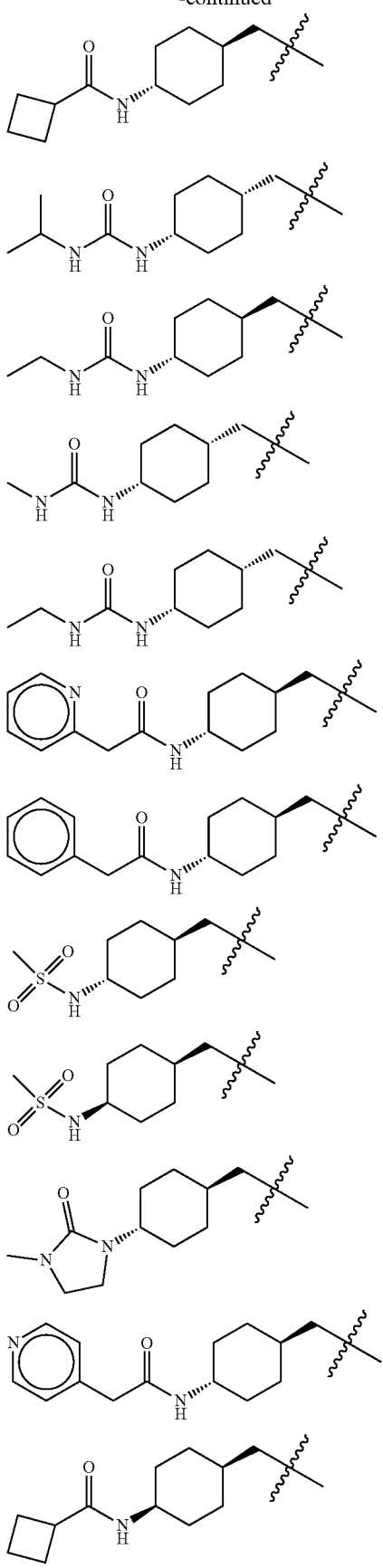
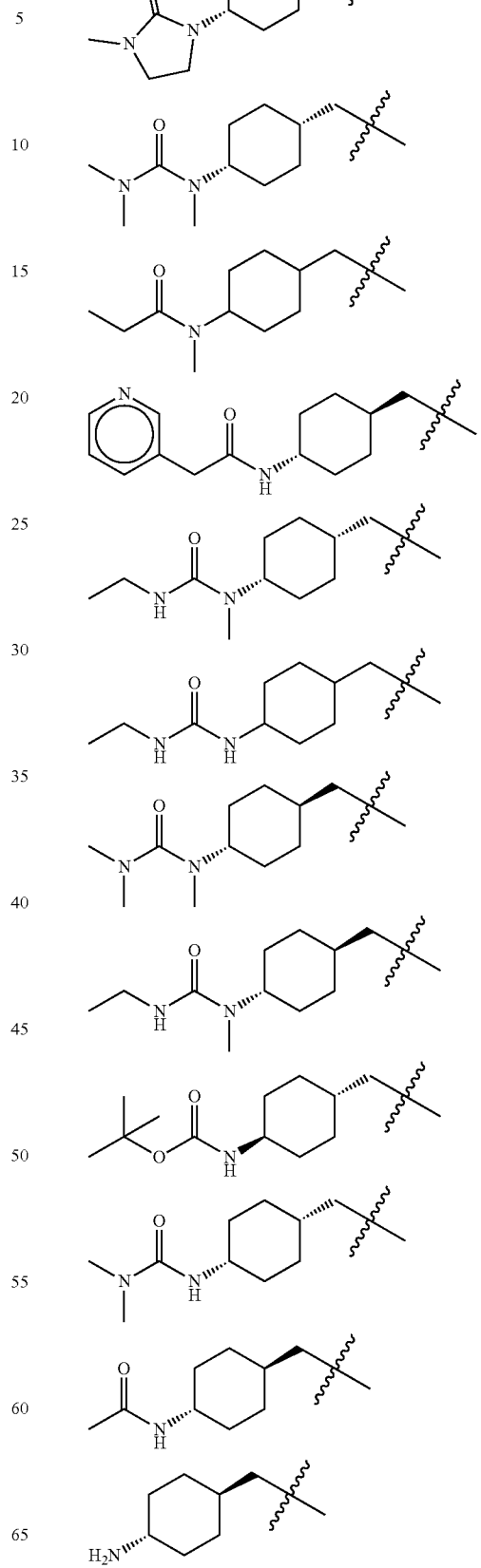

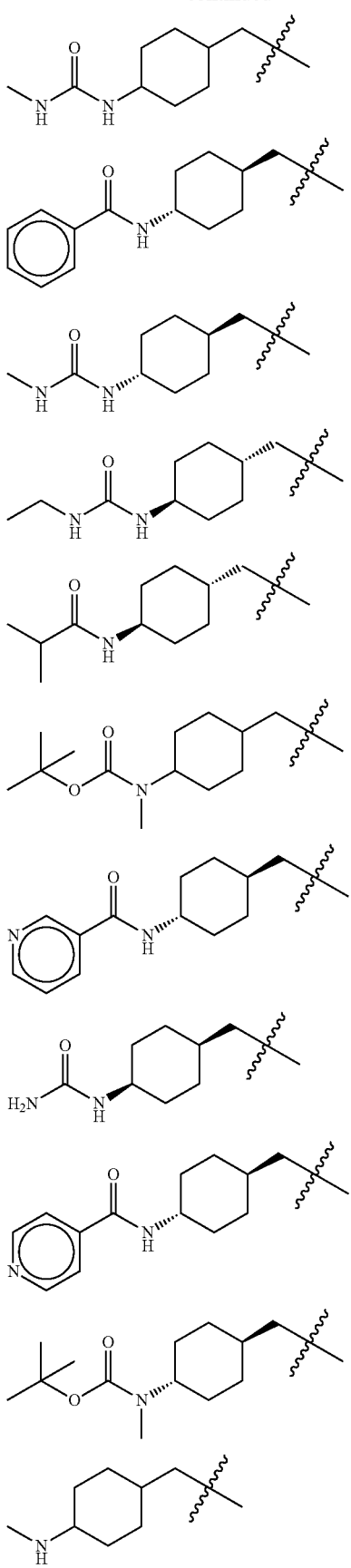
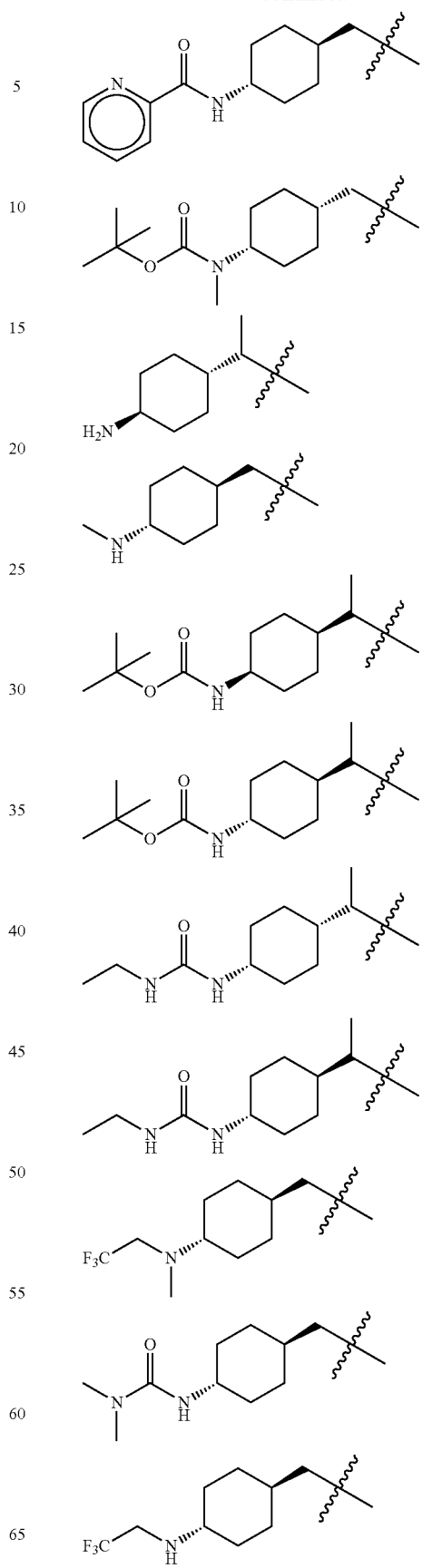

417
-continued
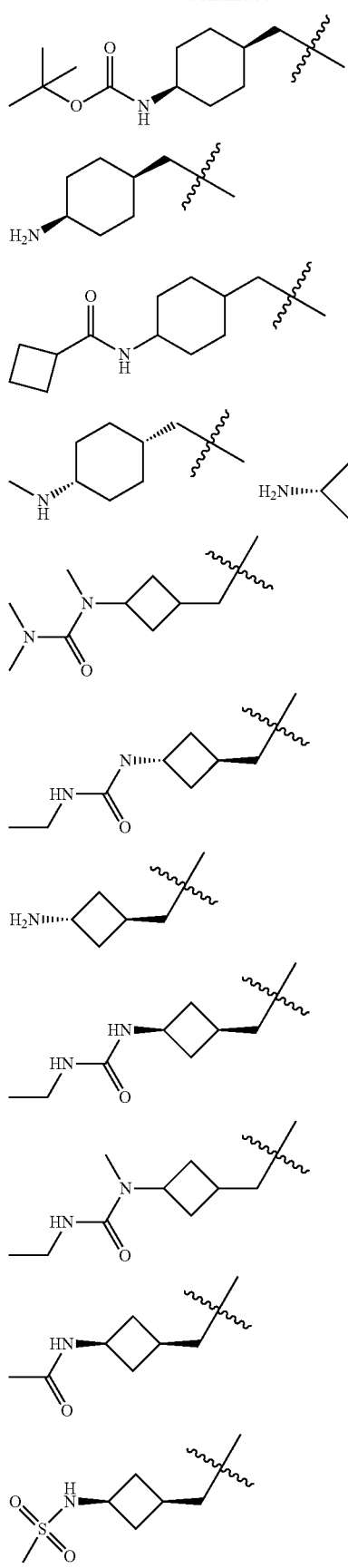
418
-continued
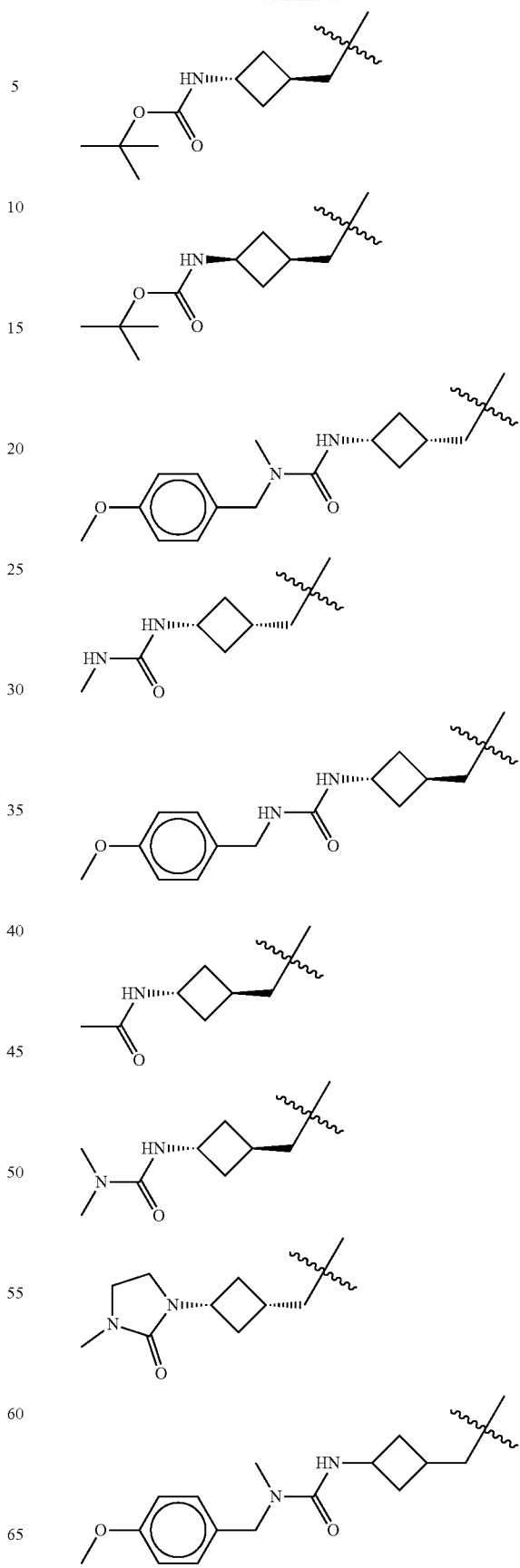

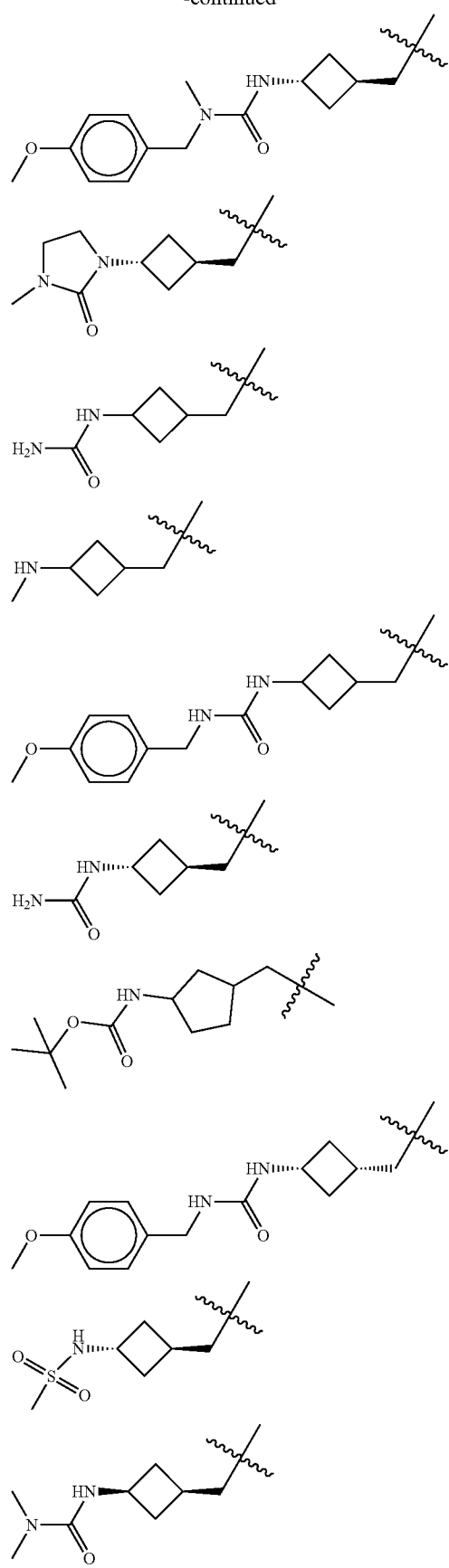
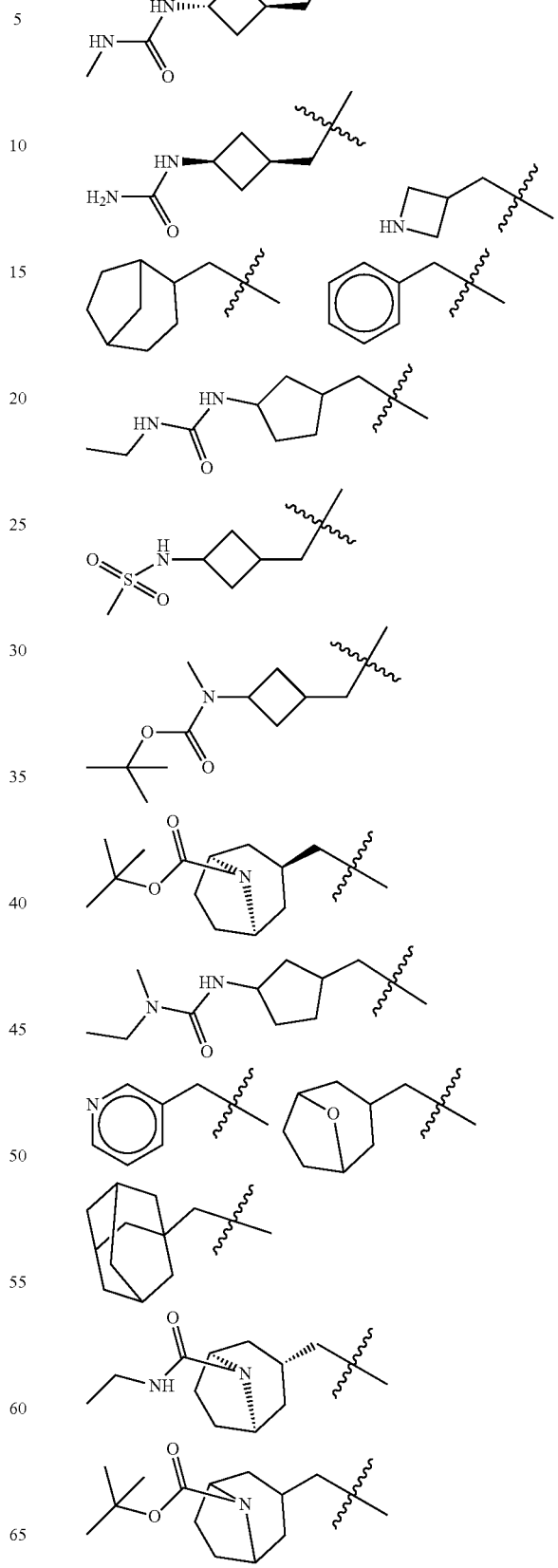

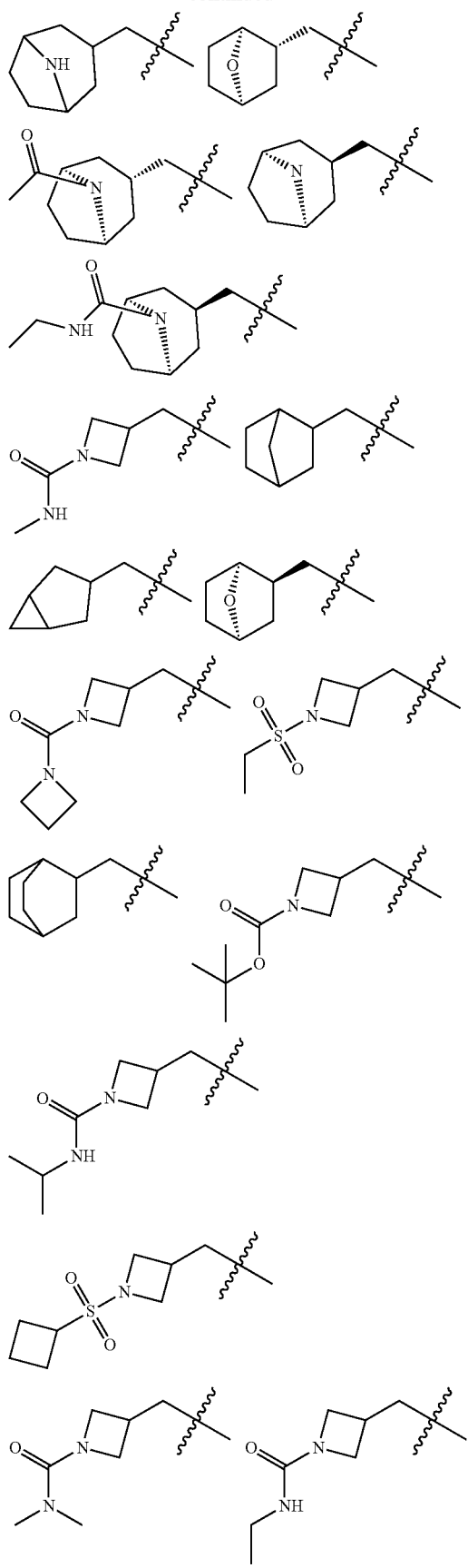
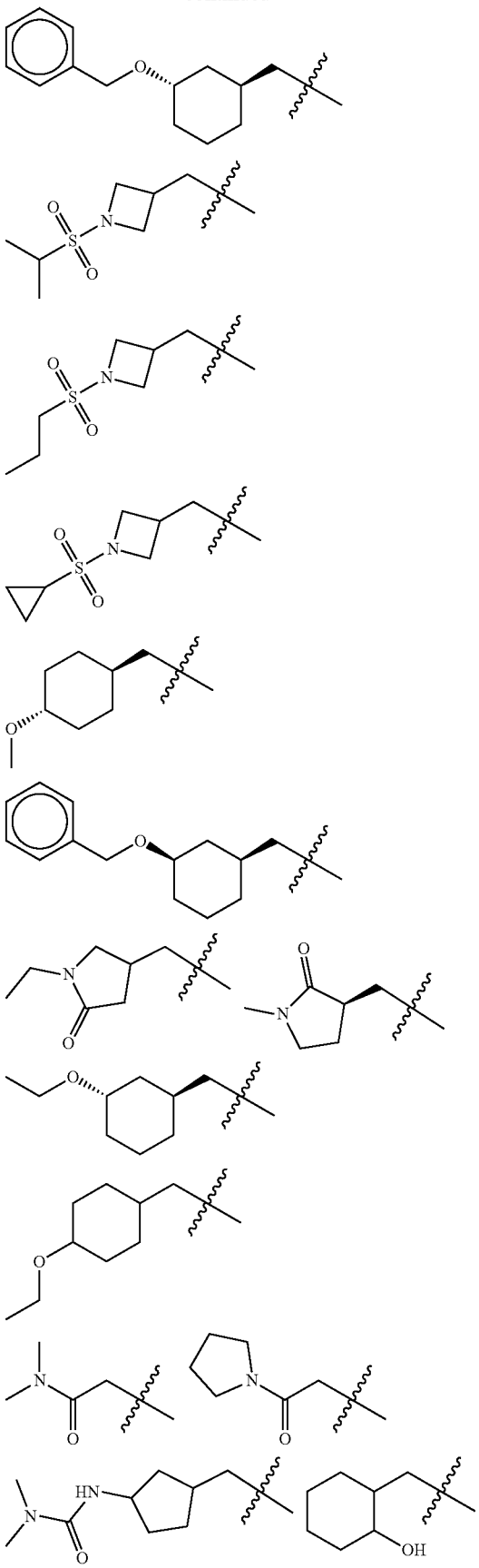

423
-continued

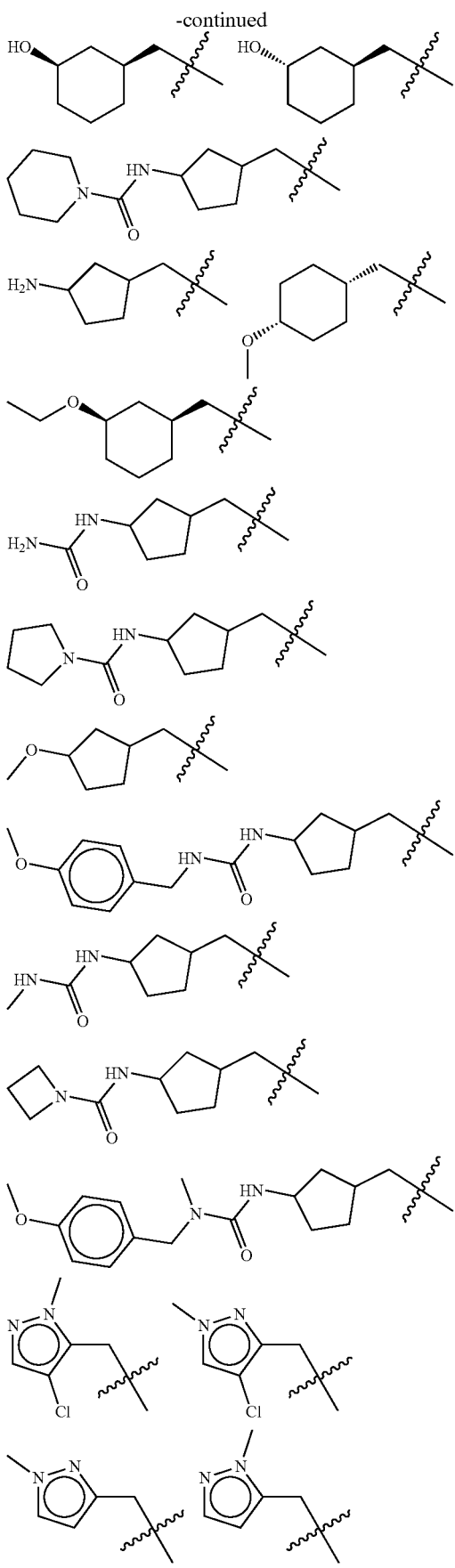

424
-continued

;

each of $R^1$ and $R^2$ is independently selected from halogen and $C_{1-4}$ aliphatic;
$R^3$ is selected from hydrogen, halogen, —CN, —$NR_2$, and optionally substituted $C_{1-4}$ aliphatic;
each R is independently selected from hydrogen, optionally substituted $C_{1-4}$ aliphatic, and —C(O)O($C_{1-4}$ aliphatic);
Ring A is an optionally substituted 5- or 6-membered heteroaryl ring having 1-4 heteroatoms independently selected from nitrogen, oxygen and sulfur;
each $R^a$ is selected from halogen and optionally substituted $C_{1-4}$ aliphatic; and
x is 0-3;
wherein optional substituents are independently selected from monovalent and divalent substituents,
each optional monovalent substituent on a substitutable carbon atom is independently selected from halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, optionally substituted with R°; —$(CH_2)_{0-4}O(CH_2)_{0-1}Ph$ optionally substituted with R°; —CH=CHPh optionally substituted with R°; —$(CH_2)_{0-4}O(CH_2)_{0-1}$-pyridyl optionally substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$; —$(CH_2)_{0-4}SC(O)R°$; —$(CH_2)_{0-4}C(O)NR°_2$; —C(S)NR°_2$; —C(S)SR°; —SC(S)SR°, —$(CH_2)_{0-4}OC(O)NR°_2$; —C(O)N(OR°)R°; —C(O)C(O)R°; —C(O)$CH_2$C(O)R°; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —S(O)$NR°_2$; —$(CH_2)_{0-4}S(O)R°$; —$N(R°)S(O)_2NR°_2$; —$N(R°)S(O)_2R°$; —N(OR°)R°; —C(NH)NR°_2$; —$P(O)_2R°$; —$P(O)R°_2$; —OP(O)$R°_2$; —OP(O)(OR°)_2$; $SiR°_3$; —($C_{1-4}$ straight or branched alkylene)O—N(R°)_2$; or —($C_{1-4}$ straight or branched alkylene)C(O)O—N(R°)_2$;
wherein each R° is optionally substituted and is independently hydrogen, $C_{1-6}$ aliphatic, —$CH_2$Ph, —$O(CH_2)_{0-1}$Ph, —$CH_2$-(5-6 membered heteroaryl ring), or a 3-6-membered saturated, partially unsaturated, or aryl ring having 0-4 heteroatoms independently selected from nitrogen, oxygen, or sulfur;
or two independent occurrences of R° are taken together with their intervening atom(s) form an optionally substituted 3- to 12-membered saturated, partially unsaturated, or aryl mono- or bicyclic ring having 0-4 heteroatoms independently selected from nitrogen, oxygen, or sulfur;
wherein each optional monovalent substituent bound to R° is independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$, —O(haloR$^\bullet$), —CN, —$N_3$, —$(CH_2)_{0-2}C(O)R^\bullet$, —$(CH_2)_{0-2}C(O)OH$, —(CH$_2$)$_{0-2}$C(O)OR$^{\bullet}$, —(CH$_2$)$_{0-2}$SR$^{\bullet}$, —(CH$_2$)$_{0-2}$SH, —(CH$_2$)$_{0-2}$NH$_2$, —(CH$_2$)$_{0-2}$NHR$^{\bullet}$, —(CH$_2$)0-2NR$^{\bullet}$$_2$, —NO$_2$, —SiR$^{\bullet}$$_3$, —OSiR$^{\bullet}$$_3$, —C(O)SR$^{\bullet}$, —(C$_{1-4}$ straight or branched alkylene)C(O)OR$^{\bullet}$, —SSR$^{\bullet}$, or -Ph optionally substituted with R$^{\bullet}$;

wherein each R$^{\bullet}$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur, =O, or =S;

wherein each optional divalent substituent on a saturated carbon atom is =O, =S, =NNR*2, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, or wherein a divalent substituent —O(CR*$_2$)$_{2-3}$O— is bound to vicinal substitutable carbons;

wherein each occurrence of R* is independently selected from hydrogen, optionally substituted C$_{1-6}$ aliphatic, or an unsubstituted 5- to 6-membered saturated, partially unsaturated, or aryl ring having 0-4 heteroatoms independently selected from nitrogen, oxygen, or sulfur;

wherein each occurrence of R* is optionally substituted with halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$$_2$, or —NO$_2$;

wherein each R$^{\bullet}$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur;

wherein each optional substituent on a substitutable nitrogen atom is independently —R$^{\dagger}$, —NR$^{\dagger}$$_2$, —C(O)R$^{\dagger}$, —C(O)OR$^{\dagger}$, —C(O)NR$^{\dagger}$$_2$, —C(O)C(O)R$^{\dagger}$, —C(O)CH$_2$C(O)R$^{\dagger}$, —S(O)$_2$R$^{\dagger}$, —S(O)$_2$NR$^{\dagger}$$_2$, —C(S)NR$^{\dagger}$$_2$, —C(NH)NR$^{\dagger}$$_2$, or —N(R$^{\dagger}$)S(O)$_2$R$^{\dagger}$;

wherein each R$^{\dagger}$ is independently hydrogen, optionally substituted C$_{1-6}$ aliphatic, unsubstituted —OPh, or an unsubstituted 5- to 6-membered saturated, partially unsaturated, or aryl ring having 0-4 heteroatoms independently selected from nitrogen, oxygen, or sulfur, or, two independent occurrences of R$^{\dagger}$ are taken together with their intervening atom(s) to form an unsubstituted 3- to 12-membered saturated, partially unsaturated, or aryl mono- or bicyclic ring having 0-4 heteroatoms independently selected from nitrogen, oxygen, or sulfur;

wherein each optional substituent on R$^{\dagger}$ is independently halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$, or —NO$_2$, wherein each R$^{\bullet}$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

2. The compound claim 1, wherein Ring A is an optionally substituted 5-membered heteroaryl ring.

3. The compound or pharmaceutically acceptable salt of claim 1, wherein Ring A is selected from

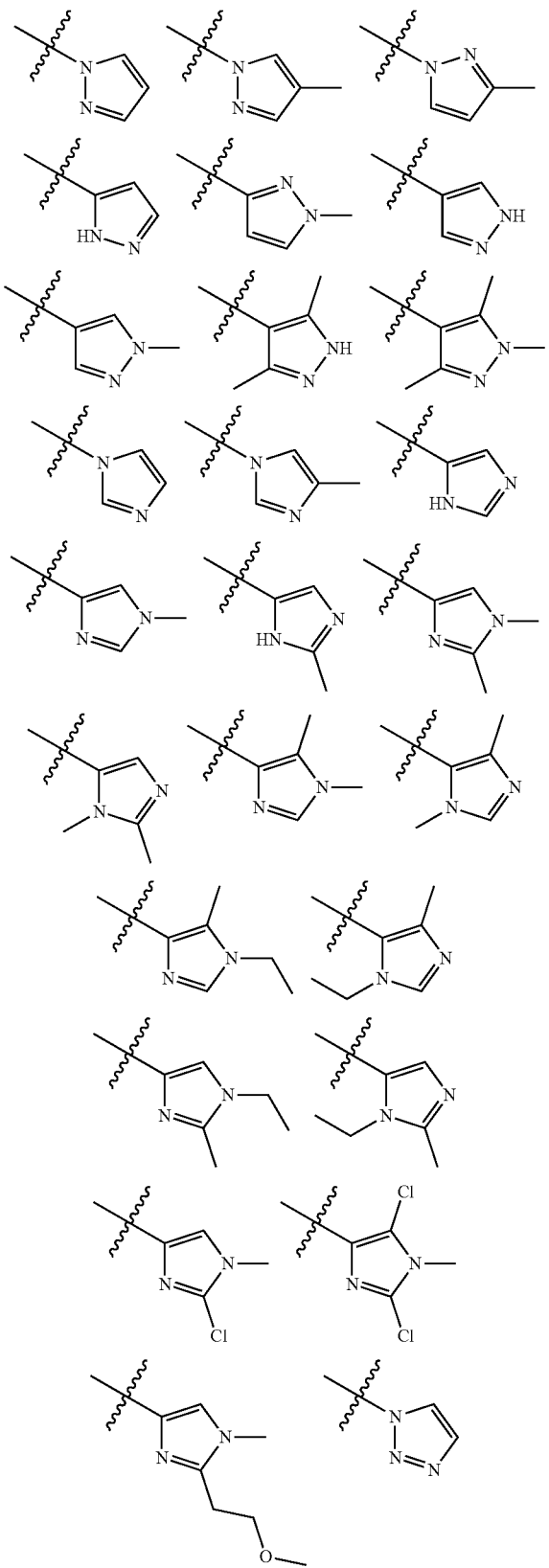

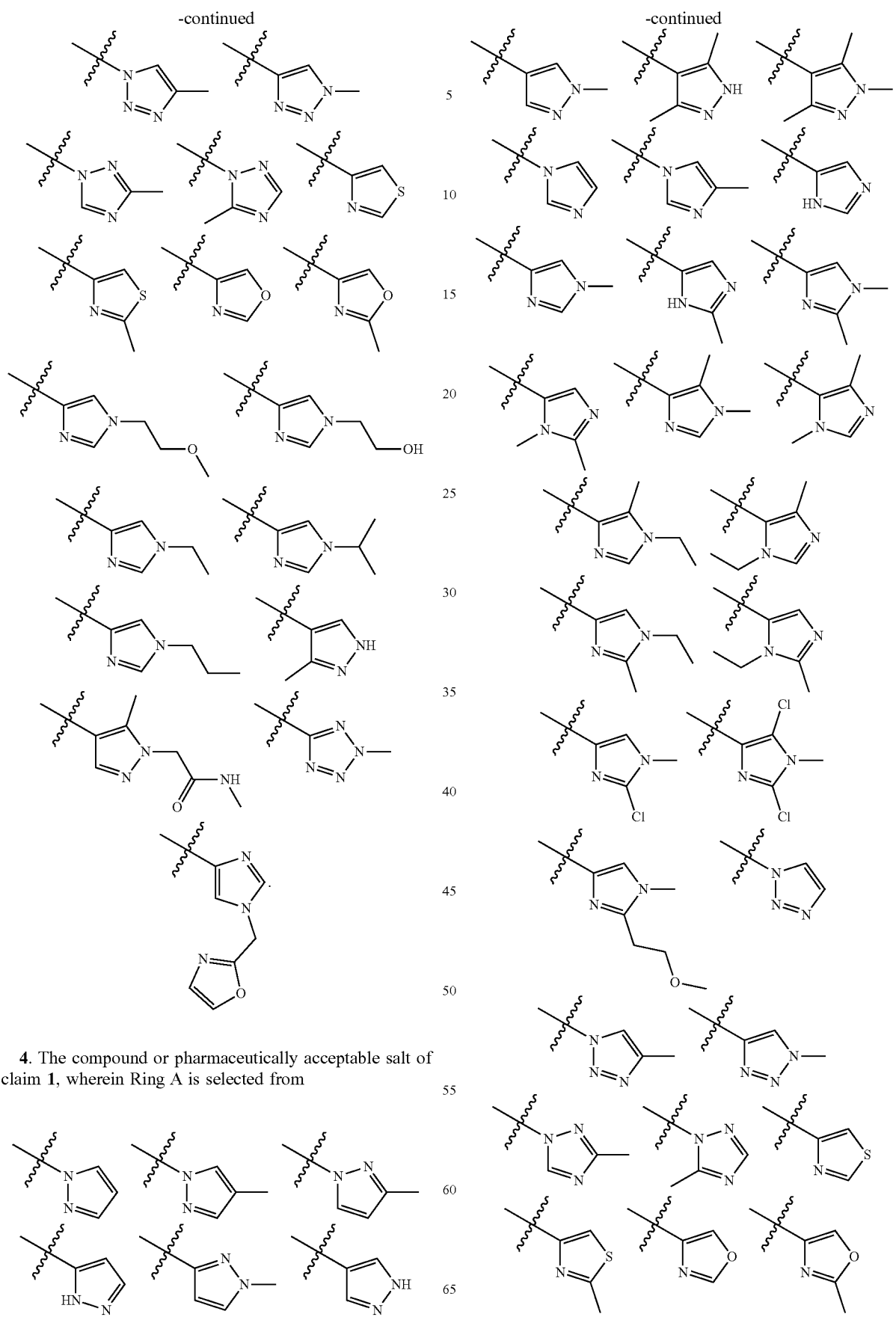
4. The compound or pharmaceutically acceptable salt of claim 1, wherein Ring A is selected from

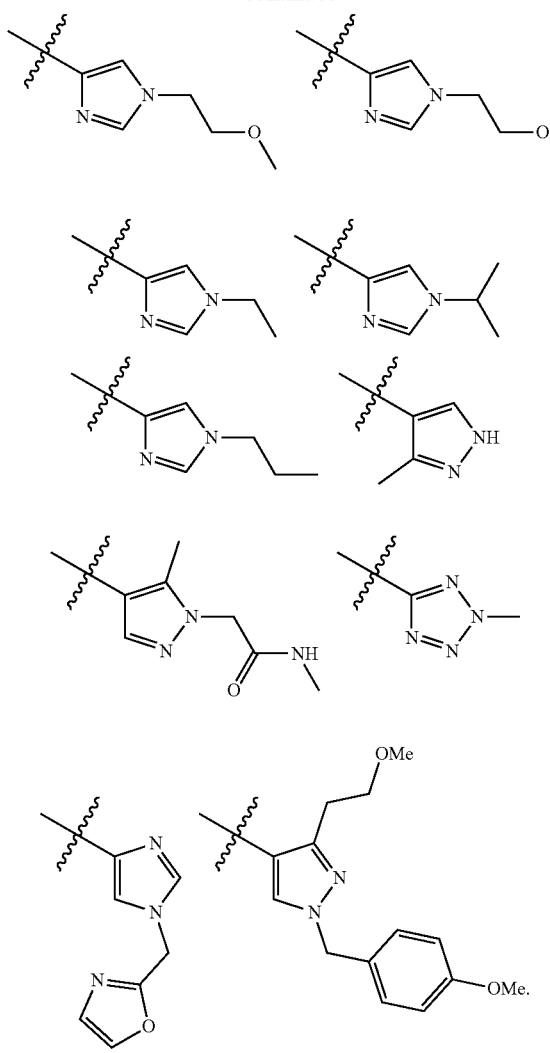

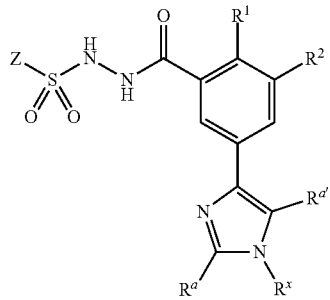

or a pharmaceutically acceptable salt thereof, wherein:
each of $R^1$ and $R^2$ is independently selected from halogen and $C_{1-4}$ aliphatic;
$R^x$ is optionally substituted $C_{1-4}$ aliphatic; and
each of $R^a$ and $R^{a'}$ is independently selected from hydrogen, halogen and optionally substituted $C_{1-4}$ aliphatic.

6. The compound of claim 1, wherein the compound is of formula III:

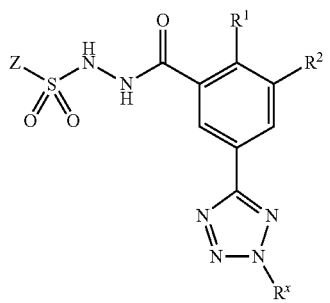

or a pharmaceutically acceptable salt thereof, wherein:
each of $R^1$ and $R^2$ is independently selected from halogen and $C_{1-4}$ aliphatic; and
$R^x$ is optionally substituted $C_{1-4}$ aliphatic.

7. The compound or pharmaceutically acceptable salt of claim 1, wherein the compound is selected from:

5. The compound of claim 1, wherein the compound is of formula II:

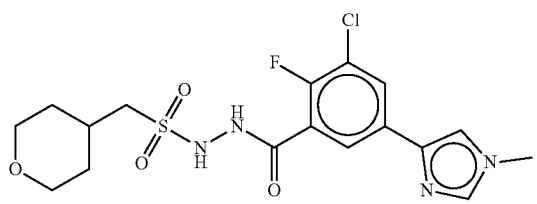

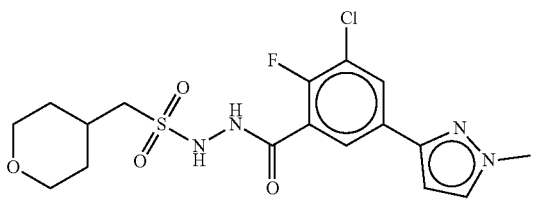

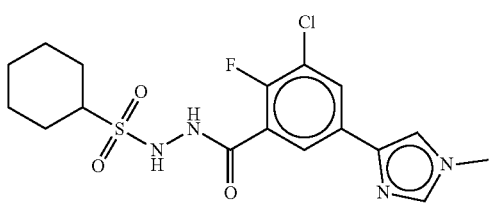

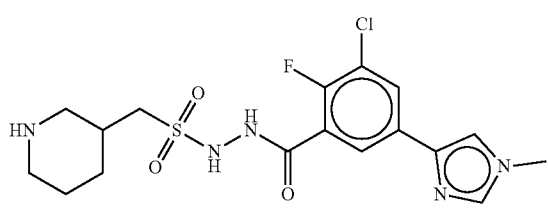

-continued
I-3
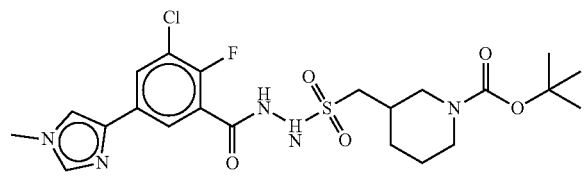
I-8
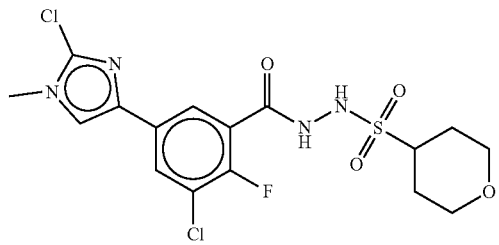
I-4
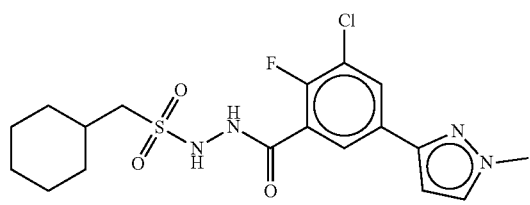
I-9
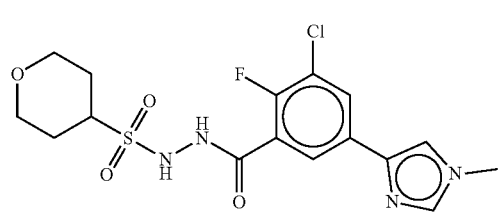
I-5
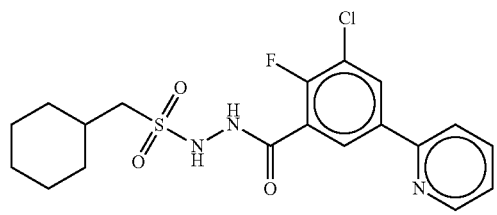
I-10
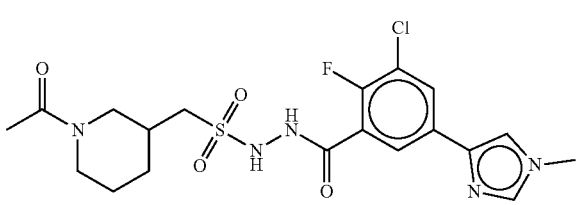
I-11
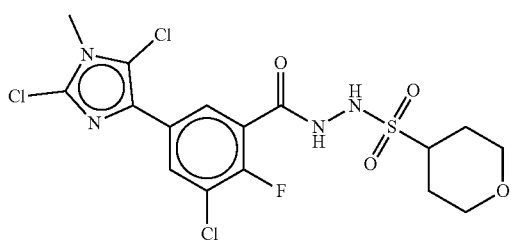
I-16
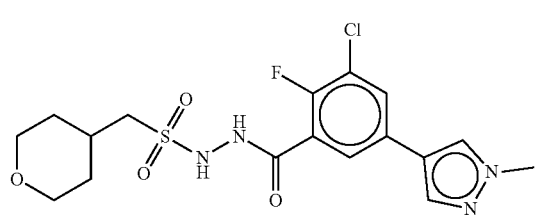
I-12
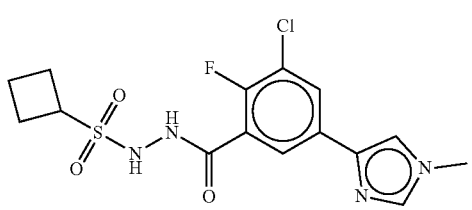
I-17
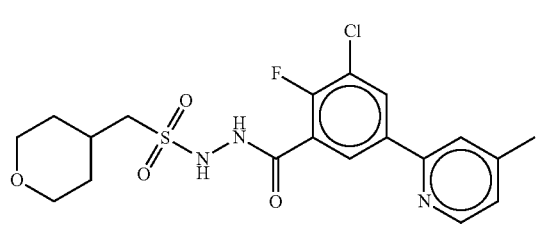
I-13
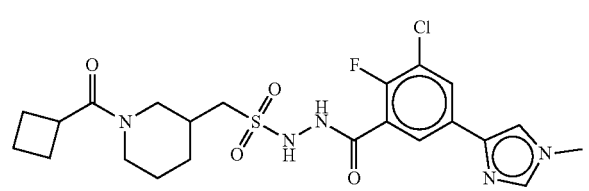
I-18
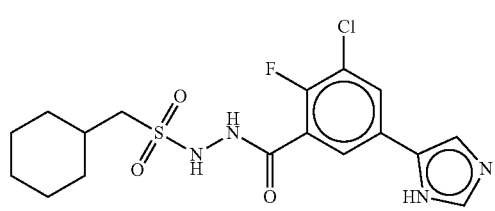

-continued
I-14
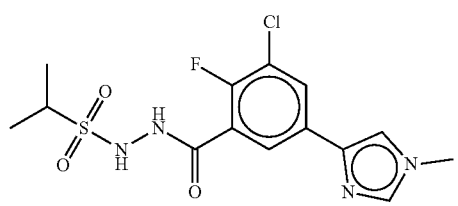
I-15
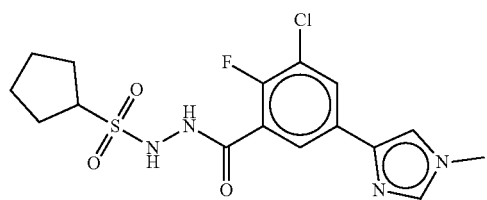
I-21
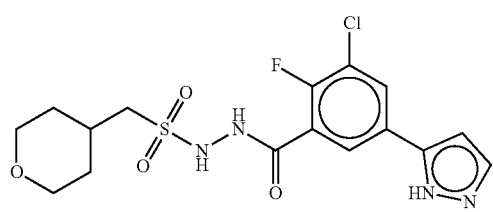
I-22
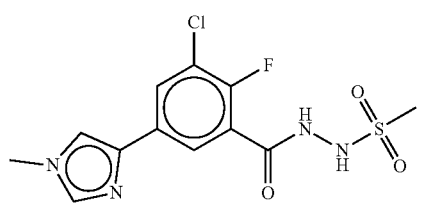
I-23
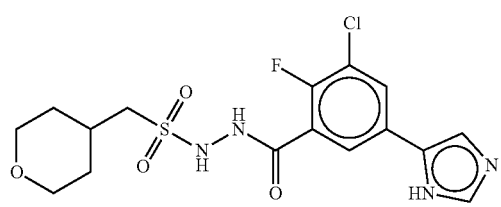
I-24
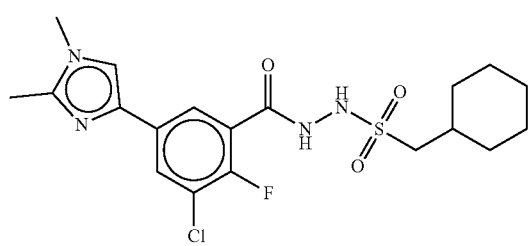
I-25
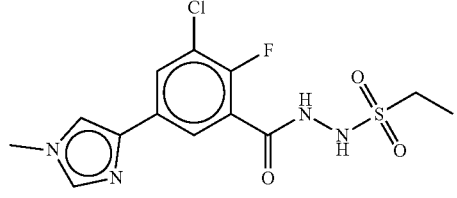
I-19
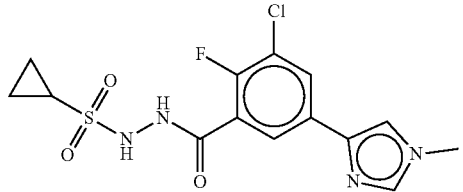
I-20
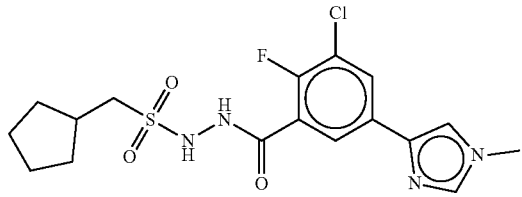
I-26
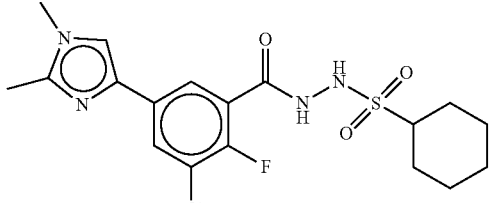
I-27
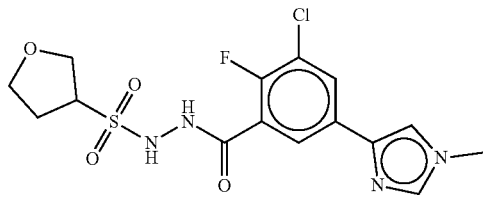
I-28
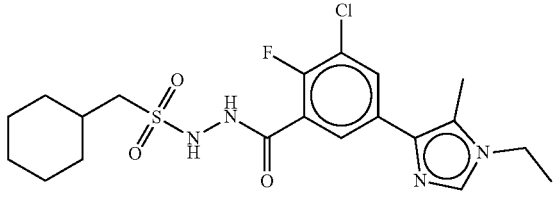
I-29
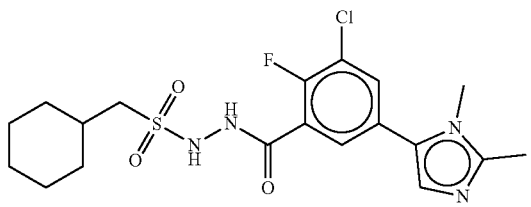
I-30
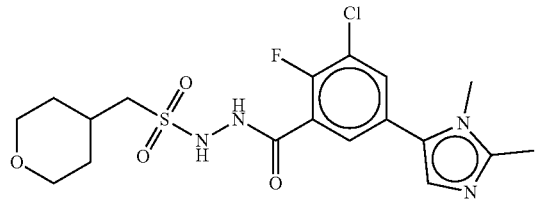

I-31
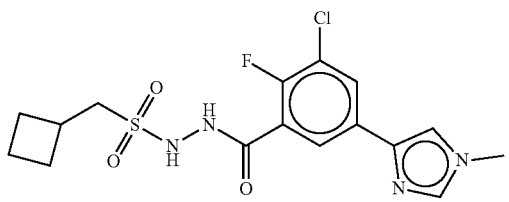
I-36
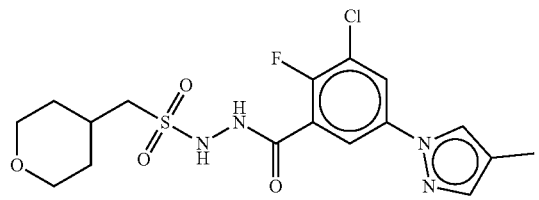
I-32
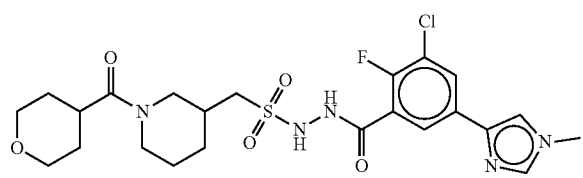
I-37
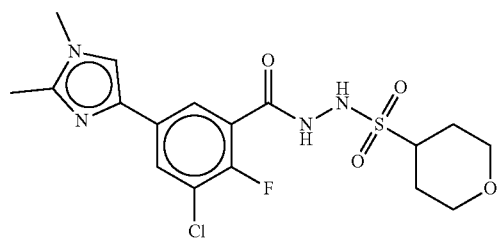
I-33
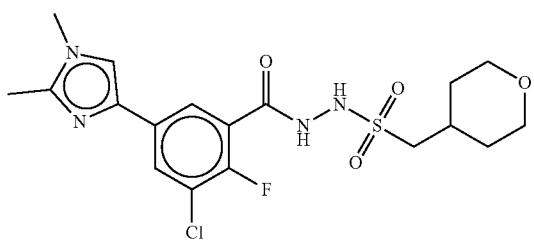
I-38
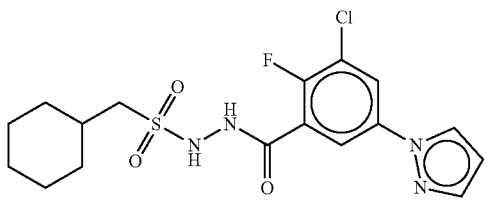
I-34
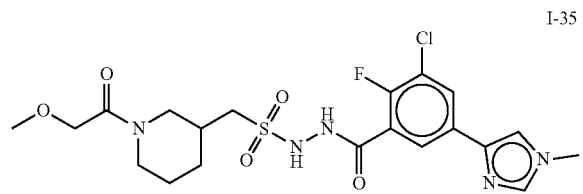
I-39
I-35
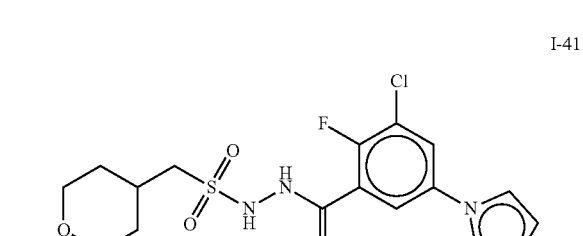
I-40
I-41
I-46
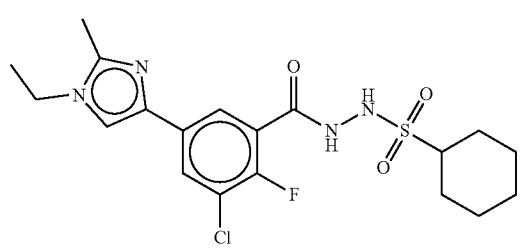

-continued
I-42
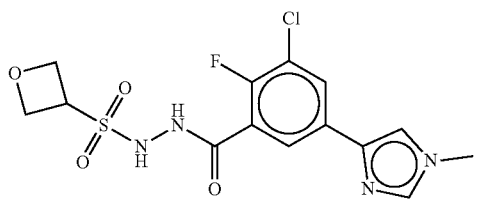
I-47
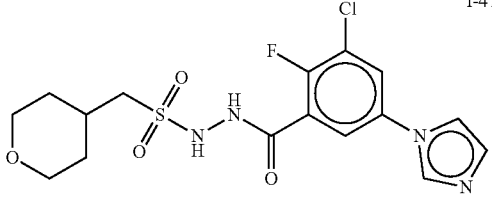
I-43
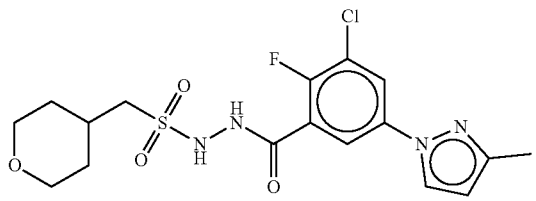
I-48
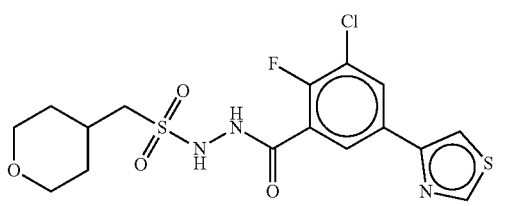
I-44
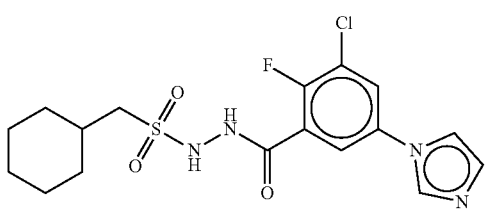
I-49
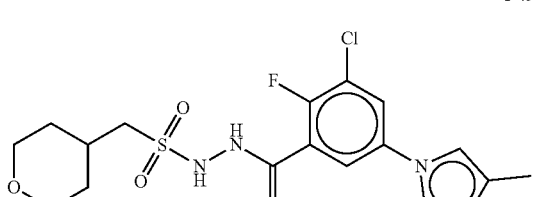
I-45
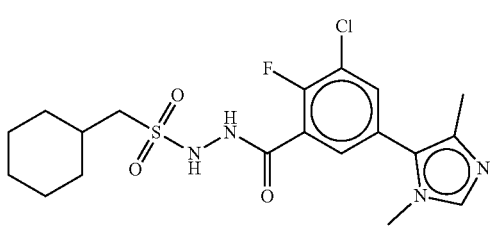
I-50
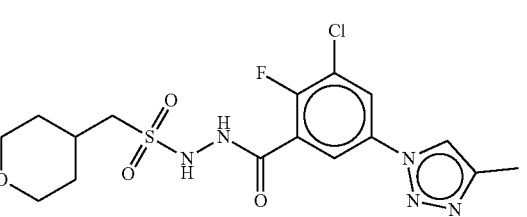
I-51
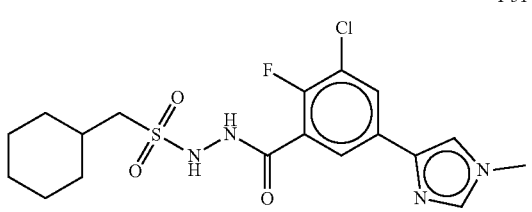
I-56
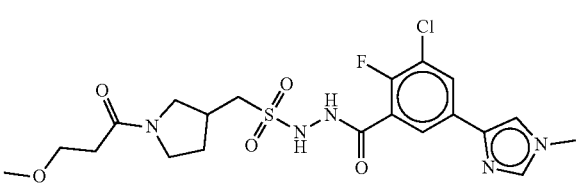
I-52
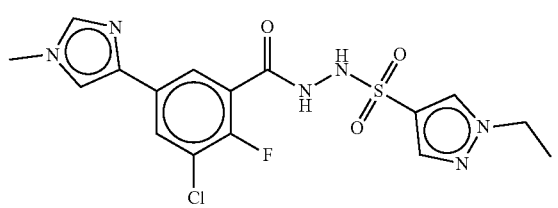
I-57
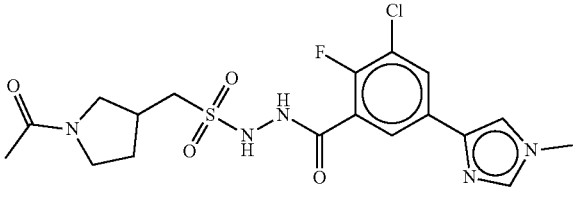
I-53
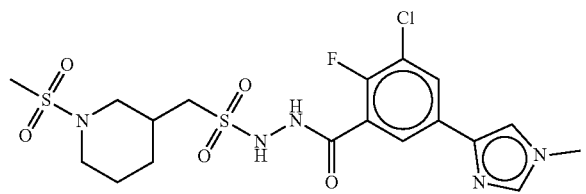
I-58
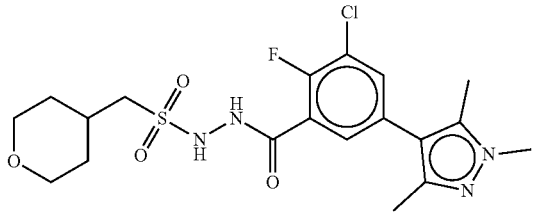

-continued
I-54
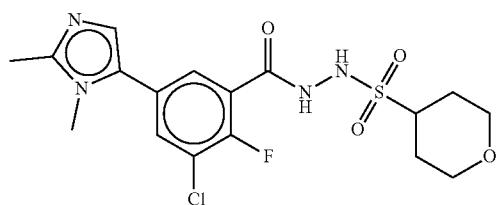
I-59
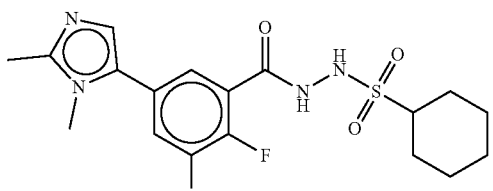
I-55
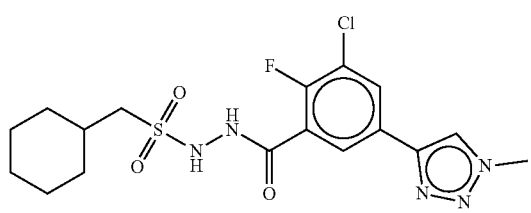
I-60
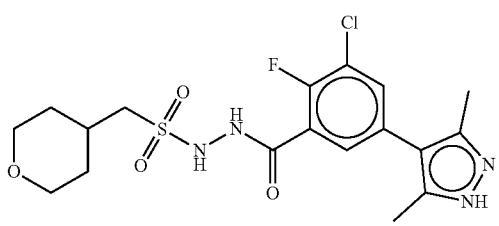
I-61
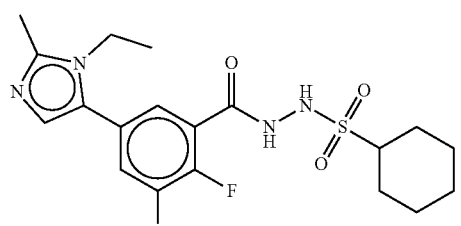
I-66
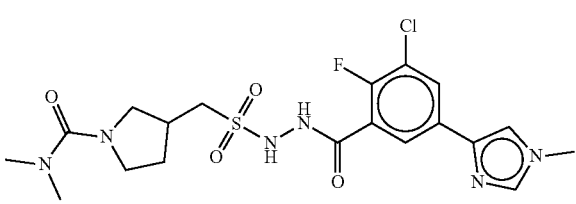
I-62
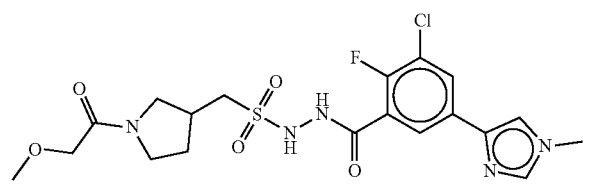
I-60
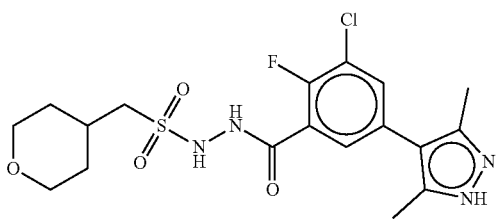
I-63
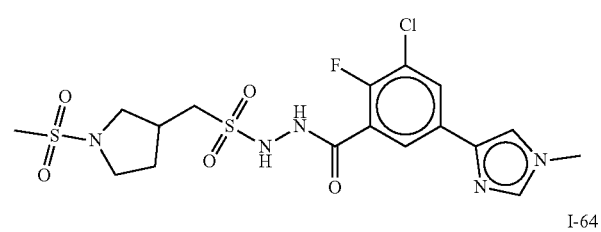
I-68
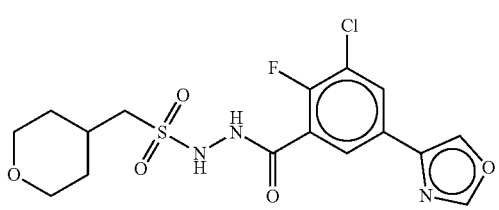
I-64
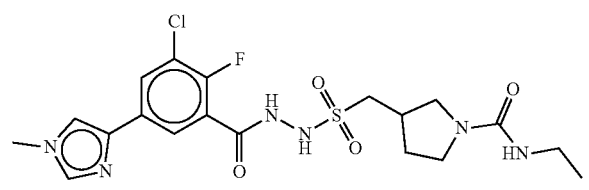
I-69
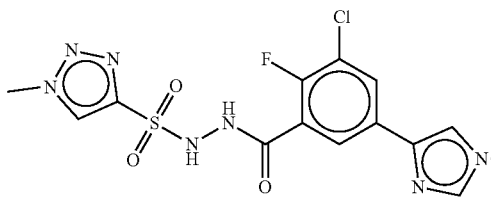
I-65
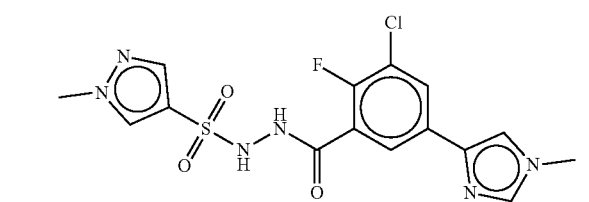
I-70
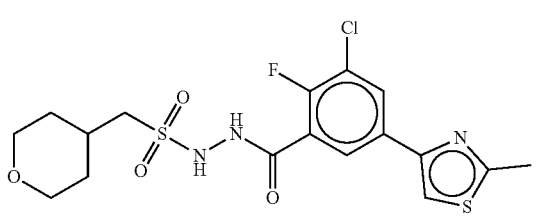

-continued
I-71
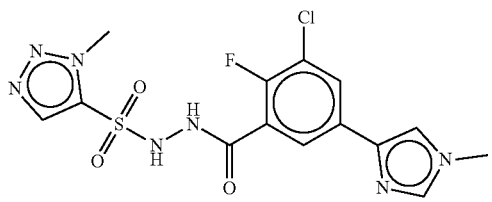
I-76
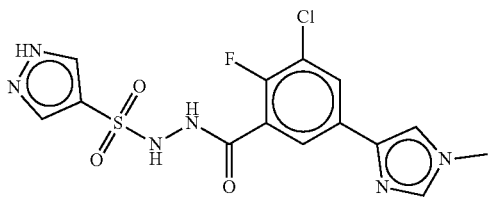
I-72
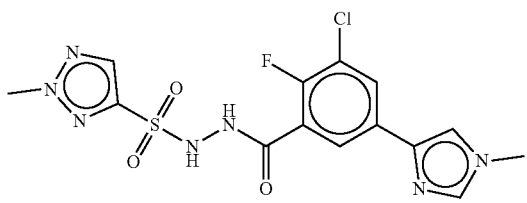
I-77
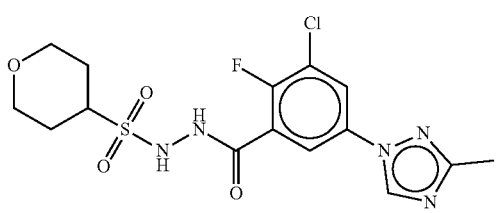
I-73
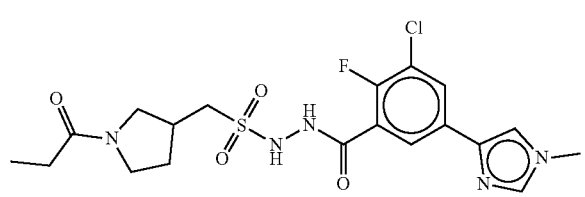
I-78
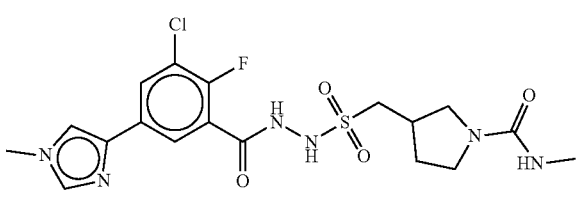
I-74
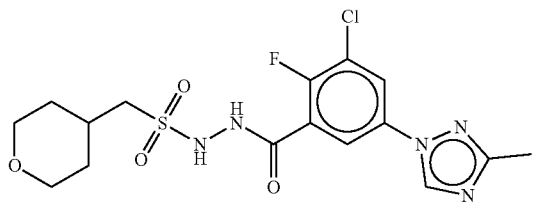
I-79
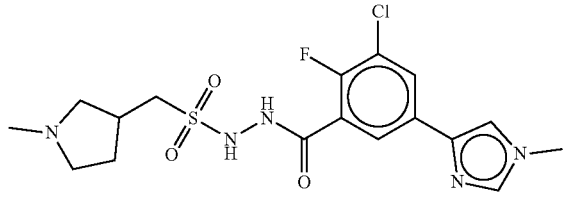
I-75
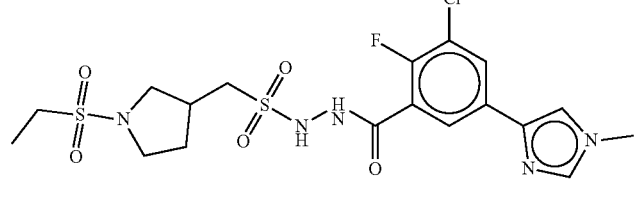
I-80
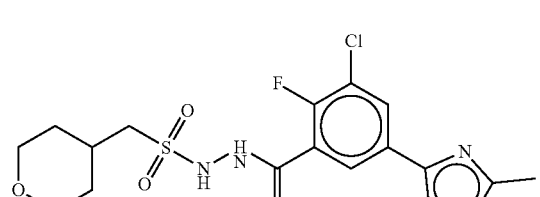
I-81
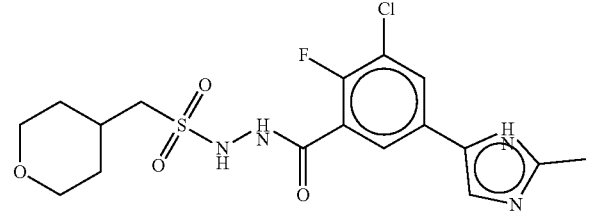
I-86
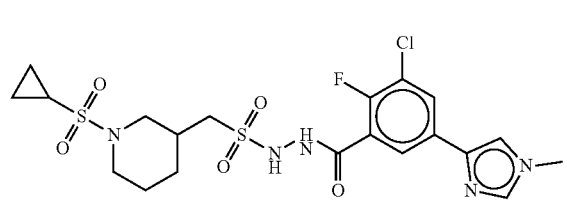
I-82
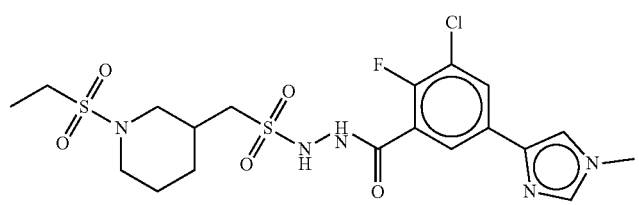
I-87
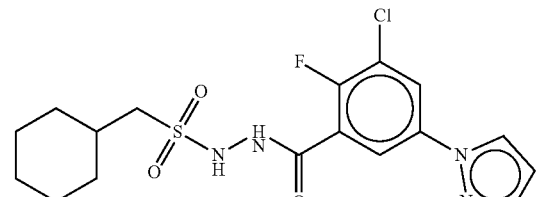

-continued
I-83
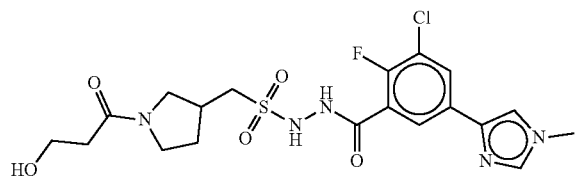
I-88
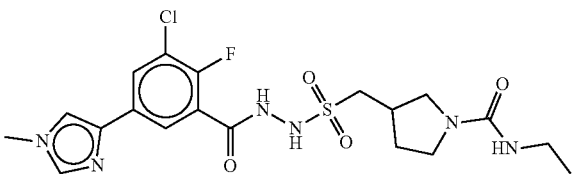
I-84
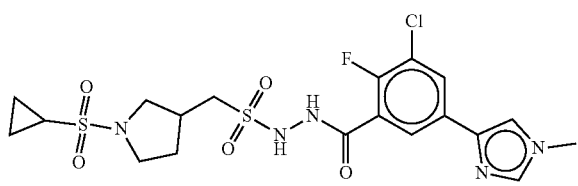
I-89
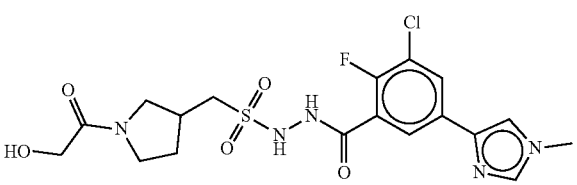
I-85
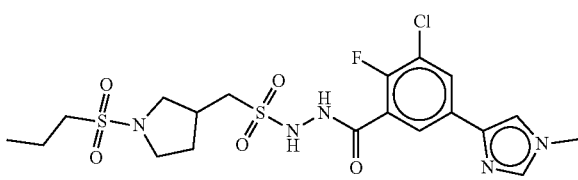
I-90
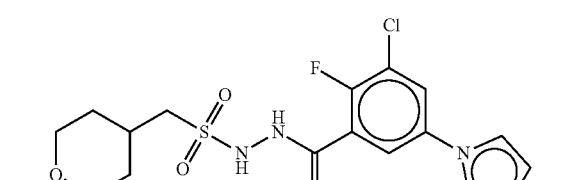
I-91
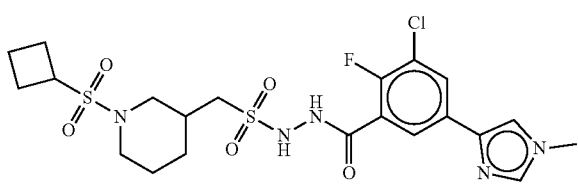
I-96
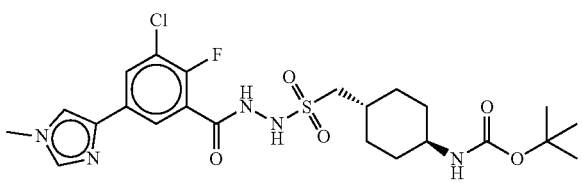
I-92
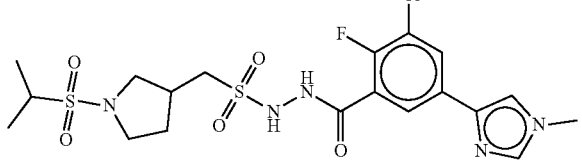
I-97
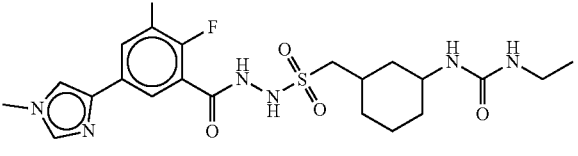
I-93
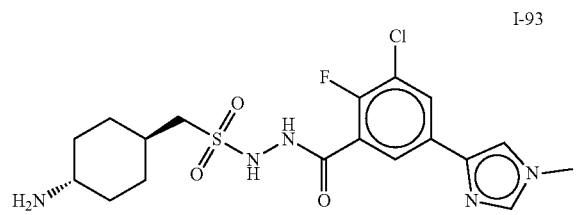
I-98
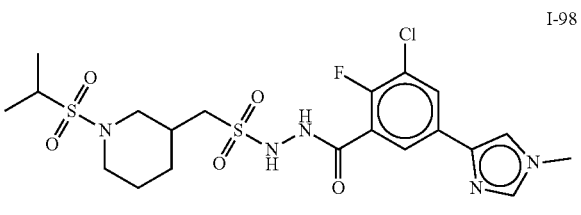
I-94
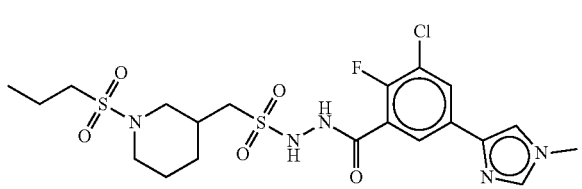
I-99
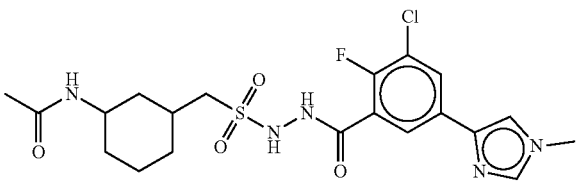

-continued
I-95
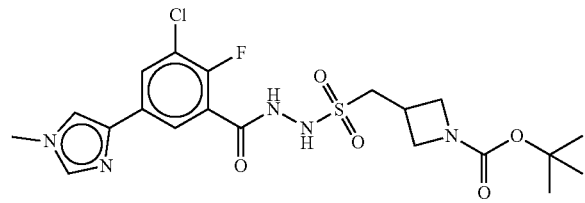
I-100
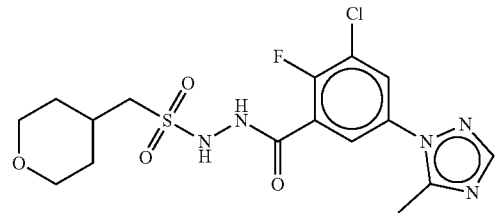
I-101
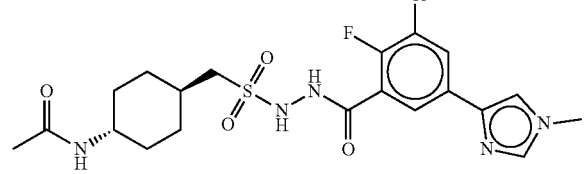
I-106
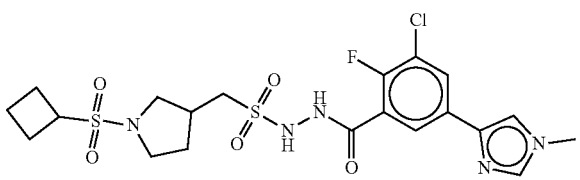
I-102
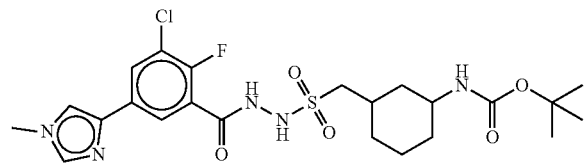
I-107
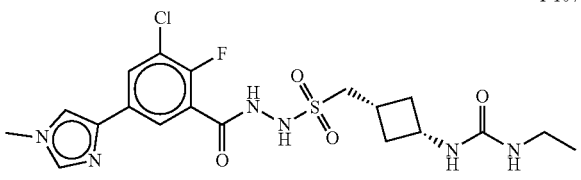
I-103
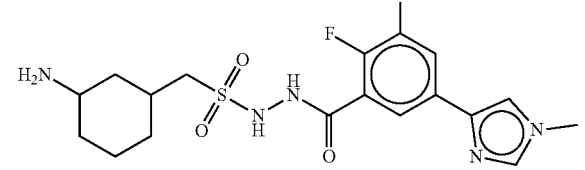
I-108
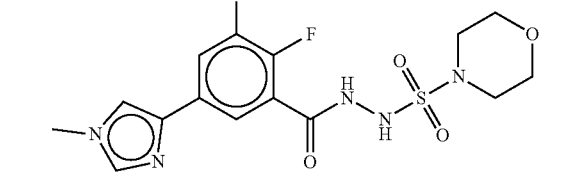
I-104
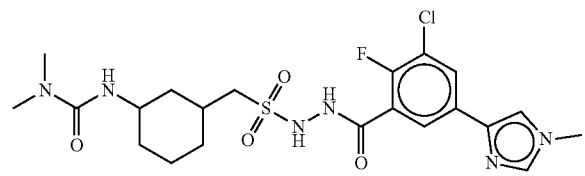
I-109
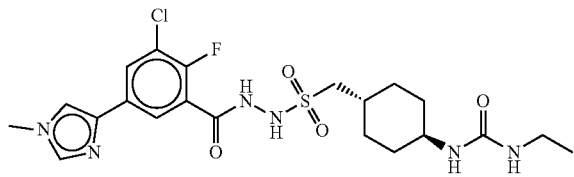
I-105
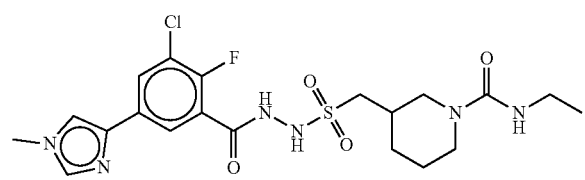
I-111
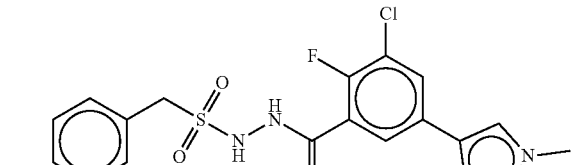
I-116
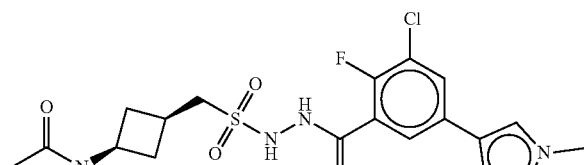
I-112
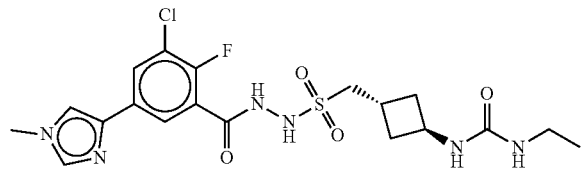

-continued
I-117
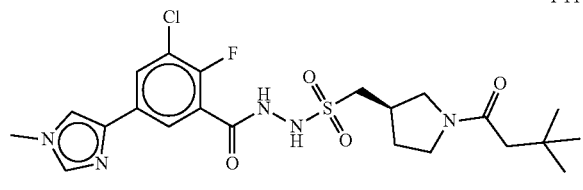
I-113
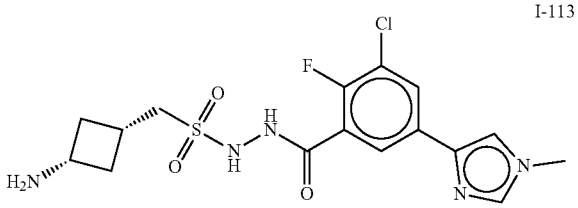
I-118
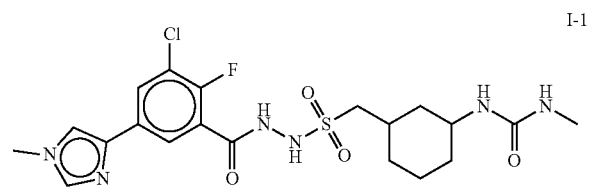
I-114
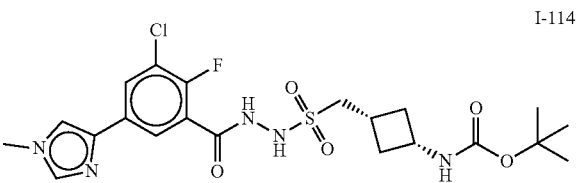
I-119
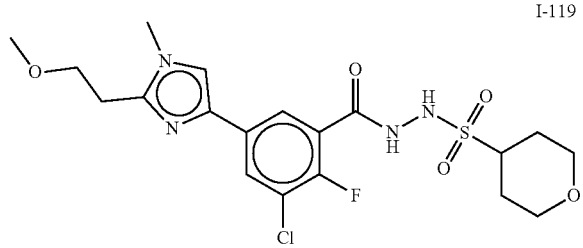
I-115
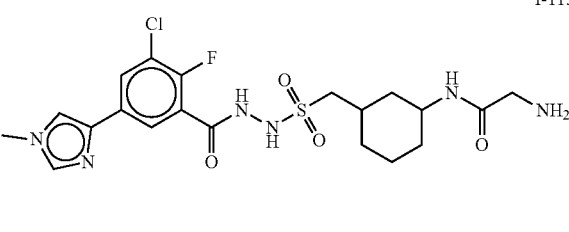
I-120
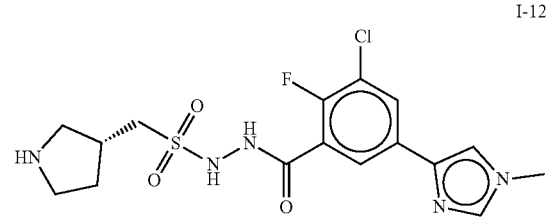
I-121
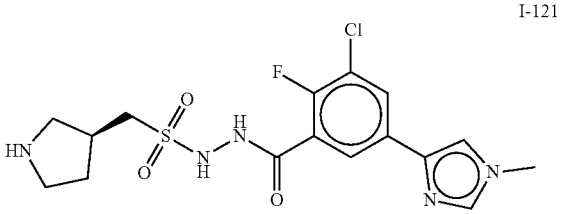
I-126
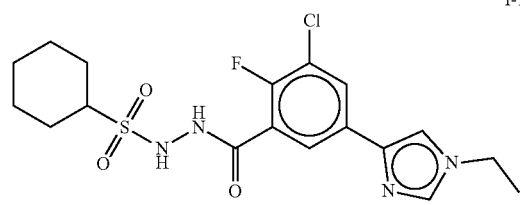
I-122
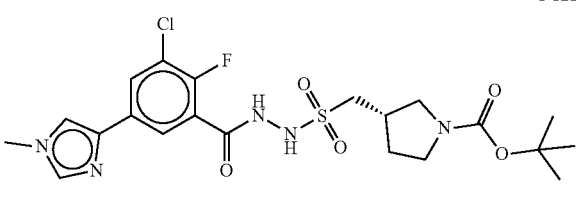
I-127
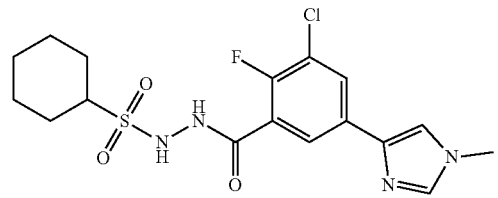
I-123
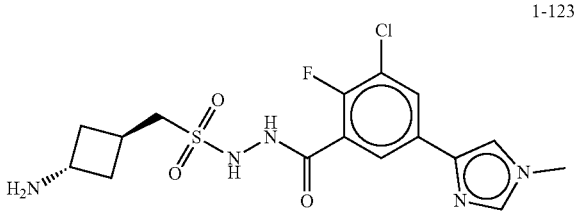
I-128
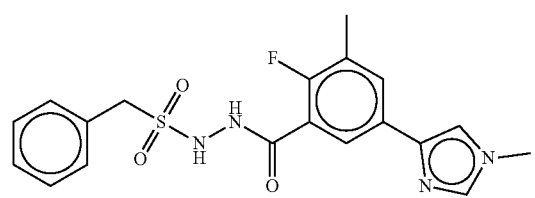
I-124
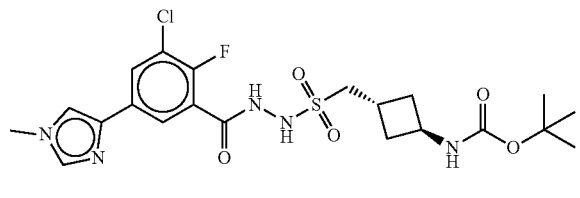

-continued
449
I-129
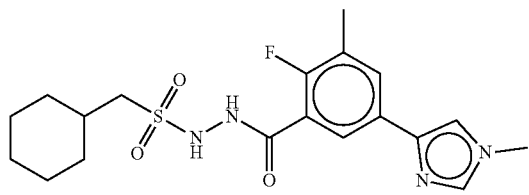
I-130
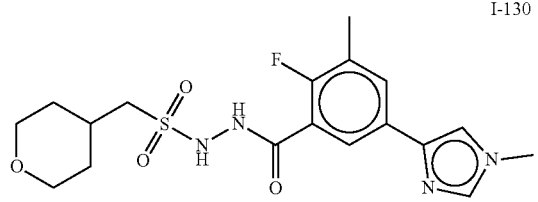
I-136
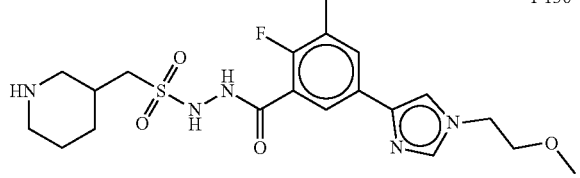
I-137
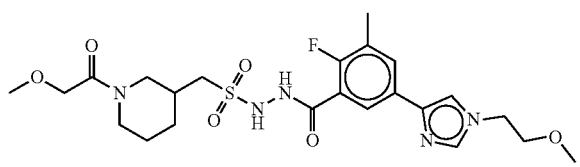
I-138
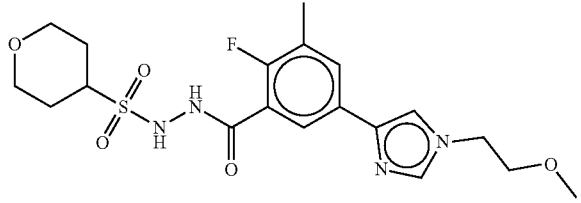
I-139
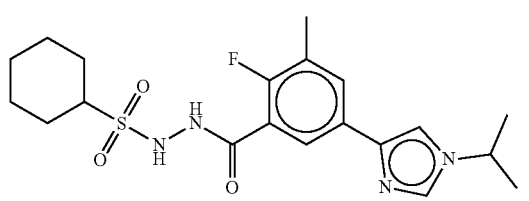
I-140
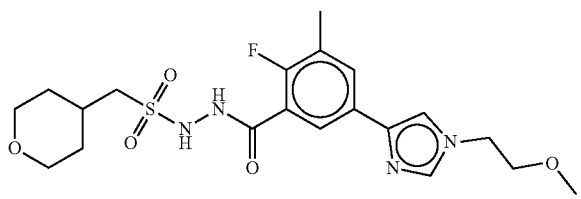
450
I-125
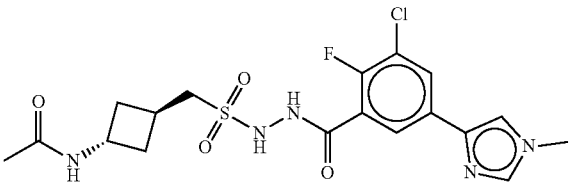
I-131
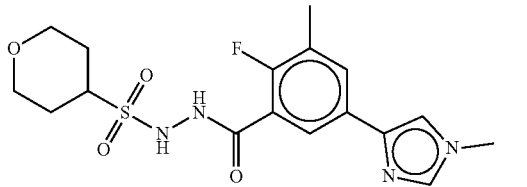
I-132
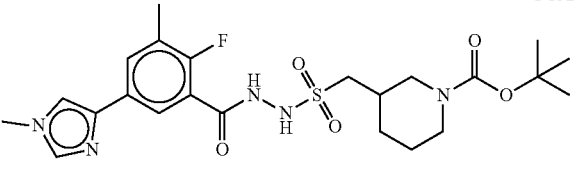
I-133
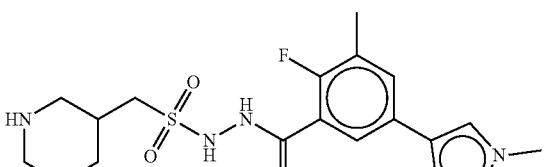
I-134
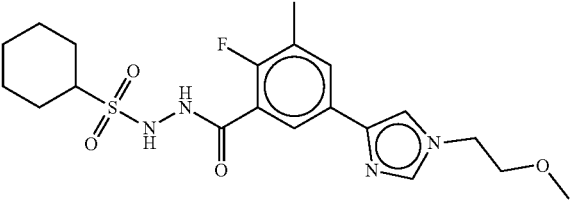
I-135
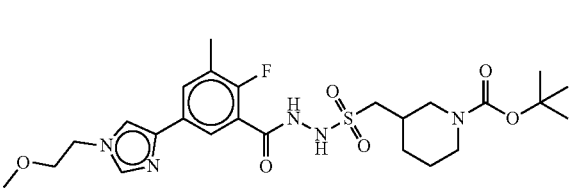
I-141
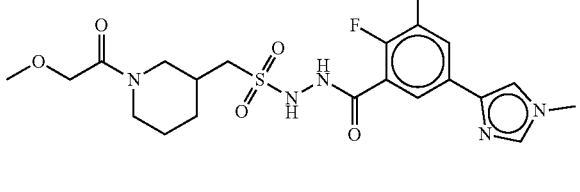

-continued
I-146
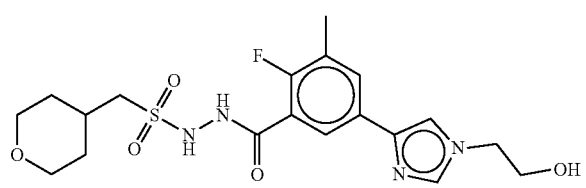
I-142
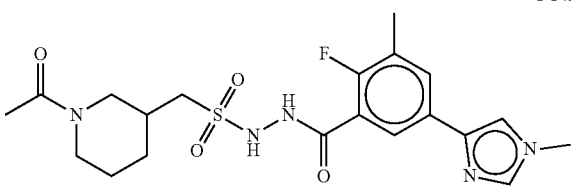
I-147
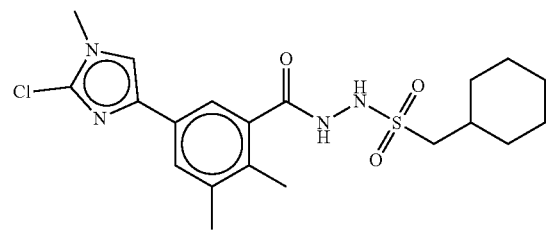
I-143
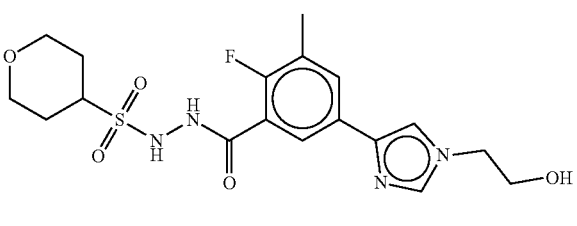
I-148
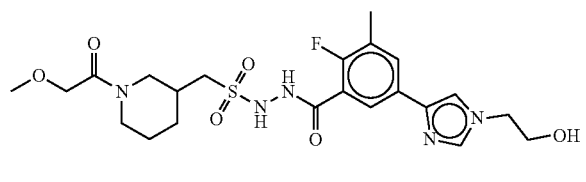
I-144
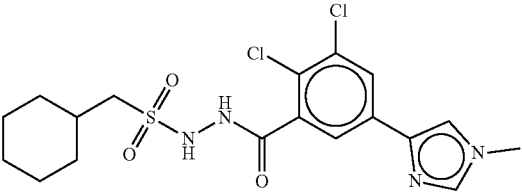
I-149
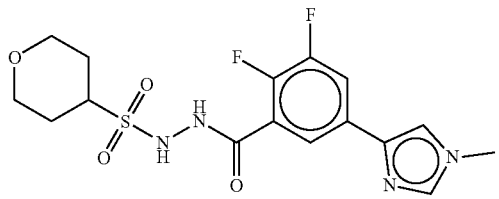
I-145
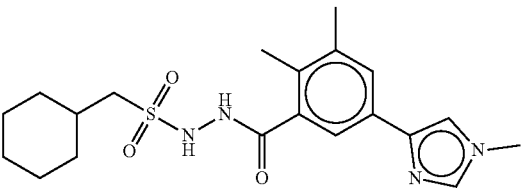
I-150
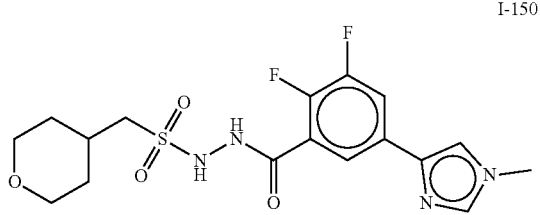
I-151
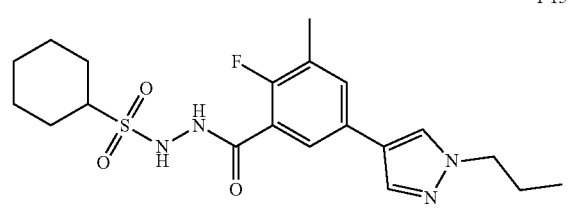
I-156
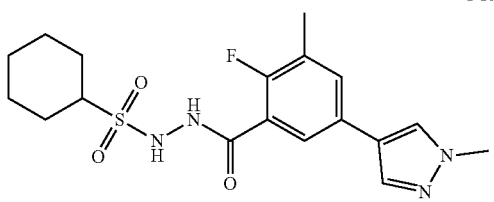
I-152
I-157
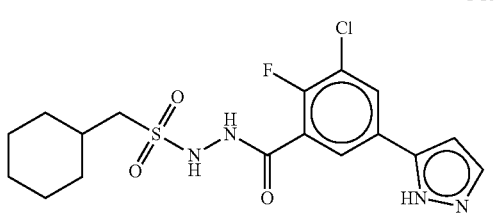
I-153
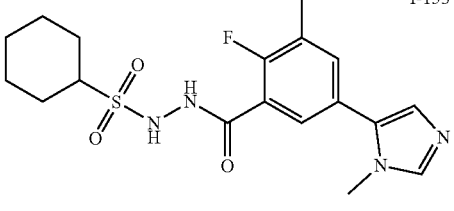

-continued
I-158
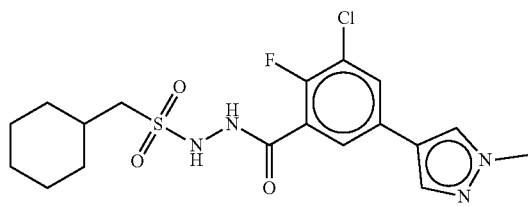
I-154
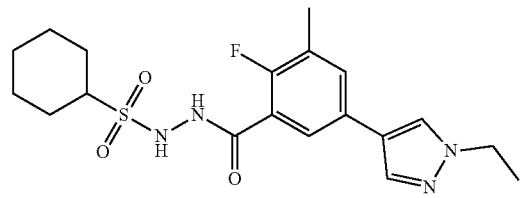
I-159
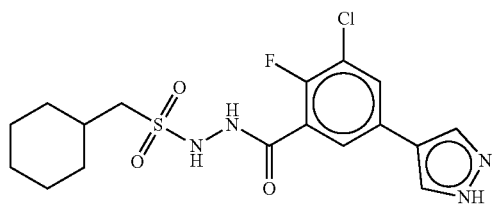
I-155
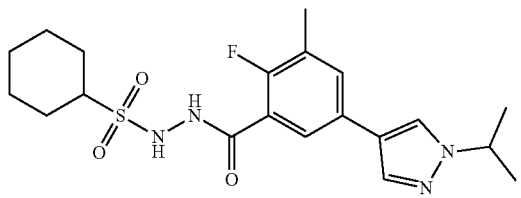
I-160
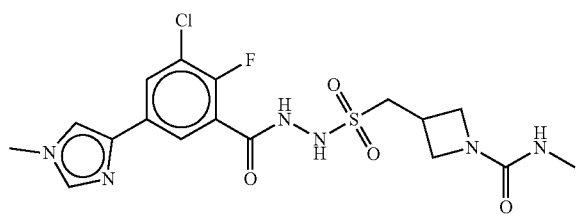
I-161
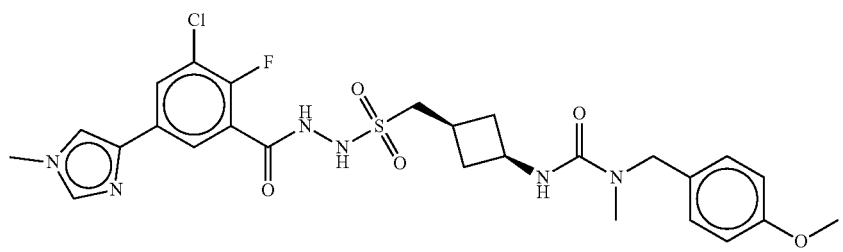
I-166
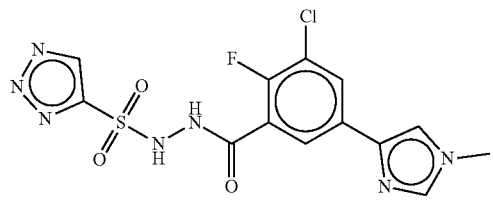
I-162
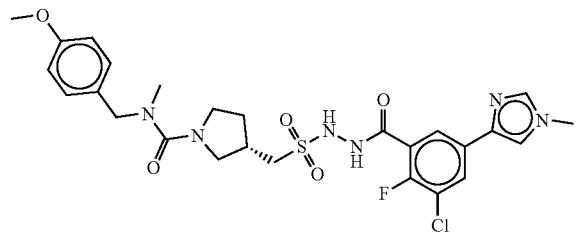
I-167
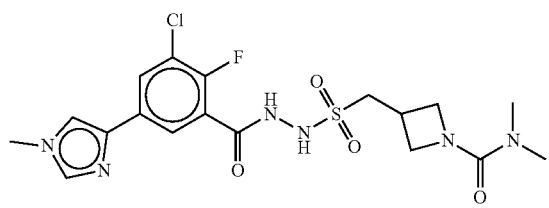
I-163
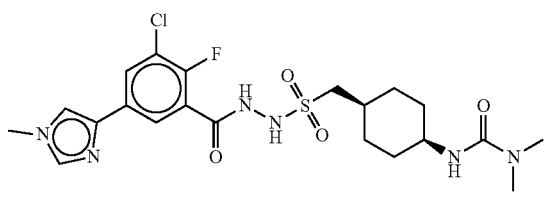

-continued
I-168
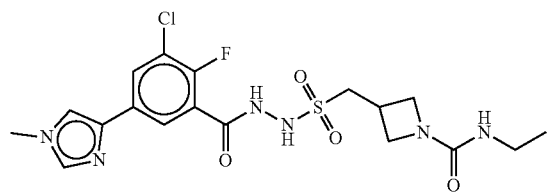
I-164
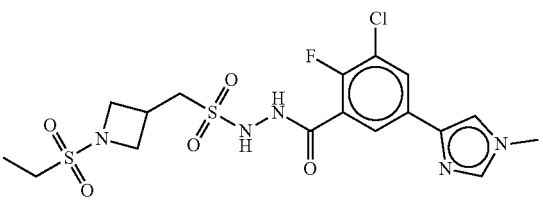
I-169
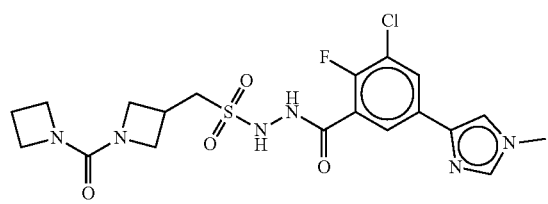
I-165
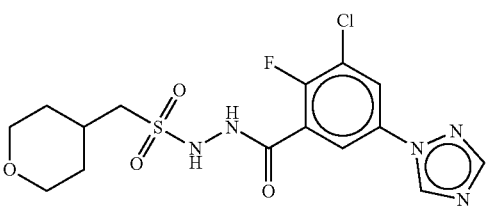
I-170
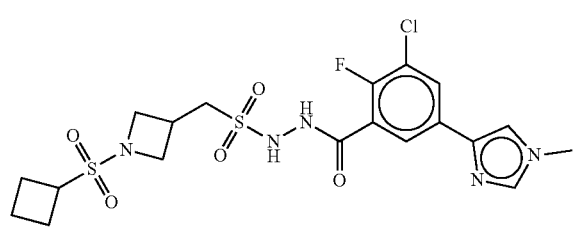
I-171
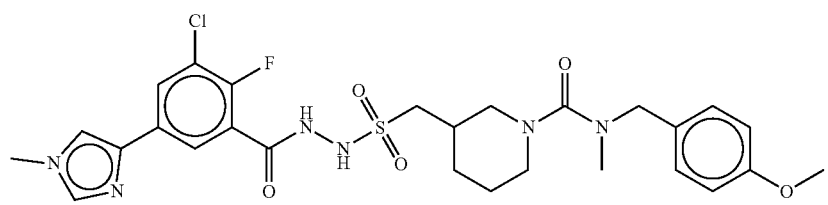
I-176
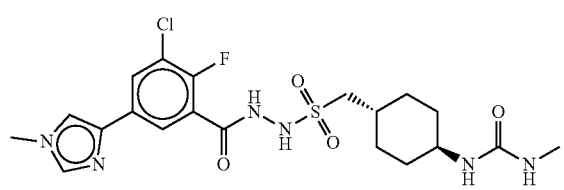
I-172
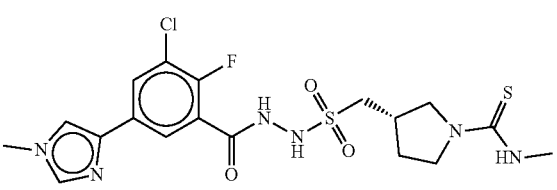
I-173
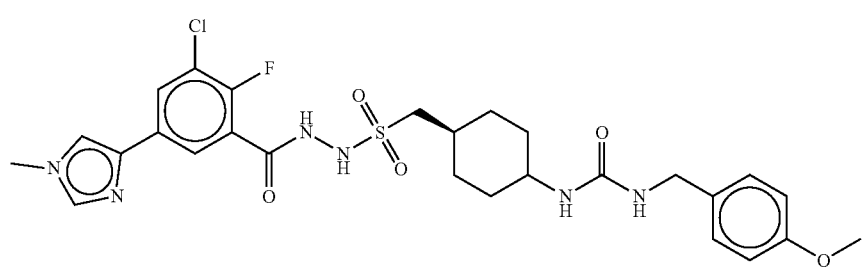
I-177
I-178
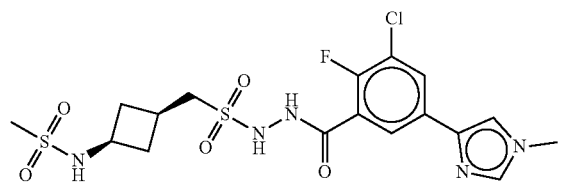
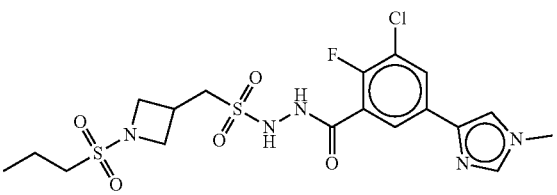

-continued
I-174
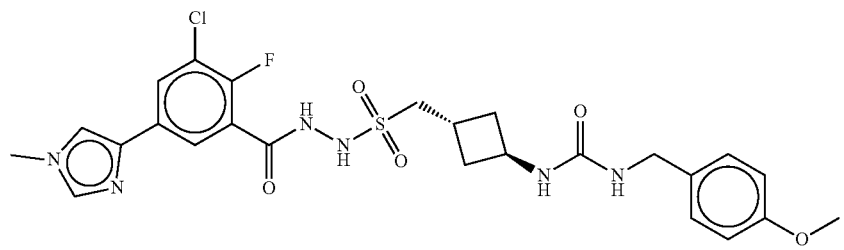
I-179
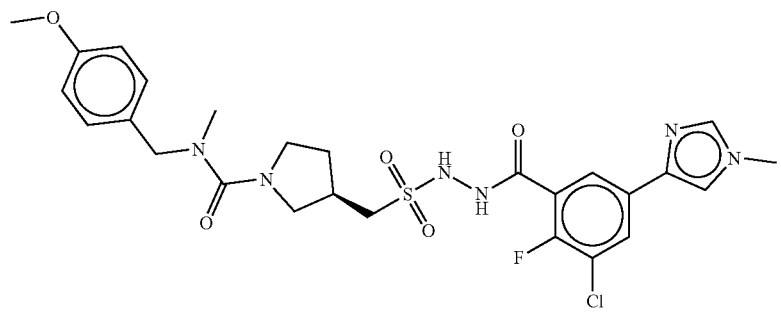
I-175
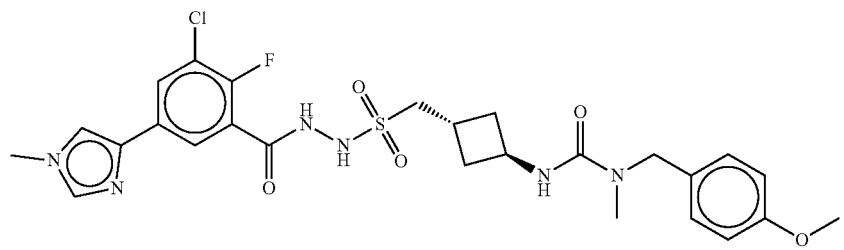
I-180        I-181
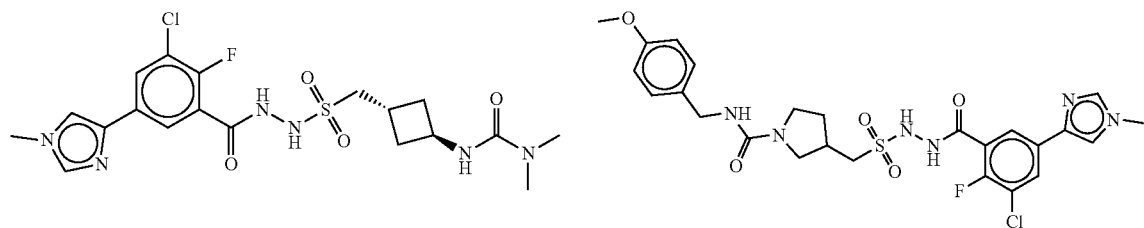
I-186        I-182
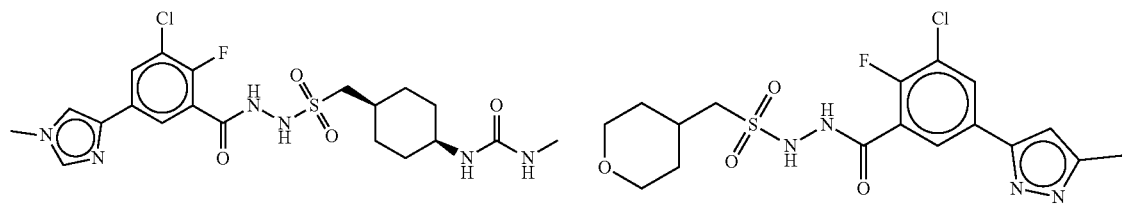
I-187        I-183
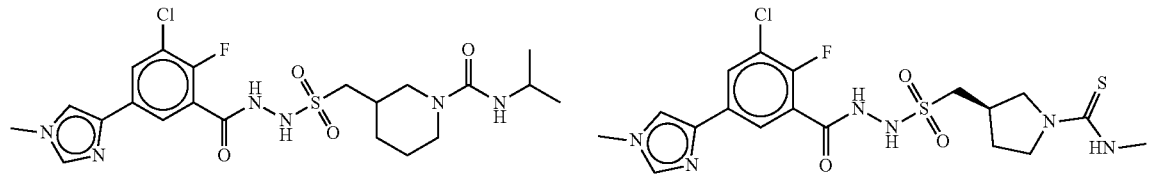

-continued
I-188
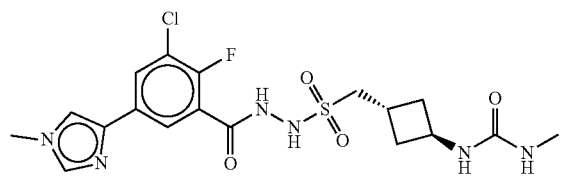
I-184
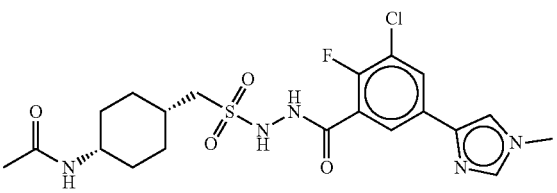
I-189
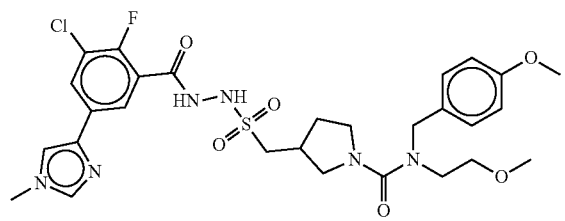
I-185
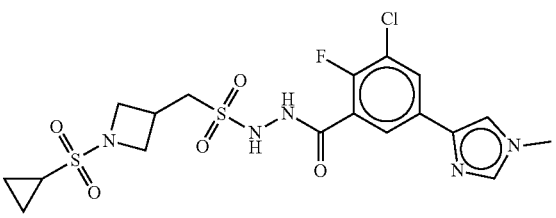
I-190
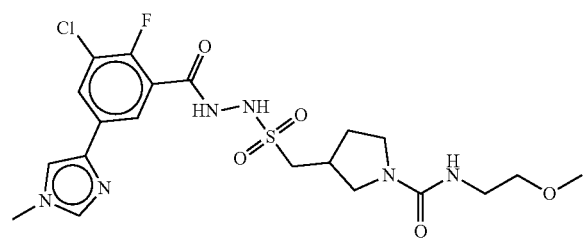
I-191
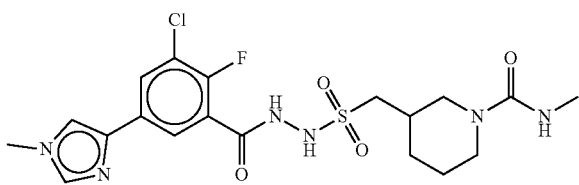
I-196
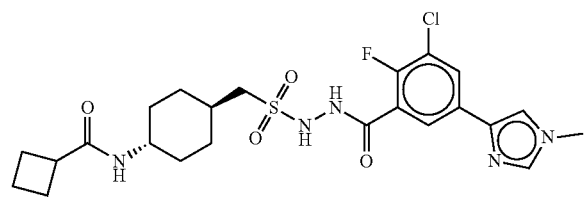
I-192
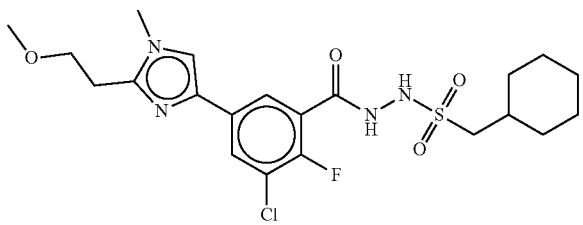
I-197
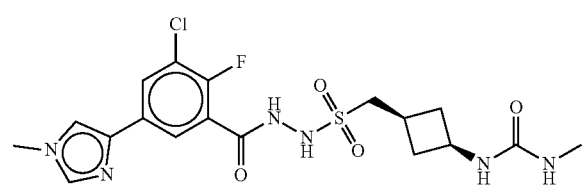
I-193
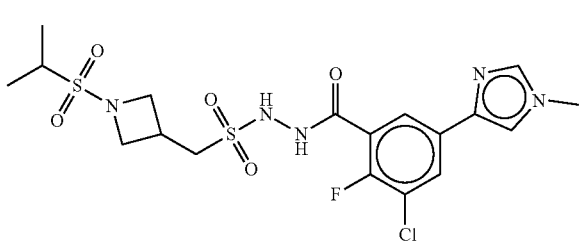
I-198
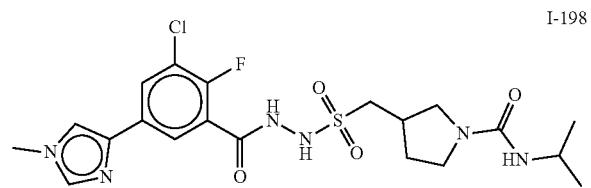
I-194
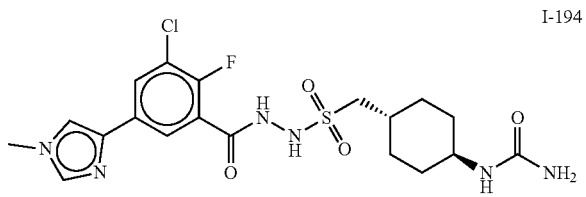

-continued
I-199
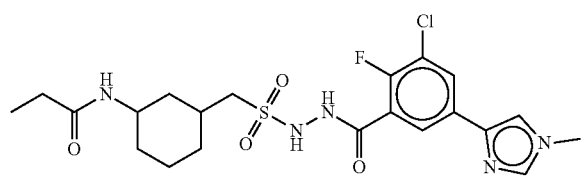
I-195
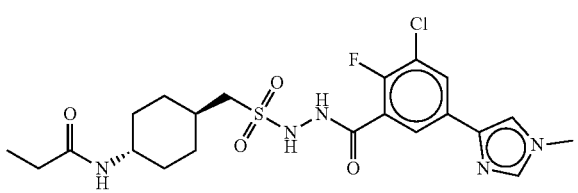
I-200
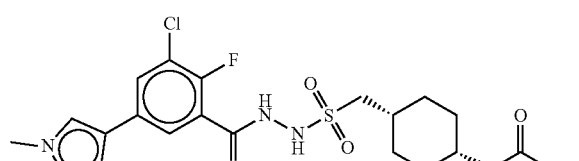
I-201
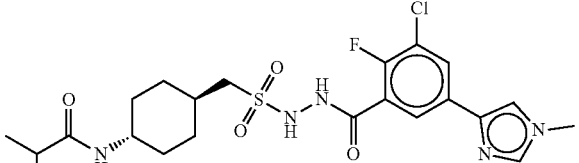
I-206
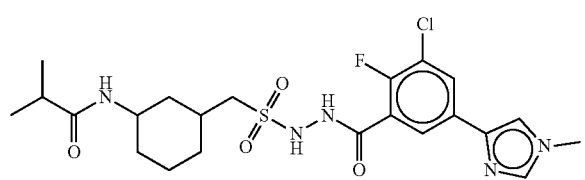
I-202
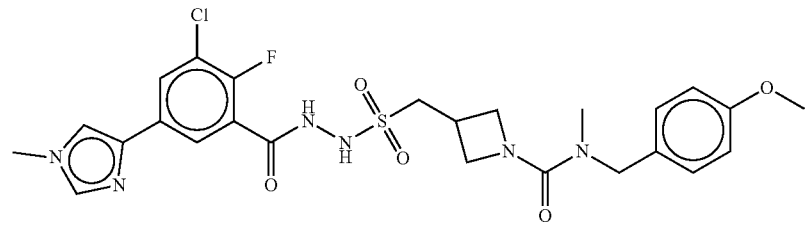
I-207
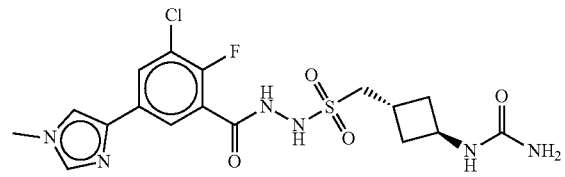
I-203
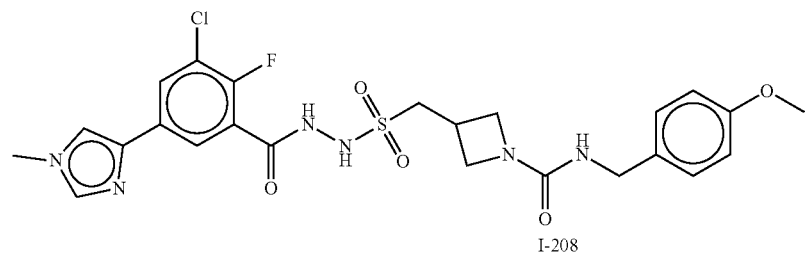
I-208
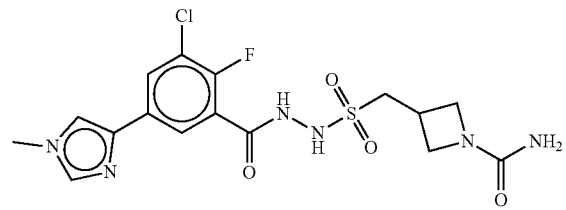
I-204
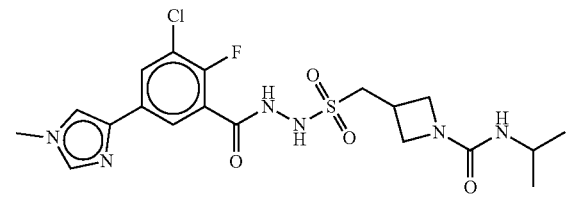

-continued
I-209
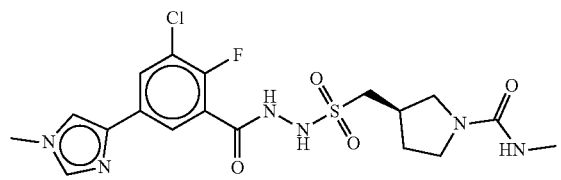
I-205
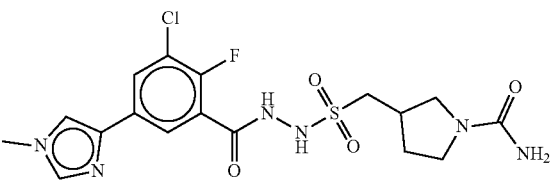
I-210
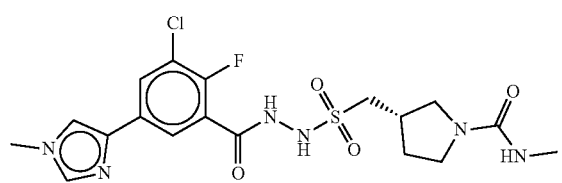
I-211
I-212
I-216
I-217
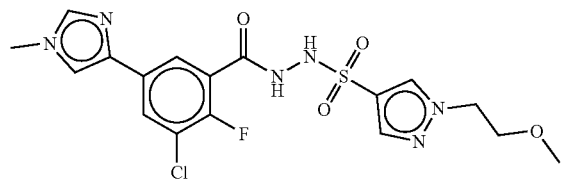
I-213
I-218
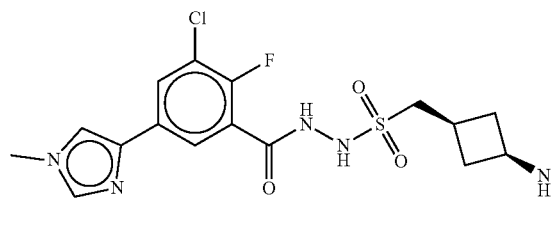
I-214
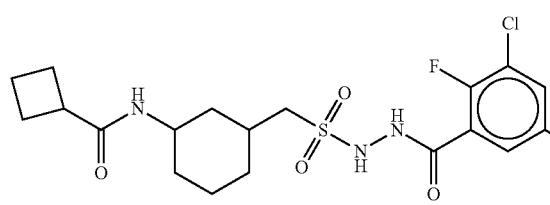
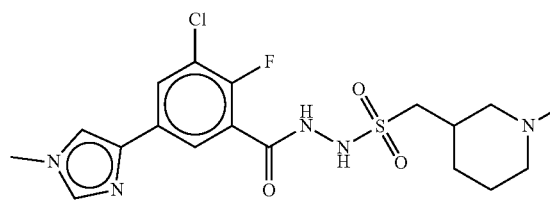

-continued
I-219
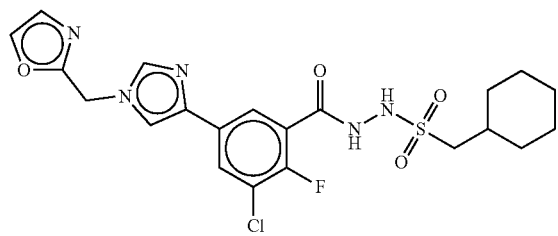
I-215
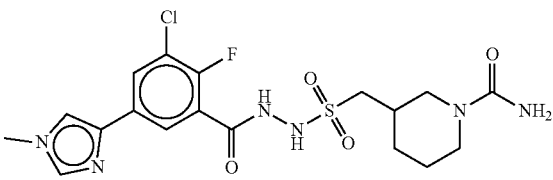
I-220
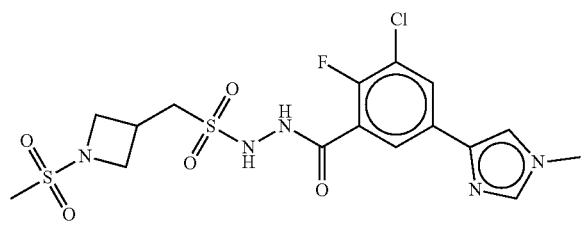
I-221
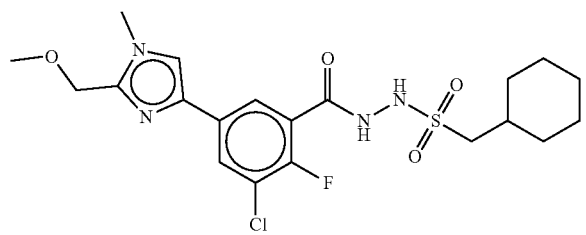
I-226
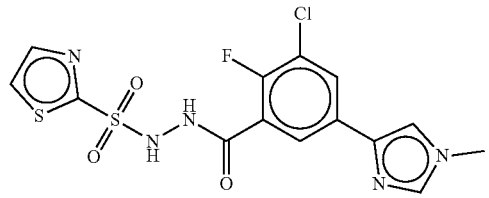
I-222
I-227
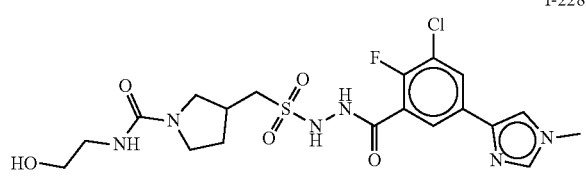
I-223
I-228
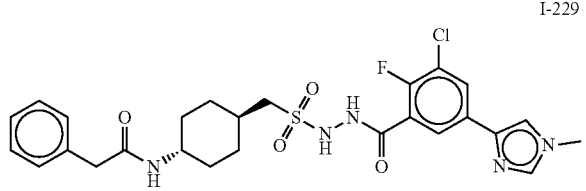
I-224
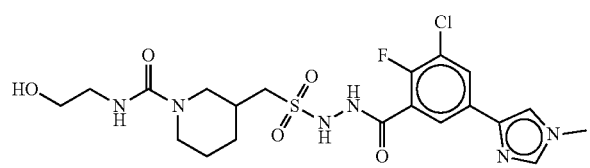
I-229
I-225
I-230
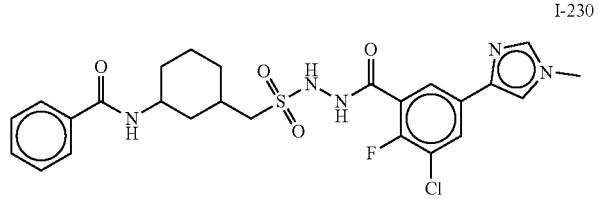
I-231
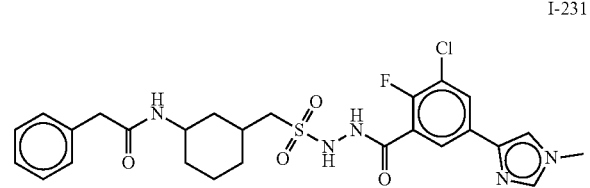

-continued
I-236
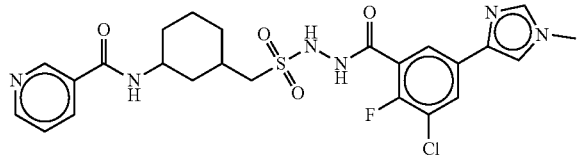
I-232
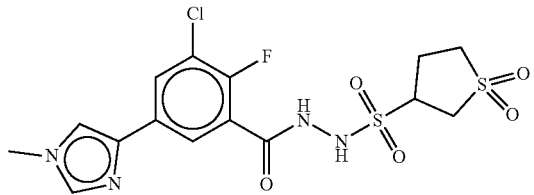
I-237
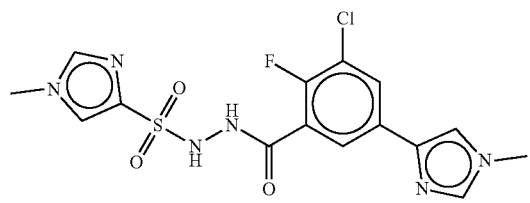
I-233
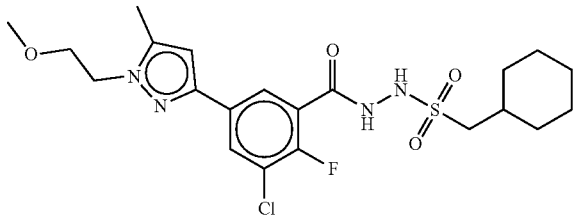
I-238
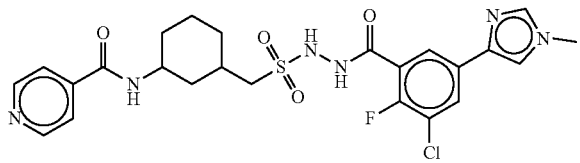
I-234
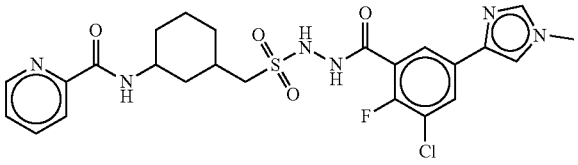
I-239
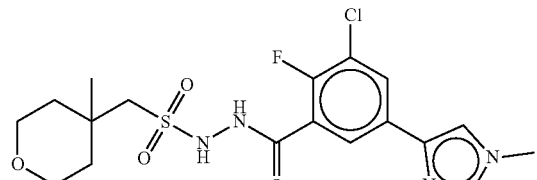
I-235
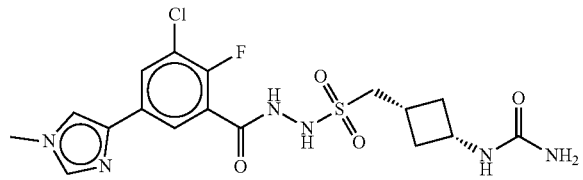
I-240
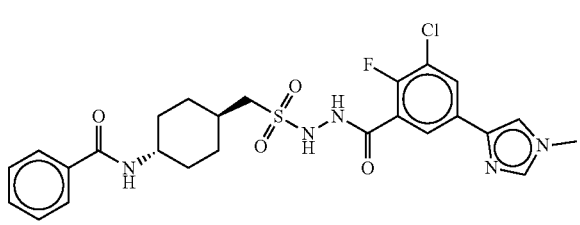
I-241
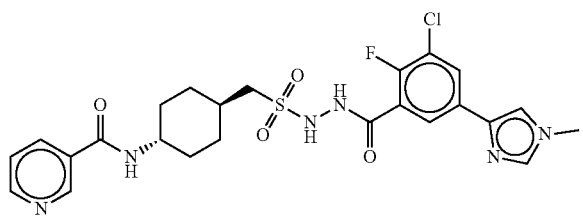
I-246
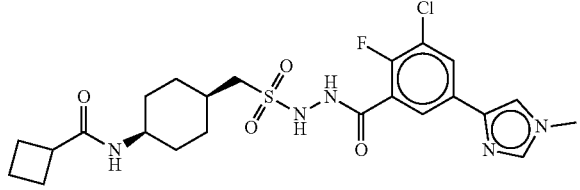
I-242
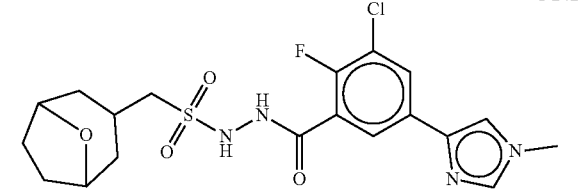
I-247
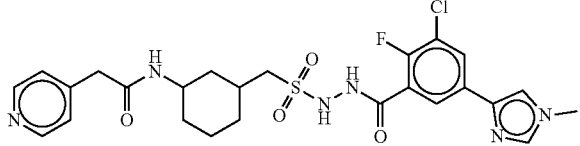
I-243
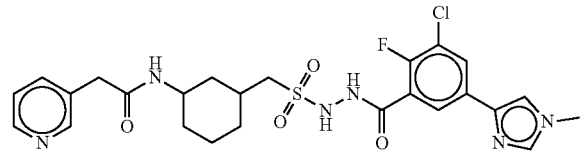

-continued
I-248
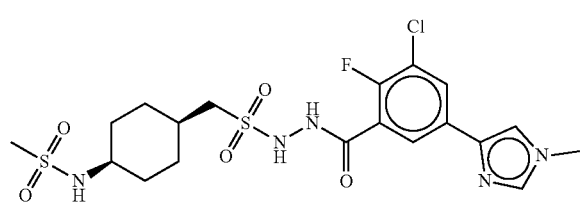
I-244
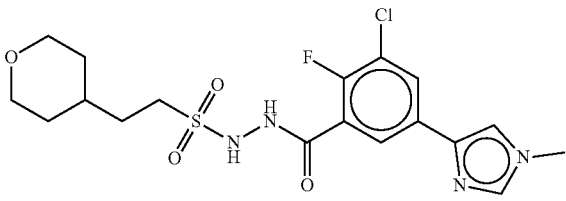
I-249
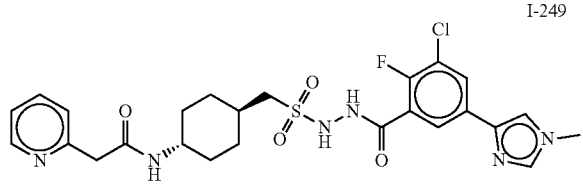
I-245
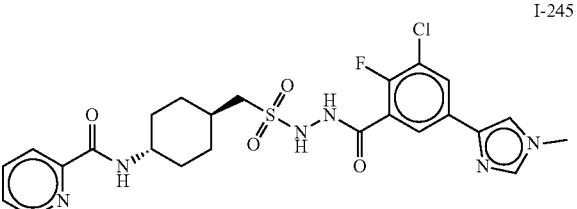
I-250
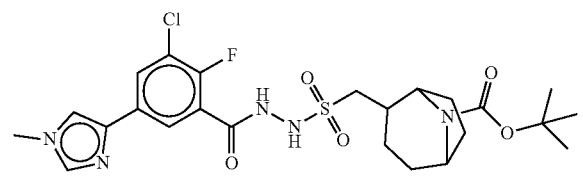
I-246
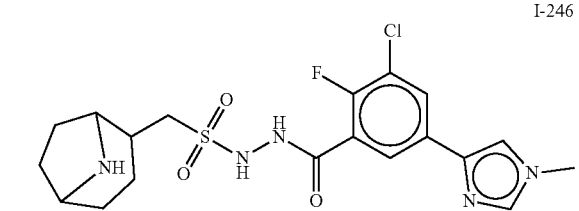
I-256
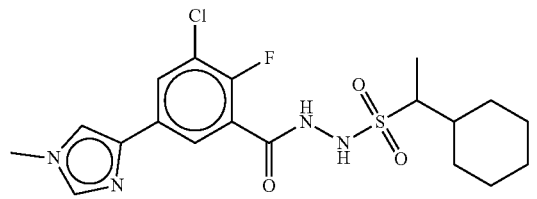
I-252
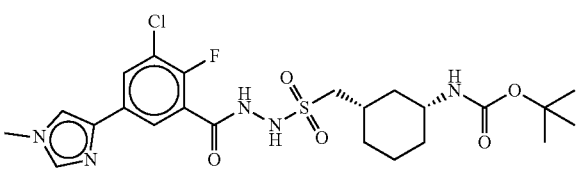
I-257
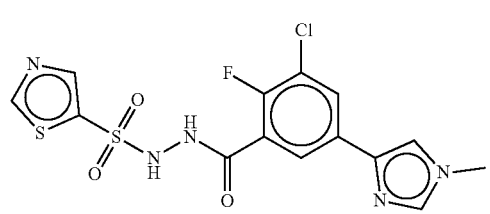
I-253
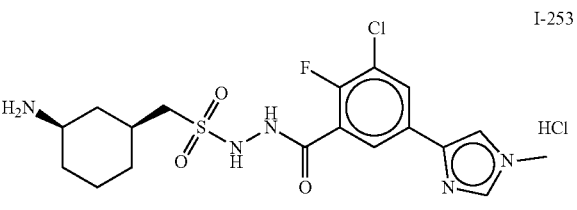
I-258
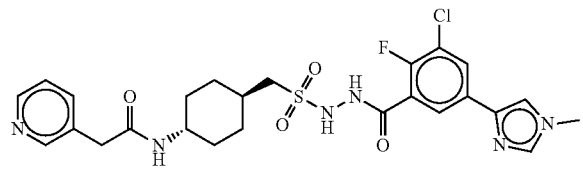
I-254
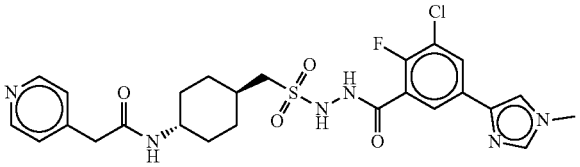
I-259
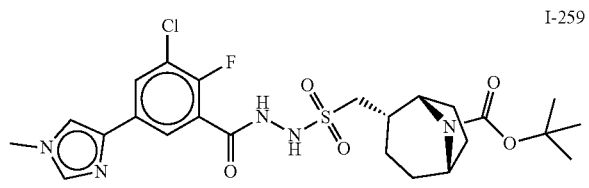
I-255
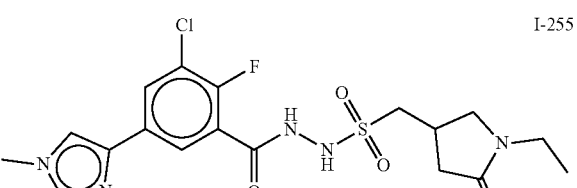

-continued
471
I-260
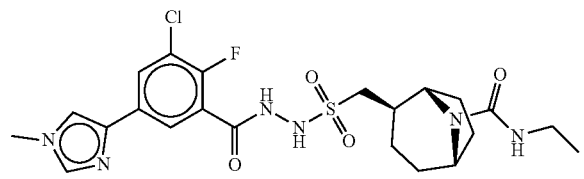
I-266
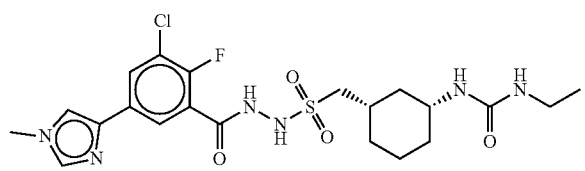
I-267
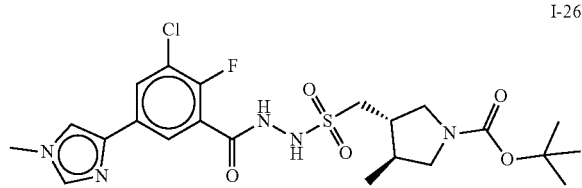
I-268
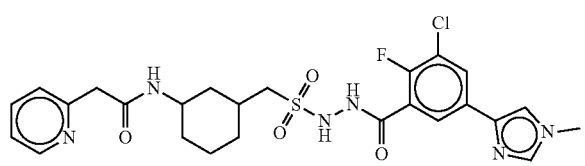
I-269
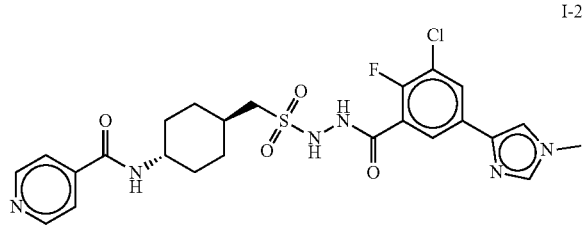
I-270
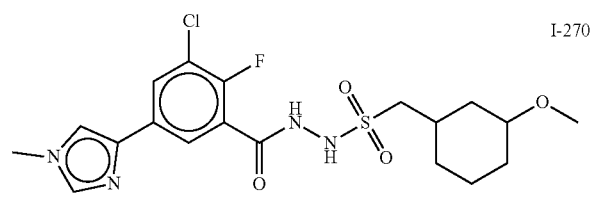
I-276
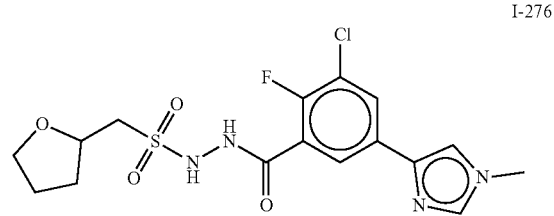
472
I-261
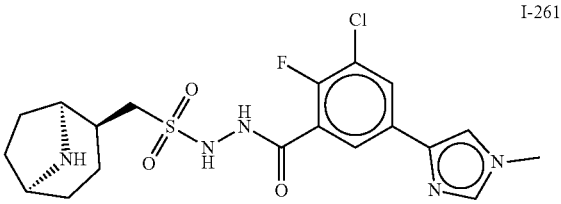
I-262
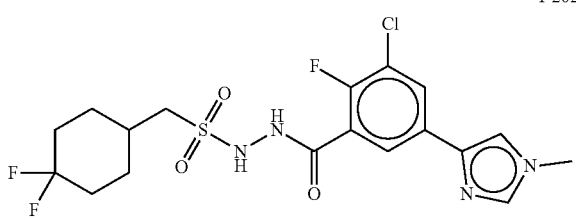
I-263
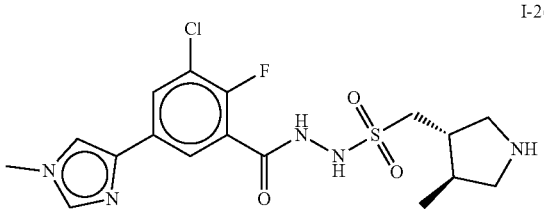
I-264
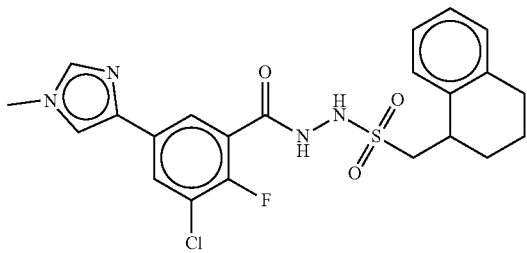
I-265
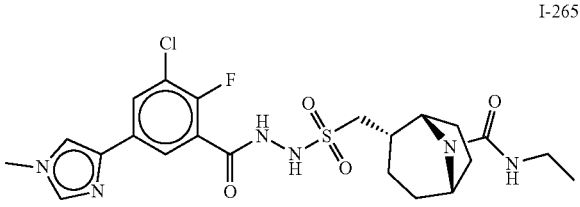
I-271
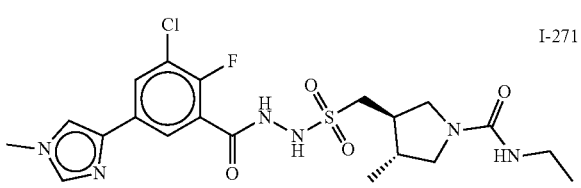
I-272
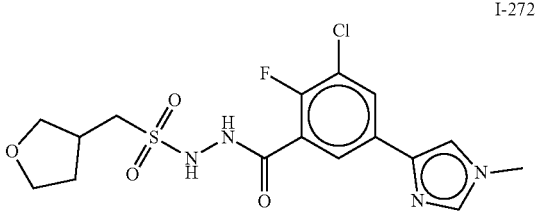

-continued
I-277
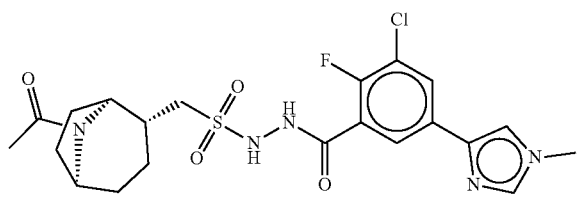
I-273
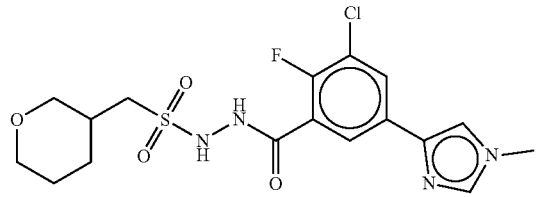
I-278
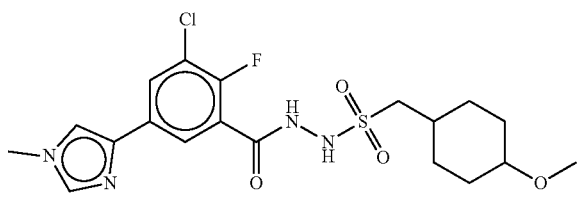
I-274
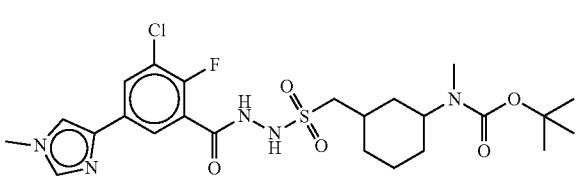
I-279
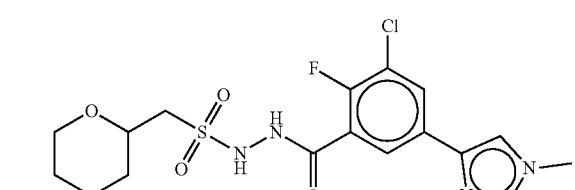
I-275
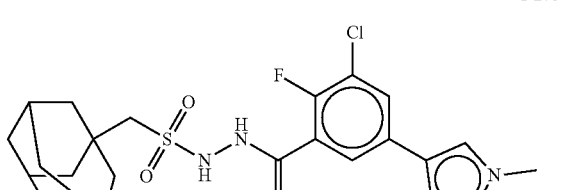
I-280
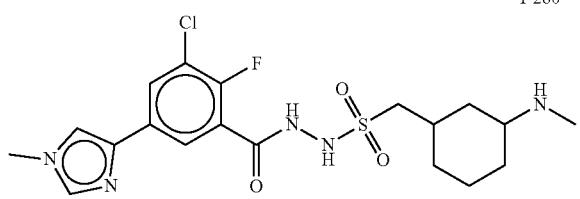
I-281
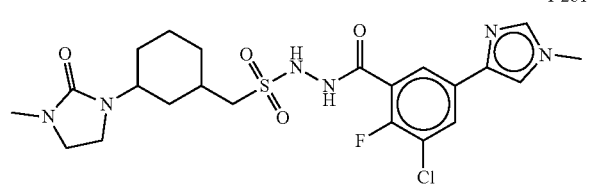
I-286
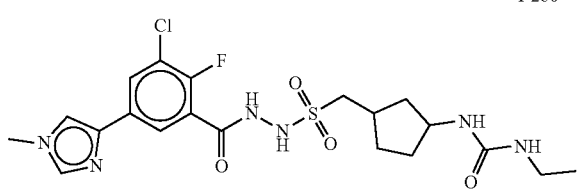
I-282
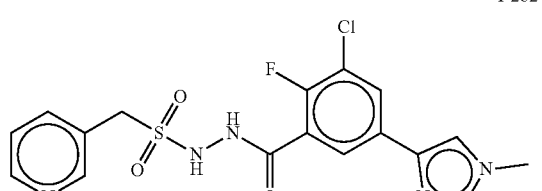
I-287
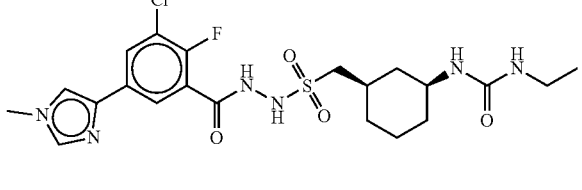
I-283
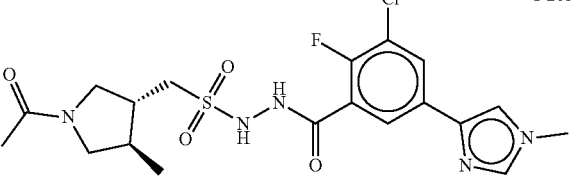
I-288
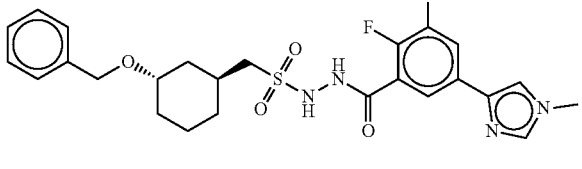
I-284
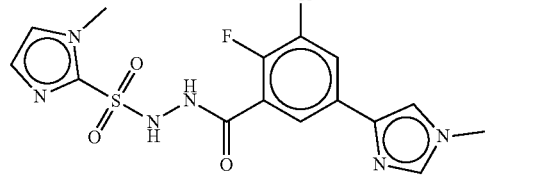

I-289
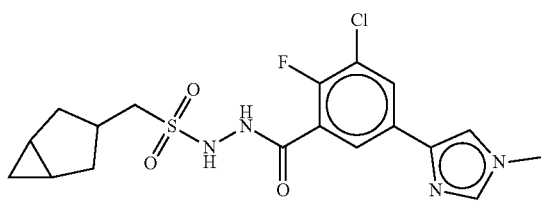
I-285
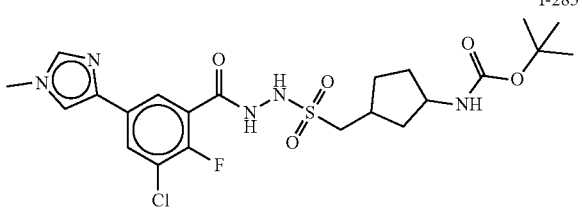
I-290
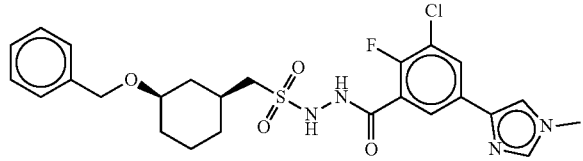
I-291
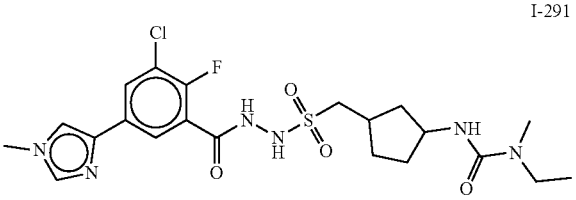
I-296
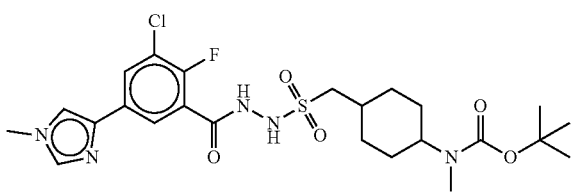
I-292
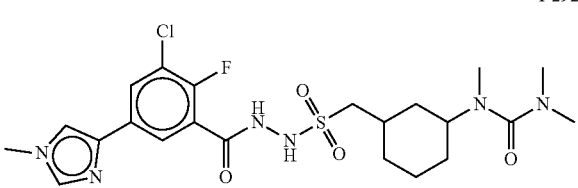
I-297
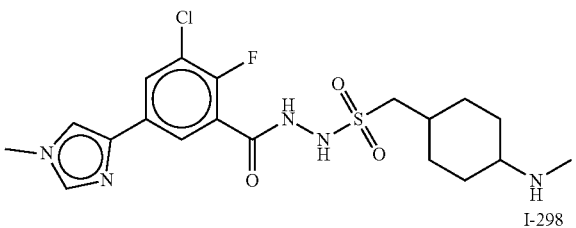
I-293
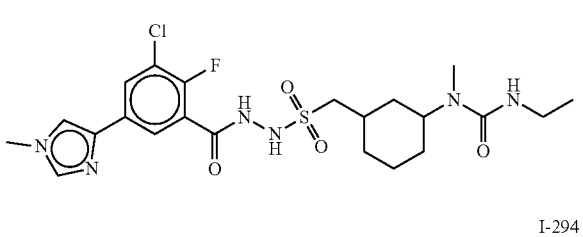
I-298
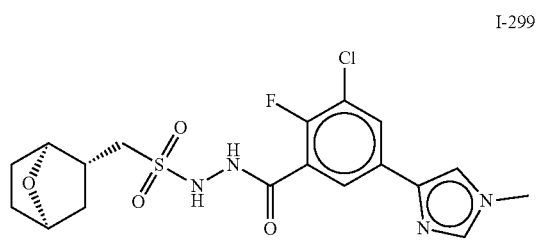
I-294
I-299
I-295
I-300
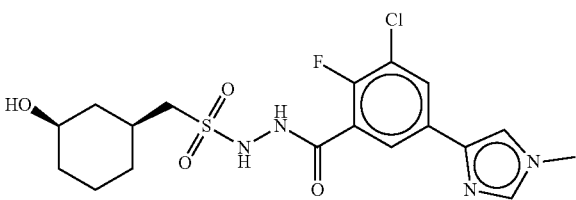
I-306
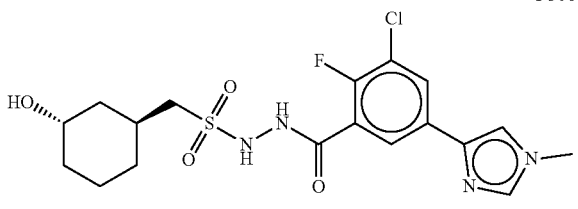

-continued
I-302
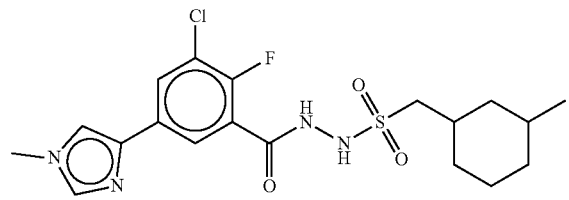
I-307
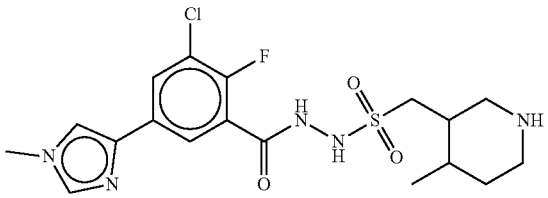
I-303
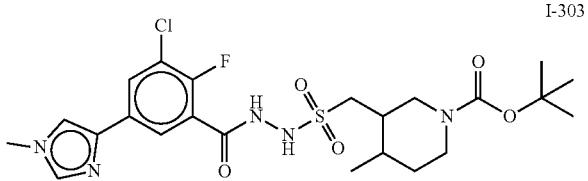
I-308
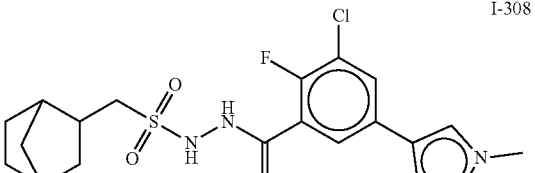
I-304
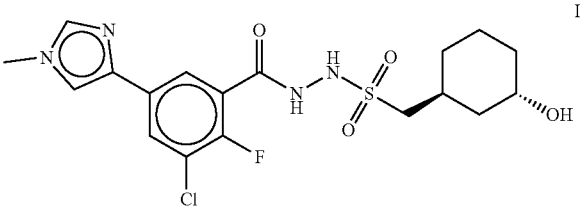
I-309
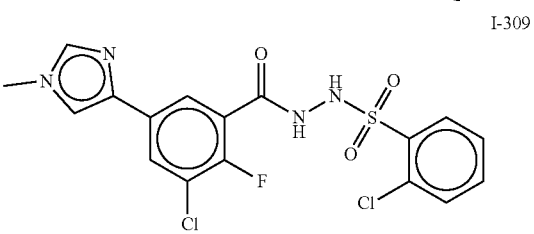
I-305
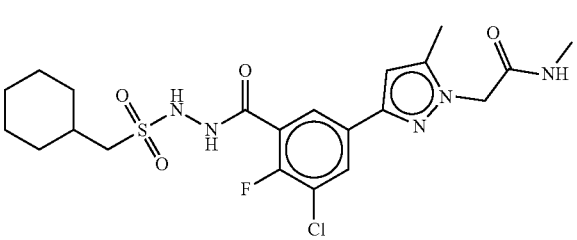
I-310
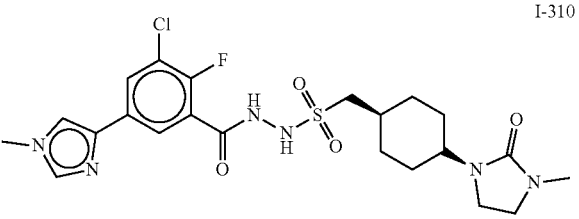
I-311
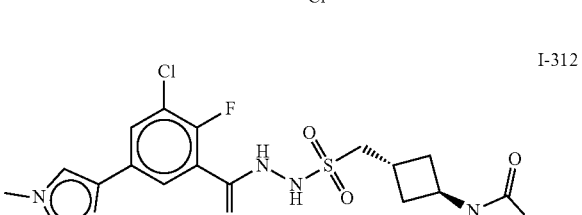
I-316
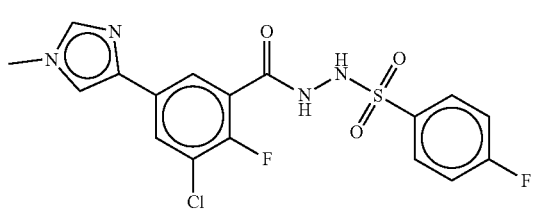
I-312
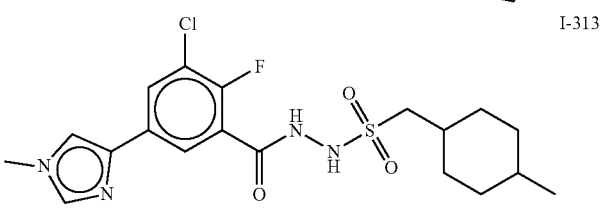
I-317
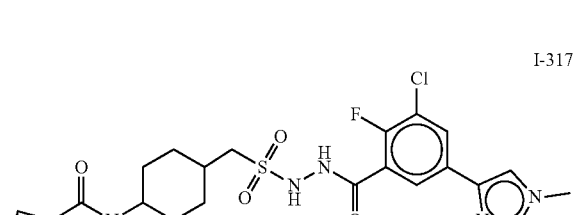
I-313
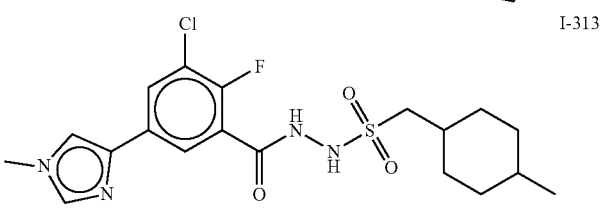
I-314
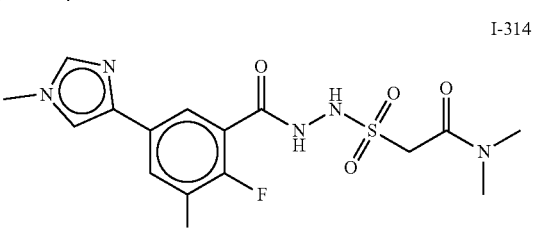

-continued
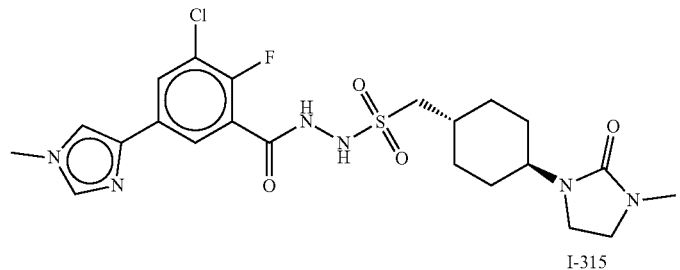
I-315
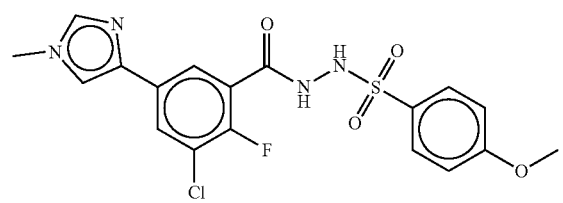
I-321
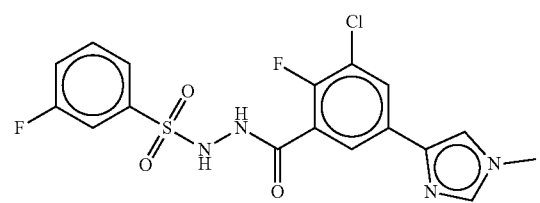
I-320
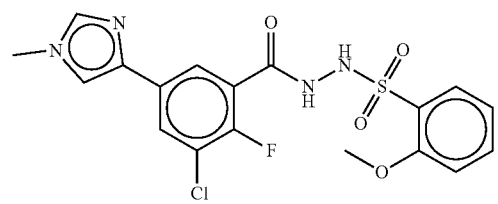
I-323
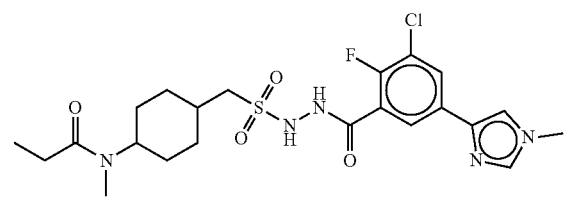
I-322
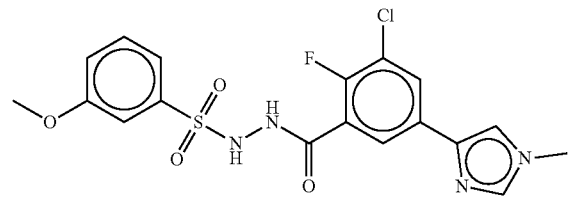
I-327
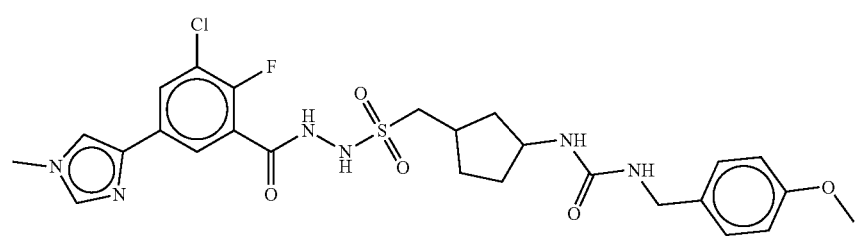
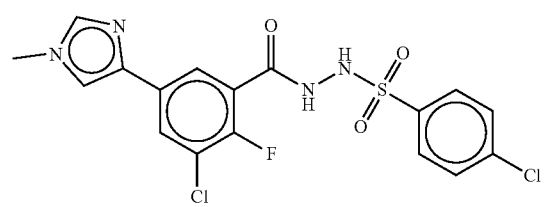
I-324
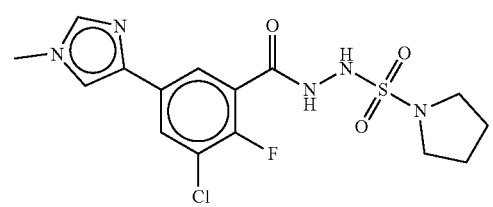
I-328
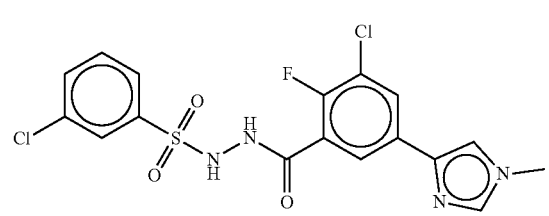
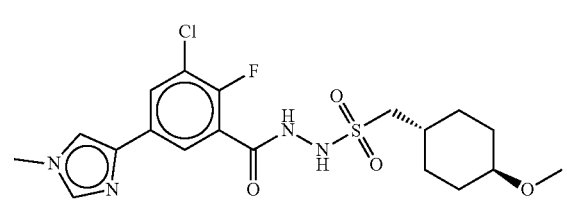
I-329
I-319
I-326

-continued
I-325
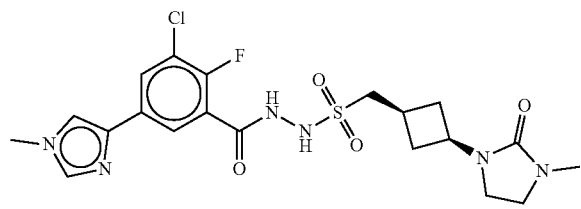
I-331
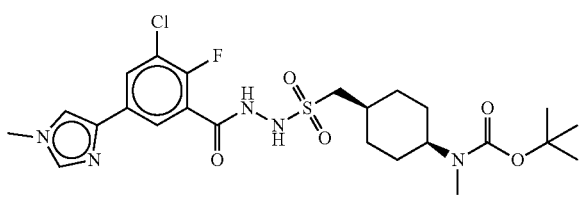
I-336
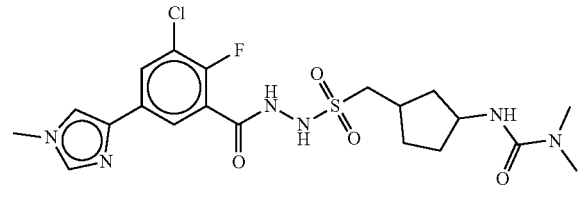
I-332
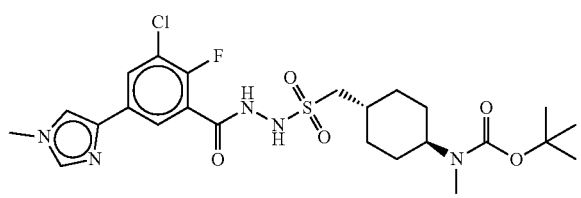
I-337
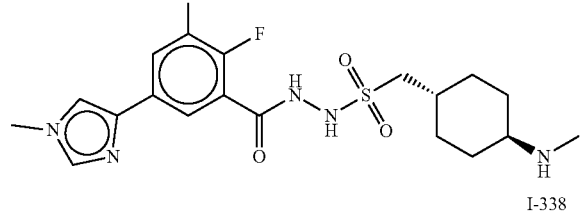
I-333
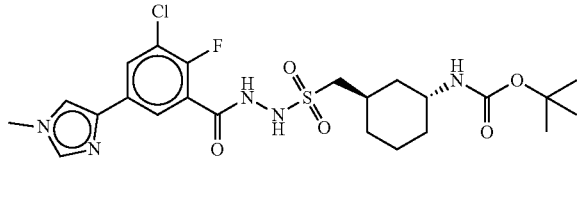
I-338
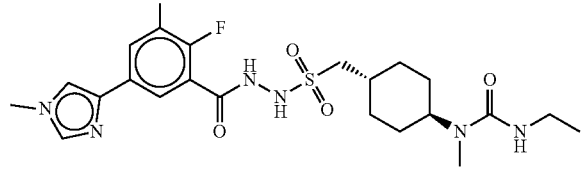
I-334
I-339
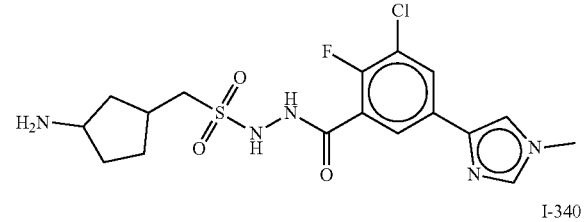
I-335
I-340
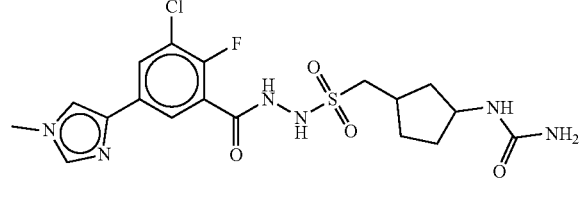
I-341
I-346
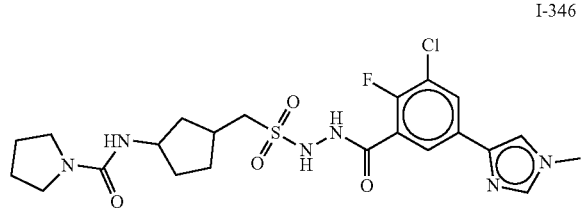
I-342

-continued
I-347
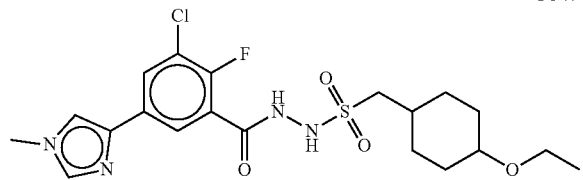
I-343
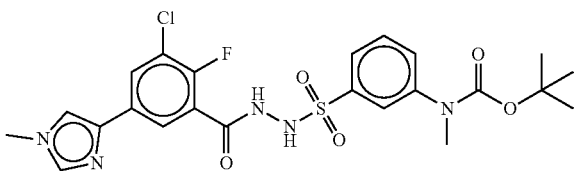
I-348
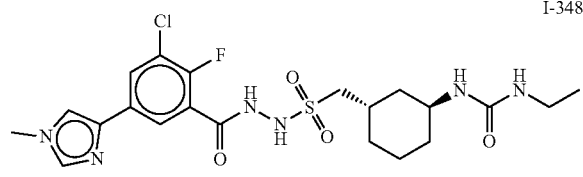
I-344
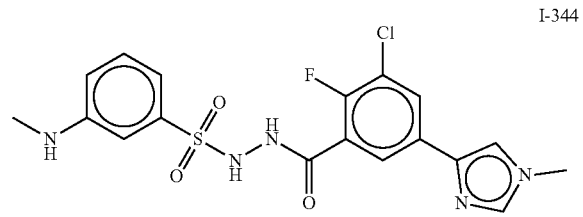
I-349
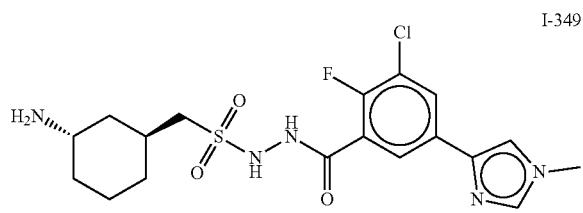
I-345
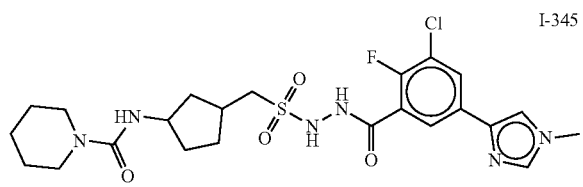
I-350
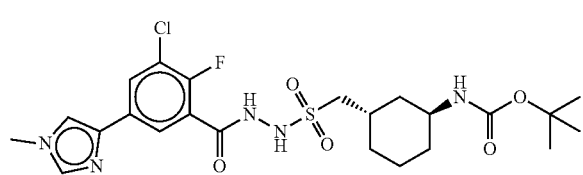
I-351
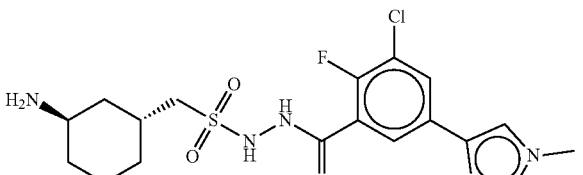
I-356
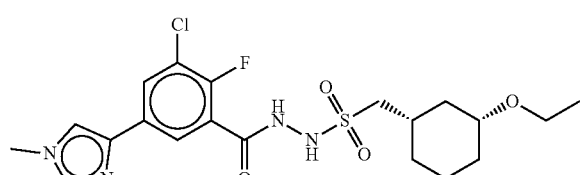
I-352
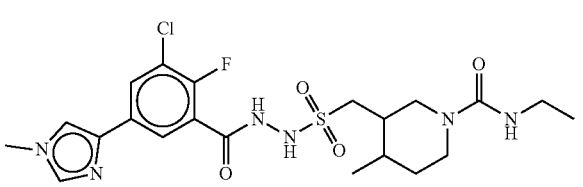
I-357
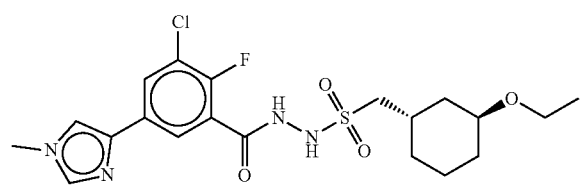
I-353
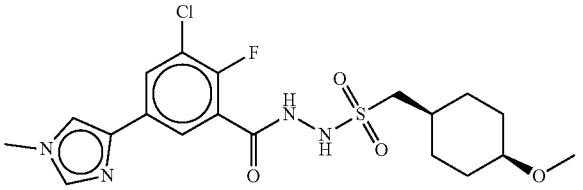
I-358
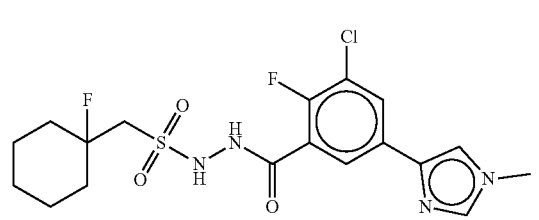

-continued
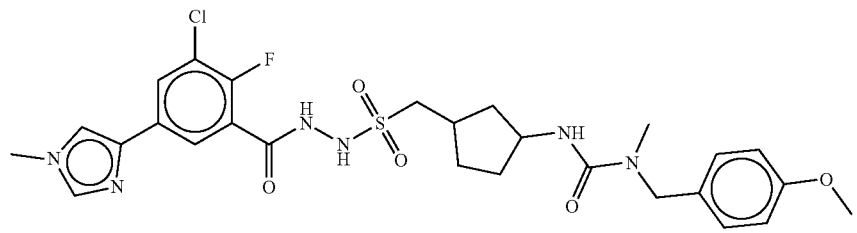
I-359
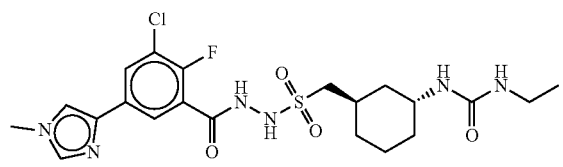
I-355
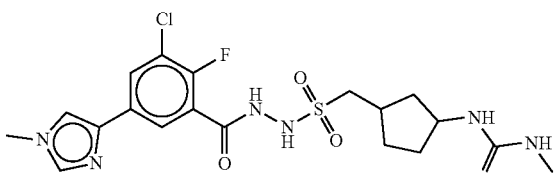
I-360
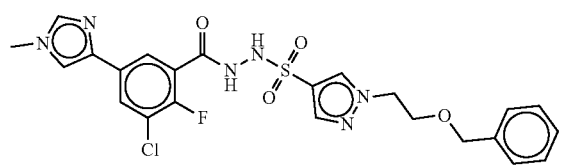
I-361
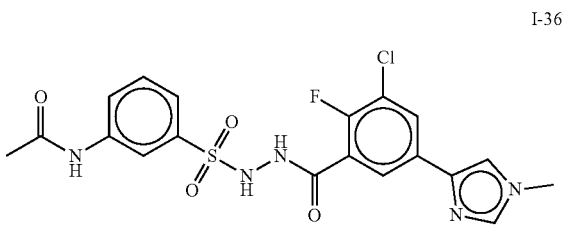
I-367
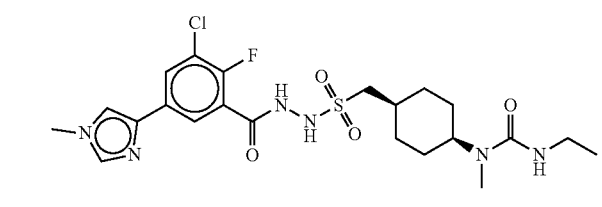
I-363
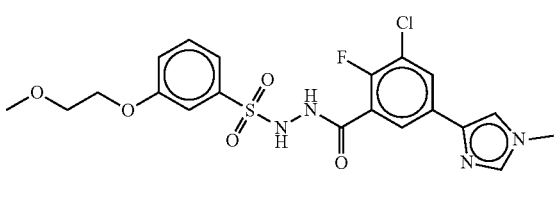
I-368
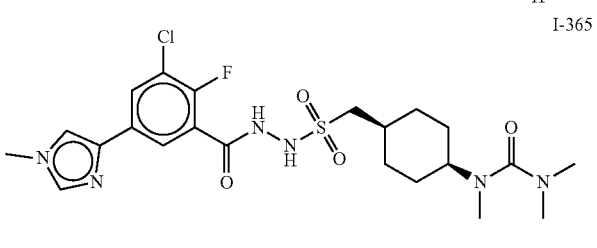
I-365
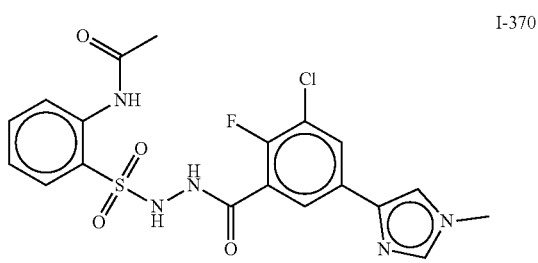
I-370

-continued
I-371
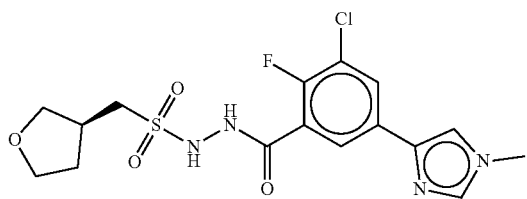
I-372
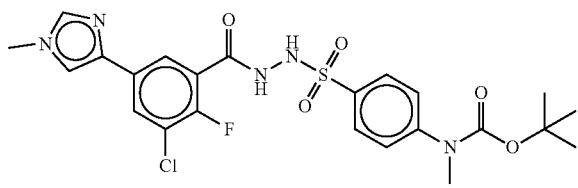
I-377
I-373
I-378
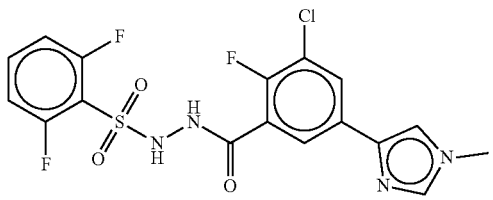
I-379
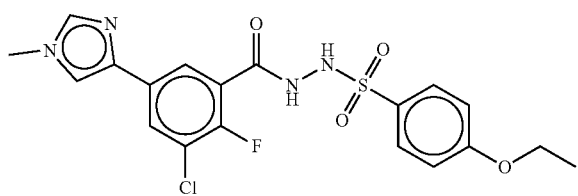
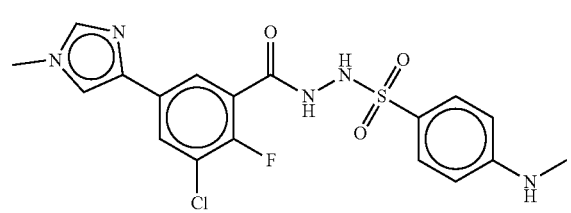
I-380
I-382
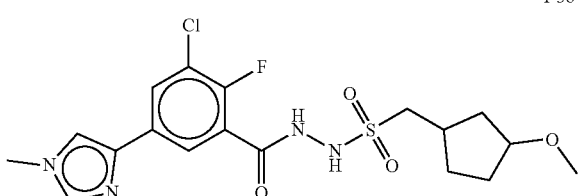
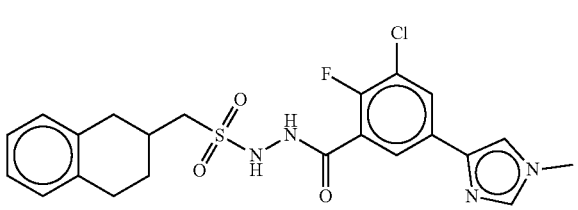
I-387
I-383
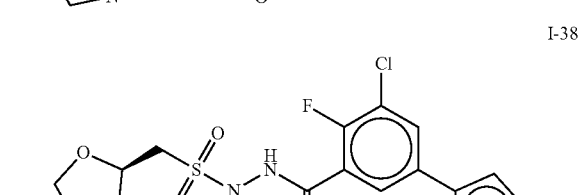
I-388
I-384
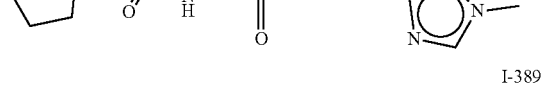
I-389
I-385
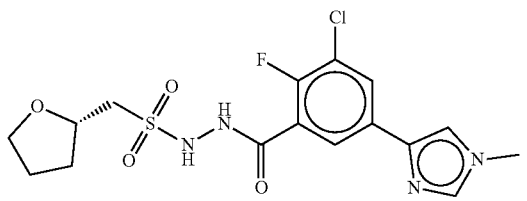
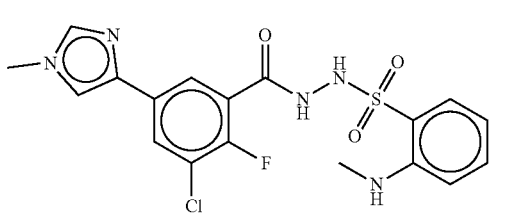

-continued
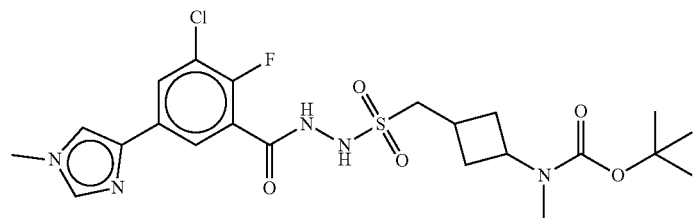
I-390
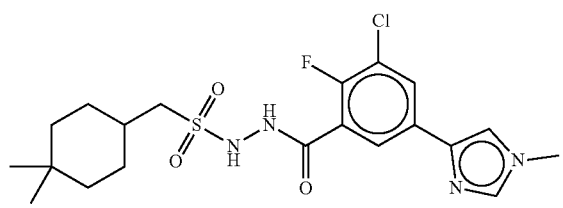
I-396
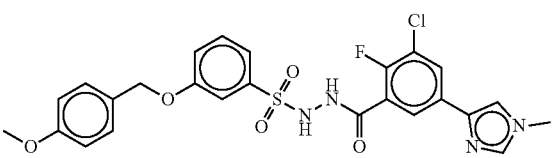
I-397
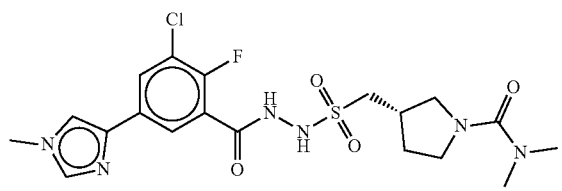
I-398
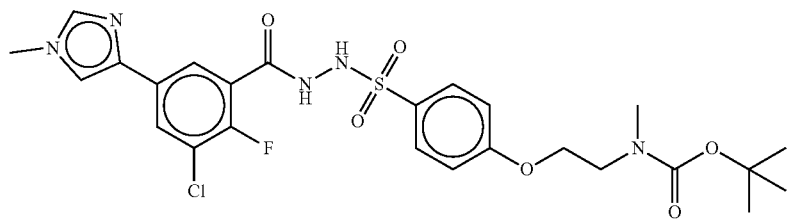
I-399
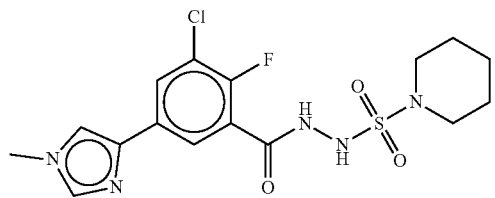
I-400
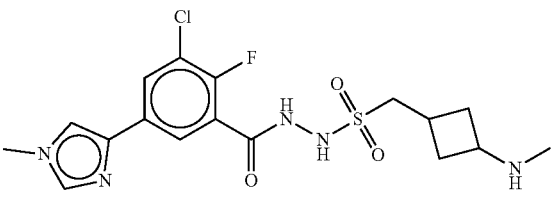
I-401
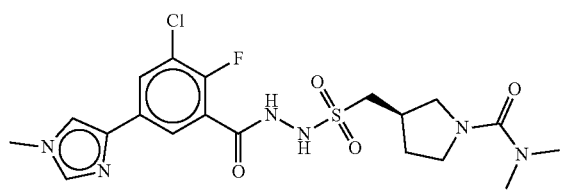
I-406
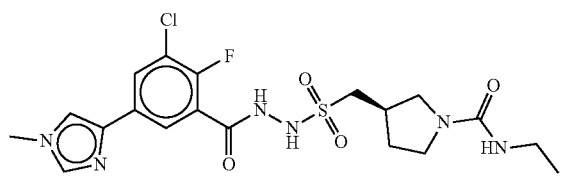
I-402
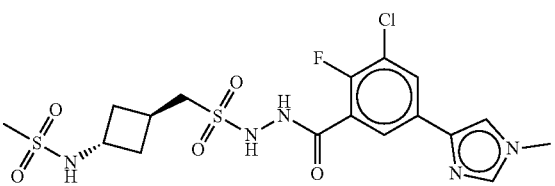

-continued
I-407
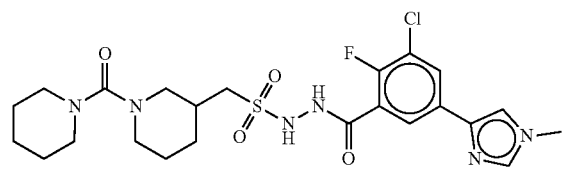
I-403
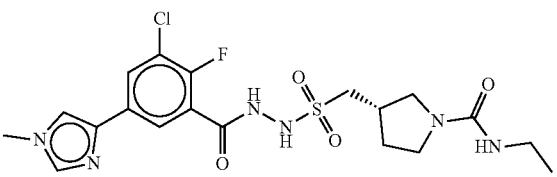
I-408
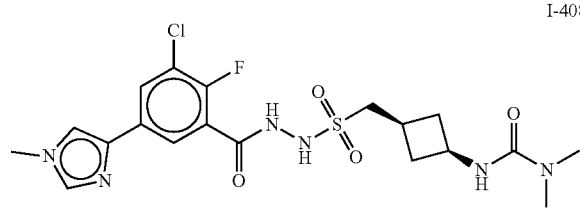
I-404
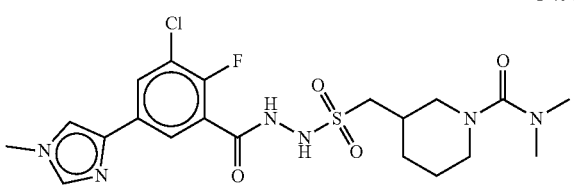
I-409
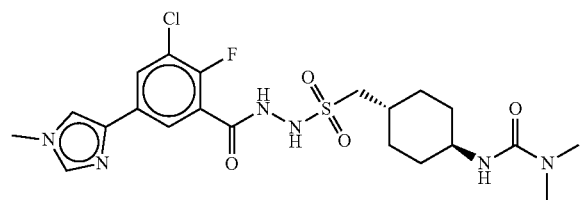
I-405
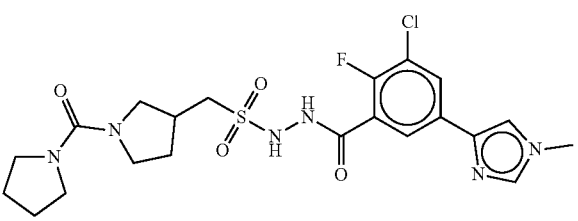
I-410
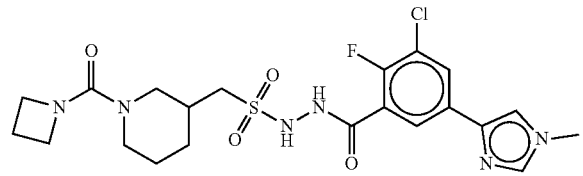
I-411
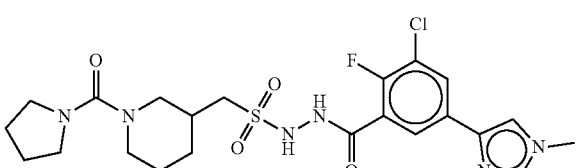
I-416
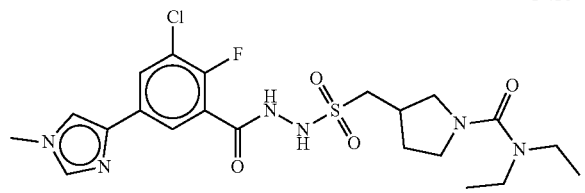
I-412
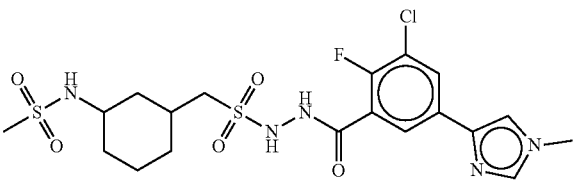
I-417
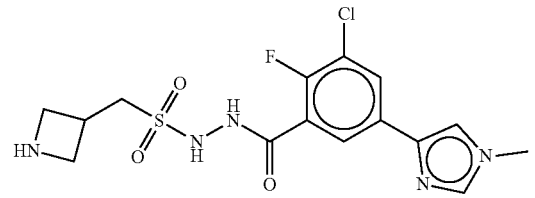
I-415
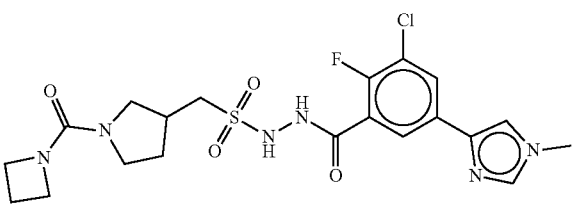
I-418
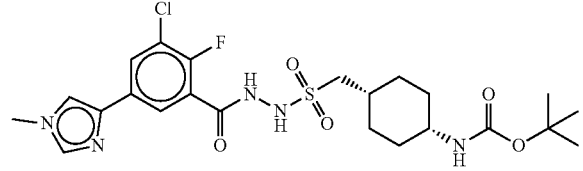
I-414
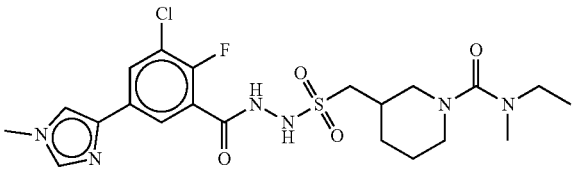

-continued
I-419
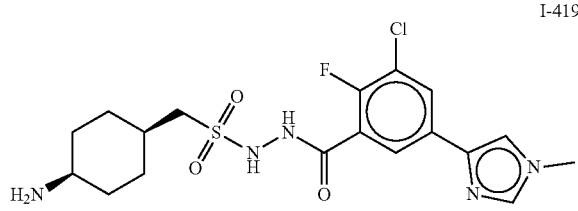
I-415
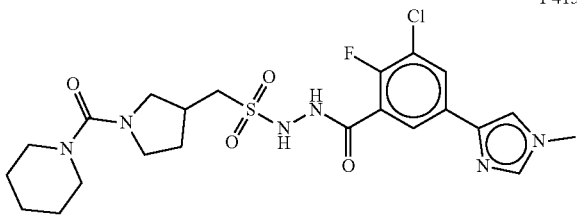
I-420
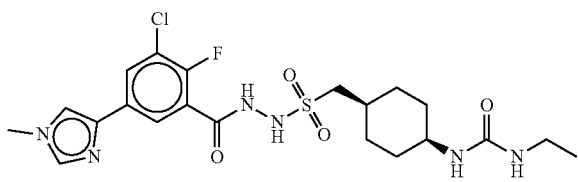
I-421
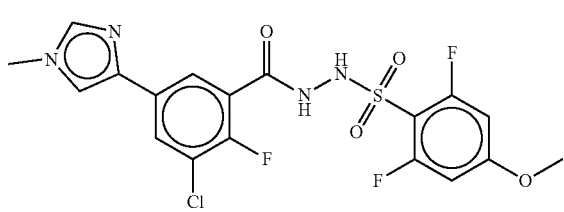
I-426
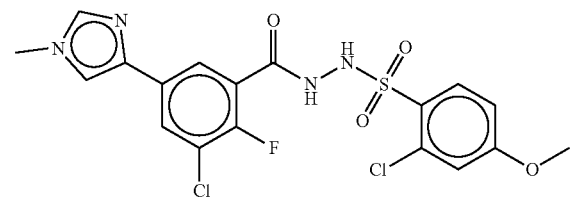
I-422
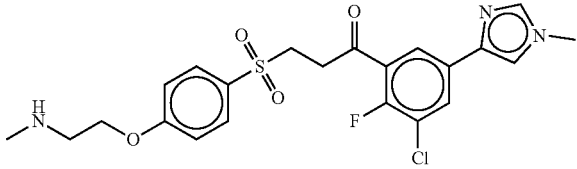
I-427
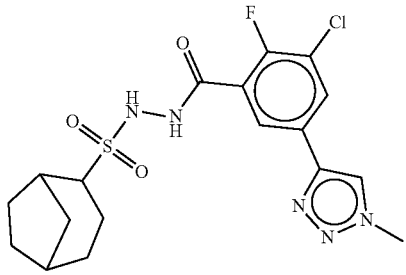
I-423
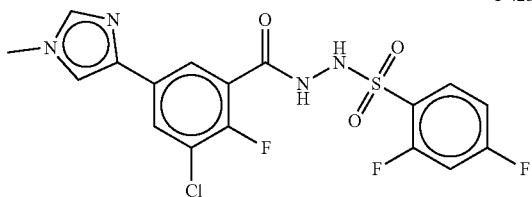
I-428
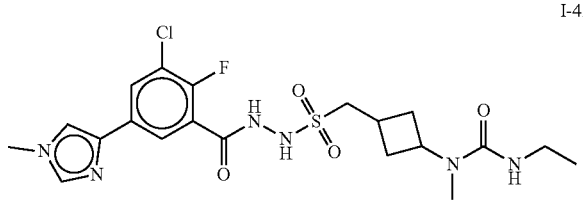
I-424
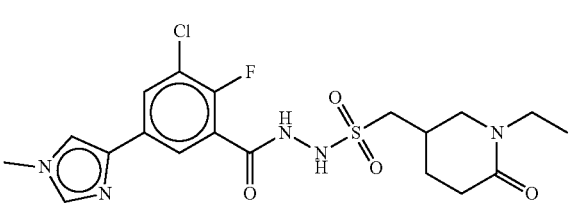
I-429
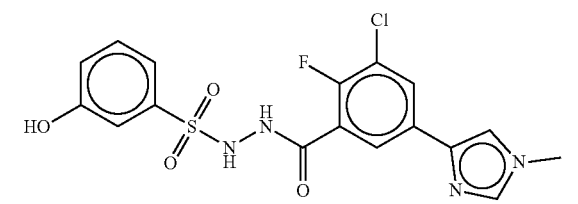
I-425
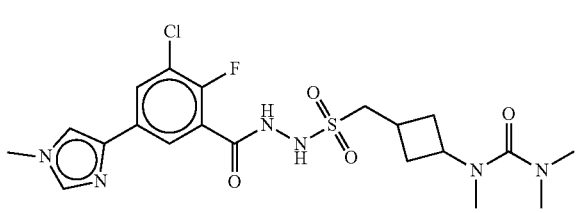

-continued
I-431
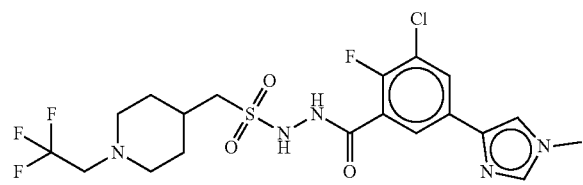
I-436
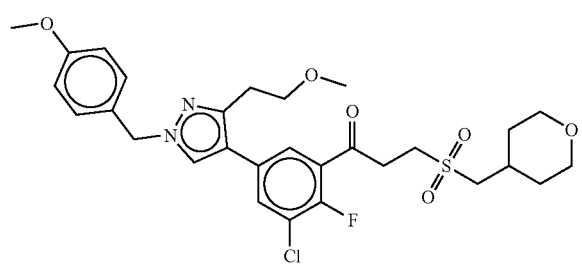
I-432
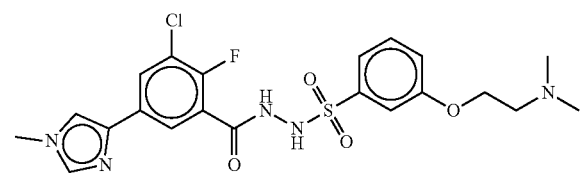
I-437
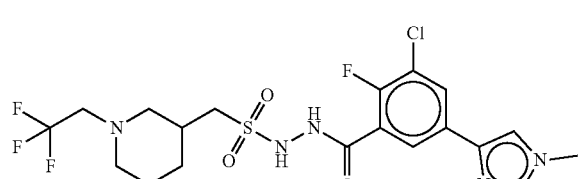
I-433
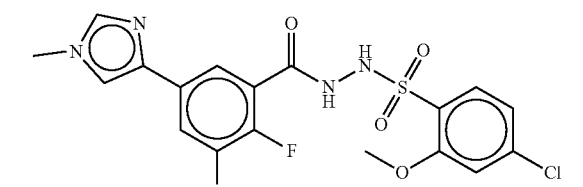
I-438
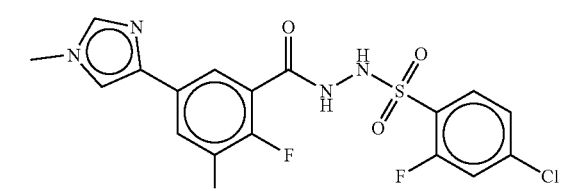
I-434
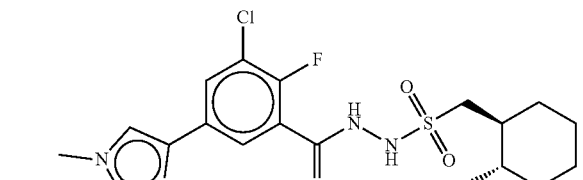
I-439
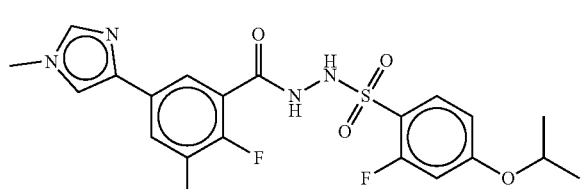
I-435
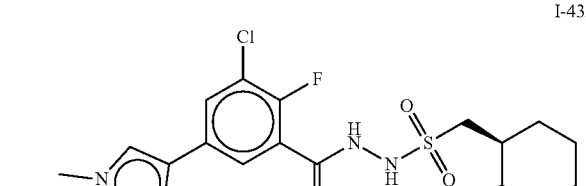
I-440
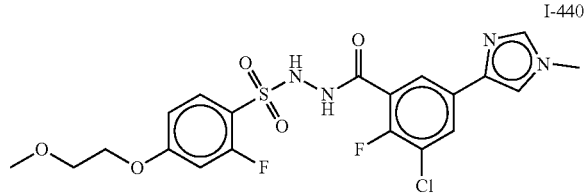
I-441
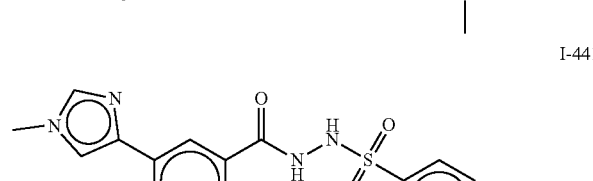
I-446
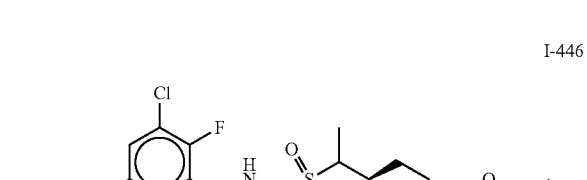
I-442
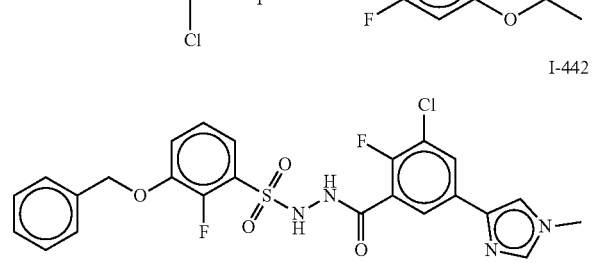
I-447
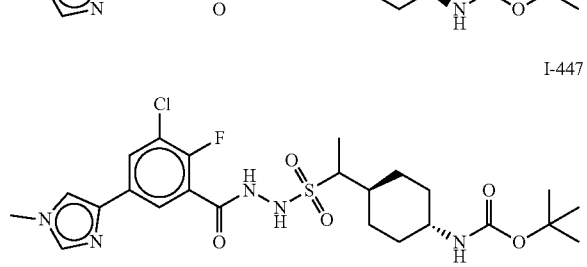

-continued
| 497 | 498 |
|---|---|
| I-443 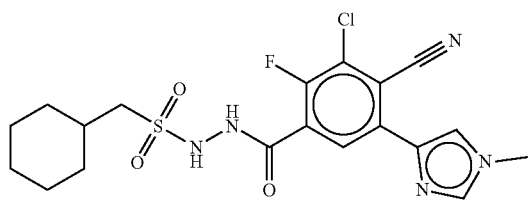 | I-448 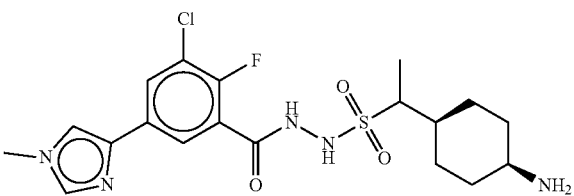 |
| I-444 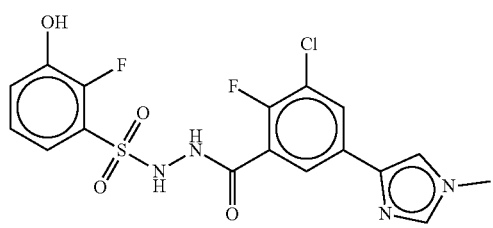 | I-449 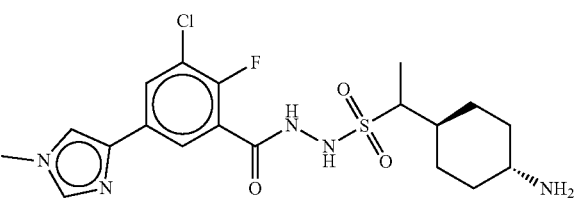 |
| I-445 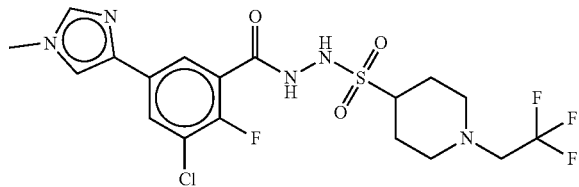 | I-450 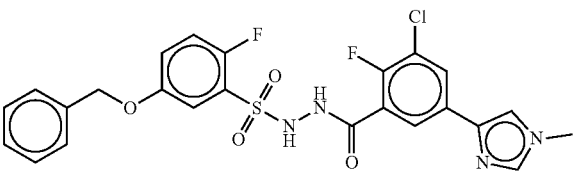 |
| I-451 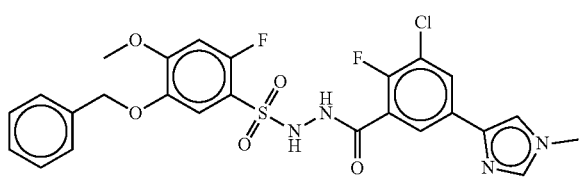 | I-456 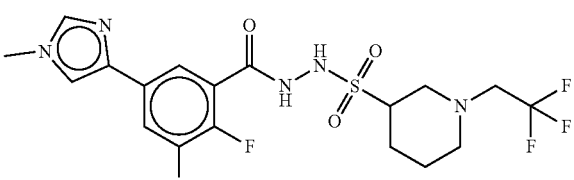 |
| I-452 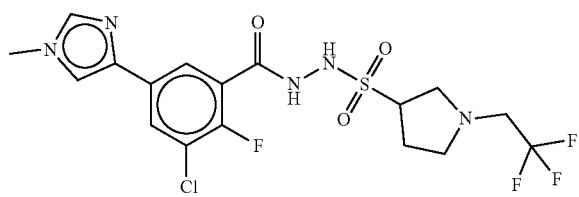 | I-457 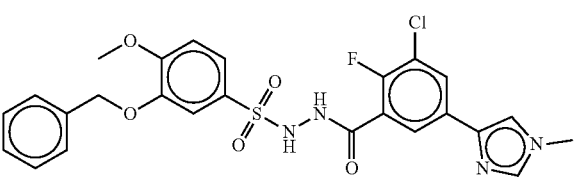 |
| I-453 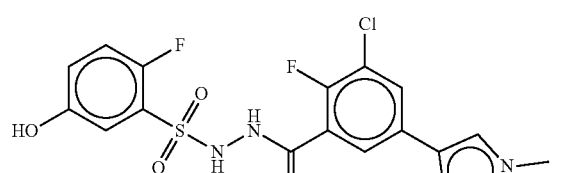 | I-458 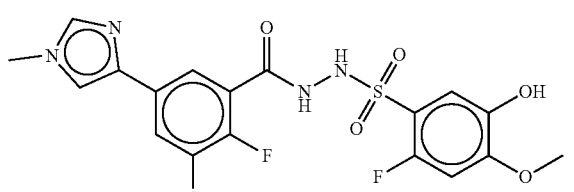 |
| I-454 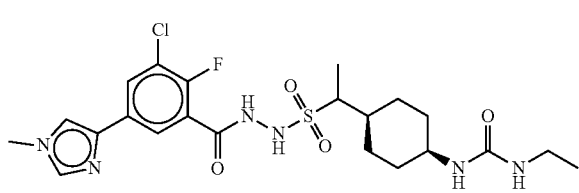 | I-459 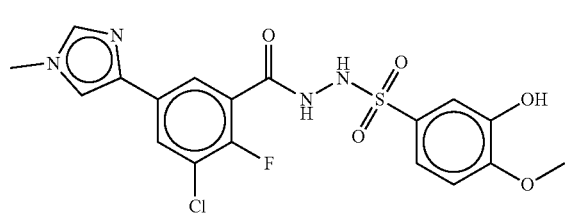 |

-continued
I-455
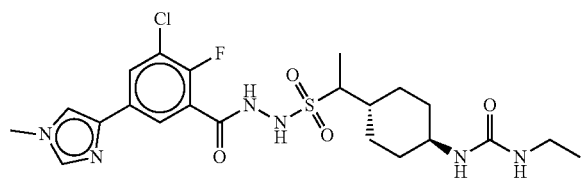
I-460
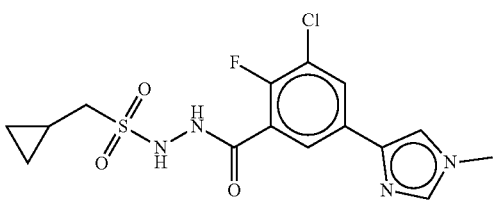
I-461
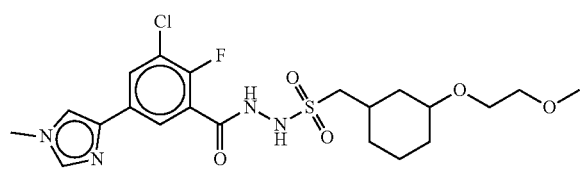
I-466
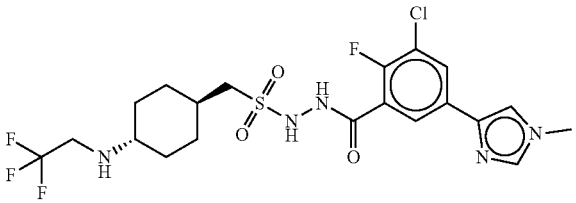
I-462
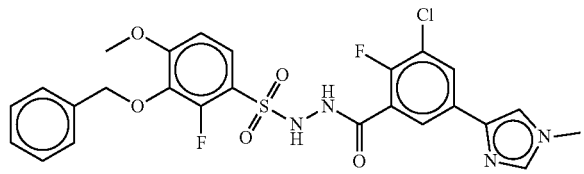
I-467
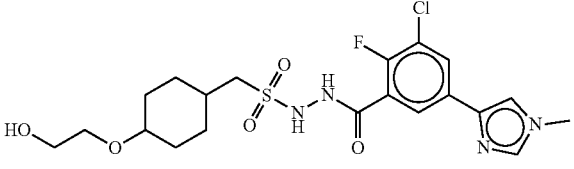
I-463
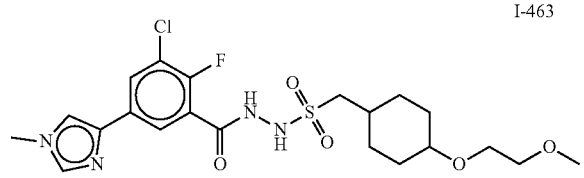
I-468
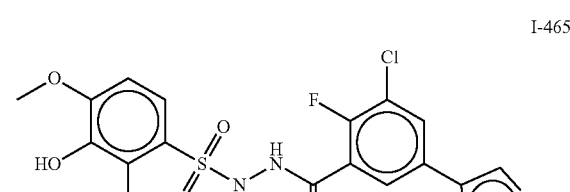
I-469
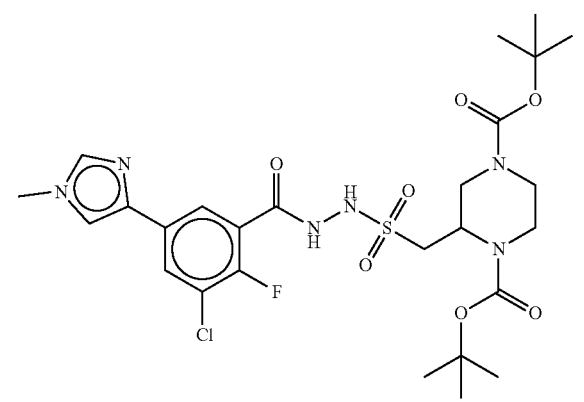
I-465
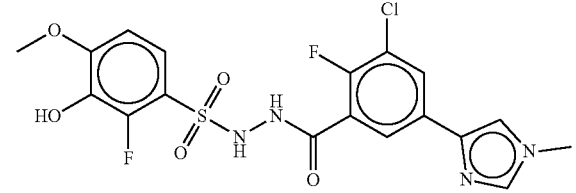
I-470
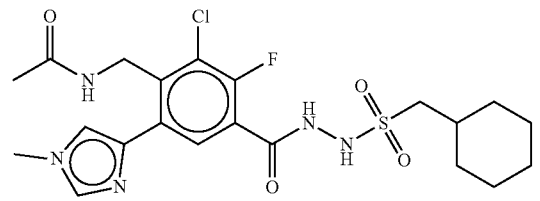
I-471
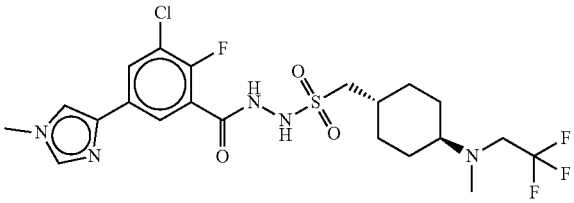

-continued
I-476
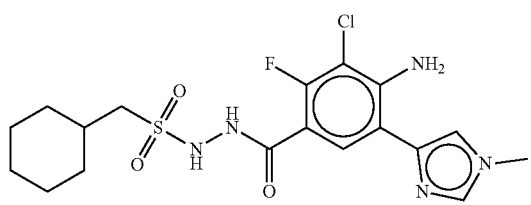
I-472
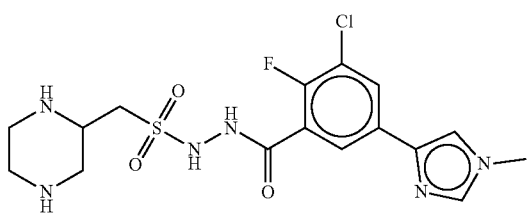
I-477
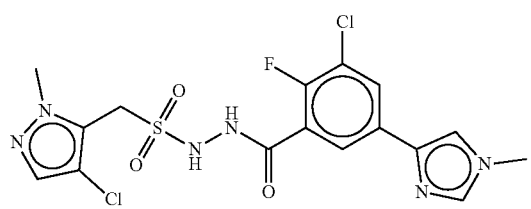
I-473
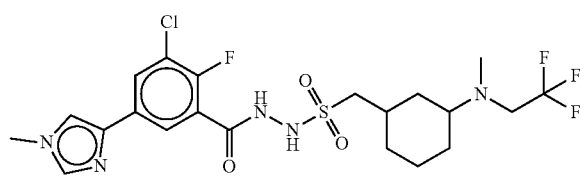
I-478
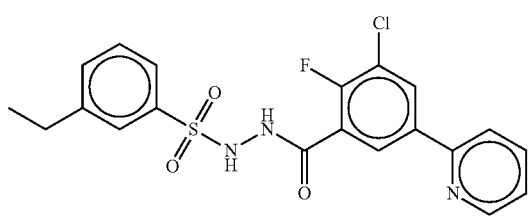
I-474
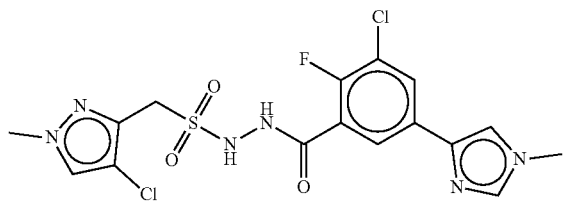
I-479
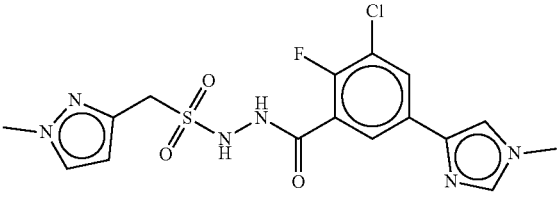
I-475
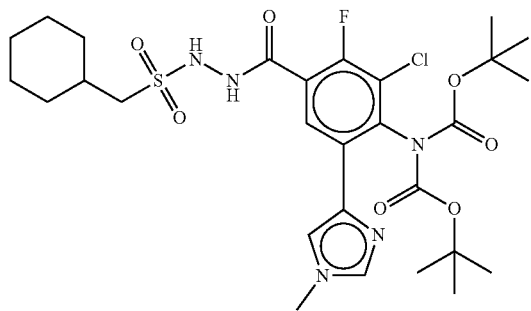
I-480
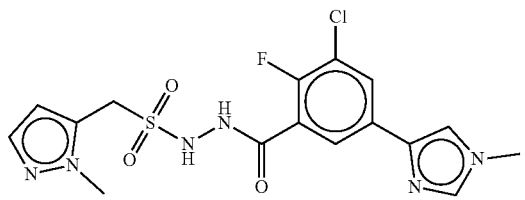
I-481
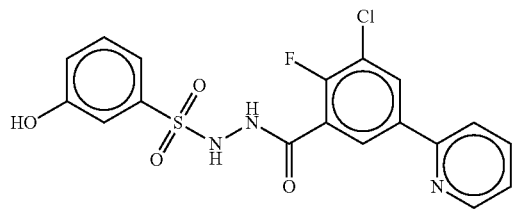
I-483
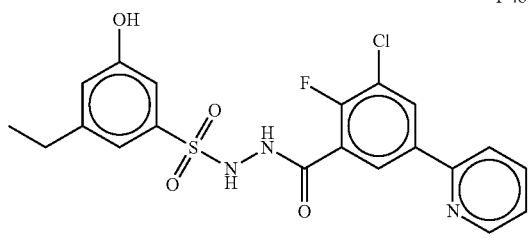

I-482
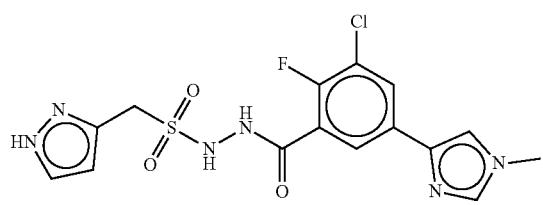
or a pharmaceutically acceptable salt thereof.
8. A pharmaceutical composition comprising a compound of claim 1, or a pharmaceutically acceptable salt thereof, and a pharmaceutically acceptable carrier or excipient.
* * * * *